(12) United States Patent
Keefe et al.

(10) Patent No.: US 12,049,455 B2
(45) Date of Patent: Jul. 30, 2024

(54) COMPOSITIONS AND METHODS FOR THE PREVENTION AND/OR TREATMENT OF MITOCHONDRIAL DISEASE, INCLUDING FRIEDREICH'S ATAXIA

(71) Applicant: Stealth BioTherapeutics Inc., Needham, MA (US)

(72) Inventors: Dennis Keefe, Needham, MA (US); Guozhu Zheng, Needham, MA (US); Pavels Arsenjans, Needham, MA (US)

(73) Assignee: STEALTH BIOTHERAPEUTICS INC., Needham, MA (US)

( * ) Notice: Subject to any disclaimer, the term of this patent is extended or adjusted under 35 U.S.C. 154(b) by 0 days.

(21) Appl. No.: 18/087,890

(22) Filed: Dec. 23, 2022

(65) Prior Publication Data
US 2023/0303506 A1    Sep. 28, 2023

Related U.S. Application Data

(62) Division of application No. 17/062,339, filed on Oct. 2, 2020, now Pat. No. 11,584,728.

(60) Provisional application No. 62/991,525, filed on Mar. 18, 2020, provisional application No. 62/911,069, filed on Oct. 4, 2019.

(51) Int. Cl.
*C07D 305/10* (2006.01)
*C07C 49/835* (2006.01)

(52) U.S. Cl.
CPC .......... *C07D 305/10* (2013.01); *C07C 49/835* (2013.01)

(58) Field of Classification Search
None
See application file for complete search history.

(56) References Cited

U.S. PATENT DOCUMENTS

| | | | |
|---|---|---|---|
| 6,133,322 A | 10/2000 | Rustin et al. | |
| 7,432,305 B2 | 10/2008 | Miller et al. | |
| 7,470,798 B2 | 12/2008 | Wang et al. | |
| 8,314,153 B2 | 11/2012 | Miller et al. | |
| 8,716,486 B2 | 5/2014 | Hinman et al. | |
| 8,716,527 B2 | 5/2014 | Hinman et al. | |
| 9,399,612 B2 | 7/2016 | Miller | |
| 9,663,485 B2 | 5/2017 | Marugan et al. | |
| 9,932,286 B2 | 4/2018 | Miller et al. | |
| 10,071,978 B2 | 9/2018 | Wesson et al. | |
| 10,105,325 B2 | 10/2018 | Miller et al. | |
| 10,189,830 B2 | 1/2019 | Hinman et al. | |
| 10,703,701 B2 | 7/2020 | Hinman et al. | |
| 2005/0065149 A1 | 3/2005 | Wang et al. | |
| 2006/0281809 A1 | 12/2006 | Miller et al. | |
| 2013/0345312 A1 | 12/2013 | Jankowski et al. | |

FOREIGN PATENT DOCUMENTS

| | | |
|---|---|---|
| EP | 2 332 534 A1 | 6/2011 |
| EP | 2 424 513 | 3/2012 |
| EP | 2 605 769 | 6/2013 |
| WO | WO-2006/130775 | 12/2006 |
| WO | WO-2007/100652 | 9/2007 |
| WO | WO-2011/025785 | 3/2011 |
| WO | WO-2012/022467 A2 | 2/2012 |
| WO | WO-2012/022468 | 2/2012 |
| WO | WO-2012/068552 | 5/2012 |
| WO | WO-2012/170773 | 12/2012 |
| WO | WO-2014/011047 A1 | 1/2014 |
| WO | WO-2014/039862 | 3/2014 |
| WO | WO-2014/078573 | 5/2014 |
| WO | WO-2014/145116 A2 | 9/2014 |
| WO | WO-2015/183963 | 12/2015 |
| WO | WO-2017/087795 A1 | 5/2017 |
| WO | WO-2017/106803 A1 | 6/2017 |
| WO | WO-2017/123822 | 7/2017 |
| WO | WO-2018/191732 A1 | 10/2018 |
| WO | WO-2018/191789 | 10/2018 |
| WO | WO-2019/118878 | 6/2019 |

OTHER PUBLICATIONS

Final Office Action on U.S. Appl. No. 17/221,463 dated Sep. 21, 2023.
Guo et al., "Rapid Deoxyfluorination of Alcohols with N-Tosyl-4-chlorobenzenesulfonimidoyl Fluoride (SulfoxFluor) at Room Temperature", Chem. Eur. J., 2019, vol. 25, pp. 7259-7264.
Non-Final Office Action on U.S. Appl. No. 17/221,463 dated Apr. 18, 2023.
Yang et al., "Protein-Ubiquinone Interaction in Bovine Heart Mitochondrial Succinate=Cytochrome c Reductase", The Journal of Biological Chemistry, vol. 266, No. 31, 1991, pp. 20863-20869.
Yu et al., "Syntheses of Biologically Active Ubiquinone Derivatives", Biochemistry, vol. 21, 1982, pp. 4096-4101.
Abeti et al., "Calcium Deregulation: Novel Insights to Understand Friedreich's Ataxia Pathophysiology", Frontiers in Cellular Neuroscience. vol. 12 Article 264 pp. 1-13 (published Oct. 2, 2018) doi: 10.3389/fncel.2018.00264.
Bodmer, et al., "Pharmacokinetics and metabolism of idebenone in healthy male subjects," Eur J Clin Pharmacol, 2009, vol. 65, pp. 493-501. DOI 10.1007/s00228-008-0596-1.
C. Varricchio et al., "The ying and yang of idebenone: Not too little, not too much—cell death in NQO1 deficient cells and the mouse retina", Free Radical Biology and Medicine, https://doi.org/10.1016/j.freeradbiomed.2019.11.030.

(Continued)

*Primary Examiner* — Samantha L Shterengarts
(74) *Attorney, Agent, or Firm* — Foley & Lardner LLP

(57) ABSTRACT

The disclosure provides therapeutic compositions (i.e., therapeutic agents) and methods of preventing or treating Friedreich's ataxia in a mammalian subject, reducing risk factors, signs and/or symptoms associated with Friedreich's ataxia (e.g., Complex I deficiency), and/or reducing the likelihood or severity of Friedreich's ataxia. The disclosure further provides novel intermediates for the production of said therapeutic compositions and related reduced versions of said therapeutic compositions, which reduce forms may also be used as therapeutic agents (or prodrugs of the therapeutic agent(s)).

5 Claims, 14 Drawing Sheets

Specification includes a Sequence Listing.

(56) References Cited

OTHER PUBLICATIONS

Daniel et al. "Novel Short-Chain Quinones to Treat Vision Loss in a Rat Model of Diabetic Retinopathy," International Journal of Molecular Sciences, vol. 22 (2021) (pp. 1-17).
Erb et al. "Features of Idebenone and Related Short-Chain Quinones that Rescue ATP Levels under Conditions of Impaired Mitochondrial Complex I", PLoS One Apr. 2012 vol. 7 Issue 4 pp. 1-8 e36153.
Gousiadou et al., "Computational Analysis of LOX1 Inhibition Identifies Descriptors Responsible for Binding Selectivity" ACS Omega 2018, 3, 2261-2272.
Haefeli et al. "NQO1-Dependent Redox Cycling of Idebenone: Effects on Cellular Redox Potential and Energy Levels", PLoS One, vol. 6, Issue 3, e17963, Mar. 2011.
Hausse et al., "Idebenone and reduced cardiac hypertrophy in Friedreich's ataxia" Heart. 2002;87:346-349.
Hinman et al., "Vitamin E hydroquinone is an endogenous regulator of ferroptosis via redox control of 15-lipoxygenase", PLOS One. Aug. 15, 2018 pp. 1-22 https://doi.org/10.1371/journal.pone.0201369.
Imounan et al., "Clinical and Genetic Study of Friedreich's Ataxia and Ataxia with Vitamin E Deficiency in 44 Moroccan Families", World Journal of Neuroscience, 4, 299-305 (2014) http://dx.doi.org/10.4236/wjns.2014.44033.
International Preliminary Report on Patentability on PCT PCT/US2020/054107 dated Apr. 14, 2022.
International Search Report and Written Opinion on PCT PCT/US2021/025558 dated Jul. 9, 2021 (15 pages).
Jabbari et al., "O-prenylated 3-carboxycoumarins as a novel class of 15-LOX-1 inhibitors" PLOS One. pp. 1-21 Feb. 9, 2017 DOI:10.1371/journal.pone.0171789.
Jaber, et al. "Idebenone and Neuroprotection: Antioxidant, Pro-oxidant, or Electron Carrier?" J Bioenerg Biomembr., Apr. 2015, vol. 47(0), pp. 111-118. doi:10.1007/s10863-014-9571-y.
Jauslin et al., "A cellular model for Friedreich Ataxia reveals small-molecule glutathione peroxidase mimetics as novel treatment strategy", Human Molecular Genetics, 2002, vol. 11, No. 24 3055-3063.
Kahn-Kirby et al. "Targeting ferroptosis: A novel therapeutic strategy for the treatment of mitochondrial disease-related epilepsy", PLoS One 14(3): e0214250. Mar. 28, 2019 https://doi.org/10.1371/journal.pone.0214250.
Lutz et al, "Enantioselective Synthesis of the Chromane Moiety of Vitamin E", European Journal of Organic Chemistry, vol. 1999, No. 5, May 1, 1999, pp. 1075-1084.
Lutz F. Tietze et al., "Enantioselective Synthesis of the Chromane Moiety of Vitamin E", European Journal of Organic Chemistry, vol. 1999, No. 5, May 1, 1999 (May 1, 1999), pp. 1075-1084, XP055760513, DE ISSN: 1434-193X, DOI: 10.1002/(SICI)1099-0690(199905)1999:5<1075 ::AID-EJOC1075>3.0.CO;2-I compound 19.
Lynch et al. "A Phase 3, Double-blind, Placebo-Controlled Trial of Idebenone in Friedreich Ataxia", Arch Neurol. 2010;67(8):941-947.
Notice of Allowance on U.S. Appl. No. 17/062,339 dated Sep. 14, 2022.
Nunez et al., "Discovery two potent and new inhibitors of 15-lipoxygenase: (E)-3-((3,4-dihydroxybenzylidene) amino)-7-hydroxy-2H-chromen-2-one and (E)-O-(4-(((7-hydroxy-2-oxo-2H-chromen-3-yl) imino)methine)phenyl)dimethylcarbamothioate", Med Chem Res. (2017) 26:2707-2717 DOI 10.1007/s00044-017-1968-9.
Pallast et al., "12/15-Lipoxygenase targets neuronal mitochondria under oxidative stress", J Neurochem. Nov. 2009 ; 111(3): 882-889. doi:10.1111/j.1471-4159.2009.06379.x.
Parkinson et al., "Co-enzyme Q10 and idebenone use in Friedreich's ataxia", J. Neurochem. (2013) 126 (Suppl. 1), 125-141 doi: 10.1111/jnc.12322.
Petrillo et al., "Targeting NRF2 for the Treatment of Friedreich's Ataxia: A Comparison among Drugs", Int. J. Mol. Sci. 2019, 20, 5211; doi:10.3390/ijms20205211.
Sadeghian et al., "15-Lipoxygenase inhibitors: a patent review", Expert Opin. Ther. Patents. (2015) 26(1) pp. 1-24 DOI: 10.1517/13543776.2016.1113259.
Sekimoto et al, "Asymmetric syntheses of daedalin A and quercinol and their tyrosinase inhibitory activity", Biorganic & Medicinal Chemistry Letters, vol. 20, No. 3, Feb. 1, 2010, pp. 1063-1064.
Sekimoto M et al., "Asymmetric syntheses of daedalin A and quercinol and their tyrosinase inhibitory activity", Biorganic & Medicinal Chemistry Letters, vol.20, No. 3, Feb. 1, 2010, pp. 1063-1064.
Stealth Biotherapeutics (*company presentation*) Leading Mitochondrial Medicine. Nov. 2019.
Stealth Biotherapeutics Corp. Form 20-F (Annual and Transition Report (foreign private issuer)). Filed Apr. 1, 2020 for the Period Ending Dec. 31, 2019. Edgar Online, a division of Donnelley Financial Solutions.
Tadokoro et al., "Mitochondria-dependent ferroptosis plays a pivotal role in doxorubicin cardiotoxicity", JCI Insight. 2020;5(9):e132747. https://doi.org/10.1172/jci.insight.132747.
U.S. Office Action—Restriction Requirements in U.S. Appl. No. 17/062,339 dated Sep. 2, 2021.
U.S. Office Action on U.S. Appl. No. 17/062,339 dated Feb. 2, 2022.
V. Giorgio, et al., "The idebenone metabolite QS10 restores electron transfer in complex I and coenzyme Q defects," BBA—Bioenergetics 1859, 2018, pp. 901-908. https://doi.org/10.1016/j.bbabio.2018.04.006.
Vafai SB et al., "Natural Product Screening Reveals NaphthoquinoneComplex | Bypass Factors", PLoS One 11(9): e0162686. doi:10.1371/journal.pone.0162686 (Sep. 13, 2016).
Walter, L, et al, Three classes of ubiquinone analogs regulate the mitochondrial permeability transition pore through a common site, Journal of Biological Chemistry, American Society for Biochemistry and Molecular Biology, US, vol. 275, No. 38, Sep. 22, 2000, pp. 29521-29527.
Worth et al. "Stable isotopes and LC-MS for monitoring metabolic disturbances in Friedreich's ataxia platelets", Bioanalysis. (2015) 7(15), 1843-1855.
Xingui Liu et al., "Synthesis and Liver Microsomal Metabolic Stability Studies of a Fluorine-Substituted [delta]-Tocotrienol Derivative", CHEMMEDCHEM, vol. 15, No. 6, Jan. 19, 2020 (Jan. 19, 2020), pp. 506-516.
Zesiewicz et al., "Double-blind, randomized and controlled trial of EPI-743 in Friedreich's ataxia", Neurodegener. Dis. Manag. Jul. 27, 2018 10.2217/nmt-2018-0013 ISSN:1758-2024.
Zhao et al. "Peptide SS-31 upregulates frataxin expression and improves the quality of mitochondria: implications in the treatment of Friedreich ataxia", Scientific Reports. 7:9840 pp. Aug. 1-11, 29, 2017 DOI:10.1038/s41598-017-10320-2.
Foreign Office Action on CN 202180040296.8, Dated Jan. 12, 2024.
Foreign Office Action on CA 3176909 Dated Feb. 14, 2024.
Jinbo Hu et al., "Rapid Deoxyfluorination of Alcohols with 4-Chloro-N-tosylbenzene-1-Sulfonimidoyl Fluoride (SulfoxFluor) at Room Temperature", Chemistry—A European Journal, 201901176, Dec. 31, 2019.
Lagishetti et al. "Construction of Bridged-Ring-Fused Naphthalenone Derivatives Through an Unexpected Zn(OTf)2-Catalyzed Cascade Transformation", Org. Lett. 2019, 21, pp. 5301-5304.
Zhao et al. "Toward a Total Synthesis of Divergolide A; Synthesis of the Amido Hydroquinone Core and the C10-C15 Fragment", SYNLETT, 2012, 23, pp. 2845-2849.

COMPOSITIONS AND METHODS FOR THE PREVENTION AND/OR TREATMENT OF MITOCHONDRIAL DISEASE, INCLUDING FRIEDREICH'S ATAXIA

CROSS-REFERENCE TO RELATED APPLICATIONS

This application is a divisional application of U.S. patent application Ser. No. 17/062,339, filed on Oct. 2, 2020, and claims the benefit of and priority to U.S. Provisional Appl. No. 62/911,069, filed Oct. 4, 2019, and U.S. Provisional Appl. No. 62/991,525, filed Mar. 18, 2020, the contents of each of which are incorporated herein by reference in their entireties for any and all purposes.

SEQUENCE LISTING

The instant application contains a Sequence Listing which has been submitted electronically in XML format and is hereby incorporated by reference in its entirety. Said XML copy, created on Jun. 14, 2023, is named 091151-1465_SL.xml and is 21,851 bytes in size.

Technical Field

The present application relates generally to compositions and methods for preventing, ameliorating and/or treating mitochondrial disease, such as Friedreich's ataxia, and/or reducing the severity of such diseases. Furthermore, the present application relates to: 1) methods for the preparation of novel therapeutic compounds and related intermediates (e.g., chromanes (benzodihydropyrans), quinones, hydroquinones, benzoquinones and hydroxybenzoquinones), and/ or 2) administering an effective amount of a novel compound disclosed herein, alone or in combination with one or more other therapeutic agents, to a subject suffering from Friedreich's ataxia or other mitochondrial disease.

INTRODUCTION

The following description is provided to assist the understanding of the reader. None of the information provided or references cited is admitted as being prior art to the compositions and methods disclosed herein.

Friedreich's ataxia (FA) is a fatal, monogenic, autosomal recessive disease caused by mutations in the gene encoding the nuclear encoded mitochondrial protein frataxin. Tissues in both the peripheral and central nervous systems are affected in FA, and include the dentate nucleus, Clark's column, spinocerebellar tract and dorsal root ganglia. Progressive degeneration of these tissues leads to a worsening ataxia which for most patients ends in loss of independent ambulation by the third decade of life.

The FXN gene encodes the protein frataxin. Frataxin is an iron binding protein responsible for forming iron-sulfur clusters. One result of frataxin deficiency is mitochondrial iron overload.

Frataxin is a highly conserved iron binding protein. Human frataxin is synthesized as a 210 amino acid precursor that is imported to the mitochondria via the mitochondrial targeting signal contained in the N-terminus. The frataxin precursor is subsequently cleaved to a mature 14 kDa protein (residues 81-210).

Frataxin binds both $Fe^{2+}$ and $Fe^{3+}$ ions in an electrostatic manner and functions as an iron chaperone during Fe—S cluster assembly. Frataxin directly binds to the central Fe—S cluster assembly complex, which is composed of Nfs1 enzyme and Isu scaffold protein. Nfs1 is a cysteine desulfurase used in the synthesis of sulfur bioorganic derivatives and Isu is the transient scaffold protein on which the Fe—S cluster assembles. Frataxin increases the efficiency of Fe—S cluster formation, which is required to activate the mitochondrial Kreb cycle enzyme aconitase. Frataxin also plays a role in mitochondrial iron storage and heme biosynthesis by incorporating mitochondrial iron into protoporphyrin (PIX).

Loss of frataxin function results in the disruption of iron-sulfur cluster biosynthesis, mitochondrial iron overload, oxidative stress, impaired aerobic electron transport chain respiration and cell death in the brain, spinal cord, dorsal root ganglia and heart. Studies have also shown that frataxin protects dopaminergic neuronal cells against MPTP-induced toxicity in a mouse model of Parkinson's disease.

Ferroptosis is an iron-dependent type of cell death that is biochemically distinct from apoptosis and typically accompanied by a large amount of iron accumulation and lipid peroxidation during the cell death process. Ferroptosis-inducing factors can directly or indirectly affect glutathione peroxidase through different pathways, resulting in a decrease in antioxidant capacity and accumulation of lipid reactive oxygen species (ROS) in cells, ultimately leading to oxidative cell death. Recent studies have shown that ferroptosis is closely related to the pathophysiological processes of many diseases, such as tumors, nervous system diseases, ischemia-reperfusion injury, kidney injury, and blood diseases. Decreased expression of frataxin (FXN) is associated with mitochondrial dysfunction, mitochondrial iron accumulation, and increased oxidative stress. Recent studies have shown that frataxin, which modulates iron homeostasis and mitochondrial function, is a key regulator of ferroptosis. As such, ferroptosis as has been identified as a therapeutic target for Friedreich's ataxia. As described above, ferroptosis is associated with glutathione depletion and production of lipid peroxides, which are generated by lipoxygenase enzymes such as lipoxygenase-15. Accordingly, targeting lipoxygenase-15 provides a therapeutic target for Friedreich's ataxia.

Mitochondrial iron overload leads to impaired intra-mitochondrial metabolism and a defective mitochondrial respiratory chain. A defective mitochondrial respiratory chain leads to increased free radical generation and oxidative damage, which may be considered as mechanisms that compromise cell viability. Some evidence suggests that frataxin might detoxify ROS via activation of glutathione peroxidase and elevation of thiols. (See e.g., Calabrese et al., Journal of the Neurological Sciences, 233(1): 145-162 (June 2005)).

Friedreich's ataxia occurs when the FXN gene contains amplified intronic GAA repeats. The mutant FXN gene contains expanded GAA triplet repeats in the first intron; in a few pedigrees, point mutations have also been detected. Since the defect is located in an intron, which is removed from the mRNA transcript between transcription and translation, the mutated FXN gene does not result in the production of abnormal proteins. Instead, the mutation causes gene silencing, i.e., the mutation decreases the transcription of the gene.

Symptoms typically begin between the ages of 5 and 15 years, although they sometimes appear in adulthood. The first symptom to appear is usually gait ataxia, or difficulty walking. The ataxia gradually worsens and slowly spreads to the arms and the trunk. There is often loss of sensation in the extremities, which may spread to other parts of the body. Other features include loss of tendon reflexes, especially in the knees and ankles. Most people with Friedreich's ataxia develop scoliosis, which often requires surgical intervention for treatment. Dysarthria (slowness and slurring of speech) develops and can get progressively worse. Many individuals with later stages of Friedreich's ataxia develop hearing and vision loss.

Heart disease often accompanies Friedreich's ataxia, such as hypertrophic cardiomyopathy, myocardial fibrosis (formation of fiber-like material in the muscles of the heart), and cardiac (heart) failure. Heart rhythm abnormalities such as tachycardia (fast heart rate) and heart block (impaired conduction of cardiac impulses within the heart) are also common. Other symptoms that may occur include chest pain, shortness of breath, and heart palpitations.

Many patients with Friedreich's ataxia will exhibit a slow decline in visual acuity in later stages of the disease. The most common ophthalmic manifestation of Friedreich's ataxia is optic neuropathy. In some cases, severe/catastrophic visual loss is experienced.

About 20 percent of people with Friedreich's ataxia develop carbohydrate intolerance and 10 percent develop diabetes. Most individuals with Friedreich's ataxia tire very easily and find that they require more rest and take a longer time to recover from common illnesses such as colds and flu.

The rate of progression varies from person to person. Generally, within 10 to 20 years after the appearance of the first symptoms, the person is confined to a wheelchair, and in later stages of the disease individuals may become completely incapacitated. Friedreich's ataxia can shorten life expectancy, and heart disease is the most common cause of death.

The five enzyme complexes (i.e. Complex I, Complex II, Complex III, Complex IV and Complex V) of the oxidative phosphorylation (OXPHOS) system are located in the mitochondrial membrane and Complex I deficiency leading to decreased levels (and decreased production) of adenosine triphosphate (ATP) is believed to be associated with Friedreich's ataxia. Indeed, it has been suggested that decreased frataxin expression in the cells of Friedreich's ataxia patients increases the pool of non-bioavailable iron within the cell, thereby leading to free radical generation, increased oxidative damage to the cell and decreased Complex I activity and associated decreases in intracellular ATP generation (Heidari et al., Complex I and ATP Content Deficiency in Lymphocytes from Friedreich's Ataxia, Can. J. Neurol. Sci. 2009: 36:26-31).

There is no known cure for Friedreich's ataxia. Generally, therapies involve treatment of the symptoms. Because patients with Friedreich's ataxia are at a risk of developing heart disease, they are often prescribed medications such as beta blockers, ACE inhibitors and/or diuretics. Because it is believed that damage caused by oxidative stress is involved in the progression of Friedreich's ataxia, antioxidants such as vitamin E, idebenone and coenzyme Q10 are often co-administered to persons diagnosed or suspected of having Friedrich's ataxia. These compounds have been used in various clinical trials.

Currently, EPI-743 (a benzoquinone compound also known as vatiquinone) is currently in phase 2 clinical trials, has yet to initiate a phase 3 clinical trial for the treatment of refractory epilepsy and has been granted orphan drug designation and fast track status by the United States Food and Drug Administration (FDA). Vatiquinone is believed to reduce oxidative stress and improve mitochondrial function.

Omaveloxolone is a second generation synthetic oleanane triterpenoid that is believed to exhibit antioxidative and anti-inflammatory activity. Omaveloxolone is currently in phase 2 clinical development for treatment of a variety of indications, including Friedreich's ataxia, mitochondrial myopathies and ophthalmic conditions/diseases.

Several other therapies for the treatment of Friedreich's ataxia are currently in clinical trials but there are no FDA approved drugs. Hence, there remains a need for better drug candidates to address the needs of patients diagnosed with Friedreich's ataxia.

SUMMARY

In an aspect, a compound of formula E-F, or pharmaceutically acceptable salts, stereoisomers, mixtures of stereoisomers, tautomers, hydrates, and/or solvates thereof, is provided wherein E is 21 or 22:

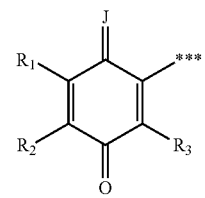

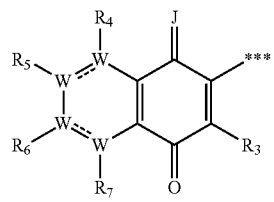

and F is 13, 14, 15, 16, 17, 18, 19 or 20:

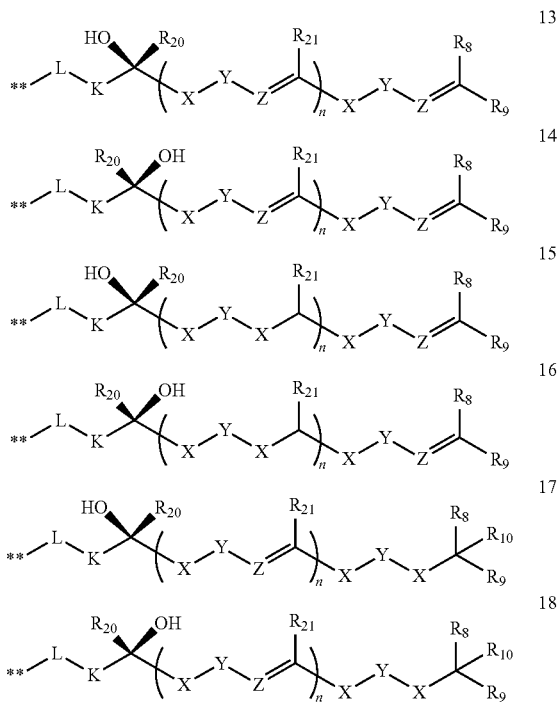

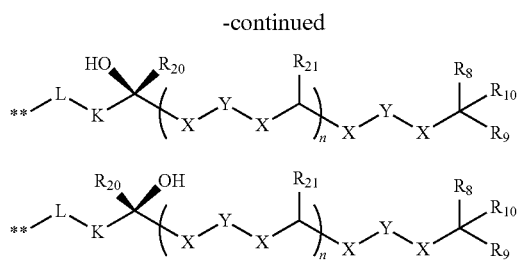

wherein, J is O, S or N—Ru; K is absent or —(CR$_{12}$R$_{13}$)—; L is —(CR$_{12}$R$_{13}$)—; each W is independently C (carbon) or N (nitrogen) and wherein for each use of w=w, the bond between each W can be a single bond or double bond and further provided that if a single bond, each C (carbon) atom will have a hydrogen atom linked hereto in addition to one of R$_4$, R$_5$, R$_6$ or R$_7$ and in either case each of R$_4$, R$_5$, R$_6$ and R$_7$ attached thereto is independently selected from H, D, F, Cl, Br, I, C$_1$-C$_6$ alkyl and C$_1$-C$_6$ alkoxy, and if W is N (nitrogen), each of R$_4$, R$_5$, R$_6$ and R$_7$ attached thereto is independently absent (if W=w is a double bond) or selected from H, D and C$_1$-C$_6$ alkyl (if W=W is a single bond); each X is independently a group of formula —(CR$_{12}$R$_{13}$)—; = each Y is independently absent or a group of formula —(CR$_{12}$R$_{13}$)—; each Z is independently a group of formula —(CR$_{14}$)—; each of R$_1$, R$_2$ and R$_3$ is independently H, D, F, Cl, Br, I, C$_1$-C$_6$ alkyl or C$_1$-C$_6$ alkoxy; or R$_1$ and R$_2$ together form a 5-membered carbocyclic ring, a 5-membered heterocyclic ring, a 5-membered aromatic or heteroaromatic ring, or a 6-membered heterocyclic ring; each R$_8$ and R$_9$ is each independently H, D, F, Cl, Br, I or C$_1$-C$_4$ alkyl; or taken together R$_8$ and R$_9$ form a 3-, 4-, 5-, 6- or 7-membered carbocyclic or heterocyclic ring; R$_{10}$ is H, D, F, C$_1$, Br, I, C$_1$-C$_6$ alkyl or C$_1$-C$_6$ alkoxy; R$_1$ is H, D or C$_1$-C$_6$ alkyl; each of R$_{12}$, R$_{13}$ and R$_{14}$ is independently H, D, F, Cl, Br, I, C$_1$-C$_6$ alkyl or C$_1$-C$_6$ alkoxy; R$_{20}$ is H, D, F or C$_1$-C$_{12}$ alkyl; each R$_{21}$ is independently H, D, F, Cl, Br, I, or C$_1$-C$_4$ alkyl; n is an integer from 0 to 12; and * indicates the point of attachment of E to F and  indicates the point of attachment of F to E; and further provided that: (i) at least one group of formula R$_1$, R$_2$, R$_3$, R$_4$, R$_5$, R$_6$, R$_7$, R$_8$, R$_9$, R$_{10}$, R$_{12}$, R$_{13}$, R$_{14}$, R$_{20}$ or R$_{21}$ comprises at least one fluorine atom; and/or (ii) R$_8$ and R$_9$ taken together form a 3-, 4-, 5-, 6- or 7-membered carbocyclic or heterocyclic ring. In any embodiment herein, it may be that E is 21 and F is 13, 14, 19 or 20. In any embodiment herein, it may be that E is 22 and F is 13, 14, 19 or 20. In any embodiment herein, it may be that E is 21 and F is 15, 16, 17 or 18. In any embodiment herein, it may be that E is 22 and F is 15, 16, 17 or 18. In any embodiment herein, it may be that J is O. In any embodiment herein, it may be that J is S. In any embodiment herein, it may be that J is N—R$_{11}$. In any embodiment herein, it may be that J is O or N—R$_{11}$ and K is absent. In some embodiments, each of K and L is independently —(CH$_2$)—, —(CD$_2$)-, —(CHF)—, —(CF$_2$)—, —(CH (CH$_3$))—, —(CD(CD$_3$))—, —(CF(CH$_3$))—, —(CH (CF$_3$))—, —(CF(CF$_3$))—, —(C(CH$_3$)$_2$)—, —(C(CD$_3$)$_2$)—, —(C(CF$_3$)$_2$), —(CH(OCH$_3$))—, —(CD(OCD$_3$))—, —(CF (OCH$_3$))—, —(CH(OCF$_3$))—, —(CF(OCF$_3$))—, —(C (OCH$_3$)$_2$)—, —(C(OCD$_3$)$_2$)—, —(C(OCF$_3$)$_2$)—, —(C (CH$_3$)(CF$_3$))—, —(C(CD$_3$)(CF$_3$))—, —(CH(CH$_2$CH$_3$))—, —(CD(CD$_2$CD$_3$))—, —(CF(CH$_2$CH$_3$))—, —(CH (CH$_2$CF$_3$))—, —(CH(CF$_2$CF$_3$))—, —(CF(CF$_2$CF$_3$))—, —(C(CH$_2$CH$_3$)$_2$)—, —(C(CD$_2$CD$_3$)$_2$)— or —(C(CF$_2$CF$_3$)$_2$)—. In some embodiments, each of K and L is independently —(CH$_2$)—, —(CD$_2$)-, —(CF$_2$)—, —(CH (CH$_3$))—, —(CD(CD$_3$))—, —(CF(CF$_3$))—, —(C (CH$_3$)$_2$)—, —(C(CD$_3$)$_2$)—, —(C(CF$_3$)$_2$)—, —(CH (OCH$_3$))—, —(CD(OCD$_3$))—, —(CF(OCF$_3$))— or —(C (OCH$_3$)$_2$)—. In some embodiments, each of K and L is independently —(CH$_2$)—, —(CD$_2$)-, —(CHF)—, —(CF$_2$)—, —(CH(CH$_3$))—, —(CF(CF$_3$))—, —(C (CH$_3$)$_2$)— or —(C(CF$_3$)$_2$)—. In some embodiments, L is —(CH$_2$)—, —(CD$_2$)-, —(CHF)—, —(CF$_2$)—, —(CH (CH$_3$))—, —(CD(CD$_3$))—, —(CF(CH$_3$))—, —(CH (CF$_3$))—, —(CF(CF$_3$))—, —(C(CH$_3$)$_2$)—, —(C(CD$_3$)$_2$)—, —(C(CF$_3$)$_2$)—, —(CH(OCH$_3$))—, —(CD(OCD$_3$))—, —(CF(OCH$_3$))—, —(CH(OCF$_3$))—, —(CF(OCF$_3$))—, —(C(OCH$_3$)$_2$)—, —(C(OCD$_3$)$_2$)—, —(C(OCF$_3$)$_2$)—, —(C (CH$_3$)(CF$_3$))—, —(C(CD$_3$)(CF$_3$))—, —(CH(CH$_2$CH$_3$))—, —(CD(CD$_2$CD$_3$))—, —(CF(CH$_2$CH$_3$))—, —(CH (CH$_2$CF$_3$))—, —(CH(CF$_2$CF$_3$))—, —(CF(CF$_2$CF$_3$))—, —(C(CH$_2$CH$_3$)$_2$)—, —(C(CD$_2$CD$_3$)$_2$)— or —(C(CF$_2$CF$_3$)$_2$)—. In some embodiments, L is —(CH$_2$)—, —(CD$_2$)-, —(CF$_2$)—, —(CH(CH$_3$))—, —(CD(CD$_3$))—, —(CF (CF$_3$))—, —(C(CH$_3$)$_2$)—, —(C(CD$_3$)$_2$)—, —(C(CF$_3$)$_2$)—, —(CH(OCH$_3$))—, —(CD(OCD$_3$))—, —(CF(OCF$_3$))— or —(C(OCH$_3$)$_2$)—. In some embodiments, L is —(CH$_2$)—, —(CD$_2$)-, —(CHF)—, —(CF$_2$)—, —(CH(CH$_3$))—, —(CF (CF$_3$))—, —(C(CH$_3$)$_2$)— or —(C(CF$_3$)$_2$)—. In some embodiments, each of R$_1$, R$_2$ and R$_3$ is independently H, D, Cl, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, —CH(CH$_3$)$_2$, —CD$_2$CD$_3$, —CD(CD$_3$)$_2$, —CF$_2$CH$_3$, CF(CH$_3$)$_2$, —CH$_2$CF$_3$, —CH(CF$_3$)$_2$, —CF$_2$CF$_3$, —CF(CF$_3$)$_2$, —C(CH$_3$)$_3$, —C(CD$_3$)$_3$, —C (CF$_3$)$_3$, —OCH$_2$CH$_3$, —OCH(CH$_3$)$_2$, —OCD$_2$CD$_3$, —OCD(CD$_3$)$_2$, —OCF$_2$CH$_3$, —OCF(CH$_3$)$_2$, —OCH$_2$CF$_3$, —OCH(CF$_3$)$_2$, —OCF$_2$(CF$_3$), —OCF(CF$_3$)$_2$, —OC(CH$_3$)$_3$, —OC(CD$_3$)$_3$, —OC(CF$_3$)$_3$, —C(CH$_3$)$_2$(CF$_3$), —C(CH$_3$) (CF$_3$)$_2$, —OC(CH$_3$)$_2$(CF$_3$), —OC(CH$_3$)(CF$_3$)$_2$, —CH$_2$CH$_2$CH$_3$, —CH(CH$_2$CH$_3$)$_2$, —CD$_2$CD$_2$CD$_3$, —CD (CD$_2$CD$_3$)$_2$, —CF$_2$CH$_2$CH$_3$, —CF(CH$_2$CH$_3$)$_2$, —CH$_2$CF$_2$CF$_3$, —CH(CF$_2$CF$_3$)$_2$, —CF$_2$CF$_2$CF$_3$, —CF (CF$_2$CF$_3$)$_2$, —OCH$_2$CH$_2$CH$_3$, —OCH(CH$_2$CH$_3$)$_2$, —OCD$_2$CD$_2$CD$_3$, —OCD(CD$_2$CD$_3$)$_2$, —OCF$_2$CH$_2$CH$_3$, —OCF(CH$_2$CH$_3$)$_2$, —OCH$_2$CF$_2$CF$_3$, —OCH(CF$_2$CF$_3$)$_2$, —OCF$_2$CF$_2$CF$_3$ or —OCF(CF$_2$CF$_3$)$_2$. In some embodiments, each of R$_1$, R$_2$ and R$_3$ is independently H, D, Cl, F, —CH$_3$, —OCH$_3$, —CD$_3$, —OCD$_3$, —CH$_2$F, —CHF$_2$, —CF$_3$, —OCF$_3$, —C(CH$_3$)$_3$, —C(CD$_3$)$_3$, —C(CF$_3$)$_3$, —OC (CH$_3$)$_3$, —OC(CD$_3$)$_3$, —OC(CF$_3$)$_3$, —CH$_2$CH$_3$, —OCH$_2$CH$_3$ or —CH(CH$_3$)$_2$. In some embodiments, each of R$_1$, R$_2$ and R$_3$ is independently H, F, —CH$_3$, —OCH$_3$, —CH$_2$F, —CHF$_2$, —CF$_3$, —OCF$_3$, —C(CH$_3$)$_3$, —C(CF$_3$)$_3$, —CH$_2$CH$_3$, —OCH$_2$CH$_3$ or —CH(CH$_3$)$_2$. In some embodiments, J is O; each of K and L is independently —(CH$_2$)—, —(CD$_2$)-, —(CHF)—, —(CF$_2$)—, —(CH(CH$_3$))—, —(CF (CF$_3$))—, —(C(CH$_3$)$_2$)— or —(C(CF$_3$)$_2$)—; and each of R$_1$, R$_2$ and R$_3$ is independently H, F, —CH$_3$, —OCH$_3$, —CH$_2$F, —CHF$_2$, —CF$_3$, —OCF$_3$, —C(CH$_3$)$_3$, —C(CF$_3$)$_3$, —CH$_2$CH$_3$, —OCH$_2$CH$_3$ or —CH(CH$_3$)$_2$. In some embodiments, R$_3$ is H, D, Cl, F, —CH$_3$, —OCH$_3$, —CD$_3$, —OCD$_3$, —CF$_3$, —OCF$_3$, —C(CH$_3$)$_3$, —C(CD$_3$)$_3$, —C(CF$_3$)$_3$, —OC (CH$_3$)$_3$, —OC(CD$_3$)$_3$, —OC(CF$_3$)$_3$, —CH$_2$CH$_3$, —OCH$_2$CH$_3$, or —CH(CH$_3$)$_2$ and R$_1$ and R$_2$ taken together form a 5-, or 6-membered carbocyclic or heterocyclic ring. In some embodiments, E is 21A, 21B, 21C, 21D, 21E or 21F:

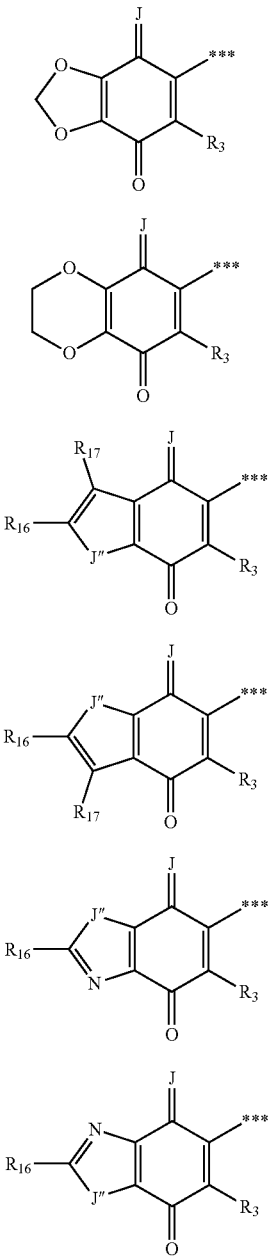

21A

21B

21C

21D

21E

21F wherein each of $R_{16}$ and $R_{17}$ is independently H, D, Cl, F, —CH$_3$, —OCH$_3$, —CD$_3$, —OCD$_3$, —CH$_2$F, —CHF$_2$, —CF$_3$, —OCF$_3$, —C(CH$_3$)$_3$, —C(CD$_3$)$_3$, —C(CF$_3$)$_3$, —OC(CH$_3$)$_3$, —OC(CD$_3$)$_3$, —OC(CF$_3$)$_3$, —CH$_2$CH$_3$, —OCH$_2$CH$_3$, —CH(CH$_3$)$_2$, —OCH(CH$_3$)$_2$, —C(CH$_3$)$_3$ or —O(CH$_3$)$_3$; and J″ is O, S or N—R$_{18}$, wherein R$_{18}$ is H, D, —CH$_3$, —CH$_2$F, —CHF$_2$ or —CF$_3$. In some embodiments, R$_3$ is H, D, Cl, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, —CH(CH$_3$)$_2$, —CD$_2$CD$_3$, —CD(CD$_3$)$_2$, —CF$_2$CH$_3$, CF(CH$_3$)$_2$, —CH$_2$CF$_3$, —CH(CF$_3$)$_2$, —CF$_2$CF$_3$, —CF(CF$_3$)$_2$, —C(CH$_3$)$_3$, —C(CD$_3$)$_3$, —C(CF$_3$)$_3$, —OCH$_2$CH$_3$, —OCH(CH$_3$)$_2$, —OCD$_2$CD$_3$, —OCD(CD$_3$)$_2$, —OCF$_2$CH$_3$, —OCF(CH$_3$)$_2$, —OCH$_2$CF$_3$, —OCH(CF$_3$)$_2$, —OCF$_2$(CF$_3$), —OCF$_2$CF$_3$, —OC(CH$_3$)$_3$, —OC(CD$_3$)$_3$, —OC(CF$_3$)$_3$, —C(CH$_3$)$_2$(CF$_3$), —C(CH$_3$)(CF$_3$)$_2$, —OC(CH$_3$)$_2$(CF$_3$), —OC(CH$_3$)(CF$_3$)$_2$, —CH$_2$CH$_2$CH$_3$, —CH(CH$_2$CH$_3$)$_2$, —CD$_2$CD$_2$CD$_3$, —CD(CD$_2$CD$_3$)$_2$, —CF$_2$CH$_2$CH$_3$, —CF(CH$_2$CH$_3$)$_2$, —CH$_2$CF$_2$CF$_3$, —CH(CF$_2$CF$_3$)$_2$, —CF$_2$CF$_2$CF$_3$, —CF(CF$_2$CF$_3$)$_2$, —OCH$_2$CH$_2$CH$_3$, —OCH(CH$_2$CH$_3$)$_2$, —OCD$_2$CD$_2$CD$_3$, —OCD(CD$_2$CD$_3$)$_2$, —OCF$_2$CH$_2$CH$_3$, —OCF(CH$_2$CH$_3$)$_2$, —OCH$_2$CF$_2$CF$_3$, —OCH(CF$_2$CF$_3$)$_2$, —OCF$_2$CF$_2$CF$_3$ or —OCF(CF$_2$CF$_3$)$_2$; and where if W is C (carbon), each of R$_4$, R$_5$, R$_6$ and R$_7$ attached thereto is independently selected from H, D, F, Cl, Br, I, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, and —CH(CH$_3$)$_2$, and where if W is N (nitrogen), each of R$_4$, R$_5$, R$_6$ and R$_7$ attached thereto is independently absent or is selected from H, D, methyl, ethyl, isopropyl and t-butyl. In some embodiments, R$_3$ is H, D, C$_1$, F, —CH$_3$, —OCH$_3$, —CD$_3$, —OCD$_3$, —CH$_2$F, —CHF$_2$, —CF$_3$, —OCF$_3$, —C(CH$_3$)$_3$, —C(CD$_3$)$_3$, —C(CF$_3$)$_3$, —OC(CH$_3$)$_3$, —OC(CD$_3$)$_3$, —OC(CF$_3$)$_3$, —CH$_2$CH$_3$, —OCH$_2$CH$_3$, or —CH(CH$_3$)$_2$; and where if W is C (carbon), each of R$_4$, R$_5$, R$_6$ and R$_7$ attached thereto is independently selected from H, D, F, C$_1$, —CH$_3$, —OCH$_3$, —CH$_2$F, —CHF$_2$, —CF$_3$, —OCF$_3$, —CH$_2$CH$_3$, and —CH(CH$_3$)$_2$, and where if W is N (nitrogen), each of R$_4$, R$_5$, R$_6$ and R$_7$ attached thereto is independently absent or is selected from H, D, methyl and ethyl. In some embodiments, each W is C and each of R$_4$, R$_5$, R$_6$ and R$_7$ is independently H, D, Cl, F, —CH$_3$, —OCH$_3$, —CH$_2$F, —CHF$_2$, —CF$_3$ or —OCF.

In any embodiment herein, it may be that each of R$_8$ and R$_9$ is independently H, D, F, Cl, Br, I, —CH$_3$, —CD$_3$, —CH$_2$F, —CHF$_2$, —CF$_3$, —CH$_2$CH$_3$, —CH(CH$_3$)$_2$, —CD$_2$CD$_3$, —CD(CD$_3$)$_2$, —CF$_2$CH$_3$, —CF(CH$_3$)$_2$, —CH$_2$CF$_3$, —CH(CF$_3$)$_2$, —CF$_2$CF$_3$, —CF(CF$_3$)$_2$, —C(CH$_3$)$_3$, —C(CD$_3$)$_3$, —C(CF$_3$)$_3$, —C(CH$_3$)$_2$(CF$_3$), —C(CH$_3$)(CF$_3$)$_2$, —CH$_2$CH$_2$CH$_3$, —CH(CH$_2$CH$_3$)$_2$, —CD$_2$CD$_2$CD$_3$, —CD(CD$_2$CD$_3$)$_2$, —CF$_2$CH$_2$CH$_3$, —CF(CH$_2$CH$_3$)$_2$, —CH$_2$CF$_2$CF$_3$, —CH(CF$_2$CF$_3$)$_2$, —CF$_2$CF$_2$CF$_3$ or —CF(CF$_2$CF$_3$)$_2$. In some embodiments, each of R$_8$ and R$_9$ is independently H, F, —CH$_3$, —CH$_2$F, —CHF$_2$, —CF$_3$, —CH$_2$CH$_3$, —CH(CH$_3$)$_2$, —CF$_2$CH$_3$, —CH$_2$CF$_3$, —CH(CF$_3$)$_2$, —CF$_2$CF$_3$, —CF(CF$_3$)$_2$, —C(CH$_3$)$_3$, —C(CF$_3$)$_3$, —CH$_2$CH$_2$CH$_3$, —CH(CH$_2$CH$_3$)$_2$, —CF$_2$CF$_2$CF$_3$ or —CF(CF$_2$CF$_3$)$_2$.

In any embodiment herein, it may be that R$_8$ and R$_9$ taken together form a 3-, 4-, 5-, 6- or 7-membered carbocyclic or heterocyclic ring can be 31, 32, 33, 34, 35, 36, 37, 38, 39, 40, 41, 42, 43, 44, 45, 46 or 47:

31

32

33

34

35

-continued

36 

37 

38 

39 

40 

41 

42 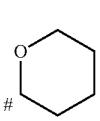

43 

44 

45 

46 

47 

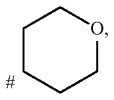

wherein # indicates the point of attachment of the carbocycle or heterocycle to the remainder of the compound. In any embodiment herein, it may be that $R_{10}$ is H, D, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, —CH(CH$_3$)$_2$, —CD$_2$CD$_3$, —CD(CD$_3$)$_2$, —CF$_2$CH$_3$, —CF(CH$_3$)$_2$, —CH$_2$CF$_3$, —CH(CF$_3$)$_2$, —CF$_2$CF$_3$, —CF(CF$_3$)$_2$, —C(CH$_3$)$_3$, —C(CD$_3$)$_3$, —C(CF$_3$)$_3$, —OCH$_2$CH$_3$, —OCH(CH$_3$)$_2$, —OCD$_2$CD$_3$, —OCD(CD$_3$)$_2$, —OCF$_2$(CF$_3$), —OCF(CF$_3$)$_2$, —OC(CH$_3$)$_3$, —OC(CD$_3$)$_3$, —OC(CF$_3$)$_3$, —C(CH$_3$)$_2$(CF$_3$), —C(CH$_3$)(CF$_3$)$_2$, —OC(CH$_3$)$_2$(CF$_3$), —OC(CH$_3$)(CF$_3$)$_2$, —CH$_2$CH$_2$CH$_3$, —CH(CH$_2$CH$_3$)$_2$, —CD$_2$CD$_2$CD$_3$, —CD(CD$_2$CD$_3$)$_2$, —CF$_2$CF$_2$CF$_3$, —CF(CF$_2$CF$_3$)$_2$, —C(CH$_2$CH$_3$)$_3$, —C(CD$_2$CD$_3$)$_3$, —C(CF$_2$CF$_3$)$_3$, —OCH$_2$CH$_2$CH$_3$, —OCH(CH$_2$CH$_3$)$_2$, —OCD$_2$CD$_2$CD$_3$, —OCD(CD$_2$CD$_3$)$_2$, —OCF$_2$CF$_2$CF$_3$ or —OCF(CF$_2$CF$_3$)$_2$. In some embodiments, $R_{10}$ is H, D, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$ or —CH(CH$_3$)$_2$. In any embodiment herein, it may be that $R_{11}$ is H, methyl or ethyl. In any embodiment herein, it may be that each of $R_{12}$, $R_{13}$ or $R_{14}$ is independently H, D, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, —CH(CH$_3$)$_2$, —CH$_2$CH$_2$CH$_3$, —CH(CH$_2$CH$_3$)$_2$, —C(CH$_3$)$_3$, —OCH$_2$CH$_3$, —OCH(CH$_3$)$_2$, —OCH$_2$CH$_2$CH$_3$, —OCH(CH$_2$CH$_3$)$_2$ or —OC(CH$_3$)$_3$. In some embodiments, each of $R_{12}$, $R_{13}$ or $R_{14}$ is independently H, D, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$ or —OCH$_2$CH$_3$. In any embodiment herein, it may be that $R_{20}$ is H, D, F, —CH$_3$, —CD$_3$, —CH$_2$F, —CHF$_2$, —CF$_3$, —CH$_2$CH$_3$, —CH$_2$CH$_2$CH$_3$, —CH(CH$_3$)$_2$, —C(CH$_3$)$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CH$_2$CH$_2$CH$_2$CH$_2$CH$_2$CH$_2$CH$_3$, —CH$_2$CH$_2$CH$_2$CH$_2$CH$_2$CH$_2$CH$_2$CH$_3$, —CH$_2$CH$_2$CH$_2$CH$_2$CH$_2$CH$_2$CH$_2$CH$_2$CH$_3$ or —CH$_2$CH$_2$CH$_2$CH$_2$CH$_2$CH$_2$CH$_2$CH$_2$CH$_2$CH$_3$. In any embodiment herein, it may be that each $R_{21}$ is independently H, D, F, —CH$_3$, —CD$_3$, —CH$_2$F, —CHF$_2$, —CF$_3$, —CH$_2$CH$_3$, —CH$_2$CH$_2$CH$_3$, —CH(CH$_3$)$_2$, —CH$_2$CH$_2$CH$_2$CH$_3$ or —C(CH$_3$)$_3$. In any embodiment herein, it may be that n is 0, 1, 2, 3 or 4.

In some embodiments, the compound is

Compound A

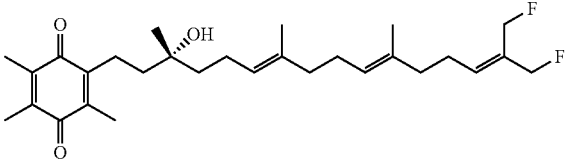

or a pharmaceutically acceptable salt, a stereoisomer, a mixture of stereoisomers, a tautomer, a hydrate, and/or a solvate thereof. In some embodiments, the compound is Compound B or a pharmaceutically acceptable salt, a stereoisomer, a mixture of stereoisomers, a tautomer, a hydrate, and/or a solvate thereof. In some embodiments, the compound is Compound C or a pharmaceutically acceptable salt, a stereoisomer, a mixture of stereoisomers, a tautomer, a hydrate, and/or a solvate thereof. In some embodiments, the compound is Compound D

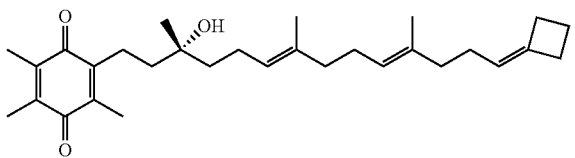

or a pharmaceutically acceptable salt, a stereoisomer, a mixture of stereoisomers, a tautomer, a hydrate, and/or a solvate thereof. In some embodiments, the compound is Compound E

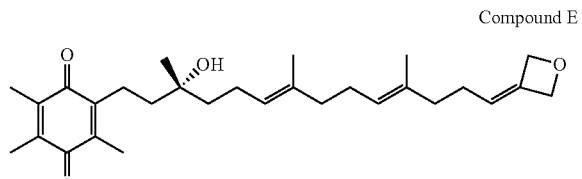

or a pharmaceutically acceptable salt, a stereoisomer, a mixture of stereoisomers, a tautomer, a hydrate, and/or a solvate thereof. In some embodiments, the compound is Compound F

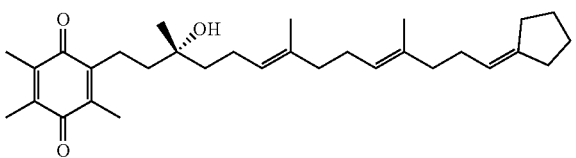

or a pharmaceutically acceptable salt, a stereoisomer, a mixture of stereoisomers, a tautomer, a hydrate, and/or a solvate thereof. In some embodiments, the compound is Compound G

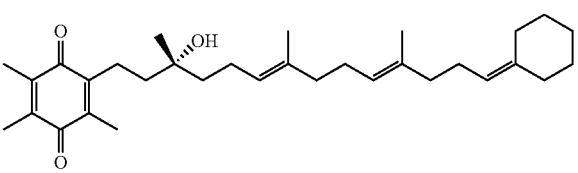

or a pharmaceutically acceptable salt, a stereoisomer, a mixture of stereoisomers, a tautomer, a hydrate, and/or a solvate thereof. In some embodiments, the compound is Compound H

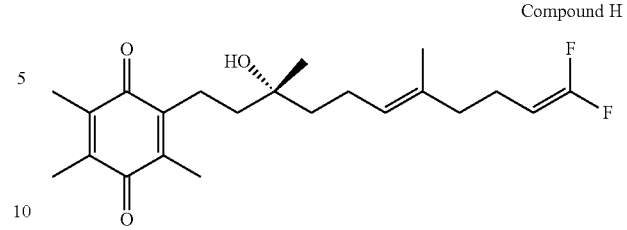

or a pharmaceutically acceptable salt, a stereoisomer, a mixture of stereoisomers, a tautomer, a hydrate, and/or a solvate thereof. In some embodiments, the compound is Compound I

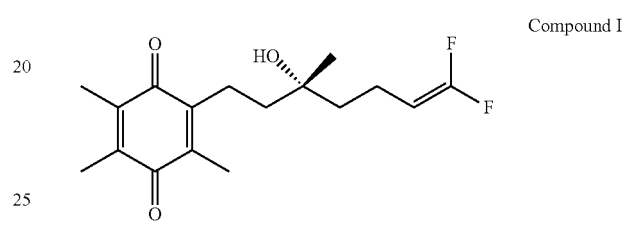

or a pharmaceutically acceptable salt, a stereoisomer, a mixture of stereoisomers, a tautomer, a hydrate, and/or a solvate thereof. In some embodiments, the compound is Compound J

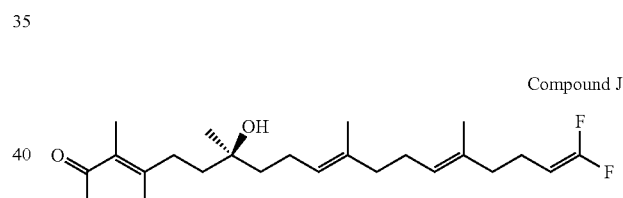

or a pharmaceutically acceptable salt, a stereoisomer, a mixture of stereoisomers, a tautomer, a hydrate, and/or a solvate thereof. In some embodiments, the compound is Compound K

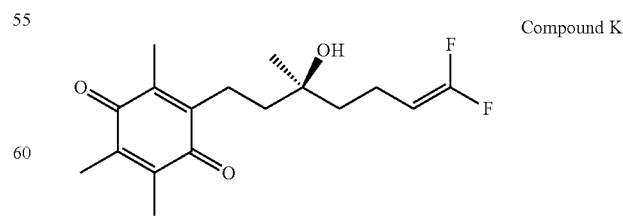

or a pharmaceutically acceptable salt, a stereoisomer, a mixture of stereoisomers, a tautomer, a hydrate, and/or a solvate thereof.

Compound L

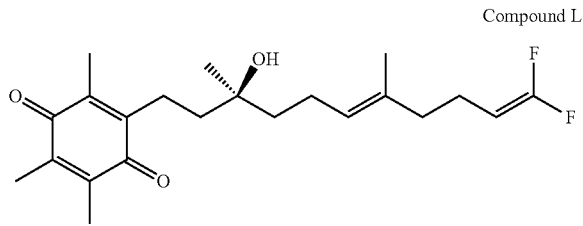 [SMILES: CC1=C(C)C(=O)C(CC[C@@](C)(O)CC/C=C(\C)CCC=C(F)F)=C(C)C1=O]

or a pharmaceutically acceptable salt, a stereoisomer, a mixture of stereoisomers, a tautomer, a hydrate, and/or a solvate thereof. In some embodiments, the compound is Compound N

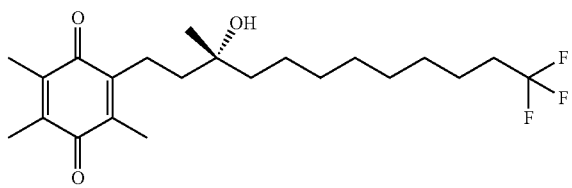

or a pharmaceutically acceptable salt, a stereoisomer, a mixture of stereoisomers, a tautomer, a hydrate, and/or a solvate thereof.

In an aspect, a compound of formula C-D, or pharmaceutically acceptable salts, stereoisomers, mixtures of stereoisomers, tautomers, hydrates, and/or solvates thereof, is provided wherein C is 11 or 12:

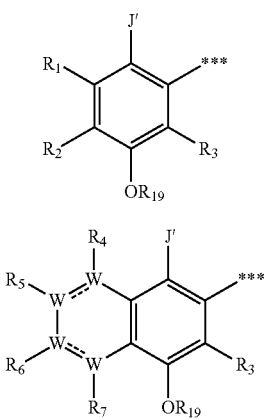

and D is 13, 14, 15, 16, 17, 18, 19 or 20:

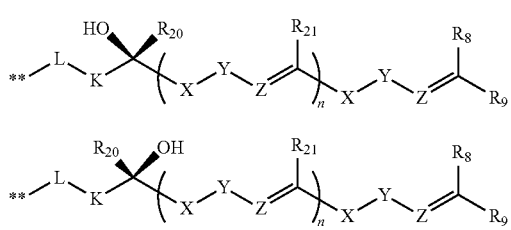

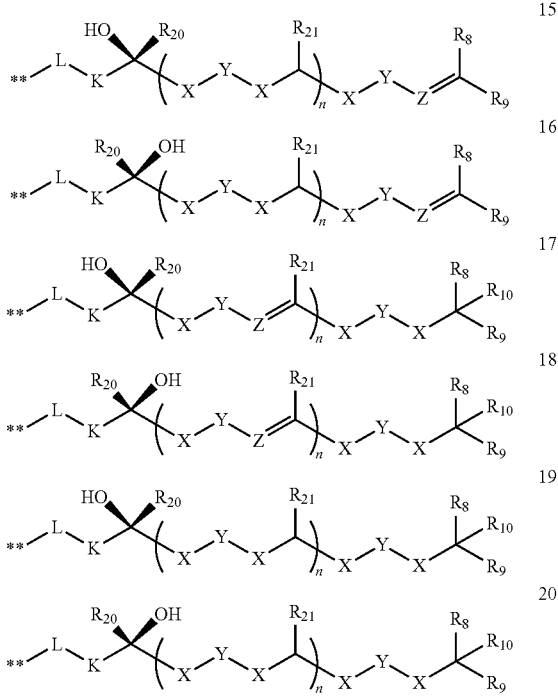

wherein, J' is OH, SH or NH—$R_{11}$; K is absent or —$(CR_{12}R_{13})$—; L is —$(CR_{12}R_{13})$—; each W is $=$ independently C (carbon) or N (nitrogen) and wherein for each use of W$=$W, the bond between each W can be a single bond or double bond and further provided that if a single bond, each C (carbon) atom will have a hydrogen atom linked hereto in addition to one of $R_4$, $R_5$, $R_6$ or $R_7$ and in either case each of $R_4$, $R_5$, $R_6$ and $R_7$ attached thereto is independently selected from H, D, F, Cl, Br, I, $C_1$-$C_6$ alkyl and $C_1$-$C_6$ alkoxy, and if W is N (nitrogen), each of $R_4$, $R_5$, $R_6$ and $R_7$ attached thereto is independently absent (if W$=$W is a double bond) or selected from H, D and $C_1$-$C_6$ alkyl (if w $=$ w is a single bond); each X is independently a group of formula —$(CR_{12}R_{13})$—; each Y is independently absent or a group of formula —$(CR_{12}R_{13})$—; each Z is independently a group of formula —$(CR_{14})$—; each of $R_1$, $R_2$ and $R_3$ is independently H, D, F, Cl, Br, I, $C_1$-$C_6$ alkyl or $C_1$-$C_6$ alkoxy; or $R_1$ and $R_2$ together form a 5-membered carbocyclic ring, a 5-membered heterocyclic ring, a 5-membered aromatic or heteroaromatic ring or a 6-membered heterocyclic ring; each of $R_8$ and $R_9$ is each independently H, D, F, Cl, Br, I or $C_1$-$C_4$ alkyl; or taken together $R_8$ and $R_9$ form a 3-, 4-, 5-, 6- or 7-membered carbocyclic or heterocyclic ring; $R_{10}$ is H, D, F, $C_1$, Br, I, $C_1$-$C_6$ alkyl or $C_1$-$C_6$ alkoxy; $R_{11}$ is H, D or $C_1$-$C_6$ alkyl; each of $R_{12}$, $R_{13}$ and $R_{14}$ is independently H, D, F, Cl, Br, I, $C_1$-$C_6$ alkyl or $C_1$-$C_6$ alkoxy; $R_{19}$ is H, $C_1$-$C_4$ alkyl or benzyl; $R_{20}$ is H, D, F, or $C_1$-$C_{12}$ alkyl; each $R_{21}$ is independently H, D, F, Cl, Br, I, or $C_1$-$C_4$ alkyl; n is an integer from 0 to 12, inclusive; and * indicates the point of attachment of C to D and  indicates the point of attachment of D to C; and further provided that: (i) at least one group of formula $R_1$, $R_2$, $R_3$, $R_4$, $R_5$, $R_6$, $R_7$, $R_8$, $R_9$, $R_{10}$, $R_{12}$, $R_{13}$, $R_{14}$, $R_{20}$ or $R_{21}$ comprises at least one fluorine atom; and/or (ii) $R_8$ and $R_9$ taken together form a 3-, 4-, 5-, 6- or 7-membered carbocyclic or heterocyclic ring.

In any embodiment herein, it may be that C is 11 and D is 13, 14, 19 or 20. In any embodiment herein, it may be that C is 12 and D is 13, 14, 19 or 20. In any embodiment herein, it may be that C is 11 and D is 15, 16, 17 or 18. In any embodiment herein, it may be that C is 12 and D is 15, 16, 17 or 18. In any embodiment herein, it may be that J' is OH. In any embodiment herein, it may be that J' is SH. In any embodiment herein, it may be that J' is NH—$R_{11}$. In any embodiment herein, it may be that J' is OH or NH—$R_{11}$ and K is absent. In some embodiments, each of K and L is independently —(CH$_2$)—, —(CD$_2$)-, —(CHF)—, —(CF$_2$)—, —(CH(CH$_3$))—, —(CD(CD$_3$))—, —(CF(CH$_3$))—, —(CH(CF$_3$))—, —(CF(CF$_3$))—, —(C(CH$_3$)$_2$)—, —(C(CD$_3$)$_2$)—, —(C(CF$_3$)$_2$), —(CH(OCH$_3$))—, —(CD(OCD$_3$))—, —(CF(OCH$_3$))—, —(CH(OCF$_3$))—, —(CF(OCF$_3$))—, —(C(OCH$_3$)$_2$)—, —(C(OCD$_3$)$_2$)—, —(C(OCF$_3$)$_2$)—, —(C(CH$_3$)(CF$_3$))—, —(C(CD$_3$)(CF$_3$))—, —(CH(CH$_2$CH$_3$))—, —(CD(CD$_2$CD$_3$))—, —(CF(CH$_2$CH$_3$))—, —(CH(CH$_2$CF$_3$))—, —(CH(CF$_2$CF$_3$))—, —(CF(CF$_2$CF$_3$))—, —(C(CH$_2$CH$_3$)$_2$)—, —(C(CD$_2$CD$_3$)$_2$)— or —(C(CF$_2$CF$_3$)$_2$)—. In some embodiments, each of K and L is independently —(CH$_2$)—, —(CD$_2$)-, —(CF$_2$)—, —(CH(CH$_3$))—, —(CD(CD$_3$))—, —(CF(CF$_3$))—, —(C(CH$_3$)$_2$)—, —(C(CD$_3$)$_2$)—, —(C(CF$_3$)$_2$)—, —(CH(OCH$_3$))—, —(CD(OCD$_3$))—, —(CF(OCF$_3$))— or —(C(OCH$_3$)$_2$)—. In some embodiments, each of K and L is independently —(CH$_2$)—, —(CD$_2$)-, —(CHF)—, —(CF$_2$)—, —(CH(CH$_3$))—, —(CF(CF$_3$))—, —(C(CH$_3$)$_2$)— or —(C(CF$_3$)$_2$)—. In some embodiments, L is —(CH$_2$)—, —(CD$_2$)-, —(CHF)—, —(CF$_2$)—, —(CH(CH$_3$))—, —(CD(CD$_3$))—, —(CF(CH$_3$))—, —(CH(CF$_3$))—, —(CF(CF$_3$))—, —(C(CH$_3$)$_2$)—, —(C(CD$_3$)$_2$)—, —(C(CF$_3$)$_2$)—, —(CH(OCH$_3$))—, —(CD(OCD$_3$))—, —(CF(OCH$_3$))—, —(CH(OCF$_3$))—, —(CF(OCF$_3$))—, —(C(OCH$_3$)$_2$)—, —(C(OCD$_3$)$_2$)—, —(C(OCF$_3$)$_2$)—, —(C(CH$_3$)(CF$_3$))—, —(C(CD$_3$)(CF$_3$))—, —(CH(CH$_2$CH$_3$))—, —(CD(CD$_2$CD$_3$))—, —(CF(CH$_2$CH$_3$))—, —(CH(CH$_2$CF$_3$))—, —(CH(CF$_2$CF$_3$))—, —(CF(CF$_2$CF$_3$))—, —(C(CH$_2$CH$_3$)$_2$)—, —(C(CD$_2$CD$_3$)$_2$)— or —(C(CF$_2$CF$_3$)$_2$)—. In some embodiments, L is —(CH$_2$)—, —(CD$_2$)-, —(CF$_2$)—, —(CH(CH$_3$))—, —(CD(CD$_3$))—, —(CF(CF$_3$))—, —(C(CH$_3$)$_2$)—, —(C(CD$_3$)$_2$)—, —(C(CF$_3$)$_2$)—, —(CH(OCH$_3$))—, —(CD(OCD$_3$))—, —(CF(OCF$_3$))— or —(C(OCH$_3$)$_2$)—. In some embodiments, L is —(CH$_2$)—, —(CD$_2$)-, —(CHF)—, —(CF$_2$)—, —(CH(CH$_3$))—, —(CF(CF$_3$))—, —(C(CH$_3$)$_2$)— or —(C(CF$_3$)$_2$)—. In some embodiments, each of $R_1$, $R_2$ and $R_3$ is independently H, D, Cl, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, —CH(CH$_3$)$_2$, —CD$_2$CD$_3$, —CD(CD$_3$)$_2$, —CF$_2$CH$_3$, CF(CH$_3$)$_2$, —CH$_2$CF$_3$, —CH(CF$_3$)$_2$, —CF$_2$CF$_3$, —CF(CF$_3$)$_2$, —C(CH$_3$)$_3$, —C(CD$_3$)$_3$, —C(CF$_3$)$_3$, —OCH$_2$CH$_3$, —OCH(CH$_3$)$_2$, —OCD$_2$CD$_3$, —OCD(CD$_3$)$_2$, —OCF$_2$CH$_3$, —OCF(CH$_3$)$_2$, —OCH$_2$CF$_3$, —OCH(CF$_3$)$_2$, —OCF$_2$(CF$_3$), —OCF(CF$_3$)$_2$, —OC(CH$_3$)$_3$, —OC(CD$_3$)$_3$, —OC(CF$_3$)$_3$, —C(CH$_3$)$_2$(CF$_3$), —C(CH$_3$)(CF$_3$)$_2$, —OC(CH$_3$)$_2$(CF$_3$), —OC(CH$_3$)(CF$_3$)$_2$, —CH$_2$CH$_2$CH$_3$, —CH(CH$_2$CH$_3$)$_2$, —CD$_2$CD$_2$CD$_3$, —CD(CD$_2$CD$_3$)$_2$, —CF$_2$CH$_2$CH$_3$, —CF(CH$_2$CH$_3$)$_2$, —CH$_2$CF$_2$CF$_3$, —CH(CF$_2$CF$_3$)$_2$, —CF$_2$CF$_2$CF$_3$, —CF(CF$_2$CF$_3$)$_2$, —OCH$_2$CH$_2$CH$_3$, —OCH(CH$_2$CH$_3$)$_2$, —OCD$_2$CD$_2$CD$_3$, —OCD(CD$_2$CD$_3$)$_2$, —OCF$_2$CH$_2$CH$_3$, —OCF(CH$_2$CH$_3$)$_2$, —OCH$_2$CF$_2$CF$_3$, —OCH(CF$_2$CF$_3$)$_2$, —OCF$_2$CF$_2$CF$_3$ or —OCF(CF$_2$CF$_3$)$_2$. In some embodiments, each of $R_1$, $R_2$ and $R_3$ is independently H, D, Cl, F, —CH$_3$, —OCH$_3$, —CD$_3$, —OCD$_3$, —CH$_2$F, —CHF$_2$, —CF$_3$, —OCF$_3$, —C(CH$_3$)$_3$, —C(CD$_3$)$_3$, —C(CF$_3$)$_3$, —OC(CH$_3$)$_3$, —OC(CD$_3$)$_3$, —OC(CF$_3$)$_3$, —CH$_2$CH$_3$, —OCH$_2$CH$_3$ or —CH(CH$_3$)$_2$. In some embodiments, each of $R_1$, $R_2$ and $R_3$ is independently H, F, —CH$_3$, —OCH$_3$, —CH$_2$F, —CHF$_2$, —CF$_3$, —OCF$_3$, —C(CH$_3$)$_3$, —C(CF$_3$)$_3$, —CH$_2$CH$_3$, —OCH$_2$CH$_3$ or —CH(CH$_3$)$_2$. In some embodiments, J' is OH; each of K and L is independently —(CH$_2$)—, —(CD$_2$)-, —(CHF)—, —(CF$_2$)—, —(CH(CH$_3$))—, —(CF(CF$_3$))—, —(C(CH$_3$)$_2$)— or —(C(CF$_3$)$_2$)—; and each of $R_1$, $R_2$ and $R_3$ is independently H, F, —CH$_3$, —OCH$_3$, —CH$_2$F, —CHF$_2$, —CF$_3$, —OCF$_3$, —C(CH$_3$)$_3$, —C(CF$_3$)$_3$, —CH$_2$CH$_3$, —OCH$_2$CH$_3$ or —CH(CH$_3$)$_2$. In some embodiments, $R_3$ is H, D, Cl, F, —CH$_3$, —OCH$_3$, —CD$_3$, —OCD$_3$, —CF$_3$, —OCF$_3$, —C(CH$_3$)$_3$, —C(CD$_3$)$_3$, —C(CF$_3$)$_3$, —OC(CH$_3$)$_3$, —OC(CD$_3$)$_3$, —OC(CF$_3$)$_3$, —CH$_2$CH$_3$, —OCH$_2$CH$_3$, or —CH(CH$_3$)$_2$ and $R_1$ and $R_2$ taken together form a 5-, or 6-membered carbocyclic or heterocyclic ring. In some embodiments, C is 11A, 11B, 11C, 11D, 11E or 11F:

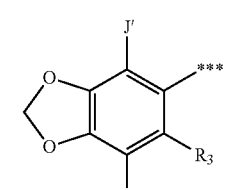

11A

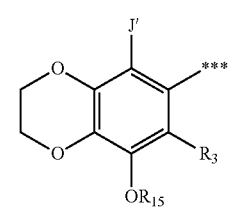

11B

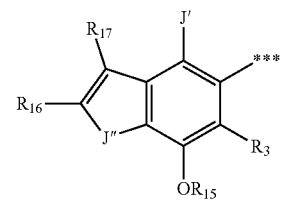

11C

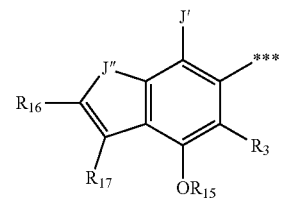

11D

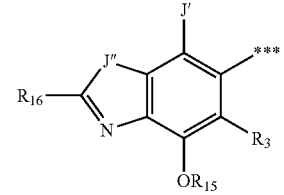

11E

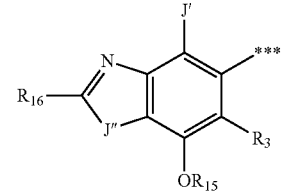

11F wherein each of $R_{16}$ and $R_{17}$ is independently H, D, Cl, F, —$CH_3$, —$OCH_3$, —$CD_3$, —$OCD_3$, —$CH_2F$, —$CHF_2$, —$CF_3$, —$OCF_3$, —$C(CH_3)_3$, —$C(CD_3)_3$, —$C(CF_3)_3$, —$OC(CH_3)_3$, —$OC(CD_3)_3$, —$OC(CF_3)_3$, —$CH_2CH_3$, —$OCH_2CH_3$, —$CH(CH_3)_2$, —$OCH(CH_3)_2$, —$C(CH_3)_3$ or —$O(CH_3)_3$; and J″ is OH, SH or NH—$R_{18}$, wherein $R_{18}$ is H, D, —$CH_3$, —$CH_2F$, —$CHF_2$ or —$CF_3$. In some embodiments, $R_3$ is H, D, Cl, F, —$CH_3$, —$OCH_3$, —$CD_3$, —$OCD_3$, —$CH_2F$, —$OCH_2F$, —$CHF_2$, —$OCHF_2$, —$CF_3$, —$OCF_3$, —$CH_2CH_3$, —$CH(CH_3)_2$, —$CD_2CD_3$, —$CD(CD_3)_2$, —$CF_2CH_3$, $CF(CH_3)_2$, —$CH_2CF_3$, —$CH(CF_3)_2$, —$CF_2CF_3$, —$CF(CF_3)_2$, —$C(CH_3)_3$, —$C(CD_3)_3$, —$C(CF_3)_3$, —$OCH_2CH_3$, —$OCH(CH_3)_2$, —$OCD_2CD_3$, —$OCD(CD_3)_2$, —$OCF_2CH_3$, —$OCF(CH_3)_2$, —$OCH_2CF_3$, —$OCH(CF_3)_2$, —$OCF_2(CF_3)$, —$OCF(CF_3)_2$, —$OC(CH_3)_3$, —$OC(CD_3)_3$, —$OC(CF_3)_3$, —$C(CH_3)_2(CF_3)$, —$C(CH_3)(CF_3)_2$, —$OC(CH_3)_2(CF_3)$, —$OC(CH_3)(CF_3)_2$, —$CH_2CH_2CH_3$, —$CH(CH_2CH_3)_2$, —$CD_2CD_2CD_3$, —$CD(CD_2CD_3)_2$, —$CF_2CH_2CH_3$, —$CF(CH_2CH_3)_2$, —$CH_2CF_2CF_3$, —$CH(CF_2CF_3)_2$, —$CF_2CF_2CF_3$, —$CF(CF_2CF_3)_2$, —$OCH_2CH_2CH_3$, —$OCH(CH_2CH_3)_2$, —$OCD_2CD_2CD_3$, —$OCD(CD_2CD_3)_2$, —$OCF_2CH_2CH_3$, —$OCF(CH_2CH_3)_2$, —$OCH_2CF_2CF_3$, —$OCH(CF_2CF_3)_2$, —$OCF_2CF_2CF_3$ or —$OCF(CF_2CF_3)_2$; and where if W is C (carbon), each of $R_4$, $R_5$, $R_6$ and $R_7$ attached thereto is independently selected from H, D, F, Cl, Br, I, —$CH_3$, —$OCH_3$, —$CD_3$, —$OCD_3$, —$CH_2F$, —$OCH_2F$, —$CHF_2$, —$OCHF_2$, —$CF_3$, —$OCF_3$, —$CH_2CH_3$, and —$CH(CH_3)_2$, and where if W is N (nitrogen), each of $R_4$, $R_5$, $R_6$ and $R_7$ attached thereto is independently absent or is selected from H, D, methyl, ethyl, isopropyl and t-butyl. In some embodiments, $R_3$ is H, D, Cl, F, —$CH_3$, —$OCH_3$, —$CD_3$, —$OCD_3$, —$CH_2F$, —$CHF_2$, —$CF_3$, —$OCF_3$, —$C(CH_3)_3$, —$C(CD_3)_3$, —$C(CF_3)_3$, —$OC(CH_3)_3$, —$OC(CD_3)_3$, —$OC(CF_3)_3$, —$CH_2CH_3$, —$OCH_2CH_3$, or —$CH(CH_3)_2$; and where if W is C (carbon), each of $R_4$, $R_5$, $R_6$ and $R_7$ attached thereto is independently H, D, F, $C_1$, —$CH_3$, —$OCH_3$, —$CH_2F$, —$CHF_2$, —$CF_3$, —$OCF_3$, —$CH_2CH_3$, or —$CH(CH_3)_2$, and where if W is N (nitrogen), each of $R_4$, $R_5$, $R_6$ and $R_7$ attached thereto is independently absent or is selected from H, D, methyl and ethyl. In some embodiments, each W is C (carbon) and each of $R_4$, $R_5$, $R_6$ and $R_7$ is independently H, D, Cl, F, —$CH_3$, —$OCH_3$, —$CH_2F$, —$CHF_2$, —$CF_3$ or —$OCF_3$.

In any embodiment herein, it may be that each of $R_8$ and $R_9$ is independently H, D, F, Cl, Br, I, —$CH_3$, —$CD_3$, —$CH_2F$, —$CHF_2$, —$CF_3$, —$CH_2CH_3$, —$CH(CH_3)_2$, —$CD_2CD_3$, —$CD(CD_3)_2$, —$CF_2CH_3$, —$CF(CH_3)_2$, —$CH_2CF_3$, —$CH(CF_3)_2$, —$CF_2CF_3$, —$CF(CF_3)_2$, —$C(CH_3)_3$, —$C(CD_3)_3$, —$C(CF_3)_3$, —$C(CH_3)_2(CF_3)$, —$C(CH_3)(CF_3)_2$, —$CH_2CH_2CH_3$, —$CH(CH_2CH_3)_2$, —$CD_2CD_2CD_3$, —$CD(CD_2CD_3)_2$, —$CF_2CH_2CH_3$, —$CF(CH_2CH_3)_2$, —$CH_2CF_2CF_3$, —$CH(CF_2CF_3)_2$, —$CF_2CF_2CF_3$ or —$CF(CF_2CF_3)_2$. In some embodiments, each of $R_8$ and $R_9$ is independently H, F, —$CH_3$, —$CH_2F$, —$CHF_2$, —$CF_3$, —$CH_2CH_3$, —$CH(CH_3)_2$, —$CF_2CH_3$, —$CH_2CF_3$, —$CH(CF_3)_2$, —$CF_2CF_3$, —$CF(CF_3)_2$, —$C(CH_3)_3$, —$C(CF_3)_3$, —$CH_2CH_2CH_3$, —$CH(CH_2CH_3)_2$, —$CF_2CF_2CF_3$ or —$CF(CF_2CF_3)_2$. In any embodiment herein, it may be that $R_8$ and $R_9$ taken together form a 3-, 4-, 5-, 6- or 7-membered carbocyclic or heterocyclic ring selected from 31, 32, 33, 34, 35, 36, 37, 38, 39, 40, 41, 42, 43, 44, 45, 46 and 47:

31

32

33

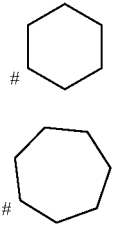

34

35

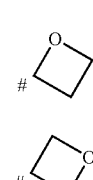

36

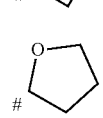

37

38

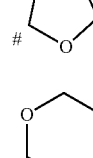

39

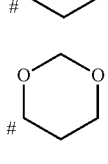

40

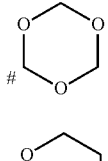

41

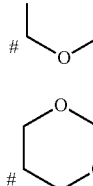

42

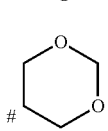

43

44

45

46

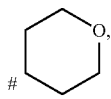

wherein # indicates the point of attachment of the carbocycle or heterocycle to the remainder of the compound.

In any embodiment herein, it may be that $R_{10}$ is H, D, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, —CH(CH$_3$)$_2$, —CD$_2$CD$_3$, —CD(CD$_3$)$_2$, —CF$_2$CH$_3$, —CF(CH$_3$)$_2$, —CH$_2$CF$_3$, —CH(CF$_3$)$_2$, —CF$_2$CF$_3$, —CF(CF$_3$)$_2$, —C(CH$_3$)$_3$, —C(CD$_3$)$_3$, —C(CF$_3$)$_3$, —OCH$_2$CH$_3$, —OCH(CH$_3$)$_2$, —OCD$_2$CD$_3$, —OCD(CD$_3$)$_2$, —OCF$_2$(CF$_3$), —OCF(CF$_3$)$_2$, —OC(CH$_3$)$_3$, —OC(CD$_3$)$_3$, —OC(CF$_3$)$_3$, —C(CH$_3$)$_2$(CF$_3$), —C(CH$_3$)(CF$_3$)$_2$, —OC(CH$_3$)$_2$(CF$_3$), —OC(CH$_3$)(CF$_3$)$_2$, —CH$_2$CH$_2$CH$_3$, —CH(CH$_2$CH$_3$)$_2$, —CD$_2$CD$_2$CD$_3$, —CD(CD$_2$CD$_3$)$_2$, —CF$_2$CF$_2$CF$_3$, —CF(CF$_2$CF$_3$)$_2$, —C(CH$_2$CH$_3$)$_3$, —C(CD$_2$CD$_3$)$_3$, —C(CF$_2$CF$_3$)$_3$, —OCH$_2$CH$_2$CH$_3$, —OCH(CH$_2$CH$_3$)$_2$, —OCD$_2$CD$_2$CD$_3$, —OCD(CD$_2$CD$_3$)$_2$, —OCF$_2$CF$_2$CF$_3$ or —OCF(CF$_2$CF$_3$)$_2$. In some embodiments, $R_{10}$ is H, D, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$ or —CH(CH$_3$)$_2$. In any embodiment herein, it may be that $R_{11}$ is H, methyl or ethyl. In any embodiment herein, it may be that each of $R_{12}$, $R_{13}$ or $R_{14}$ is independently H, D, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, —CH(CH$_3$)$_2$, —CH$_2$CH$_2$CH$_3$, —CH(CH$_2$CH$_3$)$_2$, —C(CH$_3$)$_3$, —OCH$_2$CH$_3$, —OCH(CH$_3$)$_2$, —OCH$_2$CH$_2$CH$_3$, —OCH(CH$_2$CH$_3$)$_2$ or —OC(CH$_3$)$_3$. In some embodiments, each of $R_{12}$, $R_{13}$ or $R_{14}$ is independently H, D, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$ or —OCH$_2$CH$_3$. In any embodiment herein, it may be that $R_{19}$ is H. In any embodiment herein, it may be that $R_{19}$ is —CH$_3$. In any embodiment herein, it may be that $R_{19}$ is —CH$_2$CH$_3$. In any embodiment herein, it may be that $R_{19}$ is —C(CH$_3$)$_3$. In any embodiment herein, it may be that $R_{19}$, is an unsubstituted or substituted benzyl group. In any embodiment herein, it may be that $R_{20}$ is H, D, F, —CH$_3$, —CD$_3$, —CH$_2$F, —CHF$_2$, —CF$_3$, —CH$_2$CH$_3$, —CH$_2$CH$_2$CH$_3$, —CH(CH$_3$)$_2$, —C(CH$_3$)$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CH$_2$CH$_2$CH$_2$CH$_2$CH$_2$CH$_2$CH$_3$, —CH$_2$CH$_2$CH$_2$CH$_2$CH$_2$CH$_2$CH$_2$CH$_3$, —CH$_2$CH$_2$CH$_2$CH$_2$CH$_2$CH$_2$CH$_2$CH$_2$CH$_3$ or —CH$_2$CH$_2$CH$_2$CH$_2$CH$_2$CH$_2$CH$_2$CH$_2$CH$_2$CH$_3$. In any embodiment herein, it may be that each $R_{21}$ is independently H, D, F, —CH$_3$, —CD$_3$, —CH$_2$F, —CHF$_2$, —CF$_3$, —CH$_2$CH$_3$, —CH$_2$CH$_2$CH$_3$, —CH(CH$_3$)$_2$, —CH$_2$CH$_2$CH$_2$CH$_3$ or —C(CH$_3$)$_3$. In any embodiment herein, it may be that n is 0, 1, 2, 3 or 4.

In some embodiments, the compound is

Compound A-2

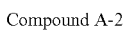

or a pharmaceutically acceptable salt, a stereoisomer, a mixture of stereoisomers, a tautomer, a hydrate, and/or a solvate thereof. In some embodiments, the compound is Compound B-2

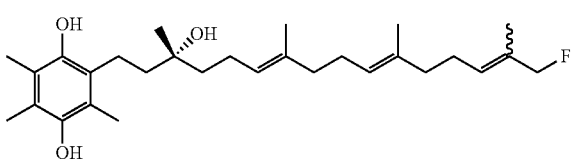

or a pharmaceutically acceptable salt, a stereoisomer, a mixture of stereoisomers, a tautomer, a hydrate, and/or a solvate thereof. In some embodiments, the compound is Compound C-2

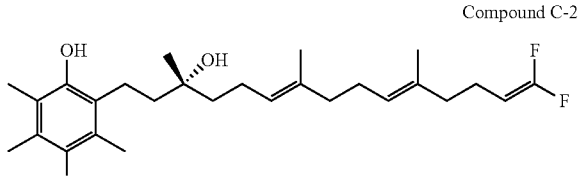

or a pharmaceutically acceptable salt, a stereoisomer, a mixture of stereoisomers, a tautomer, a hydrate, and/or a solvate thereof. In some embodiments, the compound is Compound D-2

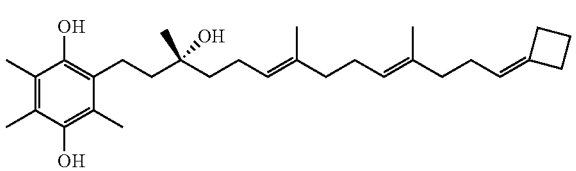

or a pharmaceutically acceptable salt, a stereoisomer, a mixture of stereoisomers, a tautomer, a hydrate, and/or a solvate thereof. In some embodiments, the compound is Compound E-2

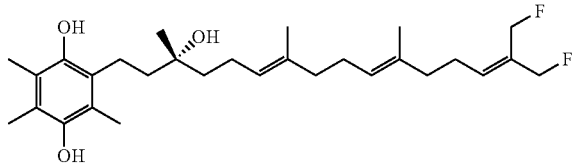

or a pharmaceutically acceptable salt, a stereoisomer, a mixture of stereoisomers, a tautomer, a hydrate, and/or a solvate thereof. In some embodiments, the compound is Compound F-2

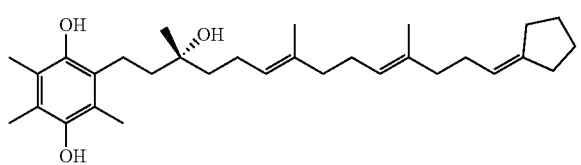

or a pharmaceutically acceptable salt, a stereoisomer, a mixture of stereoisomers, a tautomer, a hydrate, and/or a solvate thereof. In some embodiments, the compound is Compound G-2

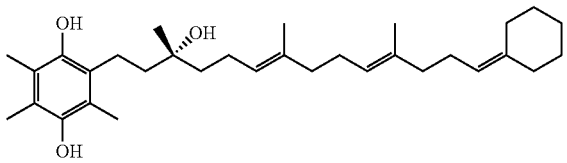

or a pharmaceutically acceptable salt, a stereoisomer, a mixture of stereoisomers, a tautomer, a hydrate, and/or a solvate thereof. In some embodiments, the compound is Compound H-2

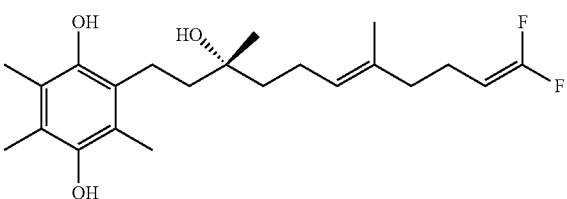

or a pharmaceutically acceptable salt, a stereoisomer, a mixture of stereoisomers, a tautomer, a hydrate, and/or a solvate thereof. In some embodiments, the compound is Compound I-2

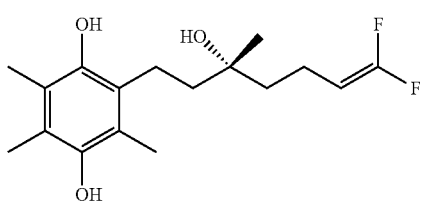

or a pharmaceutically acceptable salt, a stereoisomer, a mixture of stereoisomers, a tautomer, a hydrate, and/or a solvate thereof. In some embodiments, the compound is Compound J-2

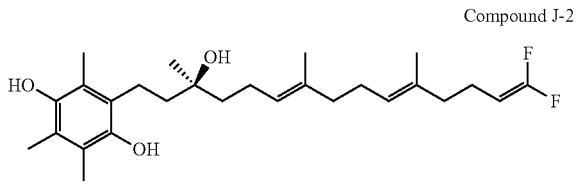 [SMILES: C/C(=C\CC/C(C)=C/CC[C@](C)(O)CCc1c(C)c(O)c(C)c(C)c1O)CCC=C(F)F]

or a pharmaceutically acceptable salt, a stereoisomer, a mixture of stereoisomers, a tautomer, a hydrate, and/or a solvate thereof. In some embodiments, the compound is Compound K-2

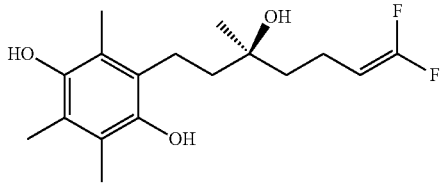

or a pharmaceutically acceptable salt, a stereoisomer, a mixture of stereoisomers, a tautomer, a hydrate, and/or a solvate thereof. In some embodiments, the compound is Compound L-2

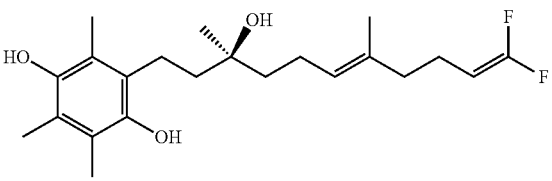

or a pharmaceutically acceptable salt, a stereoisomer, a mixture of stereoisomers, a tautomer, a hydrate, and/or a solvate thereof. In some embodiments, the compound is Compound N-2

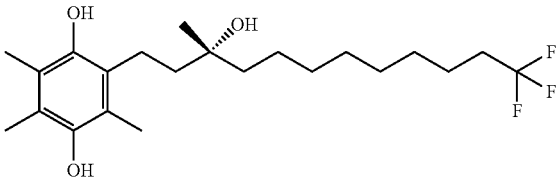

or a pharmaceutically acceptable salt, a stereoisomer, a mixture of stereoisomers, a tautomer, a hydrate, and/or a solvate thereof.

In an aspect, a compound of formula A-B, or pharmaceutically acceptable salts, stereoisomers, mixtures of stereoisomers, tautomers, hydrates, and/or solvates thereof, or of formula A-H, or pharmaceutically acceptable salts, stereoisomers, mixtures of stereoisomers, tautomers, hydrates, and/or solvates thereof, wherein A is 1, 2, 3 or 4:

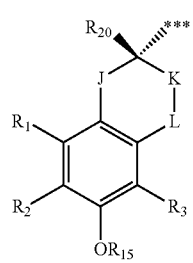

-continued

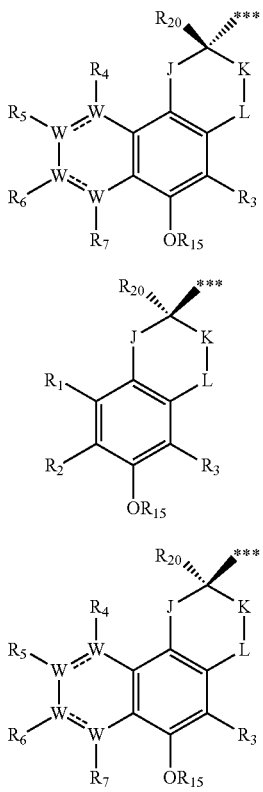

B is 5, 6, 7 or 8:

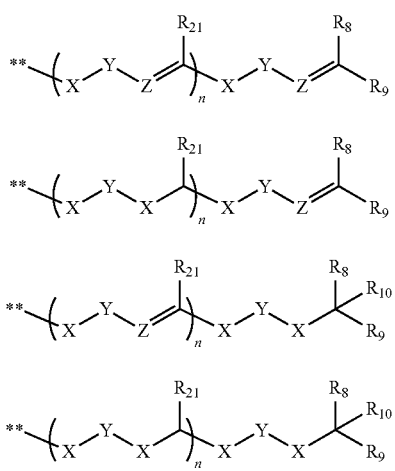

and H is 25:

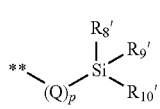

wherein, J is O, S or N—R$_{11}$; K is absent or —(CR$_{12}$R$_{13}$)—; L is —(CR$_{12}$R$_{13}$)—; each Q is independently a group of formula —(CR$_{12}$R$_{13}$)—, O or Si provided that each O and each Si is not directly bonded to O or Si; each W is independently C (carbon) or N (nitrogen) and wherein for each use of w═w, the bond between each W can be a single bond or double bond and further provided that if a single bond, each C (carbon) atom will have a hydrogen atom linked hereto in addition to one of R$_4$, R$_5$, R$_6$ or R$_7$ and in either case each of R$_4$, R$_5$, R$_6$ and R$_7$ attached thereto is independently selected from H, D, F, Cl, Br, I, C$_1$-C$_6$ alkyl and C$_1$-C$_6$ alkoxy, and if W is N (nitrogen), each of R$_4$, R$_5$, R$_6$ and R$_7$ attached thereto is independently absent (if w═w is a double bond) or selected from H, D and C$_1$-C$_6$ alkyl (if w═w is a single bond); each X is independently a group of formula —(CR$_{12}$R$_{13}$)—; each Y is independently absent or a group of formula —(CR$_{12}$R$_{13}$)—; each Z is independently a group of formula —(CR$_{14}$)—; each of R$_1$, R$_2$ and R$_3$ is independently H, D, F, Cl, Br, I, C$_1$-C$_6$ alkyl or C$_1$-C$_6$ alkoxy; or R$_1$ and R$_2$ together form a 5-membered carbocyclic ring, a 5-membered heterocyclic ring, a 5-membered aromatic or heteroaromatic ring or a 6-membered heterocyclic ring; each of R$_8$ and R$_9$ is each independently H, D, F, Cl, Br, I or C$_1$-C$_4$ alkyl; or taken together R$_8$ and R$_9$ form a 3-, 4-, 5-, 6- or 7-membered carbocyclic or heterocyclic ring; R$_{10}$ is H, D, F, Cl, Br, I, C$_1$-C$_6$ alkyl or C$_1$-C$_6$ alkoxy; each of R$_8$', R$_9$' and R$_{10}$' is independently a C$_1$-C$_4$ alkyl, or taken together R$_8$' and R$_9$' form a 3-, 4-, 5-, 6- or 7-membered carbocyclic or heterocyclic ring; R$_1$ is H, D or C$_1$-C$_6$ alkyl; each of R$_{12}$, R$_{13}$ and R$_{14}$ is independently H, D, F, Cl, Br, I, C$_1$-C$_6$ alkyl or C$_1$-C$_6$ alkoxy; R$_{15}$ is H, C$_1$-C$_4$ alkyl or PG, wherein PG is a phenol protecting group; R$_{20}$ is H, D, F or C$_1$-C$_{12}$ alkyl; each R$_{21}$ is independently H, D, F, Cl, Br, I, or C$_1$-C$_4$ alkyl; n is an integer from 0 to 12, inclusive; p is an integer from 0 to 20, inclusive; and * indicates the point of attachment of A to B or to H and  indicates the point of attachment of B to A or of H to A; and further provided that: (i) at least one group of formula R$_1$, R$_2$, R$_3$, R$_4$, R$_5$, R$_6$, R$_7$, R$_8$, R$_9$, R$_{10}$, R$_{12}$, R$_{13}$, R$_{14}$, R$_{20}$ or R$_{21}$ comprises at least one fluorine atom; and/or (ii) R$_8$ and R$_9$ taken together form a 3-, 4-, 5-, 6- or 7-membered carbocyclic or heterocyclic ring.

In any embodiment herein, it may be that A is 1 or 3 and B is 5 or 8. In any embodiment herein, it may be that A is 2 or 4 and B is 5 or 8. In any embodiment herein, it may be that A is 1 or 3 and B is 6 or 7. In any embodiment herein, it may be that A is 2 or 4 and B is 6 or 7. In any embodiment herein, it may be that J is O. In any embodiment herein, it may be that J is S. In any embodiment herein, it may be that J is N—R$_{11}$. In any embodiment herein, it may be that J is O or N—R$_{11}$ and K is absent. In some embodiments, each of K and L is independently —(CH$_2$)—, —(CD$_2$)-, —(CHF)—, —(CF$_2$)—, —(CH(CH$_3$))—, —(CD(CD$_3$))—, —(CF(CH$_3$))—, —(CH(CF$_3$))—, —(CF(CF$_3$))—, —(C(CH$_3$)$_2$)—, —(C(CD$_3$)$_2$)—, —(C(CF$_3$)$_2$), —(CH(OCH$_3$))—, —(CD(OCD$_3$))—, —(CF(OCH$_3$))—, —(CH(OCF$_3$))—, —(CF(OCF$_3$))—, —(C(OCH$_3$)$_2$)—, —(C(OCD$_3$)$_2$)—, —(C(OCF$_3$)$_2$)—, —(C(CH$_3$)(CF$_3$))—, —(C(CD$_3$)(CF$_3$))—, —(CH(CH$_2$CH$_3$))—, —(CD(CD$_2$CD$_3$))—, —(CF(CH$_2$CH$_3$))—, —(CH(CH$_2$CF$_3$))—, —(CH(CF$_2$CF$_3$))—, —(CF(CF$_2$CF$_3$))—, —(C(CH$_2$CH$_3$)$_2$)—, —(C(CD$_2$CD$_3$)$_2$)— or —(C(CF$_2$CF$_3$)$_2$)—. In some embodiments, each of K and L is independently —(CH$_2$)—, —(CD$_2$)-, —(CF$_2$)—, —(CH(CH$_3$))—, —(CD(CD$_3$))—, —(CF(CF$_3$))—, —(C(CH$_3$)$_2$)—, —(C(CD$_3$)$_2$)—, —(C(CF$_3$)$_2$)—, —(CH(OCH$_3$))—, —(CD(OCD$_3$))—, —(CF (OCF₃))— or —(C(OCH₃)₂)—. In some embodiments, each of K and L is independently —(CH₂)—, —(CD₂)-, —(CHF)—, —(CF₂)—, —(CH(CH₃))—, —(CF(CF₃))—, —(C(CH₃)₂)— or —(C(CF₃)₂)—. In some embodiments, L is —(CH₂)—, —(CD₂)-, —(CHF)—, —(CF₂)—, —(CH(CH₃))—, —(CD(CD₃))—, —(CF(CH₃))—, —(CH(CF₃))—, —(CF(CF₃))—, —(C(CH₃)₂)—, —(C(CD₃)₂)—, —(C(CF₃)₂)—, —(CH(OCH₃))—, —(CD(OCD₃))—, —(CF(OCH₃))—, —(CH(OCF₃))—, —(CF(OCF₃))—, —(C(OCH₃)₂)—, —(C(OCD₃)₂)—, —(C(OCF₃)₂)—, —(C(CH₃)(CF₃))—, —(C(CD₃)(CF₃))—, —(CH(CH₂CH₃))—, —(CD(CD₂CD₃))—, —(CF(CH₂CH₃))—, —(CH(CH₂CF₃))—, —(CH(CF₂CF₃))—, —(CF(CF₂CF₃))—, —(C(CH₂CH₃)₂)—, —(C(CD₂CD₃)₂)— or —(C(CF₂CF₃)₂)—. In some embodiments, L is —(CH₂)—, —(CD₂)-, —(CF₂)—, —(CH(CH₃))—, —(CD(CD₃))—, —(CF(CF₃))—, —(C(CH₃)₂)—, —(C(CD₃)₂)—, —(C(CF₃)₂)—, —(CH(OCH₃))—, —(CD(OCD₃))—, —(CF(OCF₃))— or —(C(OCH₃)₂)—. In some embodiments, L is —(CH₂)—, —(CD₂)-, —(CHF)—, —(CF₂)—, —(CH(CH₃))—, —(CF(CF₃))—, —(C(CH₃)₂)— or —(C(CF₃)₂)—. In some embodiments, each of R₁, R₂ and R₃ is independently H, D, C₁, F, —CH₃, —OCH₃, —CD₃, —OCD₃, —CH₂F, —OCH₂F, —CHF₂, —OCHF₂, —CF₃, —OCF₃, —CH₂CH₃, —CH(CH₃)₂, —CD₂CD₃, —CD(CD₃)₂, —CF₂CH₃, CF(CH₃)₂, —CH₂CF₃, —CH(CF₃)₂, —CF₂CF₃, —CF(CF₃)₂, —C(CH₃)₃, —C(CD₃)₃, —C(CF₃)₃, —OCH₂CH₃, —OCH(CH₃)₂, —OCD₂CD₃, —OCD(CD₃)₂, —OCF₂CH₃, —OCF(CH₃)₂, —OCH₂CF₃, —OCH(CF₃)₂, —OCF₂(CF₃), —OCF(CF₃)₂, —OC(CH₃)₃, —OC(CD₃)₃, —OC(CF₃)₃, —C(CH₃)₂(CF₃), —C(CH₃)(CF₃)₂, —OC(CH₃)₂(CF₃), —OC(CH₃)(CF₃)₂, —CH₂CH₂CH₃, —CH(CH₂CH₃)₂, —CD₂CD₂CD₃, —CD(CD₂CD₃)₂, —CF₂CH₂CH₃, —CF(CH₂CH₃)₂, —CH₂CF₂CF₃, —CH(CF₂CF₃)₂, —CF₂CF₂CF₃, —CF(CF₂CF₃)₂, —OCH₂CH₂CH₃, —OCH(CH₂CH₃)₂, —OCD₂CD₂CD₃, —OCD(CD₂CD₃)₂, —OCF₂CH₂CH₃, —OCF(CH₂CH₃)₂, —OCH₂CF₂CF₃, —OCH(CF₂CF₃)₂, —OCF₂CF₂CF₃ or —OCF(CF₂CF₃)₂. In some embodiments, each of R₁, R₂ and R₃ is independently H, D, Cl, F, —CH₃, —OCH₃, —CD₃, —OCD₃, —CH₂F, —CHF₂, —CF₃, —OCF₃, —C(CH₃)₃, —C(CD₃)₃, —C(CF₃)₃, —OC(CH₃)₃, —OC(CD₃)₃, —OC(CF₃)₃, —CH₂CH₃, —OCH₂CH₃ or —CH(CH₃)₂. In some embodiments, each of R₁, R₂ and R₃ is independently H, F, —CH₃, —OCH₃, —CH₂F, —CHF₂, —CF₃, —OCF₃, —C(CH₃)₃, —C(CF₃)₃, —CH₂CH₃, —OCH₂CH₃ or —CH(CH₃)₂. In some embodiments, J is O; each of K and L is independently —(CH₂)—, —(CD₂)-, —(CHF)—, —(CF₂)—, —(CH(CH₃))—, —(CF(CF₃))—, —(C(CH₃)₂)— or —(C(CF₃)₂)—; and each of R₁, R₂ and R₃ is independently H, F, —CH₃, —OCH₃, —CH₂F, —CHF₂, —CF₃, —OCF₃, —C(CH₃)₃, —C(CF₃)₃, —CH₂CH₃, —OCH₂CH₃ or —CH(CH₃)₂. In some embodiments, R₃ is H, D, Cl, F, —CH₃, —OCH₃, —CD₃, —OCD₃, —CF₃, —OCF₃, —C(CH₃)₃, —C(CD₃)₃, —C(CF₃)₃, —OC(CH₃)₃, —OC(CD₃)₃, —OC(CF₃)₃, —CH₂CH₃, —OCH₂CH₃, or —CH(CH₃)₂, and R₁ and R₂ taken together form a 5-, or 6-membered carbocyclic or heterocyclic ring. In some embodiments, A is 1A, 1B, 1C, 1D, 1E, 1F, 3A, 3B, 3C, 3D, 3E or 3F:

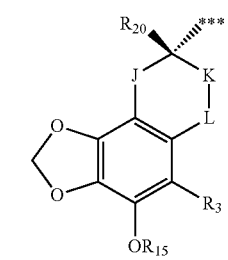

1A

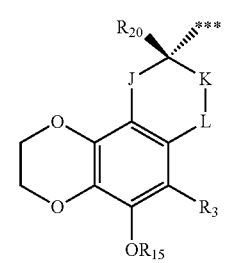

1B

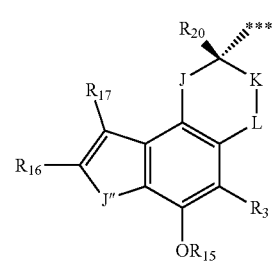

1C

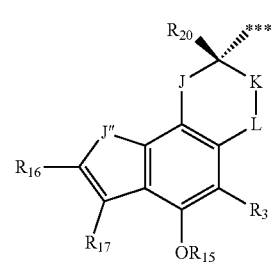

1D

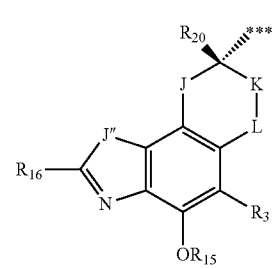

1E

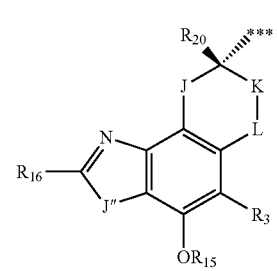

1F

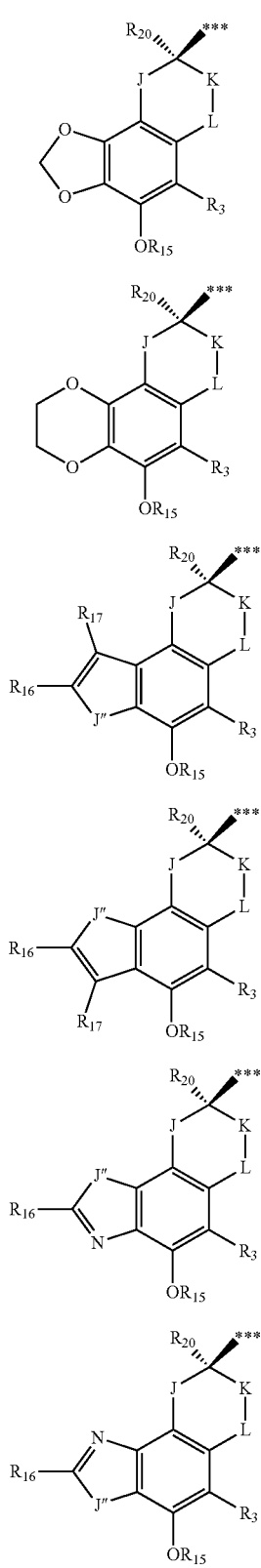

wherein each of R₁₆ and R₁₇ is independently H, D, Cl, F, —CH₃, —OCH₃, —CD₃, —OCD₃, —CH₂F, —CHF₂, —CF₃, —OCF₃, —C(CH₃)₃, —C(CD₃)₃, —C(CF₃)₃, —OC(CH₃)₃, —OC(CD₃)₃, —OC(CF₃)₃, —CH₂CH₃, —OCH₂CH₃, —CH(CH₃)₂, —OCH(CH₃)₂, —C(CH₃)₃ or —O(CH₃)₃; and J″ is O, S or N—R₁₈, wherein R₁₈ is H, D, —CH₃, —CH₂F, —CHF₂ or —CF₃. In some embodiments, R₃ is H, D, Cl, F, —CH₃, —OCH₃, —CD₃, —OCD₃, —CH₂F, —OCH₂F, —CHF₂, —OCHF₂, —CF₃, —OCF₃, —CH₂CH₃, —CH(CH₃)₂, —CD₂CD₃, —CD(CD₃)₂, —CF₂CH₃, CF(CH₃)₂, —CH₂CF₃, —CH(CF₃)₂, —CF₂CF₃, —CF(CF₃)₂, —C(CH₃)₃, —C(CD₃)₃, —C(CF₃)₃, —OCH₂CH₃, —OCH(CH₃)₂, —OCD₂CD₃, —OCD(CD₃)₂, —OCF₂CH₃, —OCF(CH₃)₂, —OCH₂CF₃, —OCH(CF₃)₂, —OCF₂(CF₃), —OCF(CF₃)₂, —OC(CH₃)₃, —OC(CD₃)₃, —OC(CF₃)₃, —C(CH₃)₂(CF₃), —C(CH₃)(CF₃)₂, —OC(CH₃)₂(CF₃), —OC(CH₃)(CF₃)₂, —CH₂CH₂CH₃, —CH(CH₂CH₃)₂, —CD₂CD₂CD₃, —CD(CD₂CD₃)₂, —CF₂CH₂CH₃, —CF(CH₂CH₃)₂, —CH₂CF₂CF₃, —CH(CF₂CF₃)₂, —CF₂CF₂CF₃, —CF(CF₂CF₃)₂, —OCH₂CH₂CH₃, —OCH(CH₂CH₃)₂, —OCD₂CD₂CD₃, —OCD(CD₂CD₃)₂, —OCF₂CH₂CH₃, —OCF(CH₂CH₃)₂, —OCH₂CF₂CF₃, —OCH(CF₂CF₃)₂, —OCF₂CF₂CF₃ or —OCF(CF₂CF₃)₂; and where if W is C (carbon), each of R₄, R₅, R₆ and R₇ attached thereto is independently H, D, F, Cl, Br, I, —CH₃, —OCH₃, —CD₃, —OCD₃, —CH₂F, —OCH₂F, —CHF₂, —OCHF₂, —CF₃, —OCF₃, —CH₂CH₃, or —CH(CH₃)₂, and where if W is N (nitrogen), each of R₄, R₅, R₆ and R₇ attached thereto is independently absent or selected from H, D, methyl, ethyl, isopropyl and t-butyl. In some embodiments, R₃ is H, D, Cl, F, —CH₃, —OCH₃, —CD₃, —OCD₃, —CH₂F, —CHF₂, —CF₃, —OCF₃, —C(CH₃)₃, —C(CD₃)₃, —C(CF₃)₃, —OC(CH₃)₃, —OC(CD₃)₃, —OC(CF₃)₃, —CH₂CH₃, —OCH₂CH₃, or —CH(CH₃)₂; and where if W is C (carbon), each of R₄, R₅, R₆ and R₇ attached thereto is independently selected from H, D, F, C₁, —CH₃, —OCH₃, —CH₂F, —CHF₂, —CF₃, —OCF₃, —CH₂CH₃, and —CH(CH₃)₂, and where if W is N (nitrogen), each of R₄, R₅, R₆ and R₇ attached thereto is independently absent or selected from H, D, methyl and ethyl. In some embodiments, each W is C (carbon) and each of R₄, R₅, R₆ and R₇ is independently H, D, Cl, F, —CH₃, —OCH₃, —CH₂F, —CHF₂, —CF₃ or —OCF₃.

In any embodiment herein, it may be that each of R₈ and R₉ is independently H, D, F, Cl, Br, I, —CH₃, —CD₃, —CH₂F, —CHF₂, —CF₃, —CH₂CH₃, —CH(CH₃)₂, —CD₂CD₃, —CD(CD₃)₂, —CF₂CH₃, —CF(CH₃)₂, —CH₂CF₃, —CH(CF₃)₂, —CF₂CF₃, —CF(CF₃)₂, —C(CH₃)₃, —C(CD₃)₃, —C(CF₃)₃, —C(CH₃)₂(CF₃), —C(CH₃)(CF₃)₂, —CH₂CH₂CH₃, —CH(CH₂CH₃)₂, —CD₂CD₂CD₃, —CD(CD₂CD₃)₂, —CF₂CH₂CH₃, —CF(CH₂CH₃)₂, —CH₂CF₂CF₃, —CH(CF₂CF₃)₂, —CF₂CF₂CF₃ or —CF(CF₂CF₃)₂. In some embodiments, each of R₈ and R₉ is independently H, F, —CH₃, —CH₂F, —CHF₂, —CF₃, —CH₂CH₃, —CH(CH₃)₂, —CF₂CH₃, —CH₂CF₃, —CH(CF₃)₂, —CF₂CF₃, —CF(CF₃)₂, —C(CH₃)₃, —C(CF₃)₃, —CH₂CH₂CH₃, —CH(CH₂CH₃)₂, —CF₂CF₂CF₃ or —CF(CF₂CF₃)₂.

In any embodiment herein, it may be that R₈ and R₉ taken together form a 3-, 4-, 5-, 6- or 7-membered carbocyclic or heterocyclic ring selected from 31, 32, 33, 34, 35, 36, 37, 38, 39, 40, 41, 42, 43, 44, 45, 46 and 47:

31

△ wherein # indicates the point of attachment of the carbocycle or heterocycle to the remainder of the compound. In any embodiment herein, it may be that $R_{10}$ is H, D, F, —$CH_3$, —$OCH_3$, —$CD_3$, —$OCD_3$, —$CH_2F$, —$OCH_2F$, —$CHF_2$, —$OCHF_2$, —$CF_3$, —$OCF_3$, —$CH_2CH_3$, —$CH(CH_3)_2$, —$CD_2CD_3$, —$CD(CD_3)_2$, —$CF_2CH_3$, —$CF(CH_3)_2$, —$CH_2CF_3$, —$CH(CF_3)_2$, —$CF_2CF_3$, —$CF(CF_3)_2$, —$C(CH_3)_3$, —$C(CD_3)_3$, —$C(CF_3)_3$, —$OCH_2CH_3$, —$OCH(CH_3)_2$, —$OCD_2CD_3$, —$OCD(CD_3)_2$, —$OCF_2(CF_3)$, —$OCF(CF_3)_2$, —$OC(CH_3)_3$, —$OC(CD_3)_3$, —$OC(CF_3)_3$, —$C(CH_3)_2(CF_3)$, —$C(CH_3)(CF_3)_2$, —$OC(CH_3)_2(CF_3)$, —$OC(CH_3)(CF_3)_2$, —$CH_2CH_2CH_3$, —$CH(CH_2CH_3)_2$, —$CD_2CD_2CD_3$, —$CD(CD_2CD_3)_2$, —$CF_2CF_2CF_3$, —$CF(CF_2CF_3)_2$, —$C(CH_2CH_3)_3$, —$C(CD_2CD_3)_3$, —$C(CF_2CF_3)_3$, —$OCH_2CH_2CH_3$, —$OCH(CH_2CH_3)_2$, —$OCD_2CD_2CD_3$, —$OCD(CD_2CD_3)_2$, —$OCF_2CF_2CF_3$ or —$OCF(CF_2CF_3)_2$. In some embodiments, $R_{10}$ is H, D, F, —$CH_3$, —$OCH_3$, —$CD_3$, —$OCD_3$, —$CH_2F$, —$OCH_2F$, —$CHF_2$, —$OCHF_2$, —$CF_3$, —$OCF_3$, —$CH_2CH_3$ or —$CH(CH_3)_2$. In any embodiment herein, it may be that $R_{11}$ is H, methyl or ethyl. In any embodiment herein, it may be that each of $R_{12}$, $R_{13}$ or $R_{14}$ is independently H, D, F, —$CH_3$, —$OCH_3$, —$CD_3$, —$OCD_3$, —$CH_2F$, —$OCH_2F$, —$CHF_2$, —$OCHF_2$, —$CF_3$, —$OCF_3$, —$CH_2CH_3$, —$CH(CH_3)_2$, —$CH_2CH_2CH_3$, —$CH(CH_2CH_3)_2$, —$C(CH_3)_3$, —$OCH_2CH_3$, —$OCH(CH_3)_2$, —$OCH_2CH_2CH_3$, —$OCH(CH_2CH_3)_2$ or —$OC(CH_3)_3$. In some embodiments, each of $R_{12}$, $R_{13}$ or $R_{14}$ is independently H, D, F, —$CH_3$, —$OCH_3$, —$CD_3$, —$OCD_3$, —$CH_2F$, —$OCH_2F$, —$CHF_2$, —$OCHF_2$, —$CF_3$, —$OCF_3$, —$CH_2CH_3$ or —$OCH_2CH_3$. In any embodiment herein, it may be that $R_{15}$ is H. In any embodiment herein, it may be that $R_{15}$ is —$CH_3$. In any embodiment herein, it may be that $R_{15}$ is a silyl-based phenol protecting group. In any embodiment herein, it may be that $R_{15}$ is triphenylmethyl-based phenol protecting group. In any embodiment herein, it may be that $R_{15}$, is an unsubstituted or substituted benzyl group.

In any embodiment herein, it may be that $R_{20}$ is H, D, F, —$CH_3$, —$CD_3$, —$CH_2F$, —$CHF_2$, —$CF_3$, —$CH_2CH_3$, —$CH_2CH_2CH_3$, —$CH(CH_3)_2$, —$C(CH_3)_3$, —$CH_2CH_2CH_2CH_3$, —$CH_2CH_2CH_2CH_2CH_3$, —$CH_2CH_2CH_2CH_2CH_2CH_3$, —$CH_2CH_2CH_2CH_2CH_2CH_2CH_3$, —$CH_2CH_2CH_2CH_2CH_2CH_2CH_2CH_3$, —$CH_2CH_2CH_2CH_2CH_2CH_2CH_2CH_2CH_3$ or —$CH_2CH_2CH_2CH_2CH_2CH_2CH_2CH_2CH_2CH_3$. In any embodiment herein, it may be that each $R_{21}$ is independently H, D, F, —$CH_3$, —$CD_3$, —$CH_2F$, —$CHF_2$, —$CF_3$, —$CH_2CH_3$, —$CH_2CH_2CH_3$, —$CH(CH_3)_2$, —$CH_2CH_2CH_2CH_3$ or —$C(CH_3)_3$. In any embodiment herein, it may be that n is 0, 1, 2, 3 or 4.

In an aspect, a compound of formula E-G, or pharmaceutically acceptable salts, stereoisomers, mixtures of stereoisomers, tautomers, hydrates, and/or solvates thereof, is provided wherein E is 21 or 22:

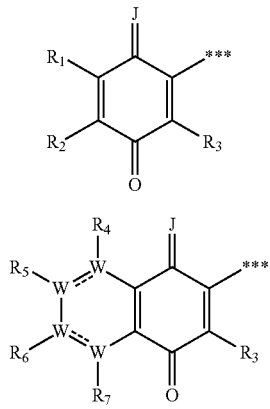

and G is 23 or 24:

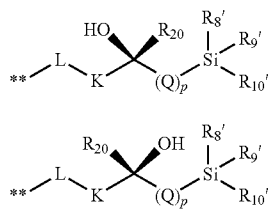

wherein, J is O, S or N—Ru; K is absent or —(CR$_{12}$R$_{13}$)—; L is —(CR$_{12}$R$_{13}$)—; each W is = independently C (carbon) or N (nitrogen) and wherein for each use of w=w, the bond between each W can be a single bond or double bond and further provided that if a single bond, each C (carbon) atom will have a hydrogen atom linked hereto in addition to one of R$_4$, R$_5$, R$_6$ or R$_7$ and in either case each of R$_4$, R$_5$, R$_6$ and R$_7$ attached thereto is independently selected from H, D, F, Cl, Br, I, C$_1$-C$_6$ alkyl and C$_1$-C$_6$ alkoxy, and if W is N (nitrogen), each of R$_4$, R$_5$, R$_6$ and R$_7$ attached thereto is independently absent (if w=w is a double bond) or selected from H, D and =C$_1$-C$_6$ alkyl (if w=w is a single bond); each Q is independently a group of formula —(CR$_{12}$R$_{13}$)—, O or Si provided that each O and each Si is not directly bonded to O or Si; each of R$_1$, R$_2$ and R$_3$ is independently H, D, F, Cl, Br, I, C$_1$-C$_6$ alkyl or C$_1$-C$_6$ alkoxy; or R$_1$ and R$_2$ together form a 5-membered carbocyclic ring, a 5-membered heterocyclic ring, a 5-membered aromatic or heteroaromatic ring, or a 6-membered heterocyclic ring; each R$_8$', R$_9$' and R$_{10}$' is independently a C$_1$-C$_4$ alkyl; or taken together R$_8$' and R$_9$' form a 3-, 4-, 5-, 6- or 7-membered carbocyclic or heterocyclic ring; R$_{11}$ is H, D or C$_1$-C$_6$ alkyl; each of R$_{12}$ and R$_{13}$ is independently H, D, F, Cl, Br, I, C$_1$-C$_6$ alkyl or C$_1$-C$_6$ alkoxy; R$_{20}$ is H, D, F or C$_1$-C$_{12}$ alkyl; p is an integer from 0 to 20, inclusive; and * indicates the point of attachment of E to G and  indicates the point of attachment of G to E.

In any embodiment herein, it may be that E is 21, J is O, K is —CH$_2$—, L is —CH$_2$— and each of R$_1$, R$_2$ and R$_3$ is independently selected from: H, D, F, —CH$_3$, —OCH$_3$ and —OCF$_3$. In any embodiment herein, it may be that the chiral center at the carbon to which R$_{20}$ is linked is an S configuration, or it may be that the chiral center at the carbon to which R$_{20}$ is linked is a R configuration. In any embodiment herein, it may be that each Q is —CH$_2$—, or at least one Q is O and each other Q is —CH$_2$—. In some embodiments, the compound is of formula Compound M-0:

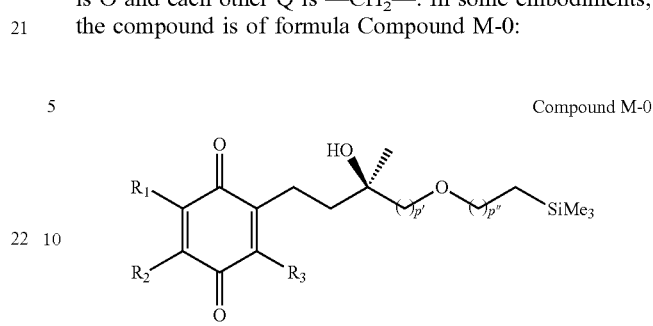

wherein each of R$_1$, R$_2$ and R$_3$ is independently H, F, —CH$_3$, —OCH$_3$, —CH$_2$CH$_3$, —OCH$_2$CH$_3$, or —OCF$_3$, p' is an integer from 1 to 9, inclusive and p" is an integer from 1 to 9, inclusive. In some embodiments, the compound is Compound M ![Compound M structure]

or a pharmaceutically acceptable salt, a stereoisomer, a mixture of stereoisomers, a tautomer, a hydrate, and/or a solvate thereof.

In an aspect, a compound of formula C-G, or pharmaceutically acceptable salts, stereoisomers, mixtures of stereoisomers, tautomers, hydrates, and/or solvates thereof, is provided wherein C is 11 or 12:

11

![Structure 11]

12

![Structure 12]

and G is 23 or 24:

23

![Structure 23]

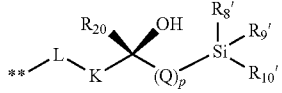

wherein, J' is OH, SH or NH—$R_{11}$; K is absent or —$(CR_{12}R_{13})$—; L is —$(CR_{12}R_{13})$—; each W is ═ independently C (carbon) or N (nitrogen) and wherein for each use of w═w, the bond between each W can be a single bond or double bond and further provided that if a single bond, each C (carbon) atom will have a hydrogen atom linked hereto in addition to one of $R_4$, $R_5$, $R_6$ or $R_7$ and in either case each of $R_4$, $R_5$, $R_6$ and $R_7$ attached thereto is independently selected from H, D, F, Cl, Br, I, $C_1$-$C_6$ alkyl and $C_1$-$C_6$ alkoxy, and if W is N (nitrogen), each of $R_4$, $R_5$, $R_6$ and $R_7$ attached thereto is independently absent (if w═w is a double bond) or selected from H, D and $C_1$-$C_6$ alkyl (if w═w is a single bond); each Q is independently a group of formula —$(CR_{12}R_{13})$—, O or Si provided that each O and each Si is not directly bonded to O or Si; each of $R_1$, $R_2$ and $R_3$ is independently H, D, F, Cl, Br, I, $C_1$-$C_6$ alkyl or $C_1$-$C_6$ alkoxy; or $R_1$ and $R_2$ together form a 5-membered carbocyclic ring, a 5-membered heterocyclic ring, a 5-membered aromatic or heteroaromatic ring, or a 6-membered heterocyclic ring; each $R_8'$, $R_9'$ and $R_{10}'$ is independently a $C_1$-$C_4$ alkyl; or taken together $R_8'$ and $R_9'$ form a 3-, 4-, 5-, 6- or 7-membered carbocyclic or heterocyclic ring; $R_{11}$ is H, D or $C_1$-$C_6$ alkyl; each of $R_{12}$ and $R_{13}$ is independently H, D, F, $C_1$, Br, I, $C_1$-$C_6$ alkyl or $C_1$-$C_6$ alkoxy; $R_{20}$ is H, D, F or $C_1$-$C_{12}$ alkyl; p is an integer from 0 to 20, inclusive; and * indicates the point of attachment of E to G and  indicates the point of attachment of G to E. In some embodiments, C is 11, J' is OH, $R_{19}$ is H, K is —$CH_2$—, L is —$CH_2$— and each of $R_1$, $R_2$ and $R_3$ is independently selected from: H, D, F, —$CH_3$, —$OCH_3$ and —$OCF_3$.

In any embodiment herein, it may be that the chiral center at the carbon to which $R_{20}$ is linked is an S configuration, or that the chiral center at the carbon to which $R_{20}$ is linked is a R configuration. In any embodiment herein, it may be that each Q is —$CH_2$—, or that at least one Q is O and each other Q is —$CH_2$—. In some embodiments, the compound is of formula Compound M-3:

Compound M-3

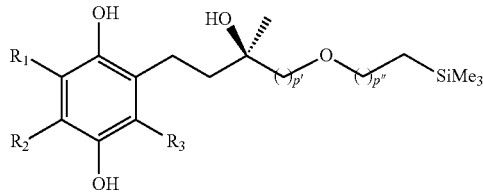

wherein each of $R_1$, $R_2$ and $R_3$ is independently H, F, —$CH_3$, —$OCH_3$, —$CH_2CH_3$, —$OCH_2CH_3$, or —$OCF_3$, p' is an integer from 1 to 9, inclusive and p" is an integer from 1 to 9, inclusive. In some embodiments, the compound is Compound M-2

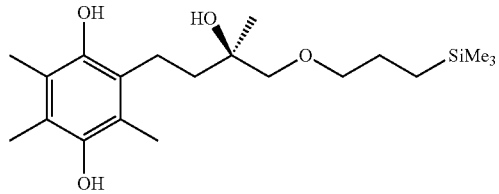

or a pharmaceutically acceptable salt, a stereoisomer, a mixture of stereoisomers, a tautomer, a hydrate, and/or a solvate thereof.

In an aspect, a compound is provided that comprises a substituted quinone or hydroquinone head group to which is covalently linked an aliphatic tail group that comprises at least one chiral center, at least one hydroxyl group and at least one silicon atom.

In an aspect, the present technology a method for treating or preventing Friedreich's ataxia or the signs or symptoms of reduced frataxin levels or activity in a subject in need thereof, the method comprising administering to the subject a therapeutically effective amount of a compound of any aspect or embodiment of the present technology disclosed herein (hereafter collectively referred to as "a compound of the present technology" or the like) or pharmaceutically acceptable salts, stereoisomers, mixtures of stereoisomers, tautomers, hydrates, and/or solvates thereof. In any embodiment herein, it may be that the subject displays reduced levels of frataxin expression compared to a normal control subject. In any embodiment herein, it may be that the compound is administered daily for 6 weeks or more. In any embodiment herein, it may be that the compound is administered daily for 12 weeks or more. In any embodiment herein, it may be that the subject has been diagnosed as having Friedreich's ataxia. In some embodiments, the Friedreich's ataxia comprises one or more of muscle weakness, loss of coordination, vision impairment, hearing impairment, slurred speech, curvature of the spine, diabetes, and heart disorders. In any embodiment herein, it may be that the subject is human. In any embodiment herein, it may be that the compound is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

In an aspect, the present technology provides a method for reducing mitochondrial iron in a mammalian subject having or suspected of having Friedreich's ataxia, the method comprising administering to the subject a therapeutically effective amount of a compound of the present technology, or pharmaceutically acceptable salts, stereoisomers, mixtures of stereoisomers, tautomers, hydrates, and/or solvates thereof. In any embodiment herein, it may be that the mammalian subject has decreased expression of frataxin compared to a normal control subject. In any embodiment herein, it may be that the compound is administered daily for 6 weeks or more. In any embodiment herein, it may be that the compound is administered daily for 12 weeks or more. In any embodiment herein, it may be that the subject has been diagnosed as having Friedreich's ataxia. In some embodiments, the Friedreich's ataxia comprises one or more of muscle weakness, loss of coordination, motor control impairment, vision impairment, hearing impairment, slurred speech, curvature of the spine, diabetes, and heart disorders.

In any embodiment herein, it may be that the subject is human. In any embodiment herein, it may be that the compound is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

In an aspect, the present technology provides a method for treating Complex I deficiency in a subject in need thereof, comprising administering to the subject a therapeutically effective amount of a compound of the present technology, or pharmaceutically acceptable salts, stereoisomers, mixtures of stereoisomers, tautomers, hydrates, and/or solvates thereof. In any embodiment herein, it may be that the compound is administered daily for 6 weeks or more. In any embodiment herein, it may be that the compound is administered daily for 12 weeks or more. In any embodiment herein, it may be that the subject has been diagnosed as having Friedreich's ataxia. In some embodiments, the Friedreich's ataxia comprises one or more of muscle weakness, loss of coordination, vision impairment, hearing impairment, slurred speech, curvature of the spine, diabetes, and heart disorders. In any embodiment herein, it may be that the subject is human. In any embodiment herein, it may be that the compound is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

In an aspect, a method is provided for reducing or inhibiting lipoxygenase-15 activity in a mammalian subject having or suspected of having Friedreich's ataxia, the method comprising administering to the subject a therapeutically effective amount of a compound of the present technology, or pharmaceutically acceptable salts, stereoisomers, mixtures of stereoisomers, tautomers, hydrates, and/or solvates thereof. In any embodiment herein, it may be that the compound is administered daily for 6 weeks or more. In any embodiment herein, it may be that the compound is administered daily for 12 weeks or more. In any embodiment herein, it may be that the Friedreich's ataxia comprises one or more of muscle weakness, loss of coordination, vision impairment, hearing impairment, slurred speech, curvature of the spine, diabetes, and heart disorders. In any embodiment herein, it may be that the subject is human. In any embodiment herein, it may be that the compound is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

In an aspect, a method is provided for reducing or inhibiting ferroptosis in a mammalian subject having or suspected of having Friedreich's ataxia, the method comprising administering to the subject a therapeutically effective amount of a compound of the present technology, or pharmaceutically acceptable salts, stereoisomers, mixtures of stereoisomers, tautomers, hydrates, and/or solvates thereof. In any embodiment herein, it may be that the compound is administered daily for 6 weeks or more. In any embodiment herein, it may be that the compound is administered daily for 12 weeks or more. In any embodiment herein, it may be that the Friedreich's ataxia comprises one or more of muscle weakness, loss of coordination, vision impairment, hearing impairment, slurred speech, curvature of the spine, diabetes, and heart disorders. In any embodiment herein, it may be that the subject is human. In any embodiment herein, it may be that the compound is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

In an aspect, the present technology provides a compound of the present technology, or pharmaceutically acceptable salts, stereoisomers, mixtures of stereoisomers, tautomers, hydrates, and/or solvates thereof, for use in treating or preventing Friedreich's ataxia in a subject in need thereof. In any embodiment herein, it may be that the compound is effective to increase or maintain frataxin levels in a subject suspected of having Friedreich's ataxia. In any embodiment herein, it may be that the compound is effective to inhibit the reduction in frataxin levels in a subject suspected of having Friedreich's ataxia. In any embodiment herein, it may be that the compound is effective to treat one or more symptoms of Friedreich's ataxia selected from the group consisting of: muscle weakness, loss of coordination, vision impairment, hearing impairment, slurred speech, curvature of the spine, diabetes, and heart disorders. In any embodiment herein, it may be that the compound is effective when administered daily for 6 weeks or more. In any embodiment herein, it may be that the compound is effective when administered daily for 12 weeks or more.

In an aspect, the present technology provides a compound of the present technology, or pharmaceutically acceptable salts, stereoisomers, mixtures of stereoisomers, tautomers, hydrates, and/or solvates thereof, for use in increasing the levels of frataxin expression in a subject in need thereof. In any embodiment herein, it may be that the compound is effective when administered daily for 6 weeks or more. In any embodiment herein, it may be that the compound is effective when administered daily for 12 weeks or more.

In an aspect, the present technology provides a compound of the present technology, or pharmaceutically acceptable salts, stereoisomers, mixtures of stereoisomers, tautomers, hydrates, and/or solvates thereof, for use in treating Complex I deficiency in a subject in need thereof. In any embodiment herein, it may be that the compound is effective when administered daily for 6 weeks or more. In any embodiment herein, it may be that the compound is effective when administered daily for 12 weeks or more. In any embodiment herein, it may be that the compound is effective to increase intracellular adenosine triphosphate (ATP) levels in tissue in a subject diagnosed as having Friedreich's ataxia.

In an aspect, the present technology provides a compound of the present technology, or pharmaceutically acceptable salts, stereoisomers, mixtures of stereoisomers, tautomers, hydrates, and/or solvates thereof, for use in reducing or inhibiting lipoxygenase-15 activity in a mammalian subject having or suspected of having Friedreich's ataxia. In any embodiment herein, it may be that the compound is effective when administered daily for 6 weeks or more. In any embodiment herein, it may be that the compound is effective when administered daily for 12 weeks or more.

In an aspect, the present technology provides a compound of the present technology, or pharmaceutically acceptable salts, stereoisomers, mixtures of stereoisomers, tautomers, hydrates, and/or solvates thereof, for use in reducing or inhibiting ferroptosis in a mammalian subject having or suspected of having Friedreich's ataxia. In any embodiment herein, it may be that the compound is effective when administered daily for 6 weeks or more. In any embodiment herein, it may be that the compound is effective when administered daily for 12 weeks or more.

In an aspect, use of a composition in the preparation of a medicament for treating or preventing Friedreich's ataxia in a subject in need thereof is provided, wherein the composition comprises a therapeutically effective amount of a compound of the present technology, or pharmaceutically acceptable salts, stereoisomers, mixtures of stereoisomers, tautomers, hydrates, and/or solvates thereof. In any embodiment herein, it may be that the medicament is effective to increase or maintain frataxin levels in a subject suspected of having Friedreich's ataxia. In any embodiment herein, it may be that the medicament is effective to inhibit the reduction in frataxin levels in a subject suspected of having Friedreich's ataxia. In any embodiment herein, it may be that the medicament is effective to treat one or more symptoms of Friedreich's ataxia selected from the group consisting of: muscle weakness, loss of coordination, vision impairment, hearing impairment, slurred speech, curvature of the spine, diabetes, and heart disorders. In any embodiment herein, it may be that the medicament is effective when administered daily for 6 weeks or more. In any embodiment herein, it may be that the medicament is effective when administered daily for 12 weeks or more.

In an aspect, use of a composition in the preparation of a medicament for increasing the levels of frataxin expression in a mammalian subject compared to a normal control subject is provided, wherein the composition comprises a therapeutically effective amount of a compound of the present technology, or pharmaceutically acceptable salts, stereoisomers, mixtures of stereoisomers, tautomers, hydrates, and/or solvates thereof. In any embodiment herein, it may be that the medicament is effective when administered daily for 6 weeks or more. In any embodiment herein, it may be that the medicament is effective when administered daily for 12 weeks or more. In any embodiment herein, it may be that the medicament is effective to increase frataxin levels in a subject diagnosed as having Friedreich's ataxia.

In an aspect, use of a composition in the preparation of a medicament for treating Complex I deficiency in a mammalian subject compared to a normal control subject is provided, wherein the composition comprises a therapeutically effective amount of a compound of the present technology, or pharmaceutically acceptable salts, stereoisomers, mixtures of stereoisomers, tautomers, hydrates, and/or solvates thereof. In any embodiment herein, it may be that the medicament is effective when administered daily for 6 weeks or more. In any embodiment herein, it may be that the medicament is effective when administered daily for 12 weeks or more. In any embodiment herein, it may be that the medicament is effective to increase intracellular adenosine triphosphate (ATP) levels in tissue in a subject diagnosed as having Friedreich's ataxia.

In an aspect, use of a composition in the preparation of a medicament for reducing or inhibiting lipoxygenase-15 activity in a mammalian subject having or suspected of having Friedreich's ataxia is provided, wherein the composition comprises a therapeutically effective amount of a compound of the present technology, or pharmaceutically acceptable salts, stereoisomers, mixtures of stereoisomers, tautomers, hydrates, and/or solvates thereof. In any embodiment herein, it may be that the medicament is effective when administered daily for 6 weeks or more. In any embodiment herein, it may be that the medicament is effective when administered daily for 12 weeks or more.

In an aspect, use of a composition in the preparation of a medicament for reducing or inhibiting ferroptosis in a mammalian subject having or suspected of having Friedreich's ataxia is provided, wherein the composition comprises a therapeutically effective amount of a compound of the present technology, or pharmaceutically acceptable salts, stereoisomers, mixtures of stereoisomers, tautomers, hydrates, and/or solvates thereof. In any embodiment herein, it may be that wherein the medicament is effective when administered daily for 6 weeks or more. In any embodiment herein, it may be that the medicament is effective when administered daily for 12 weeks or more.

BRIEF DESCRIPTION OF THE DRAWINGS

FIG. 1B is an illustration of a continuation of the chemical scheme shown in FIG. 1A for the production of novel compositions disclosed herein, wherein a species of compound 216 (i.e., 216a) is the starting material for the production of compound 226a.

FIG. 2B is an illustration of a continuation of the chemical scheme shown in FIG. 2A for the production of novel compositions disclosed herein, wherein a species of compound 316 (i.e., 316a) is the starting material for the production of compound 326a.

DETAILED DESCRIPTION

I. Chemical Definitions

Figure 1A:
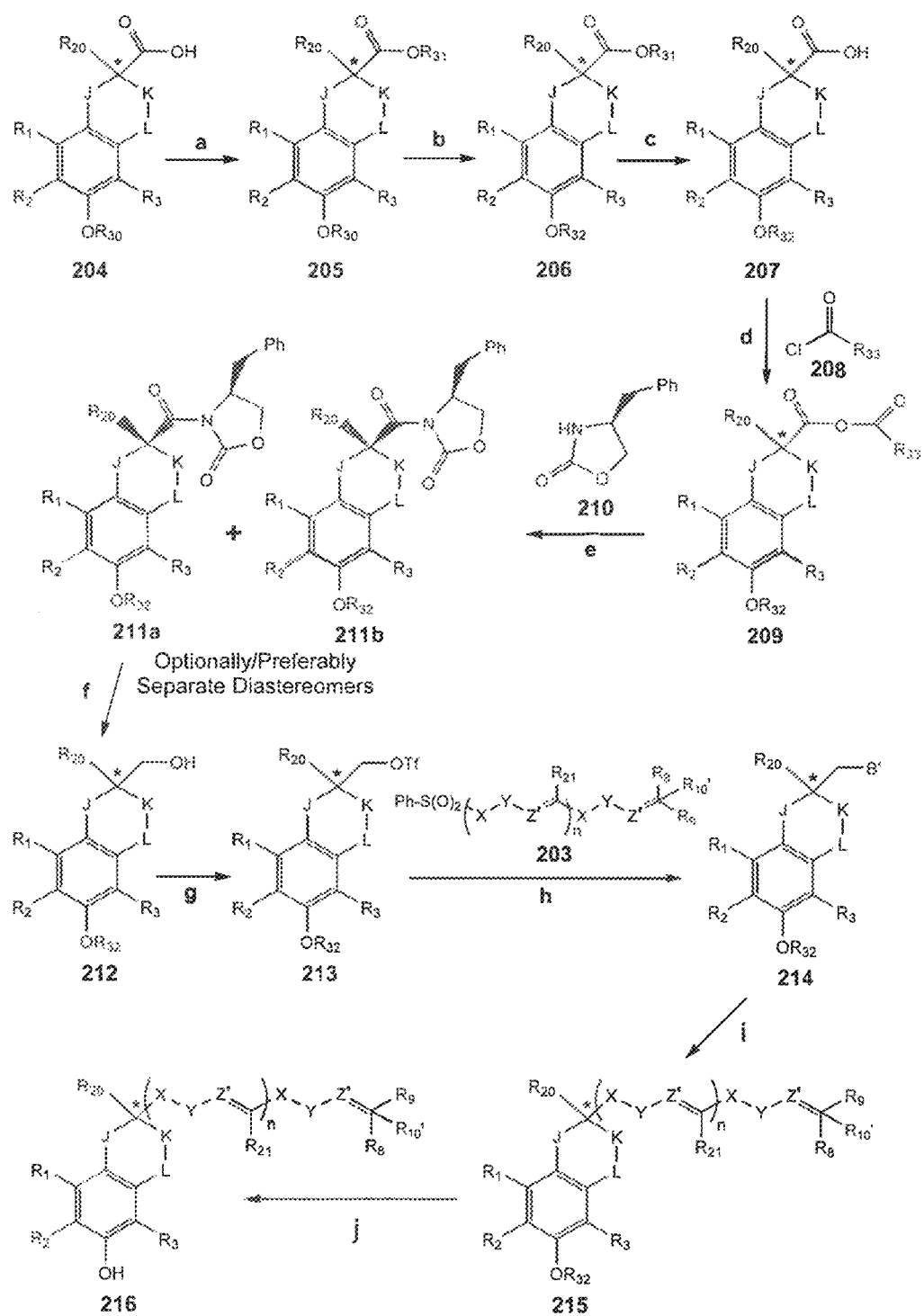
FIG. 1A an illustration of a partial chemical scheme for the production of novel compositions disclosed herein.

Definitions of specific functional groups and chemical terms are described in more detail below. The chemical elements are identified in accordance with the Periodic Table of the Elements, GAS version, Handbook of Chemistry and Physics, 7Sh Ed., inside cover. Additionally, general principles of organic chemistry, as well as specific functional moieties and reactivity, are described in Thomas Sorrell, Organic Chemistry, University Science Books, Sausalito, 1999; Smith and March, March's Advanced Organic Chemistry, 5th Edition, John Wiley & Sons, Inc., New York, 2001; Larock, Comprehensive Organic Transformations, VCH Publishers, Inc., New York, 1989; and Carruthers, Some Modern Methods of Organic Synthesis, 3rd Edition, Cambridge University Press, Cambridge, 1987.

The abbreviations used herein have their conventional meaning within the chemical and biological arts. The chemical structures and formulae set forth herein are intended to comply with the standard rules of chemical valency known in the chemical arts. When a range of values is listed, it is intended to encompass each value and subrange within the range. For example "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_5$, $C_3$-$C_4$, $C_4$-$C_6$, $C_4$-$C_5$, and $C_5$-$C_6$ alkyl. When a group or moiety is referred to as "substituted", one or more of the hydrogen atoms of the group has been replaced with a substituent. Possible "substituents" include, for example one or more: (i) deuterium (D), fluorine (F), chlorine ($C_1$), bromine (Br) or iodine (I) atoms (individually each of F, Cl, Br and I is a "halogen" and collectively F, Cl, Br and I are "halogens"); or (ii) methyl, ethyl, propyl, trichloromethyl, trifluoromethyl, carbonyl (i.e., C=O), nitrile (i.e., —C≡N), hydroxyl or protected hydroxyl (i.e., —OH or —OPG, wherein PG is a protecting group), alkoxy (i.e., —OR"), nitro (i.e., —$NO_2$) groups or amino (in protected or unprotected form, i.e., —$NH_2$ or —NHPG, wherein PG is a protecting group), each independently chosen for each possible position for substitution of a hydrogen atom. Other substituents are contemplated, such as azide, alkyl, aralkyl, alkenyl, alkynyl, cycloalkyl, alkoxy, nitro, sulfhydryl, imino, amido, phosphonate, phosphinate, carboxyl, silyl, ether, sulfonyl, sulfonamido, ketone, aldehyde, ester, heterocyclyl, aromatic or heteroaromatic moieties, fluoroalkyl (such as trifluoromethyl), cyano, or the like. A group or moiety that is not substituted is unsubstituted.

Certain compounds of the present application can exist in unsolvated forms as well as solvated forms, including hydrated forms. Solvated forms can exist, for example, because it is difficult or impossible to remove all the solvent from the compound post synthesis. In general, the solvated forms are equivalent to unsolvated forms and are encompassed within the scope of the present application. Certain compounds of the present application may exist in multiple crystalline or amorphous forms. Certain compounds of the present application may exist in various tautomeric forms. Certain compounds of the present application may exist in various salt forms. In general, all physical forms are equivalent for the uses contemplated by the present application and are intended to be within the scope of the inventive compositions disclosed herein.

As used herein "alkoxy" is one example of a heteroalkyl group and refers to an alkyl, cycloalkyl, heteroalkyl or cycloheteroalkyl group linked to a terminal oxygen of general formula:

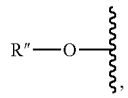

wherein R" is the alkyl, cycloalkyl, heteroalkyl or cycloheteroalkyl group and ～ identifies the bond that forms the point of attachment of the alkoxy group to another compound or moiety. Each instance of an alkoxy group may be independently optionally unsubstituted (an "unsubstituted alkoxy") or substituted (a "substituted alkoxy") with one or more substituents. For example, the substituent can be a halogen such as fluorine. A few non-limiting examples of fluorine substituted alkoxy groups used herein include: fluoromethoxy ("—$OCH_2F$"), difluoromethoxy ("—$OCHF_2$") and trifluoromethoxy ("—$OCF_3$").

As used herein, "alkyl" refers to a radical of a straight-chain or branched saturated hydrocarbon group having from 1 to 20 carbon atoms ("$C_1$-$C_{20}$ alkyl"). In some embodiments, an alkyl group has 1 to 12 carbon atoms ("$C_1$-$C_{12}$ alkyl"). In some embodiments, an alkyl group has 1 to 10 carbon atoms ("$C_1$-$C_{10}$ alkyl"). In some embodiments, an alkyl group has 1 to 8 carbon atoms ("$C_1$-$C_8$ alkyl"). In some embodiments, an alkyl group has 1 to 6 carbon atoms ("$C_1$-$C_6$ alkyl"). In some embodiments, an alkyl group has 1 to 5 carbon atoms ("$C_1$-$C_5$ alkyl"). In some embodiments, an alkyl group has 1 to 4 carbon atoms ("$C_1$-$C_4$ alkyl"). In some embodiments, an alkyl group has 1 to 3 carbon atoms ("$C_1$-$C_3$ alkyl"). In some embodiments, an alkyl group has 1 to 2 carbon atoms ("$C_1$-$C_2$ alkyl"). In some embodiments, an alkyl group has 1 carbon atom ("$C_1$ alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of higher order alkyl groups (e.g. $C_1$-$C_{12}$) include n-heptyl ($C_7$), n-octyl ($C_5$), nonyl ($C_9$), decyl ($C_{10}$), undecyl ($C_{11}$) and dodecyl ($C_{12}$) and the like. Each instance of an alkyl group may be independently optionally unsubstituted (an "unsubstituted alkyl") or substituted (a "substituted alkyl") with one or more substituents; e.g., for instance from 1 to 5 substituents, 1 to 4 substituents, 1 to 3 substituents, 1 to 2 substituents or just 1 substituent. For example, the substituent can be a halogen such as fluorine. A few non-limiting examples of substituted alkyl groups used herein include: fluoromethyl ("—$CH_2F$"), difluoromethyl ("—$CHF_2$") and trifluoromethyl ("—$CF_3$").

As used herein, "alkenyl" refers to a radical of a straight-chain or branched hydrocarbon group having from 2 to 12 carbon atoms, one or more carbon-carbon double bonds, and no triple bonds ("$C_2$-$C_{12}$ alkenyl"). In some embodiments, an alkenyl group has 1-10 carbon atoms ("$C_2$-$C_{10}$ alkenyl"). In some embodiments, an alkenyl group has 2 to 8 carbon atoms ("$C_2$-$C_8$ alkenyl"). In some embodiments, an alkenyl group has 2 to 6 carbon atoms ("$C_2$-$C_6$ alkenyl"). In some embodiments, an alkenyl group has 2 to 5 carbon atoms ("$C_2$-$C_5$ alkenyl"). In some embodiments, an alkenyl group has 2 to 4 carbon atoms ("$C_2$-$C_4$ alkenyl"). In some embodiments, an alkenyl group has 2 to 3 carbon atoms ("$C_2$-$C_3$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_2$-$C_4$ alkenyl groups as well as pentenyl ($C_5$), pentadienyl ($C_5$), hexenyl ($C_6$), and the like. Additional examples of alkenyl include heptenyl ($C_1$), octenyl ($C_8$), octatrienyl ($C_8$), and the like. Each instance of an alkenyl group may be independently optionally unsubstituted (an "unsubstituted alkenyl") or substituted (a "substituted alkenyl") with one or more substituents; e.g., for instance from 1 to 5 substituents, 1 to 4 substituents, 1 to 3 substituents, 1 to 2 substituents or just 1 substituent. For example, the substituent can be a halogen such as fluorine.

As used herein, the term "alkynyl" refers to a radical of a straight-chain or branched hydrocarbon group having from 2 to 12 carbon atoms, one or more carbon-carbon triple bonds ("$C_2$-$C_{12}$ alkynyl"). In some embodiments, an alkynyl group has 2 to 10 carbon atoms ("$C_2$-$C_{10}$ alkynyl"). In some embodiments, an alkynyl group has 2 to 8 carbon atoms ("$C_2$-$C_8$ alkynyl"). In some embodiments, an alkynyl group has 2 to 6 carbon atoms ("$C_2$-$C_6$ alkynyl"). In some embodiments, an alkynyl group has 2 to 5 carbon atoms ("$C_2$-$C_5$ alkynyl"). In some embodiments, an alkynyl group has 2 to 4 carbon atoms ("$C_2$-$C_4$ alkynyl"). In some embodiments, an alkynyl group has 2 to 3 carbon atoms ("$C_2$-$C_3$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_2$-$C_4$ alkynyl groups include ethynyl ($C_2$), 1-propynyl ($C_3$), 2-propynyl ($C_3$), 1-butynyl ($C_4$), 2-butynyl ($C_4$), and the like. Each instance of an alkynyl group may be independently optionally unsubstituted (an "unsubstituted alkynyl") or substituted (a "substituted alkynyl") with one or more substituents; e.g., for instance from 1 to 5 substituents, 1 to 4 substituents, 1 to 3 substituents, 1 to 2 substituents or just 1 substituent. For example, the substituent can be a halogen such as fluorine.

As used herein, "aprotic solvent" refers to an organic solvent that has no OH or N—H bonds. Non-limiting examples of aprotic solvents include: acetonitrile (abbreviated as ACN or MeCN), tetrahydrofuran (THF), dioxane, dichloromethane (DCM), N,N-dimethylformamide (DMF) and dimethylsulfoxide (DMSO).

As used herein, "aryl" (sometimes abbreviated as "Ar") refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include phenyl, naphthyl, indenyl, and tetrahydronaphthyl. Each instance of an aryl group may be independently optionally unsubstituted (an "unsubstituted aryl") or substituted, (a "substituted aryl") with one or more substituents; e.g., for instance from 1 to 5 substituents, 1 to 4 substituents, 1 to 3 substituents, 1 to 2 substituents or just 1 substituent. For example, the substituent can be a halogen such as fluorine or chlorine. In some embodiments, the aromatic ring may be substituted at one or more ring positions with one or more substituents, such as halogen, azide, alkyl, aralkyl, alkenyl, alkynyl, cycloalkyl, hydroxyl or protected hydroxyl (i.e., —OH or —OPG, wherein PG is a protecting group), alkoxy (i.e., —OR"), nitro, amino (in protected or unprotected form, i.e., —$NH_2$ or —NHPG, wherein PG is a protecting group), sulfhydryl, imino, amido, phosphonate, phosphinate, carbonyl, carboxyl, silyl, ether, sulfonyl, sulfonamido, ketone, aldehyde, ester, heterocyclyl, aromatic or heteroaromatic moieties, fluoroalkyl (such as trifluoromethyl, difluoromethyl and trifluoromethyl), cyano, or the like. An aryl group is sometimes referred to as an aromatic group (or aromatic moiety).

As used herein, the term "arylalkyl" refers to a radical of an aryl or heteroaryl group (which aryl or heteroaryl group may be substituted or unsubstituted) that is attached to a ($C_1$-$C_{20}$)alkyl group (which alkyl group may be substituted or unsubstituted) via an alkylene linker. The term "arylalkyl" refers to a group that may be substituted or unsubstituted. The term "arylalkyl" is also intended to refer to those compounds wherein one or more methylene groups in the alkyl chain of the arylalkyl group can be replaced by a heteroatom such as O, N, P, Si, and S, and wherein the nitrogen, phosphorus and sulfur atoms may optionally be oxidized and the nitrogen heteroatom may optionally be quaternized with one or more appended alkyl and/or aryl groups. Arylalkyl groups include for example, benzyl (in substituted or unsubstituted form).

As used herein, the term "arylheteroalkyl" refers to a radical of aryl group (which aryl group may be substituted or unsubstituted) linked to a non-cyclic stable straight or branched chain, or combinations thereof, alkyl group including at least one carbon atom and at least one heteroatom selected from the group consisting of O, N, P, Si, and S, and wherein the nitrogen, phosphorus and sulfur atoms may optionally be oxidized, and the nitrogen heteroatom may optionally be quaternized with one or more appended alkyl and/or aryl groups.

As used herein, the term "benzyl group" refers to a group of formula:

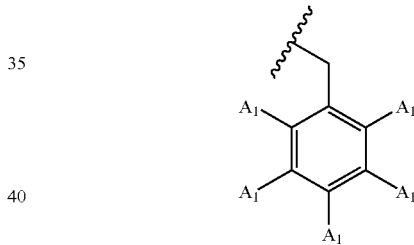

wherein each $A_1$ is independently H, D, F, Cl, Br, I, —$CH_3$, —$OCH_3$, —$CH_2CH_3$, —$OCH_2CH_3$, chloromethyl, dichloromethyl, trichloromethyl, fluoromethyl, difluoromethyl, trifluoromethyl, nitrile (—C≡N), hydroxyl/phenol (i.e., —OH or —OPG, wherein PG is a protecting group) or nitro (—$NO_2$). If each $A_1$ is H, then the benzyl group is unsubstituted. If at least one $A_1$ is not H, then the benzyl group is substituted.

As used herein, the term "carbocyclic ring" or "carbocycle" refers to a ring formed by linked carbon atoms. A carbocyclic ring may be independently optionally unsubstituted (e.g. an "unsubstituted cycloalkyl") or substituted (e.g. a "substituted cycloalkyl") with one or more substituents. For example, the substituent can be a halogen such as fluorine. A cycloalkyl group comprises a carbocyclic ring. An aryl group such as benzene comprises a carbocyclic ring. A carbocyclic ring can comprise 3 carbon atoms (a "$C_3$ carbocycle"), 4 carbon atoms (a "$C_4$ carbocycle"), 5, carbon atoms (a "$C_5$ carbocycle"), 6 carbon atoms (a "$C_6$ carbocycle"), 7 carbon atoms (a "$C_7$ carbocycle") or 8 carbon atoms (a "$C_8$ carbocycle"). A carbocyclic ring can be aromatic and therefore comprise 6 carbon atoms (a "$C_6$ carbocycle"), 10 carbon atoms (a "$C_{10}$ carbocycle") or 14 carbon atoms (a "$C_{14}$ carbocycle").

As used herein, "chiral chromatography" refers to the use of a chiral column (i.e. chiral stationary phase) for the separation of racemic, and sometimes diastereomeric, mixtures to obtain an optically enriched or optically pure product from the chromatographic separation.

As used herein, "cycloalkyl" refers to a radical of a non-aromatic cyclic hydrocarbon group having from 3 to 12 ring carbon atoms ("$C_3$-$C_{12}$ cycloalkyl"). In some embodiments, a cycloalkyl group has 3 to 10 ring carbon atoms ("$C_3$-$C_{10}$ cycloalkyl"). In some embodiments, a cycloalkyl group has 3 to 8 ring carbon atoms ("$C_3$-$C_8$ cycloalkyl"). In some embodiments, a cycloalkyl group has 3 to 6 ring carbon atoms ("$C_3$-$C_6$ cycloalkyl"). In some embodiments, a cycloalkyl group has 4 to 6 ring carbon atoms ("$C_4$-$C_6$ cycloalkyl"). In some embodiments, a cycloalkyl group has 5 to 6 ring carbon atoms ("$C_5$-$C_6$ cycloalkyl"). In some embodiments, a cycloalkyl group has 5 to 7 ring carbon atoms ("$C_5$-$C_7$ cycloalkyl"). In some embodiments, a cycloalkyl group has 6 to 7 ring carbon atoms ("$C_6$-$C_7$ cycloalkyl"). A cycloalkyl group maybe described as, e.g., a $C_4$-$C_7$-membered cycloalkyl, wherein the term "membered" refers to the non-hydrogen ring atoms within the moiety. Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_7$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), and cycloheptatrienyl ($C_7$), bicyclo[2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_7$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. Non-limiting examples of bicyclic cycloalkyl groups include 1-ethylbicyclo[1.1.1]pentane, 1-ethylbicyclo[2.2.2]octane and (3r,5r,7r)-1-ethyladamantane. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally unsubstituted (an "unsubstituted cycloalkyl") or substituted (a "substituted cycloalkyl") with one or more substituents. For example, the substituent can be a halogen such as fluorine.

As used herein, "cycloheteroalkyl" refers to a radical of a cycloalkyl group comprising at least one heteroatom (wherein the heteroatom is substituted in the ring for a carbon atom) selected from the group consisting of O, N, P, Si, and S, and wherein the nitrogen, phosphorus and sulfur atoms may optionally be oxidized, and the nitrogen heteroatom may optionally be quaternized with appended alkyl and/or aryl groups. The heteroatom(s) O, N, P, S, and Si may be placed at any position of the cycloheteroalkyl group but generally each heteroatom is linked to at least two carbon atoms of the cycloalkyl group.

As used herein, the term "heteroalkyl" refers to a radical of a non-cyclic stable straight or branched chain, or combinations thereof, including at least one carbon atom and at least one heteroatom selected from the group consisting of O, N, P, Si, and S, and wherein the nitrogen, phosphorus and sulfur atoms may optionally be oxidized, and the nitrogen heteroatom may optionally be quaternized with appended alkyl and/or aryl groups. The heteroatom(s) O, N, P, S, and Si may be placed at any position of the heteroalkyl group but generally each heteroatom is linked to at least two carbon atoms of the radical group. Exemplary heteroalkyl groups include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —$CH_2$—$CH_2$—P(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, and —O—$CH_2$—$CH_3$. Up to two heteroatoms may be consecutive, such as, for example, —$CH_2$—NH—$OCH_3$, —$CH_2CH_2$—S—S—$CH_2CH_3$ and —$CH_2$—O—Si($CH_3$)$_3$. Each instance of heteroalkyl group may be independently optionally unsubstituted (an "unsubstituted heteroalkyl") or substituted (a "substituted heteroalkyl") with one or more substituents; e.g., for instance from 1 to 5 substituents, 1 to 4 substituents, 1 to 3 substituents, 1 to 2 substituents or just 1 substituent. For example, the substituent can be a halogen such as fluorine.

As used herein, the term "heteroaryl" refers to a radical of an aromatic heterocycle that comprises 1, 2, 3 or 4 heteroatoms selected, independently of the others, from nitrogen, sulfur and oxygen. As used herein, the term "heteroaryl" refers to a group that may be substituted or unsubstituted. For example, the substituent can be a halogen such as fluorine. A heteroaryl may be fused to one or two rings, such as a cycloalkyl, an aryl, or a second heteroaryl ring. The point of attachment of a heteroaryl to a molecule may be on the heteroaryl, cycloalkyl, heterocycloalkyl or aryl ring, and the heteroaryl group may be attached through carbon or a heteroatom. Examples of heteroaryl groups include imidazolyl, furyl, pyrrolyl, thienyl, thiazolyl, isoxazolyl, isothiazolyl, thiadiazolyl, oxadiazolyl, pyridinyl, pyrimidyl, pyrazinyl, pyridazinyl, quinolyl, isoquinolinyl, indazolyl, benzoxazolyl, benzisooxazolyl, benzofuryl, benzothiazolyl, indolizinyl, imidazopyridinyl, pyrazolyl, triazolyl, oxazolyl, tetrazolyl, benzimidazolyl, benzoisothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidyl, pyrazolo[3,4]pyrimidyl or benzo(b)thienyl, each of which can be optionally substituted. The aromatic heterocycle may be substituted at one or more ring positions with one or more substituents, such as halogen, azide, alkyl, aralkyl, alkenyl, alkynyl, cycloalkyl, hydroxyl or protected hydroxyl (i.e., —OH or —OPG, wherein PG is a protecting group), alkoxy (i.e., —OR"), nitro, amino (in protected or unprotected form, i.e., —$NH_2$ or —NHPG, wherein PG is a protecting group), sulfhydryl, imino, amido, phosphonate, phosphinate, carbonyl, carboxyl, silyl, ether, sulfonyl, sulfonamido, ketone, aldehyde, ester, heterocyclyl, aromatic or heteroaromatic moieties, fluoroalkyl (such as trifluoromethyl), cyano, or the like. A heteroaryl group is sometimes referred to as a heteroaromatic group (or moiety).

As used herein, the term "heterocyclic ring" or "heterocycle" refers to a ring of atoms of at least two different elements, one of which is carbon. Additional reference is made to: Oxford Dictionary of Biochemistry and Molecular Biology, Oxford University Press, Oxford, 1997 as evidence that the term "heterocyclic ring" is a term well-established in field of organic chemistry. A heterocyclic ring can be aliphatic (e.g. tetrahydrofuran) or aromatic (e.g. pyridine).

As used herein, the term "hydrate" refers to a compound which is associated with water. The number of the water molecules contained in a hydrate of a compound may be (or may not be) in a definite ratio to the number of the compound molecules in the hydrate.

As used herein, the term "pharmaceutically acceptable salt" refers to a salt of a therapeutically active compound that can be prepared with relatively nontoxic acids or bases, depending on the particular substituents found on the compounds described herein. When compounds of the present application contain relatively acidic functionalities, base addition salts can be obtained by contacting the neutral form of such compounds with a sufficient amount of the desired base, either neat or in a suitable inert solvent. When compounds of the present application contain relatively basic functionalities, acid addition salts can be obtained by contacting the neutral form of such compounds with a sufficient amount of the desired acid, either neat or in a suitable inert solvent. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-methylmorpholine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine ($NEt_3$), trimethylamine, tripropylamine, tromethamine and the like, such as where the salt includes the protonated form of the organic base (e.g., $[HNEt_3]+$). Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucuronic, mandelic, mucic, nicotinic, orotic, pamoic, pantothenic, sulfonic acids (e.g., benzenesulfonic, camphorsulfonic, edisylic, ethanesulfonic, isethionic, methanesulfonic, naphthalenesulfonic, naphthalene-1,5-disulfonic, naphthalene-2,6-disulfonic and p-toluenesulfonic acids (PTSA)), xinafoic acid, and the like. In some embodiments, the pharmaceutically acceptable counterion is selected from the group consisting of acetate, benzoate, besylate, bromide, camphorsulfonate, chloride, chlorotheophyllinate, citrate, ethanedisulfonate, fumarate, gluceptate, gluconate, glucoronate, hippurate, iodide, isethionate, lactate, lactobionate, laurylsulfate, malate, maleate, mesylate, methylsulfate, naphthoate, sapsylate, nitrate, octadecanoate, oleate, oxalate, pamoate, phosphate, polygalacturonate, succinate, sulfate, sulfosalicylate, tartrate, tosylate, and trifluoroacetate. In some embodiments, the salt is a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt, a maleate salt, a trifluoroacetate salt, a hydrochloride salt, or a tosylate salt. Also included are salts of amino acids such as arginate and the like, and salts of organic acids such as glucuronic or galactunoric acids and the like (see, e.g., Berge et al, Journal of Pharmaceutical Science 66: 1-19 (1977)). Certain specific compounds of the present application contain both basic and acidic functionalities that allow the compounds to be converted into either base or acid addition salts or exist in zwitterionic form. These salts may be prepared by methods known to those skilled in the art. Other pharmaceutically acceptable carriers known to those of skill in the art are suitable for the inventive compositions disclosed herein.

As used herein, the term "protecting group" or "PG" refers to a chemical group that is reacted with, and bound to (at least for some period of time), a functional group (e.g. —OH, —$NH_2$ or —SH) in a molecule to prevent said functional group from participating in reactions of the molecule but which chemical group can subsequently be removed to thereby regenerate said functional group. Additional reference is made to: Oxford Dictionary of Biochemistry and Molecular Biology, Oxford University Press, Oxford, 1997 as evidence that protecting group is a term well-established in field of organic chemistry. Further reference is made to Greene's Protective Groups in Organic Synthesis, Fourth Edition, 2007, John Wiley & Sons, Inc. which is known as a primary reference for researching the suitability of various protecting groups (e.g., protecting groups (i.e., PG) for hydroxyl or amine groups) for in organic synthesis reactions.

As used herein, the term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like.

As used herein, the term "tautomer" refers to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Tautomeric forms may be relevant to the attainment of the optimal chemical reactivity and biological activity of a compound of interest.

II. Other Definitions

It is to be appreciated that certain aspects, modes, embodiments, variations and features of the technology are described below in various levels of detail in order to provide a substantial understanding of the present application. The definitions of certain terms as used in this specification are provided below. Unless defined otherwise, all technical and scientific terms used herein generally have the same meaning as commonly understood by one of ordinary skill in the art to which this technology belongs.

As used in this specification and the appended claims, the singular forms "a", "an" and "the" include plural references unless the content clearly dictates otherwise. For example, reference to "a cell" includes a combination of two or more cells, and the like.

As used herein, the "administering" or the "administration" of an agent (i.e. therapeutic agent) or drug to a subject includes any route of introducing or delivering to a subject a compound to perform its intended function. Administration can be carried out by any suitable route, such as oral administration. Administration may be carried out subcutaneously. Alternatively, administration may be carried out, topically, intranasally, systemically, intravenously, intraperitoneally, intradermally, intraocularly, ophthalmically, intrathecally, intracerebroventricularly, iontophoretically, transmucosally, intravitreally, or intramuscularly. Administration includes self-administration and the administration by another.

As used herein the terms "carrier" and "pharmaceutically acceptable carrier" refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in *Remington's Pharmaceutical Sciences* by E. W. Martin, herein incorporated by reference in its entirety.

As used herein, the phrase "delaying the onset of" refers to, in a statistical sample, postponing, hindering, or causing one or more symptoms of a disorder, symptom, condition or indication to occur more slowly than normal in a treated sample relative to an untreated control sample.

As used herein, the term "effective amount" refers to a quantity sufficient to achieve a desired therapeutic and/or prophylactic effect, e.g., an amount that reduces, ameliorates, prevents or delays the onset of the physiological symptoms of mitochondrial disease, such as Friedreich's ataxia. In the context of therapeutic or prophylactic applications, in some embodiments, the amount of a composition administered to the subject will depend on the type and severity of the disease and on the characteristics of the individual, such as general health, age, sex, body weight and tolerance to drugs. In some embodiments, it will also depend on the degree, severity and type of disease. The skilled artisan will be able to determine appropriate dosages depending on these and other factors. The compositions can also be administered in combination with one or more additional therapeutic compounds. In the methods described herein, therapeutic compounds, or pharmaceutically acceptable salts, stereoisomers, mixtures of stereoisomers, tautomers, hydrates, and/or solvates thereof, may be administered to a subject having one or more signs, symptoms, or risk factors of mitochondrial disease such as Friedreich's ataxia; e.g., muscle weakness, especially in the arms and legs, loss of coordination, motor control impairment, vision impairment, hearing impairment, slurred speech, curvature of the spine, diabetes, heart and/or ophthalmic conditions or disorders. For example, a "therapeutically effective amount" of therapeutic compound includes levels at which the presence, frequency, or severity of one or more signs, symptoms, or risk factors of mitochondrial disease, for example Friedreich's ataxia, are reduced or eliminated. In some embodiments, a therapeutically effective amount reduces or ameliorates the physiological effects of a mitochondrial disease (e.g. Friedreich's ataxia), and/or the risk factors of Friedreich's ataxia, and/or delays the progression or onset of a mitochondrial disease (e.g. Friedreich's ataxia).

As used herein, "inhibit" or "inhibiting" means reduce by an objectively measurable amount or degree compared to control. In one embodiment, inhibit or inhibiting means reduce by at least a statistically significant amount compared to control. In one embodiment, inhibit or inhibiting means reduce by at least 5 percent compared to control. In various individual embodiments, inhibit or inhibiting means reduce by at least 2, 3, 4, 5, 10, 15, 20, 25, 30, 33, 40, 50, 60, 67, 70, 75, 80, 90, 95, or 99 percent compared to control.

As used herein, the term "simultaneous" therapeutic use refers to the administration of at least two active ingredients by the same route and at the same time or at substantially the same time.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this definition.

As used herein, a "subject" refers to a living animal. In various embodiments, a subject is a mammal. In various embodiments, a subject is a non-human mammal, including, without limitation, a mouse, rat, hamster, guinea pig, rabbit, sheep, goat, cat, dog, pig, horse, cow, or non-human primate. In certain embodiments, the subject is a human.

As used herein, the terms "treating" or "treatment" or "alleviation" refers to therapeutic treatment, wherein the object is to reduce, alleviate or slow down (lessen) the targeted pathologic condition or disorder. By way of example, but not by way of limitation, a subject is successfully "treated" for a mitochondrial disease (e.g. Friedreich's ataxia) if, after receiving an effective amount of the compounds of the present application (including a pharmaceutically acceptable salt (such as hydrochloride, acetate, citrate, trifluoroacetate, benzoate, oxalate or mesylate salt), stereoisomers, mixtures of stereoisomers, tautomers, hydrates, and/or solvates thereof) according to the methods described herein, the subject shows observable and/or measurable reduction in or absence of one or more signs and symptoms of a mitochondrial disease (e.g. Friedreich's ataxia), such as but not limited to, e.g., muscle weakness, especially in the arms and legs, loss of coordination, motor control impairment, vision impairment, hearing impairment, slurred speech, curvature of the spine, diabetes, heart or ophthalmic conditions or disorders. It is also to be appreciated that the various modes of treatment of medical conditions as described are intended to mean "substantial," which includes total but also less than total treatment, and wherein some biologically or medically relevant result is achieved. Treating Friedreich's ataxia, as used herein, also refers to treating the signs and symptoms related to reduced frataxin activity or frataxin expression levels characteristic of Friedreich's ataxia.

As used herein, "prevention" or "preventing" of a disease or condition, e.g., a mitochondrial disease such as Friedreich's ataxia refers to results that, in a statistical sample, exhibit a reduction in the occurrence of the disorder or condition in the treated sample relative to an untreated control sample, or exhibit a delay in the onset of one or more symptoms of the disorder or condition relative to the untreated control sample. Such prevention is sometimes referred to as a prophylactic treatment. As used herein, preventing mitochondrial disease (e.g. Friedreich's ataxia)

includes preventing or delaying the onset of, preventing, delaying, or slowing the progression or advancement of mitochondrial disease (e.g. Friedreich's ataxia). As used herein, prevention of Friedreich's ataxia also includes preventing a recurrence of one or more signs or symptoms of Friedreich's ataxia.

III. Chiral/Stereochemistry Considerations

Compounds described herein can comprise one or more asymmetric centers, and thus can exist in various isomeric forms, e.g., enantiomers and/or diastereomers (i.e., stereoisomers). Chiral centers in illustrated structures (including the claims) may be identified herein by use of an asterisk (*). For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high-pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, Tables of Resolving Agents and Optical Resolutions p. 268 (E. L. Eliel, Ed., Univ. of Notre Dame Press, Notre Dame, IN 1972). The disclosure of the present application additionally encompasses compounds described herein as individual isomers substantially free of other isomers, and alternatively, as mixtures of various isomers.

As used herein, a pure enantiomeric compound is substantially free from other enantiomers or stereoisomers of the compound (i.e., in enantiomeric excess); as purity is a relative term in the sense that it is exceedingly difficult to achieve 100% purity. In other words, an "S" form of the compound is substantially free from the "R" form of the compound and is, thus, in enantiomeric excess of the "R" form. With respect to amino acids (which are more commonly described in terms of "D" and "L" enantiomer, it is to be understood that for a "D"-amino acid the configuration is "R" and for an "L"-amino acid, the configuration is "S". In some embodiments, 'substantially free', refers to: (i) an aliquot of an "R" form compound that contains less than 2% "S" form; or (ii) an aliquot of an "S" form compound that contains less than 2% "R" form. The term "enantiomerically pure" or "pure enantiomer" denotes that the compound comprises more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the particularly identified enantiomer (e.g. as compared with the other enantiomer). In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure "R" form compound can comprise, for example, about 90% excipient and about 10% enantiomerically pure "R" form compound. In certain embodiments, the enantiomerically pure "R" form compound in such compositions can, for example, comprise, at least about 95% by weight "R" form compound and at most about 5% by weight "S" form compound, by total weight of the compound. For example, a pharmaceutical composition comprising enantiomerically pure "S" form compound can comprise, for example, about 90% excipient and about 10% enantiomerically pure "S" form compound. In certain embodiments, the enantiomerically pure "S" form compound in such compositions can, for example, comprise, at least about 95% by weight "S" form compound and at most about 5% by weight "R" form compound, by total weight of the enantiomers of the compound. In certain embodiments, the active ingredient can be formulated with little or no excipient or carrier.

IV. Pharmaceutical Compositions, Routes of Administration, and Dosing

In certain embodiments, the present application is directed to a pharmaceutical composition. In some embodiments, the composition comprises a therapeutic compound (i.e. agent) and a pharmaceutically acceptable carrier. In certain embodiments, the pharmaceutical composition comprises a plurality of compounds and a pharmaceutically acceptable carrier. The pharmaceutical composition can be a medicament.

In certain embodiments, a pharmaceutical composition further comprises at least one additional therapeutic agent other than a compound of the present application. The at least one additional therapeutic agent can be an agent useful in the treatment of mitochondrial disease, such as Friedreich's ataxia.

Pharmaceutical compositions can be prepared by combining one or more compounds of the present application with a pharmaceutically acceptable carrier and, optionally, one or more additional therapeutic agents.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and mode of administration, an effective prophylactic (i.e. preventative) or therapeutic treatment regimen can be planned which does not cause substantial unwanted toxicity and yet is effective to remedy the condition or disease of a particular subject. The effective amount for any particular indication can vary depending on such factors as the disease or condition being treated, the particular compound of the present application being administered, the size of the subject, or the severity of the disease or condition. The effective amount may be determined during pre-clinical trials and clinical trials by methods familiar to physicians and clinicians. One of ordinary skill in the art can empirically determine the effective amount of a particular compound of the present application and/or other therapeutic agent without necessitating undue experimentation. A maximum dose may be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein. A dose can be administered by oneself, by another or by way of a device (e.g. a pump).

Compounds for use in therapy or prevention can be tested in suitable animal model systems. Similarly, for in vivo testing, any of the animal model system known in the art can be used prior to administration to human subjects. Suitable animal model systems include, but are not limited to, rats, mice, chicken, cows, monkeys, rabbits, and the like, prior to testing in human subjects.

A therapeutic compound and optionally other therapeutic agents may be administered per se (neat) or in the form of a pharmaceutically acceptable salt. When used in medicine, the salts should be pharmaceutically acceptable, but non-pharmaceutically acceptable salts may conveniently be used to prepare pharmaceutically acceptable salts thereof.

Pharmaceutical compositions of the present application contain an effective amount of a therapeutic compound as described herein and may optionally be disbursed in a pharmaceutically acceptable carrier. The components of the pharmaceutical compositions also are capable of being commingled with the compounds of the present application, and with each other, in a manner such that there is no interaction which would substantially impair the desired pharmaceutical efficiency.

Dosage, toxicity and therapeutic efficacy of any therapeutic compounds, compositions (e.g. formulations or medicaments), other therapeutic agents, or mixtures thereof can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

In some embodiments, an effective amount of a therapeutic compound disclosed herein sufficient for achieving a therapeutic or prophylactic effect, can range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In some embodiments, a single dosage of a therapeutic compound disclosed herein ranges from 0.001-10,000 micrograms per kg body weight. In some embodiments, a therapeutic compound disclosed herein dissolved or suspended in a carrier range from 0.2 to 2000 micrograms per delivered milliliter.

An exemplary treatment regime can entail administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regimen.

In some embodiments, a therapeutically effective amount of a therapeutic compound disclosed herein may be defined as a concentration of compound existing at the target tissue of $10^{-12}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, such as by single daily or weekly administration, but also including continuous administration (e.g., oral, systemic, topical, subcutaneous, parenteral infusion or transdermal application).

In some embodiments, intravenous or subcutaneous administration of a therapeutic compound may typically be from 0.01 μg/kg/day to 20 mg/kg/day. In some embodiments, intravenous or subcutaneous administration of a therapeutic compound may typically be from 0.01 μg/kg/day to 100 μg/kg/day. In some embodiments, intravenous or subcutaneous administration of a therapeutic compound may typically be from 0.1 μg/kg/day to 1 mg/kg/day. In some embodiments, intravenous or subcutaneous administration of a therapeutic compound may typically be from 10 μg/kg/day to 2 mg/kg/day. In some embodiments, intravenous or subcutaneous administration of a therapeutic compound may typically be from 500 μg/kg/day to 5 mg/kg/day. In some embodiments, intravenous or subcutaneous administration of a therapeutic compound may typically be from 1 mg/kg/day to 20 mg/kg/day. In some embodiments, intravenous or subcutaneous administration of a therapeutic compound may typically be from 1 mg/kg/day to 10 mg/kg/day.

Generally, daily oral doses of a compound will be, for human subjects, from about 0.01 micrograms/kg per day to 100 milligrams/kg per day. It is expected that oral doses in the range of 0.01 to 50 milligrams/kg, in one or more administrations per day, will yield therapeutic results. Dosage may be adjusted appropriately to achieve desired drug levels, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of the compound.

For use in therapy, an effective amount of the compound can be administered to a subject by any mode that delivers the compound to the desired surface. Administering a pharmaceutical composition may be accomplished by any means known to the skilled artisan. Routes of administration include but are not limited to oral, topical, intranasal, systemic, intravenous, subcutaneous, intraperitoneal, intradermal, intraocular, ophthalmic, intrathecal, intracerebroventricular, iontophoretic, transmucosal, intravitreal, or intramuscular administration. Administration includes self-administration, the administration by another and administration by a device.

A therapeutic compound disclosed herein can be delivered to the subject in a formulation or medicament (i.e. a pharmaceutical composition). Formulations and medicaments can be prepared by, for example, dissolving or suspending a therapeutic compound disclosed herein in water or a carrier (i.e. a pharmaceutically acceptable carrier). For example, the formulations and medicaments of the present application can be administered in pharmaceutically acceptable solutions, which may routinely contain pharmaceutically acceptable concentrations of salt, buffering agents, preservatives, compatible carriers, adjuvants, and optionally other therapeutic ingredients.

The pharmaceutical compositions (e.g. a formulation or medicament) can include a carrier, which can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Solutions or suspensions (e.g. a formulation or medicament) used for parenteral, intradermal, subcutaneous or intraocular application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided alone or in a kit containing all necessary equipment (e.g., vials of drug, vials of diluent, syringes and needles) for a treatment course (e.g., 7 days or more of treatment).

Systemic formulations include those designed for administration by injection, e.g., subcutaneous, intravenous, intramuscular, intrathecal or intraperitoneal injection, as well as those designed for transdermal, transmucosal oral or pulmonary administration.

For intravenous and other parenteral routes of administration, a compound or pharmaceutical composition of the present application can be formulated as a lyophilized preparation, as a lyophilized preparation of liposome-intercalated or -encapsulated active compound, as a lipid complex in aqueous suspension, or as a salt complex. Lyophilized formulations are generally reconstituted in suitable aqueous solution, e.g., in sterile water or saline, shortly prior to administration.

Pharmaceutical compositions (e.g. a formulation or medicament) suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). A composition for administration by injection will generally be sterile and should be fluid to the extent that easy syringability exists. It should be stable under the conditions of manufacture and storage and must be preserved against the contaminating action of microorganisms such as bacteria and fungi.

Sterile injectable solutions (e.g. a formulation or medicament) can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

The therapeutic compounds or pharmaceutical compositions, when it is desirable to deliver them systemically, may be formulated for parenteral administration by injection, e.g., by bolus injection or continuous infusion (for example by IV injection or via a pump to meter the administration over a defined time). Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical compositions for parenteral administration include aqueous solutions of the active compounds in water-soluble form. Additionally, suspensions of the therapeutic compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the therapeutic compounds to allow for the preparation of highly concentrated solutions.

For oral administration, the compounds can be formulated readily by combining the active compound(s) with pharmaceutically acceptable carriers well known in the art. Such carriers enable the compounds of the present application to be formulated as tablets, pills, dragees, capsules, liquids, gels, syrups, slurries, suspensions and the like, for oral ingestion by a subject to be treated. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel®, or corn starch; a lubricant such as magnesium stearate or sterates; a glidant such as colloidal silicon dioxide; a sweetening agent such as sucrose or saccharin; or a flavoring agent such as peppermint, methyl salicylate, or orange flavoring.

Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J. Appl Biochem* 4:185-9 (1982). Other polymers that could be used are poly-1,3-dioxolane and poly-1,3,6-tioxocane. For pharmaceutical usage, as indicated above, polyethylene glycol (PEG) moieties of various molecular weights are suitable.

For a particular therapeutic compound or pharmaceutical composition the preferred location of release may be the stomach, the small intestine (the duodenum, the jejunum, or the ileum), or the large intestine. One skilled in the art has available formulations which will not dissolve in the stomach yet will release the material in the duodenum or elsewhere in the intestine. Preferably, the release will avoid the deleterious effects of the stomach environment, either by protection of the compound of the present application (or derivative) or by release of the biologically active material beyond the stomach environment, such as in the intestine.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic compound or pharmaceutical composition can be included in the formulation as fine multiparticulates in the form of granules or pellets of particle size about 1-2 mm. The formulation of the material for capsule administration could also be as a powder, lightly compressed plugs or even as tablets. The therapeutic compound or pharmaceutical composition could be prepared by compression. Colorants and flavoring agents may all be included. For example, the therapeutic compound or pharmaceutical composition may be formulated and then further contained within an edible product, such as a refrigerated beverage containing colorants and flavoring agents.

One may dilute or increase the volume of a formulation or medicament comprising a therapeutic compound, other therapeutic agent, or mixtures thereof with an inert material.

These diluents could include carbohydrates, especially mannitol, lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo®, Emdex®, STARCH 1500®, Emcompress® and Avicel®.

Disintegrants may be included in the pharmaceutical composition to thereby provide a solid dosage form. Materials used as disintegrates include but are not limited to starch, including the commercial disintegrant based on starch, Explotab. Sodium starch glycolate, Amberlite®, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol (PEG) of various molecular weights, Carbowax™ 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic compound or pharmaceutical composition into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the present application or derivative either alone or as a mixture in different ratios.

Pharmaceutical compositions that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For topical administration, a therapeutic compound as disclosed herein may be formulated as solutions, gels, ointments, creams, suspensions, etc. as are well-known in the art.

For administration of a therapeutic compound or pharmaceutical composition by inhalation for use according to the present application, it may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In some embodiments, the formulation, medicament or therapeutic compound can be delivered in the form of an aerosol spray from a pressurized container or dispenser, which contains a suitable propellant, e.g., a gas such as carbon dioxide, or a nebulizer. Such methods include those described in U.S. Pat. No. 6,468,798. In the case of a pressurized aerosol the dosage unit may be determined by providing a valve to deliver a metered amount. Capsules and cartridges of e.g., gelatin for use in an inhaler or insufflator may be formulated containing a powder mix of the therapeutic compound and a suitable powder base such as lactose or starch.

Nasal delivery of a therapeutic compound or pharmaceutical composition of the present application is also contemplated. Nasal delivery allows the passage of a therapeutic compound or pharmaceutical composition of the present application to the blood stream directly after administering the therapeutic compound or pharmaceutical composition to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present application solution into a chamber of defined volume, which chamber has an aperture dimensioned to aerosolize and aerosol formulation by forming a spray when a liquid in the chamber is compressed. The chamber is compressed to administer the therapeutic compound or pharmaceutical composition. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the therapeutic compound or pharmaceutical composition.

Alternatively, the therapeutic compound or pharmaceutical composition may be in powder form for constitution with a suitable vehicle, e.g., sterile pyrogen-free water, before use.

Also contemplated herein is pulmonary delivery of the therapeutic compound or pharmaceutical composition disclosed herein. The compound, formulation or medicament can be delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med* 3:206-212 (1989) (al-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, *Keystone, Colorado*, March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor; incorporated by reference). A method and composition for pulmonary delivery of drugs for systemic effect is described in U.S. Pat. No. 5,451,569 (incorporated by reference), issued Sep. 19, 1995 to Wong et al.

Contemplated for use in the practice of this technology are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this technology are the Ultravent™ nebulizer, manufactured by Mallinckrodt, Inc., St. Louis, Mo.; the Acorn II® nebulizer, manufactured by Marquest Medical Products, Englewood, Colo.; the Ventolin® metered dose inhaler, manufactured by Glaxo Inc., Research Triangle Park, North Carolina; and the Spinhaler® powder inhaler, manufactured by Fisons Corp., Bedford, Mass.

All such devices require the use of formulations suitable for the dispensing of the therapeutic compounds, formulations and medicaments of the present application. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compounds, of the present application may also be prepared in different formulations and medicaments depending on the type of chemical modification or the type of device employed.

Formulations suitable for use with a nebulizer, either jet or ultrasonic, can comprise a therapeutic compound of the present application (or derivative) dissolved in water at a concentration of about 0.1 to 25 mg of biologically active compound of the present application per mL of solution. The formulation may also include a buffer and a simple sugar (e.g., for inhibitor stabilization and regulation of osmotic pressure). The nebulizer formulation may also contain a surfactant, to reduce or prevent surface induced aggregation of the compound of the present application caused by atomization of the solution in forming the aerosol.

Formulations for use with a metered-dose inhaler device may generally comprise a finely divided powder containing the compound of the present application (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device may comprise a finely divided dry powder containing therapeutic compound of the present application (or derivative) and may also include a bulking agent, such as lactose, sorbitol, sucrose, or mannitol in amounts which facilitate dispersal of the powder from the device, e.g., 50 to 90% by weight of the formulation. The therapeutic compound or pharmaceutical composition of the present application (or derivative) can advantageously be prepared in particulate form with an average particle size of less than 10 micrometers (μm), most preferably 0.5 to 5 m, for most effective delivery to the deep lung.

For ophthalmic or intraocular indications, any suitable mode of delivering the therapeutic compounds or pharmaceutical compositions to the eye or regions near the eye can be used. For ophthalmic formulations generally, see Mitra (ed.), *Ophthalmic Drug Delivery Systems*, Marcel Dekker, Inc., New York, N.Y. (1993) and also Havener, W. H., *Ocular Pharmacology*, C. V. Mosby Co., St. Louis (1983). Nonlimiting examples of pharmaceutical compositions suitable for administration in or near the eye include, but are not limited to, ocular inserts, minitablets, and topical formulations such as eye drops, ointments, and in situ gels. In one embodiment, a contact lens is coated with a pharmaceutical composition comprising a therapeutic compound disclosed herein. In some embodiments, a single dose comprises from between 0.1 ng to 5000 μg, 1 ng to μg, or 10 ng to 100 μg of the therapeutic compounds or pharmaceutical compositions administered to the eye.

Eye drops can comprise a sterile liquid formulation that can be administered directly to the eye. In some embodiments, eye drops comprise at least one therapeutic compound disclosed herein and may further comprise one or more preservatives. In some embodiments, the optimum pH for eye drops equals that of tear fluid and is about 7.4.

In situ gels are viscous liquids, showing the ability to undergo sol-to-gel transitions when influenced by external factors, such as appropriate pH, temperature, and the presence of electrolytes. This property causes slowing of drug drainage from the eyeball surface and increase of the active ingredient bioavailability. Polymers commonly used in in situ gel formulations include, but are not limited to, gellan gum, poloxamer, silicone containing formulations and cellulose acetate phthalate. In some embodiments, the therapeutic compound is formulated into an in-situ gel (as the pharmaceutical composition).

For topical ophthalmic administration, therapeutic compound or pharmaceutical composition may be formulated as solutions, gels, ointments, creams, suspensions, etc. as are well-known in the art. Ointments are semisolid dosage forms for external use such as topical use for the eye or skin. In some embodiments, ointments comprise a solid or semisolid hydrocarbon base of melting or softening point close to human core temperature. In some embodiments, an ointment applied to the eye decomposes into small drops, which stay for a longer time period in conjunctival sac, thus increasing bioavailability.

Ocular inserts are solid or semisolid dosage forms without disadvantages of traditional ophthalmic drug forms. They are less susceptible to defense mechanisms like outflow through nasolacrimal duct, show the ability to stay in conjunctival sac for a longer period, and are more stable than conventional dosage forms. They also offer advantages such as accurate dosing of one or more therapeutic compounds, slow release of one or more therapeutic compounds with constant speed and limiting of one or more therapeutic compounds' systemic absorption. In some embodiments, an ocular insert comprises one or more therapeutic compounds as disclosed herein and one or more polymeric materials. The polymeric materials can include, but are not limited to, methylcellulose and its derivatives (e.g., hydroxypropyl methylcellulose (HPMC)), ethylcellulose, polyvinylpyrrolidone (PVP K-90), polyvinyl alcohol, chitosan, carboxymethyl chitosan, gelatin, and various mixtures of the aforementioned polymers. An ocular insert can comprise silica.

Minitablets are biodegradable, solid drug forms, that transit into gels after application to the conjunctival sac, thereby extending the period of contact between active ingredient (i.e. the therapeutic compound disclosed herein) and the eyeball surface, which in turn increases a therapeutic compounds' bioavailability. The advantages of minitablets include easy application to conjunctival sac, resistance to defense mechanisms like tearing or outflow through nasolacrimal duct, longer contact with the cornea caused by presence of mucoadhesive polymers, and gradual release of the active ingredient from the formulation in the place of application due to the swelling of the outer carrier layers. Minitablets can comprise one or more of the therapeutic compounds disclosed herein and one or more polymers. Nonlimiting examples of polymers suitable for use in in a minitablet formulation include cellulose derivatives, like hydroxypropyl methylcellulose (HPMC), hydroxyethyl cellulose (HEC), sodium carboxymethyl cellulose, ethyl cellulose, acrylates (e.g., polyacrylic acid and its cross-linked forms), Carbopol® or carbomer, chitosan, and starch (e.g., drum-dried waxy maize starch). In some embodiments, minitablets further comprise one or more excipients. Nonlimiting examples of excipients include mannitol and magnesium stearate.

The ophthalmic or intraocular formulations and medicaments may contain non-toxic auxiliary substances such as antibacterial components which are non-injurious in use, for example, thimerosal, benzalkonium chloride, methyl and propyl paraben, benzyldodecinium bromide, benzyl alcohol, or phenylethanol; buffering ingredients such as sodium chloride, sodium borate, sodium acetate, sodium citrate, or gluconate buffers; and other conventional ingredients such as sorbitan monolaurate, triethanolamine, polyoxyethylene sorbitan monopalmitylate, ethylenediamine tetraacetic acid, and the like.

In some embodiments, the viscosity of the ocular formulation comprising one or more therapeutic compounds is increased to improve contact with the cornea and bioavailability in the eye. Viscosity can be increased by the addition of hydrophilic polymers of high molecular weight which do not diffuse through biological membranes and which form three-dimensional networks in the water. Nonlimiting examples of such polymers include polyvinyl alcohol, poloxamers, hyaluronic acid, carbomers, and polysaccharides, cellulose derivatives, gellan gum, and xanthan gum.

In some embodiments, the ocular formulation can be injected into the eye, for example as a sol-gel. In some embodiments, the ocular formulation is a depot formulation such as a controlled release formulation. Such controlled release formulation may comprise particles, such as microparticles or nanoparticles.

The therapeutic compound or pharmaceutical composition may also be formulated in rectal or vaginal compositions such as suppositories or retention enemas, e.g., containing conventional suppository bases such as cocoa butter or other glycerides.

In addition to the formulations described above, a therapeutic compound may also be formulated as a depot preparation. Such long acting pharmaceutical compositions may be formulated with suitable polymeric or hydrophobic materials (for example as an emulsion in an acceptable oil) or ion exchange resins, or as sparingly soluble derivatives, for example, as a sparingly soluble salt.

Suitable liquid or solid pharmaceutical depot forms can be, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions can be suitable for use in a variety of drug delivery systems. For a brief review of methods for drug delivery, see Langer R, *Science* 249:1527-33 (1990).

The therapeutic compound or pharmaceutical composition may be provided in particles. Particles as used herein means nanoparticles or microparticles (or in some instances larger particles) which can consist in whole or in part of the compound of the present application or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof. The particle may include, in addition to the therapeutic agent(s), any of those materials routinely used in the art of pharmacy and medicine, including, but not limited to, erodible, non-erodible, biodegradable, or nonbiodegradable material or combinations thereof. The particles may be microcapsules which contain the compound of the present application in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, polyethylene glycols (PEGs), polyvinylalcohols (PVAs), poly(methyl methacrylates), poly(ethyl methacrylates), poly(butylmethacrylate), poly(isobutyl methacrylate), poly(lactic-co-glycolic) acid (PLGA), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) and poly(F-caprolactone).

A therapeutic compound or other therapeutic agent or mixtures thereof can be formulated in a carrier system. The carrier can be a colloidal system. The colloidal system can be a liposome, a phospholipid bilayer vehicle. In one embodiment, therapeutic compound or other therapeutic agent or mixtures thereof can be encapsulated in a liposome while maintaining integrity of the therapeutic compound or other therapeutic agent or mixtures thereof. One skilled in the art would appreciate that there are a variety of methods to prepare liposomes. (See Lichtenberg, et al., *Methods Biochem. Anal.,* 33:337-462 (1988); Anselem, et al., *Liposome Technology,* CRC Press (1993)). Liposomal formulations can delay clearance and increase cellular uptake (See Reddy, *Ann. Pharmacother.,* 34(7-8):915-923 (2000)). For example, an active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic compound or other therapeutic agent or mixtures thereof can be embedded in the polymer matrix, while maintaining integrity of the composition. The polymer can be a nanoparticle that encapsulates the therapeutic agent or agents. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or poly lactic/glycolic acid (PLGA). The polymeric matrices can be prepared and isolated in a variety of forms and sizes, including microspheres and nanospheres. Polymer formulations can lead to prolonged duration of therapeutic effect. (See Reddy, *Ann. Pharmacother.,* 34(7-8):915-923 (2000)). A polymer formulation for human growth hormone (hGH) has been used in clinical trials. (See Kozarich and Rich, *Chemical Biology,* 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compound or other therapeutic agent or mixtures thereof are prepared with carriers that will protect the therapeutic compound, other therapeutic agent or mixtures thereof against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compound(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. The term "implant" is intended to include a single composition (such as a mesh) or composition comprising multiple components (e.g. a fibrous mesh constructed from several individual pieces of mesh material) or a plurality of individual compositions where the plurality remains localized and provide the long-term sustained release occurring from the aggregate of the plurality of compositions. "Long-term" release, as used herein, means that the implant is constructed and arranged to deliver therapeutic or prophylactic levels of the active ingredient for at least 2 days. In some embodiments, the implant is constructed and arranged to deliver therapeutic or prophylactic levels of the active ingredient for at least 7 days. In some embodiments, the implant is constructed and arranged to deliver therapeutic or prophylactic levels of the active ingredient for at least 14 days. In some embodiments, the implant is constructed and arranged to deliver therapeutic or prophylactic levels of the active ingredient for at least 30 days. In some embodiments, the implant is constructed and arranged to deliver therapeutic or prophylactic levels of the active ingredient for at least 60 days. In some embodiments, the implant is constructed and arranged to deliver therapeutic or prophylactic levels of the active ingredient for at least 90 days. In some embodiments, the implant is constructed and arranged to deliver therapeutic or prophylactic levels of the active ingredient for at least 180 days. In some embodiments, the implant is constructed and arranged to deliver therapeutic or prophylactic levels of the active ingredient for at least one year. In some embodiments, the implant is constructed and arranged to deliver therapeutic or prophylactic levels of the active ingredient for 15-30 days. In some embodiments, the implant is constructed and arranged to deliver therapeutic or prophylactic levels of the active ingredient for 30-60 days. In some embodiments, the implant is constructed and arranged to deliver therapeutic or prophylactic levels of the active ingredient for 60-90 days. In some embodiments, the implant is constructed and arranged to deliver therapeutic or prophylactic levels of the active ingredient for 90-120 days. In some embodiments, the implant is constructed and arranged to deliver therapeutic or prophylactic levels of the active ingredient for 120-180 days. In some embodiments, the Long-term sustained release implants are well-known to those of ordinary skill in the art and include some of the release systems described above. In some embodiments, such implants can be administered surgically. In some embodiments, such implants can be administered topically or by injection.

It will be understood by one of ordinary skill in the relevant arts that other suitable modifications and adaptations to the compositions and methods described herein are readily apparent from the description of the present technology contained herein in view of information known to the ordinarily skilled artisan, and may be made without departing from the scope of the present application or any embodiment thereof.

V. Compounds & Compositions Useful for Treating Mitochondrial Disease (e.g., Friedreich's Ataxia) and Intermediates Related Thereto (a) Therapeutic Compounds In some embodiments, the present application provides novel compounds and compositions useful for treating mitochondrial disease such as Friedreich's ataxia in a mammalian subject. Said compounds and compositions (e.g. formulations) can be formulated in any way suitable for administration to the subject. Said compounds and compositions can, for example, be formulated as a tablet, in solution for subcutaneous injection, in solution for intravenous injection or in a gel, cream or drop for topical or intraocular application. In some embodiments, said compounds and compositions can be used to prepare medicaments.

In some embodiments, the present application pertains to compounds represented by the formula E-F, or pharmaceutically acceptable salts, stereoisomers, mixtures of stereoisomers, tautomers, hydrates, and/or solvates thereof, wherein E is 21 or 22:

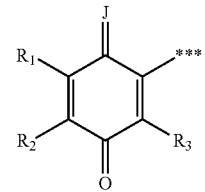

21

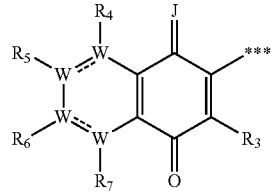

22 and F is 13, 14, 15, 16, 17, 18, 19 or 20:

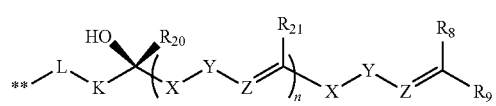

13

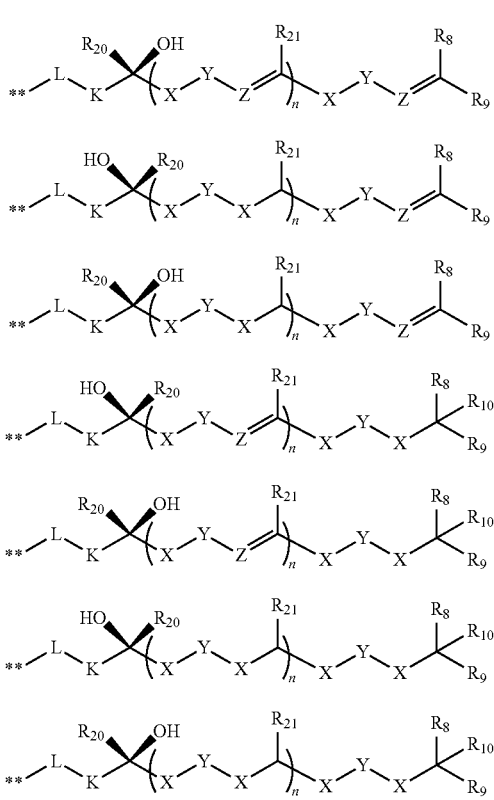

wherein, J is O, S or N—Ru; K is absent or —(CR$_{12}$R$_{13}$)—; L is —(CR$_{12}$R$_{13}$)—; each W is independently C (carbon) or N (nitrogen) and wherein for each use of w═w, the bond between each W can be a single bond or double bond and further provided that if a single bond, each C (carbon) atom will have a hydrogen atom linked hereto in addition to one of R$_4$, R$_5$, R$_6$ or R$_7$ and in either case each of R$_4$, R$_5$, R$_6$ and R$_7$ attached thereto is independently selected from H, D, F, Cl, Br, I, C$_1$-C$_6$ alkyl and C$_1$-C$_6$ alkoxy, and if W is N (nitrogen), each of R$_4$, R$_5$, R$_6$ and R$_7$ attached thereto is independently absent (if w═w is a double bond) or selected from H, D and C$_1$-C$_6$ alkyl (if w═w is a single bond); each X is independently a group of formula —(CR$_{12}$R$_{13}$)—; each Y is independently absent or a group of formula —(CR$_{12}$R$_{13}$)—; each Z is independently a group of formula —(CR$_{14}$)—; each of R$_1$, R$_2$ and R$_3$ is independently H, D, F, Cl, Br, I, C$_1$-C$_6$ alkyl or C$_1$-C$_6$ alkoxy; or R$_1$ and R$_2$ together form a 5-membered carbocyclic ring, a 5-membered heterocyclic ring, a 5-membered aromatic or heteroaromatic ring, or a 6-membered heterocyclic ring; each R$_8$ and R$_9$ is independently H, D, F, Cl, Br, I or C$_1$-C$_4$ alkyl; or taken together R$_8$ and R$_9$ form a 3-, 4-, 5-, 6-, or 7-membered carbocyclic or heterocyclic ring; R$_{10}$ is H, D, F, Cl, Br, I, C$_1$-C$_6$ alkyl or C$_1$-C$_6$ alkoxy; R$_{11}$ is H, D or C$_1$-C$_6$ alkyl; each R$_{12}$, R$_{13}$ and R$_{14}$ is independently H, D, F, Cl, Br, I, C$_1$-C$_6$ alkyl or C$_1$-C$_6$ alkoxy; R$_{20}$ is H, D, F or C$_1$-C$_{12}$ alkyl; each R$_{21}$ is H, D, F, Cl, Br, I, or C$_1$-C$_4$ alkyl; n is an integer from 0 to 12 (i.e., 0, 1, 2, 3, 4, 5, 6, 7, 8, 9, 10, 11, or 12); and * indicates the point of attachment of E to F and  indicates the point of attachment of F to E; and further provided that: (i) at least one group of formula R$_1$, R$_2$, R$_3$, R$_4$, R$_5$, R$_6$, R$_7$, R$_8$, R$_9$, R$_{10}$, R$_{12}$, R$_{13}$, R$_{14}$, R$_{20}$ or R$_{21}$ comprises at least one fluorine atom; and/or (ii) R$_8$ and R$_9$ taken together form a 3-, 4-, 5-, 6- or 7-membered carbocyclic or heterocyclic ring. In some embodiments, at least one of R$_8$ and R$_9$ is fluorine or a substituted C$_1$-C$_4$ alkyl group comprising at least one fluorine. In some embodiments, each of R$_8$ and R$_9$ is independently fluorine or a substituted C$_1$-C$_4$ alkyl group comprising at least one fluorine. In some embodiments, each of R$_8$ and R$_9$ is fluorine. In some embodiments, each of R$_8$, R$_9$ and R$_{10}$ is fluorine. In some embodiments, each of R$_8$, R$_9$ and R$_{10}$ is independently fluorine or a substituted C$_1$-C$_4$ alkyl group comprising at least one fluorine.

As used herein, in compounds such as those of formula E-F, the aromatic group such as 21 and 22 are sometimes referred to the 'head' group and the aliphatic groups such as 13, 14, 15, 16, 17, 18, 19 and 20 are referred to as the 'tail' group. Thus, the therapeutic compounds disclosed herein (not just compounds of formula E-F) generally comprise an aromatic 'head' group covalently link to an aliphatic 'tail' group, wherein the aromatic head group is a quinone or hydroquinone. The quinone (or hydroquinone in reduced form) can be a substituted benzoquinone ring, naphthoquinone ring or other aromatic ring.

Any combination of 21 and 22 with 13, 14, 15, 16, 17, 18, 19 or 20 is permissible. In some embodiments, E is 21 and F is 13, 14, 19 or 20. In some embodiments, wherein E is 22 and F is 13, 14, 19 or 20. In some embodiments, E is 21 and F is 15, 16, 17 or 18, In some embodiments, E is 22 and F is 15, 16, 17 or 18. In some embodiments, E is 21 and F is 13. In some embodiments, E is 21 and F is 14. In some embodiments, E is 21 and F is 15. In some embodiments, E is 21 and F is 16. In some embodiments, E is 21 and F is 17. In some embodiments, E is 21 and F is 18. In some embodiments, E is 21 and F is 19. In some embodiments, E is 21 and F is 20. In some embodiments, E is 22 and F is 13. In some embodiments, E is 22 and F is 14. In some embodiments, E is 22 and F is 15. In some embodiments, E is 22 and F is 16. In some embodiments, E is 22 and F is 17. In some embodiments, E is 22 and F is 18. In some embodiments, E is 22 and F is 19. In some embodiments, E is 22 and F is 20.

The atom or group represented by J can be O, S or N—R$_{11}$. In some embodiments, J is O (oxygen). In some embodiments, J is S (sulfur). In some embodiment, J is N—R$_{11}$, wherein Rn is defined above. In some embodiments, J is O or N—R$_{11}$ and K is absent.

In some embodiments, the groups represented by K and L can each independently be: —(CH$_2$)—, —(CD$_2$)-, —(CHF)—, —(CF$_2$)—, —(CH(CH$_3$))—, —(CD(CD$_3$))—, —(CF(CH$_3$))—, —(CH(CF$_3$))—, —(CF(CF$_3$))—, —(C(CH$_3$)$_2$)—, —(C(CD$_3$)$_2$)—, —(C(CF$_3$)$_2$), —(CH(OCH$_3$))—, —(CD(OCD$_3$))—, —(CF(OCH$_3$))—, —(CH(OCF$_3$))—, —(CF(OCF$_3$))—, —(C(OCH$_3$)$_2$)—, —(C(OCD$_3$)$_2$)—, —(C(OCF$_3$)$_2$)—, —(C(CH$_3$)(CF$_3$))—, —(C(CD$_3$)(CF$_3$))—, —(CH(CH$_2$CH$_3$))—, —(CD(CD$_2$CD$_3$))—, —(CF(CH$_2$CH$_3$))—, —(CH(CH$_2$CF$_3$))—, —(CH(CF$_2$CF$_3$))—, —(CF(CF$_2$CF$_3$))—, —(C(CH$_2$CH$_3$)$_2$)—, —(C(CD$_2$CD$_3$)$_2$)— or —(C(CF$_2$CF$_3$)$_2$)—. In some embodiments, K is absent and L is —(CH$_2$)—, —(CD$_2$)-, —(CHF)—, —(CF$_2$)—, —(CH(CH$_3$))—, —(CD(CD$_3$))—, —(CF(CH$_3$))—, —(CH(CF$_3$))—, —(CF(CF$_3$))—, —(C(CH$_3$)$_2$)—, —(C(CD$_3$)$_2$)—, —(C(CF$_3$)$_2$), —(CH(OCH$_3$))—, —(CD(OCD$_3$))—, —(CF(OCH$_3$))—, —(CH(OCF$_3$))—, —(CF(OCF$_3$))—, —(C(OCH$_3$)$_2$)—, —(C(OCD$_3$)$_2$)—, —(C(OCF$_3$)$_2$)—, —(C(CH$_3$)(CF$_3$))—, —(C(CD$_3$)(CF$_3$))—, —(CH(CH$_2$CH$_3$))—, —(CD(CD$_2$CD$_3$))—, —(CF(CH$_2$CH$_3$))—, —(CH(CH$_2$CF$_3$))—, —(CH(CF$_2$CF$_3$))—, —(CF(CF$_2$CF$_3$))—, —(C(CH$_2$CH$_3$)$_2$)—, —(C(CD$_2$CD$_3$)$_2$)— or —(C(CF$_2$CF$_3$)$_2$)—. In some embodiments, each of K and L is independently —(CH$_2$)—, —(CD$_2$)-, —(CF$_2$)—, —(CH(CH$_3$))—, —(CD(CD$_3$))—, —(CF(CF$_3$))—, —(C(CH$_3$)$_2$)—, —(C(CD$_3$)$_2$)—, —(C(CF$_3$)$_2$)—, —(CH(OCH$_3$))—, —(CD(OCD$_3$))—, —(CF(OCF$_3$))— or —(C(OCH$_3$)$_2$)—. In some embodiments, K is absent and L is —(CH$_2$)—, —(CD$_2$)-, —(CF$_2$)—, —(CH(CH$_3$))—, —(CD(CD$_3$))—, —(CF(CF$_3$))—, —(C(CH$_3$)$_2$)—, —(C(CD$_3$)$_2$)—, —(C(CF$_3$)$_2$)—, —(CH(OCH$_3$))—, —(CD(OCD$_3$))—, —(CF(OCF$_3$))— or —(C(OCH$_3$)$_2$)—. In some embodiments, each of K and L is independently —(CH$_2$)—, —(CD$_2$)-, —(CHF)—, —(CF$_2$)—, —(CH(CH$_3$))—, —(CF(CF$_3$))—, —(C(CH$_3$)$_2$)— or —(C(CF$_3$)$_2$)—. In some embodiments, K is absent and L is —(CH$_2$)—, —(CD$_2$)-, —(CHF)—, —(CF$_2$)—, —(CH(CH$_3$))—, —(CF(CF$_3$))—, —(C(CH$_3$)$_2$)— or —(C(CF$_3$)$_2$)—. In some embodiments, each of K and L is independently —(CH$_2$)—, —(CD$_2$)-, —(CHF)— or —(CF$_2$)—. In some embodiments, K is absent and L is —(CH$_2$)—, —(CD$_2$)-, —(CHF)— or —(CF$_2$)—. In some embodiments, each of K and L are —(CH$_2$)—. In some embodiments, K is absent and L is —(CH$_2$)—. In some embodiments, each of K and L are —(CD$_2$)-. In some embodiments, K is absent and L is —(CD$_2$)-. In some embodiments, each of K and L are —(CF$_2$)—. In some embodiments, K is absent and L is —(CF$_2$)—.

In some embodiments of the compound represented by E-F, wherein E is 21, each of $R_1$, $R_2$ and $R_3$ is independently H, D, Cl, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, —CH(CH$_3$)$_2$, —CD$_2$CD$_3$, —CD(CD$_3$)$_2$, —CF$_2$CH$_3$, —CF(CH$_3$)$_2$, —CH$_2$CF$_3$, —CH(CF$_3$)$_2$, —CF$_2$CF$_3$, —CF(CF$_3$)$_2$, —C(CH$_3$)$_3$, —C(CD$_3$)$_3$, —C(CF$_3$)$_3$, —OCH$_2$CH$_3$, —OCH(CH$_3$)$_2$, —OCD$_2$CD$_3$, —OCD(CD$_3$)$_2$, —OCF$_2$CH$_3$, —OCF(CH$_3$)$_2$, —OCH$_2$CF$_3$, —OCH(CF$_3$)$_2$, —OCF$_2$(CF$_3$), —OCF(CF$_3$)$_2$, —OC(CH$_3$)$_3$, —OC(CD$_3$)$_3$, —OC(CF$_3$)$_3$, —C(CH$_3$)$_2$(CF$_3$), —C(CH$_3$)(CF$_3$)$_2$, —OC(CH$_3$)$_2$(CF$_3$), —OC(CH$_3$)(CF$_3$)$_2$, —CH$_2$CH$_2$CH$_3$, —CH(CH$_2$CH$_3$)$_2$, —CD$_2$CD$_2$CD$_3$, —CD(CD$_2$CD$_3$)$_2$, —CF$_2$CH$_2$CH$_3$, —CF(CH$_2$CH$_3$)$_2$, —CH$_2$CF$_2$CF$_3$, —CH(CF$_2$CF$_3$)$_2$, —CF$_2$CF$_2$CF$_3$, —CF(CF$_2$CF$_3$)$_2$, —OCH$_2$CH$_2$CH$_3$, —OCH(CH$_2$CH$_3$)$_2$, —OCD$_2$CD$_2$CD$_3$, —OCD(CD$_2$CD$_3$)$_2$, —OCF$_2$CH$_2$CH$_3$, —OCF(CH$_2$CH$_3$)$_2$, —OCH$_2$CF$_2$CF$_3$, —OCH(CF$_2$CF$_3$)$_2$, —OCF$_2$CF$_2$CF$_3$ or —OCF(CF$_2$CF$_3$)$_2$. In some embodiments of the compound represented by E-F, wherein E is 21, each of $R_1$, $R_2$ and $R_3$ is independently H, D, Cl, F, —CH$_3$, —OCH$_3$, —CD$_3$, —OCD$_3$, —CH$_2$F, —CHF$_2$, —CF$_3$, —OCF$_3$, —C(CH$_3$)$_3$, —C(CD$_3$)$_3$, —C(CF$_3$)$_3$, —OC(CH$_3$)$_3$, —OC(CD$_3$)$_3$, —OC(CF$_3$)$_3$, —CH$_2$CH$_3$, —OCH$_2$CH$_3$, or —CH(CH$_3$)$_2$. In some embodiments of the compound represented by E-F, wherein E is 21, each of $R_1$, $R_2$ and $R_3$ is independently H, F, —CH$_3$, —OCH$_3$, —CH$_2$F, —CHF$_2$, —CF$_3$, —OCF$_3$, —C(CH$_3$)$_3$, —C(CF$_3$)$_3$, —CH$_2$CH$_3$, —OCH$_2$CH$_3$, or —CH(CH$_3$)$_2$. In some embodiments of the compound represented by E-F, wherein E is 21, each of $R_1$, $R_2$ and $R_3$ is independently H, F, —CH$_3$, —OCH$_3$, —CH$_2$F, —CHF$_2$, —CF$_3$ or —OCF$_3$. In some embodiments of the compound represented by E-F, wherein E is 21, each of $R_1$, $R_2$ and $R_3$ is independently H, F, —CH$_3$, —OCH$_3$, —CF$_3$ or —OCF$_3$. In some embodiments of the compound represented by E-F, wherein E is 21, each of $R_1$, $R_2$ and $R_3$ is independently H, F, —CH$_3$, —OCH$_3$ or —CF$_3$. In some embodiments of the compound represented by E-F, wherein E is 21, each of $R_1$, $R_2$ and $R_3$ is —CH$_3$. In some embodiments of the compound represented by E-F, wherein E is 21, each of $R_1$, $R_2$ and $R_3$ is H. In some embodiments of the compound represented by E-F, wherein E is 21, each of $R_1$, $R_2$ and $R_3$ is independently H or —CH$_3$. In some embodiments of the compound represented by E-F, wherein E is 21, each of $R_1$, $R_2$ and $R_3$ is independently H or —OCH$_3$. In some embodiments of the compound represented by E-F, wherein E is 21, each of $R_1$, $R_2$ and $R_3$ is independently H, —CH$_3$ or —OCH$_3$. In some embodiments of the compound represented by E-F, wherein E is 21, each of $R_1$ and $R_2$ is —OCH$_3$ and $R_3$ is —CH$_3$. In some embodiments of the compound represented by E-F, wherein E is 21, each of $R_1$ and $R_2$ is —CH$_3$ and $R_3$ is H. In some embodiments of the compound represented by E-F, wherein E is 21, each of $R_1$ and $R_2$ is —OCH$_3$ and $R_3$ is H. In some embodiments of the compound represented by E-F, wherein E is 21, at least one of $R_1$, $R_2$ and $R_3$ is F.

In some embodiments of the compound represented by E-F wherein E is 21, J is O, each of K and L is independently —(CH$_2$)—, —(CD$_2$)-, —(CHF)—, —(CF$_2$)—, —(CH(CH$_3$))—, —(CF(CF$_3$))—, —(C(CH$_3$)$_2$)— or —(C(CF$_3$)$_2$)—; and each of $R_1$, $R_2$ and $R_3$ is independently H, F, —CH$_3$, —OCH$_3$, —CH$_2$F, —CHF$_2$, —CF$_3$, —OCF$_3$, —C(CH$_3$)$_3$, —C(CF$_3$)$_3$, —CH$_2$CH$_3$, —OCH$_2$CH$_3$, or —CH(CH$_3$)$_2$. In some embodiments of the compound represented by E-F wherein E is 21, J is O, each of K and L is independently —(CH$_2$)—, —(CD$_2$)-, —(CHF)— or —(CF$_2$)—; and each of $R_1$, $R_2$ and $R_3$ is independently H, F, —CH$_3$, —OCH$_3$, —CH$_2$F, —CHF$_2$, —CF$_3$ or —OCF$_3$. In some embodiments of the compound represented by E-F wherein E is 21, J is O, each of K and L is independently —(CH$_2$)—, —(CD$_2$)-, —(CHF)— or —(CF$_2$)—; and each of $R_1$, $R_2$ and $R_3$ is independently H, F, —CH$_3$, —OCH$_3$, —CF$_3$ or —OCF$_3$. In some embodiments of the compound represented by E-F wherein E is 21, J is O; each of K and L is —(CH$_2$)—; and each of $R_1$, $R_2$ and $R_3$ is —CH$_3$. In some embodiments of the compound represented by E-F wherein E is 21, J is O; each of K and L is —(CH$_2$)—; and each of $R_1$, $R_2$ and $R_3$ is H. In some embodiments of the compound represented by E-F wherein E is 21, J is O; each of K and L is —(CH$_2$)—; and each of $R_1$, $R_2$ and $R_3$ is CH$_3$. In some embodiments of the compound represented by E-F wherein E is 21, J is O; each of K and L is —(CH$_2$)—; each of $R_1$, $R_2$ and $R_3$ is independently H or —CH$_3$. In some embodiments of the compound represented by E-F wherein E is 21, J is O; each of K and L is —(CH$_2$)—; each of $R_1$, $R_2$ and $R_3$ is independently H or —OCH$_3$. In some embodiments of the compound represented by E-F wherein E is 21, J is O; each of K and L is —(CH$_2$)—; each of $R_1$, $R_2$ and $R_3$ is independently H, —CH$_3$ or —OCH$_3$. In some embodiments of the compound represented by E-F wherein E is 21, J is O; each of K and L is —(CH$_2$)—; each of $R_1$ and $R_2$ is —OCH$_3$ and $R_3$ is —CH$_3$. In some embodiments of the compound represented by E-F wherein E is 21, J is O; each of K and L is —(CH$_2$)—; each of $R_1$ and $R_2$ is —OCH$_3$ and $R_3$ is H. In some embodiments of the compound represented by E-F wherein E is 21, J is O; each of K and L is —(CH$_2$)—; each of $R_1$ and $R_2$ is —CH$_3$ and $R_3$ is H. In some embodiments of the compound represented by E-F wherein E is 21, J is O; each of K and L is —(CH$_2$)—; each of $R_1$ and $R_2$ is —OCH$_3$ and $R_3$ is H. In some embodiments of the compound represented by E-F wherein E is 21, J is O; each of K and L is —(CH$_2$)— and at least one of $R_1$, $R_2$ and $R_3$ is F.

In some embodiments of the compound represented by E-F wherein E is 21, $R_3$ is H, D, Cl, F, —CH$_3$, —OCH$_3$, —CD$_3$, —OCD$_3$, —CF$_3$, —OCF$_3$, —C(CH$_3$)$_3$, —C(CD$_3$)$_3$, —C(CF$_3$)$_3$, —OC(CH$_3$)$_3$, —OC(CD$_3$)$_3$, —OC(CF$_3$)$_3$, —CH$_2$CH$_3$, —OCH$_2$CH$_3$, or —CH(CH$_3$)$_2$ and $R_1$ and $R_2$ taken together form a 5-, or 6-membered carbocyclic or heterocyclic ring. In some embodiments of the compound represented by E-F wherein E is 21, (i) R₃ is H, F, —CH₃, or —OCH₃, and (ii) R₁ and R₂ taken together form a 5-, or 6-membered carbocyclic or heterocyclic ring. In some embodiments of the compound represented by E-F wherein E is 21, (i) R₃ is H; and (ii) R₁ and R₂ taken together form a 5-, or 6-membered carbocyclic or heterocyclic ring. In some embodiments of the compound represented by E-F wherein E is 21, (i) R₃ is —CH₃; and (ii) R₁ and R₂ taken together form a 5-, or 6-membered carbocyclic or heterocyclic ring. In some embodiments of the compound represented by E-F wherein E is 21, (i) R₃ is —OCH₃; and (ii) R₁ and R₂ taken together form a 5-, or 6-membered carbocyclic or heterocyclic ring. In some embodiments of the compound represented by E-F wherein E is 21, (i) R₃ is F; and (ii) R₁ and R₂ taken together form a 5-, or 6-membered carbocyclic or heterocyclic ring.

In some embodiments of E-F, R₁ and R₂ of 21, taken together, form a heterocycle as represented in 21A, 21B, 21C, 21D, 21E or 21F:

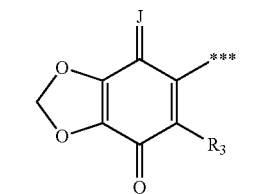

21A

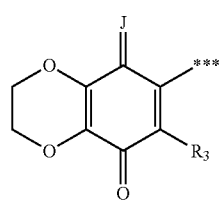

21B

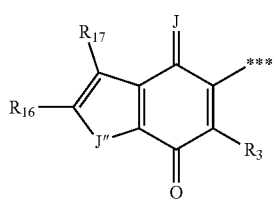

21C

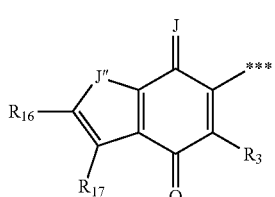

21D

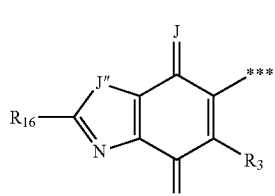

21E

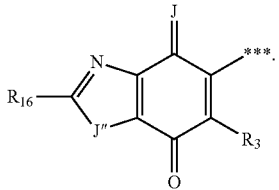

21F wherein each of R₁₆ and R₁₇ are each independently H, D, Cl, F, —CH₃, —OCH₃, —CD₃, —OCD₃, —CH₂F, —CHF₂, —CF₃, —OCF₃, —C(CH₃)₃, —C(CD₃)₃, —C(CF₃)₃, —OC(CH₃)₃, —OC(CD₃)₃, —OC(CF₃)₃, —CH₂CH₃, —OCH₂CH₃, —CH(CH₃)₂, —OCH(CH₃)₂, —C(CH₃)₃ or —O(CH₃)₃; and J" is O, S or N—R₁₈, wherein R₁₈ is H, D, —CH₃, —CH₂F, —CHF₂ or —CF₃. In some embodiments, R₁₆ and R₁₇ are each independently H, D, Cl, F, —CH₃, —OCH₃, —CD₃, —OCD₃, —CH₂F, —CHF₂, —CF₃, or —OCF₃. In some embodiments, R₁₆ and R₁₇ are each independently H, D, F, or —CH₃. In some embodiments, R₁₆ and R₁₇ are H. In some embodiments, R₁₆ and R₁₇ are F. In some embodiments, R₁₆ and R₁₇ are —CH₃. In some embodiments, R₁₈ is H or —CH₃.

In some embodiments of the compound represented by E-F wherein E is 22, R₃ is H, D, Cl, F, —CH₃, —OCH₃, —CD₃, —OCD₃, —CH₂F, —OCH₂F, —CHF₂, —OCHF₂, —CF₃, —OCF₃, —CH₂CH₃, —CH(CH₃)₂, —CD₂CD₃, —CD(CD₃)₂, —CF₂CH₃, CF(CH₃)₂, —CH₂CF₃, —CH(CF₃)₂, —CF₂CF₃, —CF(CF₃)₂, —C(CH₃)₃, —C(CD₃)₃, —C(CF₃)₃, —OCH₂CH₃, —OCH(CH₃)₂, —OCD₂CD₃, —OCD(CD₃)₂, —OCF₂CH₃, —OCF(CH₃)₂, —OCH₂CF₃, —OCH(CF₃)₂, —OCF₂(CF₃), —OCF(CF₃)₂, —OC(CH₃)₃, —OC(CD₃)₃, —OC(CF₃)₃, —C(CH₃)₂(CF₃), —C(CH₃)(CF₃)₂, —OC(CH₃)₂(CF₃), —OC(CH₃)(CF₃)₂, —CH₂CH₂CH₃, —CH(CH₂CH₃)₂, —CD₂CD₂CD₃, —CD(CD₂CD₃)₂, —CF₂CH₂CH₃, —CF(CH₂CH₃)₂, —CH₂CF₂CF₃, —CH(CF₂CF₃)₂, —CF₂CF₂CF₃, —CF(CF₂CF₃)₂, —OCH₂CH₂CH₃, —OCH(CH₂CH₃)₂, —OCD₂CD₂CD₃, —OCD(CD₂CD₃)₂, —OCF₂CH₂CH₃, —OCF(CH₂CH₃)₂, —OCH₂CF₂CF₃, —OCH(CF₂CF₃)₂, —OCF₂CF₂CF₃ or —OCF(CF₂CF₃)₂; and where if W is C (carbon), each of R₄, R₅, R₆ and R₇ attached thereto is independently H, D, F, Cl, Br, I, —CH₃, —OCH₃, —CD₃, —OCD₃, —CH₂F, —OCH₂F, —CHF₂, —OCHF₂, —CF₃, —OCF₃, —CH₂CH₃, or —CH(CH₃)₂, and where if W is N (nitrogen), each of R₄, R₅, R₆ and R₇ attached thereto is independently absent or selected from H, D, methyl, ethyl, isopropyl or t-butyl. In some embodiments, for each instance of w═w, the bond between each W is a single bond. In some embodiments, for each instance of w═w, the bond between each W is a double bond. In some embodiments, R₃ is H, D, Cl, F, —CH₃, —OCH₃, —CD₃, —OCD₃, —CH₂F, —CHF₂, —CF₃, —OCF₃, —C(CH₃)₃, —C(CD₃)₃, —C(CF₃)₃, —OC(CH₃)₃, —OC(CD₃)₃, —OC(CF₃)₃, —CH₂CH₃, —OCH₂CH₃, or —CH(CH₃)₂; and where if W is C (carbon), each of R₄, R₅, R₆ and R₇ attached thereto is independently H, D, F, C₁, —CH₃, —OCH₃, —CH₂F, —CHF₂, —CF₃, —OCF₃, —CH₂CH₃, or —CH(CH₃)₂, and where if W is N (nitrogen), each of R₄, R₅, R₆ and R₇ attached thereto is independently absent or selected from H, D, methyl and ethyl. In some embodiments, each W is C (carbon) and each of R₄, R₅, R₆ and R₇ is independently H, D, Cl, F, —CH₃, —OCH₃, —CH₂F, —CHF₂, —CF₃ or —OCF₃. In some embodiments, each W is C (carbon) and each of R₄, R₅, R₆ and R₇ is independently H, D, Cl, F, —CH₃ or —OCH₃. In some embodiments, each W is C (carbon) and each of $R_4$, $R_5$, $R_6$ and $R_7$ is independently H, —$CH_3$ or —$OCH_3$. In some embodiments, each W is C (carbon) and each of $R_4$, $R_5$, $R_6$ and $R_7$ is H. In some embodiments, each W is C (carbon) and each of $R_4$, $R_5$, $R_6$ and $R_7$ is —$CH_3$.

In some embodiments of the compound E-F, each of $R_8$ and $R_9$ can be independently H, D, F, $C_l$, Br, I, —$CH_3$, —$CD_3$, —$CH_2F$, —$CHF_2$, —$CF_3$, —$CH_2CH_3$, —$CH(CH_3)_2$, —$CD_2CD_3$, —$CD(CD_3)_2$, —$CF_2CH_3$, —$CF(CH_3)_2$, —$CH_2CF_3$, —$CH(CF_3)_2$, —$CF_2CF_3$, —$CF(CF_3)_2$, —$C(CH_3)_3$, —$C(CD_3)_3$, —$C(CF_3)_3$, —$C(CH_3)_2(CF_3)$, —$C(CH_3)(CF_3)_2$, —$CH_2CH_2CH_3$, —$CH(CH_2CH_3)_2$, —$CD_2CD_2CD_3$, —$CD(CD_2CD_3)_2$, —$CF_2CH_2CH_3$, —$CF(CH_2CH_3)_2$, —$CH_2CF_2CF_3$, —$CH(CF_2CF_3)_2$, —$CF_2CF_2CF_3$ or —$CF(CF_2CF_3)_2$. In some embodiments of the compound E-F, each of $R_8$ and $R_9$ can be independently H, F, —$CH_3$, —$CH_2F$, —$CHF_2$, —$CF_3$, —$CH_2CH_3$, —$CH(CH_3)_2$, —$CF_2CH_3$, —$CH_2CF_3$, —$CH(CF_3)_2$, —$CF_2CF_3$, —$CF(CF_3)_2$, —$C(CH_3)_3$, —$C(CF_3)_3$, —$CH_2CH_2CH_3$, —$CH(CH_2CH_3)_2$, —$CF_2CF_2CF_3$ or —$CF(CF_2CF_3)_2$. In some embodiments of the compound E-F, each of $R_8$ and $R_9$ can be independently H, F, —$CH_3$, —$CH_2F$, —$CHF_2$ or —$CF_3$.

In some embodiments of the compound E-F, each of $R_8$ and $R_9$ can be independently a $C_1$-$C_4$ alkyl group. Said alkyl group can be, for example, substituted with one or more fluorine atoms. For example, said alkyl group can be fluoromethyl, difluoromethyl or trifluoromethyl.

In some embodiments of the compound E-F, $R_8$ and $R_9$, taken together, can form a 3-, 4-, 5-, 6- or 7-membered carbocyclic or heterocyclic ring. For example, the 3-, 4-, 5-, 6- or 7-membered carbocyclic or heterocyclic ring can be 31, 32, 33, 34, 35, 36, 37, 38, 39, 40, 41, 42, 43, 44, 45, 46 or 47:

31

32

33

34

35

36

37

38

39

40

41

42

43

44

45

46

47

wherein #indicates the point of attachment of the carbocycle or heterocycle to the remainder of the compound. In some embodiments, the 3-, 4-, 5-, 6- or 7-membered carbocyclic or heterocyclic ring can comprise one or more fluorine substitutions. In some embodiments, the 3-, 4-, 5-, 6- or 7-membered carbocyclic or heterocyclic ring can comprise one or more deuterium substitutions.

In some embodiments of the compound E-F, $R_{10}$ is H, D, F, —$CH_3$, —$OCH_3$, —$CD_3$, —$OCD_3$, —$CH_2F$, —$OCH_2F$, —$CHF_2$, —$OCHF_2$, —$CF_3$, —$OCF_3$, —$CH_2CH_3$, —$CH(CH_3)_2$, —$CD_2CD_3$, —$CD(CD_3)_2$, —$CF_2CH_3$, $CF(CH_3)_2$, —$CH_2CF_3$, —$CH(CF_3)_2$, —$CF_2CF_3$, —$CF(CF_3)_2$, —$C(CH_3)_3$, —$C(CD_3)_3$, —$C(CF_3)_3$, —$OCH_2CH_3$, —$OCH(CH_3)_2$, —$OCD_2CD_3$, —$OCD(CD_3)_2$, —$OCF_2(CF_3)$, —$OCF(CF_3)_2$, —$OC(CH_3)_3$, —$OC(CD_3)_3$, —$OC(CF_3)_3$, —$C(CH_3)_2(CF_3)$, —$C(CH_3)(CF_3)_2$, —$OC(CH_3)_2(CF_3)$, —$OC(CH_3)(CF_3)_2$, —$CH_2CH_2CH_3$, —$CH(CH_2CH_3)_2$, —$CD_2CD_2CD_3$, —$CD(CD_2CD_3)_2$, —$CF_2CF_2CF_3$, —$CF(CF_2CF_3)_2$, —$C(CH_2CH_3)_3$, —$C(CD_2CD_3)_3$, —$C(CF_2CF_3)_3$, —$OCH_2CH_2CH_3$, —$OCH(CH_2CH_3)_2$, —$OCD_2CD_2CD_3$, —$OCD(CD_2CD_3)_2$, —$OCF_2CF_2CF_3$ or —$OCF(CF_2CF_3)_2$. In some embodiments of the compound E-F, $R_{10}$ is H, D, F, —$CH_3$, —$OCH_3$, —$CD_3$, —$OCD_3$, —$CH_2F$, —$OCH_2F$, —$CHF_2$, —$OCHF_2$, —$CF_3$, —$OCF_3$, —$CH_2CH_3$ or —$CH(CH_3)_2$. In some embodiments of the compound E-F, $R_{10}$ is H, D, F, —CH₃, —CH₂F, —CHF₂, or —CF₃. In some embodiments of the compound E-F, R₁₀ is H, D or F. In some embodiments of the compound E-F, R₁₀ is —CH₃ or —CF₃. In some embodiments of the compound E-F, R₁₀ is —H or —CH₃. In some embodiments of the compound E-F, R₁₀ is H. In some embodiments of the compound E-F, R₁₀ is —CH₃. In some embodiments of the compound E-F, R₁₀ is F. In some embodiments of the compound E-F, R₁₀ is absent.

In some embodiments of the compound E-F, Rn is H, methyl or ethyl. In some embodiments of the compound E-F, Rn is H. In some embodiments of the compound E-F, R₁ is methyl. In some embodiments of the compound E-F, Rn is ethyl.

In some embodiments of the compound E-F, each instance of R₁₂, R₁₃ or R₁₄ is independently H, D, F, —CH₃, —OCH₃, —CD₃, —OCD₃, —CH₂F, —OCH₂F, —CHF₂, —OCHF₂, —CF₃, —OCF₃, —CH₂CH₃, —CH(CH₃)₂, —CH₂CH₂CH₃, —CH(CH₂CH₃)₂, —C(CH₃)₃, —OCH₂CH₃, —OCH(CH₃)₂, —OCH₂CH₂CH₃, —OCH(CH₂CH₃)₂, or —OC(CH₃)₃. In some embodiments of the compound E-F, each instance of R₁₂, R₁₃ or R₁₄ is independently H, D, F, —CH₃, —OCH₃, —CD₃, —OCD₃, —CH₂F, —OCH₂F, —CHF₂, —OCHF₂, —CF₃ or —OCF₃. In some embodiments of the compound E-F, each instance of R₁₂, R₁₃ or R₁₄ is independently H, D, F, —CH₃, —CD₃ or —CF₃. In some embodiments of the compound E-F, each instance of R₁₂, R₁₃ or R₁₄ is independently H, D, or F. In some embodiments of the compound E-F, each instance of R₁₂, R₁₃ or R₁₄ is independently H, F or —CH₃. In some embodiments of the compound E-F, each instance of R₁₂, R₁₃ or R₁₄ is H. In some embodiments of the compound E-F, each instance of R₁₂, R₁₃ or R₁₄ is D. In some embodiments of the compound E-F, each instance of R₁₂, R₁₃ or R₁₄ is F.

In some embodiments of the compound E-F, R₂₀ is H, D, F, —CH₃, —CD₃, —CH₂F, —CHF₂, —CF₃, —CH₂CH₃, —CH₂CH₂CH₃, —CH(CH₃)₂, —C(CH₃)₃, —CH₂CH₂CH₂CH₃, —CH₂CH₂CH₂CH₂CH₃, —CH₂CH₂CH₂CH₂CH₂CH₃, —CH₂CH₂CH₂CH₂CH₂CH₂CH₃, —CH₂CH₂CH₂CH₂CH₂CH₂CH₂CH₃, —CH₂CH₂CH₂CH₂CH₂CH₂CH₂CH₂CH₃ or —CH₂CH₂CH₂CH₂CH₂CH₂CH₂CH₂CH₂CH₃. In some embodiments of the compound E-F, R₂₀ is H, D, F, —CH₃, —CD₃, —CH₂F, —CHF₂, —CF₃, —CH₂CH₃, —CH₂CH₂CH₃, —CH(CH₃)₂ or —C(CH₃)₃. In some embodiments of the compound E-F, R₂₀ is H, D, F, —CH₃, —CD₃, —CH₂F, —CHF₂ or —CF₃. In some embodiments of the compound E-F, R₂₀ is H, D, F, —CH₃, —CD₃, —CH₂F, —CHF₂ or —CF₃. In some embodiments of the compound E-F, R₂₀ is —CH₃, —CD₃, —CH₂F, —CHF₂ or —CF₃. In some embodiments of the compound E-F, R₂₀ is H. In some embodiments of the compound E-F, R₂₀ is —CH₃. In some embodiments of the compound E-F, R₂₀ is —CF₃. In some embodiments of the compound E-F, R₂₀ is F.

In some embodiments of the compound E-F, each R₂₁ is independently H, D, F, —CH₃, —CD₃, —CH₂F, —CHF₂, —CF₃, —CH₂CH₃, —CH₂CH₂CH₃, —CH(CH₃)₂, —CH₂CH₂CH₂CH₃ or —C(CH₃)₃. In some embodiments of the compound E-F, each R₂₁ is independently H, D, F, —CH₃, —CD₃, —CH₂F, —CHF₂ or —CF₃. In some embodiments of the compound E-F, each R₂₁ is independently H, —CH₃ or —CF₃. In some embodiments of the compound E-F, each R₂₁ is —CH₃. In some embodiments of the compound E-F, each R₂₁ is H. In some embodiments of the compound E-F, each R₂₁ is —CF₃.

In some embodiments of the compound E-F, n is 0, 1, 2, 3, 4, 5, 6, 7 or 8. In some embodiments of the compound E-F, n is 0, 1, 2, 3, 4, 5 or 6. In some embodiments of the compound E-F, n is 0, 1, 2, 3 or 4. In some embodiments of the compound E-F, n is 0. In some embodiments of the compound E-F, n is 1. In some embodiments of the compound E-F, n is 2. In some embodiments of the compound E-F, n is 3. In some embodiments of the compound E-F, n is 4. In some embodiments of the compound E-F, n is 5. In some embodiments of the compound E-F, n is 6. In some embodiments of the compound E-F, n is 7. In some embodiments of the compound E-F, n is 8. In some embodiments of the compound E-F, n is 9. In some embodiments of the compound E-F, n is 10. In some embodiments of the compound E-F, n is 11. In some embodiments of the compound E-F, n is 12.

In some embodiments of the compound E-F has the formula referred to herein as Compound A:

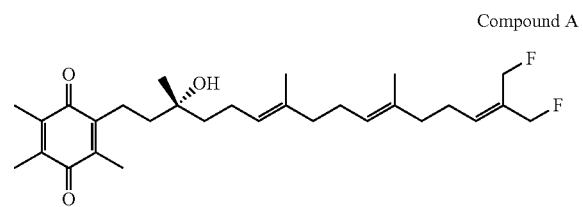 [SMILES: CC1=C(C)C(=O)C(CC[C@](C)(O)CC/C=C(\C)CC/C=C(\C)CCC=C(CF)CF)=C(C)C1=O]

Compound A

In some embodiments of the compound E-F has the formula referred to herein as Compound B:

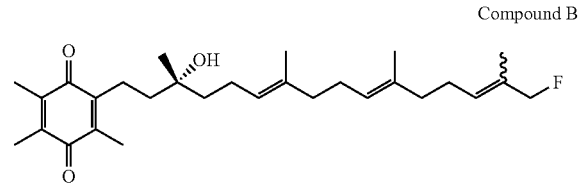

Compound B

In some embodiments of the compound E-F has the formula referred to herein as Compound C:

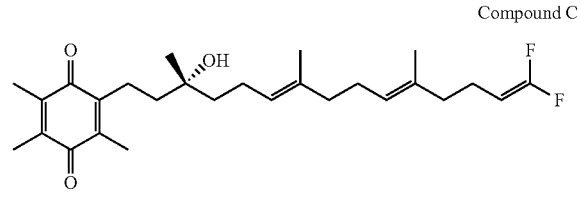 [SMILES: CC1=C(C)C(=O)C(CC[C@](C)(O)CC/C=C(\C)CC/C=C(\C)CCC=C(F)F)=C(C)C1=O]

Compound C

In some embodiments of the compound E-F has the formula referred to herein as Compound D:

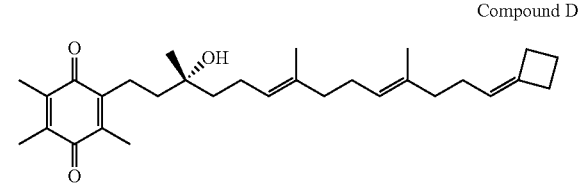 [SMILES: CC1=C(C)C(=O)C(CC[C@](C)(O)CC/C=C(\C)CC/C=C(\C)CCC=C2CCC2)=C(C)C1=O]

Compound D

In some embodiments of the compound E-F has the formula referred to herein as Compound E:

Compound E

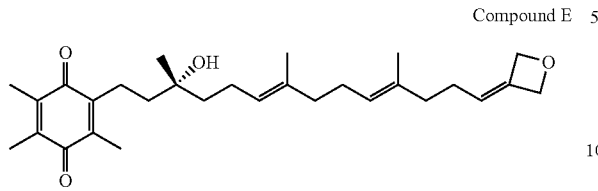

In some embodiments of the compound E-F has the formula referred to herein as Compound F:

Compound F

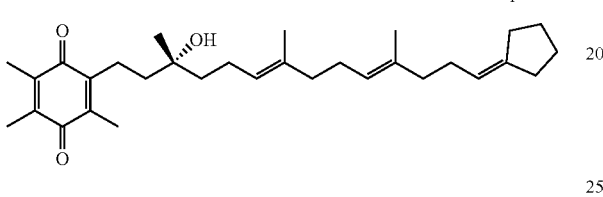

In some embodiments of the compound E-F has the formula referred to herein as Compound G:

Compound G

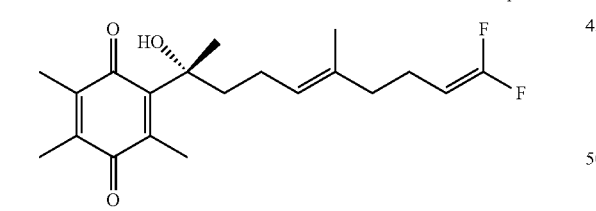

In some embodiments of the compound E-F has the formula referred to herein as Compound H:

Compound H

In some embodiments of the compound E-F has the formula referred to herein as Compound I:

Compound I

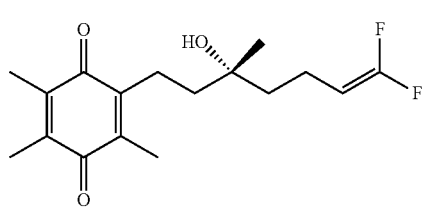

In some embodiments of the compound E-F has the formula referred to herein as Compound J:

Compound J

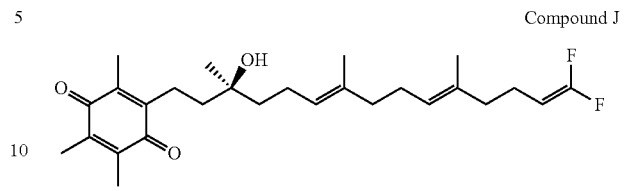

In some embodiments of the compound E-F has the formula referred to herein as Compound K:

Compound K

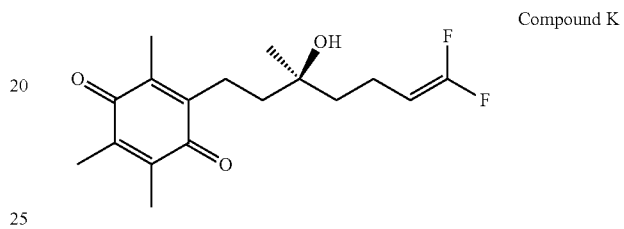

In some embodiments of the compound E-F has the formula referred to herein as Compound L:

Compound L

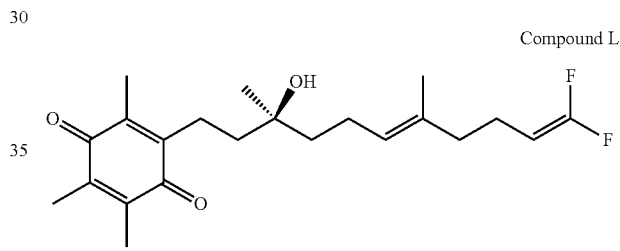

In some embodiments of the compound E-F has the formula referred to herein as Compound N:

Compound N

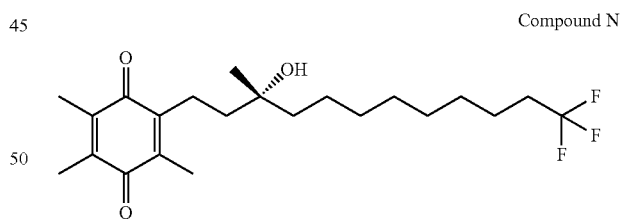

As illustrated in Examples 17 & 18, below, certain compounds disclosed herein exhibit a high degree of potency in the BSO Assay (Example 17) and in the Rotenone ATP Assay (Example 18). More specifically, for several of the compounds disclosed herein the potency and efficacy is similar to or greater than that of vatiquinone with respect to ameliorating the effects of Friedreich's ataxia in a cell-based assay (See: Example 17; BSO Assay). Similarly, several of the compounds disclosed herein are also effective in rescuing cells exhibiting an induced Complex I deficiency in the Rotenone ATP Assay (Example 18). In many cases, compounds disclosed herein have fair to good activity in both the BSO Assay and the Rotenone ATP Assay (See: Examples 17

& 18 and Table 2). By comparison, while several currently available therapeutics such as vatiquinone, idebenone or omaveloxolone may exhibit good or fair activity in one or the other of the BSO Assay or the Rotenone ATP Assay (See: Table 2, below), none of them are active in both assays, thereby suggesting that compounds disclosed herein may exhibit a unique mechanism of action and therefore be superior therapeutics as compared with compounds currently being evaluated as therapeutic agents for treatment of certain mitochondrial diseases (e.g. Friedreich's ataxia) in clinical trials. Thus, it is believed that the therapeutic compounds disclosed herein will prove to be superior agents for the treatment of certain mitochondrial diseases, such as Friedreich's ataxia. The aforementioned compounds can be used in the preparation of compositions, such as medicaments. Said compounds or compositions can thus be used in the treatment and/or prevention of mitochondrial disease, such as Friedreich's ataxia.

As further illustrated by Examples 19-22 (in combination with Examples 17 and 18), compounds disclosed herein exhibit the unique ability to protect cells from BSO induced ferroptosis; protect cells from RSL3 induced ferroptosis; and exhibit Complex I by-pass activity. No prior art compounds appear to possess this unique combination of properties that are therapeutically valuable in treating mitochrial disease, such as Freidreich's ataxia.

(b) Intermediates to Therapeutic Agents

In addition to the novel agents provided herein for the treatment of Friedreich's ataxia, novel intermediates to said novel agents are provided. In some embodiments, those intermediates are compounds of formula A-B: or pharmaceutically acceptable salts, stereoisomers, mixtures of stereoisomers, tautomers, hydrates, and/or solvates thereof, wherein A is 1, 2, 3 or 4:

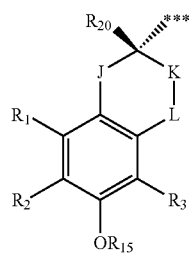

1

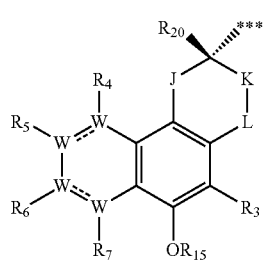

2

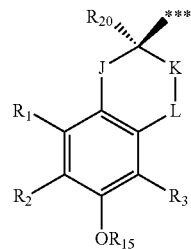

3

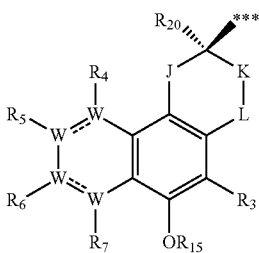

4 and B is 5, 6, 7 or 8

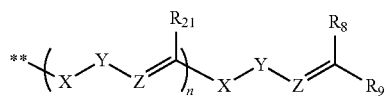

5

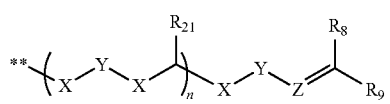

6

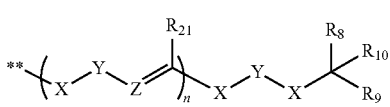

7

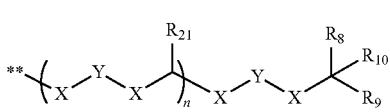

8 wherein, J is O, S or N—$R_{11}$, K is absent or —$(CR_{12}R_{13})$—, L is —$(CR_{12}R_{13})$—, each W is $=$ independently C (carbon) or N (nitrogen) and wherein for each use of w$=$w, the bond between each W can be a single bond or double bond and further provided that if a single bond, each C (carbon) atom will have a hydrogen atom linked hereto in addition to one of $R_4$, $R_5$, $R_6$ or $R_7$ and in either case each of $R_4$, $R_5$, $R_6$ and $R_7$ attached thereto is independently selected from H, D, F, Cl, Br, I, $C_1$-$C_6$ alkyl and $C_1$-$C_6$ alkoxy, and if W is N (nitrogen), each of $R_4$, $R_5$, $R_6$ and $R_7$ attached thereto is independently absent (if w$=$w is a double bond) or selected from H, D and $C_1$-$C_6$ alkyl (if w$=$w is a single bond), each X is independently a group of formula —$(CR_{12}R_{13})$—, each Y is independently absent or a group of formula —$(CR_{12}R_{13})$—, each Z is independently a group of formula —$(CR_{14})$—, each of $R_1$, $R_2$ and $R_3$ is independently H, D, F, Cl, Br, I, $C_1$-$C_6$ alkyl or $C_1$-$C_6$ alkoxy; or $R_1$ and $R_2$ together form a 5-membered carbocyclic ring, a 5-membered heterocyclic ring, a 5-membered aromatic or heteroaromatic ring or a 6-membered heterocyclic ring, each $R_8$ and $R_9$ is each independently H, D, F, Cl, Br, I or $C_1$-$C_4$ alkyl; or taken together $R_8$ and $R_9$ form a 3-, 4-, 5-, 6-, or 7-membered carbocyclic or heterocyclic ring, $R_{10}$ is H, D, F, Cl, Br, I, $C_1$-$C_6$ alkyl or $C_1$-$C_6$ alkoxy, $R_1$ is H, D or $C_1$-$C_6$ alkyl, each instance of $R_{12}$, $R_{13}$ and $R_{14}$ is independently H, D, F, Cl, Br, I, $C_1$-$C_6$ alkyl or $C_1$-$C_6$ alkoxy, $R_{15}$ is H, —$CH_3$, —$CH_2CH_3$ or PG, wherein PG is a phenol protecting group, $R_{20}$ is H, D, F or $C_1$-$C_{12}$ alkyl, each $R_{21}$ is independently H, D, F, Cl, Br, I, or $C_1$-$C_4$ alkyl, n is an integer from 0 to 12, inclusive, and indicates the point of attachment of A to B and ** indicates the point of attachment of C to D; and further provided that: (i) at least one group of formula $R_1$, $R_2$, $R_3$, $R_4$, $R_5$, $R_6$, $R_7$, $R_8$, $R_9$, $R_{10}$, $R_{12}$, $R_{13}$, $R_{14}$, $R_{20}$ or $R_{21}$ comprises at least one fluorine atom; and/or (ii) $R_8$ and $R_9$ taken together form a 3-, 4-, 5-, 6- or 7-membered carbocyclic or heterocyclic ring. In some embodiments, at least one of $R_8$ and $R_9$ is fluorine or a substituted $C_1$-$C_4$ alkyl group comprising at least one fluorine. In some embodiments, each of $R_8$ and $R_9$ is independently fluorine or a substituted $C_1$-$C_4$ alkyl group comprising at least one fluorine. In some embodiments, each of $R_8$ and $R_9$ is fluorine. In some embodiments, each of $R_8$, $R_9$ and $R_{10}$ is fluorine. In some embodiments, each of $R_8$, $R_9$ and $R_{10}$ is independently fluorine or a substituted $C_1$-$C_4$ alkyl group comprising at least one fluorine. In some embodiments of A-B, $R_{15}$ is H.

Any combination of 1, 2, 3 and 4 with 5, 6, 7 or 8 is permissible. In some embodiments, A is 1 and B is 5, 6, 7 or 8. In some embodiments, A is 2 and B is 5, 6, 7 or 8. In some embodiments, A is 3 and B is 5, 6, 7 or 8. In some embodiments, A is 4 and B is 5, 6, 7 or 8. In some embodiments, A is 1 and B is 5. In some embodiments, A is 1 and B is 6. In some embodiments, A is 1 and B is 7. In some embodiments, A is 1 and B is 8. In some embodiments, A is 2 and B is 5. In some embodiments, A is 2 and B is 6. In some embodiments, A is 2 and B is 7. In some embodiments, A is 2 and B is 8. In some embodiments, A is 3 and B is 5. In some embodiments, A is 3 and B is 6. In some embodiments, A is 3 and B is 7. In some embodiments, A is 3 and B is 8. In some embodiments, A is 4 and B is 5. In some embodiments, A is 4 and B is 6. In some embodiments, A is 4 and B is 7. In some embodiments, A is 4 and B is 8.

The atom or group represented by J can be O, S or N—$R_{11}$. In some embodiments, J is O (oxygen). In some embodiments, J is S (sulfur). In some embodiment, J is N—$R_{11}$, wherein $R_1$ is defined below. In some embodiments, J is O or N—$R_{11}$ and K is absent.

In some embodiments, the groups represented by K and L can each independently be: —($CH_2$)—, —($CD_2$)-, —(CHF)—, —($CF_2$)—, —(CH($CH_3$))—, —(CD($CD_3$))—, —(CF($CH_3$))—, —(CH($CF_3$))—, —(CF($CF_3$))—, —(C($CH_3$)$_2$)—, —(C($CD_3$)$_2$)—, —(C($CF_3$)$_2$), —(CH(O$CH_3$))—, —(CD(O$CD_3$))—, —(CF(O$CH_3$))—, —(CH(O$CF_3$))—, —(CF(O$CF_3$))—, —(C(O$CH_3$)$_2$)—, —(C(O$CD_3$)$_2$)—, —(C(O$CF_3$)$_2$)—, —(C($CH_3$)($CF_3$))—, —(C($CD_3$)($CF_3$))—, —(CH($CH_2CH_3$))—, —(CD($CD_2CD_3$))—, —(CF($CH_2CH_3$))—, —(CH($CH_2CF_3$))—, —(CH($CF_2CF_3$))—, —(CF($CF_2CF_3$))—, —(C($CH_2CH_3$)$_2$)—, —(C($CD_2CD_3$)$_2$)— or —(C($CF_2CF_3$)$_2$)—. In some embodiments, K is absent and L is —($CH_2$)—, —($CD_2$)-, —(CHF)—, —($CF_2$)—, —(CH($CH_3$))—, —(CD($CD_3$))—, —(CF($CH_3$))—, —(CH($CF_3$))—, —(CF($CF_3$))—, —(C($CH_3$)$_2$)—, —(C($CD_3$)$_2$)—, —(C($CF_3$)$_2$), —(CH(O$CH_3$))—, —(CD(O$CD_3$))—, —(CF(O$CH_3$))—, —(CH(O$CF_3$))—, —(CF(O$CF_3$))—, —(C(O$CH_3$)$_2$)—, —(C(O$CD_3$)$_2$)—, —(C(O$CF_3$)$_2$)—, —(C($CH_3$)($CF_3$))—, —(C($CD_3$)($CF_3$))—, —(CH($CH_2CH_3$))—, —(CD($CD_2CD_3$))—, —(CF($CH_2CH_3$))—, —(CH($CH_2CF_3$))—, —(CH($CF_2CF_3$))—, —(CF($CF_2CF_3$))—, —(C($CH_2CH_3$)$_2$)—, —(C($CD_2CD_3$)$_2$)— or —(C($CF_2CF_3$)$_2$)—. In some embodiments, each of K and L is independently —$CH_2$—, —$CD_2$-, —$CF_2$—, —CH($CH_3$)—, —CD($CD_3$)—, —CF($CF_3$)—, —C($CH_3$)$_2$—, —C($CD_3$)$_2$-, —C($CF_3$)$_2$, —CH(O$CH_3$)—, —CD(O$CD_3$)—, —CF(O$CF_3$)—, or —C(O$CH_3$)$_2$—. In some embodiments, K is absent and L is —($CH_2$)—, —($CD_2$)-, —($CF_2$)—, —(CH($CH_3$))—, —(CD($CD_3$))—, —(CF($CF_3$))—, —(C($CH_3$)$_2$)—, —(C($CD_3$)$_2$)—, —(C($CF_3$)$_2$)—, —(CH(O$CH_3$))—, —(CD(O$CD_3$))—, —(CF(O$CF_3$))— or —(C(O$CH_3$)$_2$)—. In some embodiments, each of K and L is independently —($CH_2$)—, —($CD_2$)-, —(CHF)—, —($CF_2$)—, —(CH($CH_3$))—, —(CF($CF_3$))—, —(C($CH_3$)$_2$)— or —(C($CF_3$)$_2$)—. In some embodiments, K is absent and L is —($CH_2$)—, —($CD_2$)-, —(CHF)—, —($CF_2$)—, —(CH($CH_3$))—, —(CF($CF_3$))—, —(C($CH_3$)$_2$)— or —(C($CF_3$)$_2$)—. In some embodiments, each of K and L is independently —($CH_2$)—, —($CD_2$)-, —(CHF)— or —($CF_2$)—. In some embodiments, K is absent and L is —($CH_2$)—, —($CD_2$)-, —(CHF)— or —($CF_2$)—. In some embodiments, each of K and L are —($CH_2$)—. In some embodiments, K is absent and L is —($CH_2$)—. In some embodiments, each of K and L are —($CD_2$)-. In some embodiments, K is absent and L is —($CD_2$)-. In some embodiments, each of K and L are —($CF_2$)—. In some embodiments, K is absent and L is —($CF_2$)—.

In some embodiments of the compound represented by A-B, wherein A is 1 or 3, each of $R_1$, $R_2$ and $R_3$ is independently H, D, Cl, F, —$CH_3$, —O$CH_3$, —$CD_3$, —O$CD_3$, —$CH_2$F, —O$CH_2$F, —$CHF_2$, —O$CHF_2$, —$CF_3$, —O$CF_3$, —$CH_2CH_3$, —CH($CH_3$)$_2$, —$CD_2CD_3$, —CD($CD_3$)$_2$, —$CF_2CH_3$, CF($CH_3$)$_2$, —$CH_2CF_3$, —CH($CF_3$)$_2$, —$CF_2CF_3$, —CF($CF_3$)$_2$, —C($CH_3$)$_3$, —C($CD_3$)$_3$, —C($CF_3$)$_3$, —O$CH_2CH_3$, —OCH($CH_3$)$_2$, —O$CD_2CD_3$, —OCD($CD_3$)$_2$, —O$CF_2CH_3$, —OCF($CH_3$)$_2$, —O$CH_2CF_3$, —OCH($CF_3$)$_2$, —O$CF_2$($CF_3$), —OCF($CF_3$)$_2$, —OC($CH_3$)$_3$, —OC($CD_3$)$_3$, —OC($CF_3$)$_3$, —C($CH_3$)$_2$($CF_3$), —C($CH_3$)($CF_3$)$_2$, —OC($CH_3$)$_2$($CF_3$), —OC($CH_3$)($CF_3$)$_2$, —$CH_2CH_2CH_3$, —CH($CH_2CH_3$)$_2$, —$CD_2CD_2CD_3$, —CD($CD_2CD_3$)$_2$, —$CF_2CH_2CH_3$, —CF($CH_2CH_3$)$_2$, —$CH_2CF_2CF_3$, —CH($CF_2CF_3$)$_2$, —$CF_2CF_2CF_3$, —CF($CF_2CF_3$)$_2$, —O$CH_2CH_2CH_3$, —OCH($CH_2CH_3$)$_2$, —O$CD_2CD_2CD_3$, —OCD($CD_2CD_3$)$_2$, —O$CF_2CH_2CH_3$, —OCF($CH_2CH_3$)$_2$, —O$CH_2CF_2CF_3$, —OCH($CF_2CF_3$)$_2$, —O$CF_2CF_2CF_3$ or —OCF($CF_2CF_3$)$_2$. In some embodiments of the compound represented by A-B, wherein A is 1 or 3, each of $R_1$, $R_2$ and $R_3$ is independently H, D, Cl, F, —$CH_3$, —O$CH_3$, —$CD_3$, —O$CD_3$, —$CH_2$F, —$CHF_2$, —$CF_2$—, —O$CF_3$, —C($CH_3$)$_3$, —C($CD_3$)$_3$, —C($CF_3$)$_3$, —OC($CH_3$)$_3$, —OC($CD_3$)$_3$, —OC($CF_3$)$_3$, —$CH_2CH_3$, —O$CH_2CH_3$, or —CH($CH_3$)$_2$. In some embodiments of the compound represented by A-B, wherein A is 1 or 3, each of $R_1$, $R_2$ and $R_3$ is independently H, F, —$CH_3$, —O$CH_3$, —$CH_2$F, —$CHF_2$, —$CF_3$, —O$CF_3$, —C($CH_3$)$_3$, —C($CF_3$)$_3$, —$CH_2CH_3$, —O$CH_2CH_3$ or —CH($CH_3$)$_2$. In some embodiments of the compound represented by A-B, wherein A is 1 or 3, each of $R_1$, $R_2$ and $R_3$ is independently H, F, —$CH_3$, —O$CH_3$, —$CH_2$F, —$CHF_2$, —$CF_3$ or —O$CF_3$. In some embodiments of the compound represented by A-B, wherein A is 1 or 3, each of $R_1$, $R_2$ and $R_3$ is independently H, F, —$CH_3$, —$CF_3$, —O$CH_3$ or —O$CF_3$. In some embodiments of the compound represented by A-B, wherein A is 1 or 3, each of $R_1$, $R_2$ and $R_3$ is independently H, F, —$CH_3$, —O$CH_3$ or —$CF_3$. In some embodiments of the compound represented by A-B, wherein A is 1 or 3, each of $R_1$, $R_2$ and $R_3$ is —$CH_3$. In some embodiments of the compound represented by A-B, wherein A is 1 or 3, each of $R_1$, $R_2$ and $R_3$ is H. In some embodiments of the compound represented by A-B, wherein A is 1 or 3, each of $R_1$, $R_2$ and $R_3$ is independently H or —$CH_3$. In some embodiments of the compound represented by A-B, wherein A is 1 or 3, each of $R_1$, $R_2$ and $R_3$ is independently H or —$OCH_3$. In some embodiments of the compound represented by A-B, wherein A is 1 or 3, each of $R_1$, $R_2$ and $R_3$ is independently H, —$CH_3$ or —$OCH_3$. In some embodiments of the compound represented by A-B, wherein A is 1 or 3, each of $R_1$ and $R_2$ is —$OCH_3$ and $R_3$ is —$CH_3$. In some embodiments of the compound represented by A-B, wherein A is 1 or 3, each of $R_1$ and $R_2$ is —$OCH_3$ and $R_3$ is H. In some embodiments of the compound represented by A-B, wherein A is 1 or 3, each of $R_1$ and $R_2$ is —$CH_3$ and $R_3$ is H. In some embodiments of the compound represented by A-B, wherein A is 1 or 3, each of $R_1$ and $R_2$ is —$OCH_3$ and $R_3$ is H. In some embodiments of the compound represented by A-B, wherein A is 1 or 3, at least one of $R_1$, $R_2$ and $R_3$ is F.

In some embodiments of the compound represented by A-B, wherein A is 1 or 3, J is O, each of K and L is independently —($CH_2$)—, —($CD_2$)-, —(CHF)—, —($CF_2$)—, —($CH(CH_3)$)—, —($CF(CF_3)$)—, —($C(CH_3)_2$)— or —($C(CF_3)_2$)—; and each of $R_1$, $R_2$ and $R_3$ is independently H, F, —$CH_3$, —$OCH_3$, —$CH_2F$, —$CHF_2$, —$CF_3$, —$OCF_3$, —$C(CH_3)_3$, —$C(CF_3)_3$, —$CH_2CH_3$, —$OCH_2CH_3$ or —$CH(CH_3)_2$. In some embodiments of the compound represented by A-B, wherein A is 1 or 3, J is O, each of K and L is independently —($CH_2$)—, —($CD_2$)-, —(CHF)— or —($CF_2$)—; and each of $R_1$, $R_2$ and $R_3$ is independently H, F, —$CH_3$, —$OCH_3$, —$CH_2F$, —$CHF_2$, —$CF_3$ or —$OCF_3$. In some embodiments of the compound represented by A-B, wherein A is 1 or 3, J is O, each of K and L is independently —($CH_2$)—, —($CD_2$)-, —(CHF)— or —($CF_2$)—; and each of $R_1$, $R_2$ and $R_3$ is independently H, F, —$CH_3$, —$OCH_3$, —$CF_3$ or —$OCF_3$. In some embodiments of the compound represented by A-B, wherein A is 1 or 3, J is O; each of K and L is —($CH_2$)—; and each of $R_1$, $R_2$ and $R_3$ is —$CH_3$. In some embodiments of the compound represented by A-B, wherein A is 1 or 3, J is O; each of K and L is —($CH_2$)—; and each of $R_1$, $R_2$ and $R_3$ is H. In some embodiments of the compound represented by A-B, wherein A is 1 or 3, J is O; each of K and L is —($CH_2$)—; each of $R_1$ and $R_2$ is —$OCH_3$ and $R_3$ is —$CH_3$. In some embodiments of the compound represented by A-B wherein A is 1 or 3, J is O; each of K and L is —($CH_2$)—; each of $R_1$, $R_2$ and $R_3$ is independently H or —$OCH_3$. In some embodiments of the compound represented by A-B wherein A is 1 or 3, J is O; each of K and L is —($CH_2$)—; each of $R_1$, $R_2$ and $R_3$ is independently H, —$CH_3$ or —$OCH_3$. In some embodiments of the compound represented by A-B wherein A is 1 or 3, J is O; each of K and L is —($CH_2$)—; each of $R_1$ and $R_2$ is —$OCH_3$ and $R_3$ is —$CH_3$. In some embodiments of the compound represented by A-B wherein A is 1 or 3, J is O; each of K and L is —($CH_2$)—; each of $R_1$ and $R_2$ is —$OCH_3$ and $R_3$ is —$CH_3$. In some embodiments of the compound represented by A-B wherein A is 1 or 3, J is O; each of K and L is —($CH_2$)—; each of $R_1$ and $R_2$ is —$CH_3$ and $R_3$ is H. In some embodiments of the compound represented by A-B, wherein A is 1 or 3, J is O; each of K and L is —($CH_2$)—; each of $R_1$ and $R_2$ is —$OCH_3$ and $R_3$ is H. In some embodiments of the compound represented by A-B, wherein A is 1 or 3, each of K and L is —($CH_2$)— and at least one of $R_1$, $R_2$ and $R_3$ is F.

In some embodiments of the compound represented by A-B, wherein A is 1 or 3, $R_3$ is H, D, $C_1$, F, —$CH_3$, —$OCH_3$, —$CD_3$, —$OCD_3$, —$CF_3$, —$OCF_3$, —$C(CH_3)_3$, —$C(CD_3)_3$, —$C(CF_3)_3$, —$OC(CH_3)_3$, —$OC(CD_3)_3$, —$OC(CF_3)_3$, —$CH_2CH_3$, —$OCH_2CH_3$, or —$CH(CH_3)_2$ and $R_1$ and $R_2$ taken together form a 5-, or 6-membered carbocyclic or heterocyclic ring. In some embodiments of the compound represented by A-B, wherein A is 1 or 3, (i) $R_3$ is H, F, —$CH_3$, or —$OCH_3$, and (ii) $R_1$ and $R_2$ taken together form a 5-, or 6-membered carbocyclic or heterocyclic ring. In some embodiments of the compound represented by A-B, wherein A is 1 or 3, (i) $R_3$ is H; and (ii) $R_1$ and $R_2$ taken together form a 5-, or 6-membered carbocyclic or heterocyclic ring. In some embodiments of the compound represented by A-B, wherein A is 1 or 3, (i) $R_3$ is —$CH_3$; and (ii) $R_1$ and $R_2$ taken together form a 5-, or 6-membered carbocyclic or heterocyclic ring. In some embodiments of the compound represented by A-B, wherein A is 1 or 3, (i) $R_3$ is —$OCH_3$; and (ii) $R_1$ and $R_2$ taken together form a 5-, or 6-membered carbocyclic or heterocyclic ring. In some embodiments of the compound represented by A-B, wherein A is 1 or 3, (i) $R_3$ is F; and (ii) $R_1$ and $R_2$ taken together form a 5-, or 6-membered carbocyclic or heterocyclic ring.

In some embodiments, $R_1$ and $R_2$ of 1 or 3, taken together, form a heterocycle as represented in 1A, 1B, 1C, 1D, 1E, 1F, 3A, 3B, 3C, 3D, 3E or 3F:

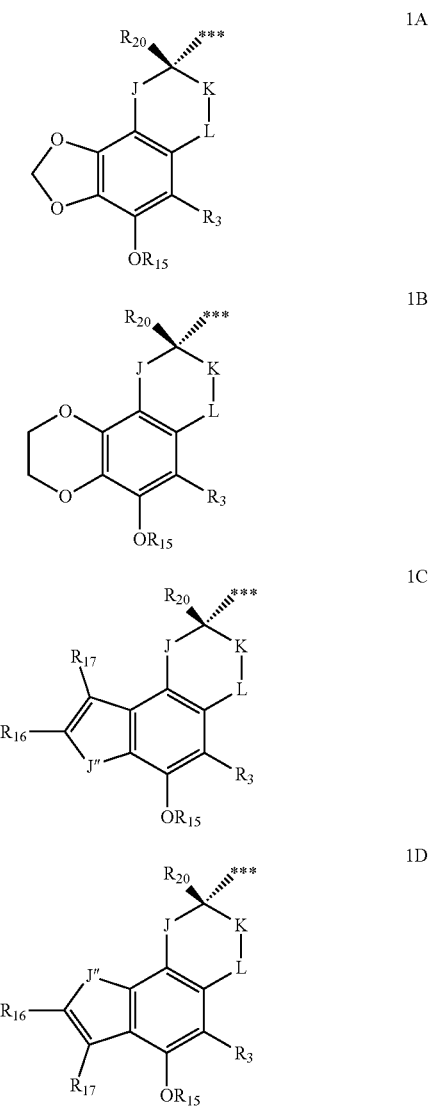

-continued

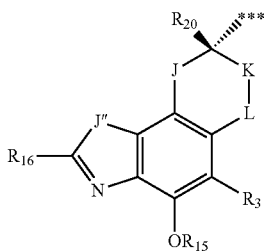
1E

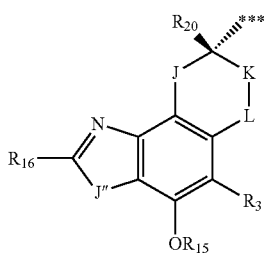
1F

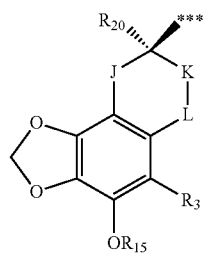
3A

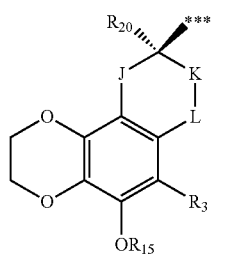
3B

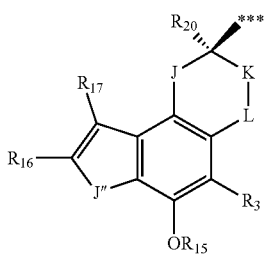
3C

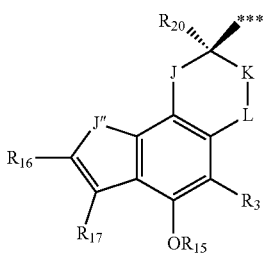
3D

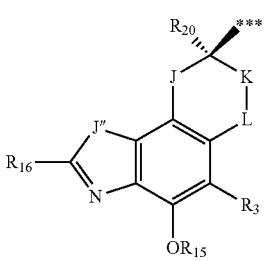
3E

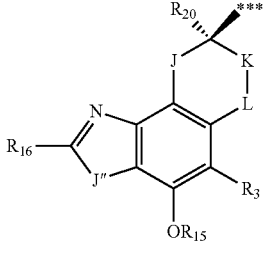
3F wherein each of $R_{16}$ and $R_{17}$ is independently H, D, Cl, F, —CH$_3$, —OCH$_3$, —CD$_3$, —OCD$_3$, —CH$_2$F, —CHF$_2$, —CF$_3$, —OCF$_3$, —C(CH$_3$)$_3$, —C(CD$_3$)$_3$, —C(CF$_3$)$_3$, —OC(CH$_3$)$_3$, —OC(CD$_3$)$_3$, —OC(CF$_3$)$_3$, —CH$_2$CH$_3$, —OCH$_2$CH$_3$, —CH(CH$_3$)$_2$, —OCH(CH$_3$)$_2$, —C(CH$_3$)$_3$ or —O(CH$_3$)$_3$; and J" is O, S or N—R$_{18}$, wherein R$_{18}$ is H, D, —CH$_3$, —CH$_2$F, —CHF$_2$ or —CF$_3$. In some embodiments, $R_{16}$ and $R_{17}$ are each independently H, D, Cl, F, —CH$_3$, —OCH$_3$, —CD$_3$, —OCD$_3$, —CH$_2$F, —CHF$_2$, —CF$_3$, or —OCF$_3$. In some embodiments, $R_{16}$ and $R_{17}$ are each independently H, D, F, or —CH$_3$. In some embodiments, $R_{16}$ and $R_{17}$ are H. In some embodiments, $R_{16}$ and $R_{17}$ are F. In some embodiments, $R_{16}$ and $R_{17}$ are —CH$_3$. In some embodiments, $R_{18}$ is H or —CH$_3$.

In some embodiments of the compound represented by A-B wherein A is 2 or 4, $R_3$ is H, D, C$_1$, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, —CH(CH$_3$)$_2$, —CD$_2$CD$_3$, —CD(CD$_3$)$_2$, —CF$_2$CH$_3$, CF(CH$_3$)$_2$, —CH$_2$CF$_3$, —CH(CF$_3$)$_2$, —CF$_2$CF$_3$, —CF(CF$_3$)$_2$, —C(CH$_3$)$_3$, —C(CD$_3$)$_3$, —C(CF$_3$)$_3$, —OCH$_2$CH$_3$, —OCH(CH$_3$)$_2$, —OCD$_2$CD$_3$, —OCD(CD$_3$)$_2$, —OCF$_2$CH$_3$, —OCF(CH$_3$)$_2$, —OCH$_2$CF$_3$, —OCH(CF$_3$)$_2$, —OCF$_2$(CF$_3$), —OCF(CF$_3$)$_2$, —OC(CH$_3$)$_3$, —OC(CD$_3$)$_3$, —OC(CF$_3$)$_3$, —C(CH$_3$)$_2$(CF$_3$), —C(CH$_3$)(CF$_3$)$_2$, —OC(CH$_3$)$_2$(CF$_3$), —OC(CH$_3$)(CF$_3$)$_2$, —CH$_2$CH$_2$CH$_3$, —CH(CH$_2$CH$_3$)$_2$, —CD$_2$CD$_2$CD$_3$, —CD(CD$_2$CD$_3$)$_2$, —CF$_2$CH$_2$CH$_3$, —CF(CH$_2$CH$_3$)$_2$, —CH$_2$CF$_2$CF$_3$, —CH(CF$_2$CF$_3$)$_2$, —CF$_2$CF$_2$CF$_3$, —CF(CF$_2$CF$_3$)$_2$, —OCH$_2$CH$_2$CH$_3$, —OCH(CH$_2$CH$_3$)$_2$, —OCD$_2$CD$_2$CD$_3$, —OCD(CD$_2$CD$_3$)$_2$, —OCF$_2$CH$_2$CH$_3$, —OCF(CH$_2$CH$_3$)$_2$, —OCH$_2$CF$_2$CF$_3$, —OCH(CF$_2$CF$_3$)$_2$, —OCF$_2$CF$_2$CF$_3$ or —OCF(CF$_2$CF$_3$)$_2$; and where if W is C (carbon), each of $R_4$, $R_5$, $R_6$ and $R_7$ attached thereto is independently H, D, F, Cl, Br, I, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, or —CH(CH$_3$)$_2$; and where if W is N (nitrogen), each of $R_4$, $R_5$, $R_6$ and $R_7$ attached thereto is independently absent or selected from H, D, methyl, ethyl, isopropyl and t-butyl. In some embodiments, for each instance of w═w, the bond between each W is a single bond. In some embodiments, for each instance of w═w, the bond between each W is a double bond. In some embodiments, $R_3$ is H, D, Cl, F, —CH$_3$, —OCH$_3$, —CD$_3$, —OCD$_3$, —CH$_2$F, —CHF$_2$, —CF$_3$, —OCF$_3$, —C(CH$_3$)$_3$, —C $CD_3)_3$, $-C(CF_3)_3$, $-OC(CH_3)_3$, $-OC(CD_3)_3$, $-OC(CF_3)_3$, $-CH_2CH_3$, $-OCH_2CH_3$ or $-CH(CH_3)_2$; and where if W is C (carbon), each of $R_4$, $R_5$, $R_6$ and $R_7$ attached thereto is independently H, D, F, $C_1$, $-CH_3$, $-OCH_3$, $-CH_2F$, $-CHF_2$, $-CF_3$, $-OCF_3$, $-CH_2CH_3$, or $-CH(CH_3)_2$; and where if W is N (nitrogen), each of $R_4$, $R_5$, $R_6$ and $R_7$ attached thereto is independently absent or selected from H, D, methyl and ethyl. In some embodiments, each W is C (carbon) and each of $R_4$, $R_5$, $R_6$ and $R_7$ is independently H, D, Cl, F, $-CH_3$, $-OCH_3$, $-CH_2F$, $-CHF_2$, $-CF_3$ or $-OCF_3$. In some embodiments, each W is C (carbon) and each of $R_4$, $R_5$, $R_6$ and $R_7$ is independently H, D, Cl, F, $-CH_3$ or $-OCH_3$. In some embodiments, each W is C (carbon) and each of $R_4$, $R_5$, $R_6$ and $R_7$ is independently H, $-CH_3$ or $-OCH_3$. In some embodiments, each W is C (carbon) and each of $R_4$, $R_5$, $R_6$ and $R_7$ is H. In some embodiments, each W is C (carbon) and each of $R_4$, $R_5$, $R_6$ and $R_7$ is $-CH_3$.

In some embodiments of the compound A-B, each of $R_8$ and $R_9$ can be independently H, D, F, Cl, Br, I, $-CH_3$, $-CD_3$, $-CH_2F$, $-CHF_2$, $-CF_3$, $-CH_2CH_3$, $-CH(CH_3)_2$, $-CD_2CD_3$, $-CD(CD_3)_2$, $-CF_2CH_3$, $-CF(CH_3)_2$, $-CH_2CF_3$, $-CH(CF_3)_2$, $-CF_2CF_3$, $-CF(CF_3)_2$, $-C(CH_3)_3$, $-C(CD_3)_3$, $-C(CF_3)_3$, $-C(CH_3)_2(CF_3)$, $-C(CH_3)(CF_3)_2$, $-CH_2CH_2CH_3$, $-CH(CH_2CH_3)_2$, $-CD_2CD_2CD_3$, $-CD(CD_2CD_3)_2$, $-CF_2CH_2CH_3$, $-CF(CH_2CH_3)_2$, $-CH_2CF_2CF_3$, $-CH(CF_2CF_3)_2$, $-CF_2CF_2CF_3$ or $-CF(CF_2CF_3)_2$. In some embodiments of the compound A-B, each of $R_8$ and $R_9$ can be independently H, F, $-CH_3$, $-CH_2F$, $-CHF_2$, $-CF_3$, $-CH_2CH_3$, $-CH(CH_3)_2$, $-CF_2CH_3$, $-CH_2CF_3$, $-CH(CF_3)_2$, $-CF_2CF_3$, $-CF(CF_3)_2$, $-C(CH_3)_3$, $-C(CF_3)_3$, $-CH_2CH_2CH_3$, $-CH(CH_2CH_3)_2$, $-CF_2CF_2CF_3$ or $-CF(CF_2CF_3)_2$. In some embodiments of the compound A-B, each of $R_8$ and $R_9$ can be independently H, F, $-CH_3$, $-CH_2F$, $-CHF_2$, or $-CF_3$.

In some embodiments of the compound A-B, each of $R_8$ and $R_9$ can be independently a $C_1$-$C_4$ alkyl group. Said alkyl group can be, for example, substituted with one or more fluorine atoms. For example, said alkyl group can be fluoromethyl, difluoromethyl or trifluoromethyl.

In some embodiments of the compound A-B, $R_8$ and $R_9$, taken together, can form a 3-, 4-, 5-, 6- or 7-membered carbocyclic or heterocyclic ring. For example, the 3-, 4-, 5-, 6- or 7-membered carbocyclic or heterocyclic ring can be 31, 32, 33, 34, 35, 36, 37, 38, 39, 40, 41, 42, 43, 44, 45, 46 or 47:

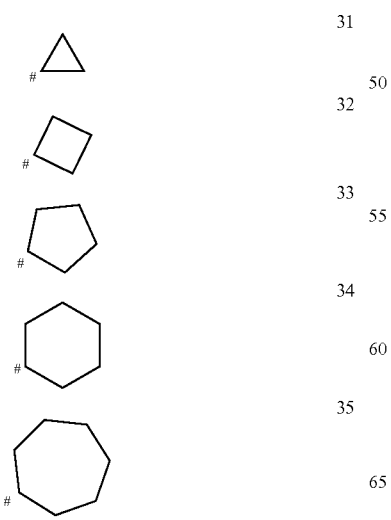

  36

  37

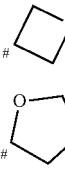  38

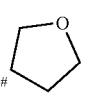  39

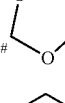  40

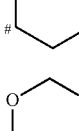  41

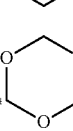  42

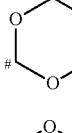  43

  44

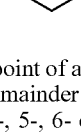  45

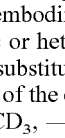  46

47 wherein #indicates the point of attachment of the carbocycle or heterocycle to the remainder of the compound. In some embodiments, the 3-, 4-, 5-, 6- or 7-membered carbocyclic or heterocyclic ring can comprise one or more fluorine substitutions. In some embodiments, the 3-, 4-, 5-, 6- or 7-membered carbocyclic or heterocyclic ring can comprise one or more deuterium substitutions.

In some embodiments of the compound A-B, $R_{10}$ is H, D, F, $-CH_3$, $-OCH_3$, $-CD_3$, $-OCD_3$, $-CH_2F$, $-OCH_2F$, $-CHF_2$, $-OCHF_2$, $-CF_3$, $-OCF_3$, $-CH_2CH_3$, $-CH(CH_3)_2$, $-CD_2CD_3$, $-CD(CD_3)_2$, $-CF_2CH_3$, $CF(CH_3)_2$, $-CH_2CF_3$, $-CH(CF_3)_2$, $-CF_2CF_3$, $-CF(CF_3)_2$, $-C(CH_3)_3$, $-C(CD_3)_3$, $-C(CF_3)_3$, $-OCH_2CH_3$, $-OCH(CH_3)_2$, $-OCD_2CD_3$, $-OCD(CD_3)_2$, $-OCF_2(CF_3)$, $-OCF(CF_3)_2$, $-OC(CH_3)_3$, $-OC(CD_3)_3$, $-OC(CF_3)_3$, $-C(CH_3)_2(CF_3)$, $-C(CH_3)(CF_3)_2$, $-OC(CH_3)_2(CF_3)$, —OC(CH$_3$)(CF$_3$)$_2$, —CH$_2$CH$_2$CH$_3$, —CH(CH$_2$CH$_3$)$_2$, —CD$_2$CD$_2$CD$_3$, —CD(CD$_2$CD$_3$)$_2$, —CF$_2$CF$_2$CF$_3$, —CF(CF$_2$CF$_3$)$_2$, —C(CH$_2$CH$_3$)$_3$, —C(CD$_2$CD$_3$)$_3$, —C(CF$_2$CF$_3$)$_3$, —OCH$_2$CH$_2$CH$_3$, —OCH(CH$_2$CH$_3$)$_2$, —OCD$_2$CD$_2$CD$_3$, —OCD(CD$_2$CD$_3$)$_2$, —OCF$_2$CF$_2$CF$_3$ or —OCF(CF$_2$CF$_3$)$_2$. In some embodiments of the compound A-B, $R_{10}$ is H, D, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$ or —CH(CH$_3$)$_2$. In some embodiments of the compound A-B, $R_{10}$ is H, D, F, —CH$_3$, —CH$_2$F, —CHF$_2$ or —CF$_3$. In some embodiments of the compound A-B, $R_{10}$ is H, D or F. In some embodiments of the compound A-B, $R_{10}$ is —CH$_3$ or —CF$_3$. In some embodiments of the compound A-B, $R_{10}$ is H or —CH$_3$. In some embodiments of the compound A-B, $R_{10}$ is H. In some embodiments of the compound A-B, $R_{10}$ is —CH$_3$. In some embodiments of the compound A-B, $R_{10}$ is absent.

In some embodiments of the compound A-B, $R_{11}$ is H, methyl or ethyl. In some embodiments of the compound A-B, $R_{11}$ is H. In some embodiments of the compound A-B, $R_{11}$ is methyl. In some embodiments of the compound A-B, $R_{11}$ is ethyl.

In some embodiments of the compound A-B, each instance of $R_{12}$, $R_{13}$ or $R_{14}$ is independently H, D, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, —CH(CH$_3$)$_2$, —CH$_2$CH$_2$CH$_3$, —CH(CH$_2$CH$_3$)$_2$, —C(CH$_3$)$_3$, —OCH$_2$CH$_3$, —OCH(CH$_3$)$_2$, —OCH$_2$CH$_2$CH$_3$, —OCH(CH$_2$CH$_3$)$_2$ or —OC(CH$_3$)$_3$. In some embodiments of the compound A-B, each instance of $R_{12}$, $R_{13}$ or $R_{14}$ is independently H, D, F, —CH$_3$, —OCH$_3$, —CD$_3$, —OCD$_3$, —CH$_2$F, —OCH$_2$F, —CHF$_2$, —OCHF$_2$, —CF$_3$ or —OCF$_3$. In some embodiments of the compound A-B, each instance of $R_{12}$, $R_{13}$ or $R_{14}$ is independently H, D, F, —CH$_3$, —CD$_3$ or —CF$_3$. In some embodiments of the compound A-B, each instance of $R_{12}$, $R_{13}$ or $R_{14}$ is independently H, D, or F. In some embodiments of the compound A-B, each instance of $R_{12}$, $R_{13}$ or $R_{14}$ is independently H, F or —CH$_3$. In some embodiments of the compound A-B, each instance of $R_{12}$, $R_{13}$ or $R_{14}$ is H. In some embodiments of the compound A-B, each instance of $R_{12}$, $R_{13}$ or $R_{14}$ is D. In some embodiments of the compound A-B, each instance of $R_{12}$, $R_{13}$ or $R_{14}$ is F.

The atom or group $R_{15}$ can vary depending on the starting material and desired product. For example, if $R_{15}$ is a $C_1$-$C_4$ alkyl group, that group is generally intended to remain in the final product as such groups are not easily removed. In some embodiments, $R_{15}$ is methyl, ethyl, isopropyl or t-butyl. In some embodiments, $R_{15}$ is —CH$_3$. Thus, if a product (intermediate or therapeutic agent) with an alkyl group is desired, the starting material will generally contain the alkyl group.

In some embodiments, $R_{15}$ is H (the unprotected phenol).

In some embodiments, $R_{15}$ is a protecting group (PG) that transiently protects the phenol during chemical synthesis—but ultimately is removed to regenerate the unprotected phenol. For example, in some embodiments, the protecting group can be a triphenylmethyl-based protecting group. In some embodiments, a triphenylmethyl-based protecting group can include: triphenylmethyl-, 4-monomethyl-triphenylmethyl-, 4,4'-dimethyl-triphenylmethyl-, 4,4',4"-trimethyl-triphenylmethyl, 4-monomethoxy-triphenylmethyl-, 4,4'-dimethoxy-triphenylmethyl-, or 4,4',4"-trimethoxy-triphenylmethyl-. Triphenylmethyl-based protecting groups can generally be removed in the presence of medium to strong acid.

In some embodiments, the protecting group can be a silyl-based protecting group. A silyl protecting group generally comprises a silicon atom to which is linked 2 to 3 (preferably 3) alkyl groups. A few non-limiting examples of silyl protecting groups include: trimethylsilyl (TMS), tert-butyldiphenylsilyl (TBDPS), tert-butyldimethylsilyl (TBS/TBDMS) and triisopropylsilyl (TIPS). Silyl protecting groups can generally be removed in the presence of fluoride ion.

In some embodiments, $R_{15}$ is a substituted or unsubstituted benzyl group. In some embodiments, the benzyl group can be left intact in the therapeutic agent. In some embodiments, the benzyl group is used as a protecting group and can be removed, for example, by hydrogenation or by treatment with strong acid.

In some embodiments of the compound A-B, $R_{20}$ is H, D, F, —CH$_3$, —CD$_3$, —CH$_2$F, —CHF$_2$, —CF$_3$, —CH$_2$CH$_3$, —CH$_2$CH$_2$CH$_3$, —CH(CH$_3$)$_2$, —C(CH$_3$)$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CH$_2$CH$_2$CH$_2$CH$_2$CH$_2$CH$_2$CH$_3$, —CH$_2$CH$_2$CH$_2$CH$_2$CH$_2$CH$_2$CH$_2$CH$_3$, —CH$_2$CH$_2$CH$_2$CH$_2$CH$_2$CH$_2$CH$_2$CH$_2$CH$_3$ or —CH$_2$CH$_2$CH$_2$CH$_2$CH$_2$CH$_2$CH$_2$CH$_2$CH$_2$CH$_3$. In some embodiments of the compound A-B, $R_{20}$ is H, D, F, —CH$_3$, —CD$_3$, —CH$_2$F, —CHF$_2$, —CF$_3$, —CH$_2$CH$_3$, —CH$_2$CH$_2$CH$_3$, —CH(CH$_3$)$_2$ or —C(CH$_3$)$_3$. In some embodiments of the compound A-B, $R_{20}$ is H, D, F, —CH$_3$, —CD$_3$, —CH$_2$F, —CHF$_2$ or —CF$_3$. In some embodiments of the compound A-B, $R_{20}$ is H, D, F, —CH$_3$, —CD$_3$, —CH$_2$F, —CHF$_2$ or —CF$_3$. In some embodiments of the compound A-B, $R_{20}$ is —CH$_3$, —CD$_3$, —CH$_2$F, —CHF$_2$ or —CF$_3$. In some embodiments of the compound A-B, $R_{20}$ is H. In some embodiments of the compound A-B, $R_{20}$ is —CH$_3$. In some embodiments of the compound A-B, $R_{20}$ is —CF$_3$. In some embodiments of the compound A-B, $R_{20}$ is F.

In some embodiments of the compound A-B, each $R_{21}$ is independently H, D, F, —CH$_3$, —CD$_3$, —CH$_2$F, —CHF$_2$, —CF$_3$, —CH$_2$CH$_3$, —CH$_2$CH$_2$CH$_3$, —CH(CH$_3$)$_2$, —CH$_2$CH$_2$CH$_2$CH$_3$ or —C(CH$_3$)$_3$. In some embodiments of the compound A-B, each $R_{21}$ is independently H, D, F, —CH$_3$, —CD$_3$, —CH$_2$F, —CHF$_2$ or —CF$_3$. In some embodiments of the compound A-B, each $R_{21}$ is independently H, —CH$_3$ or —CF$_3$. In some embodiments of the compound A-B, each $R_{21}$ is —CH$_3$. In some embodiments of the compound A-B, each $R_{21}$ is H. In some embodiments of the compound A-B, each $R_{21}$ is —CF$_3$.

In some embodiments of the compound A-B, n is 0, 1, 2, 3, 4, 5, 6, 7 or 8. In some embodiments of the compound A-B, n is 0, 1, 2, 3, 4, 5 or 6. In some embodiments of the compound A-B, n is 0, 1, 2, 3 or 4. In some embodiments of the compound A-B, n is 0. In some embodiments of the compound A-B, n is 1. In some embodiments of the compound A-B, n is 2. In some embodiments of the compound A-B, n is 3. In some embodiments of the compound A-B, n is 4. In some embodiments of the compound A-B, n is 5. In some embodiments of the compound A-B, n is 6. In some embodiments of the compound A-B, n is 7. In some embodiments of the compound A-B, n is 8. In some embodiments of the compound A-B, n is 9. In some embodiments of the compound A-B, n is 10. In some embodiments of the compound A-B, n is 11. In some embodiments of the compound A-B, n is 12.

In some embodiments of the compound A-B has the formula:

26

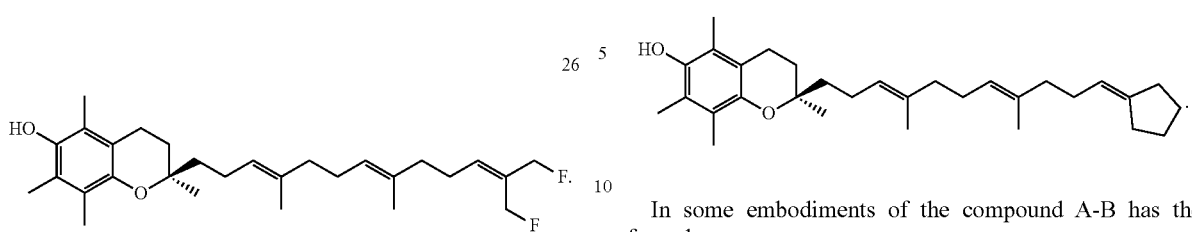

In some embodiments of the compound A-B has the formula:

29

In some embodiments of the compound A-B has the formula:

32

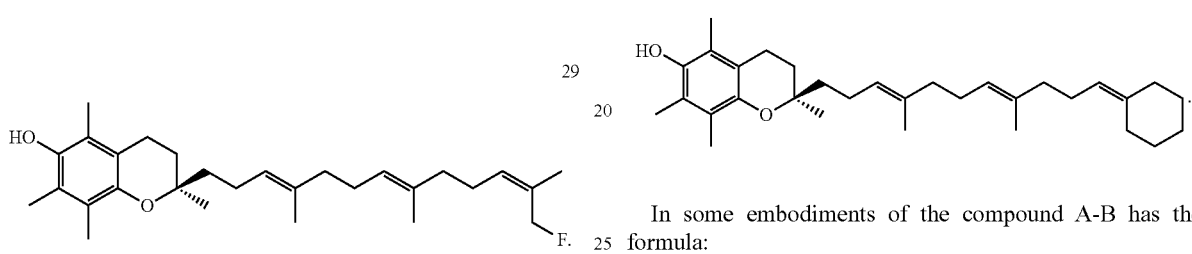

In some embodiments of the compound A-B has the formula:

35

In some embodiments of the compound A-B has the formula:

38

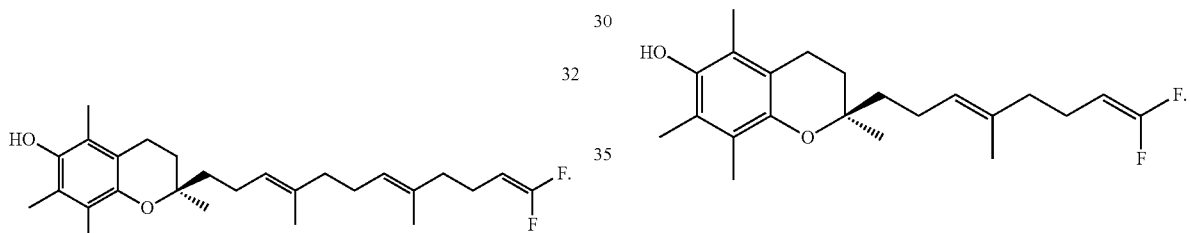

In some embodiments of the compound A-B has the formula:

41

In some embodiments of the compound A-B has the formula:

44

In some embodiments of the compound A-B has the formula:

56

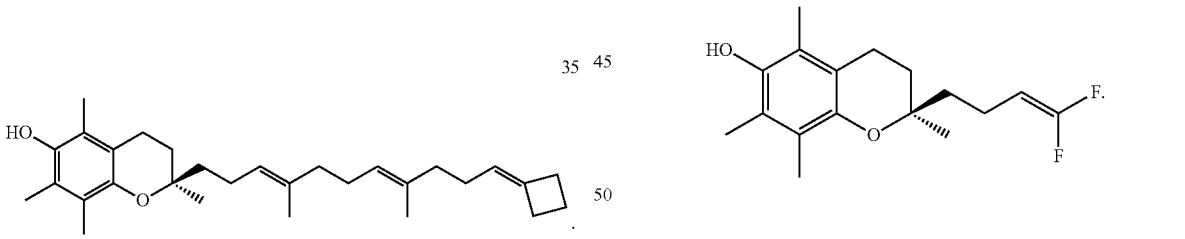

In some embodiments of the compound A-B has the formula:

67

In some embodiments of the compound A-B has the formula:

78

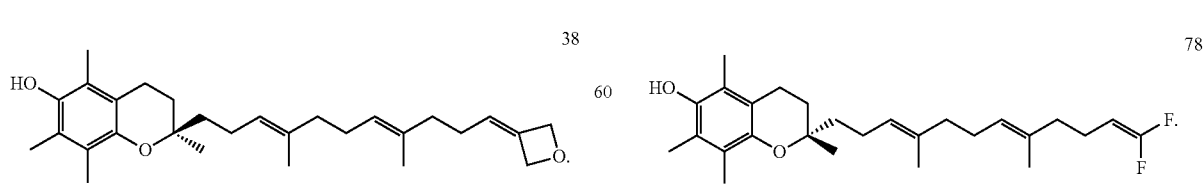

In some embodiments of the compound A-B has the formula:

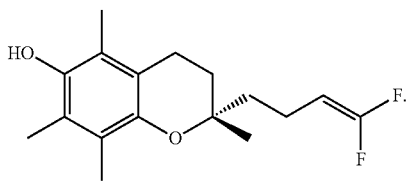

87

In some embodiments of the compound A-B has the formula:

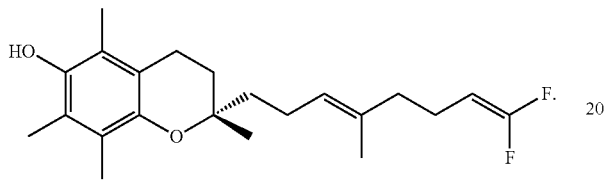

96

In some embodiments of the compound A-B has the formula:

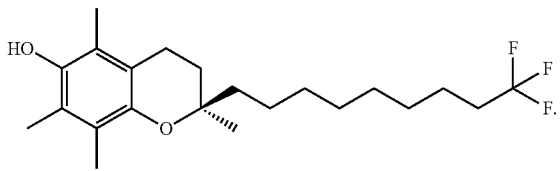

104

(c) Other Derivatives/Therapeutic Agents

In some embodiments, this application further provides therapeutic compounds of formula C-D (defined below), that can be prepared by reduction of the therapeutic compounds of formula E-F. Such reduced versions of compounds of formula E-F are believed to also be suitable for use in the treatment of mitochondrial disease, such as Friedreich's ataxia or other ataxia's (such as Ataxia with vitamin E deficiency (AVED)) because other compounds that have a hydroquinone structure, such are vitamin E, have also been shown to be clinically linked with ataxia (See: Imounan et al., Clinical and Genetic Study of Friedreich's ataxia and Ataxia with Vitamin E Deficiency in 44 Moroccan Families, World Journal of Neuroscience, 2014, 4, 299-305; and Abeti et al., Calcium Deregulation: Novel Insights to Understand Friedreich's ataxia Pathophysiology, Frontiers in Cellular Neuroscience: doi: 10.3398/fncel.2018.00264). For example, it is believed that the therapeutic compounds of formula C-D (below) can themselves be considered therapeutic agents or alternatively as prodrug forms of the therapeutic agents of formula E-F. Specifically, therapeutic compounds of formula E-F are believed to be active in the processes affecting the in vivo concentration (e.g., the internal and external mitochondrial concentration) of reactive oxygen species (ROS) and indeed may actively cycle, in vivo, between the reduced form (compounds of formula C-D) and oxidized form (compounds of formula E-F). Compounds of the formula E-F can, for example, be converted to compounds of the formula C-D as described below in Examples 8 and 9, below. Furthermore, compounds of formula C-D were shown to be effective as lipoxygenase-15 (LO-15) inhibitors in Example 22.

Thus, in some embodiments, this application further provides novel compounds of formula C-D, or pharmaceutically acceptable salts, stereoisomers, mixtures of stereoisomers, tautomers, hydrates, and/or solvates thereof, wherein C is 11 or 12:

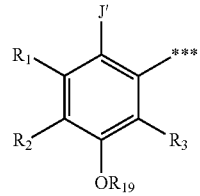

11

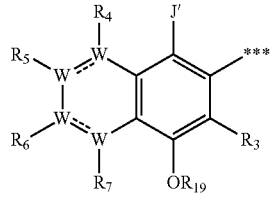

12 and D is 13, 14, 15, 16, 17, 18, 19 or 20:

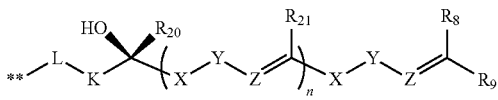

13

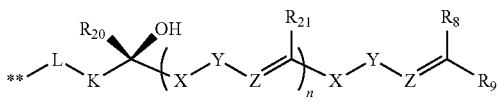

14

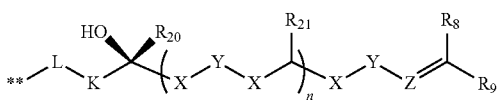

15

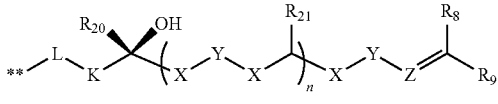

16

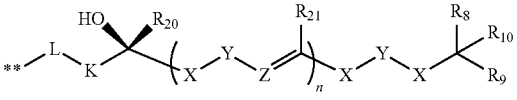

17

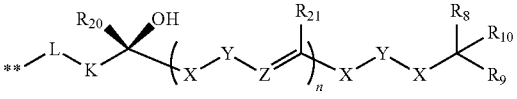

18

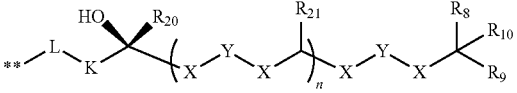

19

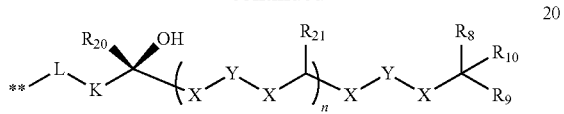

wherein, J' is OH, SH or NH—$R_{11}$, K is absent or —$(CR_{12}R_{13})$—, L is —$(CR_{12}R_{13})$—, each W is independently C (carbon) or N (nitrogen) and wherein for each use of w═w, the bond between each W can be a single bond or double bond and further provided that if a single bond, each C (carbon) atom will have a hydrogen atom linked hereto in addition to one of $R_4$, $R_5$, $R_6$ or $R_7$ and in either case each of $R_4$, $R_5$, $R_6$ and $R_7$ attached thereto is independently selected from H, D, F, Cl, Br, I, $C_1$-$C_6$ alkyl and $C_1$-$C_6$ alkoxy, and if W is N (nitrogen), each of $R_4$, $R_5$, $R_6$ and $R_7$ attached thereto is independently absent (if w═w is a double bond) or selected from H, D and $C_1$-$C_6$ alkyl (if w═w is a single bond), each X is independently a group of formula —$(CR_{12}R_{13})$—, each Y is independently absent or a group of formula —$(CR_{12}R_{13})$—, each Z is independently a group of formula —$(CR_{14})$—, each of $R_1$, $R_2$ and $R_3$ is independently H, D, F, Cl, Br, I, $C_1$-$C_6$ alkyl or $C_1$-$C_6$ alkoxy; or $R_1$ and $R_2$ together form a 5-membered carbocyclic ring, a 5-membered heterocyclic ring, a 5-membered aromatic or heteroaromatic ring or a 6-membered heterocyclic ring, each $R_8$ and $R_9$ is each independently H, D, F, Cl, Br, I or $C_1$-$C_4$ alkyl; or taken together $R_8$ and $R_9$ form a 3-, 4-, 5-, 6-, or 7-membered carbocyclic or heterocyclic ring, $R_{10}$ is H, D, F, $C_1$, Br, I, $C_1$-$C_6$ alkyl or $C_1$-$C_6$ alkoxy, $R_{11}$ is H, D or $C_1$-$C_6$ alkyl, each instance of $R_{12}$, $R_{13}$ and $R_{14}$ is independently H, D, F, Cl, Br, I, $C_1$-$C_6$ alkyl or $C_1$-$C_6$ alkoxy, $R_{19}$ is H, $C_1$-$C_4$ alkyl or benzyl (substituted or unsubstituted), $R_{20}$ is H, D, F or $C_1$-$C_{12}$ alkyl, each $R_{21}$ is independently H, D, F, Cl, Br, I, or $C_1$-$C_4$ alkyl, n is an integer from 0 to 12, inclusive, and * indicates the point of attachment of C to D and  indicates the point of attachment of C to D; and further provided that: (i) at least one group of formula $R_1$, $R_2$, $R_3$, $R_4$, $R_5$, $R_6$, $R_7$, $R_8$, $R_9$, $R_{10}$, $R_{12}$, $R_{13}$, $R_{14}$, $R_{20}$ or $R_{21}$ comprises at least one fluorine atom; and/or (ii) $R_8$ and $R_9$ taken together form a 3-, 4-, 5-, 6- or 7-membered carbocyclic or heterocyclic ring. In some embodiments, at least one of $R_8$ and $R_9$ is fluorine or a substituted $C_1$-$C_4$ alkyl group comprising at least one fluorine. In some embodiments, each of $R_8$ and $R_9$ is independently fluorine or a substituted $C_1$-$C_4$ alkyl group comprising at least one fluorine. In some embodiments, each of $R_8$ and $R_9$ is fluorine. In some embodiments, each of $R_8$, $R_9$ and $R_{10}$ is fluorine. In some embodiments, each of $R_8$, $R_9$ and $R_{10}$ is independently fluorine or a substituted $C_1$-$C_4$ alkyl group comprising at least one fluorine. In some embodiments of E-F, $R_{19}$ is H.

Any combination of 11 and 12 with 13, 14, 15, 16, 17, 18, 19 or 20 is permissible. In some embodiments, C is 12 and D is 13, 14, 15, 16, 17, 18, 19 or 20. In some embodiments, C is 11 and D is 13, 14, 19 or 20. In some embodiments, C is 12 and D is 13, 14, 19 or 20. In some embodiments, C is 11 and D is 15, 16, 17 or 18. In some embodiments, C is 12 and D is 13, 14, 19 or 20. In some embodiments, C is 12 and D is 15, 16, 17 or 18. In some embodiments, C is 11 and D is 13. In some embodiments, C is 11 and D is 14. In some embodiments, C is 11 and D is 15. In some embodiments, C is 11 and D is 16. In some embodiments, C is 11 and D is 17. In some embodiments, C is 11 and D is 18. In some embodiments, C is 11 and D is 19. In some embodiments, C is 11 and D is 20. In some embodiments, C is 12 and D is 13. In some embodiments, C is 12 and D is 14. In some embodiments, C is 12 and D is 15. In some embodiments, C is 12 and D is 16. In some embodiments, C is 12 and D is 17. In some embodiments, C is 12 and D is 18. In some embodiments, C is 12 and D is 19. In some embodiments, C is 12 and D is 20.

The atom or group represented by J' can be OH, SH or NH—$R_{11}$. In some embodiments, J' is OH. In some embodiments, J' is S. In some embodiment, J' is NH—$R_{11}$, wherein $R_1$ is defined below. In some embodiments, J' is OH or NH—$R_{11}$ and K is absent.

In some embodiments, the groups represented by K and L can each independently be: —$(CH_2)$—, —$(CD_2)$-, —$(CHF)$—, —$(CF_2)$—, —$(CH(CH_3))$—, —$(CD(CD_3))$—, —$(CF(CH_3))$—, —$(CH(CF_3))$—, —$(CF(CF_3))$—, —$(C(CH_3)_2)$—, —$(C(CD_3)_2)$—, —$(C(CF_3)_2)$, —$(CH(OCH_3))$—, —$(CD(OCD_3))$—, —$(CF(OCH_3))$—, —$(CH(OCF_3))$—, —$(CF(OCF_3))$—, —$(C(OCH_3)_2)$—, —$(C(OCD_3)_2)$—, —$(C(OCF_3)_2)$—, —$(C(CH_3)(CF_3))$—, —$(C(CD_3)(CF_3))$—, —$(CH(CH_2CH_3))$—, —$(CD(CD_2CD_3))$—, —$(CF(CH_2CH_3))$—, —$(CH(CH_2CF_3))$—, —$(CH(CF_2CF_3))$—, —$(CF(CF_2CF_3))$—, —$(C(CH_2CH_3)_2)$—, —$(C(CD_2CD_3)_2)$— or —$(C(CF_2CF_3)_2)$—. In some embodiments, K is absent and L is —$(CH_2)$—, —$(CD_2)$-, —$(CHF)$—, —$(CF_2)$—, —$(CH(CH_3))$—, —$(CD(CD_3))$—, —$(CF(CH_3))$—, —$(CH(CF_3))$—, —$(CF(CF_3))$—, —$(C(CH_3)_2)$—, —$(C(CD_3)_2)$—, —$(C(CF_3)_2)$, —$(CH(OCH_3))$—, —$(CD(OCD_3))$—, —$(CF(OCH_3))$—, —$(CH(OCF_3))$—, —$(CF(OCF_3))$—, —$(C(OCH_3)_2)$—, —$(C(OCD_3)_2)$—, —$(C(OCF_3)_2)$—, —$(C(CH_3)(CF_3))$—, —$(C(CD_3)(CF_3))$—, —$(CH(CH_2CH_3))$—, —$(CD(CD_2CD_3))$—, —$(CF(CH_2CH_3))$—, —$(CH(CH_2CF_3))$—, —$(CH(CF_2CF_3))$—, —$(CF(CF_2CF_3))$—, —$(C(CH_2CH_3)_2)$—, —$(C(CD_2CD_3)_2)$— or —$(C(CF_2CF_3)_2)$—. In some embodiments, each of K and L is independently —$(CH_2)$—, —$(CD_2)$-, —$(CF_2)$—, —$(CH(CH_3))$—, —$(CD(CD_3))$—, —$(CF(CF_3))$—, —$(C(CH_3)_2)$—, —$(C(CD_3)_2)$—, —$(C(CF_3)_2)$—, —$(C(CF_3)_2)$—, —$(CH(OCH_3))$—, —$(CD(OCD_3))$—, —$(CF(OCF_3))$— or —$(C(OCH_3)_2)$—. In some embodiments, K is absent and L is —$(CH_2)$—, —$(CD_2)$-, —$(CF_2)$—, —$(CH(CH_3))$—, —$(CD(CD_3))$—, —$(CF(CF_3))$—, —$(C(CH_3)_2)$—, —$(C(CD_3)_2)$—, —$(C(CF_3)_2)$—, —$(CH(OCH_3))$—, —$(CD(OCD_3))$—, —$(CF(OCF_3))$— or —$(C(OCH_3)_2)$—. In some embodiments, each of K and L is independently —$(CH_2)$—, —$(CD_2)$-, —$(CHF)$—, —$(CF_2)$—, —$(CH(CH_3))$—, —$(CF(CF_3))$—, —$(C(CH_3)_2)$— or —$(C(CF_3)_2)$—. In some embodiments, K is absent and L is —$(CH_2)$—, —$(CD_2)$-, —$(CHF)$—, —$(CF_2)$—, —$(CH(CH_3))$—, —$(CF(CF_3))$—, —$(C(CH_3)_2)$— or —$(C(CF_3)_2)$—. In some embodiments, each of K and L is independently —$(CH_2)$—, —$(CD_2)$-, —$(CHF)$— or —$(CF_2)$—. In some embodiments, K is absent and L is —$(CH_2)$—, —$(CD_2)$-, —$(CHF)$— or —$(CF_2)$—. In some embodiments, each of K and L are —$(CH_2)$—. In some embodiments, K is absent and L is —$(CH_2)$—. In some embodiments, each of K and L are —$(CD_2)$-. In some embodiments, K is absent and L is —$(CD_2)$-. In some embodiments, each of K and L are —$(CF_2)$—. In some embodiments, K is absent and L is —$(CF_2)$—.

In some embodiments of the compound represented by C-D, wherein C is 11, each of $R_1$, $R_2$ and $R_3$ is independently H, D, Cl, F, —$CH_3$, —$OCH_3$, —$CD_3$, —$OCD_3$, —$CH_2F$, —$OCH_2F$, —$CHF_2$, —$OCHF_2$, —$CF_3$, —$OCF_3$, —$CH_2CH_3$, —$CH(CH_3)_2$, —$CD_2CD_3$, —$CD(CD_3)_2$, —$CF_2CH_3$, —$CF(CH_3)_2$, —$CH_2CF_3$, —$CH(CF_3)_2$, —$CF_2CF_3$, —$CF(CF_3)_2$, —$C(CH_3)_3$, —$C(CD_3)_3$, —$C(CF_3)_3$, —$OCH_2CH_3$, —$OCH(CH_3)_2$, —$OCD_2CD_3$, —OCD(CD$_3$)$_2$, —OCF$_2$CH$_3$, —OCF(CH$_3$)$_2$, —OCH$_2$CF$_3$, —OCH(CF$_3$)$_2$, —OCF$_2$(CF$_3$), —OCF(CF$_3$)$_2$, —OC(CH$_3$)$_3$, —OC(CD$_3$)$_3$, —OC(CF$_3$)$_3$, —C(CH$_3$)$_2$(CF$_3$), —C(CH$_3$)(CF$_3$)$_2$, —OC(CH$_3$)$_2$(CF$_3$), —OC(CH$_3$)(CF$_3$)$_2$, —CH$_2$CH$_2$CH$_3$, —CH(CH$_2$CH$_3$)$_2$, —CD$_2$CD$_2$CD$_3$, —CD(CD$_2$CD$_3$)$_2$, —CF$_2$CH$_2$CH$_3$, —CF(CH$_2$CH$_3$)$_2$, —CH$_2$CF$_2$CF$_3$, —CH(CF$_2$CF$_3$)$_2$, —CF$_2$CF$_2$CF$_3$, —CF(CF$_2$CF$_3$)$_2$, —OCH$_2$CH$_2$CH$_3$, —OCH(CH$_2$CH$_3$)$_2$, —OCD$_2$CD$_2$CD$_3$, —OCD(CD$_2$CD$_3$)$_2$, —OCF$_2$CH$_2$CH$_3$, —OCF(CH$_2$CH$_3$)$_2$, —OCH$_2$CF$_2$CF$_3$, —OCH(CF$_2$CF$_3$)$_2$, —OCF$_2$CF$_2$CF$_3$ or —OCF(CF$_2$CF$_3$)$_2$. In some embodiments of the compound represented by C-D, wherein C is 11, each of R$_1$, R$_2$ and R$_3$ is independently H, D, Cl, F, —CH$_3$, —OCH$_3$, —CD$_3$, —OCD$_3$, —CH$_2$F, —CHF$_2$, —CF$_3$, —OCF$_3$, —C(CH$_3$)$_3$, —C(CD$_3$)$_3$, —C(CF$_3$)$_3$, —OC(CH$_3$)$_3$, —OC(CD$_3$)$_3$, —OC(CF$_3$)$_3$, —CH$_2$CH$_3$, —OCH$_2$CH$_3$ or —CH(CH$_3$)$_2$. In some embodiments of the compound represented by C-D, wherein C is 11, each of R$_1$, R$_2$ and R$_3$ is independently H, F, —CH$_3$, —OCH$_3$, —CH$_2$F, —CHF$_2$, —CF$_3$, —OCF$_3$, —C(CH$_3$)$_3$, —C(CF$_3$)$_3$, —CH$_2$CH$_3$, —OCH$_2$CH$_3$ or —CH(CH$_3$)$_2$. In some embodiments of the compound represented by C-D, wherein C is 11, each of R$_1$, R$_2$ and R$_3$ is independently H, F, —CH$_3$, —OCH$_3$, —CH$_2$F, —CHF$_2$, —CF$_3$ or —OCF$_3$. In some embodiments of the compound represented by C-D, wherein C is 11, each of R$_1$, R$_2$ and R$_3$ is independently H, F, —CH$_3$, —OCH$_3$, —CF$_3$ or —OCF$_3$. In some embodiments of the compound represented by C-D, wherein C is 11, each of R$_1$, R$_2$ and R$_3$ is independently H, F, —CH$_3$, —OCH$_3$ or —CF$_3$. In some embodiments of the compound represented by C-D, wherein C is 11, each of R$_1$, R$_2$ and R$_3$ is —CH$_3$. In some embodiments of the compound represented C-D, wherein C is 11, each of R$_1$, R$_2$ and R$_3$ is H. In some embodiments of the compound represented C-D, wherein C is 11, each of R$_1$, R$_2$ and R$_3$ is independently H or —CH$_3$. In some embodiments of the compound represented C-D, wherein C is 11, each of R$_1$, R$_2$ and R$_3$ is independently H or —OCH$_3$. In some embodiments of the compound represented C-D, wherein C is 11, each of R$_1$, R$_2$ and R$_3$ is independently H, —CH$_3$ or —OCH$_3$. In some embodiments of the compound represented by C-D, wherein C is 11, each of R$_1$ and R$_2$ is —OCH$_3$ and R$_3$ is —CH$_3$. In some embodiments of the compound represented by C-D, wherein C is 11, each of R$_1$ and R$_2$ is —CH$_3$ and R$_3$ is H. In some embodiments of the compound represented by C-D, wherein C is 11, each of R$_1$ and R$_2$ is —OCH$_3$ and R$_3$ is H. In some embodiments of the compound represented by C-D, wherein C is 11, at least one of R$_1$, R$_2$ and R$_3$ is F.

In some embodiments of the compound represented by C-D, wherein C is 11, J' is OH, each of K and L is independently —(CH$_2$)—, —(CD$_2$)-, —(CHF)—, —(CF$_2$)—, —(CH(CH$_3$))—, —(CF(CF$_3$))—, —(C(CH$_3$)$_2$)— or —(C(CF$_3$)$_2$)—; and each of R$_1$, R$_2$ and R$_3$ is independently H, F, —CH$_3$, —OCH$_3$, —CH$_2$F, —CHF$_2$, —CF$_3$, —OCF$_3$, —C(CH$_3$)$_3$, —C(CF$_3$)$_3$, —CH$_2$CH$_3$, —OCH$_2$CH$_3$, or —CH(CH$_3$)$_2$. In some embodiments of the compound represented by C-D, wherein C is 11, J' is OH, each of K and L is independently —(CH$_2$)—, —(CD$_2$)-, —(CHF)— or —(CF$_2$)—; and each of R$_1$, R$_2$ and R$_3$ is independently H, F, —CH$_3$, —OCH$_3$, —CH$_2$F, —CHF$_2$, —CF$_3$ or —OCF$_3$. In some embodiments of the compound represented by C-D wherein C is 11, J' is OH, each of K and L is independently —(CH$_2$)—, —(CD$_2$)-, —(CHF)— or —(CF$_2$)—; and each of R$_1$, R$_2$ and R$_3$ is independently H, F, —CH$_3$, —OCH$_3$, —CF$_3$ or —OCF$_3$. In some embodiments of the compound represented by C-D wherein C is 11, J' is OH; each of K and L is —(CH$_2$)—; and each of R$_1$, R$_2$ and R$_3$ is independently H or —CH$_3$. In some embodiments of the compound represented by C-D wherein C is 11, J' is OH; each of K and L is —(CH$_2$)—; and each of R$_1$, R$_2$ and R$_3$ is independently H or —CH$_3$. In some embodiments of the compound represented by C-D wherein C is 11, J is O; each of K and L is —(CH$_2$)—; each of R$_1$, R$_2$ and R$_3$ is independently H or —OCH$_3$. In some embodiments of the compound represented by C-D wherein C is 11, J' is OH; each of K and L is —(CH$_2$)— and each of R$_1$, R$_2$ and R$_3$ is independently H, —CH$_3$ or —OCH$_3$. In some embodiments of the compound represented by C-D wherein C is 11, J' is OH; each of K and L is —(CH$_2$)— and each of R$_1$ and R$_2$ is —OCH$_3$ and R$_3$ is —CH$_3$. In some embodiments of the compound represented by C-D wherein C is 11, J' is OH; each of K and L is —(CH$_2$)— and each of R$_1$ and R$_2$ is —OCH$_3$ and R$_3$ is H. In some embodiments of the compound represented by C-D wherein C is 11, J' is OH; each of K and L is —(CH$_2$)— and each of R$_1$ and R$_2$ is —CH$_3$ and R$_3$ is H. In some embodiments of the compound represented by C-D wherein C is 11, J' is OH; each of K and L is —(CH$_2$)— and each of R$_1$ and R$_2$ is —OCH$_3$ and R$_3$ is H. In some embodiments of the compound represented by C-D, wherein C is 11, J' is OH; each of K and L is —(CH$_2$)— and at least one of R$_1$, R$_2$ and R$_3$ is F.

In some embodiments of the compound represented by C-D, wherein C is 11, R$_3$ is H, D, Cl, F, —CH$_3$, —OCH$_3$, —CD$_3$, —OCD$_3$, —CF$_3$, —OCF$_3$, —C(CH$_3$)$_3$, —C(CD$_3$)$_3$, —C(CF$_3$)$_3$, —OC(CH$_3$)$_3$, —OC(CD$_3$)$_3$, —OC(CF$_3$)$_3$, —CH$_2$CH$_3$, —OCH$_2$CH$_3$, or —CH(CH$_3$)$_2$ and R$_1$ and R$_2$ taken together form a 5-, or 6-membered carbocyclic or heterocyclic ring. In some embodiments of the compound represented by C-D, wherein C is 11, (i) R$_3$ is H, F, —CH$_3$, or —OCH$_3$, and (ii) R$_1$ and R$_2$ taken together form a 5-, or 6-membered carbocyclic or heterocyclic ring. In some embodiments of the compound represented by C-D, wherein C is 11, (i) R$_3$ is H; and (ii) R$_1$ and R$_2$ taken together form a 5-, or 6-membered carbocyclic or heterocyclic ring. In some embodiments of the compound represented by C-D, wherein C is 11, (i) R$_3$ is —CH$_3$; and (ii) R$_1$ and R$_2$ taken together form a 5-, or 6-membered carbocyclic or heterocyclic ring. In some embodiments of the compound represented by C-D, wherein C is 11, (i) R$_3$ is —OCH$_3$; and (ii) R$_1$ and R$_2$ taken together form a 5-, or 6-membered carbocyclic or heterocyclic ring. In some embodiments of the compound represented by C-D, wherein C is 11, (i) R$_3$ is F; and (ii) R$_1$ and R$_2$ taken together form a 5-, or 6-membered carbocyclic or heterocyclic ring.

In some embodiments, R$_1$ and R$_2$ of 11, taken together, form a heterocycle as represented in 11A, 11B, 11C, 11D, 11E or 11F:

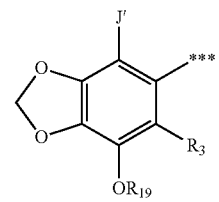

11A

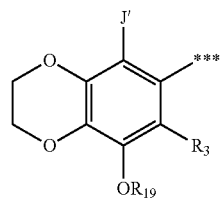

11B

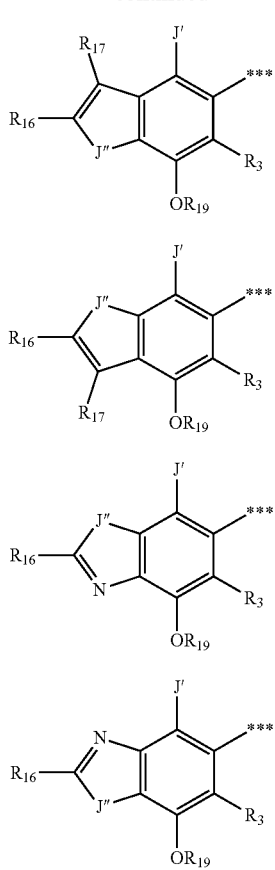

wherein each of $R_{16}$ and $R_{17}$ are each independently H, D, Cl, F, —CH$_3$, —OCH$_3$, —CD$_3$, —OCD$_3$, —CH$_2$F, —CHF$_2$, —C$_3$, —OCF$_3$, —C(CH$_3$)$_3$, —C(CD$_3$)$_3$, —C(CF$_3$)$_3$, —OC(CH$_3$)$_3$, —OC(CD$_3$)$_3$, —OC(CF$_3$)$_3$, —CH$_2$CH$_3$, —OCH$_2$CH$_3$, —CH(CH$_3$)$_2$, —OCH(CH$_3$)$_2$, —C(CH$_3$)$_3$ or —O(CH$_3$)$_3$; and J″ is OH, SH or NH—R$_{18}$, wherein R$_{18}$ is H, D, —CH$_3$, —CH$_2$F, —CHF$_2$ or —CF$_3$. In some embodiments, $R_{16}$ and $R_{17}$ are each independently H, D, Cl, F, —CH$_3$, —OCH$_3$, —CD$_3$, —OCD$_3$, —CH$_2$F, —CHF$_2$, —CF$_3$, or —OCF$_3$. In some embodiments, $R_{16}$ and $R_{17}$ are each independently H, D, F, or —CH$_3$. In some embodiments, $R_{16}$ and $R_{17}$ are H. In some embodiments, $R_{16}$ and $R_{17}$ are F. In some embodiments, $R_{16}$ and $R_{17}$ are —CH$_3$. In some embodiments, $R_{18}$ is H or —CH$_3$.

In some embodiments of the compound represented by C-D, wherein C is 12, $R_3$ is H, D, Cl, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, —CH(CH$_3$)$_2$, —CD$_2$CD$_3$, —CD(CD$_3$)$_2$, —CF$_2$CH$_3$, CF(CH$_3$)$_2$, —CH$_2$CF$_3$, —CH(CF$_3$)$_2$, —CF$_2$CF$_3$, —CF(CF$_3$)$_2$, —C(CH$_3$)$_3$, —C(CD$_3$)$_3$, —C(CF$_3$)$_3$, —OCH$_2$CH$_3$, —OCH(CH$_3$)$_2$, —OCD$_2$CD$_3$, —OCD(CD$_3$)$_2$, —OCF$_2$CH$_3$, —OCF(CH$_3$)$_2$, —OCH$_2$CF$_3$, —OCH(CF$_3$)$_2$, —OCF$_2$(CF$_3$), —OCF(CF$_3$)$_2$, —OC(CH$_3$)$_3$, —OC(CD$_3$)$_3$, —OC(CF$_3$)$_3$, —C(CH$_3$)$_2$(CF$_3$), —C(CH$_3$)(CF$_3$)$_2$, —OC(CH$_3$)$_2$(CF$_3$), —OC(CH$_3$)(CF$_3$)$_2$, —CH$_2$CH$_2$CH$_3$, —CH(CH$_2$CH$_3$)$_2$, —CD$_2$CD$_2$CD$_3$, —CD(CD$_2$CD$_3$)$_2$, —CF$_2$CH$_2$CH$_3$, —CF(CH$_2$CH$_3$)$_2$, —CH$_2$CF$_2$CF$_3$, —CH(CF$_2$CF$_3$)$_2$, —CF$_2$CF$_2$CF$_3$, —CF(CF$_2$CF$_3$)$_2$, —OCH$_2$CH$_2$CH$_3$, —OCH(CH$_2$CH$_3$)$_2$, —OCD$_2$CD$_2$CD$_3$, —OCD(CD$_2$CD$_3$)$_2$, —OCF$_2$CH$_2$CH$_3$, —OCF(CH$_2$CH$_3$)$_2$, —OCH$_2$CF$_2$CF$_3$, —OCH(CF$_2$CF$_3$)$_2$, —OCF$_2$CF$_2$CF$_3$ or —OCF(CF$_2$CF$_3$)$_2$; and where if W is C (carbon), each of $R_4$, $R_5$, $R_6$ and $R_7$ attached thereto is independently H, D, F, Cl, Br, I, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, or —CH(CH$_3$)$_2$; and where if W is N (nitrogen), each of $R_4$, $R_5$, $R_6$ and $R_7$ attached thereto is independently absent or selected from H, D, methyl, ethyl, isopropyl and t-butyl. In some embodiments, for each instance of w═w, the bond between each W is a single bond. In some embodiments, for each instance of w═w, the bond between each W is a double bond. In some embodiments, $R_3$ is H, D, Cl, F, —CH$_3$, —OCH$_3$, —CD$_3$, —OCD$_3$, —CH$_2$F, —CHF$_2$, —CF$_3$, —OCF$_3$, —C(CH$_3$)$_3$, —C(CD$_3$)$_3$, —C(CF$_3$)$_3$, —OC(CH$_3$)$_3$, —OC(CD$_3$)$_3$, —OC(CF$_3$)$_3$, —CH$_2$CH$_3$, —OCH$_2$CH$_3$, or —CH(CH$_3$)$_2$; and where if W is C (carbon), each of $R_4$, $R_5$, $R_6$ and $R_7$ attached thereto is independently H, D, F, C$_1$, —CH$_3$, —OCH$_3$, —CH$_2$F, —CHF$_2$, —CF$_3$, —OCF$_3$, —CH$_2$CH$_3$, or —CH(CH$_3$)$_2$; and where if W is N (nitrogen), each of $R_4$, $R_5$, $R_6$ and $R_7$ attached thereto is independently absent or selected from H, D, methyl and ethyl. In some embodiments, each W is C (carbon) and each of $R_4$, $R_5$, $R_6$ and $R_7$ is independently H, D, Cl, F, —CH$_3$, —OCH$_3$, —CH$_2$F, —CHF$_2$, —CF$_3$ or —OCF$_3$. In some embodiments, each W is C (carbon) and each of $R_4$, $R_5$, $R_6$ and $R_7$ is independently H, D, Cl, F, —CH$_3$ or —OCH$_3$. In some embodiments, each W is C (carbon) and each of $R_4$, $R_5$, $R_6$ and $R_7$ is independently H, —CH$_3$ or —OCH$_3$. In some embodiments, each W is C (carbon) and each of $R_4$, $R_5$, $R_6$ and $R_7$ is H. In some embodiments, each W is C (carbon) and each of $R_4$, $R_5$, $R_6$ and $R_7$ is —CH$_3$.

In some embodiments of the compound C-D, each of $R_8$ and $R_9$ can be independently H, D, F, Cl, Br, I, —CH$_3$, —CD$_3$, —CH$_2$F, —CHF$_2$, —CF$_3$, —CH$_2$CH$_3$, —CH(CH$_3$)$_2$, —CD$_2$CD$_3$, —CD(CD$_3$)$_2$, —CF$_2$CH$_3$, —CF(CH$_3$)$_2$, —CH$_2$CF$_3$, —CH(CF$_3$)$_2$, —CF$_2$CF$_3$, —CF(CF$_3$)$_2$, —C(CH$_3$)$_3$, —C(CD$_3$)$_3$, —C(CF$_3$)$_3$, —C(CH$_3$)$_2$(CF$_3$), —C(CH$_3$)(CF$_3$)$_2$, —CH$_2$CH$_2$CH$_3$, —CH(CH$_2$CH$_3$)$_2$, —CD$_2$CD$_2$CD$_3$, —CD(CD$_2$CD$_3$)$_2$, —CF$_2$CH$_2$CH$_3$, —CF(CH$_2$CH$_3$)$_2$, —CH$_2$CF$_2$CF$_3$, —CH(CF$_2$CF$_3$)$_2$, —CF$_2$CF$_2$CF$_3$ or —CF(CF$_2$CF$_3$)$_2$. In some embodiments of the compound C-D, each of $R_8$ and $R_9$ can be independently H, F, —CH$_3$, —CH$_2$F, —CHF$_2$, —CF$_3$, —CH$_2$CH$_3$, —CH(CH$_3$)$_2$, —CF$_2$CH$_3$, —CH$_2$CF$_3$, —CH(CF$_3$)$_2$, —CF$_2$CF$_3$, —CF(CF$_3$)$_2$, —C(CH$_3$)$_3$, —C(CF$_3$)$_3$, —CH$_2$CH$_2$CH$_3$, —CH(CH$_2$CH$_3$)$_2$, —CF$_2$CF$_2$CF$_3$ or —CF(CF$_2$CF$_3$)$_2$. In some embodiments of the compound C-D, each of $R_8$ and $R_9$ can be independently H, F, —CH$_3$, —CH$_2$F, —CHF$_2$, or —CF$_3$.

In some embodiments of the compound C-D, each of $R_8$ and $R_9$ can be independently a $C_1$-$C_4$ alkyl group. Said alkyl group can be, for example, substituted with one or more fluorine atoms. For example, said alkyl group can be fluoromethyl, difluoromethyl or trifluoromethyl.

In some embodiments of the compound C-D, $R_8$ and $R_9$, taken together, can form a 3-, 4-, 5-, 6- or 7-membered carbocyclic or heterocyclic ring. For example, the 3-, 4-, 5-, 6- or 7-membered carbocyclic or heterocyclic ring can be 31, 32, 33, 34, 35, 36, 37, 38, 39, 40, 41, 42, 43, 44, 45, or 47:

31

 32

 33

 34

 35

 36

 37

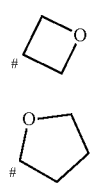 38

 39

 40

 41

 42

 43

 44

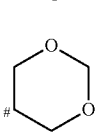 45

46

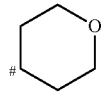 47 wherein # indicates the point of attachment of the carbocycle or heterocycle to the remainder of the compound. In some embodiments, the 3-, 4-, 5-, 6- or 7-membered carbocyclic or heterocyclic ring can comprise one or more fluorine substitutions. In some embodiments, the 3-, 4-, 5-, 6- or 7-membered carbocyclic or heterocyclic ring can comprise one or more deuterium substitutions.

In some embodiments of the compound C-D, $R_{10}$ is H, D, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, —CH(CH$_3$)$_2$, —CD$_2$CD$_3$, —CD(CD$_3$)$_2$, —CF$_2$CH$_3$, CF(CH$_3$)$_2$, —CH$_2$CF$_3$, —CH(CF$_3$)$_2$, —CF$_2$CF$_3$, —CF(CF$_3$)$_2$, —C(CH$_3$)$_3$, —C(CD$_3$)$_3$, —C(CF$_3$)$_3$, —OCH$_2$CH$_3$, —OCH(CH$_3$)$_2$, —OCD$_2$CD$_3$, —OCD(CD$_3$)$_2$, —OCF$_2$(CF$_3$), —OCF(CF$_3$)$_2$, —OC(CH$_3$)$_3$, —OC(CD$_3$)$_3$, —OC(CF$_3$)$_3$, —C(CH$_3$)$_2$(CF$_3$), —C(CH$_3$)(CF$_3$)$_2$, —OC(CH$_3$)$_2$(CF$_3$), —OC(CH$_3$)(CF$_3$)$_2$, —CH$_2$CH$_2$CH$_3$, —CH(CH$_2$CH$_3$)$_2$, —CD$_2$CD$_2$CD$_3$, —CD(CD$_2$CD$_3$)$_2$, —CF$_2$CF$_2$CF$_3$, —CF(CF$_2$CF$_3$)$_2$, —C(CH$_2$CH$_3$)$_3$, —C(CD$_2$CD$_3$)$_3$, —C(CF$_2$CF$_3$)$_3$, —OCH$_2$CH$_2$CH$_3$, —OCH(CH$_2$CH$_3$)$_2$, —OCD$_2$CD$_2$CD$_3$, —OCD(CD$_2$CD$_3$)$_2$, —OCF$_2$CF$_2$CF$_3$ or —OCF(CF$_2$CF$_3$)$_2$. In some embodiments of the compound C-D, $R_{10}$ is H, D, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$ or —CH(CH$_3$)$_2$. In some embodiments of the compound C-D, $R_{10}$ is H, D, F, —CH$_3$, —CH$_2$F, —CHF$_2$ or —CF$_3$. In some embodiments of the compound C-D, $R_{10}$ is H, D or F. In some embodiments of the compound C-D, $R_{10}$ is —CH$_3$ or —CF$_3$. In some embodiments of the compound C-D, $R_{10}$ is H or —CH$_3$. In some embodiments of the compound C-D, $R_{10}$ is H. In some embodiments of the compound E-F, $R_{10}$ is —CH$_3$. In some embodiments of the compound C-D, $R_{10}$ is absent.

In some embodiments of the compound C-D, $R_{11}$ is H, methyl or ethyl. In some embodiments of the compound C-D, $R_{11}$ is H. In some embodiments of the compound C-D, $R_{11}$ is methyl. In some embodiments of the compound C-D, $R_{11}$ is ethyl.

In some embodiments of the compound C-D, each instance of $R_{12}$, $R_{13}$ or $R_{14}$ is independently H, D, F, —CH$_3$, —OCH$_3$, —CD$_3$, —OCD$_3$, —CH$_2$F, —OCH$_2$F, —CHF$_2$, —OCHF$_2$, —CF$_3$, —OCF$_3$, —CH$_2$CH$_3$, —CH(CH$_3$)$_2$, —CH$_2$CH$_2$CH$_3$, —CH(CH$_2$CH$_3$)$_2$, —C(CH$_3$)$_3$, —OCH$_2$CH$_3$, —OCH(CH$_3$)$_2$, —OCH$_2$CH$_2$CH$_3$, —OCH(CH$_2$CH$_3$)$_2$, or —OC(CH$_3$)$_3$. In some embodiments of the compound C-D, each instance of $R_{12}$, $R_{13}$ or $R_{14}$ is independently H, D, F, —CH$_3$, —OCH$_3$, —CD$_3$, —OCD$_3$, —CH$_2$F, —OCH$_2$F, —CHF$_2$, —OCHF$_2$, —CF$_3$ or —OCF$_3$. In some embodiments of the compound C-D, each instance of $R_{12}$, $R_{13}$ or $R_{14}$ is independently H, D, F, —CH$_3$, —CD$_3$ or —CF$_3$. In some embodiments of the compound C-D, each instance of $R_{12}$, $R_{13}$ or $R_{14}$ is independently H, D, or F. In some embodiments of the compound C-D, each instance of $R_{12}$, $R_{13}$ or $R_{14}$ is independently H, F or —CH$_3$. In some embodiments of the compound C-D, each instance of $R_{12}$, $R_{13}$ or $R_{14}$ is H. In some embodiments of the compound C-D, each instance of $R_{12}$, $R_{13}$ or $R_{14}$ is D. In some embodiments of the compound C-D, each instance of $R_{12}$, $R_{13}$ or $R_{14}$ is F.

In some embodiments, $R_{19}$ is H. In some embodiments, $R_{19}$ is $C_1$-$C_4$ alkyl. For example, $R_{19}$ can be methyl, or $R_{19}$ can be ethyl, or $R_{19}$ can be isopropyl or $R_{19}$ can be tert-butyl. In some embodiments, $R_{19}$ can be benzyl (substituted or unsubstituted). For example, in some embodiments, $R_{19}$ is a group of formula:

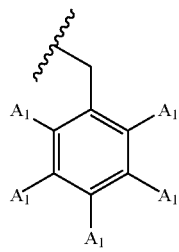

wherein each $A_1$ is independently H, D, F, Cl, Br, I, —$CH_3$, —$OCH_3$, $CH_2CH_3$, —$OCH_2CH_3$, trichloromethyl or trifluoromethyl.

In some embodiments of the compound C-D, $R_{20}$ is H, D, F, —$CH_3$, —$CD_3$, —$CH_2F$, —$CHF_2$, —$CF_3$, —$CH_2CH_3$, —$CH_2CH_2CH_3$, —$CH(CH_3)_2$, —$C(CH_3)_3$, —$CH_2CH_2CH_2CH_3$, —$CH_2CH_2CH_2CH_2CH_3$, —$CH_2CH_2CH_2CH_2CH_2CH_3$, —$CH_2CH_2CH_2CH_2CH_2CH_2CH_3$, —$CH_2CH_2CH_2CH_2CH_2CH_2CH_2CH_3$, —$CH_2CH_2CH_2CH_2CH_2CH_2CH_2CH_2CH_3$ or —$CH_2CH_2CH_2CH_2CH_2CH_2CH_2CH_2CH_2CH_3$. In some embodiments of the compound C-D, $R_{20}$ is H, D, F, —$CH_3$, —$CD_3$, —$CH_2F$, —$CHF_2$, —$CF_3$, —$CH_2CH_3$, —$CH_2CH_2CH_3$, —$CH(CH_3)_2$ or —$C(CH_3)_3$. In some embodiments of the compound C-D, $R_{20}$ is H, D, F, —$CH_3$, —$CD_3$, —$CH_2F$, —$CHF_2$ or —$CF_3$. In some embodiments of the compound C-D, $R_{20}$ is H, D, F, —$CH_3$, —$CD_3$, —$CH_2F$, —$CHF_2$ or —$CF_3$. In some embodiments of the compound C-D, $R_{20}$ is —$CH_3$, —$CD_3$, —$CH_2F$, —$CHF_2$ or —$CF_3$. In some embodiments of the compound C-D, $R_{20}$ is H. In some embodiments of the compound C-D, $R_{20}$ is —$CH_3$. In some embodiments of the compound E-F, $R_{20}$ is —$CF_3$. In some embodiments of the compound C-D, $R_{20}$ is F.

In some embodiments of the compound C-D, each $R_{21}$ is independently H, D, F, —$CH_3$, —$CD_3$, —$CH_2F$, —$CHF_2$, —$CF_3$, —$CH_2CH_3$, —$CH_2CH_2CH_3$, —$CH(CH_3)_2$, —$CH_2CH_2CH_2CH_3$ or —$C(CH_3)_3$. In some embodiments of the compound C-D, each $R_{21}$ is independently H, D, F, —$CH_3$, —$CD_3$, —$CH_2F$, —$CHF_2$ or —$CF_3$. In some embodiments of the compound C-D, each $R_{21}$ is independently H, —$CH_3$ or —$CF_3$. In some embodiments of the compound C-D, each $R_{21}$ is —$CH_3$. In some embodiments of the compound C-D, each $R_{21}$ is H. In some embodiments of the compound C-D, each $R_{21}$ is —$CF_3$.

In some embodiments of the compound C-D, n is 0, 1, 2, 3, 4, 5, 6, 7 or 8. In some embodiments of the compound C-D, n is 0, 1, 2, 3, 4, 5 or 6. In some embodiments of the compound C-D, n is 0, 1, 2, 3 or 4. In some embodiments of the compound C-D, n is 0. In some embodiments of the compound C-D, n is 1. In some embodiments of the compound C-D, n is 2. In some embodiments of the compound C-D, n is 3. In some embodiments of the compound C-D, n is 4. In some embodiments of the compound C-D, n is 5. In some embodiments of the compound C-D, n is 6. In some embodiments of the compound C-D, n is 7. In some embodiments of the compound C-D, n is 8. In some embodiments of the compound C-D, n is 9. In some embodiments of the compound C-D, n is 10. In some embodiments of the compound C-D, n is 11. In some embodiments of the compound C-D, n is 12.

In some embodiments of the compound C-D has the formula referred to herein as Compound A-2:

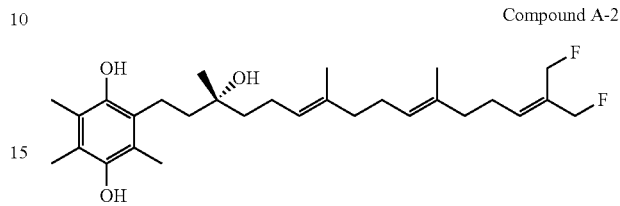

Compound A-2

In some embodiments of the compound C-D has the formula referred to herein as Compound B-2:

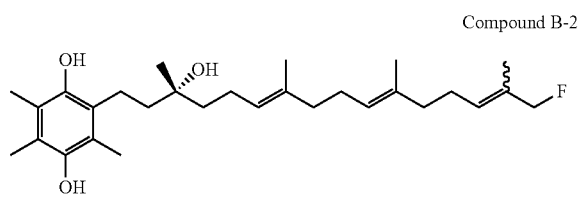

Compound B-2

In some embodiments of the compound C-D has the formula referred to herein as Compound C-2:

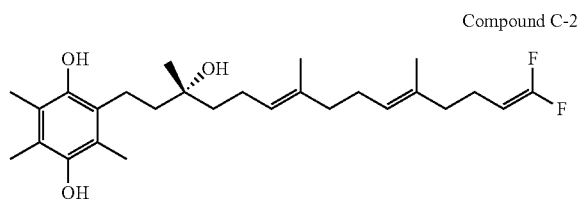 [SMILES: C/C(=C\CC/C(C)=C/CC[C@@](C)(O)CCc1c(C)c(O)c(C)c(C)c1O)CCC=C(F)F]

Compound C-2

In some embodiments of the compound C-D has the formula referred to herein as Compound D-2:

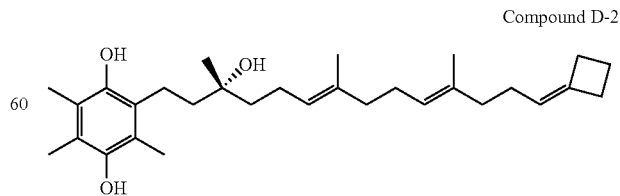

Compound D-2

In some embodiments of the compound C-D has the formula referred to herein as Compound E-2:

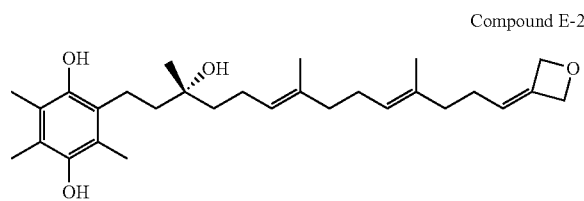 [SMILES: C/C(=C\CC/C(C)=C/CC[C@@](C)(O)CCc1c(C)c(O)c(C)c(C)c1O)CCC=C1COC1]

Compound E-2

In some embodiments of the compound C-D has the formula referred to herein as Compound F-2:

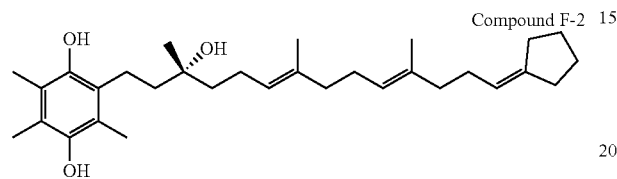

Compound F-2

In some embodiments of the compound C-D has the formula referred to herein as Compound G-2:

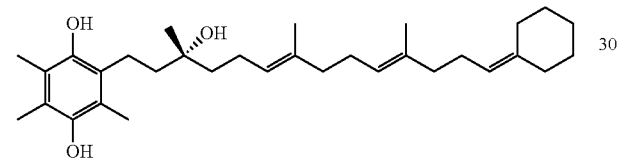

Compound G-2

In some embodiments of the compound C-D has the formula referred to herein as Compound H-2:

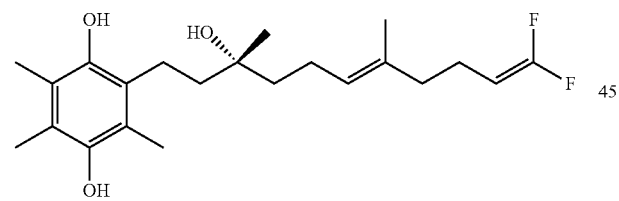

Compound H-2

In some embodiments of the compound C-D has the formula referred to herein as Compound I-2:

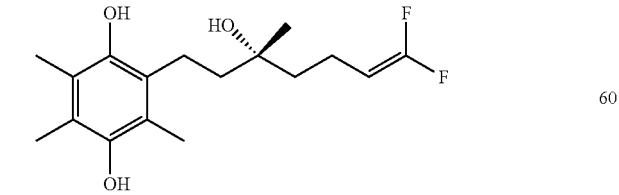

Compound I-2

In some embodiments of the compound C-D has the formula referred to herein as Compound J-2:

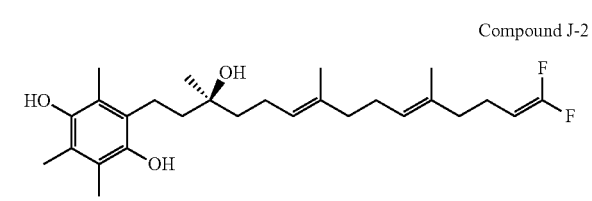 [SMILES: C/C(=C\CC/C(C)=C/CC[C@](C)(O)CCc1c(C)c(O)c(C)c(C)c1O)CCC=C(F)F]

Compound J-2

In some embodiments of the compound C-D has the formula referred to herein as Compound K-2:

Compound K-2

In some embodiments of the compound C-D has the formula referred to herein as Compound L-2:

Compound L-2

In some embodiments of the compound C-D has the formula referred to herein as Compound N-2:

Compound N-2

In some embodiments, this application further provides therapeutic compounds comprising a substituted quinone head group to which is covalently linked an aliphatic tail group that comprises at least one chiral center, at least one hydroxyl group and at least one silicon atom. In some embodiments, such compounds can have the formula E-G, or pharmaceutically acceptable salts, stereoisomers, mixtures of stereoisomers, tautomers, hydrates, and/or solvates thereof, wherein E is 21 or 22:

21

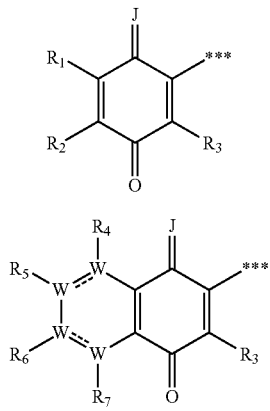

22

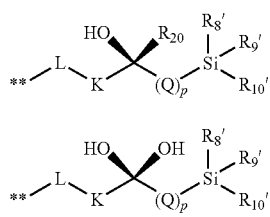

and G is 23 or 24:

23

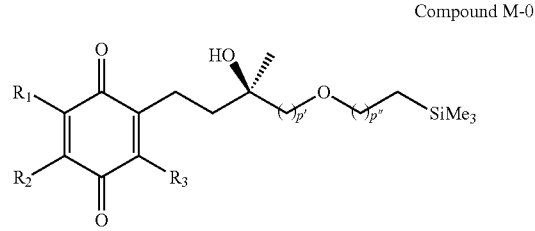

24

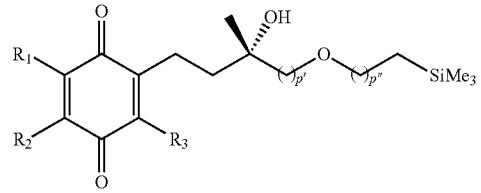

wherein, J is O, S or N—Ru; K is absent or —(CR$_{12}$R$_{13}$)—; L is —(CR$_{12}$R$_{13}$)—; each W is independently C (carbon) or N (nitrogen) and wherein for each use of w═w, the bond between each W can be a single bond or double bond and further provided that if a single bond, each C (carbon) atom will have a hydrogen atom linked hereto in addition to one of R$_4$, R$_5$, R$_6$ or R$_7$ and in either case each of R$_4$, R$_5$, R$_6$ and R$_7$ attached thereto is independently selected from H, D, F, Cl, Br, I, C$_1$-C$_6$ alkyl and C$_1$-C$_6$ alkoxy, and if W is N (nitrogen), each of R$_4$, R$_5$, R$_6$ and R$_7$ attached thereto is independently absent (if w═w is a double bond) or selected from H, D and ═C$_1$-C$_6$ alkyl (if w═w is a single bond); each Q is independently a group of formula —(CR$_{12}$R$_{13}$)—, O or Si provided that each O and each Si is not directly bonded to O or Si; each of R$_1$, R$_2$ and R$_3$ is independently H, D, F, Cl, Br, I, C$_1$-C$_6$ alkyl or C$_1$-C$_6$ alkoxy or R$_1$ and R$_2$ together form a 5-membered carbocyclic ring, a 5-membered heterocyclic ring, a 5-membered aromatic or heteroaromatic ring, or a 6-membered heterocyclic ring; each of R$_8$', R$_9$' and R$_{10}$' is independently a C$_1$-C$_4$ alkyl, or taken together R$_8$' and R$_9$' form a 3-, 4-, 5-, 6- or 7-membered carbocyclic or heterocyclic ring; R$_1$ is H, D or C$_1$-C$_6$ alkyl; each of R$_{12}$ and R$_{13}$ is independently H, D, F, Cl, Br, I, C$_1$-C$_6$ alkyl or C$_1$-C$_6$ alkoxy; R$_{20}$ is H, D, F or C$_1$-C$_{12}$ alkyl; p is an integer from 0 to 20, inclusive; and * indicates the point of attachment of E to G and  indicates the point of attachment of G to E. In some embodiments, each of R$_8$', R$_9$' and R$_{10}$' is independently methyl or ethyl.

In some embodiments, E is 21, J is O, K is —(CH$_2$)—, L is —(CH$_2$)—, each of R$_1$, R$_2$ and R$_3$ is independently selected from: H, D, F, —CH$_3$, —OCH$_3$ and —OCF$_3$, each R$_8$', R$_9$' and R$_{10}$' is independently methyl or ethyl and R$_{20}$ is C$_1$-C$_4$ alkyl. In some embodiments, each of R$_1$, R$_2$ and R$_3$ is independently H, —CH$_3$, or —OCH$_3$. In some embodiments, each of R$_1$, R$_2$ and R$_3$ is independently H, or —CH$_3$. In some embodiments, each of R$_1$, R$_2$ and R$_3$ is —CH$_3$.

In some embodiments, each Q is —(CH$_2$)—. In some embodiments, at least one Q is O and each other Q is —(CH$_2$)—. In some embodiments, at least one Q is Si and each other Q is —(CH$_2$)—. In some embodiments, only one Q is O. In some embodiments, only one Q is O and the remaining Q's are —(CH$_2$)—.

In some embodiments, E-G is Compound M-0 or M-0':

Compound M-0

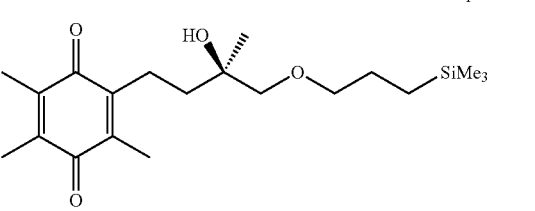

Compound M-0'

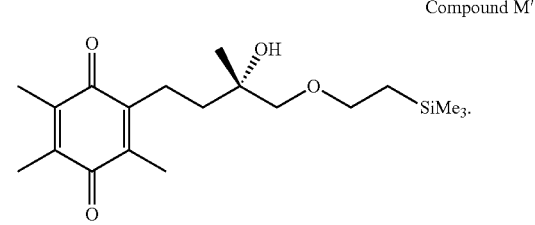

wherein, each of R$_1$, R$_2$ and R$_3$ is independently H, F, —CH$_3$, —OCH$_3$, —CH$_2$CH$_3$, —OCH$_2$CH$_3$, or —OCF$_3$, p' is an integer from 1 to 9, inclusive and p" is an integer from 1 to 9, inclusive. In some embodiments, each of R$_1$, R$_2$ and R$_3$ is independently H, —CH$_3$, or —OCH$_3$. In some embodiments, each of R$_1$, R$_2$ and R$_3$ is independently H, or —CH$_3$. In some embodiments, each of R$_1$, R$_2$ and R$_3$ is —CH$_3$. In some embodiments, each of p' and p" in independently an integer from 1-4, inclusive.

In some embodiments, E-G is Compound M or Compound M':

Compound M

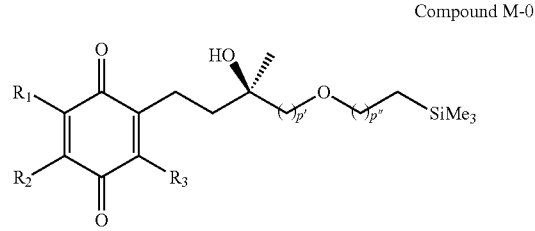

Compound M'

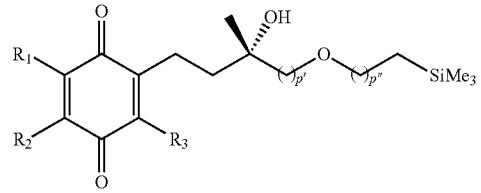

In some embodiments, this application further provides therapeutic compounds comprising a substituted hydroquinone head group to which is covalently linked an aliphatic tail group that comprises at least one chiral center, at least one hydroxyl group and at least one silicon atom. Thus, in some embodiments, this application further provides therapeutic compounds or intermediates of formula C-G, or pharmaceutically acceptable salts, stereoisomers, mixtures of stereoisomers, tautomers, hydrates, and/or solvates thereof, wherein C is 11 or 12:

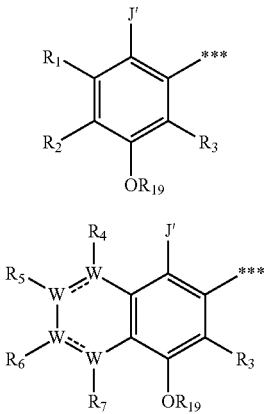

and G is 23 or 24:

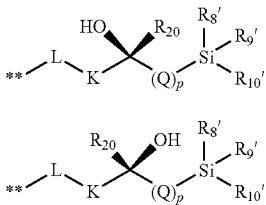

wherein, J' is OH, SH or NH—$R_{11}$; K is absent or —($CR_{12}R_{13}$)—; L is —($CR_{12}R_{13}$)—; each W is ═ independently C (carbon) or N (nitrogen) and wherein for each use of w═w, the bond between each W can be a single bond or double bond and further provided that if a single bond, each C (carbon) atom will have a hydrogen atom linked hereto in addition to one of $R_4$, $R_5$, $R_6$ or $R_7$ and in either case each of $R_4$, $R_5$, $R_6$ and $R_7$ attached thereto is independently selected from H, D, F, Cl, Br, I, $C_1$-$C_6$ alkyl and $C_1$-$C_6$ alkoxy, and if W is N (nitrogen), each of $R_4$, $R_5$, $R_6$ and $R_7$ attached thereto is independently absent (if w═w is a double bond) or selected from H, D and $C_1$-$C_6$ alkyl (if w═w is a single bond); each Q is independently a group of formula —($CR_{12}R_{13}$)—, O or Si provided that each O and each Si is not directly bonded to O or Si; each of $R_1$, $R_2$ and $R_3$ is independently H, D, F, Cl, Br, I, $C_1$-$C_6$ alkyl or $C_1$-$C_6$ alkoxy, or $R_1$ and $R_2$ together form a 5-membered carbocyclic ring, a 5-membered heterocyclic ring, a 5-membered aromatic or heteroaromatic ring, or a 6-membered heterocyclic ring; each of $R_8'$, $R_9'$ and $R_{10}'$ is independently a $C_1$-$C_4$ alkyl, or taken together $R_8'$ and $R_9'$ form a 3-, 4-, 5-, 6- or 7-membered carbocyclic or heterocyclic ring; $R_1$ is H, D or $C_1$-$C_6$ alkyl; each of $R_{12}$ and $R_{13}$ is independently H, D, F, Cl, Br, I, $C_1$-$C_6$ alkyl or $C_1$-$C_6$ alkoxy; $R_{19}$ is H, $C_1$-$C_4$ alkyl or benzyl (substituted or unsubstituted); $R_{20}$ is H, D, F or $C_1$-$C_{12}$ alkyl; p is an integer from 0 to 20, inclusive; and * indicates the point of attachment of C to G and  indicates the point of attachment of G to C. In some embodiments, each of $R_8'$, $R_9'$ and $R_{10}'$ is independently methyl or ethyl.

In some embodiments, C is 11, J' is OH, K is —($CH_2$)—, L is —($CH_2$)—, each of $R_1$, $R_2$ and $R_3$ is independently selected from: H, D, F, —$CH_3$, —$OCH_3$ and —$OCF_3$, each of $R_8'$, $R_9'$ and $R_{10}'$ is independently methyl or ethyl, $R_{19}$ is H and $R_{20}$ is $C_1$-$C_4$ alkyl. In some embodiments, each of $R_1$, $R_2$ and $R_3$ is independently H, —$CH_3$ or —$OCH_3$. In some embodiments, each of $R_1$, $R_2$ and $R_3$ is independently H, or —$CH_3$. In some embodiments, each of $R_1$, $R_2$ and $R_3$ is —$CH_3$.

In some embodiments, each Q is —($CH_2$)—. In some embodiments, at least one Q is O and each other Q is —($CH_2$)—. In some embodiments, at least one Q is Si and each other Q is —($CH_2$)—. In some embodiments, only one Q is O. In some embodiments, only one Q is O and the remaining Q's are —($CH_2$)—.

In some embodiments, C-G is a Compound M-3 or Compound M-3':

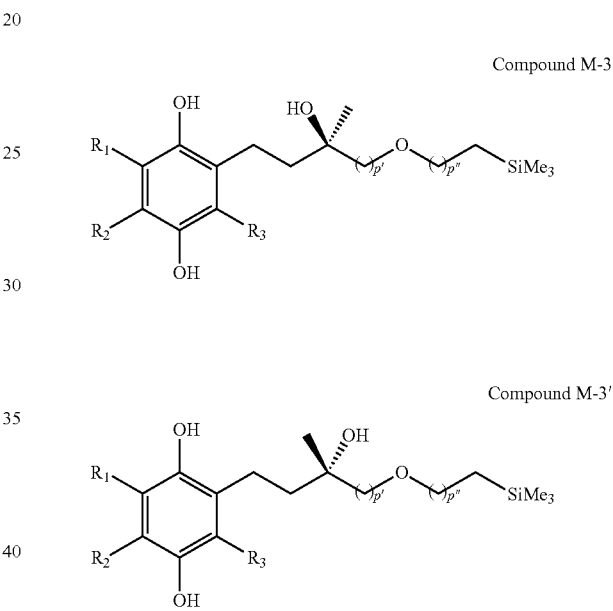

wherein, each of $R_1$, $R_2$ and $R_3$ is independently H, F, —$CH_3$, —$OCH_3$, —$CH_2CH_3$, —$OCH_2CH_3$, or $OCF_3$, p' is an integer from 1 to 9, inclusive and p" is an integer from 1 to 9, inclusive. In some embodiments, each of $R_1$, $R_2$ and $R_3$ is independently H, —$CH_3$, or —$OCH_3$. In some embodiments, each of $R_1$, $R_2$ and $R_3$ is independently H, or —$CH_3$. In some embodiments, each of $R_1$, $R_2$ and $R_3$ is —$CH_3$. In some embodiments, each of p' and p" in independently an integer from 1-4, inclusive.

In some embodiments, C-G is Compound M-2 or M-2':

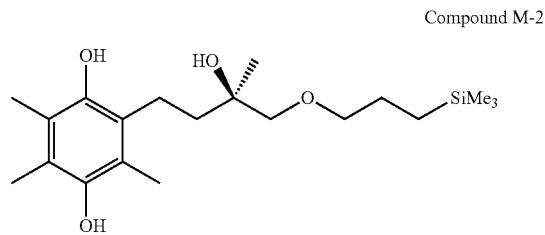

Compound M-2′

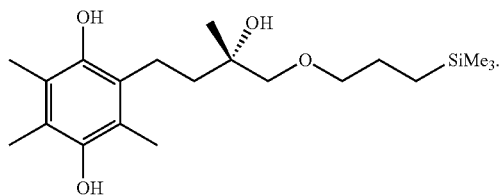

In some embodiments, this application further provides therapeutic compounds or intermediates to therapeutic compounds comprising a precursor to an aromatic quinone or hydroquinone head group to which is linked a precursor to an aliphatic tail group that comprises at least one chiral center, at least one hydroxyl group and at least one silicon atom. In some embodiments, this application pertains to compounds of formula A-H, or pharmaceutically acceptable salts, stereoisomers, mixtures of stereoisomers, tautomers, hydrates, and/or solvates thereof, wherein A is 1, 2, 3, or 4:

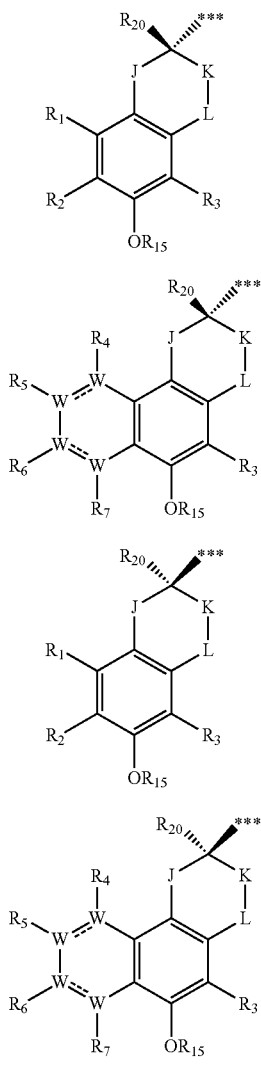

and H is 25:

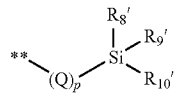

wherein, J is O, S or N—$R_{11}$; K is absent or —$(CR_{12}R_{13})$—; L is —$(CR_{12}R_{13})$—; each W is independently C (carbon) or N (nitrogen) and wherein for each use of w≡w, the bond between each W can be a single bond or double bond and further provided that if a single bond, each C (carbon) atom will have a hydrogen atom linked hereto in addition to one of $R_4$, $R_5$, $R_6$ or $R_7$ and in either case each of $R_4$, $R_5$, $R_6$ and $R_7$ attached thereto is independently selected from H, D, F, Cl, Br, I, $C_1$-$C_6$ alkyl and $C_1$-$C_6$ alkoxy, and if W is N (nitrogen), each of $R_4$, $R_5$, $R_6$ and $R_7$ attached thereto is independently absent (if w≡w is a double bond) or selected from H, D and $C_1$-$C_6$ alkyl (if w≡w is a single bond); each Q is independently a group of formula —$(CR_{12}R_{13})$—, O or Si provided that each O and each Si is not directly bonded to O or Si; each of $R_1$, $R_2$ and $R_3$ is independently H, D, F, Cl, Br, I, $C_1$-$C_6$ alkyl or $C_1$-$C_6$ alkoxy, or $R_1$ and $R_2$ together form a 5-membered carbocyclic ring, a 5-membered heterocyclic ring, a 5-membered aromatic or heteroaromatic ring, or a 6-membered heterocyclic ring; each of $R_8'$, $R_9'$ and $R_{10}'$ is independently a $C_1$-$C_4$ alkyl, or taken together $R_8'$ and $R_9'$ form a 3-, 4-, 5-, 6- or 7-membered carbocyclic or heterocyclic ring; $R_{11}$ is H, D or $C_1$-$C_6$ alkyl; each of $R_{12}$ and $R_{13}$ is independently H, D, F, Cl, Br, I, $C_1$-$C_6$ alkyl or $C_1$-$C_6$ alkoxy; $R_{15}$ is H, $C_1$-$C_4$ alkyl or PG, wherein PG is a phenol protecting group; $R_{20}$ is H, D, F or $C_1$-$C_{12}$ alkyl; p is an integer from 0 to 20, inclusive; and * indicates the point of attachment of A to H and  indicates the point of attachment of H to A. In some embodiments, each of $R_8'$, $R_9'$ and $R_{10}'$ is independently methyl or ethyl.

In some embodiments, A is 1 or 3, J is O, K is —$(CH_2)$—, L is —$(CH_2)$— and each of $R_1$, $R_2$ and $R_3$ is independently selected from: H, D, F, —$CH_3$, —$OCH_3$ and —$OCF_3$, each $R_8'$, $R_9'$ and $R_{10}'$ is independently methyl or ethyl, and $R_{15}$ is H or PG. In some embodiments, each of $R_1$, $R_2$ and $R_3$ is independently H, —$CH_3$ or —$OCH_3$. In some embodiments, each of $R_1$, $R_2$ and $R_3$ is independently H, or —$CH_3$. In some embodiments, each of $R_1$, $R_2$ and $R_3$ is —$CH_3$.

In some embodiments, each Q is —$(CH_2)$—. In some embodiments, at least one Q is O and each other Q is —$(CH_2)$—. In some embodiments, at least one Q is Si and each other Q is —$(CH_2)$—. In some embodiments, only one Q is O. In some embodiments, only one Q is O and the remaining Q's are —$(CH_2)$—.

In some embodiments, A-H is Compound M-4 or M-4′:

Compound M-4

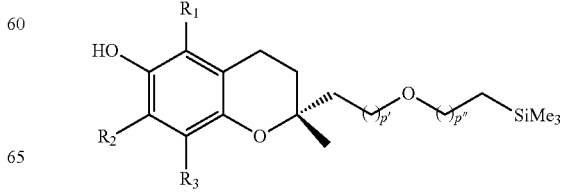

-continued

Compound M-4'

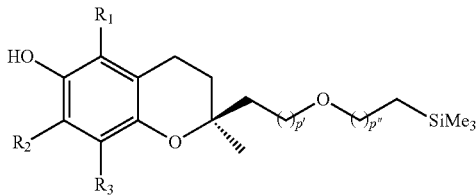

-continued

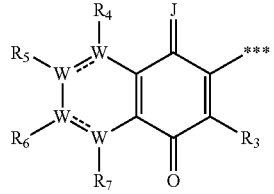

22 and I is 26 or 27:

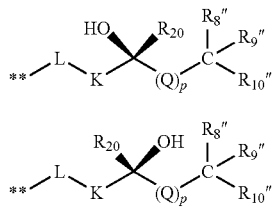

26

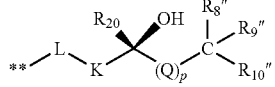

27 wherein, each of $R_1$, $R_2$ and $R_3$ is independently H, F, —$CH_3$, —$OCH_3$, —$CH_2CH_3$, —$OCH_2CH_3$, or $OCF_3$, p' is an integer from 1 to 9, inclusive and p" is an integer from 1 to 9, inclusive. In some embodiments, each of $R_1$, $R_2$ and $R_3$ is independently H, —$CH_3$, or —$OCH_3$. In some embodiments, each of $R_1$, $R_2$ and $R_3$ is independently H, or —$CH_3$. In some embodiments, each of $R_1$, $R_2$ and $R_3$ is —$CH_3$. In some embodiments, each of p' and p" in independently an integer from 1-4, inclusive.

In some embodiments, A-H is Compound M-5 or M-5':

Compound M-5

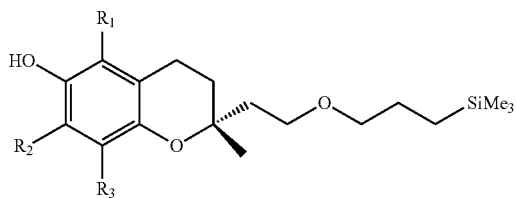

Compound M-5'

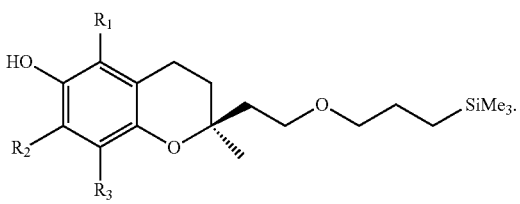

In some embodiments, this application further provides therapeutic compounds of formula E-I, or pharmaceutically acceptable salts, stereoisomers, mixtures of stereoisomers, tautomers, hydrates, and/or solvates thereof, wherein E is 21 or 22:

21

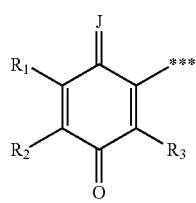

wherein, J is O, S or N—Ru; K is absent or —($CR_{12}R_{13}$)—; L is —($CR_{12}R_{13}$)—; each W is ═ independently C (carbon) or N (nitrogen) and wherein for each use of w═w, the bond between each W can be a single bond or double bond and further provided that if a single bond, each C (carbon) atom will have a hydrogen atom linked hereto in addition to one of $R_4$, $R_5$, $R_6$ or $R_7$ and in either case each of $R_4$, $R_5$, $R_6$ and $R_7$ attached thereto is independently selected from H, D, F, Cl, Br, I, $C_1$-$C_6$ alkyl and $C_1$-$C_6$ alkoxy, and if W is N (nitrogen), each of $R_4$, $R_5$, $R_6$ and $R_7$ attached thereto is independently absent (if w═w is a double bond) or selected from H, D and $C_1$-$C_6$ alkyl (if w═w is a single bond); each Q is independently a group of formula —($CR_{12}R_{13}$)—, O or Si provided that each O and each Si is not directly bonded to O or Si; each of $R_1$, $R_2$ and $R_3$ is independently H, D, F, Cl, Br, I, $C_1$-$C_6$ alkyl or $C_1$-$C_6$ alkoxy or $R_1$ and $R_2$ together form a 5-membered carbocyclic ring, a 5-membered heterocyclic ring, a 5-membered aromatic or heteroaromatic ring, or a 6-membered heterocyclic ring; each $R_8''$, $R_9''$ and $R_{10}''$ is independently H, F, or $C_1$-$C_4$ alkyl provided however that at least one of $R_8''$, $R_9''$ and $R_{10}''$ is F; $R_1$ is H, D or $C_1$-$C_6$ alkyl; each of $R_{12}$ and $R_{13}$ is independently H, D, F, Cl, Br, I, $C_1$-$C_6$ alkyl or $C_1$-$C_6$ alkoxy; $R_{20}$ is H, D, F or $C_1$-$C_{12}$ alkyl; p is an integer from 0 to 20, inclusive; and * indicates the point of attachment of E to I and  indicates the point of attachment of I to E. In some embodiments, at least one of $R_8''$, $R_9''$ and $R_{10}''$ is F. In some embodiments, each of $R_8''$, $R_9''$ and $R_{10}''$ is independently H or F. In some embodiments, each of $R_8''$, $R_9''$ and $R_{10}''$ is F.

In some embodiments, E is 21, J is O, K is —($CH_2$)—, L is —($CH_2$)—, each of $R_1$, $R_2$ and $R_3$ is independently selected from: H, D, F, —$CH_3$, —$OCH_3$ and —$OCF_3$, each $R_8''$, $R_9''$ and $R_{10}''$ is independently H or F and $R_{20}$ is $C_1$-$C_4$ alkyl. In some embodiments, each of $R_1$, $R_2$ and $R_3$ is independently H, —$CH_3$, or —$OCH_3$. In some embodiments, each of $R_1$, $R_2$ and $R_3$ is independently H, or —$CH_3$. In some embodiments, each of $R_1$, $R_2$ and $R_3$ is —$CH_3$.

In some embodiments, each Q is —($CH_2$)—. In some embodiments, at least one Q is O and each other Q is —($CH_2$)—. In some embodiments, at least one Q is Si and each other Q is —($CH_2$)—. In some embodiments, only one Q is O. In some embodiments, only one Q is O and the remaining Q's are —($CH_2$)—.

In some embodiments, E-I is Compound N-0 or N-0':

Compound N-0

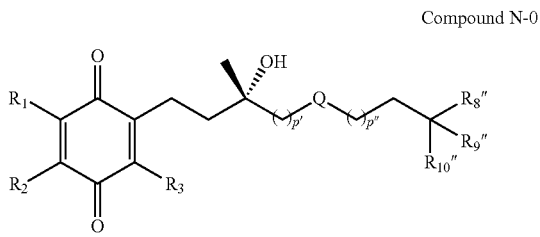

Compound N-0'

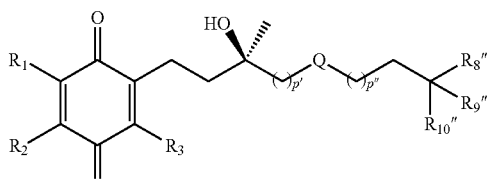

wherein, each of $R_1$, $R_2$ and $R_3$ is independently H, F, —$CH_3$, —$OCH_3$, —$CH_2CH_3$, —$OCH_2CH_3$, or —$OCF_3$, Q is —($CH_2$)—, O or Si, p' is an integer from 0 to 9, inclusive and p" is an integer from 0 to 9, inclusive. In some embodiments, Q is —($CH_2$)—. In some embodiments, each of $R_1$, $R_2$ and $R_3$ is independently H, —$CH_3$, or —$OCH_3$. In some embodiments, each of $R_1$, $R_2$ and $R_3$ is independently H, or —$CH_3$. In some embodiments, each of $R_1$, $R_2$ and $R_3$ is —$CH_3$. In some embodiments, each of p' and p" is independently an integer from 0-4, inclusive.

In some embodiments, E-I is Compound N or Compound N':

Compound N

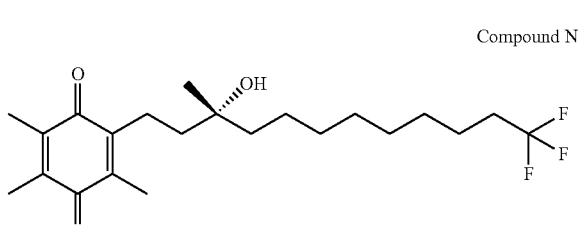

Compound N'

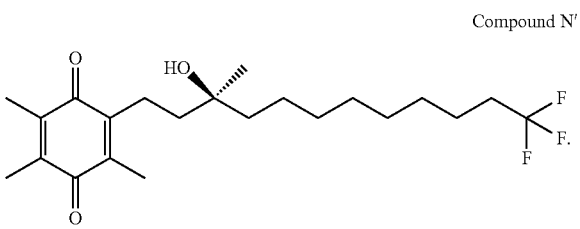

In some embodiments, this application further provides therapeutic compounds or intermediates of formula C-I, or pharmaceutically acceptable salts, stereoisomers, mixtures of stereoisomers, tautomers, hydrates, and/or solvates thereof, wherein C is 11 or 12:

11

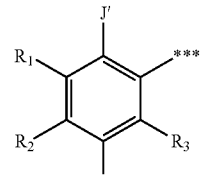

12

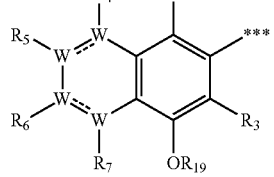

and I is 26 or 27:

26

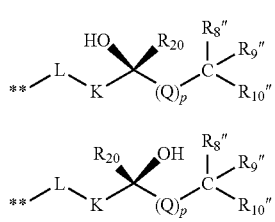

27

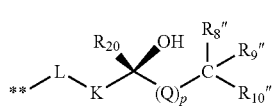

wherein, J' is OH, SH or NH—$R_{11}$; K is absent or —($CR_{12}R_{13}$)—; L is —($CR_{12}R_{13}$)—; each W is independently C (carbon) or N (nitrogen) and wherein for each use of w═w, the bond between each W can be a single bond or double bond and further provided that if a single bond, each C (carbon) atom will have a hydrogen atom linked hereto in addition to one of $R_4$, $R_5$, $R_6$ or $R_7$ and in either case each of $R_4$, $R_5$, $R_6$ and $R_7$ attached thereto is independently selected from H, D, F, Cl, Br, I, $C_1$-$C_6$ alkyl and $C_1$-$C_6$ alkoxy, and if W is N (nitrogen), each of $R_4$, $R_5$, $R_6$ and $R_7$ attached thereto is independently absent (if w═w is a double bond) or selected from H, D and $C_1$-$C_6$ alkyl (if w═w is a single bond); each Q is independently a group of formula —($CR_{12}R_{13}$)—, O or Si provided that each O and each Si is not directly bonded to O or Si; each of $R_1$, $R_2$ and $R_3$ is independently H, D, F, Cl, Br, I, $C_1$-$C_6$ alkyl or $C_1$-$C_6$ alkoxy, or $R_1$ and $R_2$ together form a 5-membered carbocyclic ring, a 5-membered heterocyclic ring, a 5-membered aromatic or heteroaromatic ring, or a 6-membered heterocyclic ring; each $R_8''$, $R_9''$ and $R_{10}''$ is independently H, F, or $C_1$-$C_4$ alkyl provided however that at least one of $R_8''$, $R_9''$ and $R_{10}''$ is F; $R_1$ is H, D or $C_1$-$C_6$ alkyl; each of $R_{12}$ and $R_{13}$ is independently H, D, F, Cl, Br, I, $C_1$-$C_6$ alkyl or $C_1$-$C_6$ alkoxy; $R_{19}$ is H, $C_1$-$C_4$ alkyl or benzyl (substituted or unsubstituted); $R_{20}$ is H, D, F or $C_1$-$C_{12}$ alkyl; p is an integer from 0 to 20, inclusive; and * indicates the point of attachment of C to I and  indicates the point of attachment of I to C. In some embodiments, each of $R_8''$, $R_9''$ and $R_{10}''$ is independently H or F. In some embodiments, at least one of $R_8''$, $R_9''$ and $R_{10}''$ is F. In some embodiments, each of $R_8''$, $R_9''$ and $R_{10}''$ is F.

In some embodiments, C is 11, J' is OH, K is —($CH_2$)—, L is —($CH_2$)—, each of $R_1$, $R_2$ and $R_3$ is independently selected from: H, D, F, —$CH_3$, —$OCH_3$ and —$OCF_3$, each $R_8''$, $R_9''$ and $R_{10}''$ is independently H or F, $R_{19}$ is H and $R_{20}$ is $C_1$-$C_4$ alkyl. In some embodiments, each of $R_1$, $R_2$ and $R_3$ is independently H, —$CH_3$ or —$OCH_3$. In some embodiments, each of $R_1$, $R_2$ and $R_3$ is independently H, or —$CH_3$. In some embodiments, each of $R_1$, $R_2$ and $R_3$ is —$CH_3$. In some embodiments, each Q is —($CH_2$)—. In some embodiments, at least one Q is O and each other Q is —($CH_2$)—. In some embodiments, at least one Q is Si and each other Q is —($CH_2$)—. In some embodiments, only one Q is O. In some embodiments, only one Q is O and the remaining Q's are —($CH_2$)—.

In some embodiments, C-I is Compound N-3 or N-3':

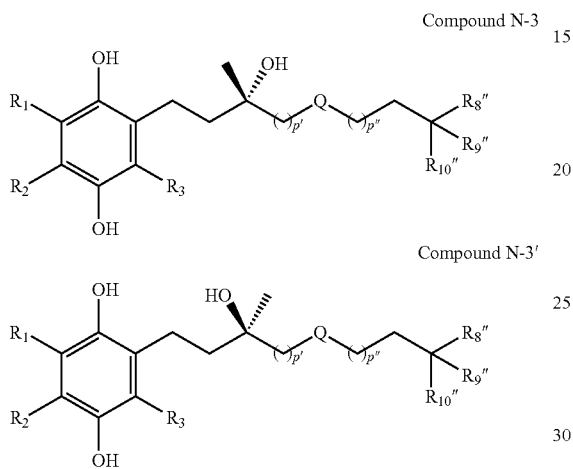

Compound N-3

Compound N-3' wherein, each of $R_1$, $R_2$ and $R_3$ is independently H, F, —$CH_3$, —$OCH_3$, —$CH_2CH_3$, —$OCH_2CH_3$, or $OCF_3$, Q is —($CH_2$)—, O or Si, p' is an integer from 0 to 9, inclusive and p" is an integer from 0 to 9, inclusive. In some embodiments, Q is —($CH_2$)—. In some embodiments, each of $R_1$, $R_2$ and $R_3$ is independently H, —$CH_3$, or —$OCH_3$. In some embodiments, each of $R_1$, $R_2$ and $R_3$ is independently H, or —$CH_3$. In some embodiments, each of $R_1$, $R_2$ and $R_3$ is —$CH_3$. In some embodiments, each of p' and p" is independently an integer from 0-4, inclusive.

In some embodiments, C-G is Compound N-2 or N-2':

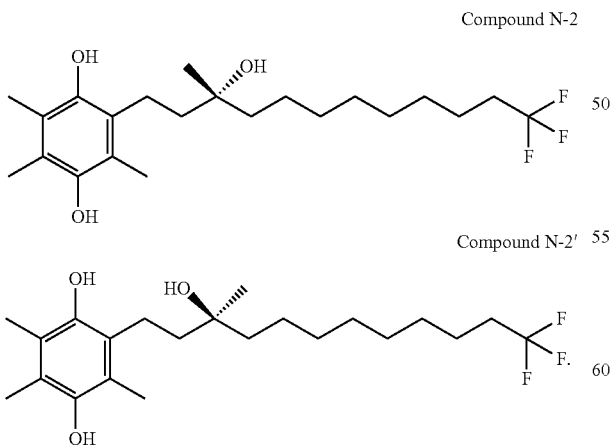

Compound N-2

Compound N-2'

In some embodiments, this application further provides therapeutic compounds or intermediates of formula A-U, or pharmaceutically acceptable salts, stereoisomers, mixtures of stereoisomers, tautomers, hydrates, and/or solvates thereof, wherein A is 1, 2, 3, or 4:

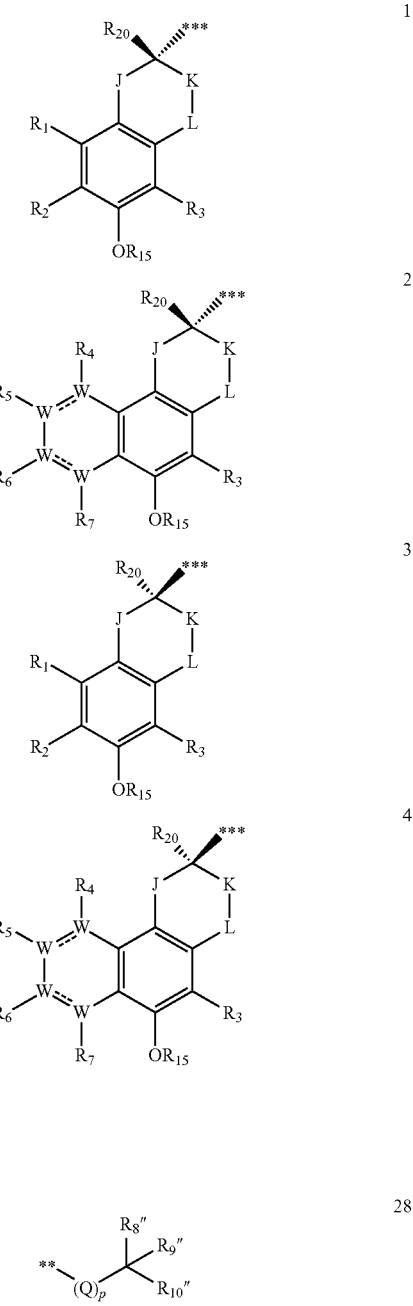

and U is 28:

28 wherein, J is O, S or N—Ru; K is absent or —($CR_{12}R_{13}$)—; L is —($CR_{12}R_{13}$)—; each W is independently C (carbon) or N (nitrogen) and wherein for each use of w═w, the bond between each W can be a single bond or double bond and further provided that if a single bond, each C (carbon) atom will have a hydrogen atom linked hereto in addition to one of $R_4$, $R_5$, $R_6$ or $R_7$ and in either case each of $R_4$, $R_5$, $R_6$ and $R_7$ attached thereto is independently selected from H, D, F, Cl, Br, I, $C_1$-$C_6$ alkyl and $C_1$-$C_6$ alkoxy, and if W is N (nitrogen), each of $R_4$, $R_5$, $R_6$ and $R_7$ attached thereto is independently absent (if w═w is a double bond) or selected from H, D and $C_1$-$C_6$ alkyl (if w═w is a single bond); each Q is independently a group of formula —(CR$_{12}$R$_{13}$)—, O or Si provided that each O and each Si is not directly bonded to O or Si; each of R$_1$, R$_2$ and R$_3$ is independently H, D, F, Cl, Br, I, C$_1$-C$_6$ alkyl or C$_1$-C$_6$ alkoxy, or R$_1$ and R$_2$ together form a 5-membered carbocyclic ring, a 5-membered heterocyclic ring, a 5-membered aromatic or heteroaromatic ring, or a 6-membered heterocyclic ring; each R$_8$", R$_9$" and R$_{10}$" is independently H, F, or C$_1$-C$_4$ alkyl provided however that at least one of R$_8$", R$_9$" and R$_{10}$" is F; R$_1$ is H, D or C$_1$-C$_6$ alkyl; each of R$_{12}$ and R$_{13}$ is independently H, D, F, Cl, Br, I, C$_1$-C$_6$ alkyl or C$_1$-C$_6$ alkoxy; R$_{15}$ is H, C$_1$-C$_4$ alkyl or PG, wherein PG is a phenol protecting group; R$_{20}$ is H, D, F or C$_1$-C$_{12}$ alkyl; p is an integer from 0 to 20, inclusive; and * indicates the point of attachment of A to U and  indicates the point of attachment of U to A. In some embodiments, each of R$_8$", R$_9$" and R$_{10}$" is independently H or F. In some embodiments, at least one of R$_8$", R$_9$" and R$_{10}$" is F. In some embodiments, each of R$_8$", R$_9$" and R$_{10}$" is F.

In some embodiments, A is 1 or 3, J is O, K is —(CH$_2$)—, L is —(CH$_2$)— and each of R$_1$, R$_2$ and R$_3$ is independently selected from: H, D, F, —CH$_3$, —OCH$_3$ and —OCF$_3$, each R$_8$", R$_9$" and R$_{10}$" is independently H or F and R$_{15}$ is H or PG. In some embodiments, each of R$_1$, R$_2$ and R$_3$ is independently H, —CH$_3$ or —OCH$_3$. In some embodiments, each of R$_1$, R$_2$ and R$_3$ is independently H, or —CH$_3$. In some embodiments, each of R$_1$, R$_2$ and R$_3$ is —CH$_3$.

In some embodiments, each Q is —(CH$_2$)—. In some embodiments, at least one Q is O and each other Q is —(CH$_2$)—. In some embodiments, at least one Q is Si and each other Q is —(CH$_2$)—. In some embodiments, only one Q is O. In some embodiments, only one Q is O and the remaining Q's are —(CH$_2$)—.

In some embodiments, A-H is Compound N-4 or Compound N-4':

Compound N-4

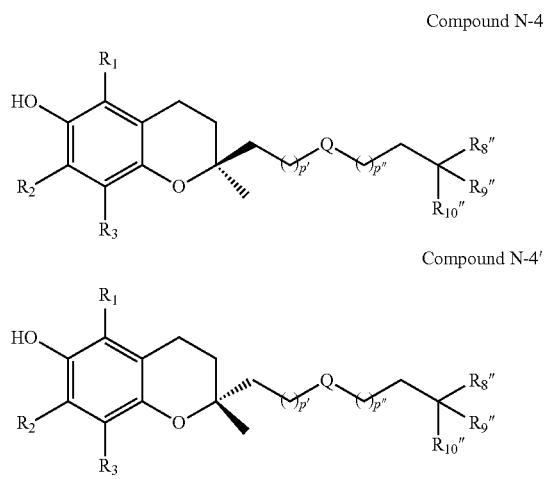

Compound N-4' wherein, each of R$_1$, R$_2$ and R$_3$ is independently H, F, —CH$_3$, —OCH$_3$, —CH$_2$CH$_3$, —OCH$_2$CH$_3$, or OCF$_3$, Q is —(CH$_2$)—, O or Si, p' is an integer from 0 to 9, inclusive and p" is an integer from 0 to 9, inclusive. In some embodiments, Q is —(CH$_2$)—. In some embodiments, each of R$_1$, R$_2$ and R$_3$ is independently H, —CH$_3$, or —OCH$_3$. In some embodiments, each of R$_1$, R$_2$ and R$_3$ is independently H, or —CH$_3$. In some embodiments, each of R$_1$, R$_2$ and R$_3$ is —CH$_3$. In some embodiments, each of p' and p" is independently an integer from 0-4, inclusive.

In some embodiments, A-U is Compound 104 or Compound 104':

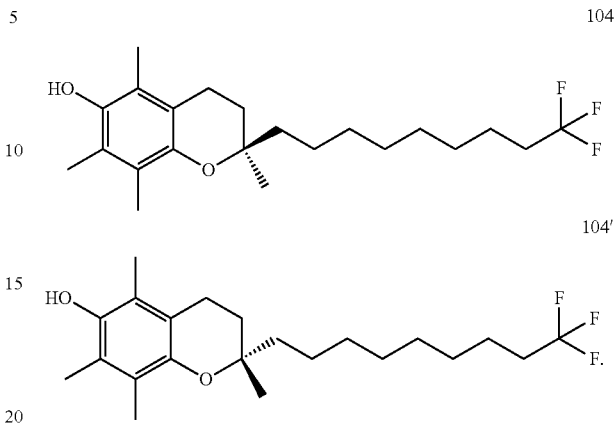

VI. Methods for Making Therapeutic Compounds and Related Intermediates

In some embodiments, the present application pertains to methods for the production of the novel compositions disclosed herein. Suitable methods are generically illustrated in FIGS. 1A, 1B, 1C, 1D, 2A, 2B, 2C, 2D and 3. Specific examples of the use of the generic methodology for the production of certain of the novel compounds can be found in Examples 1-7, and 9-10 below. The generic illustrations found in FIGS. 1A, 1B, 1C, 1D, 2A, 2B, 2C and 2D and the following description is in close alignment with Scheme 2 (below), and the associated description in Example 1. The generic illustrations found in FIG. 3 and following description for producing compound of formula 203 is in close alignment with Scheme 1 (below), and the associated description in Example 1. A general method for reducing therapeutic compounds of general Formula I-O to other therapeutic compounds of general Formula I-OR can be found in FIG. 4, and in Examples 9 and 10.

Figure 6A:
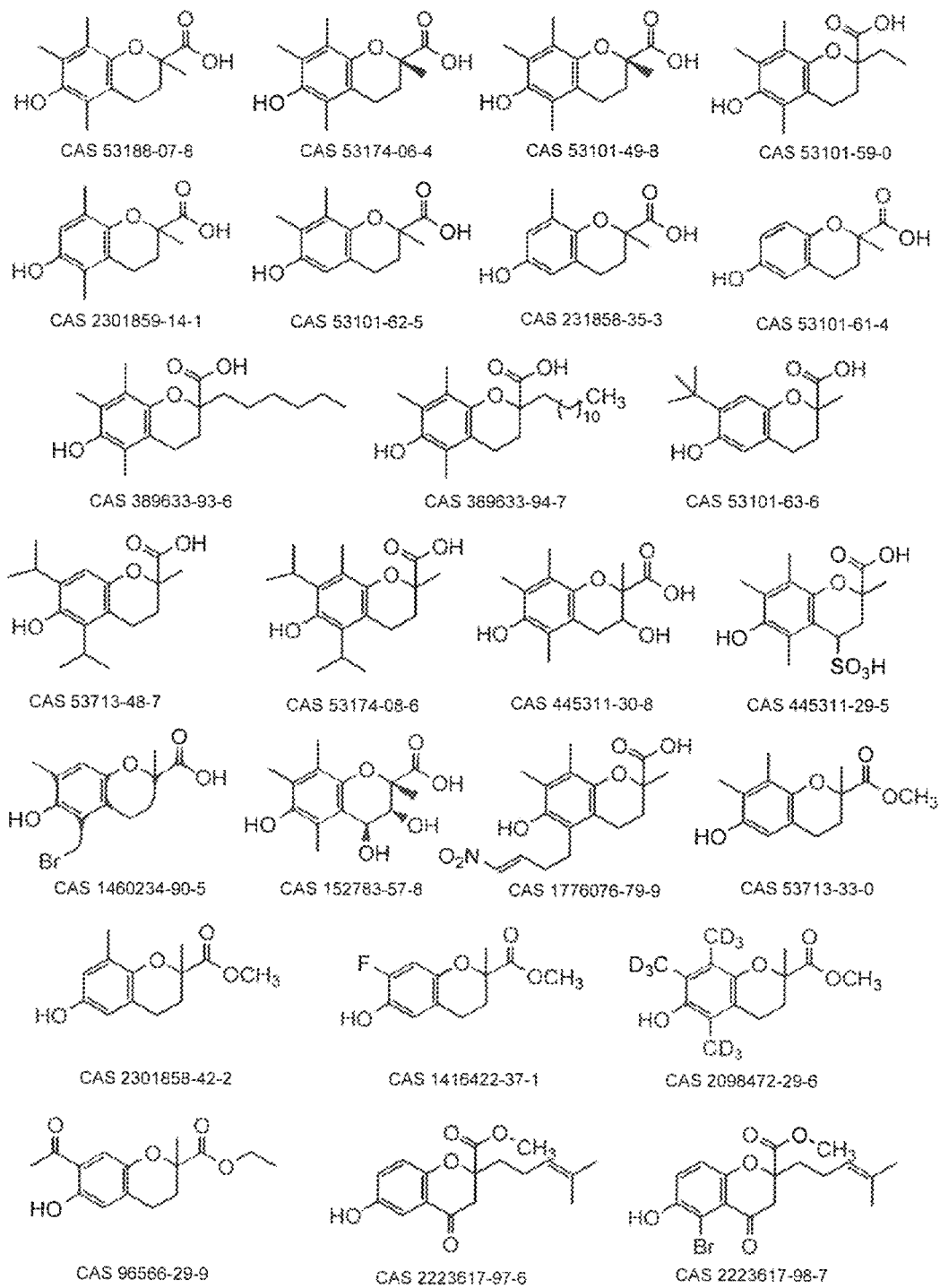
FIG. 6A is an illustration of various known heterocycles that could be used as starting materials in the methods of production of the novel compounds disclosed herein.
Figure 6B:
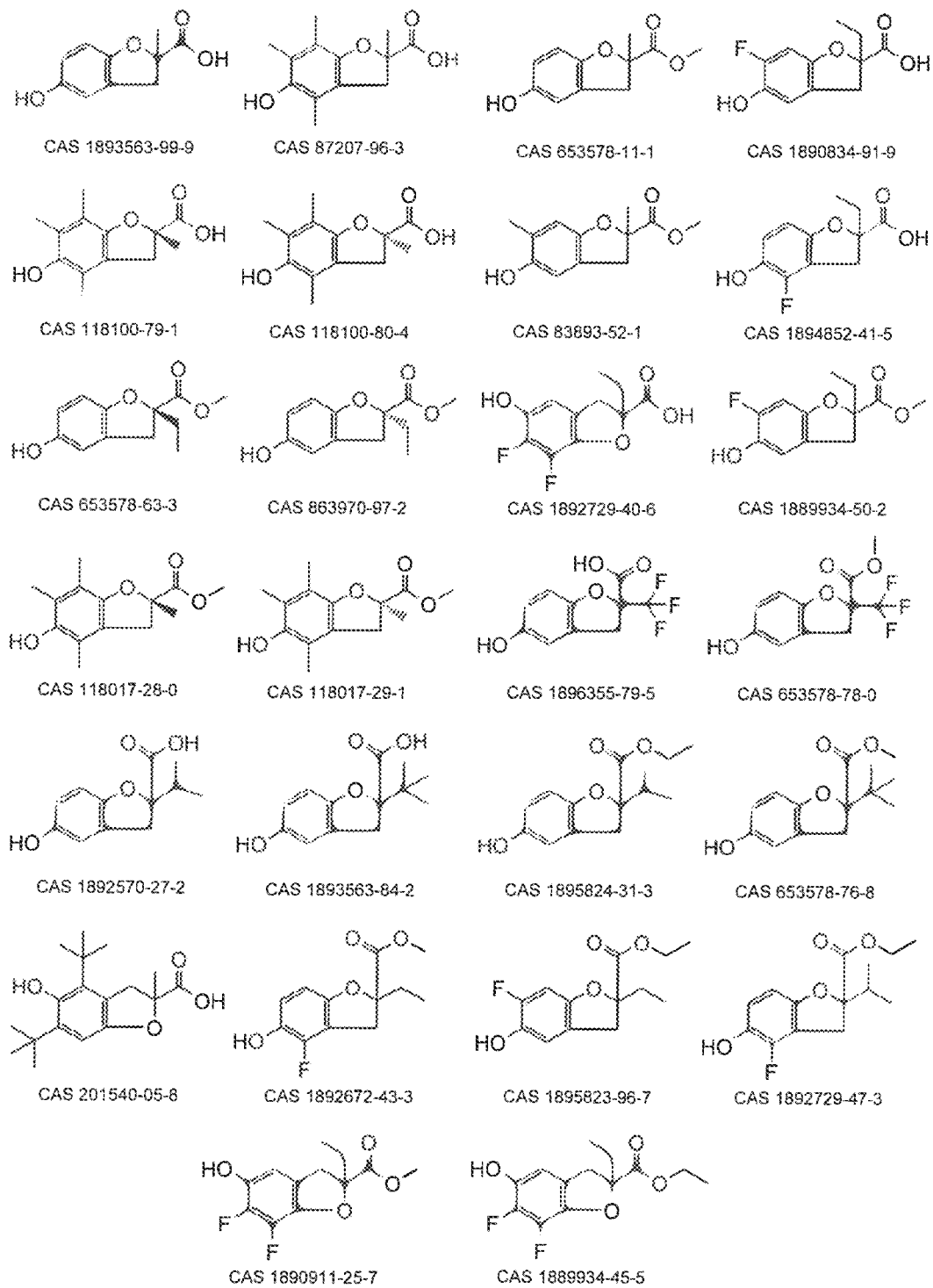
FIG. 6B is an illustration of various known heterocycles that could be used as starting materials in the methods of production of the novel compounds disclosed herein.
Figure 6C:
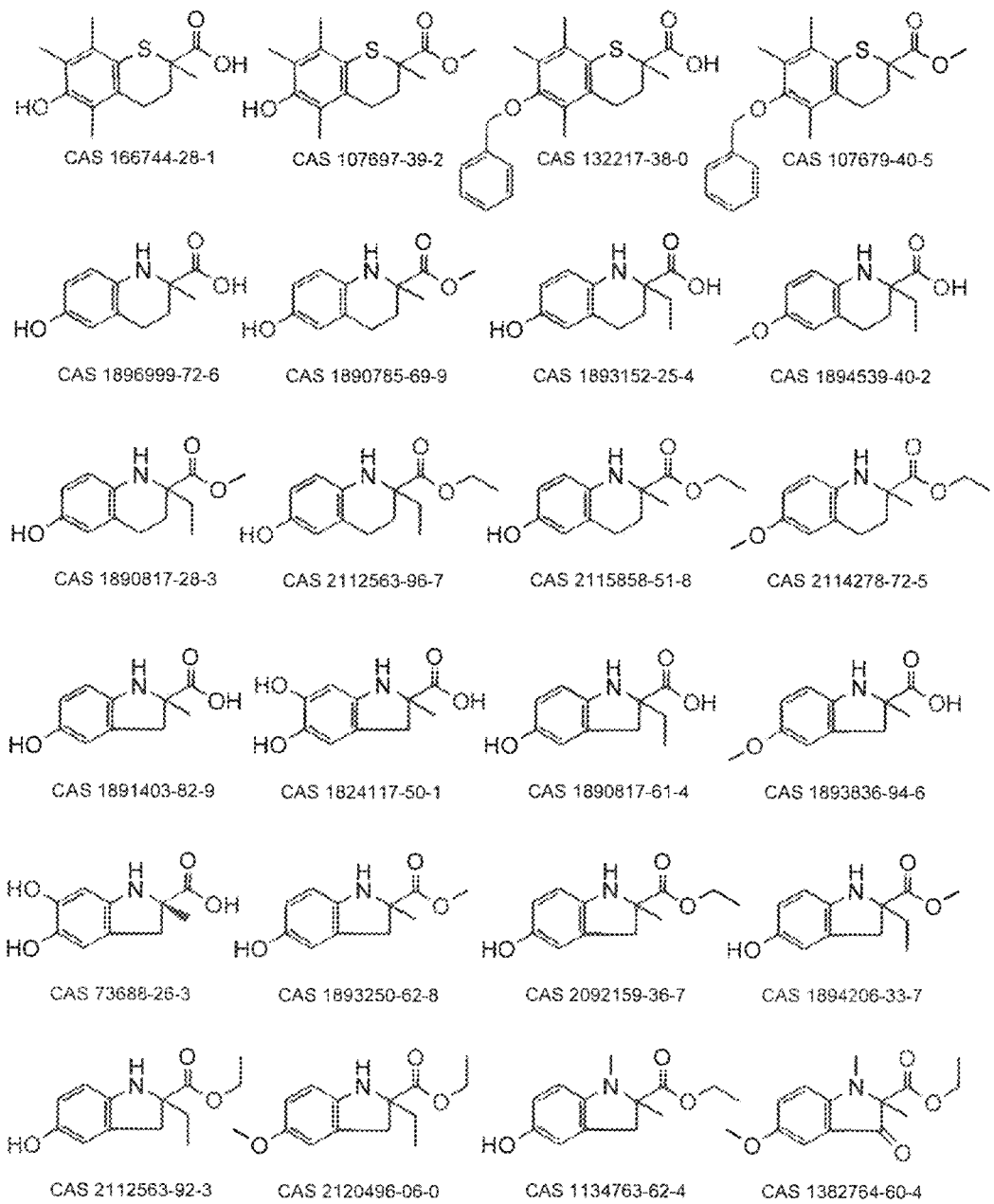
FIG. 6C is an illustration of various known heterocycles that could be used as starting materials in the methods of production of the novel compounds disclosed herein.

With reference to FIG. 1A, a compound of formula 204 is provided. Representative known compounds of formula 204 can be found in FIGS. 6A, 6B and 6C (the Chemical Abstracts Service (CAS) registration number is provided for each known composition that is illustrated). The asterisk shown in the compound of formula 204 (and for all other compounds illustrated in the FIGS.) identifies a chiral center. If available, stereochemically pure compounds of formula 204 (i.e., pure enantiomers of 204 or 205 if that is the starting material as mentioned below) can be used in the processes described herein—but that is not a requirement or limitation. Racemic mixtures of 204 (or 205) can be used as the process produces diastereomers at step d, e. (discussed below) that can be separated by chromatographic (or other) techniques, including in the examples discussed herein.

In the compounds of formula 204, J, K, L, R$_1$, R$_2$, R$_3$ and R$_{20}$ are as defined above. In some embodiments, R$_{30}$ is H. In some embodiments, the phenol is already protected (either transiently (in which case R$_{30}$ is a protecting group PG) or with a more permanent group such as a methyl, ethyl, isopropyl or tert-butyl ether (in which case R$_{30}$ can be a C$_1$-C$_6$ alkyl group). In those cases, R$_{30}$ represents the phenolic protecting group. For those cases wherein the phenol is already protected, performing step b. (below) need not be performed to obtain compound of formula 206.

The carboxylic acid compounds of formula 204 can be converted to esters of formula 205 under suitable conditions. The conversion of a carboxylic acid to an ester is well-known chemistry. Any suitable method known in the art may be used to effect this conversion of a carboxylic acid to an ester but in particular the methodology discussed in step a. under Scheme 2 in Example 1 is illustrative. As discussed in step a. under Scheme 2 in Example 1, the methyl ester (5) is produced by heating (4) in methanol in the presence of p-toluenesulfonic acid (PTSA) to thereby yield (5). Higher order esters can be prepared by using the appropriate alternative alcohol or by application of other processes well-known in the art. Alternatively, with reference to FIG. 1A, an ester compound of formula 205 is provided. As can be seen from FIGS. 6A, 6B and 6C, various esters of formula 205 are commercially known and/or available.

In the compounds of formula 205, J, K, L, $R_1$, $R_2$, $R_3$, $R_{20}$ and $R_{30}$ are as defined above. The group $R_{31}$ represents any $C_1$-$C_6$ alkyl or benzyl group, but typically will be methyl, ethyl or benzyl. If $R_{30}$ is not H, then the compound of formula 205 is synonymous with the compound of formula 206, discussed below.

With reference to FIG. 1A, it can be seen that compounds of formula 205 (where $R_{30}$ is H) can be converted to compounds of formula 206 by protection of the exocyclic phenol. Any suitable method known in the art may be used to effect this conversion of a phenol to a protected phenol but in particular the methodology discussed in step b. under Scheme 2 in Example 1 is illustrative. In Example 1 step b., benzyl bromide in DMF (as solvent) in the presence of $K_2CO_3$ (as a base) was used at room temperature to alkylate the phenol of (5) and thereby produce the benzyl ether (6). Any benzyl halide could be used to produce a substituted or unsubstituted benzyl protecting group linked to the phenol. Generally, the protection reaction will proceed in a dry, aprotic solvent in the presence of a (inorganic or organic) base. However, any protecting group and any suitable conditions can be used. For example, the phenol could be protected with a triphenylmethyl-based protecting group by use of, for example, triphenylmethyl chloride and similar conditions. Alternatively, the phenol could be protected with a silyl-based protecting group by use of, for example, tert-butyldimethylsilyl chloride and similar conditions. In some embodiments, the phenol can optionally be reacted with a reagent that produces a more permanent modification, such as for example, methyl iodide, ethyl iodide or isopropyl iodide to thereby produce the methyl ether, ethyl ether or isopropyl ether, respectively.

In the compounds of formula 206, J, K, L, $R_1$, $R_2$, $R_3$, $R_{20}$ and $R_{31}$ are as defined above. The group $R_{32}$ represents any phenol protecting group (e.g., a $C_1$-$C_4$ alkyl group, a triphenylmethyl-based protecting group, a silyl protecting group or a benzyl protecting group), but $R_{32}$ is not hydrogen (H).

With reference to FIG. 1A, it can be seen that compounds of formula 206 can be converted to compounds of formula 207 by conversion of the ester group back to a carboxylic acid (the process being known as saponification of an ester). Saponification of an ester is well-known chemistry. Any suitable method known in the art may be used to effect this conversion of an ester to a carboxylic acid but in particular the methodology discussed in step c. under Scheme 2 in Example 1 is illustrative. Generally this process involves treatment of the ester in a mixture of water or water and water miscible organic solvent (e.g., methanol, ethanol, tetrahydrofuran and/or acetonitrile) with a strong base such as sodium hydroxide, potassium hydroxide or lithium hydroxide for a period necessary to saponify the ester, followed by neutralization with an acid (generally a strong acid such as hydrochloric acid) to generate the carboxylic acid from the carboxylate anion. Depending on the nature of the starting material, the reaction can be carried out at reduced temperature, room temperature or at elevated temperature. In the compounds of formula 207, J, K, L, $R_1$, $R_2$, $R_3$, $R_{20}$ and $R_{32}$ are as defined above.

With reference to FIG. 1A, it can be seen that compounds of formula 207 can be converted to compounds of formula 209 by, for example, conversion of the acid group to a mixed anhydride. Formation of mixed anhydrides is well-known chemistry. Any suitable method known in the art may be used to effect this conversion of the carboxylic acid to a mixed anhydride but in particular the methodology discussed in step d., under Scheme 2 in Example 1 is illustrative. Generally, this conversion can be effected by treatment of the carboxylic acid (7) an dry, aprotic solvent (e.g., THF) in the presence of a (inorganic or organic) base and an acid chloride (illustrated as a compound of formula 208 (in FIG. 1A), wherein $R_{33}$ is any alkyl, alkenyl, alkynyl, aryl, arylalkyl, arylheteroalkyl, cycloalkyl, cycloheteroalkyl, heteroalkyl, or heteroaryl group known in the art; and illustrated as 8 in Scheme 2). The reaction can be carried out at reduced temperature (e.g., −30° C.). In the compounds of formula 209, J, K, L, $R_1$, $R_2$, $R_3$, $R_{20}$ and $R_{32}$ are as defined above. Generally, $R_{33}$ is a bulky group such as t-butyl or adamantyl. As mixed anhydrides tend to be unstable (especially prone to hydrolysis in the presence of any water), the mixed anhydride is typically (but not necessarily) used directly in the subsequent reaction without isolation or purification.

With reference to FIG. 1A, it can be seen that compounds of formula 209 can be converted to diastereomers of formula 211a or 211b by reaction with an appropriate chiral oxazolidine-2-one (in FIG. 1A, the compound of formula 210 is illustrative). Any suitable method known in the art may be used to effect this conversion but in particular the methodology discussed in step d, e, under Scheme 2 in Example 1 is illustrative. Generally, as provided in Example 1, the mixed anhydride is further reacted with the oxazolidine-2-one in the presence of n-butyl lithium ("BuLi) in an aprotic solvent under anhydrous conditions and at reduced temperature (e.g. −78° C.). In the compounds of formula 211a and 211b, J, K, L, $R_1$, $R_2$, $R_3$, $R_{20}$ and $R_{32}$ are as defined above. While it is possible to proceed to the subsequent steps with the mixture of stereoisomers, use of the chiral compound 210 produces diastereoisomers that can be chromatographically (or otherwise) separated. As therapeutic agents are generally stereochemically pure, the mixture will most often be chromatographically separated to produce an isolated compound of formula 211a and an isolated compound of formula 211b, but that is not a requirement or limitation. The process may proceed with stereochemically pure compounds or stereochemical mixtures. The products of subsequent reactions will thus be stereochemically pure or stereochemical mixtures based on the nature of the starting materials (unless purified in subsequent reactions). If stereochemical mixtures are obtained, the compounds can optionally be purified by appropriate means (e.g., chromatography or chiral chromatography, as appropriate) if stereochemically pure product is desired.

With reference to FIG. 1A, it can be seen that compounds of formula 211a and/or 211b can be converted to compounds of formula 212 by conversion of the amide to an alcohol. Any suitable method known in the art may be used to effect this conversion but in particular the methodology discussed in step f. under Scheme 2 in Example 1 is illustrative. Generally, as seen in Example 1, a stereochemically pure 11b can be treated with lithium aluminum hydride (LiH) in an aprotic solvent under anhydrous conditions and at reduced temperature to produce the alcohol (12). In the compounds of formula 212, J, K, L, $R_1$, $R_2$, $R_3$, $R_{20}$ and $R_{32}$ are as defined above. Compounds of formula 212 can be stereochemically pure or stereochemical mixtures. If stereochemical mixtures, the compounds can optionally be purified by appropriate means (e.g., chromatography or chiral chromatography, as appropriate) if stereochemically pure product is desired.

With reference to FIG. 1A, it can be seen that compounds of formula 212 can be converted to compounds of formula 213 by reaction of the alcohol group with trifluoromethane sulfonic anhydride (or other group (e.g., tosyl) that renders the alcohol derivative subject to nucleophilic attach). Any suitable method known in the art may be used to effect this conversion but in particular the methodology discussed in step g. under Scheme 2 in Example 1 is illustrative. Generally, as seen in Example 1, (12) can be converted to (13) by treatment with trifluoromethanesulfonic anhydride and pyridine in DCM at reduced temperature (e.g., 0° C.). In the compounds of formula 213, J, K, L, $R_1$, $R_2$, $R_3$, $R_{20}$ and $R_{32}$ are as defined above and "OTf" refers to the trifluoromethanesulfonyl protected hydroxyl group. Compounds of formula 213 can be stereochemically pure or stereochemical mixtures. If stereochemical mixtures, the compounds can optionally be purified by appropriate means (e.g., chromatography or chiral chromatography, as appropriate) if stereochemically pure product is desired.

Figure 3:
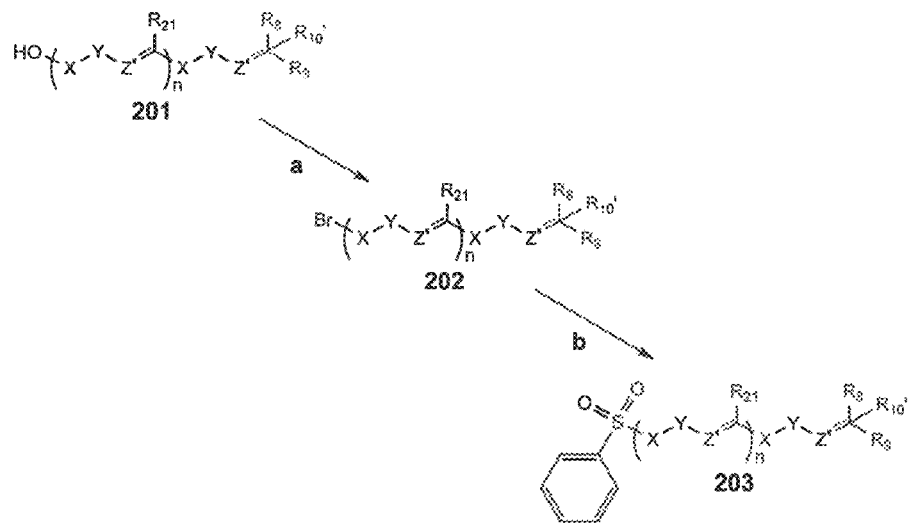
FIG. 3 is an illustration of a chemical scheme for the production of intermediate compound 203 used/disclosed herein.

With reference to FIG. 1A, it can be seen that compounds of formula 213 can be converted to compounds of formula 214 by reaction with a compound of formula 203. Compounds of formula 203 can be purchased from available sources or otherwise produced as described below with reference to FIG. 3, and Scheme 1 and the associated discussion in Example 1. Any suitable method known in the art may be used to effect this conversion but in particular the methodology discussed in step h. under Scheme 2 in Example 1 is illustrative. Generally as seen in Example 1, the reaction is performed by dissolving or suspending (3) and hexamethylphosphoramide in an aprotic solvent (e.g. THF) at reduced temperature (e.g., −78° C.) and then adding "BuLi dropwise followed by the trifluoromethane sulfonate (13). In the compounds of formula 214, J, K, L, $R_1$, $R_2$, $R_3$, $R_{20}$ and $R_{32}$ are as defined above. In the compounds of formula 214, the group B' has the formula:

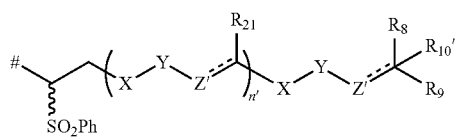

wherein, X, Y, $R_8$, $R_9$, $R_{21}$ are as defined above, n' is 0-11, inclusive, and # indicates the point of attachment. Each bond represented as === is either a single bond or a double bond. If === is a double bond, then each Z' is Z as defined above and $R_{10}'$ is absent. If === is a sing each Z' is X as defined above and $R_{10}'$ is $R_{10}$ as defined above. The abbreviation Ph refers to a phenyl group (full structure of 203 is illustrated in FIG. 3). Compounds of formula 214 can be stereochemically pure or stereochemical mixtures. If stereochemical mixtures, the compounds can optionally be purified by appropriate means (e.g., chromatography or chiral chromatography, as appropriate) if stereochemically pure product is desired.

With reference to FIG. 1A, it can be seen that compounds of formula 214 can be converted to compounds of formula 215. Any suitable method known in the art may be used to effect this conversion but in particular the methodology discussed in step i. under Scheme 2 in Example 1 is illustrative. Generally, as seen in Example 1, (14) is treated, in the presence of a palladium catalyst (e.g., bis[(diphenylphosphino)ferrocene]palladium(II) chloride, with lithium triethylborohydride to thereby yield (15). The reaction can be performed in an aprotic solvent (e.g. THF) at reduced temperature (e.g., 0° C.). In the compounds of formula 215, each bond represented as ===, n, J, K, L, X, Y, Z', $R_1$, $R_2$, $R_3$, $R_8$, $R_9$, $R_{10}'$, $R_{20}$, $R_{21}$ and $R_{32}$ are as defined above. Compounds of formula 215 can be stereochemically pure or contain stereochemical mixtures. If stereochemical mixtures, the compounds can optionally be purified by appropriate means (e.g., chromatography or chiral chromatography, as appropriate) if stereochemically pure product is desired.

With reference to FIG. 1A, it can be seen that compounds of formula 215 can be converted to compounds of formula 216 by removal of the group $R_{32}$ to thereby regenerate the unprotected phenol (—OH). The exact conditions used to remove $R_{32}$ will depend on the nature of $R_{32}$. If $R_{32}$ is alkyl, generally it is not removed and hence, the compound of formula 215 is not converted to a compound of formula 216. If $R_{32}$ is a silyl-based protecting group, it generally can be removed by treatment in the presence of fluoride ion, such as by treatment with tetra-n-butyl ammonium fluoride (TBAF). If $R_{32}$ is a triphenylmethyl-based protecting group, it generally can be removed by treatment with an acid, such as dichloroacetic acid, trichloroacetic acid or trifluoroacetic acid (neat or diluted in a compatible organic solvent such as DCM). Other phenol protecting groups, methods for their production (i.e. protection of a phenol) and deprotection (regeneration of the phenol from the protected phenol) are well-known to those of ordinary skill in the art.

In the compounds illustrated in Example 1, the group $R_{32}$ is benzyl. Any suitable method known in the art may be used to effect removal of the benzyl group but in particular the methodology discussed in step j. under Scheme 2 in Example 1 is illustrative. Generally, (15) is treated with a suspension of lithium (metal) in n-propylamine in an aprotic solvent such as diethyl ether to give (16). The reaction can be quenched by the addition of sat. aq. ammonium chloride and alcohol (e.g., methanol). In the compounds of formula 216, each bond represented as ===, n, J, K, L, X, Y, Z', $R_1$, $R_2$, $R_3$, $R_8$, $R_9$, $R_{10}'$, $R_{20}$ and $R_{21}$ are as defined above. Compounds of formula 216 can be stereochemically pure or stereochemical mixtures. If stereochemical mixtures, the compounds can optionally be purified by appropriate means (e.g., chromatography or chiral chromatography, as appropriate) if stereochemically pure product is desired.

Figure 1B:
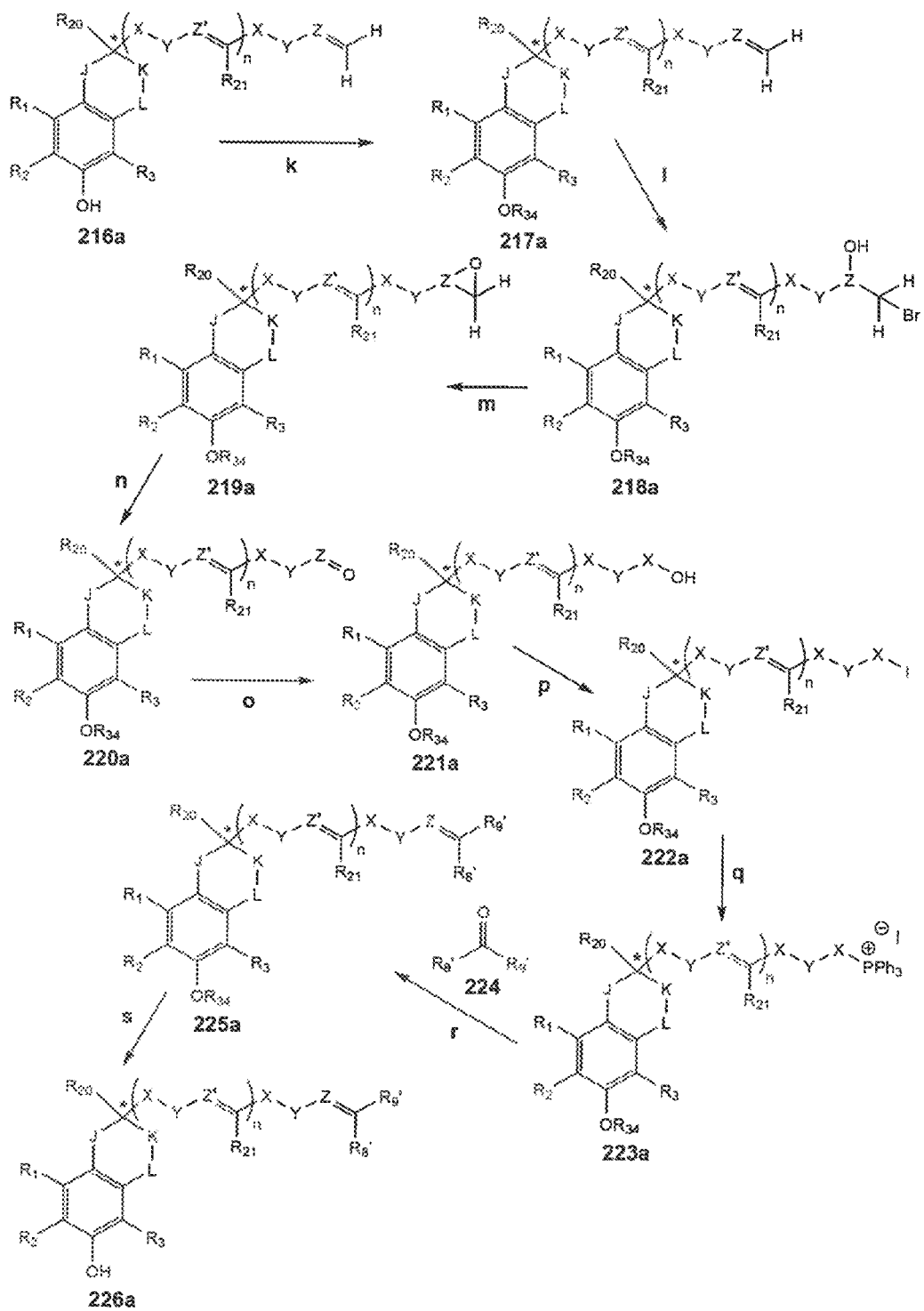

In some embodiments, in compounds of formula 216, $R_8$ and $R_9$ are H and $R_{10}'$ is absent. Preparation of compounds of this structure will typically result from the availability of suitable alcohols of formula 201 as illustrated in FIG. 3 and discussed in more detail below with respect to the production of compounds of formula 203 (as discussed above in the production of compounds of formula 214). Species of compounds of formula 216, where $R_8$ and $R_9$ are H and $R_{10}'$ is absent are illustrated in FIG. 1B and identified as compounds of formula 216a. Because the availability of compounds of formula 201 may be limited, the process described in FIG. 1B illustrates an alternative approach to the production of compounds having desired groups $R_8$ an $R_9$ (that are not H) from starting material where $R_8$ and $R_9$ are H.

With reference to FIG. 1B, a compound of formula 216a is provided. Compounds of this formula can be prepared as described above, and as illustrated in FIG. 1A. The asterisk shown in the compound of formula 216a (and for all other compounds illustrated in FIG. 1B) identifies a chiral center. If available, stereochemically pure compounds of formula 216a (i.e., pure enantiomers of 216a) can be used in the processes described herein—but that is not a requirement or limitation. Racemic mixtures of 216a can be used but generally the products will also be a mixture of stereochemically impure compounds. If stereochemical mixtures, the compounds can optionally be purified by appropriate means (e.g., chromatography or chiral chromatography, as appropriate) if stereochemically pure product is desired. In the compounds of formula 216a, each bond represented as ===, n, J, K, L, X, Y, Z, Z', $R_1$, $R_2$, $R_3$, $R_{20}$ and $R_{21}$ are as defined above.

With reference to FIG. 1B, it can be seen that compounds of formula 216a can be converted to compounds of formula 217a by protection of the exocyclic phenol. Any suitable method known in the art may be used to effect this conversion of a phenol to a protected phenol but in particular the methodology discussed in step k. under Scheme 2 in Example 1 is illustrative. In Example 1 step k., tert-butyldimethylsilyl chloride in DMF (as solvent) in the presence of imidazole (as a base) was used to protect the phenol of (16) and thereby produce the tert-butyldimethylsilyl protected product (17). Generally, the protection reaction will proceed in a dry, aprotic (e.g. DMF) solvent in the presence of a (inorganic or organic) base. However, any suitable protecting group and any suitable conditions can be used. For example, the phenol could be protected with a (substituted or unsubstituted) benzyl protecting group by use of, for example, (substituted or unsubstituted) benzyl chloride and similar conditions (such as described above for producing compound 206). Alternatively, the phenol could be protected with a triphenylmethyl-based protecting group by use of, for example, triphenylmethyl chloride and similar conditions. In some embodiments, the phenol can optionally (but not preferably) be reacted with a reagent that produces a more permanent modification, such as methyl iodide, ethyl iodide or isopropyl iodide to thereby produce the methyl ether, ethyl ether or isopropyl ether, respectively.

If available, stereochemically pure compounds of formula 216a (i.e., pure enantiomers of 216a) can be used in the processes described herein—but that is not a requirement or limitation). Racemic mixtures of 216a can be used but generally the products (i.e., 217a) will also be a mixture of stereochemically impure compounds. If stereochemical mixtures, the compounds can optionally be purified by appropriate means (e.g., chromatography or chiral chromatography, as appropriate) if stereochemically pure product is desired. In the compounds of formula 217a, each bond represented as ===, n, J, K, L, X, Y, Z, Z', $R_1$, $R_2$, $R_3$, $R_{20}$ and $R_{21}$ are as defined above. In the compounds of formula 217a, the group $R_{34}$ represents any phenol protecting group (e.g., a $C_1$-$C_4$ alkyl group, a triphenylmethyl-based protecting group, a silyl protecting group or a benzyl protecting group), but $R_{34}$ is not hydrogen (H)). For example, $R_{34}$ can be a silyl-based protecting group such as tert-butyldimethylsilyl.

With reference to FIG. 1B, it can be seen that compounds of formula 217a can be converted to compounds of formula 218a. Any suitable method known in the art may be used to effect this conversion but in particular the methodology discussed in step l. under Scheme 2 in Example 1 is illustrative. Generally as seen in Example 1, compound (17) can be treated with N-bromosuccinimide in a mixture of organic solvent (e.g., THF) and water at reduced temperature (e.g., 0° C.) to yield (18). However, any suitable conditions can be used. If available, stereochemically pure compounds of formula 217a (i.e., pure enantiomers of 217a) can be used in the processes described herein—but that is not a requirement or limitation. Racemic mixtures of 217a can be used but generally the products (218a) will also be a mixture of stereochemically impure compounds. If stereochemical mixtures, the compounds can optionally be purified by appropriate means (e.g., chromatography or chiral chromatography, as appropriate) if stereochemically pure product is desired. In the compounds of formula 218a, each bond represented as ===, n, J, K, L, X, Y, Z, Z', $R_1$, $R_2$, $R_3$, $R_{20}$, $R_{21}$ and $R_{34}$ are as defined above. With reference to FIG. 1B, it can be seen that compounds of formula 218a can be converted to epoxide compounds of formula 219a by treatment with a base. Any suitable method known in the art may be used to effect this conversion but in particular the methodology discussed in step m. under Scheme 2 in Example 1 is illustrative. Generally as seen in Example 1, compound (18) can be reacted in an alcohol such as methanol or ethanol (or an aqueous mixture of alcohol) in the presence of an inorganic base such as sodium carbonate, potassium carbonate or cesium carbonate at reduced temperature (e.g., 0° C.) to give the epoxide (19). However, any suitable conditions can be used. If available, stereochemically pure compounds of formula 218a (i.e., pure enantiomers of 218a) can be used in the processes described herein—but that is not a requirement or limitation. Racemic mixtures of 218a can be used but generally the products (219a) will also be a mixture of stereochemically impure compounds. If stereochemical mixtures, the compounds can optionally be purified by appropriate means (e.g., chromatography or chiral chromatography, as appropriate) if stereochemically pure product is desired. In the compounds of formula 219a, each bond represented as ===, n, J, K, L, X, Y, Z, Z', $R_1$, $R_2$, $R_3$, $R_{20}$, $R_{21}$ and $R_{34}$ are as defined above.

With reference to FIG. 1B, it can be seen that compounds of formula 219a can be converted to an aldehyde of formula 220a by treatment an oxidizing agent such as sodium periodate. Any suitable method known in the art may be used to effect this conversion but in particular the methodology discussed in step n. under Scheme 2 in Example 1 is illustrative. Generally and shown in Example 1, the epoxide (19) is treated in water or a mixture of water and organic solvent at reduced temperature (e.g., 0° C.) with sodium periodate and periodic acid to give (20). However, any suitable conditions can be used. If available, stereochemically pure compounds of formula 219a (i.e., pure enantiomers of 219a) can be used in the processes described herein— but that is not a requirement or limitation. Racemic mixtures of 219a can be used but generally the products (220a) will also be a mixture of stereochemically impure compounds. If stereochemical mixtures, the compounds can optionally be purified by appropriate means (e.g., chromatography or chiral chromatography, as appropriate) if stereochemically pure product is desired. In the compounds of formula 220a, each bond represented as ===, n, J, K, L, X, Y, Z, Z', $R_1$, $R_2$, $R_3$, $R_{20}$, $R_{21}$ and $R_{34}$ are as defined above.

With reference to FIG. 1B, it can be seen that aldehydes of formula 220a can be converted to an alcohol of formula 221a by treatment with a reducing agent such as sodium borohydride. Any suitable method known in the art may be used to effect this conversion but in particular the methodology discussed in step o. under Scheme 2 in Example 1 is illustrative. Generally as shown in Example 1, the aldehyde (20) is treated with sodium borohydride in alcohol (e.g. ethanol) or a mixture of water and alcohol at reduced temperature (e.g., 0° C.) to give the alcohol (21). However, any suitable conditions can be used. If available, stereochemically pure compounds of formula 220a (i.e., pure enantiomers of 220a) can be used in the processes described herein—but that is not a requirement or limitation. Racemic mixtures of 220a can be used but generally the products (221a) will also be a mixture of stereochemically impure compounds. If stereochemical mixtures, the compounds can optionally be purified by appropriate means (e.g., chromatography or chiral chromatography, as appropriate) if stereochemically pure product is desired. In the compounds of formula 221a, each bond represented as ≡, n, J, K, L, X, Y, Z', $R_1$, $R_2$, $R_3$, $R_{20}$, $R_{21}$ and $R_{34}$ are as defined above.

With reference to FIG. 1B, it can be seen that alcohols of formula 221a can be converted to an iodide of formula 222a by treatment with imidazole and iodine. Any suitable method known in the art may be used to effect this conversion but in particular the methodology discussed in step p under Scheme 2 in Example 1 is illustrative. Generally as illustrated in Example 1 the alcohol (21), can be treated with triphenylphosphine, imidazole and iodine in an aprotic solvent (e.g., DCM) at room temperature to give the iodide (22). However, any suitable conditions can be used. If available, stereochemically pure compounds of formula 221a (i.e., pure enantiomers of 221a) can be used in the processes described herein—but that is not a requirement or limitation. Racemic mixtures of 221a can be used but generally the products (222a) will also be a mixture of stereochemically impure compounds. If stereochemical mixtures, the compounds can optionally be purified by appropriate means (e.g., chromatography or chiral chromatography, as appropriate) if stereochemically pure product is desired. In the compounds of formula 222a, each bond represented as ≡, n, J, K, L, X, Y, Z', $R_1$, $R_2$, $R_3$, $R_{20}$, $R_{21}$ and $R_{34}$ are as defined above.

With reference to FIG. 1B, it can be seen that iodides of formula 222a can be converted to a triphenylphosphonium iodide salt of formula 223a by treatment with a large excess of triphenylphosphine. Any suitable method known in the art may be used to effect this conversion but in particular the methodology discussed in step a. under Scheme 2 in Example 1 is illustrative. Generally as illustrated in Example 1, the iodide (22) can be treated with a large excess of triphenylphosphine in an aprotic solvent (e.g., ACN) at elevated temperature (e.g., 85° C.) to give the triphenylphosphonium iodide salt (23). However, any suitable conditions can be used. If available, stereochemically pure compounds of formula 222a (i.e., pure enantiomers of 222a) can be used in the processes described herein—but that is not a requirement or limitation. Racemic mixtures of 222a can be used but generally the products (223a) will also be a mixture of stereochemically impure compounds. If stereochemical mixtures, the compounds can optionally be purified by appropriate means (e.g., chromatography or chiral chromatography, as appropriate) if stereochemically pure product is desired. In the compounds of formula 223a, each bond represented as ≡, n, J, K, L, X, Y, Z', $R_1$, $R_2$, $R_3$, $R_{20}$, $R_{21}$ and $R_{34}$ are as defined above.

With reference to FIG. 1B, it can be seen that triphenylphosphonium iodide salts of formula 223a can be converted to a compounds of formula 225a by treatment with hexamethyldisilazide followed by addition of a compound of formula 224. In the compounds of formula 224, $R_8$' embodies any definition of $R_8$ set forth above and $R_9$' embodies any definition of $R_9$ set forth above, provided however that both of $R_8$ and $R_9$ cannot be H (because that would regenerate compound 216a; the starting material of the process illustrated in FIG. 1). Any suitable method known in the art may be used to effect this conversion but in particular the methodology discussed in (i) step r. under Scheme 2 in Example 1 is illustrative, or (ii) step a. under Scheme 3 in Example 2 is illustrative. Generally as illustrated in Example 1, step r., the triphenylphosphonium iodide salt (23) is treated with hexamethyldisilazide and the ketone (24) an aprotic solvent (e.g., THF) at reduced (e.g., −78° C.) temperature to give the compound (25). However, any suitable conditions can be used. If available, stereochemically pure compounds of formula 223a (i.e., pure enantiomers of 223a) can be used in the processes described herein—but that is not a requirement or limitation. Racemic mixtures of 223a can be used but generally the products (225a) will also be a mixture of stereochemically impure compounds. If stereochemical mixtures, the compounds can optionally be purified by appropriate means (e.g., chromatography or chiral chromatography, as appropriate) if stereochemically pure product is desired. In the compounds of formula 225a, each bond represented as ≡, n, J, K, L, X, Y, Z, Z', $R_1$, $R_2$, $R_3$, $R_8$', $R_9$', $R_{20}$, $R_{21}$ and $R_{34}$ are as defined above. It is further noted that compounds wherein both $R_8$' and $R_9$' are fluorine can be generated essentially by following the simplified procedure illustrated in Example 3, below.

With reference to FIG. 1B, it can be seen that compounds of formula 225a can be converted to a compounds of formula 226a by removal of the phenol protecting group, $R_{34}$, to thereby regenerate the unprotected phenol (—OH). The exact conditions used to remove $R_{34}$ will depend on the nature of $R_{34}$. If $R_{34}$ is alkyl, generally it is not removed and hence, the compound of formula 225a is not converted to a compound of formula 226a. If $R_{34}$ is a silyl-based protecting group, it generally can be removed by treatment in the presence of fluoride ion, such as by treatment with tetra-n-butyl ammonium fluoride (TBAF). If $R_{34}$ is a triphenylmethyl-based protecting group, it generally can be removed by treatment with an acid, such as dichloroacetic acid, trichloroacetic acid or trifluoroacetic acid (neat or diluted in a compatible organic solvent such as DCM). If $R_{34}$ is a benzyl protecting group, it generally can be removed as described in Example 1, Scheme 2, step j.

Any suitable method known in the art may be used to effect the conversion of 225a to 226a but in particular the methodology discussed in Example 1, Scheme 2, step s. is illustrative for removing a tert-butyldimethylsilyl group. Generally as illustrated in Example 1, step s., the protected compound (25) is treated with tetra-n-butylammonium fluoride (TBAF) an aprotic solvent (e.g., THF) at room temperature to give the deprotected compound (26). However, any suitable conditions can be used. If available, stereochemically pure compounds of formula 225a (i.e., pure enantiomers of 225a) can be used in the processes described herein—but that is not a requirement or limitation. Racemic mixtures of 225a can be used but generally the products (226a) will also be a mixture of stereochemically impure compounds. If stereochemical mixtures, the compounds can optionally be purified by appropriate means (e.g., chromatography or chiral chromatography, as appropriate) if stereochemically pure product is desired. In the compounds of formula 226a, each bond represented as ≡, n, J, K, L, X, Y, Z, Z', $R_1$, $R_2$, $R_3$, $R_8$', $R_9$', $R_{20}$, and $R_{21}$ are as defined above. It is further noted that compounds wherein both $R_8'$ and $R_9'$ are fluorine can be generated by essentially by following the simplified procedure illustrated in Example 3, below.

Compounds of general formula 216 (product of the process illustrated in FIG. 1A) and 226a (product of the process illustrated FIG. 1B) differ in the makeup of groups ===, $Z'$, $R_8$, $R_9$, $R_{10}'$ for compound 216 as compared with groups Z, $R_8'$ and $R_9'$ for compound 226a. Thus, compounds 216 and 226a can be converted to therapeutically active compounds of Formula I or Formula II, respectively, by following the process illustrated in FIGS. 1C and 1D, respectively.

Any suitable method known in the art may be used to effect the conversion of 216 to compounds of Formula I and to convert 226a to compounds of Formula II, but in particular the methodology discussed in Example 1, Scheme 2, step t. is illustrative. Generally as illustrated in Example 1, step t., the unprotected phenolic compound (26) in an aprotic solvent (e.g., isopropylacetate) is treated with ammonium cerium(IV) nitrate at room temperature to give the therapeutic agent (Compound A), which is isolated after quenching the reaction at reduced temperature (e.g., 0° C.), extraction and column chromatography. However, any suitable conditions can be used. If available, stereochemically pure compounds of formula 216 or 226a (i.e., pure enantiomers of or 226a, respectively) can be used in the processes described herein—but that is not a requirement or limitation. Racemic mixtures of 216 or 226a can be used but generally the products (Formula I or II) will also be a mixture of stereochemically impure compounds. If stereochemical mixtures, the compounds can optionally be purified by appropriate means (e.g., chromatography or chiral chromatography, as appropriate) if stereochemically pure product is desired.

Figure 1C:
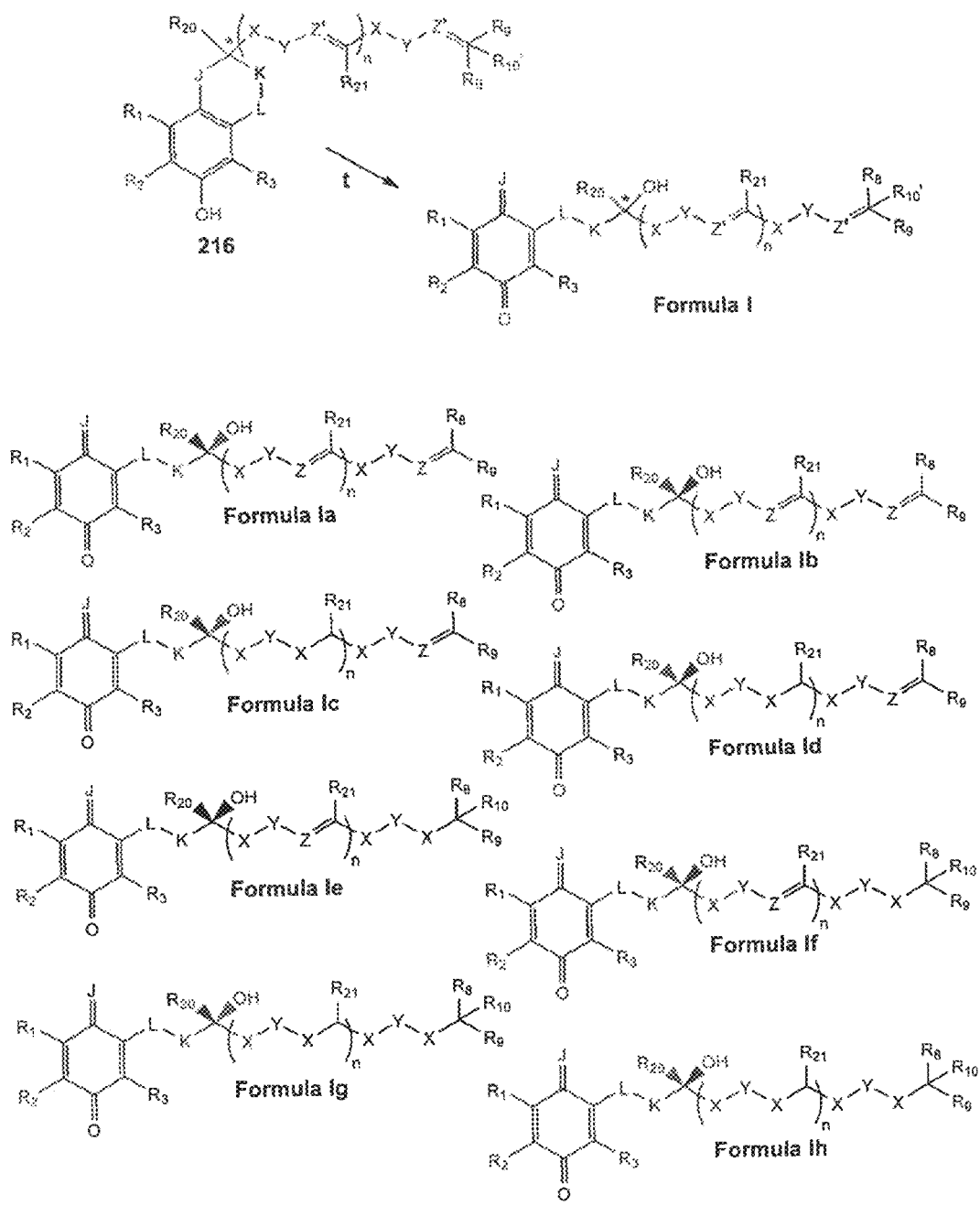
FIG. 1C is an illustration of a continuation of the chemical scheme shown in FIG. 1A for the production of novel compositions of formula I (and formula Ia-Ih).
Figure 1D:
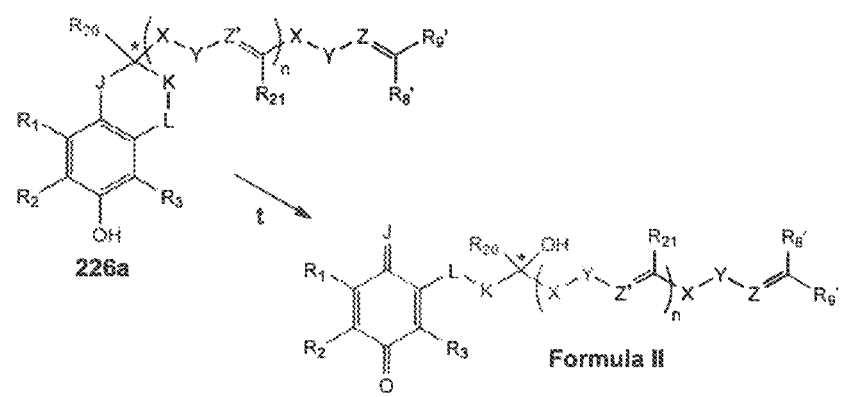
FIG. 1D is an illustration of the continuation of the chemical scheme shown in FIG. 1B, wherein compound 226a is converted to compositions of formula II (including formula IIa-IId).
Figure 1D:
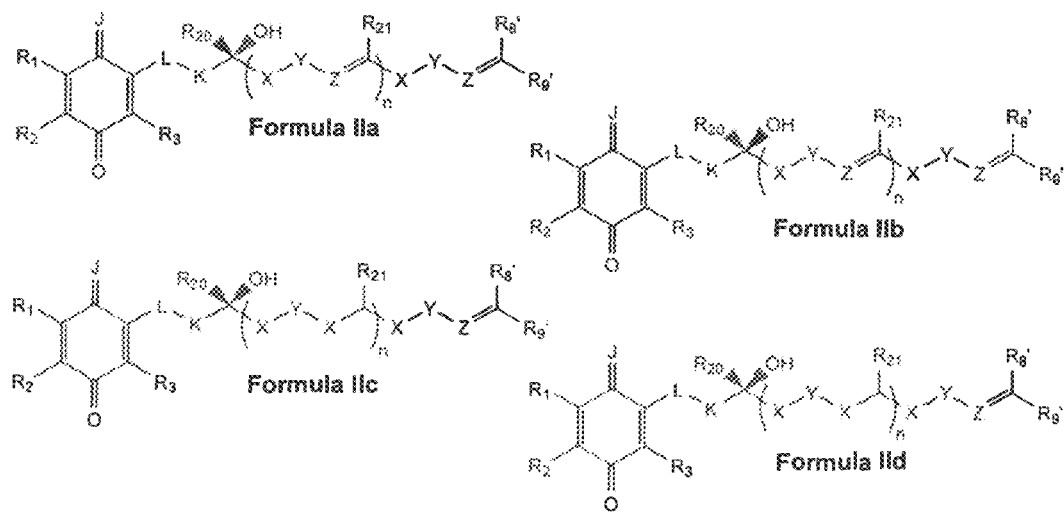

In some embodiments, compounds of Formula I can have exist as Formula Ia, Formula Ib, Formula Ic, Formula Id, Formula Ie, Formula If, Formula Ig or Formula Ih (all as illustrated in FIG. 1C). In some embodiments, compounds of Formula II can exist as Formula IIa, Formula IIb, Formula IIc, or Formula IId (all as illustrated in FIG. 1D). For all of compounds of Formula I, Formula Ia, Formula Ib, Formula Ic, Formula Id, Formula Ie, Formula If, Formula Ig or Formula Ih illustrated in FIG. 1C as well as Formula IIa, Formula IIb, Formula IIc, or Formula IId as illustrated in FIG. 1D, each bond represented as ===, n, J, K, L, X, Y, Z, $Z'$, $R_1$, $R_2$, $R_3$, $R_8$, $R_9$, $R_{10}$, $R_8'$, $R_9'$, $R_{10}'$, $R_{20}$, and $R_{21}$ are as defined above.

In some embodiments of the foregoing, the group represented by $R_1$ and $R_2$ can form a 6-membered carbocyclic or heterocyclic ring, such that instead of starting with a compound of formula 204:

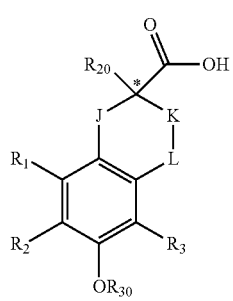

204 as illustrated in FIG. 1A, the starting material can be a compound of formula 304:

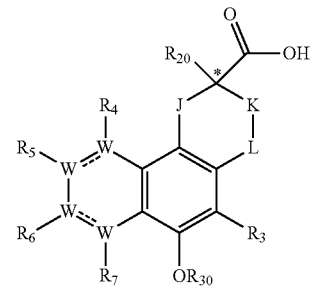

Figure 2A:
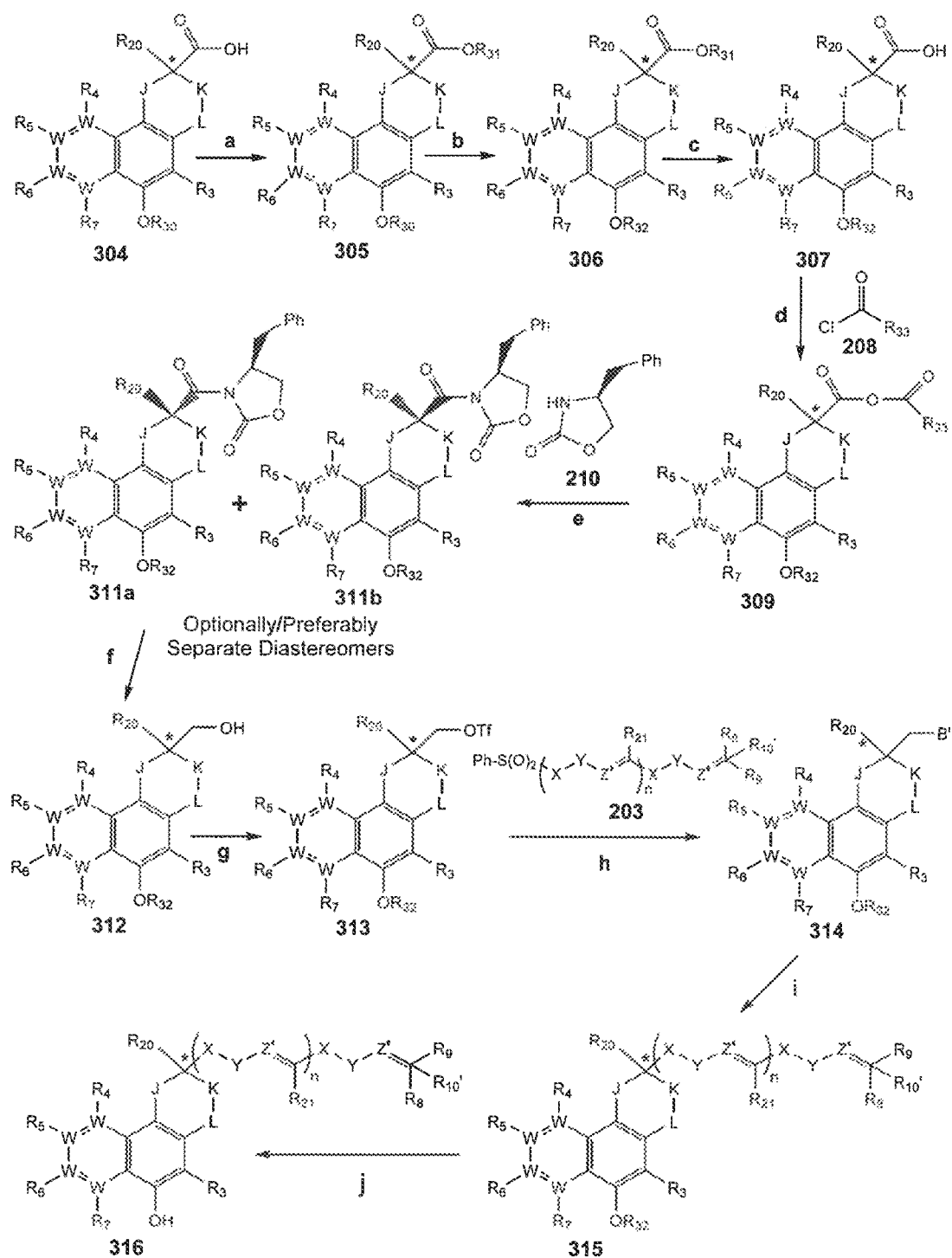
FIG. 2A an illustration of a partial chemical scheme for the production of novel compositions disclosed herein.

304 as illustrated in FIG. 2A, wherein, each bond represented by w == w, each W, and the groups J, K, L, $R_3$, $R_4$, $R_5$, $R_6$, $R_7$, $R_{20}$ and $R_{30}$ are as previously defined. As illustrated in FIG. 2A, the compounds of formula 304 can be converted to compounds of formula 316

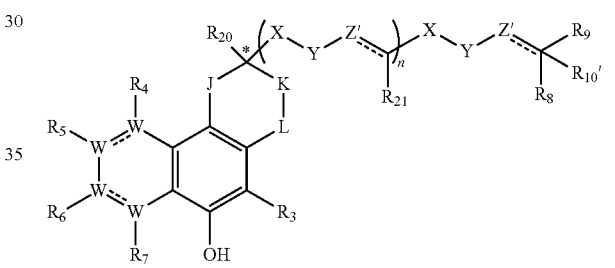

Figure 2B:
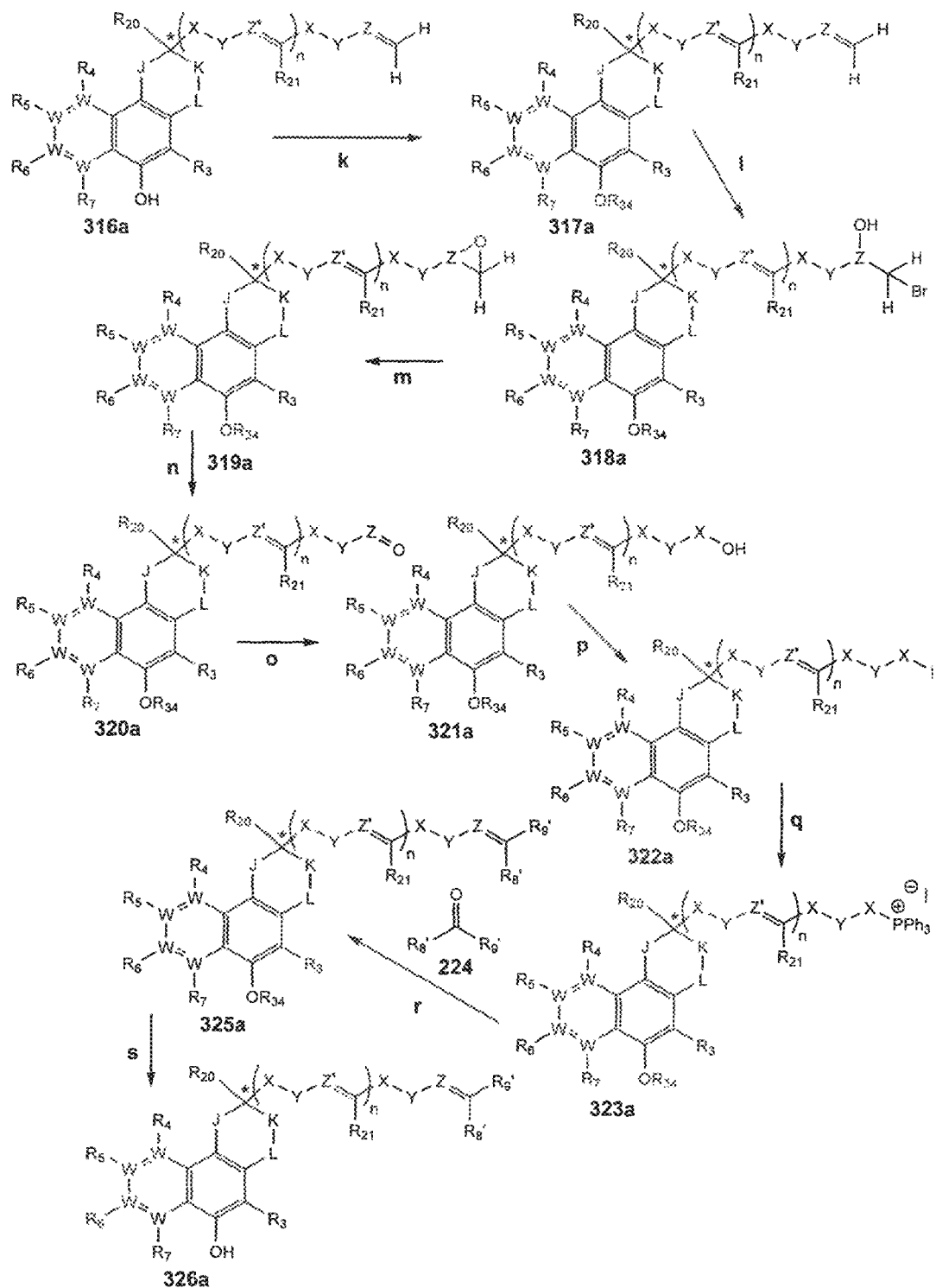

316 by an analogous multi-step process to that which is illustrated in FIG. 1A, as described above for the conversion of compounds of formula 204 to compounds of formula 216, with the only difference being the nature of the carbocyclic or heterocyclic ring formed by (and therefore substituting for) $R_1$ and $R_2$. Similarly, as illustrated in FIG. 2B, the compounds of formula 316a

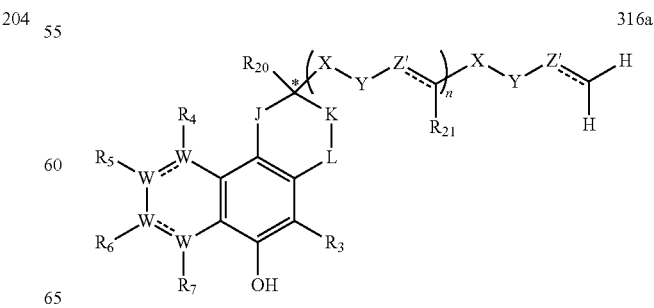

316a can be converted to compounds of formula 326a

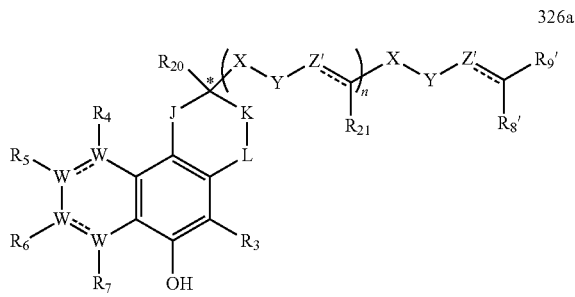

Figure 2C:
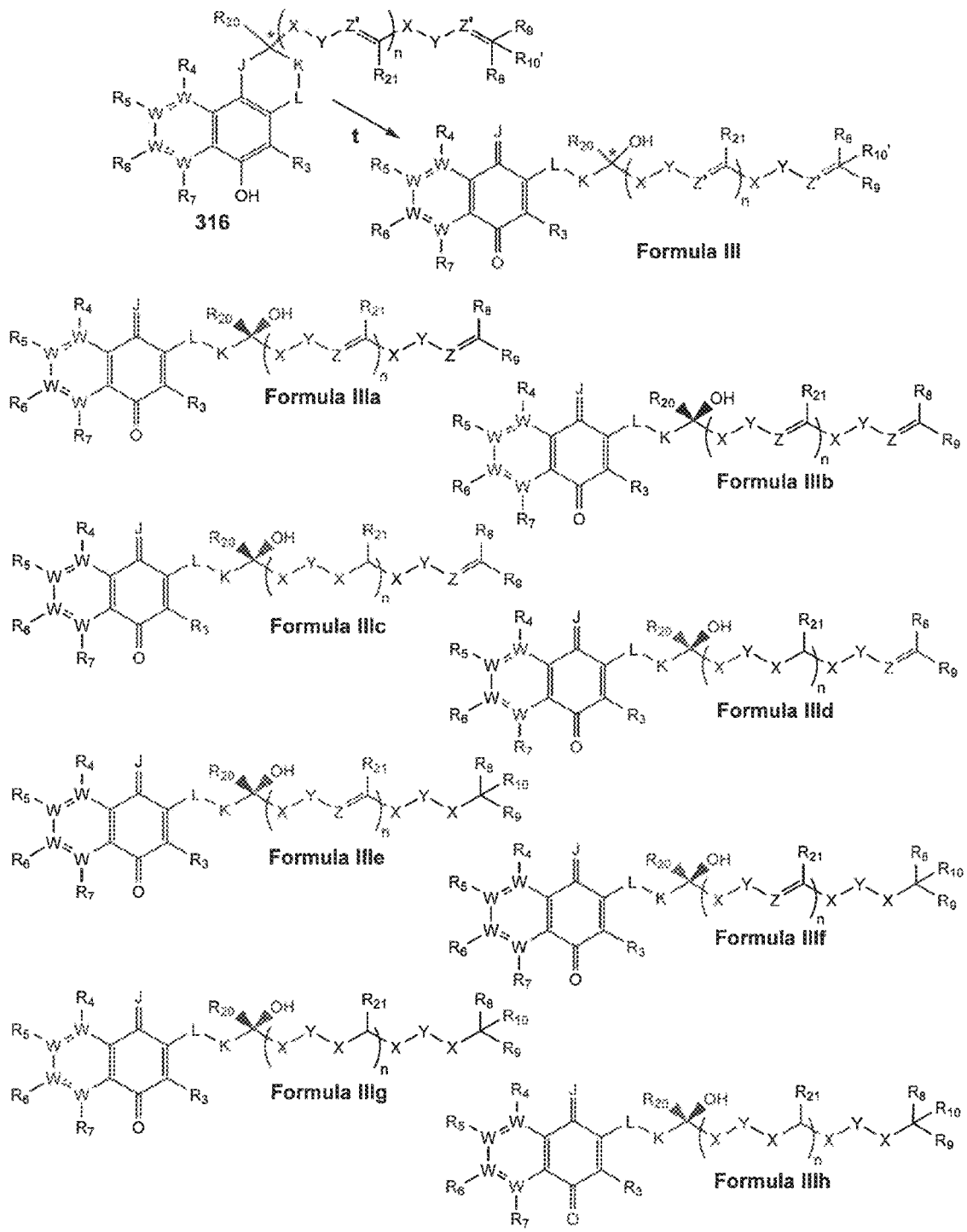
FIG. 2C is an illustration of a continuation of the chemical scheme shown in FIG. 2A for the production of novel compositions of formula III (including formula IIIa-IIIh).

326a by an analogous multi-step process to that which is illustrated in FIG. 1B, as described above for the conversion of compounds of formula 216a to compounds of formula 226a, with the only difference being the nature of the carbocyclic or heterocyclic ring formed by (and therefore substituting for) $R_1$ and $R_2$. As illustrated in FIG. 2C, compounds of formula 316 can be converted to compounds of Formula III, Formula III

Figure 2D:
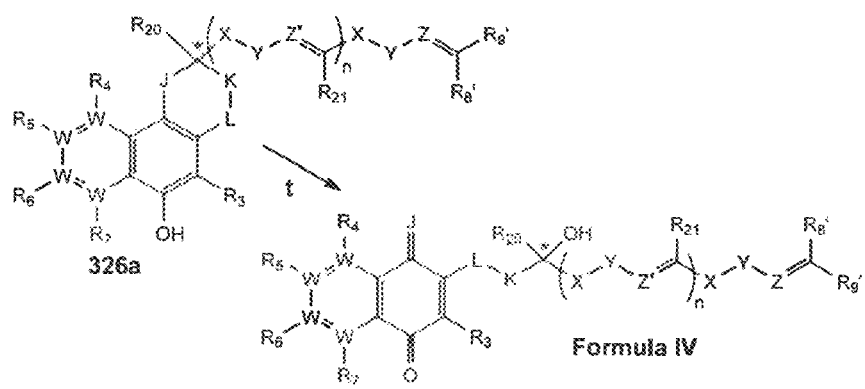
FIG. 2D is an illustration of the continuation of the chemical scheme shown in FIG. 2B, wherein compound 316a is converted to compositions of formula IV (including formula IVa-IVd).
Figure 2D:
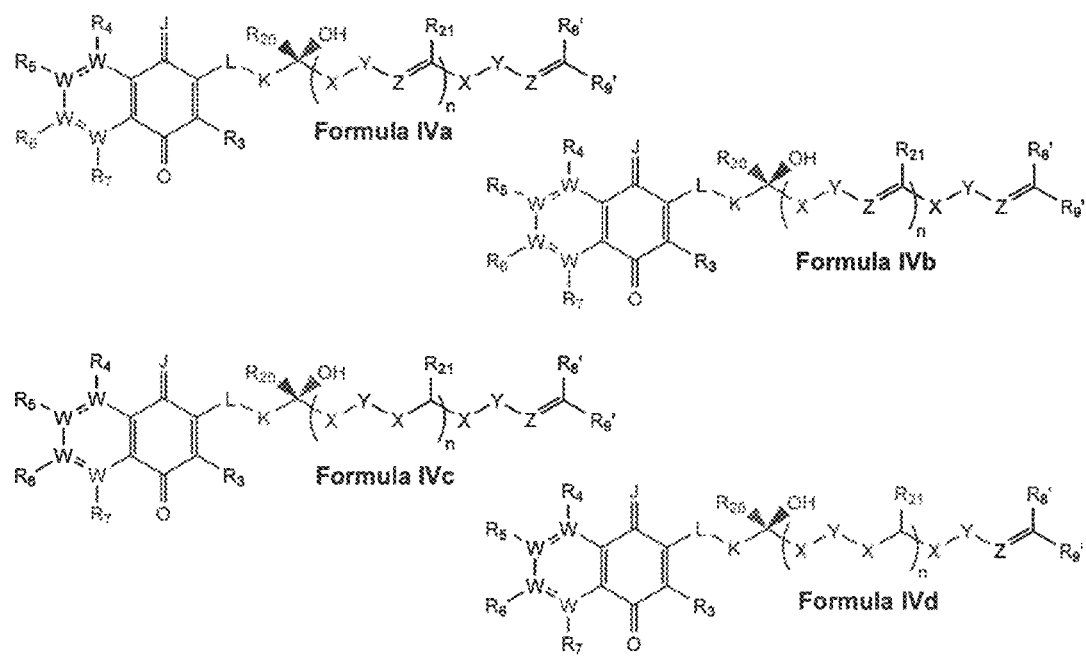

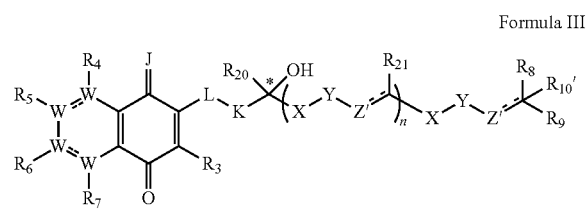

including those of Formula IIIa, IIIb, IIIc, IIId, IIe, IIIf, IIIg and IIIh by an analogous process to that illustrated in FIG. 1C, as described above for the conversion of compounds of formula 216 to compounds of Formula I, with the only difference being the nature of the carbocyclic or heterocyclic ring formed by (and therefore substituting for) $R_1$ and $R_2$. Furthermore, as illustrated in FIG. 2D, compounds of formula 326a can be converted to compounds of Formula IV, Formula IV

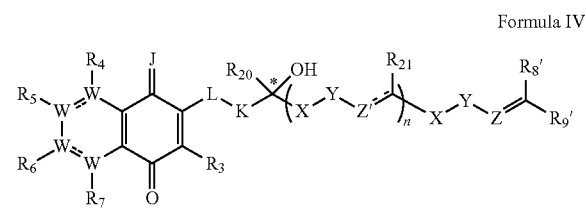

including those of Formula IVa, IVb, IVc, and IVd by an analogous process to that illustrated in FIG. 1D, as described above for the conversion of compounds of formula 226a to compounds of Formula TI, with the only difference being the nature of the carbocyclic or heterocyclic ring formed by (and therefore substituting for) $R_1$ and $R_2$. For the avoidance of doubt, any of: each bond represented as ===, each bond represented by w=w, each W, n, and the groups B', J, K, L, X, Y, Z, Z', $R_3$, $R_4$, $R_5$, $R_6$, $R_7$, $R_8$, $R_9$, $R_{10}$, $R_8'$, $R_9'$, $R_{10}'$, $R_{20}$, $R_{21}$, $R_{30}$, $R_{31}$, $R_{32}$, $R_{33}$ and $R_{34}$ as used in any of FIG. 2A, 2B, 2C or 2D are in any form as previously defined.

As noted above, compounds of formula 203

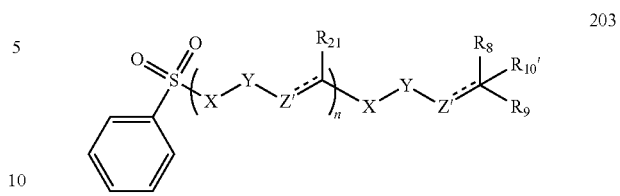

203 are useful, for example, in the preparation of compounds of formula 214 (FIG. 1A) or 314 (FIG. 2A), wherein each bond represented as ===, n, X, Y, Z', $R_8$, $R_9$, $R_{10}'$ and $R_{21}$ are as defined above. Such compounds of formula 203 can be obtained commercially or be prepared for use in the methods herein described.

For, example and with reference to FIG. 3, compounds of formula 203 can be prepared in a two-step process starting from alcohols of formula 201. More specifically, with reference to FIG. 3, it can be seen that alcohols of formula 201 can be converted to an alkyl bromide of formula 202. Any suitable method known in the art may be used to effect this conversion but in particular the methodology discussed in step a. under Scheme 1 in Example 1 is illustrative. Generally as illustrated in Example 1, step. a, Scheme 1 and the accompanying description, the alcohol (1) can be treated with phosphorus tribromide in an aprotic solvent (e.g., THF) at reduced temperature (e.g., 0° C.) to give the alkyl bromide (2). However, any suitable conditions can be used. In the compounds of formula 201 and 202, each bond represented as ===, d, n, X, Y, Z', $R_8$, $R_9$, $R_{10}'$ and $R_{21}$ are as defined above.

Next, and again with reference to FIG. 3, it can be seen that the alkyl bromides of formula 202 can be converted to compounds of formula 203. Any suitable method known in the art may be used to effect this conversion but in particular the methodology discussed in step b. under Scheme 1 in Example 1 is illustrative. Generally as illustrated in Example 1, step. b, Scheme 1 and the accompanying description, the alkyl bromide (2) can be treated with phenylsulfinic acid, sodium salt in an aprotic solvent (e.g., DMF) at room temperature to give the desired compound (3). However, any suitable conditions can be used. In the compound of formula 203, each bond represented as ===, n, X, Y, Z', $R_8$, $R_9$, $R_{10}'$ and $R_{21}$ are as defined above. Thus, from the forgoing it is possible for prepare any of the therapeutic agents represented by the formula E-F, or pharmaceutically acceptable salts, stereoisomers, mixtures of stereoisomers, tautomers, hydrates, and/or solvates thereof, wherein E is 21 or 22:

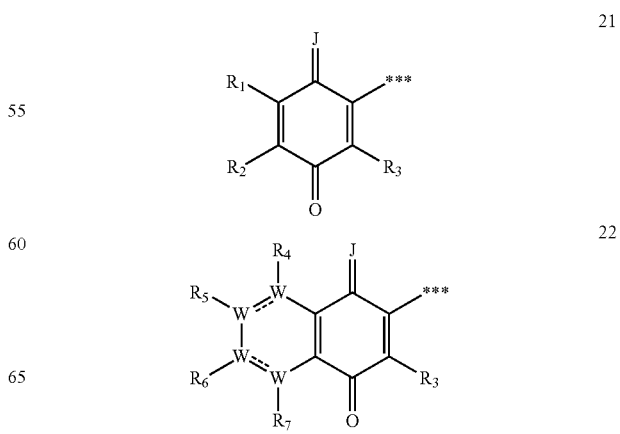

and F is 13, 14, 15, 16, 17, 18, 19 or 20:

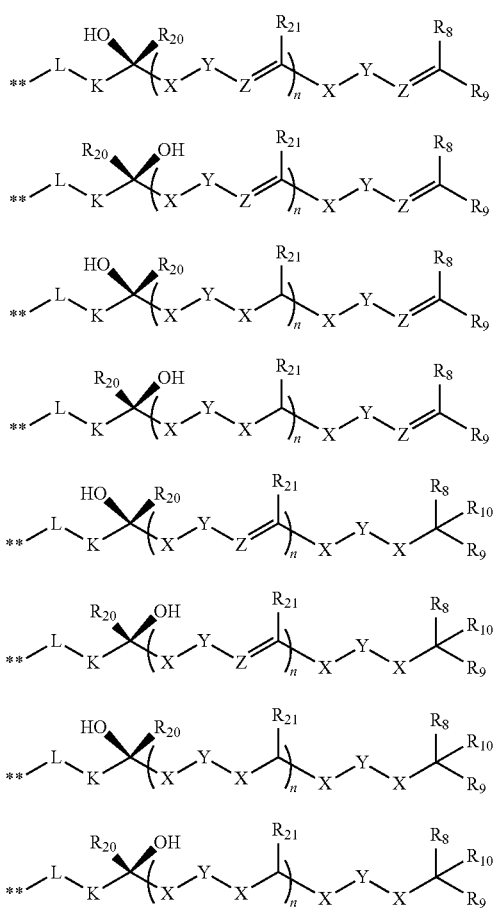

wherein, J is O, S or N—$R_{11}$, K is absent or —$(CR_{12}R_{13})$—, L is —$(CR_{12}R_{13})$—, each W is ═ independently C (carbon) or N (nitrogen) and wherein for each use of w═w, the bond between each W can be a single bond or double bond and further provided that if a single bond, each C (carbon) atom will have a hydrogen atom linked hereto in addition to one of $R_4$, $R_5$, $R_6$ or $R_7$ and in either case each of $R_4$, $R_5$, $R_6$ and $R_7$ attached thereto is independently selected from H, D, F, Cl, Br, I, $C_1$-$C_6$ alkyl and $C_1$-$C_6$ alkoxy, and if W is N (nitrogen), each of $R_4$, $R_5$, $R_6$ and $R_7$ attached thereto is independently absent (if w═w is a double bond) or selected from H, D and $C_1$-$C_6$ alkyl (if w═w is a single bond), each X is independently a group of formula —$(CR_{12}R_{13})$—, each Y is independently absent or a group of formula —$(CR_{12}R_{13})$—, each Z is independently a group of formula —$(CR_{14})$—, each of $R_1$, $R_2$ and $R_3$ is independently H, D, F, Cl, Br, I, $C_1$-$C_6$ alkyl or $C_1$-$C_6$ alkoxy; or $R_1$ and $R_2$ together form a 5-membered carbocyclic ring, a 5-membered heterocyclic ring, a 5-membered aromatic or heteroaromatic ring or a 6-membered heterocyclic ring, each $R_8$ and $R_9$ is each independently H, D, F, Cl, Br, I or $C_1$-$C_4$ alkyl; or taken together $R_8$ and $R_9$ form a 3-, 4-, 5-, 6-, or 7-membered carbocyclic or heterocyclic ring, $R_{10}$ is H, D, F, Cl, Br, I, $C_1$-$C_6$ alkyl or $C_1$-$C_6$ alkoxy, $R_{11}$ is H, D or $C_1$-$C_6$ alkyl, each instance of $R_{12}$, $R_{13}$ and $R_{14}$ is independently H, D, F, Cl, Br, I, $C_1$-$C_6$ alkyl or $C_1$-$C_6$ alkoxy, $R_{20}$ is H, D, F or $C_1$-$C_{12}$ alkyl, each $R_{21}$ is H, D, F, Cl, Br, I, or $C_1$-$C_4$ alkyl, n is an integer from 0 to 12, inclusive, and * indicates the point of attachment of E to F and  indicates the point of attachment of F to E; and further provided that: (i) at least one group of formula $R_1$, $R_2$, $R_3$, $R_4$, $R_5$, $R_6$, $R_7$, $R_8$, $R_9$, $R_{10}$, $R_{12}$, $R_{13}$, $R_{14}$, $R_{20}$ or $R_{21}$ comprises at least one fluorine atom; and/or (ii) $R_8$ and $R_9$ taken together form a 3-, 4-, 5-, 6- or 7-membered carbocyclic or heterocyclic ring.

By way of example, this process can, in particular, be used to prepare:

Compound A

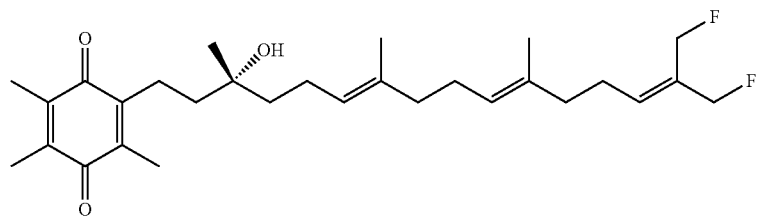

Compound B

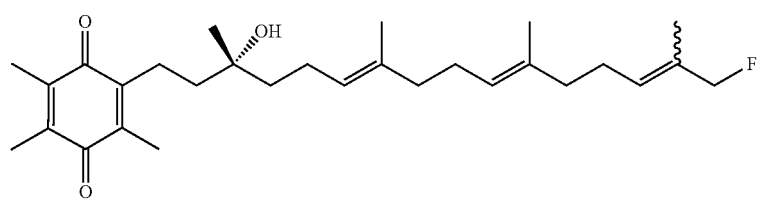

-continued
Compound C
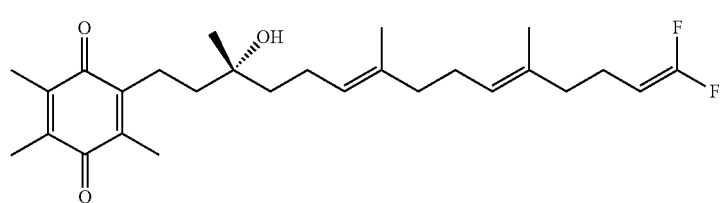
Compound D
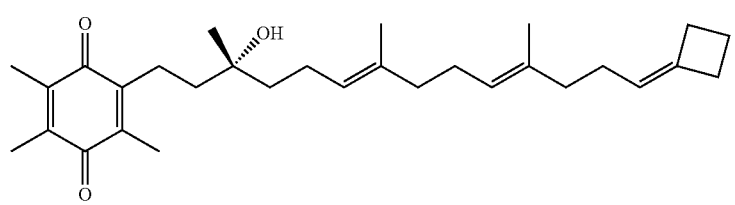
Compound E
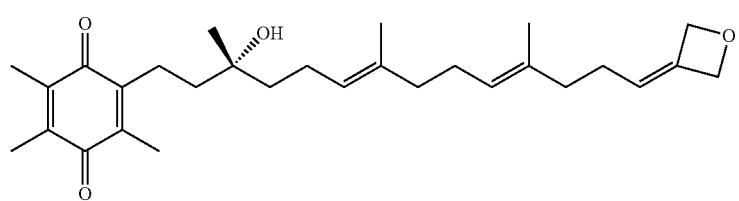
Compound F
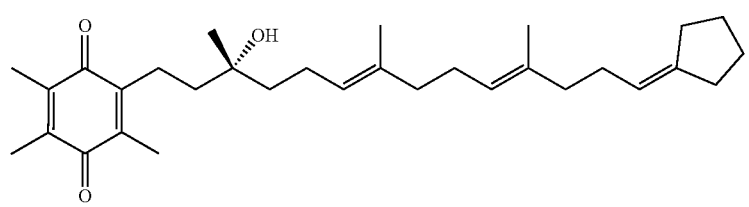
Compound G
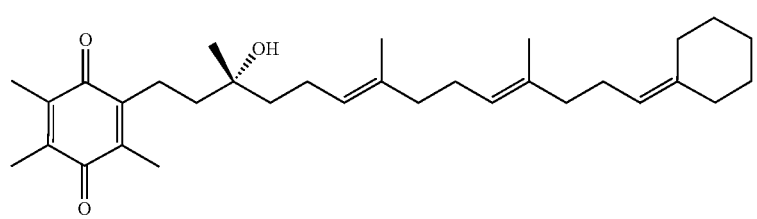
Compound H
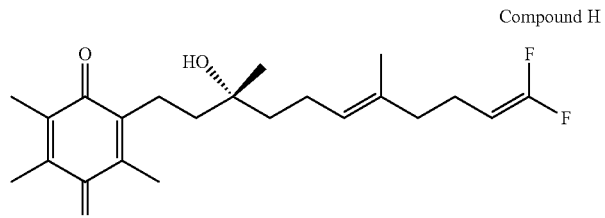
Compound I
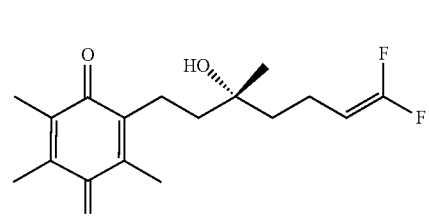

Compound J

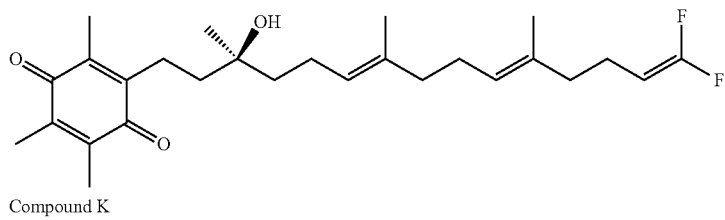

Compound K

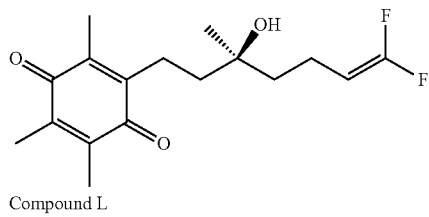

Compound L

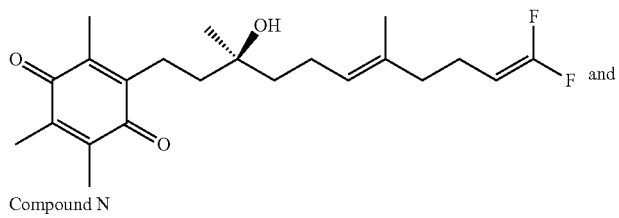

Compound N

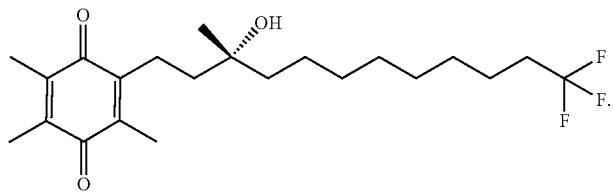

and

Compounds A, B, C, D, E, F, G, H, I, J, K, L and N are all compounds of Formula II.

Included in the compounds of Formula Ih and IIIh, made using the above recited methods are compounds of formula E-I, or pharmaceutically acceptable salts, stereoisomers, mixtures of stereoisomers, tautomers, hydrates, and/or solvates thereof, wherein E is 21 or 22:

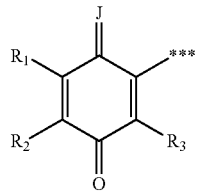

21

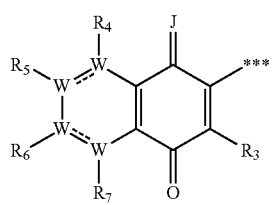

22 and I is 26 or 27:

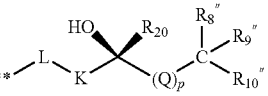

26

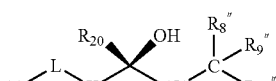

27 wherein, J is O, S or N—Ru; K is absent or —(CR$_{12}$R$_{13}$)—; L is —(CR$_{12}$R$_{13}$)—; each W is independently C (carbon) or N (nitrogen) and wherein for each use of w═w, the bond between each W can be a single bond or double bond and further provided that if a single bond, each C (carbon) atom will have a hydrogen atom linked hereto in addition to one of R$_4$, R$_5$, R$_6$ or R$_7$ and in either case each of R$_4$, R$_5$, R$_6$ and R$_7$ attached thereto is independently selected from H, D, F, Cl, Br, I, C$_1$-C$_6$ alkyl and C$_1$-C$_6$ alkoxy, and if W is N (nitrogen), each of R$_4$, R$_5$, R$_6$ and R$_7$ attached thereto is independently absent (if w═w is a double bond) or selected from H, D and ═C$_1$-C$_6$ alkyl (if w═w is a single bond); each Q is independently a group of formula —(CR$_{12}$R$_{13}$)—, O or Si provided that each O and each Si is not directly bonded to O or Si; each of $R_1$, $R_2$ and $R_3$ is independently H, D, F, Cl, Br, I, $C_1$-$C_6$ alkyl or $C_1$-$C_6$ alkoxy or $R_1$ and $R_2$ together form a 5-membered carbocyclic ring, a 5-membered heterocyclic ring, a 5-membered aromatic or heteroaromatic ring, or a 6-membered heterocyclic ring; each $R_8''$, $R_9''$ and $R_{10}''$ is independently H, F, or $C_1$-$C_4$ alkyl provided however that at least one of $R_8''$, $R_9''$ and $R_{10}''$ is F; $R_1$ is H, D or $C_1$-$C_6$ alkyl; each of $R_{12}$ and $R_{13}$ is independently H, D, F, Cl, Br, I, $C_1$-$C_6$ alkyl or $C_1$-$C_6$ alkoxy; $R_{20}$ is H, D, F or $C_1$-$C_{12}$ alkyl; p is an integer from 0 to 20, inclusive; and * indicates the point of attachment of E to I and  indicates the point of attachment of I to E.

Likewise, from the forgoing it is possible for prepare any of the intermediates to therapeutic agents represented by the formula A-B, or pharmaceutically acceptable salts, stereoisomers, mixtures of stereoisomers, tautomers, hydrates, and/or solvates thereof, wherein A is 1, 2, 3 or 4:

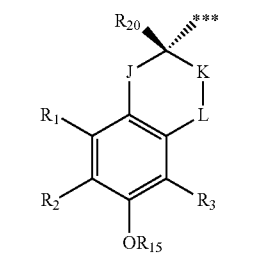

1

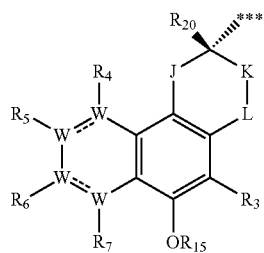

2

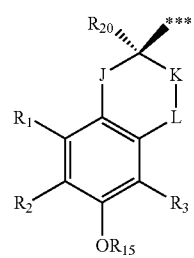

3

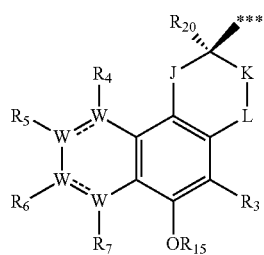

4 and B is 5, 6, 7 or 8

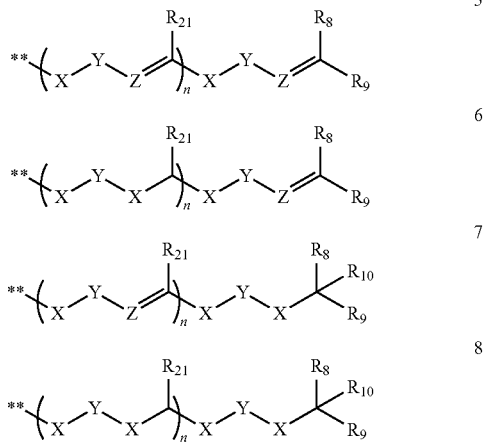

5

6

7

8 wherein, J is O, S or N—$R_{11}$, K is absent or —$(CR_{12}R_{13})$—, L is —$(CR_{12}R_{13})$—, each W is ═ independently C (carbon) or N (nitrogen) and wherein for each use of w═w, the bond between each W can be a single bond or double bond and further provided that if a single bond, each C (carbon) atom will have a hydrogen atom linked hereto in addition to one of $R_4$, $R_5$, $R_6$ or $R_7$ and in either case each of $R_4$, $R_5$, $R_6$ and $R_7$ attached thereto is independently selected from H, D, F, Cl, Br, I, $C_1$-$C_6$ alkyl and $C_1$-$C_6$ alkoxy, and if W is N (nitrogen), each of $R_4$, $R_5$, $R_6$ and $R_7$ attached thereto is independently absent (if w═w is a double bond) or selected from H, D and $C_1$-$C_6$ alkyl (if w═w is a single bond), each X is independently a group of formula —$(CR_{12}R_{13})$—, each Y is independently absent or a group of formula —$(CR_{12}R_{13})$—, each Z is independently a group of formula —$(CR_{14})$—, each of $R_1$, $R_2$ and $R_3$ is independently H, D, F, Cl, Br, I, $C_1$-$C_6$ alkyl or $C_1$-$C_6$ alkoxy; or $R_1$ and $R_2$ together form a 5-membered carbocyclic ring, a 5-membered heterocyclic ring, a 5-membered aromatic or heteroaromatic ring or a 6-membered heterocyclic ring, each $R_8$ and $R_9$ is each independently H, D, F, Cl, Br, I or $C_1$-$C_4$ alkyl; or taken together $R_8$ and $R_9$ form a 3-, 4-, 5-, 6-, or 7-membered carbocyclic or heterocyclic ring, $R_{10}$ is H, D, F, Cl, Br, I, $C_1$-$C_6$ alkyl or $C_1$-$C_6$ alkoxy, $R_1$ is H, D or $C_1$-$C_6$ alkyl, each instance of $R_{12}$, $R_{13}$ and $R_{14}$ is independently H, D, F, Cl, Br, I, $C_1$-$C_6$ alkyl or $C_1$-$C_6$ alkoxy, $R_{15}$ is H, —$CH_3$, —$CH_2CH_3$ or PG, wherein PG is a phenol protecting group, $R_{20}$ is H, D, F or $C_1$-$C_{12}$ alkyl, each $R_{21}$ is independently H, D, F, Cl, Br, I, or $C_1$-$C_4$ alkyl, n is an integer from 0 to 12, inclusive, and indicates the point of attachment of A to B and ** indicates the point of attachment of C to D; and further provided that: (i) at least one group of formula $R_1$, $R_2$, $R_3$, $R_4$, $R_5$, $R_6$, $R_7$, $R_8$, $R_9$, $R_{10}$, $R_{12}$, $R_{13}$, $R_{14}$, $R_{20}$ or $R_{21}$ comprises at least one fluorine atom; and/or (ii) $R_8$ and $R_9$ taken together form a 3-, 4-, 5-, 6- or 7-membered carbocyclic or heterocyclic ring. Said intermediates of formula A-B include, but are not limited to:

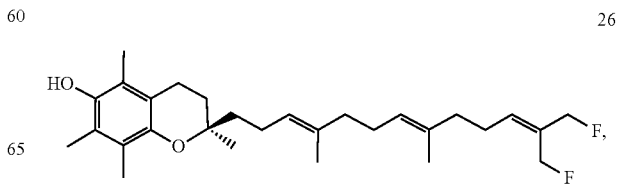

26

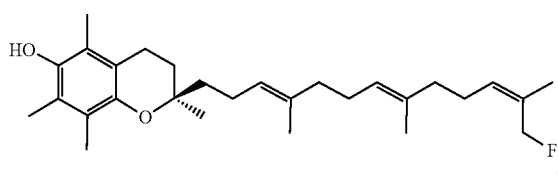
29
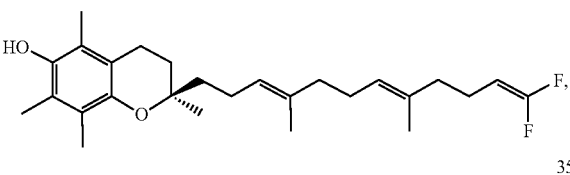
32
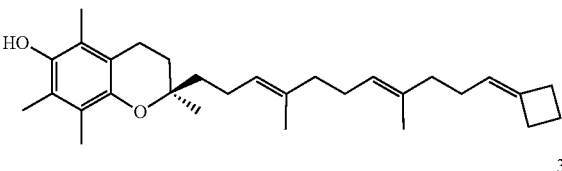
38
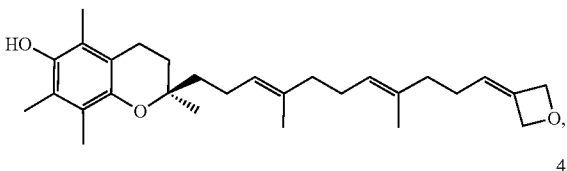
41
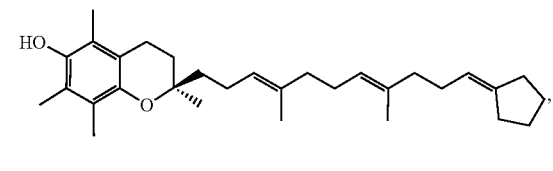
44
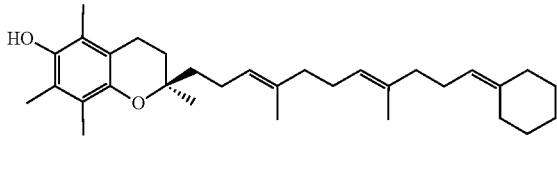
56
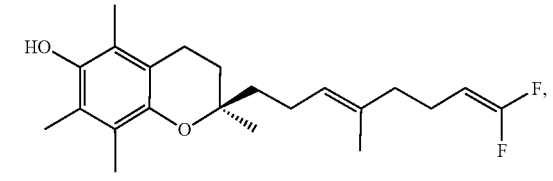
67
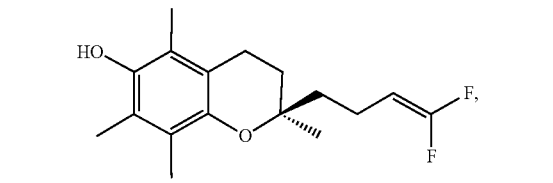
78
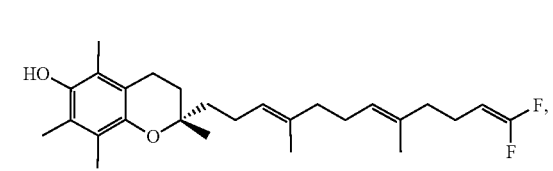
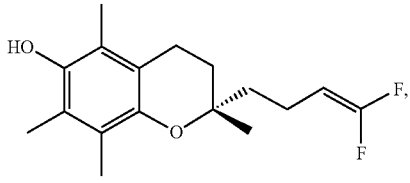
87
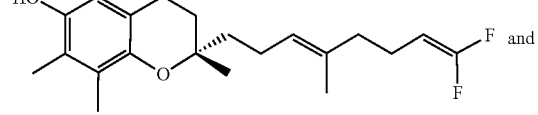
96
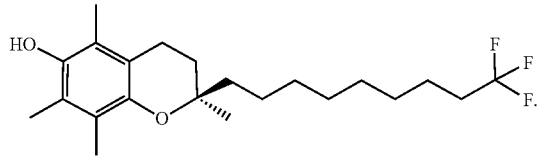
104
In some embodiments, a compound of formula A-B made using the above recited methods is a compound of formula A-U, or pharmaceutically acceptable salts, stereoisomers, mixtures of stereoisomers, tautomers, hydrates, and/or solvates thereof, wherein A is 1, 2, 3, or 4:
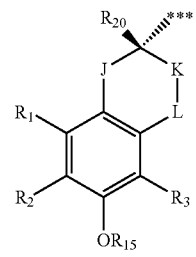
1
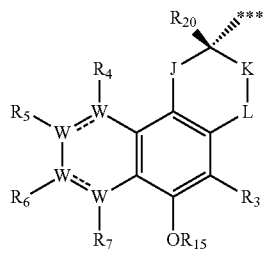
2
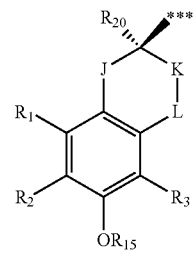
3

4

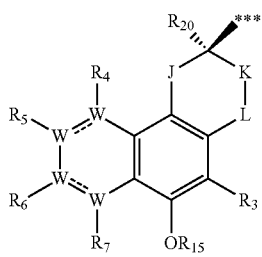

and U is 28:

28

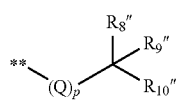

wherein, J is O, S or N—Ru; K is absent or —(CR$_{12}$R$_{13}$)—; L is —(CR$_{12}$R$_{13}$)—; each W is independently C (carbon) or N (nitrogen) and wherein for each use of w═w, the bond between each W can be a single bond or double bond and further provided that if a single bond, each C (carbon) atom will have a hydrogen atom linked hereto in addition to one of R$_4$, R$_5$, R$_6$ or R$_7$ and in either case each of R$_4$, R$_5$, R$_6$ and R$_7$ attached thereto is independently selected from H, D, F, Cl, Br, I, C$_1$-C$_6$ alkyl and C$_1$-C$_6$ alkoxy, and if W is N (nitrogen), each of R$_4$, R$_5$, R$_6$ and R$_7$ attached thereto is independently absent (if w═w is a double bond) or selected from H, D and C$_1$-C$_6$ alkyl (if w═w is a single bond); each Q is independently a group of formula —(CR$_{12}$R$_{13}$)—, O or Si provided that each O and each Si is not directly bonded to O or Si; each of R$_1$, R$_2$ and R$_3$ is independently H, D, F, Cl, Br, I, C$_1$-C$_6$ alkyl or C$_1$-C$_6$ alkoxy, or R$_1$ and R$_2$ together form a 5-membered carbocyclic ring, a 5-membered heterocyclic ring, a 5-membered aromatic or heteroaromatic ring, or a 6-membered heterocyclic ring; each R$_8$", R$_9$" and R$_{10}$" is independently H, F, or C$_1$-C$_4$ alkyl provided however that at least one of R$_8$", R$_9$" and R$_{10}$" is F; R$_1$ is H, D or C$_1$-C$_6$ alkyl; each of R$_{12}$ and R$_{13}$ is independently H, D, F, Cl, Br, I, C$_1$-C$_6$ alkyl or C$_1$-C$_6$ alkoxy; R$_{15}$ is H, C$_1$-C$_4$ alkyl or PG, wherein PG is a phenol protecting group; R$_{20}$ is H, D, F or C$_1$-C$_{12}$ alkyl; p is an integer from 0 to 20, inclusive; and * indicates the point of attachment of A to U and  indicates the point of attachment of U to A.

VII. Methods for Making Reduced Versions of Therapeutic Compounds

Furthermore and by analogy, from the forgoing it is possible for prepare therapeutic agents (which could be considered to be reduced forms or prodrugs of E-F) represented by the formula C-D, or pharmaceutically acceptable salts, stereoisomers, mixtures of stereoisomers, tautomers, hydrates, and/or solvates thereof, wherein C is 11 or 12:

11

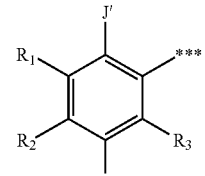

12

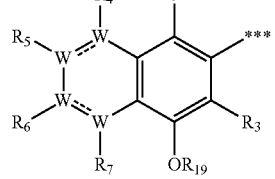

and D is 13, 14, 15, 16, 17, 18, 19 or 20:

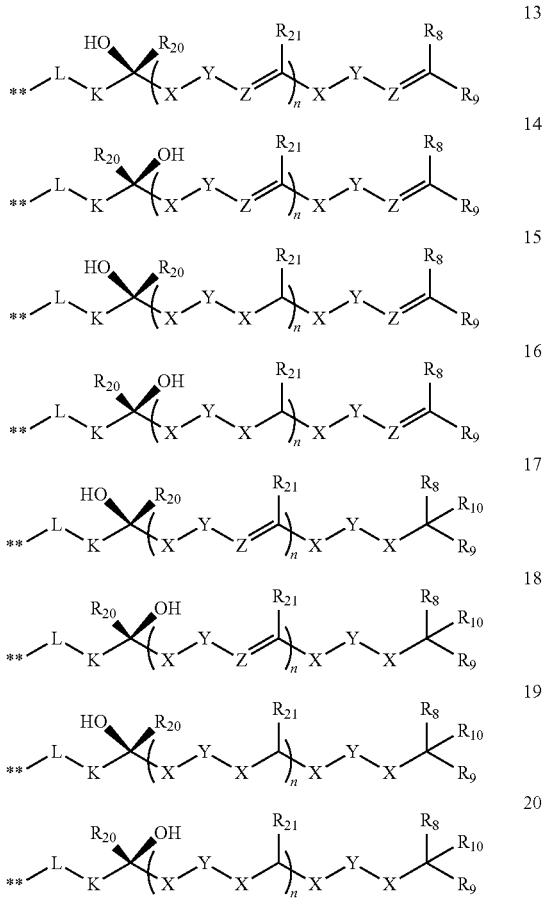

wherein, J' is OH, SH or NH—R$_{11}$, K is absent or —(CR$_{12}$R$_{13}$)—, L is —(CR$_{12}$R$_{13}$)—, each W is independently C (carbon) or N (nitrogen) and wherein for each use of w═w, the bond between each W can be a single bond or double bond and further provided that if a single bond, each C (carbon) atom will have a hydrogen atom linked hereto in addition to one of R$_4$, R$_5$, R$_6$ or R$_7$ and in either case each of R$_4$, R$_5$, R$_6$ and R$_7$ attached thereto is independently selected from H, D, F, Cl, Br, I, C$_1$-C$_6$ alkyl and C$_1$-C$_6$ alkoxy, and if W is N (nitrogen), each of R$_4$, R$_5$, R$_6$ and R$_7$ attached thereto is independently absent (if w═w is a double bond) or selected from H, D and $C_1$-$C_6$ alkyl (if w═w is a single bond), each X is independently a group of formula —$(CR_{12}R_{13})$—, each Y is independently absent or a group of formula —$(CR_{12}R_{13})$—, each Z is independently a group of formula —$(CR_{14})$—, each of $R_1$, $R_2$ and $R_3$ is independently H, D, F, Cl, Br, I, $C_1$-$C_6$ alkyl or $C_1$-$C_6$ alkoxy; or $R_1$ and $R_2$ together form a 5-membered carbocyclic ring, a 5-membered heterocyclic ring, a 5-membered aromatic or heteroaromatic ring or a 6-membered heterocyclic ring, each of $R_4$, $R_5$, $R_6$ and $R_7$ attached thereto is independently absent or selected from H, D and $C_1$-$C_6$ alkyl, each $R_8$ and $R_9$ is each independently H, D, F, Cl, Br, I or $C_1$-$C_4$ alkyl; or taken together $R_8$ and $R_9$ form a 3-, 4-, 5-, 6-, or 7-membered carbocyclic or heterocyclic ring, $R_{10}$ is H, D, F, Cl, Br, I, $C_1$-$C_6$ alkyl or $C_1$-$C_6$ alkoxy, $R_1$ is H, D or $C_1$-$C_6$ alkyl, each instance of $R_{12}$, $R_{13}$ and $R_{14}$ is independently H, D, F, Cl, Br, I, $C_1$-$C_6$ alkyl or $C_1$-$C_6$ alkoxy, $R_{19}$ is H, $C_1$-$C_4$ alkyl or benzyl (substituted or unsubstituted), $R_{20}$ is H, D, F or $C_1$-$C_{12}$ alkyl, each $R_{21}$ is independently H, D, F, Cl, Br, I, or $C_1$-$C_4$ alkyl, n is an integer from 0 to 12, inclusive, and * indicates the point of attachment of C to D and  indicates the point of attachment of C to D; and further provided that: (i) at least one group of formula $R_1$, $R_2$, $R_3$, $R_4$, $R_5$, $R_6$, $R_7$, $R_8$, $R_9$, $R_{10}$, $R_{12}$, $R_{13}$, $R_{14}$, $R_{20}$ or $R_{21}$ comprises at least one fluorine atom; and/or (ii) $R_8$ and $R_9$ taken together form a 3-, 4-, 5-, 6- or 7-membered carbocyclic or heterocyclic ring.

For example, the method can be used to convert:

Compound A
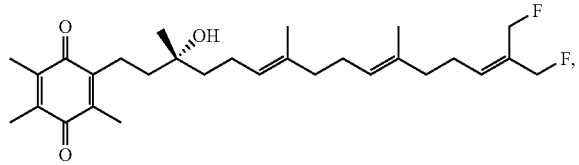

Compound B
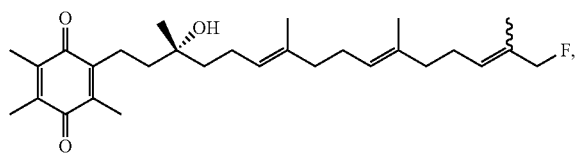

Compound C
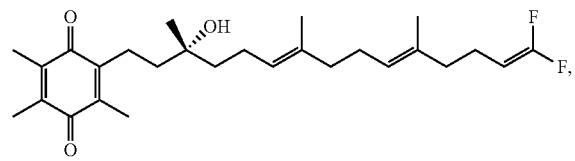

Compound D
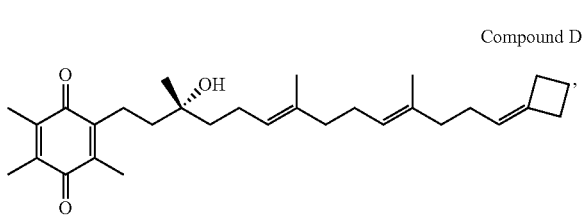 [SMILES: CC1=C(C)C(=O)C(CC[C@](C)(O)CC/C=C(\C)CC/C=C(\C)CCC=C2COC2)=C(C)C1=O]

-continued

Compound E
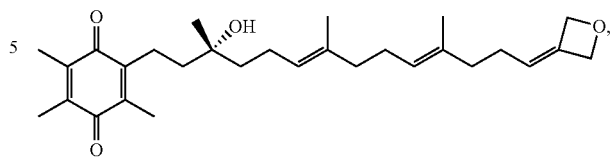

Compound F
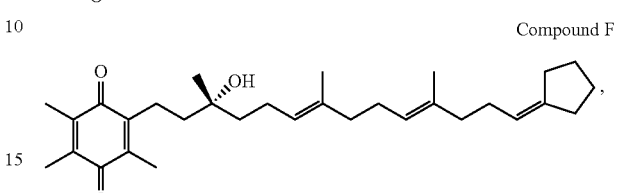

Compound G
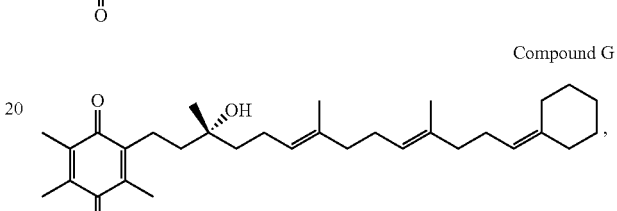

Compound H
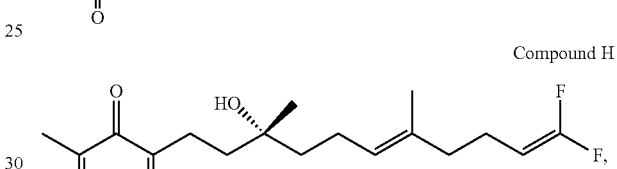

Compound I

Compound J
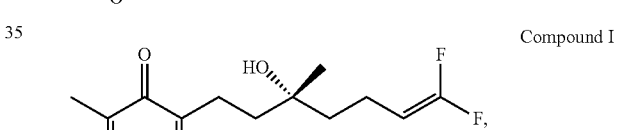

Compound K

Compound L
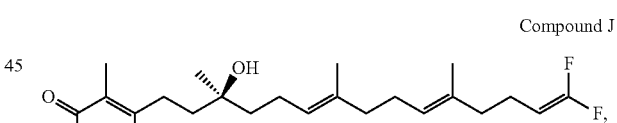

Compound N

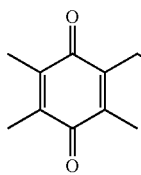

Compound A-2

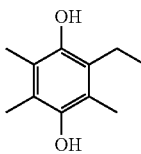

Compound B-2

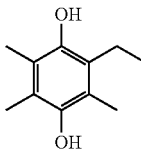

Compound C-2

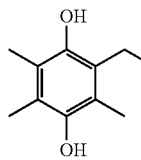

Compound D-2

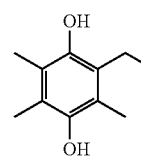

Compound E-2

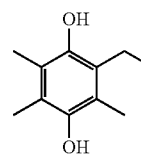

Compound F-2

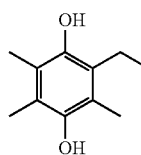

Compound G-2

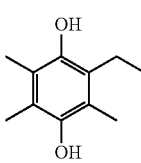

Compound H-2

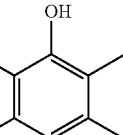

Compound I-2

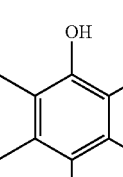

Compound J-2

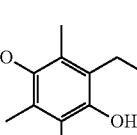

Compound K-2

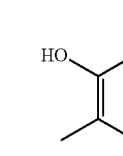

Compound L-2

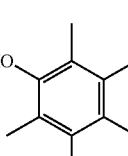

and

Compound N-2

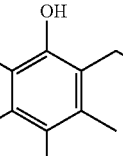

Figure 4:
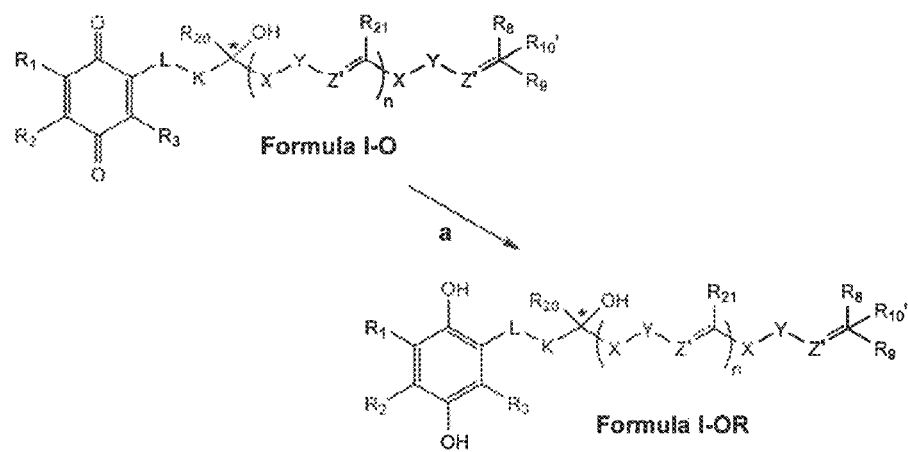
FIG. 4 is an illustration of a chemical scheme for the reduction of certain therapeutic compositions disclosed herein.

The method of conversion involves reduction of the two substituted heteroatoms of the aromatic ring. With reference to FIG. 4, it can be seen that the therapeutically active reagents of Formula I-O (a compound of Formula I, wherein J is O) can be converted to a compounds of Formula I-OR (the reduced form of the compound of Formula I-O) by treatment with a suitable reducing agent (e.g., sodium borohydride). In the compounds of Formula I-O or Formula I-OR, each bond represented as ===, n, K, L, X, Y, Z', $R_1$, $R_2$, $R_3$, $R_8$, $R_9$, $R_{10}'$, $R_{20}$ and $R_{21}$ are as defined above. Any suitable method known in the art may be used to effect this conversion but in particular the methodology discussed in step a. under Scheme 9 in Example 9 is illustrative.

Generally as illustrated in Example 9, Scheme 9, step a., the quinone compound (Compound C) is treated with sodium borohydride in an alcohol (e.g., ethanol) under an inert atmosphere at reduced temperature (e.g., −15° C.) to thereby produce the hydroquinone. However, any suitable conditions can be used. If available, stereochemically pure compounds of Formula I-O (i.e., pure enantiomers of Formula I-O) can be used in the processes described herein— but that is not a requirement or limitation. Racemic mixtures of Formula I-O can be used but generally the products (Formula I-OR) will also be a mixture of stereochemically impure compounds.

In some embodiments, the compound of formula C-D prepared as described herein is a compound of formula C-I, or pharmaceutically acceptable salts, stereoisomers, mixtures of stereoisomers, tautomers, hydrates, and/or solvates thereof, wherein C is 11 or 12:

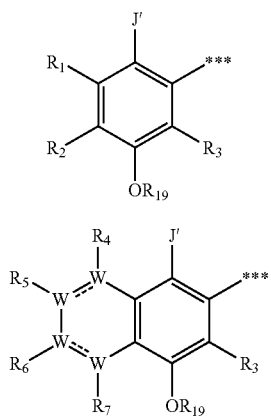

and I is 26 or 27:

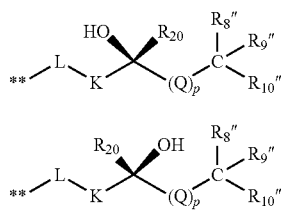

wherein, J' is OH, SH or NH—$R_{11}$; K is absent or —$(CR_{12}R_{13})$—; L is —$(CR_{12}R_{13})$—; each W is independently C (carbon) or N (nitrogen) and wherein for each use of w⩵w, the bond between each W can be a single bond or double bond and further provided that if a single bond, each C (carbon) atom will have a hydrogen atom linked hereto in addition to one of $R_4$, $R_5$, $R_6$ or $R_7$ and in either case each of $R_4$, $R_5$, $R_6$ and $R_7$ attached thereto is independently selected from H, D, F, Cl, Br, I, $C_1$-$C_6$ alkyl and $C_1$-$C_6$ alkoxy, and if W is N (nitrogen), each of $R_4$, $R_5$, $R_6$ and $R_7$ attached thereto is independently absent (if w⩵w is a double bond) or selected from H, D and $C_1$-$C_6$ alkyl (if w ⩵ w is a single bond); each Q is independently a group of formula —$(CR_{12}R_{13})$—, O or Si provided that each O and each Si is not directly bonded to O or Si; each of $R_1$, $R_2$ and $R_3$ is independently H, D, F, Cl, Br, I, $C_1$-$C_6$ alkyl or $C_1$-$C_6$ alkoxy, or $R_1$ and $R_2$ together form a 5-membered carbocyclic ring, a 5-membered heterocyclic ring, a 5-membered aromatic or heteroaromatic ring, or a 6-membered heterocyclic ring; each $R_8''$, $R_9''$ and $R_{10}''$ is independently H, F, or $C_1$-$C_4$ alkyl provided however that at least one of $R_8''$, $R_9''$ and $R_{10}''$ is F; $R_1$ is H, D or $C_1$-$C_6$ alkyl; each of $R_{12}$ and $R_{13}$ is independently H, D, F, Cl, Br, I, $C_1$-$C_6$ alkyl or $C_1$-$C_6$ alkoxy; $R_{19}$ is H, $C_1$-$C_4$ alkyl or benzyl (substituted or unsubstituted); $R_{20}$ is H, D, F or $C_1$-$C_{12}$ alkyl; p is an integer from 0 to 20, inclusive; and * indicates the point of attachment of C to I and  indicates the point of attachment of I to C.

IX. Methods for Making Silicon Containing Tail Groups

In some embodiments, this application relates to making compounds therapeutic compounds of formula E-G, or pharmaceutically acceptable salts, stereoisomers, mixtures of stereoisomers, tautomers, hydrates, and/or solvates thereof, wherein E is 21 or 22:

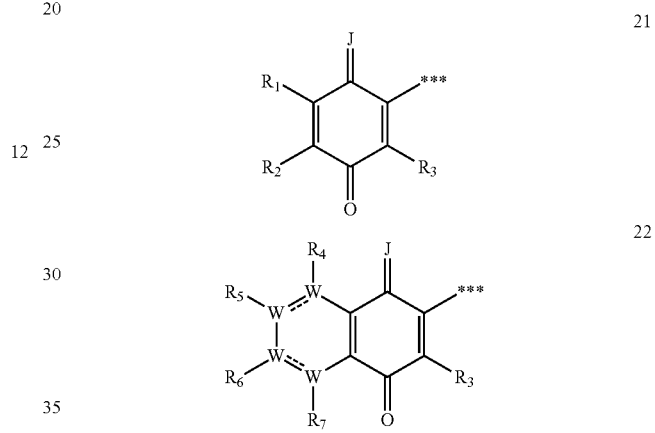

and G is 23 or 24:

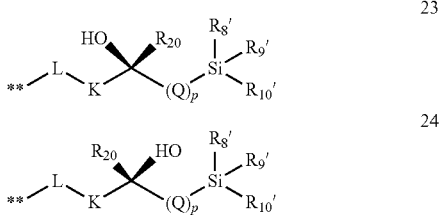

wherein, J is O, S or N—Ru; K is absent or —$(CR_{12}R_{13})$—; L is —$(CR_{12}R_{13})$—; each W is independently C (carbon) or N (nitrogen) and wherein for each use of w⩵w, the bond between each W can be a single bond or double bond and further provided that if a single bond, each C (carbon) atom will have a hydrogen atom linked hereto in addition to one of $R_4$, $R_5$, $R_6$ or $R_7$ and in either case each of $R_4$, $R_5$, $R_6$ and $R_7$ attached thereto is independently selected from H, D, F, Cl, Br, I, $C_1$-$C_6$ alkyl and $C_1$-$C_6$ alkoxy, and if W is N (nitrogen) each of $R_4$, $R_5$, $R_6$ and $R_7$ attached thereto is independently absent (if w⩵w is a double bond) or selected from H, D and $C_1$-$C_6$ alkyl (if w⩵w is a single bond); each Q is independently a group of formula —$(CR_{12}R_{13})$—, O or Si provided that each O and each Si is not directly bonded to O or Si; each of $R_1$, $R_2$ and $R_3$ is independently H, D, F, Cl, Br, I, $C_1$-$C_6$ alkyl or $C_1$-$C_6$ alkoxy or $R_1$ and $R_2$ together form a 5-membered carbocyclic ring, a 5-membered heterocyclic ring, a 5-membered aromatic or heteroaromatic ring, or a 6-membered heterocyclic ring; each of $R_8'$, $R_9'$ and $R_{10}'$ is independently a $C_1$-$C_4$ alkyl, or taken together $R_8'$ and $R_9'$ form a 3-, 4-, 5-, 6- or 7-membered carbocyclic or heterocyclic ring; $R_1$ is H, D or $C_1$-$C_6$ alkyl; each of $R_{12}$ and $R_{13}$ is independently H, D, F, Cl, Br, I, $C_1$-$C_6$ alkyl or $C_1$-$C_6$ alkoxy; $R_{20}$ is H, D, F or $C_1$-$C_{12}$ alkyl; p is an integer from 0 to 20, inclusive; and * indicates the point of attachment of E to G and  indicates the point of attachment of G to E.

Compounds of formula E-G, or pharmaceutically acceptable salts, stereoisomers, mixtures of stereoisomers, tautomers, hydrates, and/or solvates thereof, can be prepared substantially as described above for producing compounds of formula E-F, provided however, that the compound of formula 203, as described herein, is substituted with a compound of formula 203-Si, wherein the compound of formula 203-Si has the formula:

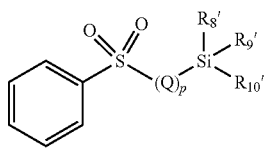

wherein p is an integer from 0 to 20, inclusive; each Q is independently a group of formula —$(CR_{12}R_{13})$—, O or Si provided that each O and each Si is not directly bonded to O or Si; and each of $R_8'$, $R_9'$ and $R_{10}'$ is independently a $C_1$-$C_4$ alkyl group. Alternatively, the process described in Example 15, below can be used as an alternative and adapted if one desires that the aliphatic tail further comprises an oxygen atom.

Similarly and by analogy, it is possible for prepare compounds of formula C-G (which are reduced forms of the compounds of formula E-G) using substantially any process used to produce compounds of formula C-D. Thus, in some embodiments, this application relates to making compounds therapeutic compounds of formula C-G, or pharmaceutically acceptable salts, stereoisomers, mixtures of stereoisomers, tautomers, hydrates, and/or solvates thereof, wherein C is 11 or 12:

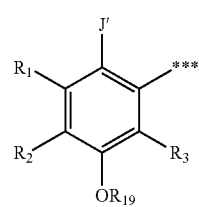

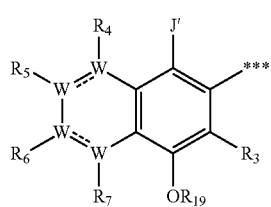

and G is 23 or 24:

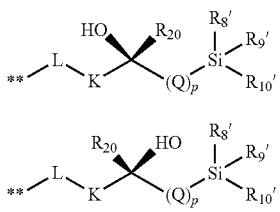

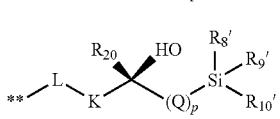

wherein, J' is OH, SH or NH—$R_{11}$; K is absent or —$(CR_{12}R_{13})$—; L is —$(CR_{12}R_{13})$—; each W is independently C (carbon) or N (nitrogen) and wherein for each use of w≕w, the bond between each W can be a single bond or double bond and further provided that if a single bond, each C (carbon) atom will have a hydrogen atom linked hereto in addition to one of $R_4$, $R_5$, $R_6$ or $R_7$ and in either case each of $R_4$, $R_5$, $R_6$ and $R_7$ attached thereto is independently selected from H, D, F, Cl, Br, I, $C_1$-$C_6$ alkyl and $C_1$-$C_6$ alkoxy, and if W is N (nitrogen), each of $R_4$, $R_5$, $R_6$ and $R_7$ attached thereto is independently absent (if w≕w is a double bond) or selected from H, D and $C_1$-$C_6$ alkyl (if w ≕ w is a single bond); each Q is independently a group of formula —$(CR_{12}R_{13})$—, O or Si provided that each O and each Si is not directly bonded to O or Si; each of $R_1$, $R_2$ and $R_3$ is independently H, D, F, Cl, Br, I, $C_1$-$C_6$ alkyl or $C_1$-$C_6$ alkoxy, or $R_1$ and $R_2$ together form a 5-membered carbocyclic ring, a 5-membered heterocyclic ring, a 5-membered aromatic or heteroaromatic ring, or a 6-membered heterocyclic ring; each of $R_8'$, $R_9'$ and $R_{10}'$ is independently a $C_1$-$C_4$ alkyl, or taken together $R_8'$ and $R_9'$ form a 3-, 4-, 5-, 6- or 7-membered carbocyclic or heterocyclic ring; $R_1$ is H, D or $C_1$-$C_6$ alkyl; each of $R_{12}$ and $R_{13}$ is independently H, D, F, Cl, Br, I, $C_1$-$C_6$ alkyl or $C_1$-$C_6$ alkoxy; $R_{19}$ is H, $C_1$-$C_4$ alkyl or benzyl (substituted or unsubstituted); $R_{20}$ is H, D, F or $C_1$-$C_{12}$ alkyl; p is an integer from 0 to 20, inclusive; and * indicates the point of attachment of C to G and  indicates the point of attachment of G to C.

For example, compounds of formula C-G, or pharmaceutically acceptable salts, stereoisomers, mixtures of stereoisomers, tautomers, hydrates, and/or solvates thereof, can be prepared substantially as described above for producing compounds of formula E-G and then reducing said compounds as disclosed herein.

Similarly and by analogy, it is possible for prepare compounds of formula A-H using substantially any process disclosed herein to produce compounds of formula A-B. Thus, in some embodiments, this application relates to making compounds therapeutic compounds of formula A-H, or pharmaceutically acceptable salts, stereoisomers, mixtures of stereoisomers, tautomers, hydrates, and/or solvates thereof, wherein A is 1, 2, 3, or 4:

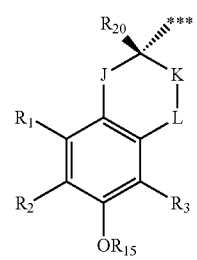

-continued

2

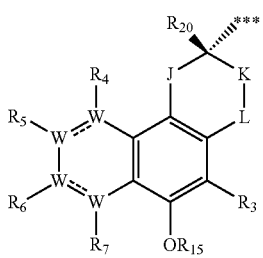

3

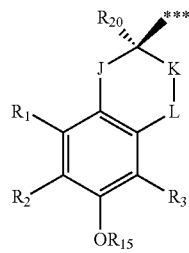

4

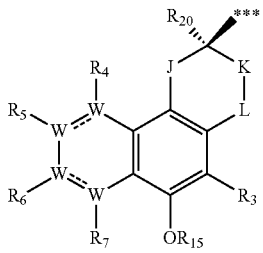

and H is 25:

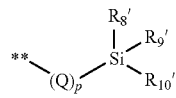

wherein, J is O, S or N—Ru; K is absent or —(CR$_{12}$R$_{13}$)—; L is —(CR$_{12}$R$_{13}$)—; each W is independently C (carbon) or N (nitrogen) and wherein for each use of w≡w, the bond between each W can be a single bond or double bond and further provided that if a single bond, each C (carbon) atom will have a hydrogen atom linked hereto in addition to one of R$_4$, R$_5$, R$_6$ or R$_7$ and in either case each of R$_4$, R$_5$, R$_6$ and R$_7$ attached thereto is independently selected from H, D, F, Cl, Br, I, C$_1$-C$_6$ alkyl and C$_1$-C$_6$ alkoxy, and if W is N (nitrogen), each of R$_4$, R$_5$, R$_6$ and R$_7$ attached thereto is independently absent (if w≡w is a double bond) or selected from H, D and C$_1$-C$_6$ alkyl (if w≡w is a single bond); each Q is independently a group of formula —(CR$_{12}$R$_{13}$)—, O or Si provided that each O and each Si is not directly bonded to O or Si; each of R$_1$, R$_2$ and R$_3$ is independently H, D, F, Cl, Br, I, C$_1$-C$_6$ alkyl or C$_1$-C$_6$ alkoxy, or R$_1$ and R$_2$ together form a 5-membered carbocyclic ring, a 5-membered heterocyclic ring, a 5-membered aromatic or heteroaromatic ring, or a 6-membered heterocyclic ring; each of R$_8$', R$_9$' and R$_{10}$' is independently a C$_1$-C$_4$ alkyl, or taken together R$_8$' and R$_9$' form a 3-, 4-, 5-, 6- or 7-membered carbocyclic or heterocyclic ring; R$_1$ is H, D or C$_1$-C$_6$ alkyl; each of R$_{12}$ and R$_{13}$ is independently H, D, F, Cl, Br, I, C$_1$-C$_6$ alkyl or C$_1$-C$_6$ alkoxy; R$_{15}$ is H, C$_1$-C$_4$ alkyl or PG, wherein PG is a phenol protecting group; R$_{20}$ is H, D, F or C$_1$-C$_{12}$ alkyl; p is an integer from 0 to 20, inclusive; and * indicates the point of attachment of A to H and  indicates the point of attachment of H to A.

For example, compounds of formula A-H, or pharmaceutically acceptable salts, stereoisomers, mixtures of stereoisomers, tautomers, hydrates, and/or solvates thereof, can be prepared substantially as described above for producing compounds of formula A-B, as described above provided however, that the compound of formula 203, as described herein, is substituted with a compound of formula 203-Si, wherein the compound of formula 203-Si has the formula:

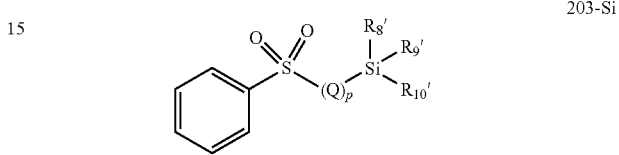

203-Si wherein p is an integer from 0 to 20, inclusive; each Q is independently a group of formula —(CR$_{12}$R$_{13}$)—, O or Si provided that each O and each Si is not directly bonded to O or Si; and each of R$_8$', R$_9$' and R$_{10}$' is independently a C$_1$-C$_4$ alkyl group.

The composition of formula 203-Si can be produced as described in FIG. 3 for the transition from 201 to 203, wherein the starting material is 201-Si of formula:

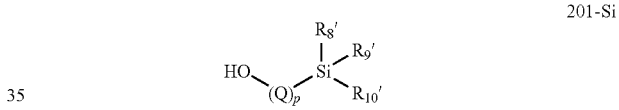

201-Si and the intermediate 202 is 202-Si having the formula:

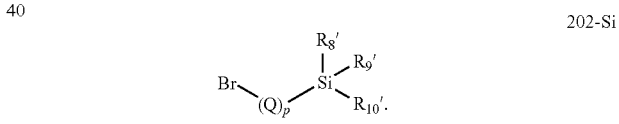

202-Si

X. Methods for Treating Friedrich's Ataxia and Associated Methods for Use

The following discussion is presented by way of example only and is not intended to be limiting.

(a) Methods of Treatment

One aspect of the present application includes methods of treating reduced frataxin expression in a subject diagnosed as having, suspected as having, or at risk of having reduced frataxin expression levels. One aspect of the present application includes methods of treating Friedreich's ataxia in a subject diagnosed as having, suspected as having, or at risk of having Friedreich's ataxia. In any embodiment disclosed herein, compounds of formula C-D or E-F (as disclosed in more detail above) or compositions or medicaments comprising a compound of formula C-D or E-F, or pharmaceutically acceptable salts, stereoisomers, mixtures of stereoisomers, tautomers, hydrates, and/or solvates thereof, may be administered to a subject suspected of, or already suffering from said mitochondrial disease (e.g., decreased frataxin expression levels or Friedreich's ataxia), in an amount sufficient to reduce the severity of or at least partially arrest or delay the onset of one or more of the symptoms of the disease, including its complications and intermediate pathological phenotypes in development of the disease. In any embodiment disclosed herein, compounds of formula C-G or E-G (as disclosed in more detail above) or compositions or medicaments comprising a compound of formula C-G or E-G, or pharmaceutically acceptable salts, stereoisomers, mixtures of stereoisomers, tautomers, hydrates, and/or solvates thereof, are administered to a subject suspected of, or already suffering from said mitochondrial disease (e.g., decreased frataxin expression levels or Friedreich's ataxia), in an amount sufficient to reduce the severity of or at least partially arrest or delay the onset of one or more of the symptoms of the disease, including its complications and intermediate pathological phenotypes in development of the disease.

Subjects suffering from decreased frataxin expression levels or Friedreich's ataxia can be identified by any or a combination of diagnostic or prognostic assays known in the art. For example, typical symptoms of Friedreich's ataxia include symptoms such as, e.g., muscle weakness, especially in the arms and legs, loss of coordination, motor control impairment, vision impairment, hearing impairment, slurred speech, curvature of the spine, diabetes, and heart disorders. In some embodiments, the subject may exhibit reduced levels of frataxin expression compared to a normal subject, which are measurable using techniques known in the art. In some embodiments, the subject may exhibit one or more mutations in the FN gene associated with Friedreich's ataxia, which are detectable using techniques known in the art.

(b) Prophylactic Methods

In one aspect, the present application provides a method for preventing or delaying the onset of Friedreich's ataxia or symptoms of Friedreich's ataxia in a subject at risk of having reduced levels of frataxin expression compared to a normal subject. In some embodiments, the subject may exhibit one or more mutations in the FXN gene associated with Friedreich's ataxia, which are detectable using techniques known in the art. Subjects at risk for reduced frataxin expression levels or Friedreich's ataxia can be identified by, e.g., any or a combination of diagnostic or prognostic assays known in the art. In any embodiment disclosed herein of prophylactic applications, compounds of formula C-D or E-F or pharmaceutical compositions or medicaments comprising a compound of formula C-D or E-F, or pharmaceutically acceptable salts, stereoisomers, mixtures of stereoisomers, tautomers, hydrates, and/or solvates thereof, may be administered to a subject susceptible to, or otherwise at risk of a mitochondrial disease or condition such as e.g., Friedreich's ataxia, in an amount sufficient to eliminate or reduce the risk, lessen the severity, or delay the onset of the disease, including biochemical, histologic and/or behavioral symptoms of the disease, its complications and intermediate pathological phenotypes presenting during development of the disease. In any embodiment disclosed herein of prophylactic applications, compounds of formula C-G or E-G or pharmaceutical compositions or medicaments comprising a compound of formula C-G or E-G, or pharmaceutically acceptable salts, stereoisomers, mixtures of stereoisomers, tautomers, hydrates, and/or solvates thereof, may be administered to a subject susceptible to, or otherwise at risk of a mitochondrial disease or condition such as e.g., Friedreich's ataxia, in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. Prophylactic administration of a compound of the present technology can occur prior to the manifestation of symptoms characteristic of the disease or disorder, such that the disease or disorder is prevented or, alternatively, delayed in its progression.

Subjects at risk for reduced frataxin expression levels or Friedreich's ataxia may exhibit one or more of the following non-limiting risk factors: cardiomyopathy, skeletal muscle abnormalities, neutropenia, slow development, weak muscle tone, increased levels of organic acids in the urine and blood, and/or frequent bacterial infections, such as pneumonia.

For therapeutic and/or prophylactic applications, a compound of the present technology or a composition comprising a compound of the present technology (as disclosed in more detail above), or pharmaceutically acceptable salts, stereoisomers, mixtures of stereoisomers, tautomers, hydrates, and/or solvates thereof, is administered to the subject. In some embodiments, the composition is administered one, two, three, four, or five times per day. In some embodiments, the composition is administered more than five times per day. Additionally or alternatively, in some embodiments, the composition is administered every day, every other day, every third day, every fourth day, every fifth day, or every sixth day. In some embodiments, the composition is administered weekly, bi-weekly, tri-weekly, or monthly. In some embodiments, the composition is administered for a period of one, two, three, four, or five weeks. In some embodiments, the composition is administered for six weeks or more. In some embodiments, the composition is administered for twelve weeks or more. In some embodiments, the composition is administered for a period of less than one year. In some embodiments, the composition is administered for a period of more than one year. In some embodiments, the composition is administered for the remainder of the subject's life.

For therapeutic and/or prophylactic applications, a composition comprising a compound of the present technology (as disclosed in more detail above), or pharmaceutically acceptable salts, stereoisomers, mixtures of stereoisomers, tautomers, hydrates, and/or solvates thereof, may be administered in combination with one or more additional agents. In some embodiments, there is a synergistic effect between the compounds of the present application and the one or more additional agents.

(c) Determination of the Biological Effect of the Therapeutic

In various embodiments, suitable in vitro or in vivo assays can be performed to determine the effect of a specific compound of the present technology or composition comprising a compound of the present technology (as disclosed in more detail above), or pharmaceutically acceptable salts, stereoisomers, mixtures of stereoisomers, tautomers, hydrates, and/or solvates thereof, and whether its administration is indicated for treatment. Such an in-vitro assay can be found in, for example, Examples 17-22, below. In various embodiments, in vivo assays can be performed with representative animal models, to determine if a given compound of the present technology (as disclosed in more detail above), or pharmaceutically acceptable salts, stereoisomers, mixtures of stereoisomers, tautomers, hydrates, and/or solvates thereof exerts the desired effect of increasing frataxin expression, and preventing or treating Friedreich's ataxia. Compounds (and compositions comprising said compounds) for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects. In some embodiments, in vitro or in vivo testing is directed to the biological function of a compound of the present technology (or a composition comprising said compound), or pharmaceutically acceptable salts, stereoisomers, mixtures of stereoisomers, tautomers, hydrates, and/or solvates of such a compound (or a composition comprising said compound).

(d) Modes of Administration and Effective Dosages

Any method known to those in the art for contacting a cell, organ or tissue with a compound of the present technology (or a composition comprising said compound), or pharmaceutically acceptable salts, stereoisomers, mixtures of stereoisomers, tautomers, hydrates, and/or solvates of such a compound (or a composition comprising said compound), may be employed. Suitable methods include in vitro, ex vivo, or in vivo methods. In vivo methods typically include the administration of a compound of the present technology (as disclosed in more detail above), or pharmaceutically acceptable salts, stereoisomers, mixtures of stereoisomers, tautomers, hydrates, and/or solvates thereof, such as those described above, to a subject, suitably a mammal or human. When used in vivo for therapy, a compound of the present technology (as disclosed in more detail above), or pharmaceutically acceptable salts, stereoisomers, mixtures of stereoisomers, tautomers, hydrates, and/or solvates thereof, may be administered to the subject in an effective amount (i.e., an amount that produces a desired therapeutic effect). The dose and dosage regimen will depend upon the degree of the disease in the subject, the characteristics of the particular compound of the present technology (as disclosed in more detail above), or pharmaceutically acceptable salts, stereoisomers, mixtures of stereoisomers, tautomers, hydrates, and/or solvates thereof, e.g., its therapeutic index, the subject, and the subject's history.

The effective amount may be determined during preclinical trials and clinical trials by methods familiar to physicians and clinicians. An effective amount of a compound useful in the methods may be administered to a mammal in need thereof by any of a number of well-known methods for administering pharmaceutical compounds. The therapeutically active compounds may be administered systemically or locally.

A compound of the present technology (as disclosed in more detail above), or pharmaceutically acceptable salts, stereoisomers, mixtures of stereoisomers, tautomers, hydrates, and/or solvates thereof, can be incorporated into pharmaceutical compositions for administration, singly or in combination, to a subject for the treatment or prevention of a disorder described herein. Such compositions typically include the active agent and a pharmaceutically acceptable carrier. Pharmaceutical compositions are typically formulated to be compatible with its intended route of administration. Exemplary routes of administration have been previously described herein.

(e) Embodiments

Thus, in some embodiments, the present application pertains to a method for treating or preventing Friedreich's ataxia or the signs or symptoms of reduced frataxin levels or activity in a subject in need thereof, comprising administering to the subject a therapeutically effective amount of a compound of formula E-F (as described above), or pharmaceutically acceptable salts, stereoisomers, mixtures of stereoisomers, tautomers, hydrates, and/or solvates thereof. Because they are believed to be alternative therapeutic embodiments (i.e. they can cycle in-vivo between reduced and oxidized forms: C-D↔E-F, respectively), in some embodiments, the present application pertains to a method for treating or preventing Friedreich's ataxia or the signs or symptoms of reduced frataxin levels or activity in a subject in need thereof, comprising administering to the subject a therapeutically effective amount of a compound of formula C-D (as described above), or pharmaceutically acceptable salts, stereoisomers, mixtures of stereoisomers, tautomers, hydrates, and/or solvates thereof.

In some embodiments, a compound of formula E-F or a compound of formula C-D is administered daily for 6 weeks or more. In some embodiments, a compound of formula E-F or a compound of formula C-D is administered daily for 12 weeks or more. In some embodiments, a compound of formula E-F or a compound of formula C-D is administered to a subject that has been diagnosed as having Friedreich's ataxia, wherein in some cases, the Friedreich's ataxia comprises one or more of muscle weakness, loss of coordination, vision impairment, hearing impairment, slurred speech, curvature of the spine, diabetes, and heart disorders. In some embodiments, the subject is a mammal. In some embodiments, the subject is human. In some embodiments, the compound of formula E-F or a compound of formula C-D is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

In some embodiments, the present application pertains to a method for reducing mitochondrial iron in a mammalian subject having or suspected of having Friedreich's ataxia, the method comprising: administering to the subject a therapeutically effective amount of a compound of formula E-F (as described above), or pharmaceutically acceptable salts, stereoisomers, mixtures of stereoisomers, tautomers, hydrates, and/or solvates thereof. In some embodiments, the present application pertains to a method for method for reducing mitochondrial iron in a mammalian subject having or suspected of having Friedreich's ataxia, the method comprising: administering to the subject a therapeutically effective amount of a compound of formula C-D (as described above), or pharmaceutically acceptable salts, stereoisomers, mixtures of stereoisomers, tautomers, hydrates, and/or solvates thereof. In some embodiments, mammalian subject to which the compound of formula E-F or C-D is administered has decreased expression of frataxin compared to a normal control subject.

In some embodiments, a compound of formula E-F or a compound of formula C-D is administered daily for 6 weeks or more. In some embodiments, a compound of formula E-F or a compound of formula C-D is administered daily for 12 weeks or more. In some embodiments, a compound of formula E-F or a compound of formula C-D is administered to a subject that has been diagnosed as having Friedreich's ataxia, wherein in some cases, the Friedreich's ataxia comprises one or more of muscle weakness, loss of coordination, vision impairment, hearing impairment, slurred speech, curvature of the spine, diabetes, and heart disorders. In some embodiments, the subject is human. In some embodiments, the compound of formula E-F or a compound of formula C-D is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

The present application further pertains to: (i) compositions comprising compounds of formula E-F; or (ii) compounds of formula C-D, used to treat or prevent Friedreich's ataxia in a subject in need thereof. In some embodiments, the compound or composition is effective to increase or maintain frataxin levels in a subject suspected of having Friedreich's ataxia. In some embodiments, the compound or composition is effective to slow the reduction in frataxin levels in a subject suspected of having Friedreich's ataxia. In some embodiments, the composition or compound is effective to treat one or more symptoms of Friedreich's ataxia selected from the group consisting of: muscle weakness, loss of coordination, vision impairment, hearing impairment, slurred speech, curvature of the spine, diabetes, and heart disorders. In some embodiments, the composition or compound is effective when administered daily for 6 weeks or more. In some embodiments, the composition or compound is effective when administered daily for 12 weeks or more.

The present application further pertains to: (i) compositions comprising compounds of formula E-F; or (ii) compounds of formula C-D, used to increase the levels of frataxin expression in a subject in need thereof. In some embodiments, the compound or composition is effective to treat one or more symptoms of Friedreich's ataxia selected from the group consisting of: muscle weakness, loss of coordination, vision impairment, hearing impairment, slurred speech, curvature of the spine, diabetes, and heart disorders. In some embodiments, the composition or compound is effective when administered daily for 6 weeks or more. In some embodiments, the composition or compound is effective when administered daily for 12 weeks or more.

The present application further pertains to use of a composition in the preparation of a medicament for treating or preventing Friedreich's ataxia in a subject in need thereof, wherein the composition comprises a therapeutically effective amount of; (i) a compound of formula E-F, or (ii) of formula C-D, pharmaceutically acceptable salts, stereoisomers, mixtures of stereoisomers, tautomers, hydrates, and/or solvates thereof. The present application further pertains to use of a composition in the preparation of a medicament for increasing the levels of frataxin expression in a mammalian subject compared to a normal control subject, wherein the composition comprises a therapeutically effective amount of; (i) a compound of formula E-F, or (ii) of formula C-D, pharmaceutically acceptable salts, stereoisomers, mixtures of stereoisomers, tautomers, hydrates, and/or solvates thereof.

In some embodiments, the medicament is effective when administered daily for 6 weeks or more. In some embodiments, the medicament is effective when administered daily for 12 weeks or more. In some embodiments, the medicament is effective to increase frataxin levels in a subject diagnosed as having Friedreich's ataxia.

In some embodiments, the present application pertains to a method for treating or preventing Complex I deficiency in a subject in need thereof, comprising administering to the subject a therapeutically effective amount of a compound of formula E-F (as described above), or pharmaceutically acceptable salts, stereoisomers, mixtures of stereoisomers, tautomers, hydrates, and/or solvates thereof. Because they are believed to be alternative therapeutic embodiments (i.e. they can cycle in-vivo between reduced and oxidized forms: C-D↔E-F, respectively), in some embodiments, the present application pertains to a method for treating or preventing Complex I deficiency in a subject in need thereof, comprising administering to the subject a therapeutically effective amount of a compound of formula C-D (as described above), or pharmaceutically acceptable salts, stereoisomers, mixtures of stereoisomers, tautomers, hydrates, and/or solvates thereof.

In some embodiments, a compound of formula E-F or a compound of formula C-D is administered daily for 6 weeks or more. In some embodiments, a compound of formula E-F or a compound of formula C-D is administered daily for 12 weeks or more. In some embodiments, a compound of formula E-F or a compound of formula C-D is administered to a subject that has been diagnosed as Complex I deficiency, wherein in some cases, the Complex I deficiency comprises one or more of muscle weakness, loss of coordination, vision impairment, hearing impairment, slurred speech, curvature of the spine, diabetes, and heart disorders. In some embodiments, the subject is a mammal. In some embodiments, the subject is human. In some embodiments, the compound of formula E-F or a compound of formula C-D is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

The present application further pertains to: (i) compositions comprising compounds of formula E-F; or (ii) compounds of formula C-D, used to treat Complex I deficiency in a mammalian subject. The efficacy of such use can be determined by comparison with that of a normal control subject. In some embodiments, the composition or compound is effective to treat one or more symptoms of Complex I deficiency selected from the group consisting of: muscle weakness, loss of coordination, vision impairment, hearing impairment, slurred speech, curvature of the spine, diabetes, and heart disorders. In some embodiments, the composition or compound is effective when administered daily for 6 weeks or more. In some embodiments, the composition or compound is effective when administered daily for 12 weeks or more.

The present application further pertains to use of a composition in the preparation of a medicament for treating or preventing Complex I deficiency in a subject in need thereof, wherein the composition comprises a therapeutically effective amount of; (i) a compound of formula E-F, or (ii) of formula C-D, pharmaceutically acceptable salts, stereoisomers, mixtures of stereoisomers, tautomers, hydrates, and/or solvates thereof. In some embodiments, the medicament is effective when administered daily for 6 weeks or more. In some embodiments, the medicament is effective when administered daily for 12 weeks or more. In some embodiments, the medicament is effective to increase intracellular adenosine triphosphate (ATP) levels in a subject diagnosed as having Complex I deficiency. In some embodiments, the medicament is effective to increase intracellular adenosine triphosphate (ATP) levels in tissue in a subject, such as a subject diagnosed as having Friedreich's ataxia.

In some embodiments, the present application pertains to a method for reducing or inhibiting lipoxygenase-15 activity in a mammalian subject having or suspected of having Friedreich's ataxia, the method comprising: administering to the subject a therapeutically effective amount of a compound of formula E-F (as described above), or pharmaceutically acceptable salts, stereoisomers, mixtures of stereoisomers, tautomers, hydrates, and/or solvates thereof. In some embodiments, the present application pertains to a method for method for reducing or inhibiting lipoxygenase-15 activity in a mammalian subject having or suspected of having Friedreich's ataxia, the method comprising: administering to the subject a therapeutically effective amount of a compound of formula C-D (as described above), or pharmaceutically acceptable salts, stereoisomers, mixtures of stereoisomers, tautomers, hydrates, and/or solvates thereof. In some embodiments, mammalian subject to which the compound of formula E-F or C-D is administered has decreased expression of frataxin compared to a normal control subject.

In some embodiments, a compound of formula E-F or a compound of formula C-D is administered daily for 6 weeks or more. In some embodiments, a compound of formula E-F or a compound of formula C-D is administered daily for 12 weeks or more. In some embodiments, a compound of formula E-F or a compound of formula C-D is administered to a subject that has been diagnosed as having Friedreich's ataxia, wherein in some cases, the Friedreich's ataxia comprises one or more of muscle weakness, loss of coordination, vision impairment, hearing impairment, slurred speech, curvature of the spine, diabetes, and heart disorders. In some embodiments, the subject is human. In some embodiments, the compound of formula E-F or a compound of formula C-D is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

In some embodiments, the present application pertains to a method for reducing or inhibiting ferroptosis in a mammalian subject having or suspected of having Friedreich's ataxia, the method comprising: administering to the subject a therapeutically effective amount of a compound of formula E-F (as described above), or pharmaceutically acceptable salts, stereoisomers, mixtures of stereoisomers, tautomers, hydrates, and/or solvates thereof. In some embodiments, the present application pertains to a method for method for reducing or inhibiting ferroptosis in a mammalian subject having or suspected of having Friedreich's ataxia, the method comprising: administering to the subject a therapeutically effective amount of a compound of formula C-D (as described above), or pharmaceutically acceptable salts, stereoisomers, mixtures of stereoisomers, tautomers, hydrates, and/or solvates thereof. In some embodiments, mammalian subject to which the compound of formula E-F or C-D is administered has decreased expression of frataxin compared to a normal control subject.

In some embodiments, a compound of formula E-F or a compound of formula C-D is administered daily for 6 weeks or more. In some embodiments, a compound of formula E-F or a compound of formula C-D is administered daily for 12 weeks or more. In some embodiments, a compound of formula E-F or a compound of formula C-D is administered to a subject that has been diagnosed as having Friedreich's ataxia, wherein in some cases, the Friedreich's ataxia comprises one or more of muscle weakness, loss of coordination, vision impairment, hearing impairment, slurred speech, curvature of the spine, diabetes, and heart disorders. In some embodiments, the subject is human. In some embodiments, the compound of formula E-F or a compound of formula C-D is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

Thus, in some embodiments, the present application pertains to a method for treating or preventing Friedreich's ataxia or the signs or symptoms of reduced frataxin levels or activity in a subject in need thereof, comprising administering to the subject a therapeutically effective amount of a compound of formula E-G (as described above), or pharmaceutically acceptable salts, stereoisomers, mixtures of stereoisomers, tautomers, hydrates, and/or solvates thereof. Because they are believed to be alternative therapeutic embodiments (i.e. they can cycle in-vivo between reduced and oxidized forms: C-G↔E-G, respectively), in some embodiments, the present application pertains to a method for treating or preventing Friedreich's ataxia or the signs or symptoms of reduced frataxin levels or activity in a subject in need thereof, comprising administering to the subject a therapeutically effective amount of a compound of formula C-G (as described above), or pharmaceutically acceptable salts, stereoisomers, mixtures of stereoisomers, tautomers, hydrates, and/or solvates thereof.

In some embodiments, a compound of formula E-G or a compound of formula C-G is administered daily for 6 weeks or more. In some embodiments, a compound of formula E-G or a compound of formula C-G is administered daily for 12 weeks or more. In some embodiments, a compound of formula E-G or a compound of formula C-G is administered to a subject that has been diagnosed as having Friedreich's ataxia, wherein in some cases, the Friedreich's ataxia comprises one or more of muscle weakness, loss of coordination, vision impairment, hearing impairment, slurred speech, curvature of the spine, diabetes, and heart disorders. In some embodiments, the subject is a mammal. In some embodiments, the subject is human. In some embodiments, the compound of formula E-G or a compound of formula C-G is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

In some embodiments, the present application pertains to a method for reducing mitochondrial iron in a mammalian subject having or suspected of having Friedreich's ataxia, the method comprising: administering to the subject a therapeutically effective amount of a compound of formula E-G (as described above), or pharmaceutically acceptable salts, stereoisomers, mixtures of stereoisomers, tautomers, hydrates, and/or solvates thereof. In some embodiments, the present application pertains to a method for method for reducing mitochondrial iron in a mammalian subject having or suspected of having Friedreich's ataxia, the method comprising: administering to the subject a therapeutically effective amount of a compound of formula C-G (as described above), or pharmaceutically acceptable salts, stereoisomers, mixtures of stereoisomers, tautomers, hydrates, and/or solvates thereof. In some embodiments, mammalian subject to which the compound of formula E-G or C-G is administered has decreased expression of frataxin compared to a normal control subject.

In some embodiments, a compound of formula E-G or a compound of formula C-G is administered daily for 6 weeks or more. In some embodiments, a compound of formula E-G or a compound of formula C-G is administered daily for 12 weeks or more. In some embodiments, a compound of formula E-G or a compound of formula C-G is administered to a subject that has been diagnosed as having Friedreich's ataxia, wherein in some cases, the Friedreich's ataxia comprises one or more of muscle weakness, loss of coordination, vision impairment, hearing impairment, slurred speech, curvature of the spine, diabetes, and heart disorders. In some embodiments, the subject is human. In some embodiments, the compound of formula E-G or a compound of formula C-G is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

The present application further pertains to: (i) compositions comprising compounds of formula E-G; or (ii) compounds of formula C-G, used to treat or prevent Friedreich's ataxia in a subject in need thereof. In some embodiments, the compound or composition is effective to increase or maintain frataxin levels in a subject suspected of having Friedreich's ataxia. In some embodiments, the compound or composition is effective to slow the reduction in frataxin levels in a subject suspected of having Friedreich's ataxia. In some embodiments, the composition or compound is effective to treat one or more symptoms of Friedreich's ataxia selected from the group consisting of: muscle weakness, loss of coordination, vision impairment, hearing impairment, slurred speech, curvature of the spine, diabetes, and heart disorders. In some embodiments, the composition or compound is effective when administered daily for 6 weeks or more. In some embodiments, the composition or compound is effective when administered daily for 12 weeks or more.

The present application further pertains to: (i) compositions comprising compounds of formula E-G; or (ii) compounds of formula C-G, used to increase the levels of frataxin expression in a subject in need thereof. In some embodiments, the compound or composition is effective to treat one or more symptoms of Friedreich's ataxia selected from the group consisting of: muscle weakness, loss of coordination, vision impairment, hearing impairment, slurred speech, curvature of the spine, diabetes, and heart disorders. In some embodiments, the composition or compound is effective when administered daily for 6 weeks or more. In some embodiments, the composition or compound is effective when administered daily for 12 weeks or more.

The present application further pertains to use of a composition in the preparation of a medicament for treating or preventing Friedreich's ataxia in a subject in need thereof, wherein the composition comprises a therapeutically effective amount of; (i) a compound of formula E-G, or (ii) of formula C-G, pharmaceutically acceptable salts, stereoisomers, mixtures of stereoisomers, tautomers, hydrates, and/or solvates thereof. The present application further pertains to use of a composition in the preparation of a medicament for increasing the levels of frataxin expression in a mammalian subject compared to a normal control subject, wherein the composition comprises a therapeutically effective amount of; (i) a compound of formula E-G, or (ii) of formula C-G, pharmaceutically acceptable salts, stereoisomers, mixtures of stereoisomers, tautomers, hydrates, and/or solvates thereof.

In some embodiments, the medicament is effective when administered daily for 6 weeks or more. In some embodiments, the medicament is effective when administered daily for 12 weeks or more. In some embodiments, the medicament is effective to increase frataxin levels in a subject diagnosed as having Friedreich's ataxia.

In some embodiments, the present application pertains to a method for treating or preventing Complex I deficiency in a subject in need thereof, comprising administering to the subject a therapeutically effective amount of a compound of formula E-G (as described above), or pharmaceutically acceptable salts, stereoisomers, mixtures of stereoisomers, tautomers, hydrates, and/or solvates thereof. Because they are believed to be alternative therapeutic embodiments (i.e. they can cycle in-vivo between reduced and oxidized forms: C-G↔E-G, respectively), in some embodiments, the present application pertains to a method for treating or preventing Complex I deficiency in a subject in need thereof, comprising administering to the subject a therapeutically effective amount of a compound of formula C-G (as described above), or pharmaceutically acceptable salts, stereoisomers, mixtures of stereoisomers, tautomers, hydrates, and/or solvates thereof.

In some embodiments, a compound of formula E-G or a compound of formula C-G is administered daily for 6 weeks or more. In some embodiments, a compound of formula E-G or a compound of formula C-G is administered daily for 12 weeks or more. In some embodiments, a compound of formula E-G or a compound of formula C-G is administered to a subject that has been diagnosed as Complex I deficiency, wherein in some cases, the Complex I deficiency comprises one or more of muscle weakness, loss of coordination, vision impairment, hearing impairment, slurred speech, curvature of the spine, diabetes, and heart disorders. In some embodiments, the subject is a mammal. In some embodiments, the subject is human. In some embodiments, the compound of formula E-G or a compound of formula C-G is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

The present application further pertains to: (i) compositions comprising compounds of formula E-G; or (ii) compounds of formula C-G, used to treat Complex I deficiency in a mammalian subject. The efficacy of such use can be determined by comparison with that of a normal control subject. In some embodiments, the composition or compound is effective to treat one or more symptoms of Complex I deficiency selected from the group consisting of: muscle weakness, loss of coordination, vision impairment, hearing impairment, slurred speech, curvature of the spine, diabetes, and heart disorders. In some embodiments, the composition or compound is effective when administered daily for 6 weeks or more. In some embodiments, the composition or compound is effective when administered daily for 12 weeks or more.

The present application further pertains to use of a composition in the preparation of a medicament for treating or preventing Complex I deficiency in a subject in need thereof, wherein the composition comprises a therapeutically effective amount of; (i) a compound of formula E-G, or (ii) of formula C-G, pharmaceutically acceptable salts, stereoisomers, mixtures of stereoisomers, tautomers, hydrates, and/or solvates thereof. In some embodiments, the medicament is effective when administered daily for 6 weeks or more. In some embodiments, the medicament is effective when administered daily for 12 weeks or more. In some embodiments, the medicament is effective to increase intracellular adenosine triphosphate (ATP) levels in a subject diagnosed as having Complex I deficiency. In some embodiments, the medicament is effective to increase intracellular adenosine triphosphate (ATP) levels in tissue in a subject, such as a subject diagnosed as having Friedreich's ataxia.

In some embodiments, the present application pertains to a method for reducing or inhibiting lipoxygenase-15 activity in a mammalian subject having or suspected of having Friedreich's ataxia, the method comprising: administering to the subject a therapeutically effective amount of a compound of formula E-G (as described above), or pharmaceutically acceptable salts, stereoisomers, mixtures of stereoisomers, tautomers, hydrates, and/or solvates thereof. In some embodiments, the present application pertains to a method for method for reducing or inhibiting lipoxygenase-15 activity in a mammalian subject having or suspected of having Friedreich's ataxia, the method comprising: administering to the subject a therapeutically effective amount of a compound of formula C-G (as described above), or pharmaceutically acceptable salts, stereoisomers, mixtures of stereoisomers, tautomers, hydrates, and/or solvates thereof. In some embodiments, mammalian subject to which the compound of formula E-G or C-G is administered has decreased expression of frataxin compared to a normal control subject.

In some embodiments, a compound of formula E-G or a compound of formula C-G is administered daily for 6 weeks or more. In some embodiments, a compound of formula E-G or a compound of formula C-G is administered daily for 12 weeks or more. In some embodiments, a compound of formula E-G or a compound of formula C-G is administered to a subject that has been diagnosed as having Friedreich's ataxia, wherein in some cases, the Friedreich's ataxia comprises one or more of muscle weakness, loss of coordination, vision impairment, hearing impairment, slurred speech, curvature of the spine, diabetes, and heart disorders. In some embodiments, the subject is human. In some embodiments, the compound of formula E-G or a compound of formula C-G is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

In some embodiments, the present application pertains to a method for reducing or inhibiting ferroptosis in a mammalian subject having or suspected of having Friedreich's ataxia, the method comprising: administering to the subject a therapeutically effective amount of a compound of formula E-G (as described above), or pharmaceutically acceptable salts, stereoisomers, mixtures of stereoisomers, tautomers, hydrates, and/or solvates thereof. In some embodiments, the present application pertains to a method for method for reducing or inhibiting ferroptosis in a mammalian subject having or suspected of having Friedreich's ataxia, the method comprising: administering to the subject a therapeutically effective amount of a compound of formula C-G (as described above), or pharmaceutically acceptable salts, stereoisomers, mixtures of stereoisomers, tautomers, hydrates, and/or solvates thereof. In some embodiments, mammalian subject to which the compound of formula E-G or C-G is administered has decreased expression of frataxin compared to a normal control subject.

In some embodiments, a compound of formula E-G or a compound of formula C-G is administered daily for 6 weeks or more. In some embodiments, a compound of formula E-G or a compound of formula C-G is administered daily for 12 weeks or more. In some embodiments, a compound of formula E-G or a compound of formula C-G is administered to a subject that has been diagnosed as having Friedreich's ataxia, wherein in some cases, the Friedreich's ataxia comprises one or more of muscle weakness, loss of coordination, vision impairment, hearing impairment, slurred speech, curvature of the spine, diabetes, and heart disorders. In some embodiments, the subject is human. In some embodiments, the compound of formula E-G or a compound of formula C-G is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

In some embodiments, the present application pertains to a method for treating or preventing Friedreich's ataxia or the signs or symptoms of reduced frataxin levels or activity in a subject in need thereof, comprising administering to the subject a therapeutically effective amount of a compound of formula E-I (as described above), or pharmaceutically acceptable salts, stereoisomers, mixtures of stereoisomers, tautomers, hydrates, and/or solvates thereof. Because they are believed to be alternative therapeutic embodiments (i.e. they can cycle in-vivo between reduced and oxidized forms: C-I↔E-I, respectively), in some embodiments, the present application pertains to a method for treating or preventing Friedreich's ataxia or the signs or symptoms of reduced frataxin levels or activity in a subject in need thereof, comprising administering to the subject a therapeutically effective amount of a compound of formula C-I (as described above), or pharmaceutically acceptable salts, stereoisomers, mixtures of stereoisomers, tautomers, hydrates, and/or solvates thereof.

In some embodiments, a compound of formula E-I or a compound of formula C-I is administered daily for 6 weeks or more. In some embodiments, a compound of formula E-I or a compound of formula C-I is administered daily for 12 weeks or more. In some embodiments, a compound of formula E-I or a compound of formula C-I is administered to a subject that has been diagnosed as having Friedreich's ataxia, wherein in some cases, the Friedreich's ataxia comprises one or more of muscle weakness, loss of coordination, vision impairment, hearing impairment, slurred speech, curvature of the spine, diabetes, and heart disorders. In some embodiments, the subject is a mammal. In some embodiments, the subject is human. In some embodiments, the compound of formula E-I or a compound of formula C-I is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

In some embodiments, the present application pertains to a method for reducing mitochondrial iron in a mammalian subject having or suspected of having Friedreich's ataxia, the method comprising: administering to the subject a therapeutically effective amount of a compound of formula E-I (as described above), or pharmaceutically acceptable salts, stereoisomers, mixtures of stereoisomers, tautomers, hydrates, and/or solvates thereof. In some embodiments, the present application pertains to a method for method for reducing mitochondrial iron in a mammalian subject having or suspected of having Friedreich's ataxia, the method comprising: administering to the subject a therapeutically effective amount of a compound of formula C-I (as described above), or pharmaceutically acceptable salts, stereoisomers, mixtures of stereoisomers, tautomers, hydrates, and/or solvates thereof. In some embodiments, mammalian subject to which the compound of formula E-I or C-I is administered has decreased expression of frataxin compared to a normal control subject.

In some embodiments, a compound of formula E-I or a compound of formula C-I is administered daily for 6 weeks or more. In some embodiments, a compound of formula E-I or a compound of formula C-I is administered daily for 12 weeks or more. In some embodiments, a compound of formula E-I or a compound of formula C-I is administered to a subject that has been diagnosed as having Friedreich's ataxia, wherein in some cases, the Friedreich's ataxia comprises one or more of muscle weakness, loss of coordination, vision impairment, hearing impairment, slurred speech, curvature of the spine, diabetes, and heart disorders. In some embodiments, the subject is human. In some embodiments, the compound of formula E-I or a compound of formula C-I is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

The present application further pertains to: (i) compositions comprising compounds of formula E-I; or (ii) compounds of formula C-I, used to treat or prevent Friedreich's ataxia in a subject in need thereof. In some embodiments, the compound or composition is effective to increase or maintain frataxin levels in a subject suspected of having Friedreich's ataxia. In some embodiments, the compound or composition is effective to slow the reduction in frataxin levels in a subject suspected of having Friedreich's ataxia. In some embodiments, the composition or compound is effective to treat one or more symptoms of Friedreich's ataxia selected from the group consisting of: muscle weakness, loss of coordination, vision impairment, hearing impairment, slurred speech, curvature of the spine, diabetes, and heart disorders. In some embodiments, the composition or compound is effective when administered daily for 6 weeks or more. In some embodiments, the composition or compound is effective when administered daily for 12 weeks or more.

The present application further pertains to: (i) compositions comprising compounds of formula E-I; or (ii) compounds of formula C-I, used to increase the levels of frataxin expression in a subject in need thereof. In some embodiments, the compound or composition is effective to treat one or more symptoms of Friedreich's ataxia selected from the group consisting of: muscle weakness, loss of coordination, vision impairment, hearing impairment, slurred speech, curvature of the spine, diabetes, and heart disorders. In some embodiments, the composition or compound is effective when administered daily for 6 weeks or more. In some embodiments, the composition or compound is effective when administered daily for 12 weeks or more.

The present application further pertains to use of a composition in the preparation of a medicament for treating or preventing Friedreich's ataxia in a subject in need thereof, wherein the composition comprises a therapeutically effective amount of; (i) a compound of formula E-I, or (ii) of formula C-I, pharmaceutically acceptable salts, stereoisomers, mixtures of stereoisomers, tautomers, hydrates, and/or solvates thereof. The present application further pertains to use of a composition in the preparation of a medicament for increasing the levels of frataxin expression in a mammalian subject compared to a normal control subject, wherein the composition comprises a therapeutically effective amount of; (i) a compound of formula E-I, or (ii) of formula C-I, pharmaceutically acceptable salts, stereoisomers, mixtures of stereoisomers, tautomers, hydrates, and/or solvates thereof.

In some embodiments, the medicament is effective when administered daily for 6 weeks or more. In some embodiments, the medicament is effective when administered daily for 12 weeks or more. In some embodiments, the medicament is effective to increase frataxin levels in a subject diagnosed as having Friedreich's ataxia.

In some embodiments, the present application pertains to a method for treating or preventing Complex I deficiency in a subject in need thereof, comprising administering to the subject a therapeutically effective amount of a compound of formula E-I (as described above), or pharmaceutically acceptable salts, stereoisomers, mixtures of stereoisomers, tautomers, hydrates, and/or solvates thereof. Because they are believed to be alternative therapeutic embodiments (i.e. they can cycle in-vivo between reduced and oxidized forms: C-I↔E-I, respectively), in some embodiments, the present application pertains to a method for treating or preventing Complex I deficiency in a subject in need thereof, comprising administering to the subject a therapeutically effective amount of a compound of formula C-I (as described above), or pharmaceutically acceptable salts, stereoisomers, mixtures of stereoisomers, tautomers, hydrates, and/or solvates thereof.

In some embodiments, a compound of formula E-I or a compound of formula C-I is administered daily for 6 weeks or more. In some embodiments, a compound of formula E-I or a compound of formula C-I is administered daily for 12 weeks or more. In some embodiments, a compound of formula E-I or a compound of formula C-I is administered to a subject that has been diagnosed as Complex I deficiency, wherein in some cases, the Complex I deficiency comprises one or more of muscle weakness, loss of coordination, vision impairment, hearing impairment, slurred speech, curvature of the spine, diabetes, and heart disorders. In some embodiments, the subject is a mammal. In some embodiments, the subject is human. In some embodiments, the compound of formula E-I or a compound of formula C-I is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

The present application further pertains to: (i) compositions comprising compounds of formula E-I; or (ii) compounds of formula C-I, used to treat Complex I deficiency in a mammalian subject. The efficacy of such use can be determined by comparison with that of a normal control subject. In some embodiments, the composition or compound is effective to treat one or more symptoms of Complex I deficiency selected from the group consisting of: muscle weakness, loss of coordination, vision impairment, hearing impairment, slurred speech, curvature of the spine, diabetes, and heart disorders. In some embodiments, the composition or compound is effective when administered daily for 6 weeks or more. In some embodiments, the composition or compound is effective when administered daily for 12 weeks or more.

The present application further pertains to use of a composition in the preparation of a medicament for treating or preventing Complex I deficiency in a subject in need thereof, wherein the composition comprises a therapeutically effective amount of; (i) a compound of formula E-I, or (ii) of formula C-I, pharmaceutically acceptable salts, stereoisomers, mixtures of stereoisomers, tautomers, hydrates, and/or solvates thereof. In some embodiments, the medicament is effective when administered daily for 6 weeks or more. In some embodiments, the medicament is effective when administered daily for 12 weeks or more. In some embodiments, the medicament is effective to increase intracellular adenosine triphosphate (ATP) levels in a subject diagnosed as having Complex I deficiency. In some embodiments, the medicament is effective to increase intracellular adenosine triphosphate (ATP) levels in tissue in a subject, such as a subject diagnosed as having Friedreich's ataxia.

In some embodiments, the present application pertains to a method for reducing or inhibiting lipoxygenase-15 activity in a mammalian subject having or suspected of having Friedreich's ataxia, the method comprising: administering to the subject a therapeutically effective amount of a compound of formula E-I (as described above), or pharmaceutically acceptable salts, stereoisomers, mixtures of stereoisomers, tautomers, hydrates, and/or solvates thereof. In some embodiments, the present application pertains to a method for method for reducing or inhibiting lipoxygenase-15 activity in a mammalian subject having or suspected of having Friedreich's ataxia, the method comprising: administering to the subject a therapeutically effective amount of a compound of formula C-I (as described above), or pharmaceutically acceptable salts, stereoisomers, mixtures of stereoisomers, tautomers, hydrates, and/or solvates thereof. In some embodiments, mammalian subject to which the compound of formula E-I or C-I is administered has decreased expression of frataxin compared to a normal control subject.

In some embodiments, a compound of formula E-I or a compound of formula C-I is administered daily for 6 weeks or more. In some embodiments, a compound of formula E-I or a compound of formula C-I is administered daily for 12 weeks or more. In some embodiments, a compound of formula E-I or a compound of formula C-I is administered to a subject that has been diagnosed as having Friedreich's ataxia, wherein in some cases, the Friedreich's ataxia comprises one or more of muscle weakness, loss of coordination, vision impairment, hearing impairment, slurred speech, curvature of the spine, diabetes, and heart disorders. In some embodiments, the subject is human. In some embodiments, the compound of formula E-I or a compound of formula C-I is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

In some embodiments, the present application pertains to a method for reducing or inhibiting ferroptosis in a mammalian subject having or suspected of having Friedreich's ataxia, the method comprising: administering to the subject a therapeutically effective amount of a compound of formula E-I (as described above), or pharmaceutically acceptable salts, stereoisomers, mixtures of stereoisomers, tautomers, hydrates, and/or solvates thereof. In some embodiments, the present application pertains to a method for method for reducing or inhibiting ferroptosis in a mammalian subject having or suspected of having Friedreich's ataxia, the method comprising: administering to the subject a therapeutically effective amount of a compound of formula C-I (as described above), or pharmaceutically acceptable salts, stereoisomers, mixtures of stereoisomers, tautomers, hydrates, and/or solvates thereof. In some embodiments, mammalian subject to which the compound of formula E-I or C-I is administered has decreased expression of frataxin compared to a normal control subject.

In some embodiments, a compound of formula E-I or a compound of formula C-I is administered daily for 6 weeks or more. In some embodiments, a compound of formula E-I or a compound of formula C-I is administered daily for 12 weeks or more. In some embodiments, a compound of formula E-I or a compound of formula C-I is administered to a subject that has been diagnosed as having Friedreich's ataxia, wherein in some cases, the Friedreich's ataxia comprises one or more of muscle weakness, loss of coordination, vision impairment, hearing impairment, slurred speech, curvature of the spine, diabetes, and heart disorders. In some embodiments, the subject is human. In some embodiments, the compound of formula E-I or a compound of formula C-I is administered orally, topically, intranasally, systemically, intravenously, subcutaneously, intraperitoneally, intradermally, intraocularly, ophthalmically, intrathecally, intracerebroventricularly, iontophoretically, transmucosally, intravitreally, or intramuscularly.

EXAMPLES

Example 1: Synthesis of 2-((R,6E,10E)-16-fluoro-15-(fluoromethyl)-3-hydroxy-3,7,11-trimethylhexadeca-6,10,14-trien-1-yl)-3,5,6-trimethylcyclohexa-2,5-diene-1,4-dione (Compound A)

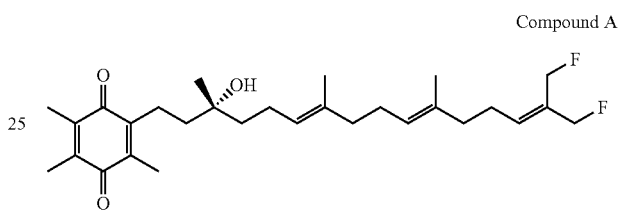

Compound A

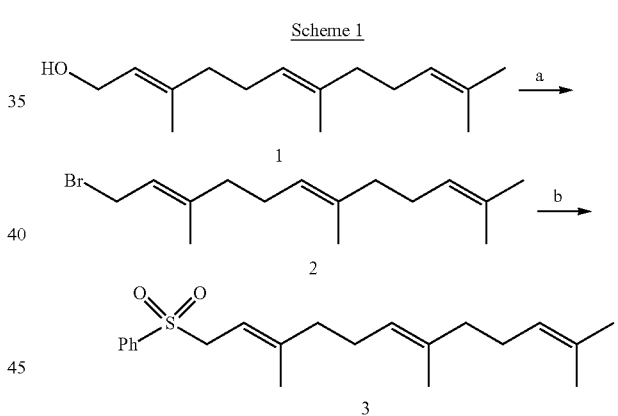

Scheme 1

Step a. Synthesis of (2E,6E)-1-bromo-3,7,11-trimethyldodeca-2,6,10-triene (2)

To a cooled (0° C.) solution of (2E,6E)-3,7,11-trimethyldodeca-2,6,10-trien-1-ol (1, 2 g, 8.99 mmol) in dry tetrahydrofuran (THF, 30 mL) dropwise was added phosphorus tribromide ($PBr_3$, 1.02 mL, 10.8 mmol) and the reaction mixture was stirred at 0° C. for 1 hour (hr.). The reaction mixture was poured on ice (50 g) and extracted with diethyl ether ($Et_2O$, 3×80 mL). The combined organic phases were dried over anhydrous (anh.) $Na_2SO_4$ and concentrated under reduced pressure to give 2 (2.5 g) in 98% yield.

Step b. Synthesis of (((2E,6E)-3,7,11-trimethyldodeca-2,6,10-trien-1-yl)sulfonyl)benzene (3)

To a cooled (0° C.) solution of 2 (2.5 g, 8.81 mmol) in dry N,N-dimethylformamide (DMF, 30 mL) was added phenylsulfinic acid sodium salt (1.89 g, 11.5 mmol) in one portion and the reaction mixture was stirred at room temperature (r.t.) overnight. The reaction mixture was quenched by addition of saturated aqueous (sat. aq.) $NH_4C_1$ (80 mL) and ethyl acetate (EtOAc, 500 mL) and stirred at r.t. for 15 minutes (min.). The aqueous phase was removed and the organic phase was washed with saturated NaCl (brine, 4×80 mL), dried over anh. $Na_2SO_4$ and concentrated under reduced pressure. The crude product was purified by silica gel flash column chromatography using a mixture of petroleum ether and EtOAc (1:0→10:1) as an eluent to give 3 (1.36 g) in 45% yield.

$^1$H-NMR ($CDCl_3$, 400 MHz): δ=7.90-7.83 (m, 2H), 7.68-7.48 (m, 3H), 5.24-5.00 (m, 3H), 3.84-3.77 (m, 2H), 2.11-1.93 (m, 8H), 1.62-1.53 (m, 9H), 1.32-1.29 ppm (m, 3H).

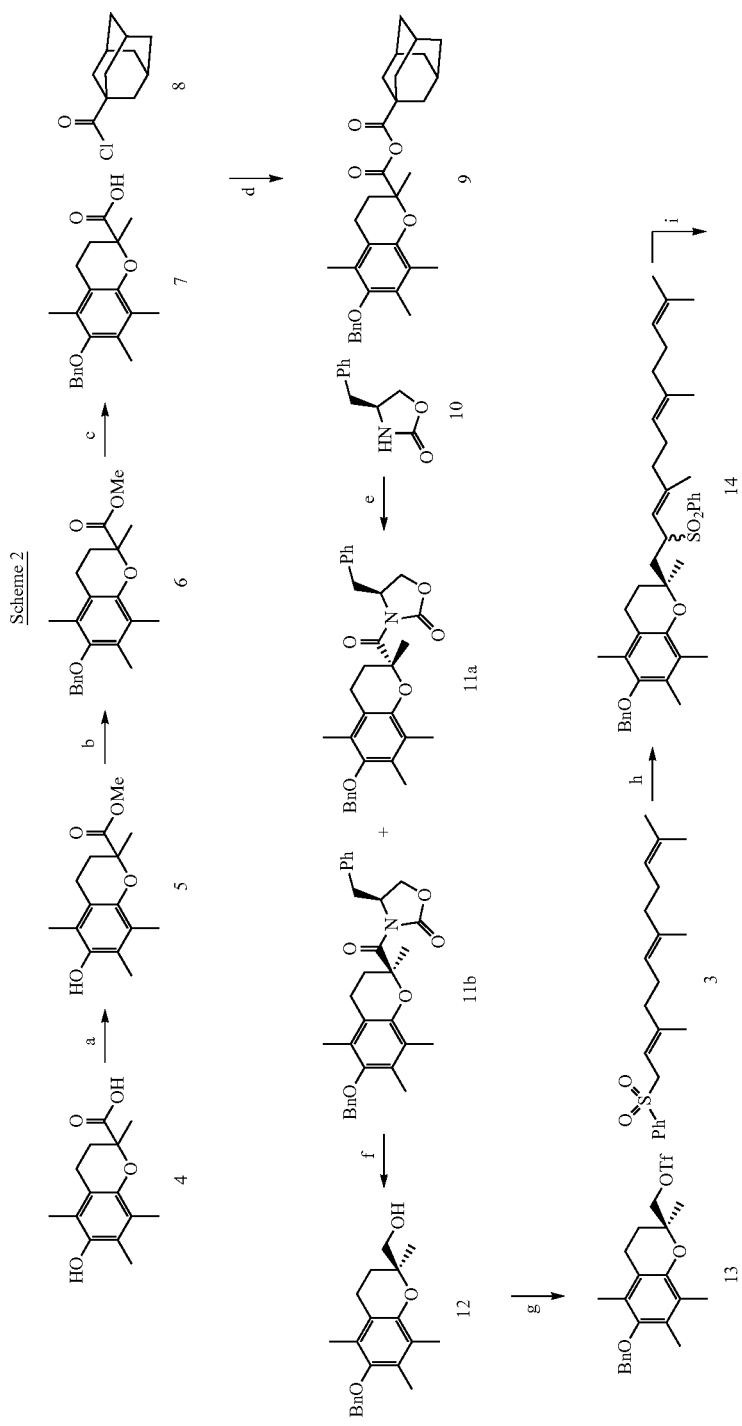

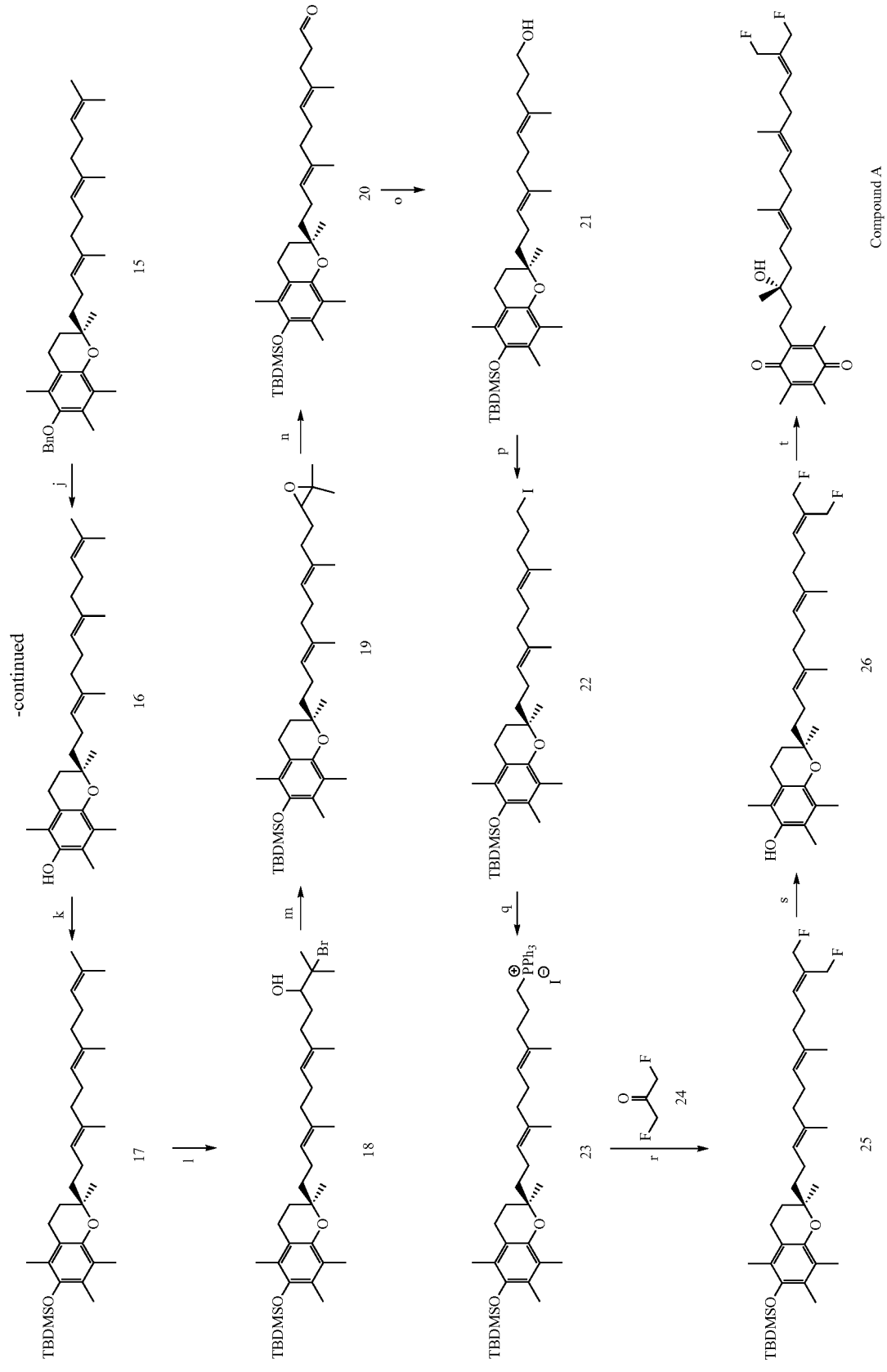

Step a. Synthesis of Methyl 6-hydroxy-2,5,7,8-tetramethylchromane-2-carboxylate (5)

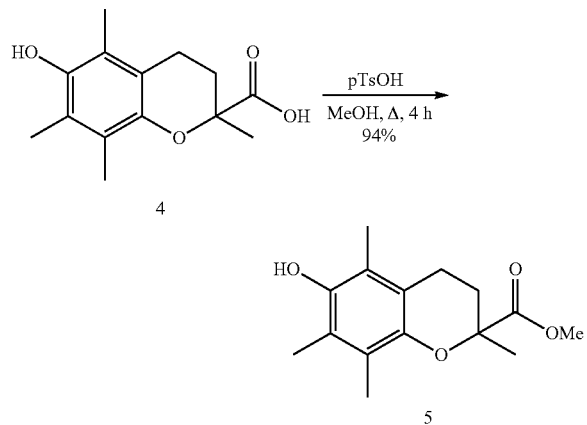

To a mixture of 4 (10 g, 40 mmol) and p-toluenesulfonic acid (3.8 g, 20 mmol) was added dry methanol (80 mL) and the reaction mixture was stirred under reflux for 4 hr. After cooling to r.t., methanol (MeOH) was removed under reduced pressure. Then, EtOAc (600 mL) and sat. aq. Na$_2$CO$_3$ (200 mL) were added and the resulting mixture was stirred at r.t. for 15 min. The aqueous phase was separated and the organic phase was washed with sat. aq. Na$_2$CO$_3$ (3×100 mL) and brine (100 mL) and dried over anh. Na$_2$SO$_4$. After evaporation of volatile matters under reduced pressure, 5 (9.9 g) was obtained in 94% yield.

$^1$H-NMR (DMSO-d$_6$, 400 MHz): δ=7.45 (br s, 1H), 3.59 (s, 3H), 2.62-2.46 (m, 1H), 2.42-2.23 (m, 2H), 2.06 (s, 3H), 2.04 (s, 3H), 1.97 (s, 3H), 1.86-1.71 (m, 1H), 1.51 ppm (s, 3H).

Step b. Synthesis of Methyl 6-(benzyloxy)-2,5,7,8-tetramethylchromane-2-carboxylate (6)

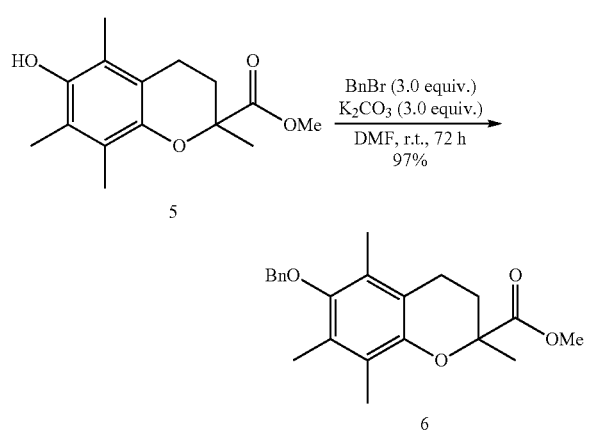

To a suspension of 5 (5.0 g, 18.9 mmol) and K$_2$CO$_3$ (7.8 g, 56.7 mmol) in dry DMF (30 mL) was added benzyl bromide (6.7 mL, 56.7 mmol) and the reaction mixture was stirred at r.t. for 72 hr. The volatile matters were removed under reduced pressure and the residue was quenched by the addition of EtOAc (600 mL), water (100 mL), and brine (100 mL) and stirred at r.t. for 15 min. After separation of the aqueous phase, the organic phase was washed with brine (3×150 mL), dried over anh. Na$_2$SO$_4$, and concentrated under reduced pressure. The crude product was purified by silica gel flash column chromatography using a mixture of petroleum ether and EtOAc (20:1) as an eluent to give 6 (6.5 g) in 97% yield.

$^1$H-NMR (CDCl$_3$, 400 MHz): δ=7.53-7.29 (m, 5H), 4.69 (s, 2H), 3.69 (s, 3H), 2.70-2.38 (m, 3H), 2.23 (s, 3H), 2.18 (s, 3H), 2.13 (s, 3H), 1.94-1.81 (m, 1H), 1.62 ppm (s, 3H).

Step c. Synthesis of 6-(Benzyloxy)-2,5,7,8-tetramethylchromane-2-carboxylic acid (7)

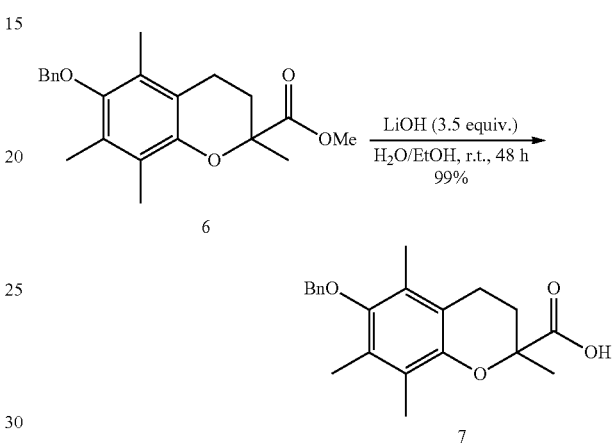

To a suspension of 6 (3.6 g, 10.2 mmol) in H$_2$O/EtOH (70 mL; 1:2.5) was added LiOH (1.50 g, 35.7 mmol) and the resulting mixture was stirred at r.t. for 48 hr. After removal of ethanol under reduced pressure, the residual aqueous solution was diluted with water (10 mL) and acidified to pH 2. The resulting white precipitate was filtered, washed with water (3×15 mL), and dried under vacuum to give 7 (3.44 g) in 99% yield.

$^1$H-NMR (DMSO-d$_6$, 400 MHz): δ=7.52-7.29 (m, 5H), 4.62 (s, 2H), 2.66-2.24 (m, 3H), 2.14 (s, 3H), 2.09-2.03 (m, 6H), 1.81-1.68 (m, 1H), 1.51 ppm (s, 3H).

Steps d, e. Synthesis of (S)-4-benzyl-3-((S)-6-(benzyloxy)-2,5,7,8-tetramethylchromane-2-carbonyl)oxazolidin-2-one (mixture of 11a and 11b)

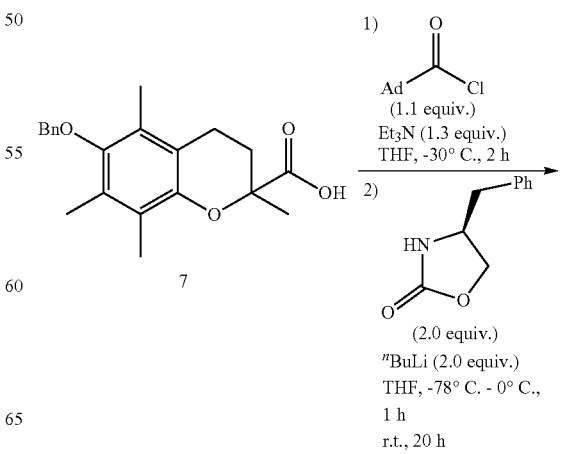

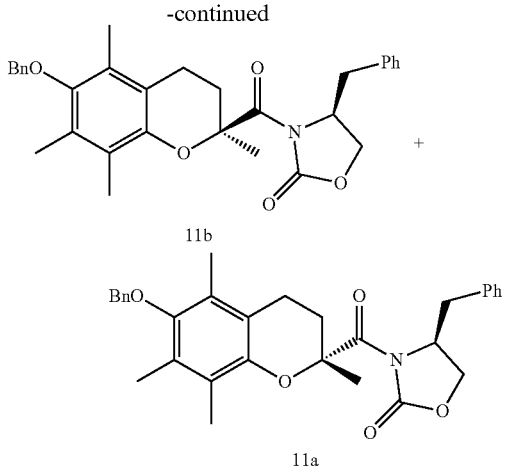

To a cooled (−30° C.) solution of 7 (6.62 g, 19.5 mmol) in dry THF (120 mL) under argon atmosphere was added solution of 1-adamantanecarbonyl chloride (4.25 g, 21.4 mmol) in dry THF (20 mL) and Et₃N (3.5 mL, 25.4 mmol) and the resulting mixture was stirred at the same temperature for 2 hr. Then, reaction mixture was cooled to −78° C. To a cooled (−78° C.) solution of (S)-4-benzyl-2-oxazolidinone (6.91 g, 39 mmol) in dry THF (100 mL), dropwise was added n-butyl lithium ("BuLi, 2.3 M in hexanes, 17 mL, 39 mmol) and the resulting mixture was transferred by cannula to the activated acid solution over 10 min. Then, the reaction mixture was placed in ice bath and stirred for 1 h. After removal of cooling bath, the reaction mixture was stirred at r.t. for 20 hr. The reaction mixture was quenched by the addition of EtOAc (500 mL) and water (100 mL) and the resulting mixture was stirred at r.t. for 15 min. After separation of the aqueous phase, the organic phase was washed with sat. aq. Na₂CO₃ (3×100 mL) and brine (100 mL), dried over anh. Na₂SO₄, and concentrated under reduced pressure. The obtained crude mixture of diastereomers was separated by silica gel flash column chromatography using a mixture of petroleum ether and EtOAc as an eluent. The less polar diastereomer 11a came out of the column by PE/EtOAc (40:3), but the required more polar 11b by PE/EtOAc (10:1). Thus, 11b (2.9 g) was obtained in 60% yield and the less polar 11a (3.4 g) in 70% yield.

¹H-NMR of 11b: (CDCl₃, 400 MHz): δ=7.50-7.17 (m, 8H), 7.09-7.04 (m, 2H), 4.72-4.60 (m, 3H), 4.16-4.08 (m, 1H), 3.95-3.89 (m, 1H), 3.12-3.04 (m, 1H), 2.91-2.82 (m, 1H), 2.69-2.49 (m, 2H), 2.26 (s, 3H), 2.20 (s, 3H), 2.19-2.07 (m, 4H), 2.01-1.91 (m, 1H), 1.87 ppm (s, 3H).

Step f. Synthesis of (S)-(6-(benzyloxy)-2,5,7,8-tetramethylchroman-2-yl)methanol (12)

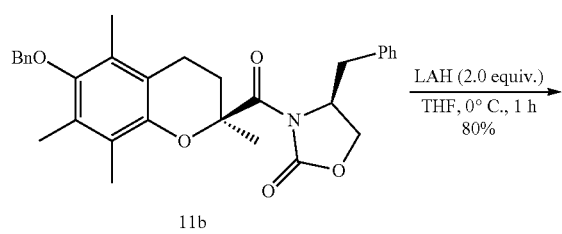

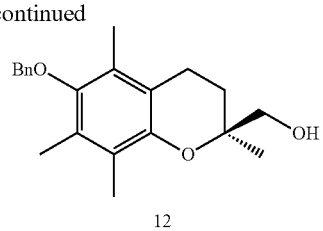

To a cooled (0° C.) solution of 11b (14.4 g, 28.8 mmol) in dry THF (150 mL) dropwise was added lithium aluminum hydride solution in THF (1 M, 58 mL, 57.6 mmol) and the reaction mixture was stirred at 0° C. for 1 hr. Under continuous cooling, ethanol was added dropwise until excess of lithium aluminum hydride was quenched. Then, 1 M aqueous (aq.) NaOH (230 mL) was added dropwise and stirred at r.t. for 15 min. After re-cooling to 0° C., 1M aq. Hydrochloric acid (HCl) was added until the resulting mixture reached about pH 4. Then, dichloromethane (DCM, 500 mL) was added and the resulting mixture was stirred at r.t. for 15 min. After separation of the organic phase, the aqueous phase was extracted with DCM (2×150 mL). The combined organic phases were washed with brine (150 mL), dried over anh. Na₂SO₄ and concentrated under reduced pressure. The crude product was purified by silica gel flash column chromatography using a mixture of petroleum ether and EtOAc (1:0→40:7) as an eluent to give 12 (7.5 g) in 80% yield.

¹H-NMR (CDCl₃, 400 MHz): δ=7.53-7.47 (m, 2H), 7.45-7.30 (m, 3H), 4.70 (s, 2H), 3.70-3.57 (m, 2H), 2.70-2.61 (m, 2H), 2.23 (s, 3H), 2.18 (s, 3H), 2.11 (s, 3H), 2.08-1.95 (m, 1H), 1.80-1.69 (m, 1H), 1.25-1.23 ppm (m, 3H).

Step g. Synthesis of (S)-(6-(benzyloxy)-2,5,7,8-tetramethylchroman-2-yl)methyl trifluoromethanesulfonate (13)

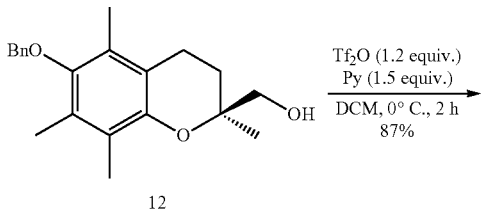

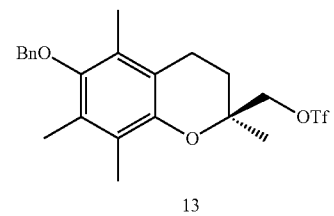

To a solution of 12 (7.5 g, 23.0 mmol) in dry DCM (100 mL) was added pyridine (2.8 ml, 34.5 mmol). After cooling to 0° C., trifluoromethanesulfonic anhydride (4.6 mL, 27.6 mmol) was added dropwise and the reaction mixture was stirred at 0° C. for 2 hr. The reaction mixture was quenched by the addition of ice (30 g) and allowed to warm to r.t. Then, EtOAc (600 mL) and water (150 mL) were added and the resulting mixture was stirred at r.t. for 15 min. The aqueous phase was separated and the organic phase was washed with brine (2×150 mL) and dried over anh. Na₂SO₄. After removal of volatile matters, 13 (9.15 g) was obtained in 87% yield.

¹H-NMR (CDCl₃, 400 MHz): δ=7.55-7.30 (m, 5H), 4.70 (s, 2H), 4.53-4.40 (m, 2H), 2.72-2.61 (m, 2H), 2.23 (s, 3H), 2.18 (s, 3H), 2.10 (s, 3H), 2.04-1.93 (m, 1H), 1.92-1.80 (m, 1H), 1.38 ppm (s, 3H).

Step h. Synthesis of (2S)-6-(Benzyloxy)-2,5,7,8-tetramethyl-2-((3E,7E)-4,8,12-trimethyl-2-(phenylsulfonyl)trideca-3,7,11-trien-1-yl)chromane (14)

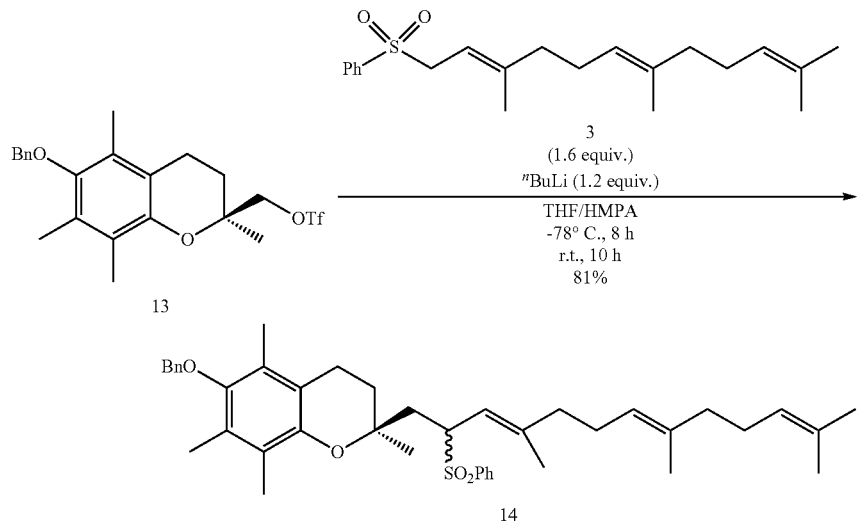

To a solution of 3 (5.30 g, 15.3 mmol, prepared as described in Scheme 1 and the accompanying description) in dry THF (50 mL) under argon was added hexamethylphosphoramide (12.7 mmol) and the resulting mixture was cooled to −78° C. Then, $^n$BuLi (2.3 M in hexanes, 5.0 mL, 11.5 mmol) was added dropwise and the reaction mixture was stirred at the same temperature for 30 min. After dropwise addition of 13 (4.38 g, 9.56 mmol) solution in dry THF (50 mL), the reaction mixture was stirred at −78° C. for 8 hr. and stirring was continued at r.t. for 20 hr. The reaction mixture was diluted with Et$_2$O (500 mL), washed with brine (2×100 mL), dried over anh. Na$_2$SO$_4$ and concentrated under reduced pressure. The crude product was purified by silica gel flash column chromatography using a mixture of petroleum ether and EtOAc (1:0→20:3) as an eluent and repurified by reversed phase flash chromatography (Acetonitrile (MeCN)/H$_2$O; 80-95%) to give 14 (5.1 g) as a mixture of diastereomers in 81% yield.

$^1$H-NMR (CDCl$_3$, 400 MHz): δ=7.89-7.71 (m, 4H), 7.67-7.28 (m, 16H), 5.23-4.96 (m, 6H), 4.68 (s, 2H), 4.20-3.99 (m, 2H), 2.64-2.45 (m, 4H), 2.23-1.45 (m, 56H), 1.34-1.09 ppm (m, 16H).

Step i. Synthesis of (R)-6-(Benzyloxy)-2,5,7,8-tetramethyl-2-((3E,7E)-4,8,12-trimethyltrideca-3,7,11-trien-1-yl)chromane (15)

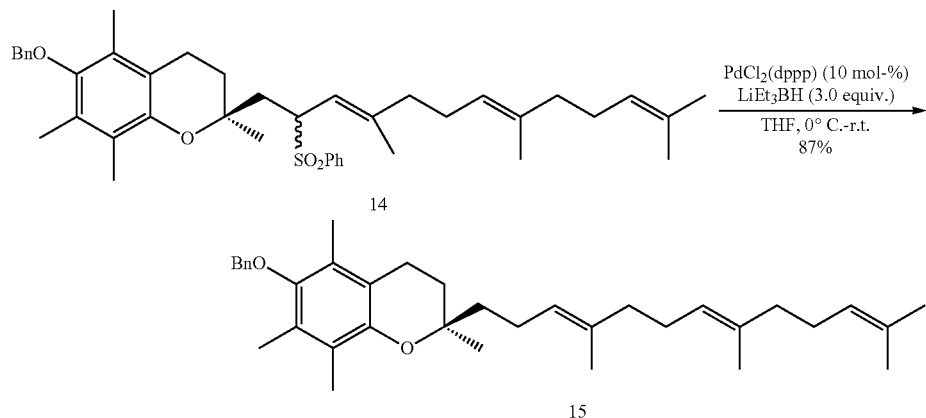

To a mixture of 14 (5.1 g, 7.79 mmol) and bis(diphenylphosphino)ferrocene]palladium(II) dichloride (PdCl$_2$dppp, 459 mg, 0.779 mmol) under argon was added dry THF (250 mL) and the resulting suspension was cooled to 0° C. Then, lithium triethylborohydride (LiEt$_3$BH, 1.7 M in THF, 13.8 mL, 23.4 mmol) was added dropwise and the reaction mixture was stirred at 0° C. for 5 hr. and overnight at r.t. The reaction mixture was diluted with Et$_2$O (500 mL) and successively washed with 1 M aq. NaCN (100 mL), water (100 mL), and brine (100 mL). After drying over anh. Na$_2$SO$_4$, the volatile matters were removed under reduced pressure and the crude product was purified by silica gel flash column chromatography using a mixture of petroleum ether and EtOAc (1:0→50:1) as an eluent to give 15 (3.5 g) in 87% yield.

¹H-NMR (CDCl₃, 400 MHz): δ=7.53-7.47 (m, 2H), 7.43-7.30 (m, 3H), 5.18-5.06 (m, 3H), 4.70 (s, 2H), 2.64-2.57 (m, 2H), 2.22 (s, 3H), 2.19-2.02 (m, 12H), 2.02-1.92 (m, 4H), 1.89-1.73 (m, 2H), 1.70-1.52 (m, 14H), 1.27 ppm (s, 3H).

Step i. Synthesis of (R)-2,5,7,8-tetramethyl-2-((3E, 7E)-4,8,12-trimethyltrideca-3,7,11-trien-1-yl)chroman-6-ol (16)

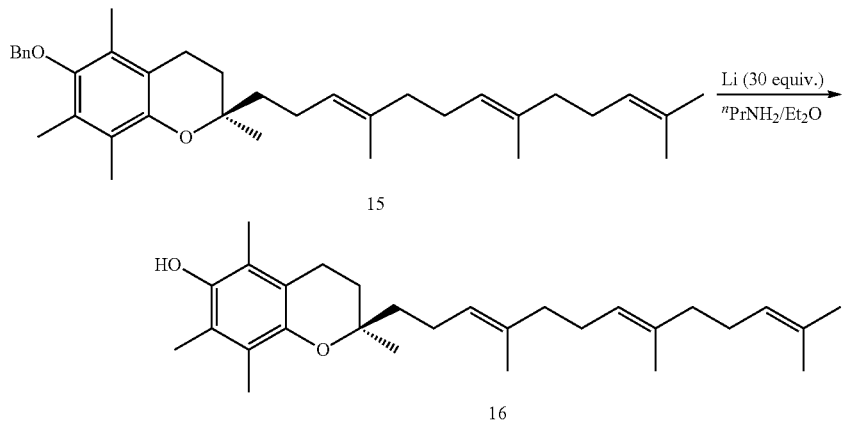

To a cooled (0° C.) suspension of lithium (1.21 g, 175 mmol) in n-propylamine (100 mL) and diethyl ether (60 mL) under argon was added a solution of 15 (3.0 g, 5.83 mmol) in Et₂O (40 mL) and the reaction mixture was stirred at r.t. for 3 hr. After re-cooling to 0° C., the reaction mixture was carefully quenched by the addition of sat. aq. NH₄C₁ (50 mL) and methanol (50 mL). The organic solvents were removed under reduced pressure at r.t. and the residue was diluted with water (50 mL) and extracted with Et₂O (3×200 mL). The combined organic phases were washed with brine (50 mL), dried over anh. Na₂SO₄ and concentrated under reduced pressure. The crude product was purified by silica gel flash column chromatography using a mixture of petroleum ether and EtOAc (1:0→20:1) as an eluent to give 16 (2.48 g) in quantitative yield.

¹H-NMR (CDCl₃, 400 MHz): δ=5.17-5.05 (m, 3H), 4.16 (br s, 1H), 2.66-2.56 (m, 2H), 2.18-1.93 (m, 19H), 1.87-1.72 (m, 2H), 1.70-1.49 (m, 14H), 1.25 ppm (s, 3H).

Step k. Synthesis of tert-Butyldimethyl(((R)-2,5,7,8-tetramethyl-2-((3E,7E)-4,8,12-trimethyltrideca-3,7,11-trien-1-yl)chroman-6-yl)oxy)silane (17)

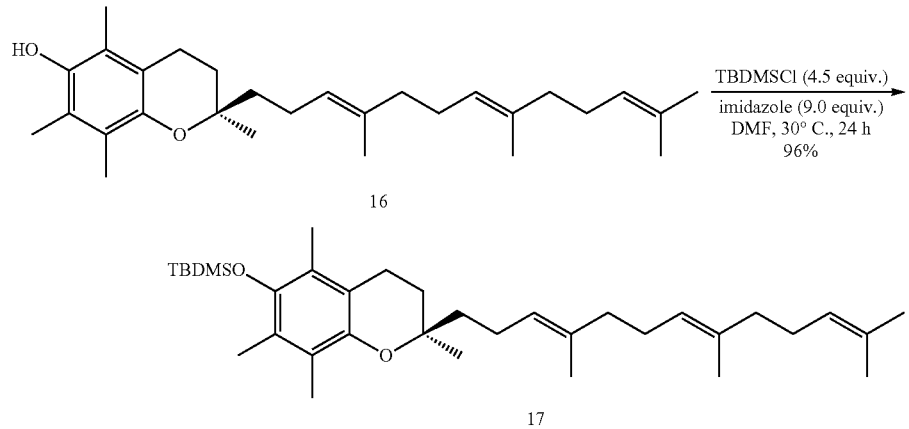

A solution of tert-butyldimethylsilyl chloride (TBDMSCl, 3.95 g g, 26.2 mmol) in dry DMF (10.0 mL) was added to a cooled (0° C.) solution of 16 (2.48 g, 5.83 mmol) and imidazole (3.57 g, 52.5 mmol) in dry DMF (10 mL) and the reaction mixture was stirred at r.t. for 20 hr. Then, the reaction mixture was diluted with EtOAc (600 mL) and water (100 mL) and stirred at r.t. for 15 min. The aqueous phase was separated and the organic phase was washed with water (3×100 mL) and brine (100 mL), dried over anh. Na$_2$SO$_4$, and concentrated under reduced pressure. The crude product was purified by silica gel column flash chromatography using a mixture of petroleum ether and EtOAc as eluent (1:0→50:1) to give 17 (3.00 g) in 96% yield as colorless oil.

$^1$H-NMR (400 MHz, CDCl$_3$): δ=5.17-5.06 (m, 3H), 2.60-2.52 (m, 2H), 2.18-2.02 (m, 15H), 2.01-1.93 (m, 4H), 1.87-1.73 (m, 2H), 1.70-1.48 (m, 14H), 1.25 (s, 3H), 1.04 (s, 9H), 0.11 ppm (s, 6H).

Step 1. Synthesis of (6E,10E)-2-bromo-13-((R)-6-((tert-butyldimethylsilyl)-oxy)-2,5,7,8-tetramethyl chroman-2-yl)-2,6,10-trimethyltrideca-6,10-dien-3-ol (18)

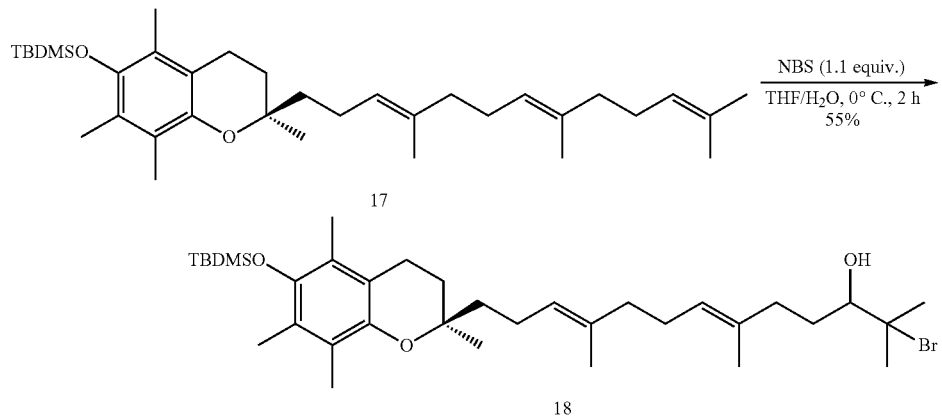

To a solution of 17 (1.2 g, 2.23 mmol) in THF (30 mL) and H$_2$O (12 mL) at 0° C., dropwise was added solution of N-bromosuccinimide (436 mg, 2.45 mmol) in THF (10 mL). After the reaction mixture was stirred for 2 hr. at 0° C., the reaction mixture was quenched by the addition of Et$_2$O (300 mL) and water (100 mL) and the resulting mixture was stirred at r.t. for 15 min. The organic phase was separated and the aqueous phase was extracted with Et$_2$O (2×100 mL). The combined organic phases were washed with brine (80 mL) and dried over anh. Na$_2$SO$_4$. After evaporation of the solvent under reduced pressure, crude product was purified by silica gel column flash chromatography using a mixture of petroleum ether and EtOAc as eluent (1:0→100:3) to give 18 (0.78 g) in 55% yield as colorless oil.

$^1$H-NMR (400 MHz, CDCl$_3$): δ=5.22-5.10 (m, 2H), 4.00-3.94 (m, 1H), 2.60-2.52 (m, 2H), 2.36-2.25 (m, 1H), 2.18-1.91 (m, 18H), 1.87-1.72 (m, 3H), 1.69-1.47 (m, 9H), 1.34 (s, 3H), 1.32 (s, 3H), 1.25 (s, 3H), 1.04 (s, 9H), 0.11 ppm (s, 6H).

Step m. Synthesis of tert-butyl(((2R)-2-((3E,7E)-10-(3,3-dimethyloxiran-2-yl)-4,8-dimethyldeca-3,7-dien-1-yl)-2,5,7,8-tetramethylchroman-6-yl)oxy)dimethylsilane (19)

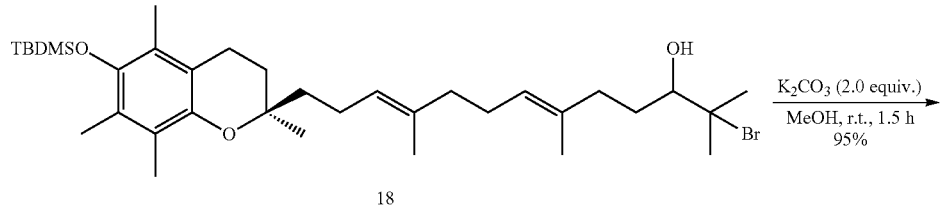

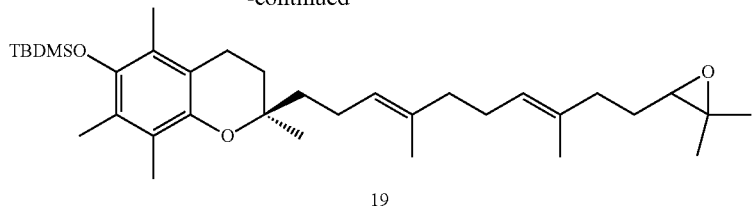

19

To a solution of 18 (2.1 g, 3.30 mmol) in MeOH (30 mL) was added $K_2CO_3$ (0.912 g, 6.60 mmol) and the resulting mixture was stirred at r.t. for 1.5 hr. Then, the reaction mixture was quenched with water (100 mL), and the resulting aqueous phase was extracted with $Et_2O$ (3×150 mL). The combined organic phases were washed with brine (80 mL), dried over anh. $Na_2SO_4$, and concentrated under reduced pressure to give crude 19 (1.74 g) in 95% yield, which was used in the next step without further purification.

$^1$H-NMR (400 MHz, $CDCl_3$): δ=5.18-5.09 (m, 2H), 2.73-2.67 (m, 1H), 2.60-2.52 (m, 2H), 2.18-2.02 (m, 15H), 2.01-1.93 (m, 2H), 1.87-1.72 (m, 2H), 1.70-1.47 (m, 10H), 1.30 (s, 3H), 1.25 (s, 3H), 1.24 (s, 3H), 1.04 (s, 9H), 0.11 ppm (s, 6H).

Step n. Synthesis of (4E,8E)-11-((R)-6-((tert-butyldimethylsilyl)oxy)-2,5,7,8-tetramethylchroman-2-yl)-4,8-dimethylundeca-4,8-dienal (20)

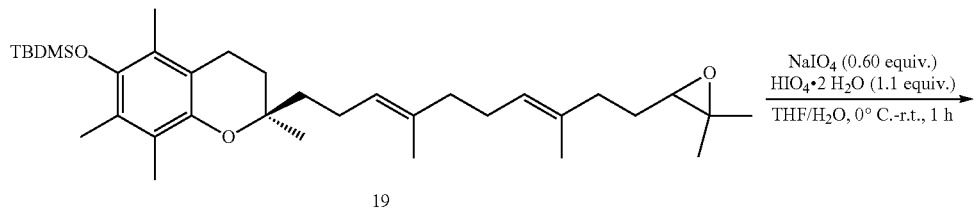

19

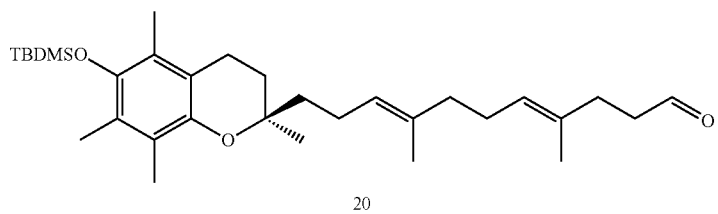

20

A stirred mixture of 19 (1.74 g, 3.14 mmol), THF (20 mL), and water (4.0 mL) at 0° C. was sequentially treated with sodium periodate (402 mg, 1.88 mmol) and periodic acid (786 mg, 3.45 mmol). The resulting mixture was stirred at 0° C. for 10 min. and, then, warmed to room temperature. After 1 hr., the reaction mixture was quenched by the addition of saturated aqueous sodium bicarbonate solution (100 mL) and the resulting mixture was stirred at r.t. for 5 min. The biphasic layers were separated and the aqueous layer was extracted with $Et_2O$ (3×200 mL). The combined organic layers were washed with brine (80 mL), dried over anh. $Na_2SO_4$, filtered and concentrated under reduced pressure. The crude 20 (1.61 g) was used in the next step without further purification.

$^1$H-NMR (400 MHz, $CDCl_3$): δ=9.73 (t, $^3J_{(H,H)}$=1.9 Hz, 1H), 5.16-5.08 (m, 2H), 2.60-2.45 (m, 4H), 2.34-2.27 (m, 2H), 2.16-2.00 (m, 13H), 1.99-1.92 (m, 2H), 1.87-1.73 (m, 2H), 1.68-1.48 (m, 8H), 1.25 (s, 3H), 1.04 (s, 9H), 0.11 ppm (s, 6H).

Step o. Synthesis of (4E,8E)-11-((R)-6-((tert-butyldimethylsilyl)oxy)-2,5,7,8-tetramethylchroman-2-yl)-4,8-dimethylundeca-4,8-dien-1-ol (21)

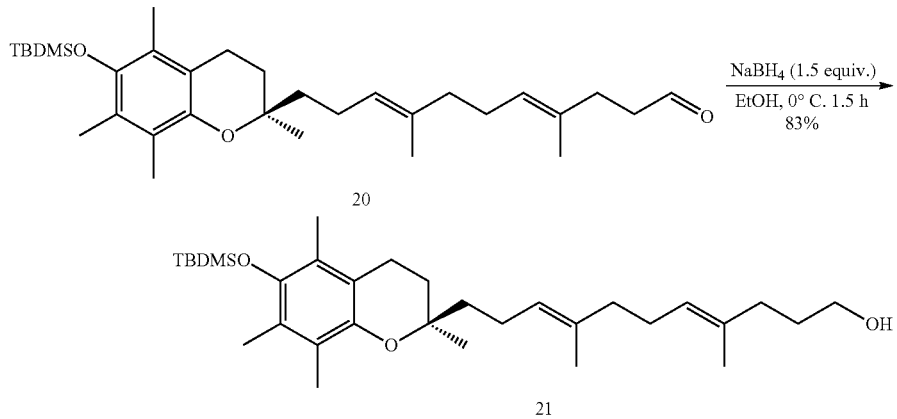

To a solution of 20 (1.61 g, 3.14 mmol) in ethanol (25 mL) at 0° C. was added NaBH$_4$ (178 mg, 4.71 mmol). After stirring for 1.5 h at r.t., the reaction mixture was quenched by addition of saturated aqueous NH$_4$C$_1$ (100 mL) and extracted with diethyl ether (3×200 mL). The combined organic phases were washed with brine, dried over anh. Na$_2$SO$_4$, and concentrated under reduced pressure. The crude product was purified by silica gel column flash chromatography (petroleum ether/ethyl acetate 1/0→20:3) to give 21 (1.34 g, 83%) as colorless oil.

$^1$H-NMR (400 MHz, CDCl$_3$): δ=5.17-5.10 (m, 2H), 3.65-3.58 (m, 2H), 2.60-2.53 (m, 2H), 2.17-1.93 (m, 17H), 1.87-1.72 (m, 2H), 1.70-1.46 (m, 10H), 1.25 (s, 3H), 1.04 (s, 9H), 0.11 ppm (s, 6H).

Step p. Synthesis of tert-butyl(((R)-2-((3E,7E)-11-iodo-4,8-dimethylundeca-3,7-dien-1-yl)-2,5,7,8-tetramethylchroman-6-yl)oxy)dimethyl-silane (22)

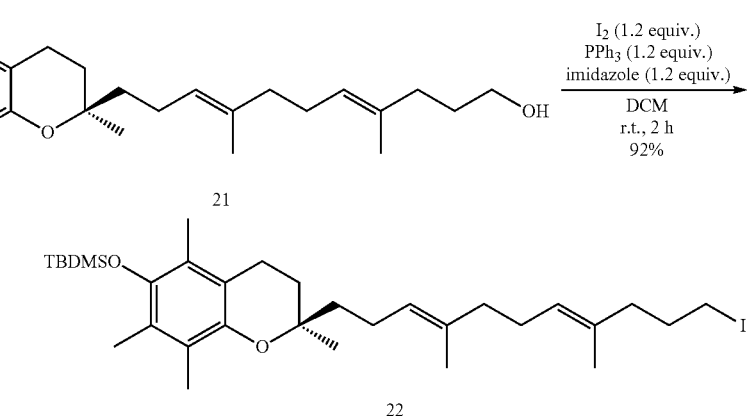

To a solution of PPh$_3$ (818 mg, 3.12 mmol) and imidazole (212 mg, 3.12 mmol) in dry DCM (30 mL) was added solution of 21 (1.34 g, 2.60 mmol) in dry DCM (20 mL). Then, iodine (792 mg, 3.12 mmol) was added and the reaction mixture was stirred at r.t. for 2 hr. The reaction mixture was diluted with petroleum ether (200 mL) and the resulting suspension was filtered through a silica gel layer. The silica gel was washed with additional portion of mixture of petroleum ether and DCM (5:1; 50 mL) and the obtained filtrate was concentrated under reduced pressure. The crude product was purified by silica gel column chromatography (hexane/ethyl acetate 1:0→50:1) to give 22 (1.49 g, 92%) as colorless oil.

$^1$H-NMR (400 MHz, CDCl$_3$): δ=5.18-5.09 (m, 2H), 3.13 (t, $^3$J$_{(H,H)}$=7.0 Hz, 2H), 2.60-2.52 (m, 2H), 2.18-1.72 (m, 21H), 1.68-1.47 (m, 8H), 1.25 (s, 3H), 1.04 (s, 9H), 0.11 ppm (s, 6H).

Step q. Synthesis of (((4E,8E)-11-((R)-6-((tert-butyldimethylsilyl)oxy)-2,5,7,8-tetramethylchroman-2-yl)-4,8-dimethylundeca-4,8-dien-1-yl)triphenylphosphonium iodide (23)

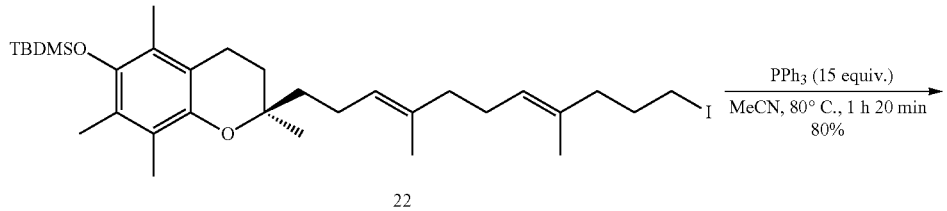

A solution of 22 (0.6 g, 0.960 mmol) and PPh₃ (3.78 g, 14.4 mmol) in dry MeCN (12 mL) was stirred at 85° C. for 1 hr. and 20 min. After cooling to r.t., the reaction mixture was concentrated under reduced pressure. The crude product was purified by silica gel flash column chromatography using a mixture of DCM and EtOAc (1:0→1:1) as an eluent to give 23 (0.68 g) in 80% yield.

$^1$H-NMR (400 MHz, CDCl₃): δ=7.88-7.63 (m, 15H), 5.17-5.04 (m, 2H), 3.74-3.63 (m, 2H), 2.59-2.50 (m, 2H), 2.34-2.26 (m, 2H), 2.12-1.97 (m, 13H), 1.95-1.87 (m, 2H), 1.84-1.69 (m, 4H), 1.65-1.41 (m, 8H), 1.22 (s, 3H), 1.04 (s, 9H), 0.11 ppm (s, 6H).

Step r. Synthesis of tert-butyl(((R)-2-((3E,7E)-13-fluoro-12-(fluoromethyl)-4,8-dimethyltrideca-3,7,11-trien-1-yl)-2,5,7,8-tetramethylchroman-6-yl)oxy)dimethylsilane (25)

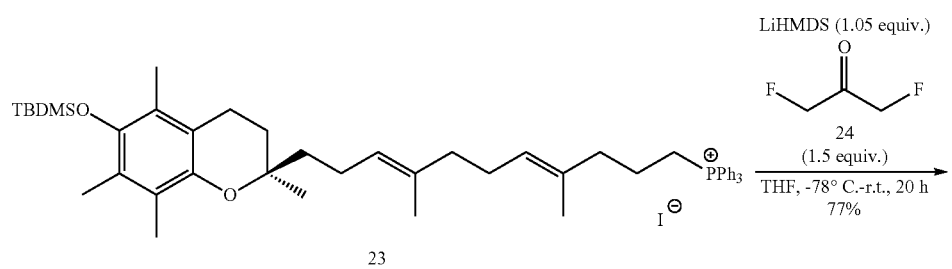

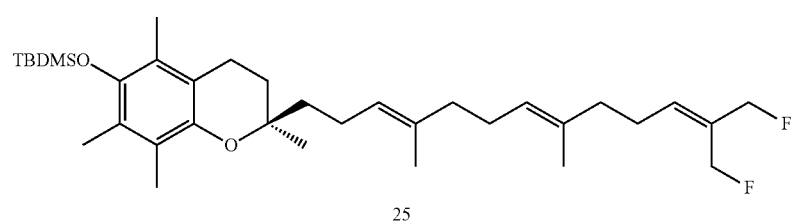

To a cooled (−78° C.) and stirred solution of 23 (0.800 g, 0.902 mmol) in dry THF (20 mL) under argon atmosphere was added lithium hexamethyldisilazide (1M solution in THF, 0.95 mL, 0.947 mmol). After stirring at the same temperature for 30 min., a solution of 1,3-difluoroacetone (24, 97 μL, 1.35 mmol) in dry THF (2.0 mL) was added dropwise. After continuous stirring at the same temperature for 1 hr., the reaction mixture was slowly (in approximately 4 hr.) warmed to r.t. and stirred overnight. The reaction mixture was diluted with Et$_2$O (150 mL) and water (50 mL) and the resulting mixture was stirred at r.t. for 5 min. Then, organic phase was separated and the aqueous phase was extracted with Et$_2$O (2×80 mL). The combined organic phases were washed with brine (80 mL), dried over anh. Na$_2$SO$_4$, and concentrated under reduced pressure. The crude product was purified by silica gel flash column chromatography (petroleum ether/EtOAc 1:0→100:1) to give 25 (0.4 g) in 77% yield.

$^1$H-NMR (400 MHz, CDCl$_3$): δ=5.88-5.80 (m, 1H), 5.18-5.07 (m, 2H), 4.99 (d, $^2$J(H,F)=48 Hz, 2H), 4.87 (d, $^2$J(H,F)=48 Hz, 2H), 2.60-2.52 (m, 2H), 2.32-2.20 (m, 2H), 2.18-1.92 (m, 17H), 1.87-1.72 (m, 2H), 1.69-1.48 (m, 8H), 1.25 (s, 3H), 1.05 (s, 9H), 0.12 ppm (s, 6H).

Step s. Synthesis of (R)-2-((3E,7E)-13-fluoro-12-(fluoromethyl)-4,8-dimethyltrideca-3,7,11-trien-1-yl)-2,5,7,8-tetramethylchroman-6-ol (26)

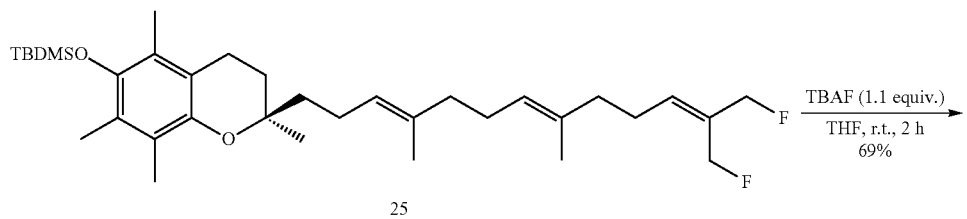

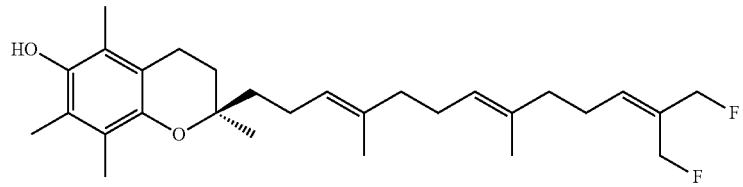

A solution of 25 (0.4 g, 0.696 mmol) in dry THF (20 mL) was cooled in ice bath while 1 M tetra-n-butylammonium fluoride (TBAF) solution in THF (0.77 mL, 0.766 mmol) was added dropwise. The reaction mixture was stirred at r.t. for 2 hr. After completion of the reaction (as determined by thin layer chromatography (TLC)), the cooled (ice bath) reaction mixture was quenched by the addition of Et$_2$O (150 mL) and water (50 mL) and the resulting mixture was stirred at r.t. for 5 min. Then, the organic phase was separated and the aqueous phase was extracted with Et$_2$O (2×80 mL). The combined organic phases were washed with brine (80 mL), dried over anh. Na$_2$SO$_4$, and concentrated under reduced pressure. The crude product was purified by silica gel flash column chromatography (petroleum ether/EtOAc 1:0→40:3) and re-purified by reversed phase flash chromatography (MeCN/H$_2$O; 85-100% of MeCN) to give 26 (220 mg) in 69% yield.

$^1$H-NMR (400 MHz, CDCl$_3$): δ=5.88-7.79 (m, 1H), 5.17-5.08 (m, 2H), 4.99 (d, $^2$J(H,F)=47.7 Hz, 2H), 4.86 (d, $^2$J(H,F)=47.6 Hz, 2H), 4.17 (br s, 1H), 2.66-2.57 (m, 2H), 2.32-2.20 (m, 2H), 2.19-1.92 (m, 17H), 1.88-1.72 (m, 2H), 1.69-1.48 (m, 8H), 1.25 ppm (s, 3H).

Step t. Synthesis of 2-((R,6E,10E)-16-fluoro-15-(fluoromethyl)-3-hydroxy-3,7,11-trimethylhexadeca-6,10,14-trien-1-yl)-3,5,6-trimethylcyclohexa-2,5-diene-1,4-dione (Compound A)

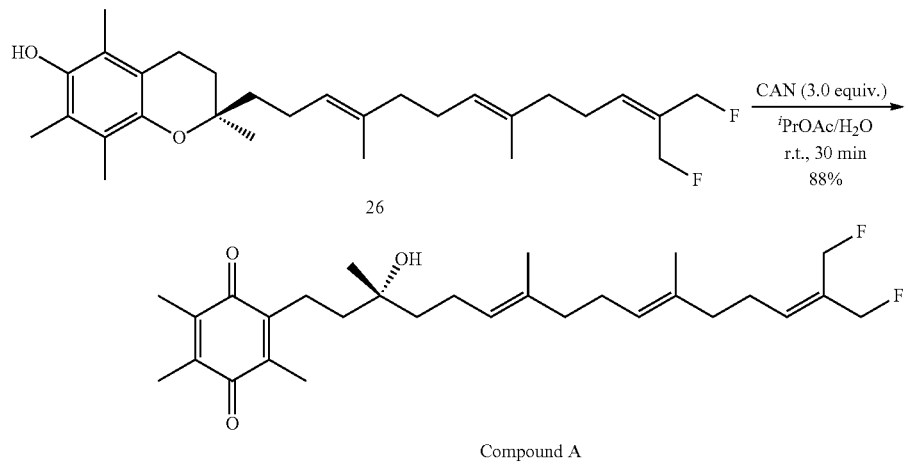

To a solution of 26 (220 mg, 0.478 mmol) in isopropyl acetate ($^i$PrOAc, 6.0 mL) at r.t. was added solution of ammonium cerium(IV) nitrate (CAN, 784 mg, 1.43 mmol) in water (1.4 mL) and the reaction mixture was stirred at r.t. for 25 min. After cooling to 0° C., the reaction mixture was quenched by brine (50 mL) and EtOAc (200 mL). The resulting mixture was stirred at r.t. for 5 min. Then, aqueous phase was separated and the organic phase was washed with brine (30 mL), dried over anh. Na$_2$SO$_4$ and concentrated under reduced pressure. The crude product was purified by silica gel flash column chromatography using a mixture of petroleum ether and EtOAc (1:0→20:3) as an eluent to give Compound A (200 mg) in 88% yield.

$^1$H-NMR (CDCl$_3$, 400 MHz): δ=5.89-5.80 (m, 1H), 5.19-5.08 (m, 2H), 4.99 (d, $^2$J(H,F)=47.6 Hz, 2H), 4.86 (d, $^2$J(H,F)=47.6 Hz, 2H), 2.60-2.49 (m, 2H), 2.33-2.21 (m, 2H), 2.15-1.94 (m, 17H), 1.64 (s, 3H), 1.60 (s, 3H), 1.58-1.45 (m, 4H), 1.25 ppm (s, 3H).

Example 2: Synthesis of 2-((R,6E,10E)-16-fluoro-3-hydroxy-3,7,11,15-tetramethylhexadeca-6,10,14-trien-1-yl)-3,5,6-trimethylcyclohexa-2,5-diene-1,4-dione (Compound B)

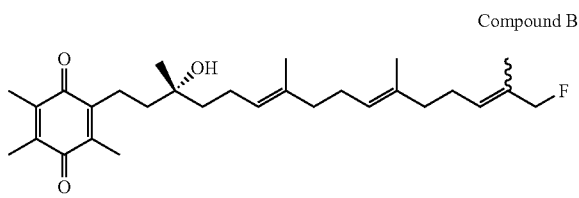

Compound B

Scheme 3

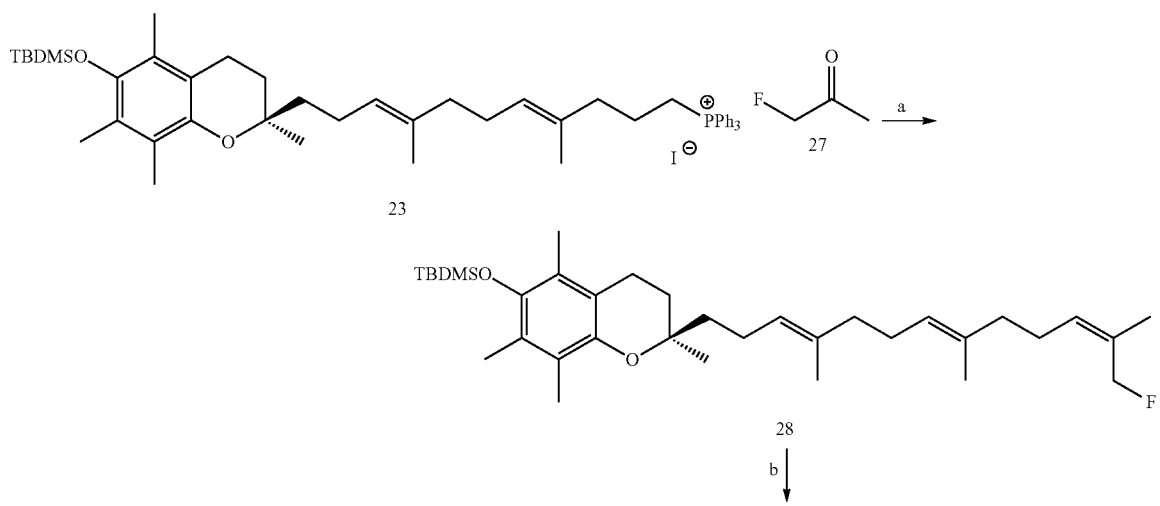

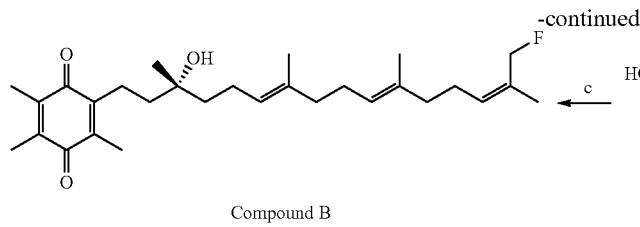

Compound B

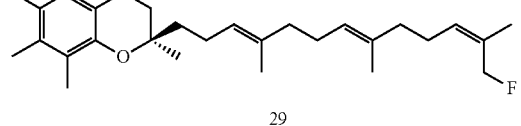

29

1 Step a. Synthesis of tert-butyl(((R)-2-((3E,7E)-13-fluoro-4,8,12-trimethyltrideca-3,7,11-trien-1-yl)-2,5,7,8-tetramethylchroman-6-yl)oxy)dimethylsilane (28)

To a cooled (−78° C.) and stirred solution of 23 (0.750 g, 0.845 mmol, made according to the procedures described above in Example 1) in dry THF (15 mL) under argon atmosphere was added lithium hexamethyldisilazide (1M solution in THF, 0.89 mL, 0.887 mmol). After stirring at the same temperature for 30 min, a solution of fluoroacetone (27, 92 µL, 1.27 mmol) in dry THF (2.0 mL) was added dropwise. After continuous stirring at the same temperature for 1 hr., the reaction mixture was slowly (in approximately 4 hr.) warmed to r.t. and stirred overnight. The reaction mixture was diluted with diethyl ether (150 mL) and water (50 mL) and the resulting mixture was stirred at r.t. for 5 min. Then, the organic phase was separated and the aqueous phase was extracted with diethyl ether (2×80 mL). The combined organic phases were washed with brine (80 mL), dried over anh. $Na_2SO_4$, and concentrated under reduced pressure. The crude product was purified by silica gel flash column chromatography (petroleum ether/EtOAc 1:0→100:1) to give 28 (0.37 g, 11Z/11E dr≈6:1, determined by $^1$H-NMR) in 79% yield as a mixture of diastereomers.

$^1$H-NMR of the major 11Z-diastereomer (400 MHz, $CDCl_3$): δ=5.43-5.36 (m, 1H), 5.18-5.06 (m, 2H), 4.87 (d, $^2$J(H,F)=47.7 Hz, 2H), 2.62-2.50 (m, 2H), 2.20-1.91 (m, 17H), 1.88-1.72 (m, 4H), 1.71-1.46 (m, 11H), 1.25 (s, 3H), 1.04 (s, 9H), 0.11 ppm (s, 6H).

Step b. Synthesis of (R)-2-((3E,7E)-13-fluoro-4,8,12-trimethyltrideca-3,7,11-trien-1-yl)-2,5,7,8-tetramethylchroman-6-ol (29)

A solution of 28 (0.37 g, 0.664 mmol) in dry THF (15 mL) was cooled in ice bath while 1 M TBAF solution in THF (0.66 mL, 0.664 mmol) was added dropwise. The reaction mixture was stirred at 0° C. for 2 hr. After completion of the reaction (as determined by TLC), the cooled (ice bath) reaction mixture was quenched by addition of $Et_2O$ (150 mL) and water (50 mL) and the resulting mixture was stirred at r.t. for 5 min. Then, the organic phase was separated and the aqueous phase was extracted with diethyl ether (2×80 mL). The combined organic phases were washed with brine (80 mL), dried over anh. $Na_2SO_4$, and concentrated under reduced pressure. The crude product was purified by silica gel flash column chromatography (petroleum ether/EtOAc 1:0→40:3) to give 29 (270 mg, dr≈ 7:1, determined by $^1$H-NMR) in 92% yield as a mixture of diastereomers.

$^1$H-NMR of the major 11Z-diastereomer (400 MHz, $CDCl_3$): δ=5.44-5.34 (m, 1H), 5.17-5.06 (m, 2H), 4.86 (d, $^2$J(H,F)=47.7 Hz, 2H), 4.18 (s, 1H), 2.67-2.55 (m, 2H), 2.23-1.91 (m, 17H), 1.88-1.72 (m, 4H), 1.70-1.49 (m, 11H), 1.25 ppm (s, 3H).

Step c. Synthesis of 2-((R,6E,10E)-16-fluoro-3-hydroxy-3,7,11,15-tetramethylhexadeca-6,10,14-trien-1-yl)-3,5,6-trimethylcyclohexa-2,5-diene-1,4-dione (Compound B)

To a solution of 29 (222 mg, 0.502 mmol) in $^i$PrOAc (5.9 mL) at r.t. was added a solution of ammonium cerium(IV) nitrate (828 mg, 1.51 mmol) in water (1.3 mL) and the reaction mixture was stirred at r.t. for 25 min. After cooling to 0° C., the reaction mixture was quenched by addition of brine (50 mL) and EtOAc (200 mL). The resulting mixture was stirred at r.t. for 5 min. Then, the aqueous phase was separated and the organic phase was washed with brine (30 mL), dried over anh. $Na_2SO_4$ and concentrated under reduced pressure. The crude product was purified by silica gel flash column chromatography using a mixture of petroleum ether and EtOAc (1:0→10:1) as an eluent to give Compound B (150 mg) in 65% yield as a mixture of diastereomers (14Z:14E dr≈8:1, determined by $^1$H-NMR).

$^1$H-NMR of the major 14Z-diastereomer ($CDCl_3$, 400 MHz): δ=5.37-5.28 (m, 1H), 5.13-4.98 (m, 2H), 4.80 (d, $^2$J(H,F)=47.7 Hz, 2H), 2.53-2.43 (m, 2H), 2.15-1.85 (m, 17H), 1.75-1.68 (m, 3H), 1.57 (s, 3H), 1.54-1.39 (m, 9H), 1.18 (s, 3H). MS (M+H): 459.3266.

Example 3: Synthesis of 2-((R,6E,10E)-15,15-difluoro-3-hydroxy-3,7,11-trimethylpentadeca-6,10,14-trien-1-yl)-3,5,6-trimethylcyclohexa-2,5-diene-1,4-dione (Compound C)

Compound C

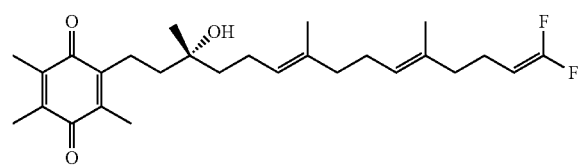

Scheme 4

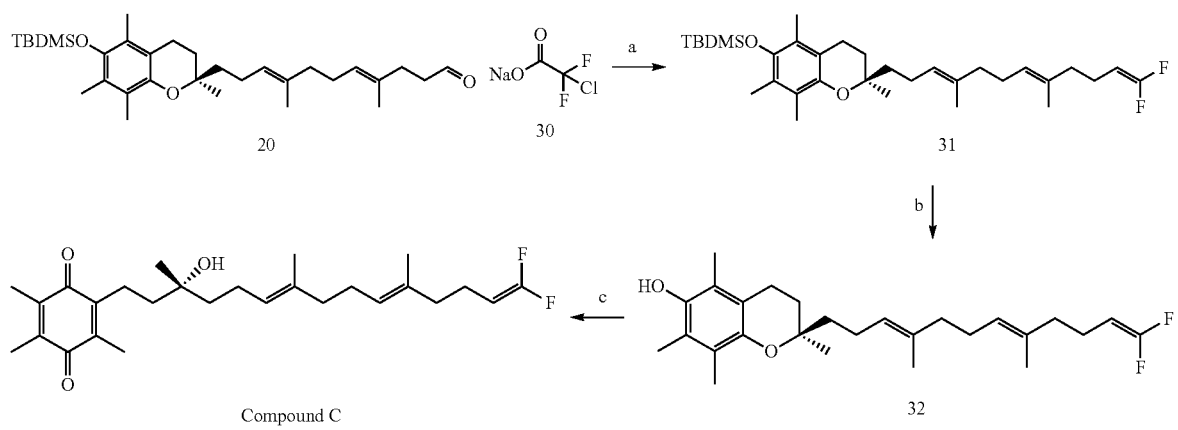

Step a. Synthesis of tert-butyl(((R)-2-((3E,7E)-12,12-difluoro-4,8-dimethyldodeca-3,7,11-trien-1-yl)-2,5,7,8-tetramethylchroman-6-yl)oxy)dimethylsilane (31)

To a mixture of 20 (1.30 g, 2.53 mmol, made according to the procedures described in Example 1), sodium 2-chloro-2,2-difluoroacetate (30, 771 mg, 5.06 mmol), and triphenylphosphine ($PPh_3$, 1.33 g, 5.06 mmol) under argon was added dry DMF (5.2 mL) and the reaction mixture was stirred at 105° C. for 2 hrs. After cooling in ice bath, water (5.0 mL) was added slowly. Then, the resulting mixture was diluted by water (60 mL) and $Et_2O$ (400 mL) and stirred at r.t. for 5 min. The aqueous phase was separated and the organic phase was washed with water (3×60 mL) and brine (60 mL). After drying over anh. $Na_2SO_4$, the volatile matters were removed under reduced pressure and the crude product was purified by silica gel column flash chromatography using a mixture of petroleum ether and EtOAc as eluent (1:0-200:3) to give 31 (0.8 g) together with approximately 1 equiv. of $PPh_3$ in 39% yield. The obtained product was used in the next step without further purification.

$^1$H-NMR (400 MHz, $CDCl_3$): δ=5.17-5.06 (m, 2H), 4.15-4.01 (m, 1H), 2.60-2.52 (m, 2H), 2.18-1.93 (m, 19H), 1.88-1.71 (m, 2H), 1.69-1.45 (m, 8H), 1.25 (s, 3H), 1.04 (s, 9H), 0.11 ppm (s, 6H).

Step b. Synthesis of (R)-2-((3E,7E)-12,12-difluoro-4,8-dimethyldodeca-3,7,11-trien-1-yl)-2,5,7,8-tetramethylchroman-6-ol (32)

A solution of 31 containing approximately 1.0 equivalents (eq.) of $PPh_3$ (0.70 g, 0.865 mmol) in dry THF (30 mL) was cooled in ice bath while 1 M TBAF solution in THF (0.86 mL, 0.865 mmol) was added dropwise. The reaction mixture was stirred at 0° C. for 2 hr. After completion of the reaction (as determined by TLC), the cooled (ice bath) reaction mixture was quenched by the addition of $Et_2O$ (150 mL) and water (50 mL) and the resulting mixture was stirred at r.t. for 5 min. Then, the organic phase was separated and the aqueous phase was extracted with diethyl ether (2×100 mL). The combined organic phases were washed with brine (80 mL), dried over anh. $Na_2SO_4$, and concentrated under reduced pressure. The crude product was purified by silica gel flash column chromatography (petroleum ether/EtOAc 1:0→20:1) to give 32 (260 mg) in 74% yield.

$^1$H-NMR (400 MHz, $CDCl_3$): δ=5.16-5.06 (m, 2H), 4.18 (s, 1H), 4.15-4.02 (m, 1H), 2.65-2.57 (m, 2H), 2.18-1.94 (m, 19H), 1.87-1.72 (m, 2H), 1.68-1.47 (m, 8H), 1.25 ppm (s, 3H).

Step c. Synthesis of 2-((R,6E,10E)-15,15-difluoro-3-hydroxy-3,7,11-trimethylpentadeca-6,10,14-trien-1-yl)-3,5,6-trimethylcyclohexa-2,5-diene-1,4-dione (Compound C)

To a solution of 32 (260 mg, 0.601 mmol) in $^i$PrOAc (7.0 mL) at r.t. was added a solution of ammonium cerium(IV) nitrate (987 mg, 1.80 mmol) in water (1.6 mL) and the reaction mixture was stirred at r.t. for 25 min. After cooling to 0° C., the reaction mixture was quenched by the addition of brine (60 mL) and EtOAc (300 mL). The resulting mixture was stirred at r.t. for 5 min. Then, the aqueous phase was separated and the organic phase was washed with brine (30 mL), dried over anh. $Na_2SO_4$ and concentrated under reduced pressure. The crude product was purified by silica gel flash column chromatography using a mixture of petroleum ether and EtOAc (1:0→10:1) as an eluent to give Compound C (150 mg) in 56% yield.

$^1$H-NMR ($CDC_3$, 400 MHz): δ=5.18-5.06 (m, 2H), 4.16-4.01 (m, 1H), 2.58-2.50 (m, 2H), 2.14-1.93 (m, 19H), 1.67-1.44 (m, 10H), 1.24 ppm (s, 3H). MS (M+H): 449.2859.

Example 4: Synthesis of 2-((R,6E,10E)-14-cyclobutylidene-3-hydroxy-3,7,11-trimethyltetradeca-6,10-dien-1-yl)-3,5,6-trimethylcyclohexa-2,5-diene-1,4-dione (Compound D)

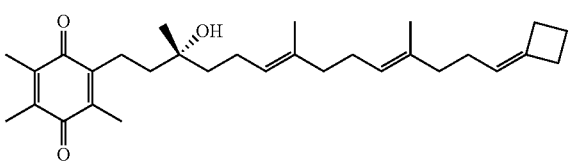

Compound D

Scheme 5

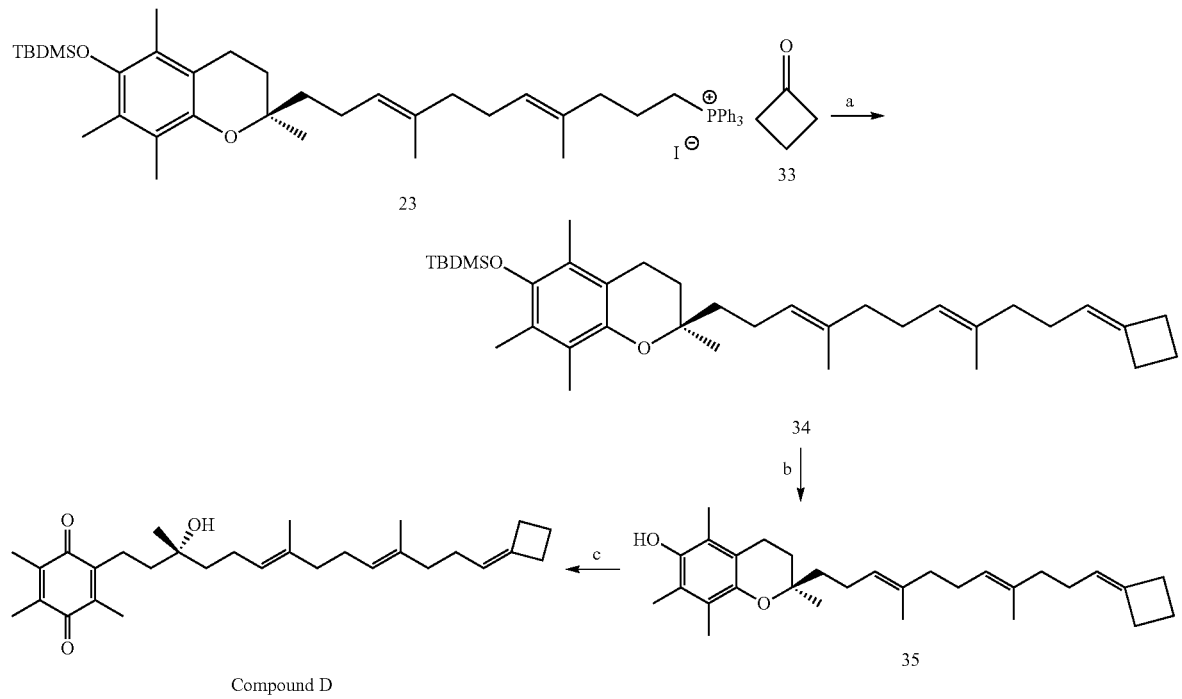

Step a. Synthesis of tert-butyl(((R)-2-((3E,7E)-11-cyclobutylidene-4,8-dimethylundeca-3,7-dien-1-yl)-2,5,7,8-tetramethylchroman-6-yl)oxy)dimethylsilane (34)

To a cooled (−78° C.) and stirred solution of 23 (0.750 g, 0.845 mmol, made according to the procedures described in Example 1) in dry THF (15 mL) under argon atmosphere was added lithium hexamethyldisilazide (1M solution in THF, 0.89 mL, 0.887 mmol). After stirring at the same temperature for 30 min, a solution of cyclobutanone (33, 93 μL, 1.27 mmol) in dry THF (2.0 mL) was added dropwise. After continuous stirring at the same temperature for hr., the reaction mixture was slowly (in approximately 4 hr.) warmed to r.t. and stirred overnight. The reaction mixture was diluted with diethyl ether (150 mL) and water (50 mL) and the resulting mixture was stirred at r.t. for 5 min. Then, the organic phase was separated and the aqueous phase was extracted with diethyl ether (2×80 mL). The combined organic phases were washed with brine (80 mL), dried over anh. $Na_2SO_4$, and concentrated under reduced pressure. The crude product was purified by silica gel flash column chromatography (petroleum ether/EtOAc 1:0→100:1) to give 34 (0.37 g) in 80% yield.

$^1$H-NMR (400 MHz, $CDCl_3$): δ=5.18-5.07 (m, 2H), 5.05-5.00 (m, 1H), 2.67-2.52 (m, 6H), 2.17-2.02 (m, 13H), 2.02-1.87 (m, 8H), 1.86-1.72 (m, 2H), 1.70-1.48 (m, 8H), 1.26 (s, 3H), 1.05 (s, 9H), 0.12 ppm (s, 6H).

Step b. Synthesis of (R)-2-((3E,7E)-11-cyclobutylidene-4,8-dimethylundeca-3,7-dien-1-yl)-2,5,7,8-tetramethylchroman-6-ol (35)

A solution of 34 (0.37 g, 0.672 mmol) in dry THF (20 mL) was cooled in ice bath while 1 M TBAF solution in THF (0.74 mL, 0.739 mmol) was added dropwise. The reaction mixture was stirred at r.t. for 2 hr. After completion of the reaction (as determined by TLC), the cooled (ice bath) reaction mixture was quenched by the addition of $Et_2O$ (150 mL) and water (50 mL) and the resulting mixture was stirred at r.t. for 5 min. Then, organic phase was separated and the aqueous phase was extracted with diethyl ether (2×80 mL). The combined organic phases were washed with brine (80 mL), dried over anh. $Na_2SO_4$, and concentrated under reduced pressure. The crude product was purified by silica gel flash column chromatography (petroleum ether/EtOAc 1:0→30:1) and re-purified by reversed phase flash chromatography (100% of MeCN) to give 35 (206 mg) in 70% yield.

$^1$H-NMR (400 MHz, $CDCl_3$): δ=5.17-5.07 (m, 2H), 5.05-4.99 (m, 1H), 4.18 (br s, 1H), 2.67-2.58 (m, 6H), 2.20-2.03 (m, 13H), 2.02-1.88 (m, 8H), 1.88-1.73 (m, 2H), 1.70-1.50 (m, 8H), 1.26 (s, 3H).

Step c. Synthesis of 2-((R,6E,10E)-14-cyclohexylidene-3-hydroxy-3,7,11-trimethyltetradeca-6,10-dien-1-yl)-3,5,6-trimethylcyclohexa-2,5-diene-1,4-dione (Compound D)

To a solution of 35 (206 mg, 0.472 mmol) in $^i$PrOAc (5.5 mL) at r.t. was added a solution of ammonium cerium(IV) nitrate (778 mg, 1.42 mmol) in water (1.3 mL) and the reaction mixture was stirred at r.t. for 25 min. After cooling to 0° C., the reaction mixture was quenched by the addition of brine (50 mL) and EtOAc (200 mL). The resulting mixture was stirred at r.t. for 5 min. Then, aqueous phase was separated and the organic phase was washed with brine (30 mL), dried over anh. $Na_2SO_4$ and concentrated under reduced pressure. The crude product was purified by silica gel flash column chromatography using a mixture of petroleum ether and EtOAc (1:0→40:3) as an eluent and re-purified by reversed phase flash chromatography (100% of MeCN) to give Compound D (142 mg) in 66% yield.

¹H-NMR (CDCl₃, 400 MHz): δ=5.18-5.11 (m, 1H), 5.11-5.05 (m, 1H), 5.04-4.97 (m, 1H), 2.65-2.50 (m, 6H), 2.14-1.85 (m, 21H), 1.66-1.45 (m, 10H), 1.24 ppm (s, 3H). MS (M+H): 453.3357.

Example 5: Synthesis of 2-((R,6E,10E)-3-hydroxy-3,7,11-trimethyl-14-(oxetan-3-ylidene)tetradeca-6,10-dien-1-yl)-3,5,6-trimethylcyclohexa-2,5-diene-1,4-dione (Compound E)

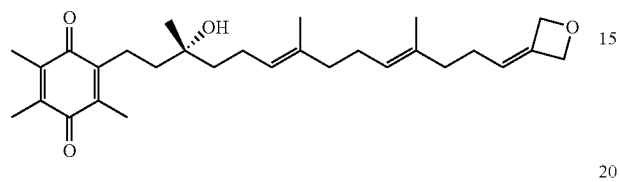

Compound E

Scheme 6

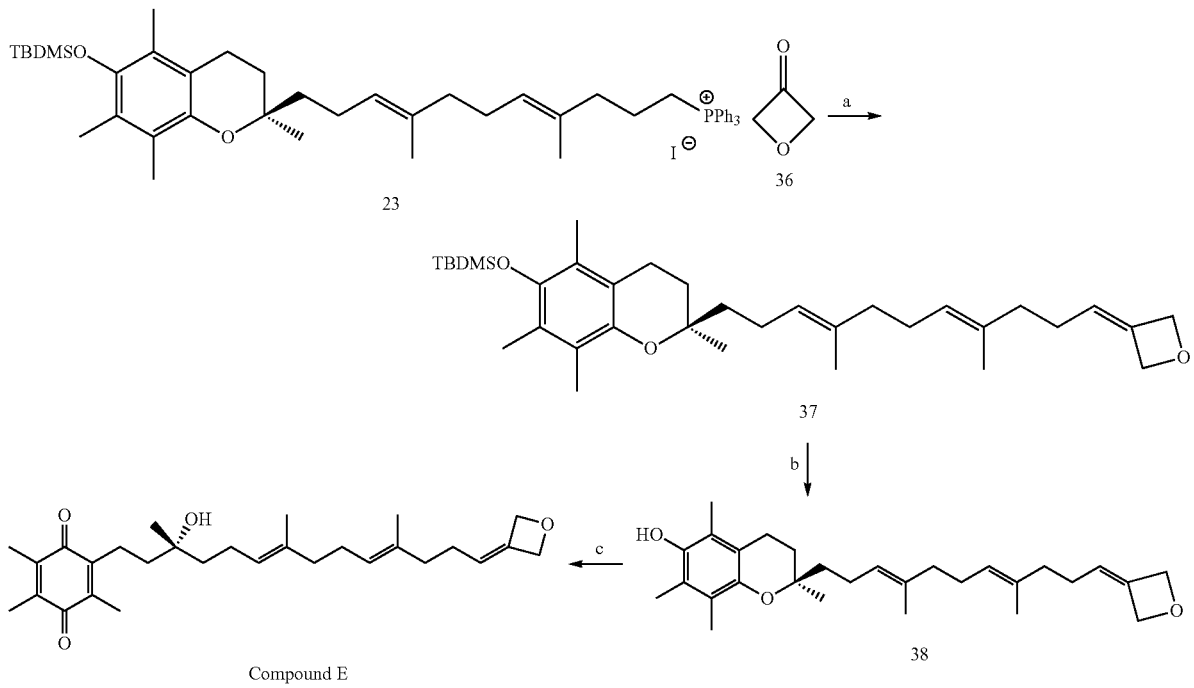

Step a. Synthesis of tert-butyl(((R)-2-((3E,7E)-4,8-dimethyl-11-(oxetan-3-ylidene)undeca-3,7-dien-1-yl)-2,5,7,8-tetramethylchroman-6-yl)oxy)dimethylsilane (37)

To a cooled (−78° C.) and stirred solution of 23 (0.750 g, 0.845 mmol, made according to the procedures described in Example 1) in dry THF (15 mL) under argon atmosphere was added lithium hexamethyldisilazide (1M solution in THF, 0.89 mL, 0.887 mmol). After stirring at the same temperature for 30 min, a solution of oxetan-3-one (36, 81 μL, 1.27 mmol) in dry THF (2.0 mL) was added dropwise. After continuous stirring at the same temperature for 1 hr., the reaction mixture was slowly (in approximately 4 hr.) warmed to r.t. and stirred overnight. The reaction mixture was diluted with diethyl ether (150 mL) and water (50 mL) and the resulting mixture was stirred at r.t. for 5 min. Then, organic phase was separated and the aqueous phase was extracted with diethyl ether (2×80 mL). The combined organic phases were washed with brine (80 mL), dried over anh. Na₂SO₄, and concentrated under reduced pressure. The crude product was purified by silica gel flash column chromatography (petroleum ether/EtOAc 1:0→200:3) to give 37 (0.316 g) in 68% yield.

¹H-NMR (400 MHz, CDC₃): δ=5.24-5.19 (m, 2H), 5.19-5.06 (m, 5H), 2.61-2.52 (m, 2H), 2.18-1.89 (m, 19H), 1.87-1.72 (m, 2H), 1.70-1.47 (m, 8H), 1.25 (s, 3H), 1.05 (s, 9H), 0.12 ppm (s, 6H).

Step b. Synthesis of (R)-2-((3E,7E)-4,8-dimethyl-11-(oxetan-3-ylidene)undeca-3,7-dien-1-yl)-2,5,7,8-tetramethylchroman-6-ol (38)

A solution of 37 (0.31 g, 0.561 mmol) in dry THF (20 mL) was cooled in ice bath while 1 M tetra-n-butylammonium fluoride solution in THF (0.56 mL, 0.561 mmol) was added dropwise. The reaction mixture was stirred at 0° C. for 2 hr. After completion of the reaction (as determined by TLC), the cooled (ice bath) reaction mixture was quenched by the addition of Et$_2$O (150 mL) and water (50 mL) and the resulting mixture was stirred at r.t. for 5 min. Then, organic phase was separated and the aqueous phase was extracted with diethyl ether (2×80 mL). The combined organic phases were washed with brine (80 mL), dried over anh. Na$_2$SO$_4$, and concentrated under reduced pressure. The crude product was purified by silica gel flash column chromatography (petroleum ether/EtOAc 1:0→10:1) to give 38 (216 mg) in 88% yield.

$^1$H-NMR (400 MHz, CDCl$_3$): δ=5.25-5.05 (m, 7H), 4.29 (s, 1H), 2.66-2.57 (m, 2H), 2.25-1.89 (m, 19H), 1.88-1.72 (m, 2H), 1.70-1.49 (m, 8H), 1.25 ppm (s, 3H).

Step c. Synthesis of 2-((R,6E,10E)-3-hydroxy-3,7,11-trimethyl-14-(oxetan-3-ylidene)tetradeca-6,10-dien-1-yl)-3,5,6-trimethylcyclohexa-2,5-diene-1,4-dione (Compound E)

To a solution of 38 (210 mg, 0.479 mmol) in $^i$PrOAc (5.9 mL) at r.t. was added a solution of ammonium cerium(IV) nitrate (789 mg, 1.44 mmol) in water (1.3 mL) and the reaction mixture was stirred at r.t. for 25 min. After cooling to 0° C., the reaction mixture was quenched by the addition of brine (50 mL) and EtOAc (200 mL). The resulting mixture was stirred at r.t. for 5 min. Then, aqueous phase was separated and the organic phase was washed with brine (30 mL), dried over anh. Na$_2$SO$_4$ and concentrated under reduced pressure. The crude product was purified by silica gel flash column chromatography using a mixture of petroleum ether and EtOAc (1:0-20:3) as an eluent to give Compound E (155 mg) in 71% yield.

$^1$H-NMR (CDCl$_3$, 400 MHz): δ=5.25-5.05 (m, 7H), 2.59-2.51 (m, 2H), 2.15-1.88 (m, 19H), 1.64 (s, 3H), 1.61-1.45 (m, 7H), 1.25 ppm (s, 3H). MS (M+H): 455.3152.

Example 6: Synthesis of 2-((R,6E,10E)-14-cyclopentylidene-3-hydroxy-3,7,11-trimethyltetradeca-6,10-dien-1-yl)-3,5,6-trimethylcyclohexa-2,5-diene-1,4-dione (Compound F)

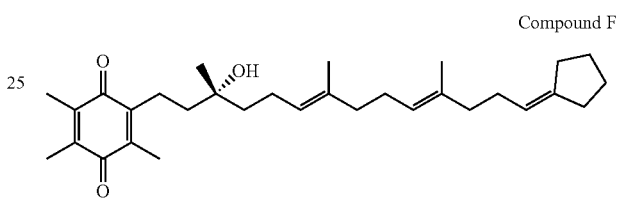

Compound F

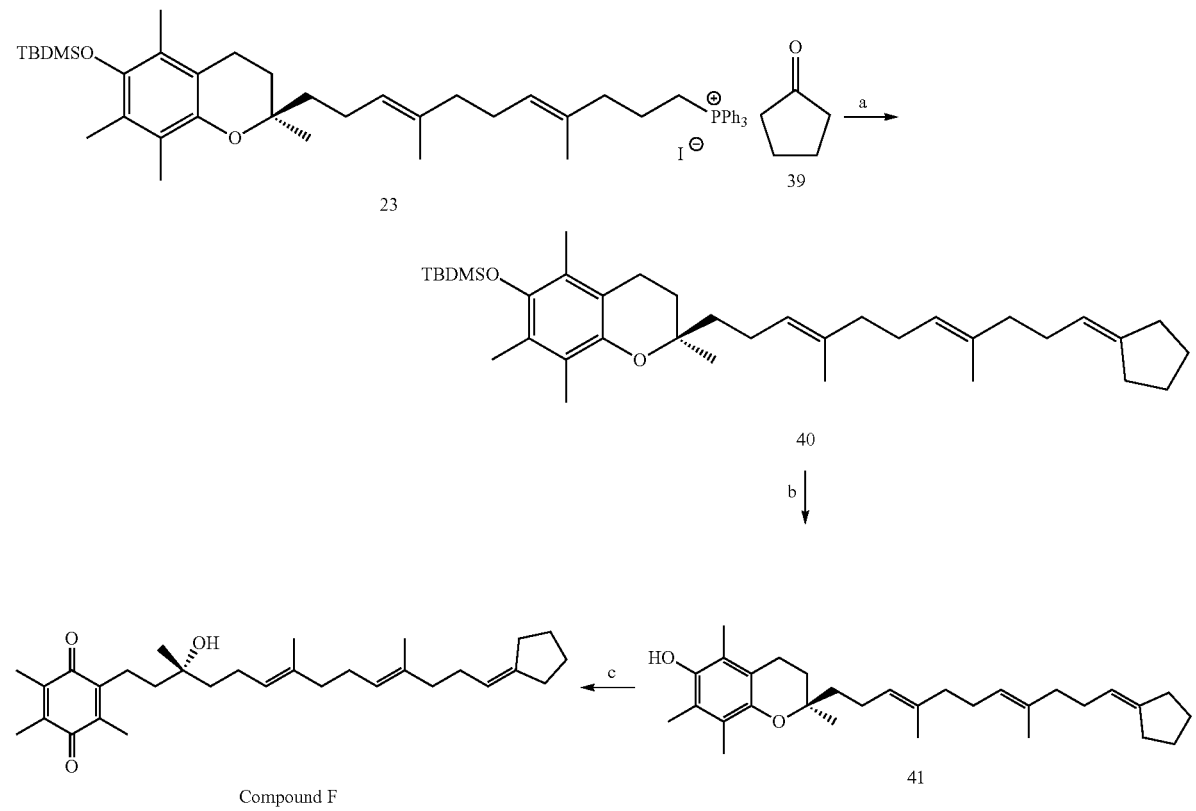

Scheme 7

Step a. Synthesis of tert-butyl(((R)-2-((3E,7E)-11-cyclopentylidene-4,8-dimethylundeca-3,7-dien-1-yl)-2,5,7,8-tetramethylchroman-6-yl)oxy)dimethylsilane (40)

To a cooled (−78° C.) and stirred solution of 23 (0.750 g, 0.845 mmol, made according to the procedures described in Example 1) in dry THF (15 mL) under argon atmosphere was added lithium hexamethyldisilazide (1M solution in THF, 0.89 mL, 0.887 mmol). After stirring at the same temperature for 30 min, solution of cyclopentanone (39, 112 µL, 1.27 mmol) in dry THF (2.0 mL) was added dropwise. After continuous stirring at the same temperature for 1 hr., the reaction mixture was slowly (in approximately 4 hr.) warmed to r.t. and stirred overnight. The reaction mixture was diluted with diethyl ether (150 mL) and water (50 mL) and the resulting mixture was stirred at r.t. for 5 min. Then, organic phase was separated and the aqueous phase was extracted with diethyl ether (2×80 mL). The combined organic phases were washed with brine (80 mL), dried over anh. $Na_2SO_4$, and concentrated under reduced pressure. The crude product was purified by silica gel flash column chromatography (petroleum ether/EtOAc 1:0→100:1) to give 40 (0.32 g) in 67% yield.
$^1$H-NMR (400 MHz, $CDCl_3$): δ=5.17-5.07 (m, 3H), 2.59-2.53 (m, 2H), 2.25-1.93 (m, 23H), 1.87-1.73 (m, 2H), 1.69-1.45 (m, 12H), 1.25 (s, 3H), 1.05 (s, 9H), 0.12 (s, 6H).

Step b. Synthesis of (R)-2-((3E,7E)-11-cyclopentylidene-4,8-dimethylundeca-3,7-dien-1-yl)-2,5,7,8-tetramethylchroman-6-ol (41)

A solution of 40 (0.300 g, 0.531 mmol) in dry THF (15 mL) was cooled in ice bath while 1 M TBAF solution in THF (0.58 mL, 0.584 mmol) was added dropwise. The reaction mixture was stirred at r.t. for 2 hr. After completion of the reaction (as determined by TLC), the cooled (ice bath) reaction mixture was quenched by the addition of $Et_2O$ (150 mL) and water (50 mL) and the resulting mixture was stirred at r.t. for 5 min. Then, organic phase was separated and the aqueous phase was extracted with diethyl ether (2×80 mL). The combined organic phases were washed with brine (80 mL), dried over anh. $Na_2SO_4$, and concentrated under reduced pressure. The crude product was purified by silica gel flash column chromatography (petroleum ether/EtOAc 1:0→30:1) and re-purified by reversed phase flash chromatography (100% of MeCN) to give 41 (170 mg) in 71% yield.
$^1$H-NMR (400 MHz, $CDCl_3$): δ=5.18-5.07 (m, 3H), 4.20 (s, 1H), 2.66-2.58 (m, 2H), 2.27-1.94 (m, 23H), 1.88-1.73 (m, 2H), 1.69-1.44 (m, 12H), 1.26 (s, 3H).

Step c. Synthesis of 2-((R,6E,10E)-14-cyclopentylidene-3-hydroxy-3,7,11-trimethyltetradeca-6,10-dien-1-yl)-3,5,6-trimethylcyclohexa-2,5-diene-1,4-dione (Compound F)

To a solution of 41 (170 mg, 0.377 mmol) in $^i$PrOAc (4.4 mL) at r.t. was added solution of ammonium cerium(IV) nitrate (619 mg, 1.13 mmol) in water (1.0 mL) and the reaction mixture was stirred at r.t. for 25 min. After cooling to 0° C., the reaction mixture was quenched by brine (50 mL) and EtOAc (200 mL). The resulting mixture was stirred at r.t. for 5 min. Then, aqueous phase was separated, and the organic phase was washed with brine (30 mL), dried over anh. $Na_2SO_4$ and concentrated under reduced pressure. The crude product was purified by silica gel flash column chromatography using a mixture of petroleum ether and EtOAc (1:0→10:1) as an eluent and re-purified by reversed phase flash chromatography (100% of MeCN) to give Compound F (57 mg) in 32% yield.
$^1$H-NMR ($CDCl_3$, 400 MHz): δ=5.18-5.07 (m, 3H), 2.58-2.51 (m, 2H), 2.23-2.14 (m, 4H), 2.13-1.95 (m, 19H), 1.65-1.43 (m, 14H), 1.24 (s, 3H). MS (M+H): 465.3377.

Example 7: Synthesis of 2-((R,6E,10E)-14-cyclohexylidene-3-hydroxy-3,7,11-trimethyltetradeca-6,10-dien-1-yl)-3,5,6-trimethylcyclohexa-2,5-diene-1,4-dione (Compound G)

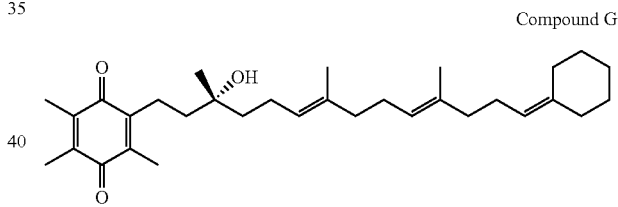

Compound G

Scheme 8

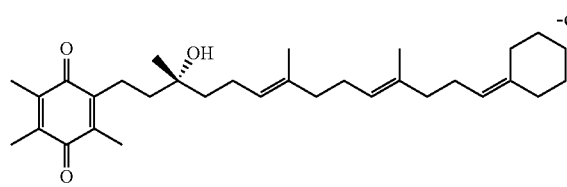

Compound G

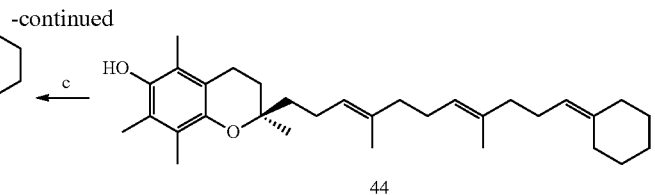

44

-continued

Step a. Synthesis of tert-butyl(((R)-2-((3E,7E)-11-cyclohexylidene-4,8-dimethylundeca-3,7-dien-1-yl)-2,5,7,8-tetramethylchroman-6-yl)oxy)dimethylsilane (43)

To a cooled (−78° C.) and stirred solution of 23 (0.780 g, 0.879 mmol, made according to the procedures described in Example 1) in dry THF (15 mL) under argon atmosphere was added lithium hexamethyldisilazide (1M solution in THF, 0.92 mL, 0.923 mmol). After stirring at the same temperature for 30 min, solution of cyclohexanone (42, 137 µL, 1.32 mmol) in dry THF (2.0 mL) was added dropwise. After continuous stirring at the same temperature for hr., the reaction mixture was slowly (in approximately 4 hr.) warmed to r.t. and stirred overnight. The reaction mixture was diluted with diethyl ether (150 mL) and water (50 mL) and the resulting mixture was stirred at r.t. for 5 min. Then, the organic phase was separated, and the aqueous phase was extracted with diethyl ether (2×80 mL). The combined organic phases were washed with brine (80 mL), dried over anh. Na$_2$SO$_4$, and concentrated under reduced pressure. The crude product was purified by silica gel flash column chromatography (petroleum ether/EtOAc 1:0→400:3) to give 43 (0.46 g) in 90% yield.

$^1$H-NMR (400 MHz, CDCl$_3$): δ=5.18-5.01 (m, 3H), 2.60-2.53 (m, 2H), 2.17-2.02 (m, 19H), 2.01-1.93 (m, 4H), 1.88-1.73 (m, 2H), 1.69-1.43 (m, 14H), 1.26 (s, 3H), 1.05 (s, 9H), 0.12 ppm (s, 6H).

Step b. Synthesis of (R)-2-((3E,7E)-11-cyclohexylidene-4,8-dimethylundeca-3,7-dien-1-yl)-2,5,7,8-tetramethylchroman-6-ol (44)

A solution of 43 (0.44 g, 0.760 mmol) in dry THF (25 mL) was cooled in ice bath while 1 M TBAF solution in THF (0.84 mL, 0.836 mmol) was added dropwise. The reaction mixture was stirred at r.t. for 2 hr. After completion of the reaction (as determined by TLC), the cooled (ice bath) reaction mixture was quenched by the addition of Et$_2$O (150 mL) and water (50 mL) and the resulting mixture was stirred at r.t. for 5 min. Then, the organic phase was separated and the aqueous phase was extracted with diethyl ether (2×80 mL). The combined organic phases were washed with brine (80 mL), dried over anh. Na$_2$SO$_4$, and concentrated under reduced pressure. The crude product was purified by silica gel flash column chromatography (petroleum ether/EtOAc 1:0→40:3) and re-purified by reversed phase flash chromatography (100% of MeCN) to give 44 (260 mg) in 74% yield.

$^1$H-NMR (400 MHz, CDCl$_3$): δ=5.18-5.00 (m, 3H), 4.19 (br s, 1H), 2.66-2.58 (m, 2H), 2.21-1.91 (m, 23H), 1.89-1.72 (m, 2H), 1.72-1.41 (m, 14H), 1.26 (s, 3H).

Step c. Synthesis of 2-((R,6E,10E)-14-cyclohexylidene-3-hydroxy-3,7,11-trimethyltetradeca-6,10-dien-1-yl)-3,5,6-trimethylcyclohexa-2,5-diene-1,4-dione (Compound G)

To a solution of 44 (260 mg, 0.559 mmol) in $^i$PrOAc (6.5 mL) at r.t. was added a solution of ammonium cerium(IV) nitrate (921 mg, 1.68 mmol) in water (1.5 mL) and the reaction mixture was stirred at r.t. for 25 min. After cooling to 0° C., the reaction mixture was quenched by the addition of brine (50 mL) and EtOAc (200 mL). The resulting mixture was stirred at r.t. for 5 min. Then, the aqueous phase was separated and the organic phase was washed with brine (30 mL), dried over anh. Na$_2$SO$_4$ and concentrated under reduced pressure. The crude product was purified by silica gel flash column chromatography using a mixture of petroleum ether and EtOAc (1:0→10:1) as an eluent and re-purified by reversed phase flash chromatography (100% of MeCN) to give Compound G (205 mg) in 76% yield.

$^1$H-NMR (CDCl$_3$, 400 MHz): δ=5.19-5.01 (m, 3H), 2.59-2.51 (m, 2H), 2.14-1.93 (m, 21H), 1.64 (s, 3H), 1.59 (s, 3H), 1.58-1.43 (m, 12H), 1.25 ppm (s, 3H). MS (M+H): 481.3667.

Example 8: Preparation of Reduced Form of Vatiquinone ("Vatiquinone-R")

Scheme 9

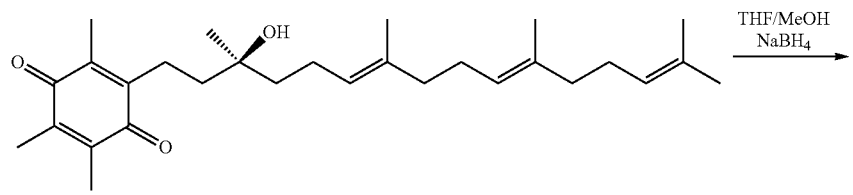

Vatiquinone

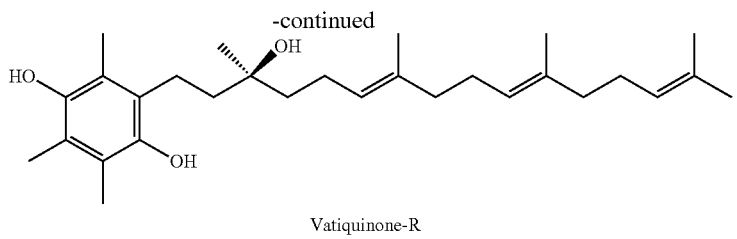

Vatiquinone-R

Vatiquinone (20 mg) was dissolved in mixture of MeOH/THF (1 mL+1 mL) under an argon atmosphere. Then NaBH$_4$ (3 mg) was added and the reaction mixture was stirred at r.t. for 1 hr. Next, the reaction mixture was quenched by the addition of Et$_2$O (30 mL) and aq. NH$_4$C$_1$ (10 mL) with stirring at r.t. for 2 min. The aqueous phase was separated and organic phase was washed with brine (10 mL), dried over anhydrous Na$_2$SO$_4$ and concentrated under reduced pressure. The crude product was purified by column chromatography to yield 0.015 g (74% yield) of reduced vatiquinone (Vatiquinone-R).

$^1$H-NMR (CDCl$_3$, 400 MHz): δ=5.17-5.08 (m, 3H), 2.74-2.71 (m, 2H), 2.19-2.16 (m, 9H), 2.11-1.96 (m, 11H), 1.71-1.68 (m, 5H), 1.62-1.56 (m, 11H), 1.25 (s, 4H).

$^{13}$C-NMR (101 MHz, Chloroform-d) δ 145.9, 145.5, 136.1, 135.3, 131.4, 125.9, 124.5, 124.2, 124.0, 121.8, 120.7, 119.1, 74.0, 41.9, 41.0, 40.0, 30.5, 26.9, 26.7, 26.7, 25.8, 23.0, 20.7, 17.8, 16.2, 16.2, 12.5, 12.4, 12.2.

HRMS, [M+H]: C$_{29}$H$_{47}$O$_3$ (calculated: 443.3525). Found: 443.3516.

Example 9: Synthesis of 2-((R,6E,10E)-14-cyclohexylidene-3-hydroxy-3,7,11-trimethyltetradeca-6,10-dien-1-yl)-3,5,6-trimethylcyclohexa-2,5-diene-1,4-dione (Compound C$_2$; i.e., reduced form of Compound C)

Scheme 10

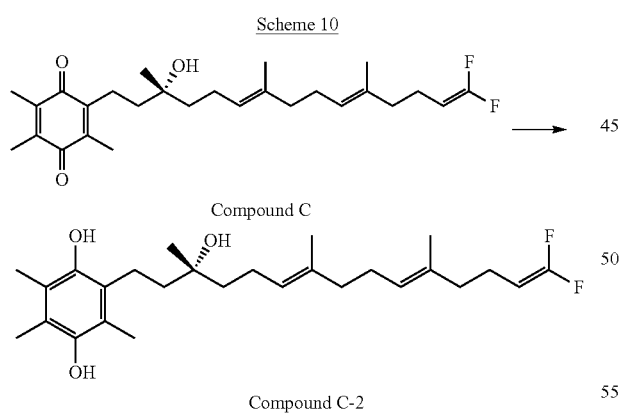

Compound C

Compound C-2

To a cooled (–15° C.) and stirred solution of Compound C (0.225 g, 0.50 mmol, made according to the procedures described in Scheme 4) in EtOH (12 ml) under argon atmosphere was added NaBH$_4$ (10 mg 0.25 mmol). After stirring for 10 min at –15° C., the reaction was quenched by the addition of 5% (aq.) diluted HCl solution. The reaction mixture was extracted with EtOAc (3×20 mL). The combined organic layers were washed with brine and dried over anhydrous Na$_2$SO$_4$. The organic phase was filtered, and solvent was evaporated. The crude mixture was then purified via chromatography (petroleum ether/EtOAc 1:0→40:3 and EtOAc (1:0-10:1) to give a pure Compound C-2.

As this procedure is generally adaptable to both Compound C and Vatiquinone, it should be suitable for converting any of the quinone compounds disclosed herein to their corresponding hydroquinone derivatives.

Example 10: Synthesis of (R,E)-2-(11,11-difluoro-3-hydroxy-3,7-dimethylundeca-6,10-dien-1-(1-yl)-3,5,6-trimethylcyclohexa-2,5-diene-1,4-dione (Compound H)

Compound H

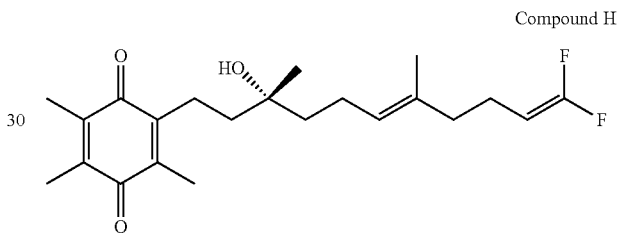

Scheme 11

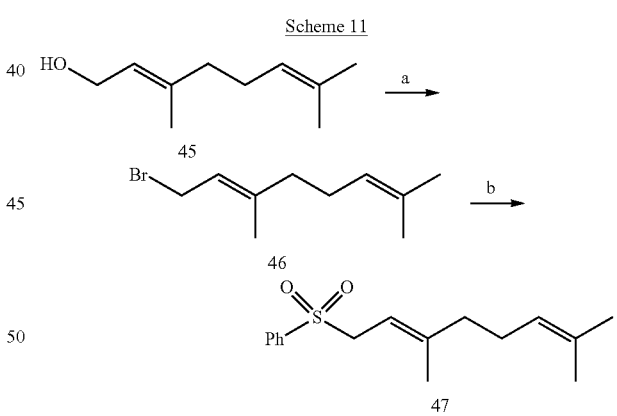

Step a. Synthesis of (E)-1-bromo-3,7-dimethylocta-2,6-diene (46)

To a cooled (0° C.) solution of 45 (10 g, 64.8 mmol) in dry THF (100 mL) dropwise was added PBr$_3$ (7.39 ml, 77.8 mmol) and the reaction mixture was stirred at 0° C. for 40 min. The reaction mixture was then poured on ice (200 g) and extracted with Et$_2$O (3×200 mL). The combined organic phases were dried over anh. Na$_2$SO$_4$ and concentrated under reduced pressure to give 46 (13.4 g) in 95% yield. This material was used in the next step (step b) without further purification.

Step b. Synthesis of (E)-((3,7-dimethylocta-2,6-dien-1-yl)sulfonyl)benzene (47)

To a cooled (0° C.) solution of 46 (13.4 g, 61.7 mmol) in dry DMF (130 mL) was added phenylsulfinic acid sodium salt (13.2 g, 80.2 mmol) in one portion and the reaction mixture was stirred at r.t. overnight. The reaction mixture was quenched by the addition of sat. aq. $NH_4Cl$ (200 mL) and EtOAc (1200 mL) and stirred at r.t. for 15 min. The aqueous phase was removed and the organic phase was washed with brine (4×150 mL), dried over anh. $Na_2SO_4$ and concentrated under reduced pressure. The crude product was purified by silica gel flash column chromatography using a mixture of petroleum ether and EtOAc (1:0-10:1) as an eluent to give 47 (13.4 g) in 78% yield.

$^1$H-NMR (CDCl$_3$, 400 MHz): δ=7.90-7.83 (m, 2H), 7.67-7.59 (m, 1H), 7.57-7.48 (m, 2H), 5.22-5.14 (m, 1H), 5.07-4.98 (m, 1H), 3.80 (d, J=8.0 Hz, 2H), 2.03-1.96 (m, 4H), 1.70-1.65 (m, 3H), 1.59-1.57 (m, 3H), 1.32-1.29 ppm (m, 3H).

Scheme 12

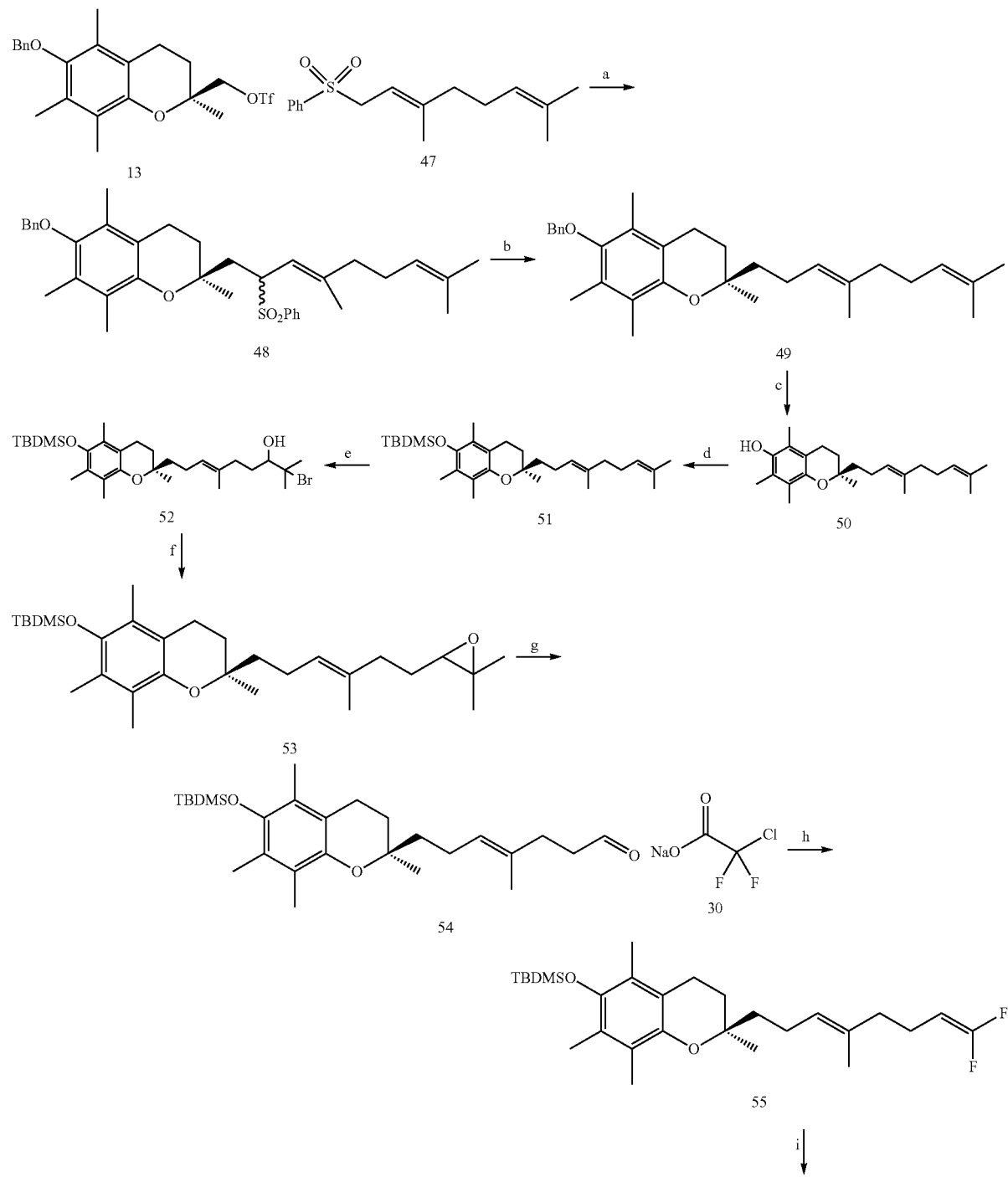

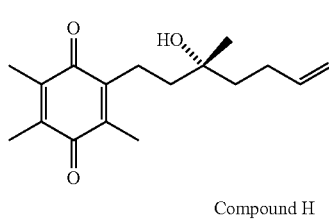

Compound H

-continued

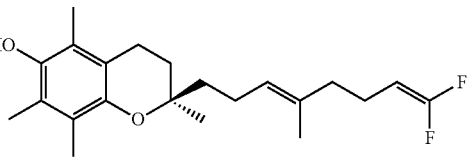

56

Step a. Synthesis of (2S)-6-(benzyloxy)-2-((E)-4,8-dimethyl-2-(phenylsulfonyl)nona-3,7-dien-1-yl)-2,5,7,8-tetramethylchromane (48)

To a solution of 47 (4.84 g, 17.4 mmol) in dry THF (60 mL) under argon was added hexamethylphosphoramide (15.9 mmol) and the resulting mixture was cooled to −78° C. Then, "BuLi (2.3 M in hexanes, 5.7 mL, 13.1 mmol) was added dropwise and the reaction mixture was stirred at the same temperature for 30 min. After dropwise addition of 13 (5.00 g, 10.9 mmol) solution in dry THF (60 mL), the reaction mixture was stirred at −78° C. for 8 hrs. and stirring was continued at r.t. for 20 hrs. The reaction mixture was diluted with Et$_2$O (1000 mL), washed with water (2×150 mL), brine (150 mL), dried over anh. Na$_2$SO$_4$ and concentrated under reduced pressure. The crude product was purified by silica gel flash column chromatography using a mixture of petroleum ether and EtOAc (1:0→5:1) as an eluent to give 48 (7.73 g) as a mixture of diastereomers, containing premix of the remaining 47 (about 0.5 equiv.). This material was used in the next step (Step b) without further purification.

Step b. Synthesis of (R)-6-(Benzyloxy)-2,5,7,8-tetramethyl-2-((3E,7E)-4,8,12-trimethyltrideca-3,7,11-trien-1-yl)chromane (49)

To a mixture of 48 (containing approx. 0.5 equivalents of 47) (7.73 g, approx. 13.2 mmol) and PdCl$_2$dppp (779 mg, 1.32 mmol) under argon was added dry THF (100 mL) and the resulting suspension was cooled to 0° C. Then, LiEt$_3$BH (1.7 M in THF, 23.3 mL, 39.6 mmol) was added dropwise and the reaction mixture was stirred at 0° C. for 5 hrs. and overnight at r.t. The reaction mixture was the diluted with Et$_2$O (800 mL) and successively washed with 1 M aq. NaCN (100 mL), water (100 mL), and brine (100 mL). After drying over anh. Na$_2$SO$_4$, the volatile matters were removed under reduced pressure and the crude product was purified by silica gel flash column chromatography using a mixture of petroleum ether and EtOAc (1:0-40:1) as an eluent to give 49 (3.83 g) in 79% yield over two steps.

$^1$H-NMR (CDCl$_3$, 400 MHz): δ=7.56-7.50 (m, 2H), 7.46-7.29 (m, 3H), 5.21-5.08 (m, 2H), 4.73 (s, 2H), 2.67-2.59 (m, 2H), 2.25 (s, 3H), 2.23-2.05 (m, 10H), 2.05-1.96 (m, 2H), 1.93-1.76 (m, 2H), 1.75-1.54 (m, 11H), 1.30 ppm (s, 3H).

Step c. Synthesis of (R,E)-2-(4,8-dimethylnona-3,7-dien-1-yl)-2,5,7,8-tetramethylchroman-6-ol (50)

To a cooled (0° C.) suspension of lithium (1.77 g, 255 mmol) in n-propylamine (100 mL) and diethylether (60 mL) under argon was added solution of 49 (3.8 g, 8.51 mmol) in diethylether (40 mL) and the reaction mixture was stirred at r.t. for 3 hrs. After re-cooling to 0° C., the reaction mixture was carefully quenched by the addition of sat. aq. NH$_4$C$_1$ (50 mL) and methanol (50 mL). The organic solvents were removed under reduced pressure at r.t. and the residue was diluted with water (100 mL) and extracted with diethylether (3×200 mL). The combined organic phases were washed with brine (100 mL), dried over anh. Na$_2$SO$_4$ and concentrated under reduced pressure. The crude product was purified by silica gel flash column chromatography using a mixture of petroleum ether and EtOAc (1:0-40:3) as an eluent to give 50 (2.92 g) in 96% yield.

$^1$H-NMR (CDCl$_3$, 400 MHz): δ=5.18-5.06 (m, 2H), 4.19 (s, 1H), 2.67-2.58 (m, 2H), 2.21-2.02 (m, 13H), 2.01-1.94 (m, 2H), 1.90-1.73 (m, 2H), 1.73-1.49 (m, 11H), 1.26 ppm (s, 2H).

Step d. Synthesis of (R,E)-tert-butyl((2-(4,8-dimethylnona-3,7-dien-1-yl)-2,5,7,8-tetramethylchroman-6-yl)oxy)dimethylsilane (51)

A solution of TBDMSCl (5.14 g, 34.1 mmol) in dry DMF (18 mL) was added to a cooled (0° C.) solution of 50 (2.70 g, 7.57 mmol) and imidazole (4.64 g, 68.1 mmol) in dry DMF (18 mL) and the reaction mixture was stirred at r.t. for 20 hrs. Then, the reaction mixture was diluted with EtOAc (1000 mL) and water (150 mL) and stirred at r.t. for 15 min. The aqueous phase was separated and the organic phase was washed with water (3×150 mL) and brine (150 mL), dried over anh. Na$_2$SO$_4$, and concentrated under reduced pressure. The crude product was purified by silica gel column flash chromatography using a mixture of petroleum ether and EtOAc as eluent (1:0-50:1) to give 51 (3.28 g) in 92% yield as colorless oil.

$^1$H-NMR (400 MHz, CDCl$_3$): δ=5.18-5.06 (m, 2H), 2.61-2.54 (m, 2H), 2.19-2.02 (m, 13H), 2.01-1.93 (m, 2H), 1.89-1.73 (m, 2H), 1.72-1.48 (m, 11H), 1.26 (s, 3H), 1.06 (s, 9H), 0.13 ppm (s, 6H).

Step e. Synthesis of (E)-2-bromo-9-((R)-6-((tert-butyldimethylsilyl)oxy)-2,5,7,8-tetramethyl-chroman-2-yl)-2,6-dimethylnon-6-en-3-ol (52)

To a solution of 51 (3.2 g, 6.80 mmol) in THF (81 mL) and H$_2$O (30 mL) at 0° C. dropwise was added solution of N-bromosuccinimide (1.33 g, 7.48 mmol) in THF (24.3 mL). After the reaction mixture was stirred for 2 hrs. at 0° C., the reaction mixture was quenched by the addition of Et$_2$O (300 mL) and water (100 mL) and the resulting mixture was stirred at r.t. for 15 min. The organic phase was separated and the aqueous phase was extracted with Et$_2$O (2×100 mL). The combined organic phases were washed with brine (80 mL) and dried over anh. Na$_2$SO$_4$. After evaporation of the solvent under reduced pressure, crude product was purified by silica gel column flash chromatography using a mixture of petroleum ether and EtOAc as eluent (1:0→40:3) to give 52 (2.63 g) in 68% yield as colorless oil.

$^1$H-NMR (400 MHz, CDCl$_3$): δ=5.26-5.19 (m, 1H), 4.02-3.93 (m, 1H), 2.61-2.53 (m, 2H), 2.37-2.27 (m, 1H), 2.22-

2.03 (m, 13H), 2.01-1.91 (m, 1H), 1.88-1.72 (m, 3H), 1.70-1.46 (m, 5H), 1.40-1.30 (m, 6H), 1.25 (s, 3H), 1.05 (s, 9H), 0.12 ppm (s, 6H).

Step f. Synthesis of tert-butyl(((2R)-2-((E)-6-(3,3-dimethyloxiran-2-yl)-4-methylhex-3-en-1-yl)-2,5,7,8-tetramethylchroman-6-yl)oxy)dimethylsilane (53)

To a solution of 52 (2.60 g, 4.58 mmol) in MeOH (42 mL) was added $K_2CO_3$ (1.27 g, 9.16 mmol) and the resulting mixture was stirred at r.t. for 1.5 h. Then, the reaction mixture was quenched with water (200 mL), and the resulting aqueous phase was extracted with $Et_2O$ (3×200 mL). The combined organic phases were washed with brine (100 mL), dried over anh. $Na_2SO_4$, and concentrated under reduced pressure to give crude 53 (2.17 g) in 98% yield, which was used in the next step without further purification.

$^1$H-NMR (400 MHz, $CDCl_3$): δ=5.23-5.15 (m, 1H), 2.73-2.66 (m, 1H), 2.60-2.53 (m, 2H), 2.20-2.01 (m, 13H), 1.88-1.72 (m, 2H), 1.71-1.48 (m, 7H), 1.33-1.21 (m, 9H), 1.05 (s, 9H), 0.12 ppm (s, 6H).

Step g. Synthesis of (R,E)-7-(6-((tert-butyldimethylsilyl)oxy)-2,5,7,8-tetramethylchroman-2-yl)-4-methylhept-4-enal (54)

A stirred mixture of 53 (2.17 g, 4.46 mmol), THF (28 mL), and water (5.6 mL) at 0° C. was sequentially treated with sodium periodate (573 mg, 2.68 mmol) and periodic acid (1.12 g, 4.91 mmol). The resulting mixture was stirred at 0° C. for 10 min. and, then, warmed to room temperature. After 1 hr., the reaction mixture was quenched by the addition of saturated aqueous sodium bicarbonate solution (100 mL) and diethyl ether (200 mL) and the resulting mixture was stirred at r.t. for 5 min. The biphasic layers were separated and the aqueous layer was extracted with diethyl ether (2×200 mL). The combined organic layers were washed with brine (100 mL), dried over anh. $Na_2SO_4$, filtered and concentrated under reduced pressure to give crude 54 (1.80 g) in 91% yield. It was used in the next step without further purification.

$^1$H-NMR (400 MHz, $CDCl_3$): δ=9.75 (t, J=1.9 Hz, 1H), 5.22-5.13 (m, 1H), 2.59-2.53 (m, 2H), 2.53-2.47 (m, 1H), 2.34-2.27 (m, 1H), 2.18-2.03 (m, 11H), 1.88-1.72 (m, 2H), 1.72-1.46 (m, 7H), 1.25 (s, 3H), 1.05 (s, 9H), 0.12 ppm (s, 6H).

Step h. Synthesis of (R,E)-tert-butyl((2-(8,8-difluoro-4-methylocta-3,7-dien-1-yl)-2,5,7,8-tetramethylchroman-6-yl)oxy)dimethylsilane (55)

To a mixture of 54 (1.70 g, 3.82 mmol), sodium 2-chloro-2,2-difluoroacetate (30, 1.16 g, 7.64 mmol), and $PPh_3$ (2.00 g, 7.64 mmol) under argon was added dry DMF (7.9 mL) and the reaction mixture was stirred at 105° C. for 2 hrs. After cooling in ice bath, water (5.0 L was added slowly. Then, the resulting mixture was diluted by water (100 mL) and $Et_2O$ (600 mL) and stirred at r.t. for 5 min. The aqueous phase was separated and the organic phase was washed with water (3×80 mL) and brine (80 mL). After drying over anh. $Na_2SO_4$, the volatile matters were removed under reduced pressure and the crude product was purified by silica gel column flash chromatography using a mixture of petroleum ether and EtOAc as eluent (1:0-100:1) to give 55 (0.86 g) together with approximately 0.2 equiv. of $PPh_3$ in 47% yield. The obtained product was used in the next step without further purification.

$^1$H-NMR (400 MHz, $CDCl_3$): δ=5.20-5.13 (m, 1H), 4.18-4.03 (m, 1H), 2.62-2.55 (m, 2H), 2.20-1.99 (m, 15H), 1.89-1.74 (m, 2H), 1.71-1.49 (m, 5H), 1.27 (s, 3H), 1.07 (s, 9H), 0.14 ppm (s, 6H).

Step i. Synthesis of (R,E)-2-(8,8-difluoro-4-methylocta-3,7-dien-1-yl)-2,5,7,8-tetramethylchroman-6-ol (56)

A solution of 55 containing approximately 0.2 equiv. of $PPh_3$ (0.80 g, 1.67 mmol) in dry THF (40 mL) was cooled in ice bath while 1 M tetra-n-butylammonium fluoride solution in THF (1.7 mL, 1.67 mmol) was added dropwise. The reaction mixture was stirred at 0° C. for 30 min. After completion of the reaction (TLC), cooled (ice bath) reaction mixture was quenched by the addition of $Et_2O$ (200 mL) and water (100 mL) and the resulting mixture was stirred at r.t. for 5 min. Then, organic phase was separated and the aqueous phase was extracted with diethyl ether (2×100 mL). The combined organic phases were washed with brine (80 mL), dried over anh. $Na_2SO_4$, and concentrated under reduced pressure. The crude product was purified by silica gel flash column chromatography (petroleum ether/EtOAc 1:0→20:1) to give 56 (0.49 g) in 80% yield.

$^1$H-NMR (400 MHz, $CDC_3$): δ=5.20-5.12 (m, 1H), 4.20 (s, 1H), 4.17-4.02 (m, 1H), 2.67-2.58 (m, 2H), 2.21-1.98 (m, 15H), 1.89-1.73 (m, 2H), 1.71-1.49 (m, 5H), 1.26 ppm (s, 3H). MS: 364.2.

Step j. Synthesis of Synthesis of (R,E)-2-(11,11-difluoro-3-hydroxy-3,7-dimethylundeca-6,10-dien-1-yl)-3,5,6-trimethylcyclohexa-2,5-diene-1,4-dione (Compound H)

To a cooled (ice bath) solution of 56 (390 mg, 1.07 mmol) in PrOAc (13.3 ml) was added a solution of ammonium cerium(IV) nitrate (1.76 g, 3.21 mmol) in water (3.2 mL) and the reaction mixture was stirred at r.t. for 25 min. After cooling to 0° C., the reaction mixture was quenched by brine (60 mL) and EtOAc (300 mL). The resulting mixture was stirred at r.t. for 5 min. Then, aqueous phase was separated and the organic phase was washed with water (80 mL) and brine (80 mL), dried over anh. $Na_2SO_4$ and concentrated under reduced pressure. The crude product was purified by silica gel flash column chromatography using a mixture of petroleum ether and EtOAc (1:0→10:1) as an eluent and re-purified by reversed phase flash chromatography (100% MeCN) to give Compound H (300 mg) in 74% yield.

$^1$H-NMR ($CDCl_3$, 400 MHz): δ=5.19-5.13 (m, 1H), 4.16-4.02 (m, 1H), 2.58-2.51 (m, 2H), 2.14-1.98 (m, 13H), 1.65-1.61 (m, 3H), 1.59-1.45 (m, 6H), 1.25 ppm (s, 3H). MS (M+H$^+$): 381.2242

3H). MS (M+H$^+$): 381.2242.

Example 11: Synthesis of (R)-2-(7,7-difluoro-3-hydroxy-3-methylhept-6-en-1-yl)-3,5,6-trimethylcyclo-hexa-2,5-diene-1,4-dione (Compound I)

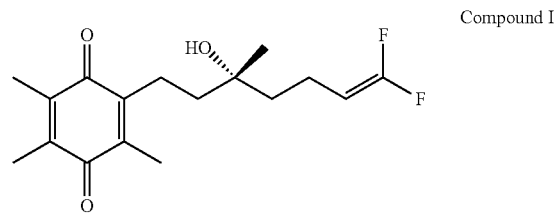 [SMILES: CC1=C(C)C(=O)C(CC[C@](C)(O)CCC=C(F)F)=C(C)C1=O]

Compound I

Scheme 13

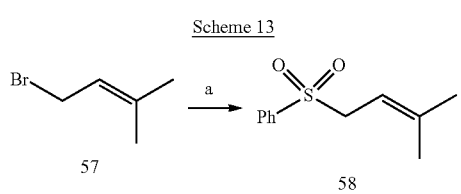

Step a. Synthesis of ((3-methylbut-2-en-1-yl)sulfonyl)benzene (58)

To a cooled (0° C.) solution of 57 (20 g, 134 mmol) in dry DMF (200 mL) was added phenylsulfinic acid sodium salt (28.6 g, 174 mmol) in one portion and the reaction mixture was stirred at r.t. over night. Most of the solvent was removed under reduced pressure and the residue was quenched by sat. aq. $NH_4C_1$ (200 mL) and EtOAc (1200 mL) and stirred at r.t. for 15 min. The aqueous phase was removed and the organic phase was washed with water (4×150 mL) and brine (100 mL), dried over anh. $Na_2SO_4$ and concentrated under reduced pressure. The crude product was purified by silica gel flash column chromatography using a mixture of petroleum ether and EtOAc (1:0-20:3) as an eluent to give 57 (20.9 g) in 74% yield as white solid.

$^1$H-NMR (CDCl$_3$, 400 MHz): δ=7.90-7.82 (m, 2H), 7.67-7.59 (m, 1H), 7.57-7.49 (m, 2H), 5.22-5.14 (m, 1H), 3.81-3.75 (m, 2H), 1.73-1.68 (m, 3H), 1.32-1.29 ppm (m, 3H).

Scheme 14

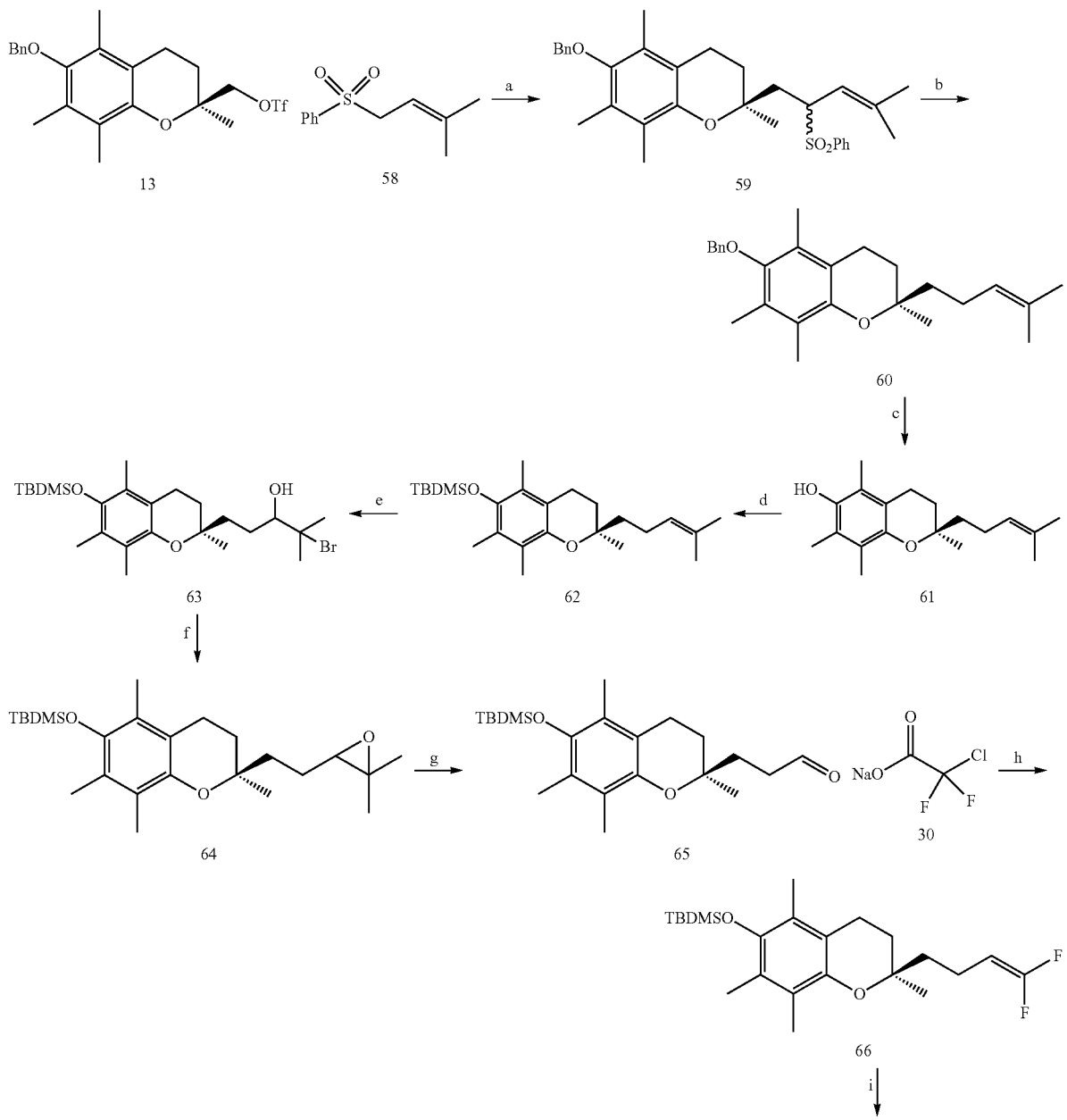

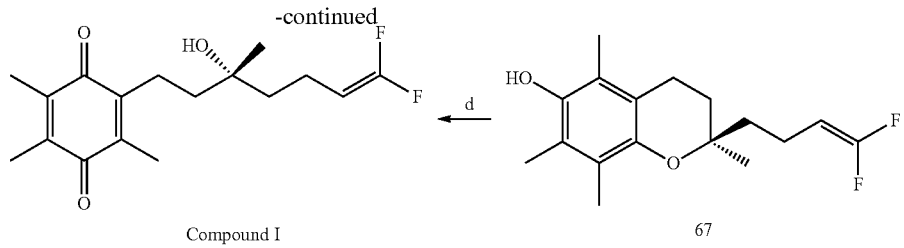

Compound I  67

Step a. Synthesis of (2S)-6-(benzyloxy)-2,5,7,8-tetramethyl-2-(4-methyl-2-(phenylsulfonyl)pent-3-en-1-yl)chromane (59)

To a solution of 58 (3.66 g, 17.4 mmol) in dry THF (60 mL) under argon was added hexamethylphosphoramide (15.9 mmol) and the resulting mixture was cooled to −78° C. Then, "BuLi (2.3 M in hexanes, 5.7 mL, 13.1 mmol) was added dropwise and the reaction mixture was stirred at the same temperature for 30 min. After dropwise addition of 13 (5.00 g, 10.9 mmol) solution in dry THF (60 mL), the reaction mixture was stirred at −78° C. for 8 hrs. and stirring was continued at r.t. for 20 hrs. The reaction mixture was diluted with $Et_2O$ (1000 mL), washed with water (2×150 mL), brine (150 mL), dried over anh. $Na_2SO_4$ and concentrated under reduced pressure. The crude product was purified by silica gel flash column chromatography using a mixture of petroleum ether and EtOAc (1:0→5:1) as an eluent to give 59 (4.95 g) as a mixture of diastereomers, containing premix of the remaining 58 (about 1.3 equiv.). This product was used in the next step without further purification.

Step b. Synthesis of (R)-6-(benzyloxy)-2,5,7,8-tetramethyl-2-(4-methylpent-3-en-1-yl)chromane (60)

To a mixture of 59 (containing approx. 1.3 equivalents of 58) (4.95 g, approx. 14.5 mmol) and $PdCl_2dppp$ (855 mg, 1.45 mmol) under argon was added dry THF (100 mL) and the resulting suspension was cooled to 0° C. Then, $LiEt_3BH$ (1.7 M in THF, 25.6 mL, 43.5 mmol) was added dropwise and the reaction mixture was stirred at 0° C. for 5 hrs. and overnight at r.t. The reaction mixture was diluted with $Et_2O$ (800 mL) and successively washed with 1 M aq. NaCN (100 mL), water (100 mL), and brine (100 mL). After drying over anh. $Na_2SO_4$, the volatile matters were removed under reduced pressure and the crude product was purified by silica gel flash column chromatography using a mixture of petroleum ether and EtOAc (1:0→40:1) as an eluent to give 60 (1.87 g) in 45% yield over two steps.

$^1$H-NMR ($CDCl_3$, 400 MHz): δ=7.55-7.50 (m, 2H), 7.45-7.39 (m, 2H), 7.39-7.32 (m, 1H), 5.19-5.12 (m, 1H), 4.72 (s, 2H), 2.66-2.58 (m, 2H), 2.24 (s, 3H), 2.21-2.10 (m, 8H), 1.93-1.75 (m, 2H), 1.73-1.53 (m, 8H), 1.29 ppm (s, 3H).

Step c. Synthesis of (R)-2,5,7,8-tetramethyl-2-(4-methylpent-3-en-1-yl)chroman-6-ol (61)

To a cooled (0° C.) suspension of lithium (1.03 g, 148 mmol) in n-propylamine (50 mL) and diethylether (20 mL) under argon was added solution of 60 (1.87 g, 4.94 mmol) in diethylether (30 mL) and the reaction mixture was stirred at r.t. for 3 hrs. After re-cooling to 0° C., the reaction mixture was carefully quenched by the addition of sat. aq. $NH_4C_1$ (30 mL) and methanol (30 mL). The organic solvents were removed under reduced pressure at r.t. and the residue was diluted with water (100 mL) and extracted with diethylether (3×200 mL). The combined organic phases were washed with brine (100 mL), dried over anh. $Na_2SO_4$ and concentrated under reduced pressure. The crude product was purified by silica gel flash column chromatography using a mixture of petroleum ether and EtOAc (1:0→40:3) as an eluent to give 61 (1.25 g) in 88% yield.

$^1$H-NMR ($CDCl_3$, 400 MHz): δ=5.18-5.10 (m, 1H), 4.21 (s, 1H), 2.68-2.58 (m, 2H), 2.22-2.07 (m, 11H), 1.90-1.73 (m, 2H), 1.72-1.50 (m, 8H), 1.26 ppm (s, 3H).

Step d. Synthesis of (R)-tert-butyldimethyl((2,5,7,8-tetramethyl-2-(4-methylpent-3-en-1-yl)chroman-6-yl)oxy)silane (62)

A solution of TBDMSCl (2.71 g, 18.0 mmol) in dry DMF (10 mL) was added to a cooled (0° C.) solution of 61 (1.15 g, 3.99 mmol) and imidazole (2.44 g, 35.9 mmol) in dry DMF (7 mL) and the reaction mixture was stirred at r.t. for 20 hrs. Then, the reaction mixture was diluted with EtOAc (800 mL) and water (100 mL) and stirred at r.t. for 15 min. The aqueous phase was separated and the organic phase was washed with water (3×150 mL) and brine (150 mL), dried over anh. $Na_2SO_4$, and concentrated under reduced pressure. The crude product was purified by silica gel column flash chromatography using a mixture of petroleum ether and EtOAc as eluent (1:0→40:1) to give 62 (1.46 g) in 91% yield as colorless oil.

$^1$H-NMR (400 MHz, $CDCl_3$): δ=5.17-5.10 (m, 1H), 2.60-2.54 (m, 2H), 2.17-2.04 (m, 11H), 1.89-1.74 (m, 2H), 1.72-1.48 (m, 8H), 1.26 (s, 3H), 1.06 (s, 9H), 0.13 ppm (s, 6H).

Step e. Synthesis of 4-bromo-1-((S)-6-((tert-butyldimethylsilyl)oxy)-2,5,7,8-tetramethyl-chroman-2-yl)-4-methylpentan-3-ol (63)

To a solution of 62 (1.46 g, 3.63 mmol) in THF (43 mL) and $H_2O$ (15.9 mL) at 0° C. dropwise was added solution of N-bromosuccinimide (710 mg, 3.99 mmol) in THF (12.9 mL). After the reaction mixture was stirred for 2 hrs. at 0° C., the reaction mixture was quenched by the addition of $Et_2O$ (300 mL) and water (100 mL) and the resulting mixture was stirred at r.t. for 15 min. The organic phase was separated and the aqueous phase was extracted with $Et_2O$ (2×100 mL). The combined organic phases were washed with brine (80 mL) and dried over anh. $Na_2SO_4$. After evaporation of the solvent under reduced pressure, crude product was purified by silica gel column flash chromatography using a mixture of petroleum ether and EtOAc as eluent (1:0→20:1) to give 63 (1.49 g) in 82% yield as colorless oil.

¹H-NMR (400 MHz, CDCl₃): δ=4.08-3.94 (m, 1H), 2.63-2.54 (m, 2H), 2.22-2.01 (m, 11H), 1.97-1.58 (m, 5H), 1.41-1.31 (m, 6H), 1.27-1.22 (m, 3H), 1.05 (s, 9H), 0.12 (s, 6H).

Step f. Synthesis of tert-butyl(((2S)-2-(2-(3,3-dimethyloxiran-2-yl)ethyl)-2,5,7,8-tetramethyl-chroman-6-yl)oxy)dimethylsilane (64)

To a solution of 63 (1.40 g, 2.80 mmol) in MeOH (25 mL) was added K₂CO₃ (774 mg, 5.60 mmol) and the resulting mixture was stirred at r.t. for 1.5 hrs. Then, the reaction mixture was quenched by the addition of water (200 mL), and the resulting aqueous phase was extracted with Et₂O (3×200 mL). The combined organic phases were washed with brine (100 mL), dried over anh. Na₂SO₄, and concentrated under reduced pressure to give crude 64 (1.1 g) in 94% yield, which was used in the next step without further purification.

¹H-NMR (400 MHz, CDCl₃): δ=2.78-2.69 (m, 1H), 2.63-2.54 (m, 2H), 2.13-2.03 (m, 9H), 1.89-1.55 (m, 6H), 1.34-1.20 (m, 9H), 1.05 (s, 9H), 0.12 ppm (s, 6H).

Step g. Synthesis of (S)-3-(6-((tert-butyldimethylsilyl)oxy)-2,5,7,8-tetramethylchroman-2-yl)propanal (65)

A stirred mixture of 64 (1.07 g, 2.56 mmol), THF (16 mL), and water (3.2 mL) at 0° C. was sequentially treated with sodium periodate (329 mg, 1.54 mmol) and periodic acid (643 mg, 2.82 mmol). The resulting mixture was stirred at 0° C. for 10 min. and, then, warmed to room temperature. After 1 hr., the reaction mixture was quenched by the addition of saturated aqueous sodium bicarbonate solution (60 mL) and diethyl ether (100 mL) and the resulting mixture was stirred at r.t. for 5 min. The biphasic layers were separated and the aqueous layer was extracted with diethyl ether (2×100 mL). The combined organic layers were washed with brine (80 mL), dried over anh. Na₂SO₄, filtered and concentrated under reduced pressure to give crude 65 (0.96 g) in 99% yield. This material was used in the next step without further purification.

¹H-NMR (400 MHz, CDCl₃): δ=9.80 (t, J=1.7 Hz, 1H), 2.65-2.55 (m, 3H), 2.13-1.99 (m, 10H), 1.93-1.75 (m, 2H), 1.32-1.12 (m, 5H), 1.05 (s, 9H), 0.12 ppm (s, 6H).

Step h. Synthesis of (R)-tert-butyl((2-(4,4-difluorobut-3-en-1-yl)-2,5,7,8-tetramethylchroman-6-yl)oxy)dimethylsilane (66)

To a mixture of 65 (0.9 g, 2.39 mmol), sodium 2-chloro-2,2-difluoroacetate (30, 729 mg, 4.78 mmol), and PPh₃ (1.25 g, 4.78 mmol) under argon was added dry DMF (4.9 mL) and the reaction mixture was stirred at 105° C. for 2 hrs. After cooling in ice bath, water (5.0 mL) was added slowly. Then, the resulting mixture was diluted by water (80 mL) and Et₂O (400 mL) and stirred at r.t. for 5 min. The aqueous phase was separated and the organic phase was washed with water (3×60 mL) and brine (60 mL). After drying over anh. Na₂SO₄, the volatile matters were removed under reduced pressure and the crude product was purified by silica gel column flash chromatography using a mixture of petroleum ether and EtOAc as eluent (1:0→100:1) to give 66 (0.68 g) together with approximately 1.1 equiv. of PPh₃ in 42% yield. The obtained product was used in the next step without further purification.

¹H-NMR (400 MHz, CDCl₃): δ=4.22-4.09 (m, 1H), 2.61-2.53 (m, 2H), 2.19-2.02 (m, 11H), 1.87-1.51 (m, 4H), 1.25 (s, 3H), 1.05 (s, 9H), 0.12 ppm (s, 6H).

Step i. Synthesis of (R)-2-(4,4-difluorobut-3-en-1-yl)-2,5,7,8-tetramethylchroman-6-ol (67)

A solution of 67 containing approximately 1.1 equiv. of PPh₃ (0.68 g, approx. 1.07 mmol) in dry THF (20 mL) was cooled in ice bath while 1 M tetra-n-butylammonium fluoride solution in THF (1.7 mL, 1.1 mmol) was added dropwise. The reaction mixture was stirred at 0° C. for 30 min. After completion of the reaction (TLC), cooled (ice bath) reaction mixture was quenched by the addition of Et₂O (150 mL) and water (80 mL) and the resulting mixture was stirred at r.t. for 5 min. Then, organic phase was separated and the aqueous phase was extracted with diethyl ether (2×100 mL). The combined organic phases were washed with brine (60 mL), dried over anh. Na₂SO₄, and concentrated under reduced pressure. The crude product was purified by silica gel flash column chromatography (petroleum ether/EtOAc 1:0→50:1) to give 67 (257 mg) in 81% yield.

¹H-NMR (400 MHz, CDC₃): δ=4.26-4.09 (m, 2H), 2.67-2.59 (m, 2H), 2.21-2.08 (m, 11H), 1.88-1.66 (m, 3H), 1.65-1.53 (m, 1H), 1.25 ppm (s, 3H). MS: 296.1.

Step j. Synthesis of (R)-2-(7,7-difluoro-3-hydroxy-3-methylhept-6-en-1-yl)-3,5,6-trimethylcyclo-hexa-2,5-diene-1,4-dione (Compound I)

To a cooled (ice bath) solution of 67 (160 mg, 0.540 mmol) in ⁱPrOAc (6.7 mL) was added solution of ammonium cerium(IV) nitrate (888 mg, 1.62 mmol) in water (1.6 mL) and the reaction mixture was stirred at r.t. for 25 min. After cooling to 0° C., the reaction mixture was quenched by the addition of brine (30 mL) and EtOAc (150 mL). The resulting mixture was stirred at r.t. for 5 min. Then, aqueous phase was separated and the organic phase was washed with water (30 mL) and brine (30 mL), dried over anh. Na₂SO₄ and concentrated under reduced pressure. The crude product was purified by silica gel flash column chromatography using a mixture of petroleum ether and EtOAc (1:0→10:1) as an eluent and re-purified by reversed phase flash chromatography (100% MeCN) to give Compound I (122 mg) in 72% yield.

¹H-NMR (CDCl₃, 400 MHz): δ=4.24-4.11 (m, 1H), 2.58-2.50 (m, 2H), 2.14-1.97 (m, 11H), 1.62-1.46 (m, 4H), 1.25 ppm (s, 3H). MS (M+H⁺): 313.1622.

Example 12: Synthesis of 2-((S,6E,10E)-15,15-difluoro-3-hydroxy-3,7,11-trimethylpentadeca-6,10,14-trien-1-yl)-3,5,6-trimethylcyclohexa-2,5-diene-1,4-dione (Compound J)

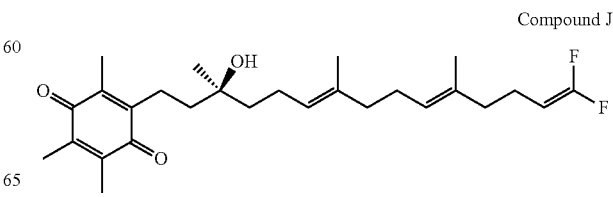

Compound J

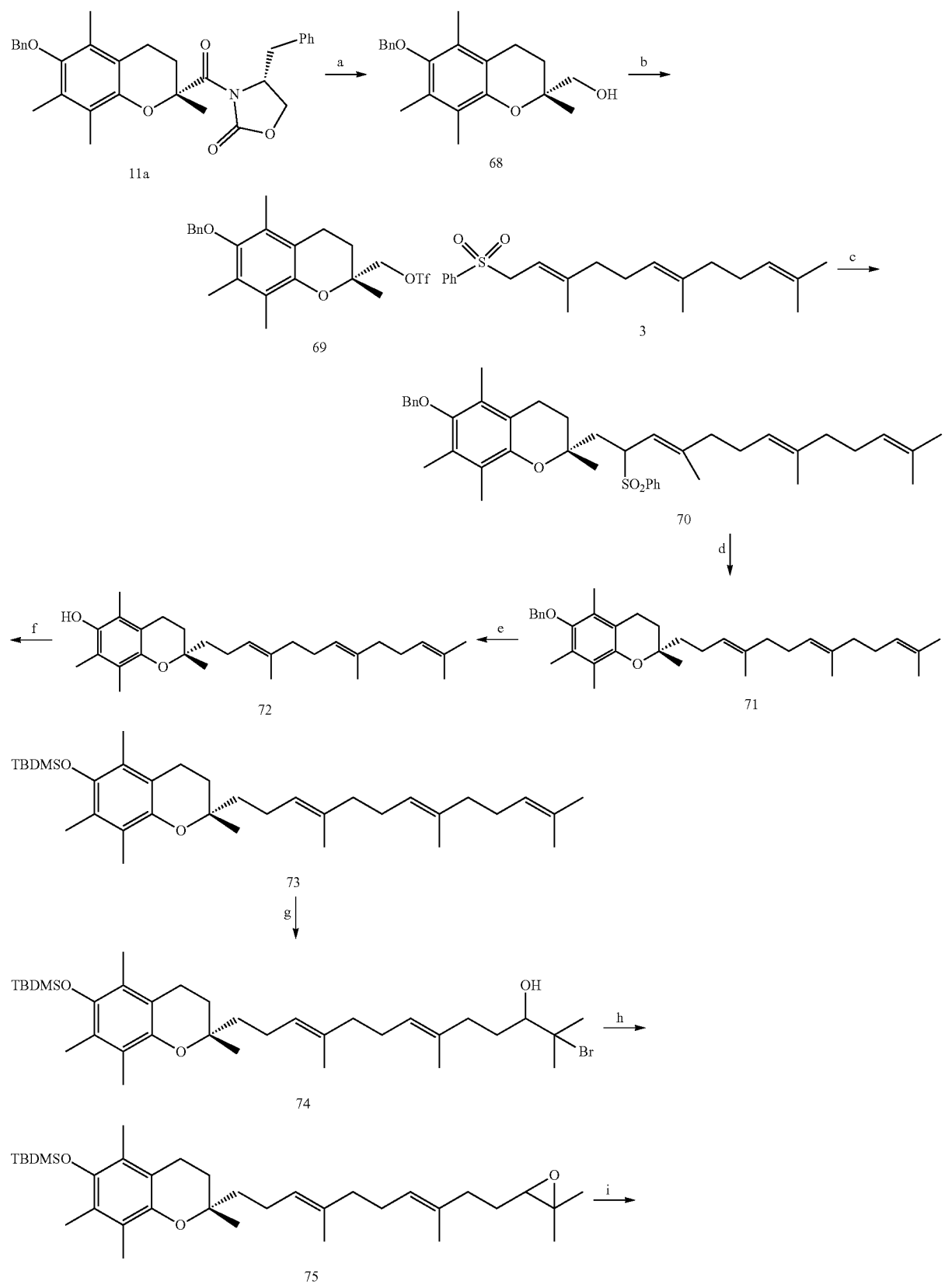
Scheme 15

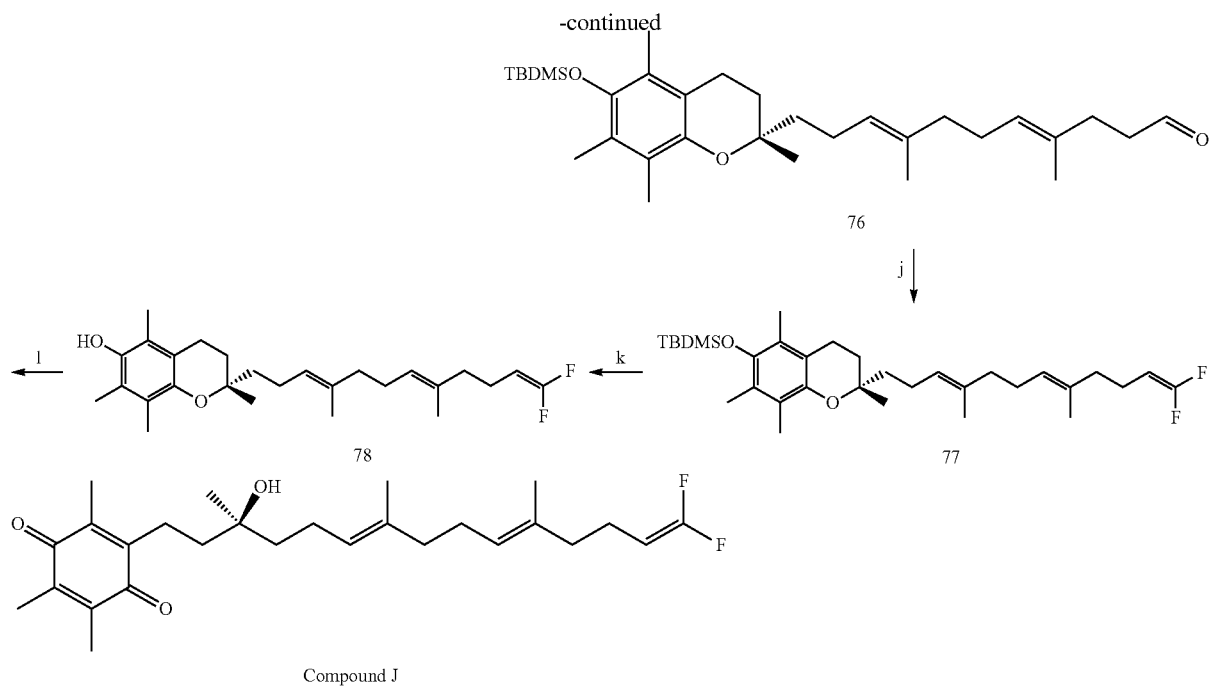

Compound J

Step a. Synthesis of (R)-(6-(benzyloxy)-2,5,7,8-tetramethylchroman-2-yl)methanol (68)

To a cooled (0° C.) solution of 11a (38.6 g, 77.35 mmol) in dry THF (300 mL) dropwise was added lithium aluminum hydride solution in THF (1 M, 155 mL, 154.7 mmol) and the reaction mixture was stirred at 0° C. for 1 hr. Under continuous cooling, ethanol was added dropwise until excess of lithium aluminum hydride was quenched. Then, 1 M aq. NaOH (615 mL) was added dropwise and stirred at r.t. for 15 min. After re-cooling to 0° C., 1M aq. HCl was added until the resulting mixture reached about pH 4. Then, DCM (700 mL) was added and the resulting mixture was stirred at r.t. for 15 min. After separation of the organic phase, the aqueous phase was extracted with DCM (2×350 mL). The combined organic phases were washed with brine (300 mL), dried over anh. $Na_2SO_4$ and concentrated under reduced pressure. The crude product was purified by silica gel flash column chromatography using a mixture of petroleum ether and EtOAc (1:0-40:7) as an eluent to give 68 (23 g) in 92% yield.
$^1$H-NMR ($CDCl_3$, 400 MHz): δ=7.52-7.49 (m, 2H), 7.43-7.32 (m, 3H), 4.70 (s, 2H), 3.69-3.59 (m, 2H), 2.69-2.63 (m, 2H), 2.23 (s, 3H), 2.18 (s, 3H), 2.11 (s, 3H), 2.05 (s, 3H).

Step b. Synthesis of (R)-(6-(benzyloxy)-2,5,7,8-tetramethylchroman-2-yl)methyl trifluoromethanesulfonate (69)

To a solution of 68 (22 g, 67.0 mmol) in dry DCM (100 mL) was added pyridine (8.15 mL, 100.0 mmol). After cooling to 0° C., trifluoromethanesulfonic anhydride (13.52 mL, 80.0 mmol) was added dropwise and the reaction mixture was stirred at 0° C. for 2 hrs. The reaction mixture was quenched by the addition of ice (200 g) and allowed to warm to r.t. Then, EtOAc (900 mL) and water (300 mL) were added and the resulting mixture was stirred at r.t. for 15 min. The aqueous phase was separated and the organic phase was washed with brine (2×350 mL) and dried over anh. $Na_2SO_4$. After removal of volatile matters, 69 (29.4 g) was obtained in 96% yield.
$^1$H-NMR ($CDCl_3$, 400 MHz): δ=7.52-7.51 (m, 2H), 7.44-7.32 (m, 3H), 4.70 (s, 2H), 4.51-4.42 (m, 2H), 2.70-2.65 (m, 2H), 2.23 (s, 3H), 2.18 (s, 3H), 2.10 (s, 3H), 2.03-1.96 (m, 1H), 1.91-1.82 (m, 1H), 1.38 ppm (s, 3H).

Step c. Synthesis of (2S)-6-(benzyloxy)-2,5,7,8-tetramethyl-2-((3E,7E)-4,8,12-trimethyl-2-(phenylsulfonyl)trideca-3,7,11-trien-1-yl)chromane (70)

To a solution of 3 (5.30 g, 15.3 mmol) in dry THF (50 mL) under argon was added hexamethylphosphoramide (12.7 mmol) and the resulting mixture was cooled to −78° C. Then, $^n$BuLi (2.3 M in hexanes, 5.0 mL, 11.5 mmol) was added dropwise and the reaction mixture was stirred at the same temperature for 30 min. After dropwise addition of 69 (4.38 g, 9.56 mmol) solution in dry THF (50 mL), the reaction mixture was stirred at −78° C. for 8 hrs. and stirring was continued at r.t. for 20 hrs. The reaction mixture was diluted with $Et_2O$ (500 mL), washed with brine (2×100 mL), dried over anh. $Na_2SO_4$ and concentrated under reduced pressure. The crude product was purified by silica gel flash column chromatography using a mixture of petroleum ether and EtOAc (1:0→20:3) as an eluent to give 70 (7.2 g) as a mixture of diastereomers.
$^1$H-NMR ($CDCl_3$, 400 MHz): δ=7.89-7.71 (m, 4H), 7.67-7.28 (m, 16H), 5.23-4.96 (m, 6H), 4.68 (s, 2H), 4.20-3.99 (m, 2H), 2.64-2.45 (m, 4H), 2.23-1.45 (m, 6H), 1.34-1.09 ppm (m, 16H).

Step d. Synthesis of (R)-6-(Benzyloxy)-2,5,7,8-tetramethyl-2-((3E,7E)-4,8,12-trimethyltrideca-3,7,11-trien-1-yl)chromane (71)

To a mixture of 70 (7.2 g, 10.99 mmol) and $PdCl_2$dppp (643 mg, 1.09 mmol) under argon was added dry THF (350 mL) and the resulting suspension was cooled to 0° C. Then, LiEt$_3$BH (1.7 M in THF, 19.39 mL, 32.97 mmol) was added dropwise and the reaction mixture was stirred at 0° C. for 5 hrs. and overnight at r.t. The reaction mixture was diluted with Et$_2$O (700 mL) and successively washed with 1 M aq. NaCN (100 mL), water (100 mL), and brine (100 mL). After drying over anh. Na$_2$SO$_4$, the volatile matters were removed under reduced pressure and the crude product was purified by silica gel flash column chromatography using a mixture of petroleum ether and EtOAc (1:0→50:1) as an eluent to give 71 (4.8 g).

$^1$H-NMR (CDCl$_3$, 400 MHz): δ=7.53-7.47 (m, 2H), 7.43-7.30 (m, 3H), 5.18-5.06 (m, 3H), 4.70 (s, 2H), 2.64-2.57 (m, 2H), 2.22 (s, 3H), 2.19-2.02 (m, 12H), 2.02-1.92 (m, 4H), 1.89-1.73 (m, 2H), 1.70-1.52 (m, 14H), 1.27 ppm (s, 3H).

Step e. Synthesis of (S)-2,5,7,8-tetramethyl-2-((3E,7E)-4,8,12-trimethyltrideca-3,7,11-trien-1-(1-yl)chroman-6-ol (72)

To a cooled (0° C.) suspension of lithium (1.53 g, 219 mmol) in n-propylamine (100 mL) and diethylether (60 mL) under argon was added solution of 71 (4.8 g, 7.32 mmol) in diethylether (40 mL) and the reaction mixture was stirred at r.t. for 3 hrs. After re-cooling to 0° C., the reaction mixture was carefully quenched by the addition of sat. aq. NH$_4$C$_1$ (50 mL) and methanol (50 mL). The organic solvents were removed under reduced pressure at r.t. and the residue was diluted with water (50 mL) and extracted with diethylether (3×250 mL). The combined organic phases were washed with brine (50 mL), dried over anh. Na$_2$SO$_4$ and concentrated under reduced pressure. The crude product was purified by silica gel flash column chromatography using a mixture of petroleum ether and EtOAc (1:0→20:1) as an eluent to give 72 (3.5 g) in 93% yield.

$^1$H-NMR (CDCl$_3$, 400 MHz): δ=5.16-5.07 (m, 3H), 4.17 (br s, 1H), 2.63-2.60 (m, 2H), 2.16-1.95 (m, 19H), 1.87-1.73 (m, 2H), 1.68-1.10 (m, 14H), 1.25 ppm (s, 3H).

Step f. Synthesis of tert-butyldimethyl(((S)-2,5,7,8-tetramethyl-2-((3E,7E)-4,8,12-trimethyltrideca-3,7,11-trien-1-yl)chroman-6-yl)oxy)silane (73)

A solution of TBDMSCl (5.59 g, 37.14 mmol) in dry DMF (15.0 mL) was added to a cooled (0° C.) solution of 72 (3.5 g, 8.25 mmol) and imidazole (5.0 g, 74.3 mmol) in dry DMF (13 mL) and the reaction mixture was stirred at r.t. for 20 hrs. Then, the reaction mixture was diluted with EtOAc (650 mL) and water (120 mL) and stirred at r.t. for 15 min. The aqueous phase was separated and the organic phase was washed with water (3×120 mL) and brine (150 mL), dried over anh. Na$_2$SO$_4$, and concentrated under reduced pressure. The crude product was purified by silica gel column flash chromatography using a mixture of petroleum ether and EtOAc as eluent (1:0→50:1) to give 73 (3.89 g) in 88% yield as colorless oil.

$^1$H-NMR (400 MHz, CDCl$_3$): δ=5.16-5.07 (m, 3H), 2.58-2.54 (m, 2H), 2.15-2.04 (m, 15H), 1.99-1.95 (m, 4H), 1.87-1.73 (m, 2H), 1.68-1.49 (m, 14H), 1.25 (s, 3H), 1.05 (s, 9H), 0.11 ppm (s, 6H).

Step g. Synthesis of (6E,10E)-2-bromo-13-((S)-6-((tert-butyldimethylsilyl)oxy)-2,5,7,8-tetramethylchroman-2-yl)-2,6,10-trimethyltrideca-6,10-dien-3-ol (74)

To a solution of 73 (3.8 g, 7.05 mmol) in THF (60 mL) and H$_2$O (24 mL) at 0° C. dropwise was added solution of N-bromosuccinimide (1.25 g, 7.05 mmol) in THF (15 mL). After the reaction mixture was stirred for 2 hrs. at 0° C., the reaction mixture was quenched with Et$_2$O (400 mL) and water (150 mL) and the resulting mixture was stirred at r.t. for 15 min. The organic phase was separated and the aqueous phase was extracted with Et$_2$O (2×200 mL). The combined organic phases were washed with brine (150 mL) and dried over anh. Na$_2$SO$_4$. After evaporation of the solvent under reduced pressure, crude product was purified by silica gel column flash chromatography using a mixture of petroleum ether and EtOAc as eluent (1:0-100:3) to give 74 (2.4 g) in 53% yield as colorless oil.

$^1$H-NMR (400 MHz, CDCl$_3$): δ=5.22-5.10 (m, 2H), 4.00-3.94 (m, 1H), 2.60-2.52 (m, 2H), 2.36-2.25 (m, 1H), 2.18-1.91 (m, 18H), 1.87-1.72 (m, 3H), 1.69-1.47 (m, 9H), 1.34 (s, 3H), 1.32 (s, 3H), 1.25 (s, 3H), 1.04 (s, 9H), 0.11 ppm (s, 6H).

Step h. Synthesis of tert-butyl(((2S)-2-((3E,7E)-10-(3,3-dimethyloxiran-2-yl)-4,8-dimethyldeca-3,7-dien-1-yl)-2,5,7,8-tetramethylchroman-6-yl)oxy)dimethylsilane (75)

To a solution of 74 (2.4 g, 3.77 mmol) in MeOH (30 mL) was added K$_2$CO$_3$ (1.04 g, 7.54 mmol) and the resulting mixture was stirred at r.t. for 1.5 hrs. Then, the reaction mixture was quenched by the addition of water (100 mL), and the resulting aqueous phase was extracted with Et$_2$O (3×150 mL). The combined organic phases were washed with brine (100 mL), dried over anh. Na$_2$SO$_4$, and concentrated under reduced pressure to give crude 75 (2 g) in 95% yield, which was used in the next step without further purification.

$^1$H-NMR (400 MHz, CDCl$_3$): δ=5.16-5.11 (m, 2H), 2.71-2.68 (m, 1H), 2.58-2.54 (m, 2H), 2.17-2.06 (m, 15H), 1.99-1.95 (m, 2H), 1.84-1.75 (m, 2H), 1.66-1.54 (m, 10H), 1.30 (s, 3H), 1.25 (s, 3H), 1.24 (s, 3H), 1.04 (s, 9H), 0.11 ppm (s, 6H).

Step i. Synthesis of (4E,8E)-11-((S)-6-((tert-butyldimethylsilyl)oxy)-2,5,7,8-tetramethylchroman-2-yl)-4,8-dimethylundeca-4,8-dienal (76)

A stirred mixture of 75 (2 g, 3.6 mmol), THF (20 mL), and water (4.0 mL) at 0° C. was sequentially treated with sodium periodate (460 mg, 2.1 mmol) and periodic acid (900 mg, 3.96 mmol). The resulting mixture was stirred at 0° C. for 10 min. and, then, warmed to room temperature. After 1 hrs., the reaction mixture was quenched by the addition of saturated aqueous sodium bicarbonate solution (110 mL) and the resulting mixture was stirred at r.t. for 5 min. The biphasic layers were separated and the aqueous layer was extracted with diethyl ether (3×200 mL). The combined organic layers were washed with brine (80 mL), dried over anh. Na$_2$SO$_4$, filtered and concentrated under reduced pressure. The crude 76 (1.8 g) was used in the next step without further purification.

$^1$H-NMR (400 MHz, CDCl$_3$): δ=9.73 (t, $^3$J$_{(H,H)}$=1.9 Hz, 1H), 5.15-5.10 (m, 2H), 2.58-2.47 (m, 4H), 2.32-2.28 (m, 2H), 2.15-2.05 (m, 13H), 1.98-1.94 (m, 2H), 1.87-1.73 (m, 2H), 1.65-1.50 (m, 8H), 1.25 (s, 3H), 1.04 (s, 9H), 0.11 ppm (s, 6H).

Step j. Synthesis of tert-butyl(((S)-2-((3E,7E)-12,12-difluoro-4,8-dimethyldodeca-3,7,11-trien-1-yl)-2,5,7,8-tetramethylchroman-6-yl)oxy)dimethylsilane (77)

To a mixture of 76 (1.8 g, 3.51 mmol), sodium 2-chloro-2,2-difluoroacetate (30, 1.07 g, 7.02 mmol), and PPh$_3$ (1.83 g, 7.02 mmol) under argon was added dry DMF (7 mL) and the reaction mixture was stirred at 105° C. for 2 hrs. After cooling in ice bath, water (6.0 mL) was added slowly. Then, the resulting mixture was diluted by water (60 mL) and Et$_2$O (400 mL) and stirred at r.t. for 5 min. The aqueous phase was separated and the organic phase was washed with water (3×60 mL) and brine (60 mL). After drying over anh. Na$_2$SO$_4$, the volatile matters were removed under reduced pressure and the crude product was purified by silica gel column flash chromatography using a mixture of petroleum ether and EtOAc as eluent (1:0-200:2) to give 77 (0.91 g) together with approximately 1 equiv. of PPh$_3$ in 39% yield. The obtained product was used in the next step without further purification.

$^1$H-NMR (400 MHz, CDCl$_3$): δ=5.15-5.09 (m, 2H), 4.15-4.04 (m, 1H), 2.58-2.54 (m, 2H), 2.15-1.96 (m, 19H), 1.87-1.74 (m, 2H), 1.68-1.49 (m, 8H), 1.25 (s, 3H), 1.04 (s, 9H), 0.11 ppm (s, 6H).

Step k. Synthesis of (S)-2-((3E,7E)-12,12-difluoro-4,8-dimethyldodeca-3,7,11-trien-1-yl)-2,5,7,8-tetramethylchroman-6-ol (78)

A solution of 77 containing approximately 1.0 equiv. of PPh$_3$ (0.91 g) in dry THF (30 mL) was cooled in ice bath while 1 M tetra-n-butylammonium fluoride solution in THF (1.2 mL) was added dropwise. The reaction mixture was stirred at 0° C. for 2 hrs. After completion of the reaction (TLC), the cooled (ice bath) reaction mixture was quenched by the addition of Et$_2$O (150 mL) and water (50 mL) and the resulting mixture was stirred at r.t. for 5 min. Then, organic phase was separated and the aqueous phase was extracted with diethyl ether (2×100 mL). The combined organic phases were washed with brine (80 mL), dried over anh. Na$_2$SO$_4$, and concentrated under reduced pressure. The crude product was purified by silica gel flash column chromatography (petroleum ether/EtOAc 1:0→25:1) to give 78 (400 mg).

$^1$H-NMR (400 MHz, CDCl$_3$): δ=5.15-5.08 (m, 2H), 4.18 (s, 1H), 4.14-4.04 (m, 1H), 2.63-2.60 (m, 2H), 2.16-1.96 (m, 19H), 1.87-1.74 (m, 2H), 1.68-1.50 (m, 8H), 1.25 ppm (s, 3H).

Step 1. Synthesis of 2-((S,6E,10E)-15,15-difluoro-3-hydroxy-3,7,11-trimethylpentadeca-6,10,14-trien-1-yl)-3,5,6-trimethylcyclohexa-2,5-diene-1,4-dione (Compound J)

To a solution of 78 (400 mg, 0.925 mmol) in $^i$PrOAc (13.0 mL) at r.t. was added solution of ammonium cerium(IV) nitrate (1.5 g, 2.77 mmol) in water (3 mL) and the reaction mixture was stirred at r.t. for 25 min. After cooling to 0° C., the reaction mixture was quenched by the addition of brine (70 mL) and EtOAc (400 mL). The resulting mixture was stirred at r.t. for 5 min. Then, aqueous phase was separated and the organic phase was washed with brine (30 mL), dried over anh. Na$_2$SO$_4$ and concentrated under reduced pressure. The crude product was purified by silica gel flash column chromatography using a mixture of petroleum ether and EtOAc (1:0→10:1) as an eluent to give Compound J (326 mg) in 78% yield.

$^1$H-NMR (CDCl$_3$, 400 MHz): δ=5.17-5.09 (m, 2H), 4.15-4.04 (m, 1H), 2.57-2.53 (m, 2H), 2.12-1.98 (m, 19H), 1.63 (s, 3H), 1.59 (s, 3H), 1.57-1.48 (m, 4H), 1.25 ppm (s, 3H). MS (M+H$^+$): 449.2854.

Example 13: Synthesis of 2-((S,6E,10E)-15,15-difluoro-3-hydroxy-3,7,11-trimethylpentadeca-6,10, 14-trien-1-yl)-3,5,6-trimethylcyclohexa-2,5-diene-1, 4-dione (Compound K)

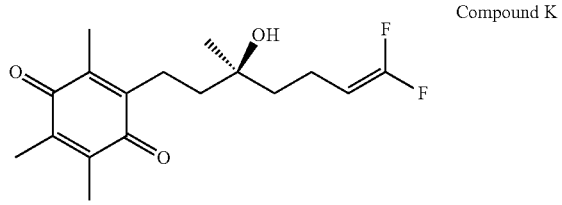 [SMILES: CC1=C(C)C(=O)C(CC[C@@](C)(O)CCC=C(F)F)=C(C)C1=O]

Compound K

Scheme 16

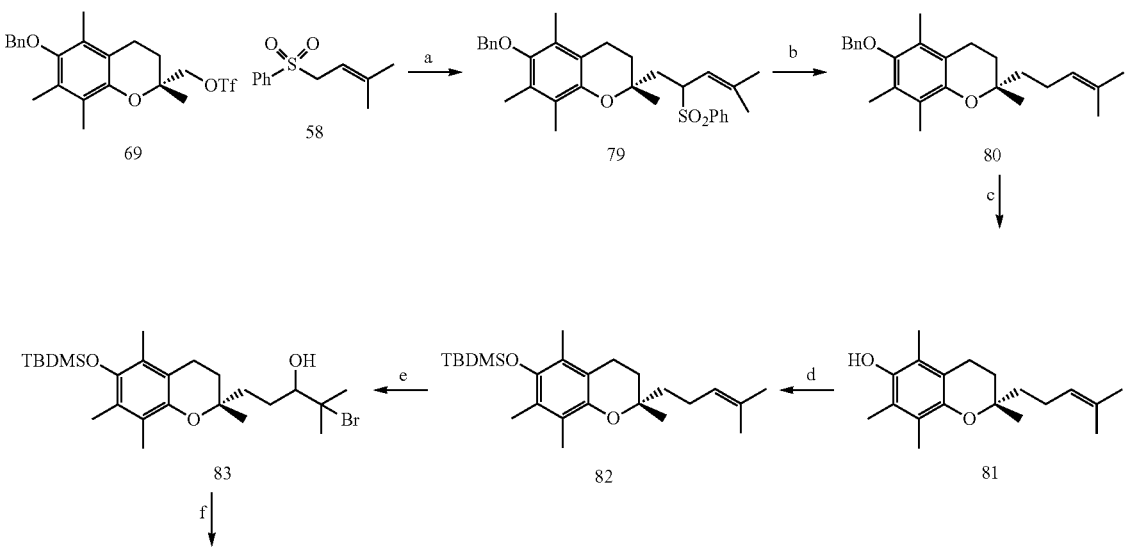

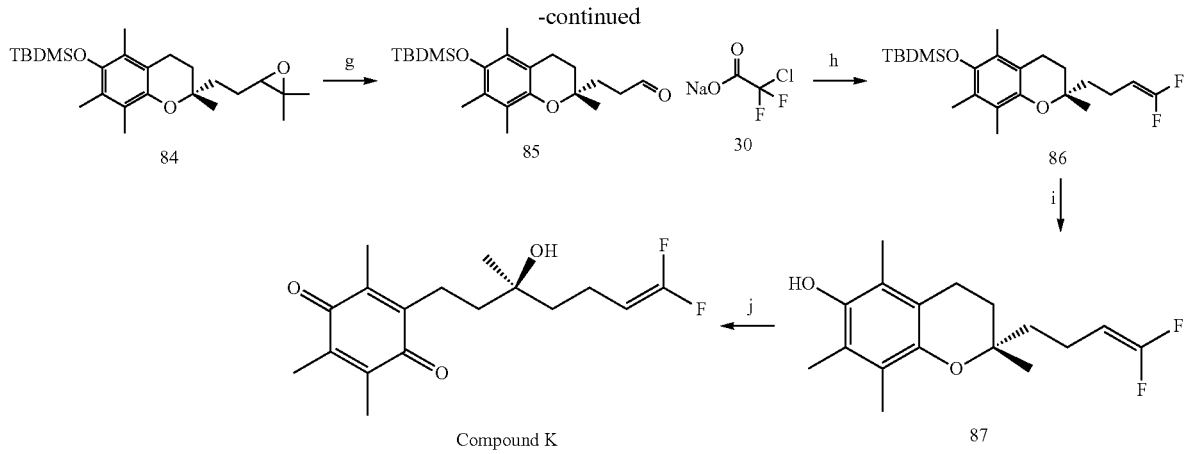

Compound K

Step a. Synthesis of (2R)-6-(benzyloxy)-2,5,7,8-tetramethyl-2-(4-methyl-2-(phenylsulfonyl)pent-3-en-1-yl)chromane (79)

To a solution of 58 (3.21 g, 15.3 mmol) in dry THF (60 mL) under argon was added hexamethylphosphoramide (15.9 mmol) and the resulting mixture was cooled to −78° C. Then, "BuLi (2.3 M in hexanes, 5.4 mL, 12.4 mmol) was added dropwise and the reaction mixture was stirred at the same temperature for 30 min. After dropwise addition of 69 (4.38 g, 9.56 mmol) solution in dry THF (60 mL), the reaction mixture was stirred at −78° C. for 8 hrs. and stirring was continued at r.t. for 20 hrs. The reaction mixture was diluted with Et₂O (800 mL), washed with water (2×150 mL), brine (150 mL), dried over anh. Na₂SO₄ and concentrated under reduced pressure. The crude product was purified by silica gel flash column chromatography using a mixture of petroleum ether and EtOAc (1:0→5:1) as an eluent to give 79 (6 g) as a mixture of diastereomers, containing premix of the remaining 58 (about 1.3 equiv.). This material was used in the next step without further purification.

Step b. Synthesis of (S)-6-(benzyloxy)-2,5,7,8-tetramethyl-2-(4-methylpent-3-en-1-yl)chromane (80)

To a mixture of 79 (containing approx. 1.3 equivalents of 58) (6 g, approx. 11.6 mmol) and PdCl₂dppp (680 mg, 1.15 mmol) under argon was added dry THF (100 mL) and the resulting suspension was cooled to 0° C. Then, LiEt₃BH (1.7 M in THF, 20.4 mL, 34.7 mmol) was added dropwise and the reaction mixture was stirred at 0° C. for 5 hrs. and overnight at r.t. The reaction mixture was diluted with Et₂O (800 mL) and successively washed with 1 M aq. NaCN (100 mL), water (100 mL), and brine (100 mL). After drying over anh. Na₂SO₄, the volatile matters were removed under reduced pressure and the crude product was purified by silica gel flash column chromatography using a mixture of petroleum ether and EtOAc (1:0→40:1) as an eluent to give 80 (2.2 g).

$^1$H-NMR (CDCl₃, 400 MHz): δ=7.52-7.50 (m, 2H), 7.43-7.39 (m, 2H), 7.36-7.32 (m, 1H), 5.16-5.12 (m, 1H), 4.70 (s, 2H), 2.63-2.59 (m, 2H), 2.23 (s, 3H), 2.17-2.10 (m, 8H), 1.89-1.75 (m, 2H), 1.69-1.53 (m, 8H), 1.27 ppm (s, 3H).

Step c. Synthesis of (S)-2,5,7,8-tetramethyl-2-(4-methylpent-3-en-1-yl)chroman-6-ol (81)

To a cooled (0° C.) suspension of lithium (1.2 g, 174 mmol) in n-propylamine (50 mL) and diethylether (20 mL) under argon was added solution of 80 (2.2 g, 5.8 mmol) in diethylether (30 mL) and the reaction mixture was stirred at r.t. for 3 hrs. After re-cooling to 0° C., the reaction mixture was carefully quenched by the addition of sat. aq. NH₄Cl (30 mL) and methanol (30 mL). The organic solvents were removed under reduced pressure at r.t. and the residue was diluted with water (100 mL) and extracted with diethylether (3×200 mL). The combined organic phases were washed with brine (100 mL), dried over anh. Na₂SO₄ and concentrated under reduced pressure. The crude product was purified by silica gel flash column chromatography using a mixture of petroleum ether and EtOAc (1:0→40:3) as an eluent to give 81 (1.55 g) in 92% yield. $^1$H-NMR (CDCl₃, 400 MHz): δ=5.14-5.10 (m, 1H), 4.17 (s, 1H), 2.63-2.60 (m, 2H), 2.16-2.09 (m, 11H), 1.87-1.73 (m, 2H), 1.68-1.50 (m, 8H), 1.25 ppm (s, 3H).

Step d. Synthesis of (S)-tert-butyldimethyl((2,5,7,8-tetramethyl-2-(4-methylpent-3-en-1-yl)chroman-6-yl)oxy)silane (82)

A solution of TBDMSCl (2.9 g, 19.5 mmol) in dry DMF (10 mL) was added to a cooled (0° C.) solution of 81 (1.25 g, 4.33 mmol) and imidazole (2.65 g, 38.9 mmol) in dry DMF (7 mL) and the reaction mixture was stirred at r.t. for 20 hrs. Then, the reaction mixture was diluted with EtOAc (700 mL) and water (100 mL) and stirred at r.t. for 15 min. The aqueous phase was separated and the organic phase was washed with water (3×150 mL) and brine (150 mL), dried over anh. Na₂SO₄, and concentrated under reduced pressure. The crude product was purified by silica gel column flash chromatography using a mixture of petroleum ether and EtOAc as eluent (1:0→40:1) to give 82 (1.55 g) in 89% yield as colorless oil.

$^1$H-NMR (400 MHz, CDCl₃): δ=5.14-5.10 (m, 1H), 2.58-2.54 (m, 2H), 2.14-2.05 (m, 11H), 1.86-1.73 (m, 2H), 1.67-1.48 (m, 8H), 1.25 (s, 3H), 1.05 (s, 9H), 0.11 ppm (s, 6H).

Step e. Synthesis of 4-bromo-1-((R)-6-((tert-butyldimethylsilyl)oxy)-2,5,7,8-tetramethylchroman-2-yl)-4-methylpentan-3-ol (83)

To a solution of 82 (1.55 g, 3.72 mmol) in THF (30 mL) and H₂O (12 mL) at 0° C. dropwise was added solution of N-bromosuccinimide (660 mg, 3.72 mmol) in THF (10 mL). After the reaction mixture was stirred for 2 h at 0° C., the reaction mixture was quenched by the addition of Et$_2$O (300 mL) and water (100 mL) and the resulting mixture was stirred at r.t. for 15 min. The organic phase was separated and the aqueous phase was extracted with Et$_2$O (2×100 mL). The combined organic phases were washed with brine (80 mL) and dried over anh. Na$_2$SO$_4$. After evaporation of the solvent under reduced pressure, crude product was purified by silica gel column flash chromatography using a mixture of petroleum ether and EtOAc as eluent (1:0-20:1) to give 83 (1.25 g) in 67% yield as colorless oil.

$^1$H-NMR (400 MHz, CDCl$_3$): δ=4.06-3.96 (m, 1H), 2.60-2.57 (m, 2H), 2.16-2.05 (m, 11H), 1.93-1.61 (m, 5H), 1.38-1.33 (m, 6H), 1.23-1.22 (m, 3H), 1.04 (s, 9H), 0.12 (s, 6H).

Step f. Synthesis of tert-butyl(((2R)-2-(2-(3,3-dimethyloxiran-2-yl)ethyl)-2,5,7,8-tetramethyl-chroman-6-yl)oxy)dimethylsilane (84)

To a solution of 83 (1.19 g, 2.52 mmol) in MeOH (25 mL) was added K$_2$CO$_3$ (689 mg, 5.04 mmol) and the resulting mixture was stirred at r.t. for 1.5 hrs. Then, the reaction mixture was quenched with water (200 mL), and the resulting aqueous phase was extracted with Et$_2$O (3×200 mL). The combined organic phases were washed with brine (100 mL), dried over anh. Na$_2$SO$_4$, and concentrated under reduced pressure to give crude 84 (1.1 g) in 96% yield, which was used in the next step without further purification.

$^1$H-NMR (400 MHz, CDCl$_3$): δ=2.76-2.70 (m, 1H), 2.59-2.55 (m, 2H), 2.09-2.05 (m, 9H), 1.86-1.58 (m, 6H), 1.30-1.22 (m, 9H), 1.04 (s, 9H), 0.12 ppm (s, 6H).

Step g. Synthesis of (R)-3-(6-((tert-butyldimethylsilyl)oxy)-2,5,7,8-tetramethylchroman-2-yl)propanal (85)

A stirred mixture of 84 (1 g, 2.38 mmol), THF (15 mL), and water (3 mL) at 0° C. was sequentially treated with sodium periodate (300 mg, 1.43 mmol) and periodic acid (590 mg, 2.22 mmol). The resulting mixture was stirred at 0° C. for 10 min. and then warmed to room temperature. After 1 hr., the reaction mixture was quenched by the addition of saturated aqueous sodium bicarbonate solution (60 mL) and diethyl ether (100 mL) and the resulting mixture was stirred at r.t. for 5 min. The biphasic layers were separated and the aqueous layer was extracted with diethyl ether (2×100 mL). The combined organic layers were washed with brine (80 mL), dried over anh. Na$_2$SO$_4$, filtered and concentrated under reduced pressure to give crude 85 (0.9 g) in 94% yield. This material was used in the next step without further purification.

$^1$H-NMR (400 MHz, CDCl$_3$): δ=9.79 (t, J=1.7 Hz, 1H), 2.64-2.55 (m, 3H), 2.09-1.99 (m, 10H), 1.91-1.77 (m, 2H), 1.26-1.20 (m, 5H), 1.04 (s, 9H), 0.11 ppm (s, 6H).

Step h. Synthesis of (S)-tert-butyl((2-(4,4-difluorobut-3-en-1-yl)-2,5,7,8-tetramethylchroman-6-yl)oxy)dimethylsilane (86)

To a mixture of 85 (0.9 g, 2.22 mmol), sodium 2-chloro-2,2-difluoroacetate (30, 676 mg, 4.44 mmol), and PPh$_3$ (1.16 g, 4.44 mmol) under argon was added dry DMF (4.9 mL) and the reaction mixture was stirred at 105° C. for 2 hrs. After cooling in ice bath, water (5.0 mL) was added slowly. Then, the resulting mixture was diluted by water (80 mL) and Et$_2$O (400 mL) and stirred at r.t. for 5 min. The aqueous phase was separated and the organic phase was washed with water (3×60 mL) and brine (60 mL). After drying over anh. Na$_2$SO$_4$, the volatile matters were removed under reduced pressure and the crude product was purified by silica gel column flash chromatography using a mixture of petroleum ether and EtOAc as eluent (1:0→100:1) to give 86 (0.396 g) together with approximately 3 equiv. of PPh$_3$ in 28% yield. The obtained product was used in the next step without further purification.

$^1$H-NMR (400 MHz, CDCl$_3$): δ=4.21-4.10 (m, 1H), 2.59-2.50 (m, 2H), 2.18-2.04 (m, 11H), 1.86-1.67 (m, 4H), 1.25 (s, 3H), 1.05 (s, 9H), 0.12 ppm (s, 6H).

Step i. Synthesis of (S)-2-(4,4-difluorobut-3-en-1-yl)-2,5,7,8-tetramethylchroman-6-ol (87)

A solution of 86 containing approximately 3 equiv. of PPh$_3$ (0.396 g) in dry THF (20 mL) was cooled in ice bath while 1 M tetra-n-butylammonium fluoride solution in THF (0.8 mL) was added dropwise. The reaction mixture was stirred at 0° C. for 30 min. After completion of the reaction (TLC), cooled (ice bath) reaction mixture was quenched by the addition of Et$_2$O (150 mL) and water (80 mL) and the resulting mixture was stirred at r.t. for 5 min. Then, organic phase was separated and the aqueous phase was extracted with diethyl ether (2×100 mL). The combined organic phases were washed with brine (60 ml), dried over anh. Na$_2$SO$_4$, and concentrated under reduced pressure. The crude product was purified by silica gel flash column chromatography (petroleum ether/EtOAc 1:0→50:1) to give 87 (110 mg).

$^1$H-NMR (400 MHz, CDCl$_3$): δ=4.21-4.10 (m, 2H), 2.64-2.60 (m, 2H), 2.22-2.08 (m, 11H), 1.85-1.77 (m, 3H), 1.62-1.58 (m, 1H), 1.24 ppm (s, 3H).

1) Step j. Synthesis of (S)-2-(7,7-difluoro-3-hydroxy-3-methylhept-6-en-1-yl)-3,5,6-trimethylcyclohexa-2,5-diene-1,4-dione (Compound K)

To a cooled (ice bath) solution of 87 (111 mg, 0.370 mmol) in $^i$PrOAc (4 mL) was added solution of ammonium cerium(IV) nitrate (610 mg, 1.11 mmol) in water (1 mL) and the reaction mixture was stirred at r.t. for 25 min. After cooling to 0° C., the reaction mixture was quenched by brine (30 mL) and EtOAc (150 mL). The resulting mixture was stirred at r.t. for 5 min. Then, aqueous phase was separated and the organic phase was washed with water (30 mL) and brine (30 mL), dried over anh. Na$_2$SO$_4$ and concentrated under reduced pressure. The crude product was purified by silica gel flash column chromatography using a mixture of petroleum ether and EtOAc (1:0→10:1) as an eluent and re-purified by reversed phase flash chromatography (100% MeCN) to give Compound K (54 mg) in 48% yield.

$^1$H-NMR (CDCl$_3$, 400 MHz): δ=4.25-4.10 (m, 1H), 2.57-2.51 (m, 2H), 2.13-2.00 (m, 11H), 1.60-1.47 (m, 4H), 1.25 ppm (s, 3H). MS (M+H$^+$): 313.1615.

Example 14: Synthesis of 2-((S,6E,10E)-15,15-difluoro-3-hydroxy-3,7,11-trimethylpentadeca-6,10,14-trien-1-yl)-3,5,6-trimethylcyclohexa-2,5-diene-1,4-dione (Compound L)
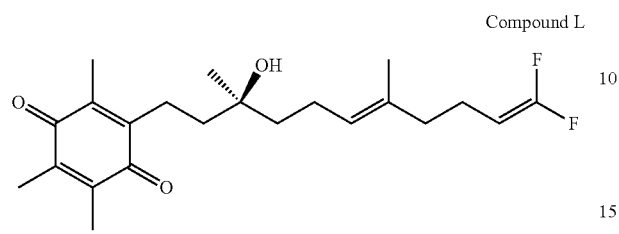
Compound L
Scheme 17
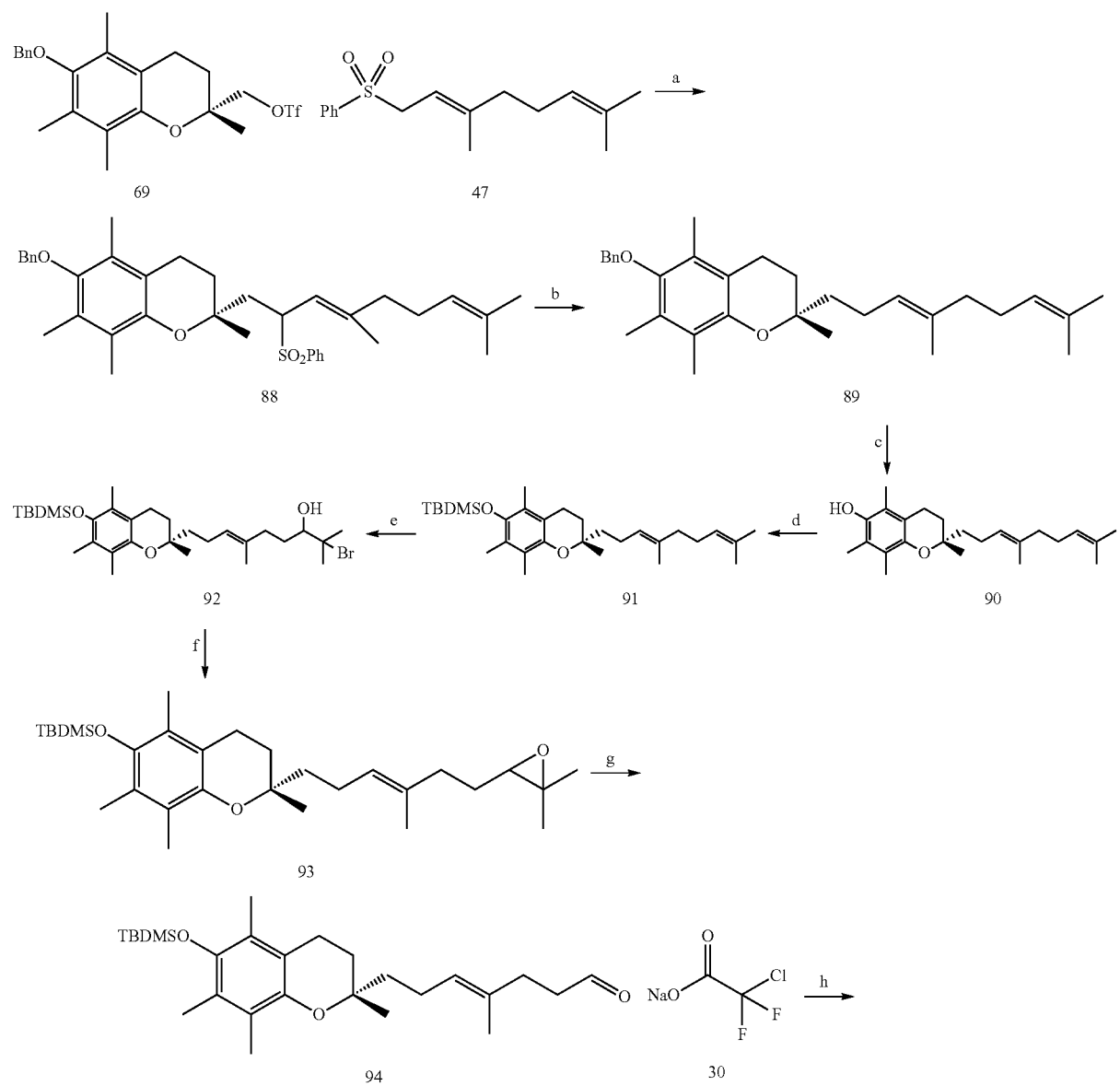

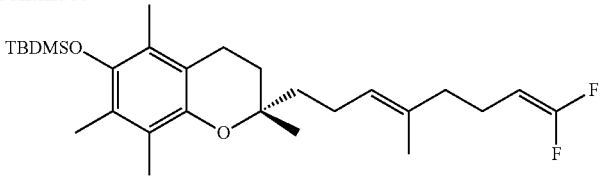

95

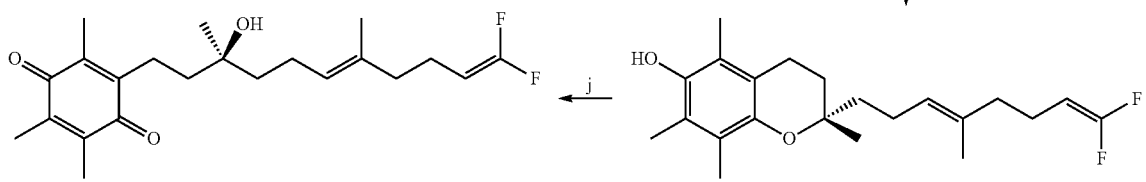

Compound L                                96

Step a. Synthesis of (2R)-6-(benzyloxy)-2-((E)-4,8-dimethyl-2-(phenylsulfonyl)nona-3,7-dien-1-yl)-2,5,7,8-tetramethylchromane (88)

To a solution of 47 (4.25 g, 15.3 mmol) in dry THF (60 mL) under argon was added hexamethylphosphoramide (15.9 mmol) and the resulting mixture was cooled to −78° C. Then, "BuLi (2.3 M in hexanes, 5.4 mL, 12.4 mmol) was added dropwise and the reaction mixture was stirred at the same temperature for 30 min. After dropwise addition of 69 (4.38 g, 9.56 mmol) solution in dry THF (60 mL), the reaction mixture was stirred at −78° C. for 8 hrs. and stirring was continued at r.t. for 20 hrs. The reaction mixture was diluted with $Et_2O$ (1000 mL), washed with water (2×150 mL), brine (150 mL), dried over anh. $Na_2SO_4$ and concentrated under reduced pressure. The crude product was purified by silica gel flash column chromatography using a mixture of petroleum ether and EtOAc (1:0→5:1) as an eluent to give 88 (6.79 g) as a mixture of diastereomers, containing premix of the remaining 47 (about 0.5 equiv.). This material was used in the next step without further purification.

Step b. Synthesis of (S,E)-6-(benzyloxy)-2-(4,8-dimethylnona-3,7-dien-1-yl)-2,5,7,8-tetramethylchromane (89)

To a mixture of 88 (containing approx. 0.5 equivalents of 47) (6.79 g, approx. 11.5 mmol) and $PdCl_2$dppp (682 mg, 1.11 mmol) under argon was added dry THF (100 mL) and the resulting suspension was cooled to 0° C. Then, $LiEt_3BH$ (1.7 M in THF, 20.4 mL, 34.7 mmol) was added dropwise and the reaction mixture was stirred at 0° C. for 5 hrs. and overnight at r.t. The reaction mixture was diluted with $Et_2O$ (800 mL) and successively washed with 1 M aq. NaCN (100 mL), water (100 mL), and brine (100 mL). After drying over anh. $Na_2SO_4$, the volatile matters were removed under reduced pressure and the crude product was purified by silica gel flash column chromatography using a mixture of petroleum ether and EtOAc (1:0-40:1) as an eluent to give 89 (3.9 g).
$^1$H-NMR (CDCl$_3$, 400 MHz): δ=7.52-7.49 (m, 2H), 7.43-7.32 (m, 3H), 5.17-5.07 (m, 2H), 4.70 (s, 2H), 2.63-2.59 (m, 2H), 2.23 (s, 3H), 2.17-2.04 (m, 10H), 2.00-1.96 (m, 2H), 1.89-1.75 (m, 2H), 1.70-1.53 (m, 11H), 1.28 ppm (s, 3H).

Step c. Synthesis of (S,E)-2-(4,8-dimethylnona-3,7-dien-1-yl)-2,5,7,8-tetramethylchroman-6-ol (90)

To a cooled (0° C.) suspension of lithium (1.8 g, 260 mmol) in n-propylamine (70 mL) and diethylether (70 mL) under argon was added solution of 89 (3.9 g, 8.71 mmol) in diethylether (30 mL) and the reaction mixture was stirred at r.t. for 3 hrs. After re-cooling to 0° C., the reaction mixture was carefully quenched by the addition of sat. aq. $NH_4C_1$ (50 mL) and methanol (50 mL). The organic solvents were removed under reduced pressure at r.t. and the residue was diluted with water (100 mL) and extracted with diethylether (3×200 mL). The combined organic phases were washed with brine (100 mL), dried over anh. $Na_2SO_4$ and concentrated under reduced pressure. The crude product was purified by silica gel flash column chromatography using a mixture of petroleum ether and EtOAc (1:0→40:3) as an eluent to give 90 (2.6 g) in 83% yield.
$^1$H-NMR (CDCl$_3$, 400 MHz): δ=5.16-5.07 (m, 2H), 4.18 (s, 1H), 2.64-2.60 (m, 2H), 2.16-2.03 (m, 13H), 1.99-1.95 (m, 2H), 1.87-1.74 (m, 2H), 1.68-1.51 (m, 11H), 1.26 ppm (s, 3H).

Step d. Synthesis of (S,E)-tert-butyl((2-(4,8-dimethylnona-3,7-dien-1-yl)-2,5,7,8-tetramethyl-chroman-6-yl)oxy)dimethylsilane (91)

A solution of TBDMSCl (4.39 g, 29.1 mmol) in dry DMF (15 mL) was added to a cooled (0° C.) solution of 90 (2.3 g, 6.48 mmol) and imidazole (3.9 g, 58.0 mmol) in dry DMF (15 mL) and the reaction mixture was stirred at r.t. for 20 hrs. Then, the reaction mixture was diluted with EtOAc (1000 mL) and water (150 mL) and stirred at r.t. for 15 min. The aqueous phase was separated and the organic phase was washed with water (3×150 mL) and brine (150 mL), dried over anh. $Na_2SO_4$, and concentrated under reduced pressure. The crude product was purified by silica gel column flash chromatography using a mixture of petroleum ether and EtOAc as eluent (1:0→50:1) to give 91 (2.99 g) in 98% yield as colorless oil.
$^1$H-NMR (400 MHz, CDCl$_3$): δ=5.16-5.06 (m, 2H), 2.58-2.55 (m, 2H), 2.15-2.03 (m, 13H), 1.98-1.94 (m, 2H), 1.87-1.74 (m, 2H), 1.79-1.49 (m, 11H), 1.25 (s, 3H), 1.05 (s, 9H), 0.12 ppm (s, 6H).

Step e. Synthesis of (E)-2-bromo-9-((S)-6-((tert-butyldimethylsilyl)oxy)-2,5,7,8-tetramethyl-chroman-2-yl)-2,6-dimethylnon-6-en-3-ol (92)

To a solution of 91 (2.9 g, 6.1 mmol) in THF (40 mL) and H$_2$O (20 mL) at 0° C. dropwise was added solution of N-bromosuccinimide (1.09 g, 6.16 mmol) in THF (20 mL). After the reaction mixture was stirred for 2 hrs. at 0° C., the reaction mixture was quenched by the addition of Et$_2$O (300 mL) and water (100 mL) and the resulting mixture was stirred at r.t. for 15 min. The organic phase was separated and the aqueous phase was extracted with Et$_2$O (2×100 mL). The combined organic phases were washed with brine (80 mL) and dried over anh. Na$_2$SO$_4$. After evaporation of the solvent under reduced pressure, crude product was purified by silica gel column flash chromatography using a mixture of petroleum ether and EtOAc as eluent (1:0→40:3) to give 92 (2.63 g) in 63% yield as colorless oil.

Step f. Synthesis of tert-butyl(((2S)-2-((E)-6-(3,3-dimethyloxiran-2-yl)-4-methylhex-3-en-1-yl)-2,5,7,8-tetramethylchroman-6-yl)oxy)dimethylsilane (93)

To a solution of 92 (2.2 g, 3.87 mmol) in MeOH (35 mL) was added K$_2$CO$_3$ (1.07 g, 7.75 mmol) and the resulting mixture was stirred at r.t. for 1.5 hrs. Then, the reaction mixture was quenched by the addition of water (200 mL), and the resulting aqueous phase was extracted with Et$_2$O (3×200 mL). The combined organic phases were washed with brine (100 mL), dried over anh. Na$_2$SO$_4$, and concentrated under reduced pressure to give crude 93 (2 g) in 98% yield, which was used in the next step without further purification.
$^1$H-NMR (400 MHz, CDCl$_3$): δ=5.20-5.16 (m, 1H), 2.71-2.67 (m, 1H), 2.58-2.54 (m, 2H), 2.18-2.02 (m, 13H), 1.86-1.73 (m, 2H), 1.67-1.53 (m, 7H), 1.29-1.24 (m, 9H), 1.04 (s, 9H), 0.11 ppm (s, 6H).

Step g. Synthesis of (S,E)-7-(6-((tert-butyldimethylsilyl)oxy)-2,5,7,8-tetramethylchroman-2-yl)-4-methylhept-4-enal (94)

A stirred mixture of 93 (2.0 g, 4.11 mmol), THF (30 mL), and water (6 mL) at 0° C. was sequentially treated with sodium periodate (520 mg, 2.46 mmol) and periodic acid (1.02 g, 4.51 mmol). The resulting mixture was stirred at 0° C. for 10 min. and then warmed to room temperature. After 1 hr., the reaction mixture was quenched by the addition of saturated aqueous sodium bicarbonate solution (100 mL) and diethyl ether (200 mL) and the resulting mixture was stirred at r.t. for 5 min. The biphasic layers were separated and the aqueous layer was extracted with diethyl ether (2×200 mL). The combined organic layers were washed with brine (100 mL), dried over anh. Na$_2$SO$_4$, filtered and concentrated under reduced pressure to give crude 94 (1.5 g) in 83% yield. This material was used in the next step without further purification.
$^1$H-NMR (400 MHz, CDCl$_3$): δ=9.74 (t, J=1.9 Hz, 1H), 5.19-5.14 (m, 1H), 2.57-2.54 (m, 2H), 2.52-2.48 (m, 1H), 2.32-2.28 (m, 1H), 2.15-2.05 (m, 11H), 1.85-1.74 (m, 2H), 1.66-1.49 (m, 7H), 1.24 (s, 3H), 1.04 (s, 9H), 0.11 ppm (s, 6H).

Step h. Synthesis of (S,E)-tert-butyl((2-(8,8-difluoro-4-methylocta-3,7-dien-1-yl)-2,5,7,8-tetramethylchroman-6-yl)oxy)dimethylsilane (95)

To a mixture of 94 (1.5 g, 3.37 mmol), sodium 2-chloro-2,2-difluoroacetate (30, 1.02 g, 6.74 mmol), and PPh$_3$ (1.76 g, 6.74 mmol) under argon was added dry DMF (8 mL) and the reaction mixture was stirred at 105° C. for 2 hrs. After cooling in ice bath, water (5.0 mL) was added slowly. Then, the resulting mixture was diluted by water (100 mL) and Et$_2$O (600 mL) and stirred at r.t. for 5 min. The aqueous phase was separated and the organic phase was washed with water (3×80 mL) and brine (80 mL). After drying over anh. Na$_2$SO$_4$, the volatile matters were removed under reduced pressure and the crude product was purified by silica gel column flash chromatography using a mixture of petroleum ether and EtOAc as eluent (1:0→100:1) to give 95 (0.95 g) together with approximately 1 equiv. of PPh$_3$. The obtained product was used in the next step without further purification.
$^1$H-NMR (400 MHz, CDCl$_3$): δ=5.20-5.13 (m, 1H), 4.18-4.03 (m, 1H), 2.62-2.55 (m, 2H), 2.20-1.99 (m, 15H), 1.89-1.74 (m, 2H), 1.71-1.49 (m, 5H), 1.27 (s, 3H), 1.07 (s, 9H), 0.14 ppm (s, 6H).

Step i. Synthesis of (S,E)-2-(8,8-difluoro-4-methylocta-3,7-dien-1-yl)-2,5,7,8-tetramethyl-chroman-6-ol (96)

A solution of 95 containing approximately 0.5 equiv. of PPh$_3$ (0.95 g) in dry THF (40 mL) was cooled in ice bath while 1 M tetra-n-butylammonium fluoride solution in THF (1 mL) was added dropwise. The reaction mixture was stirred at 0° C. for 30 min. After completion of the reaction (TLC), cooled (ice bath) reaction mixture was quenched by the addition of Et$_2$O (200 mL) and water (100 mL) and the resulting mixture was stirred at r.t. for 5 min. Then, organic phase was separated and the aqueous phase was extracted with diethyl ether (2×100 mL). The combined organic phases were washed with brine (80 mL), dried over anh. Na$_2$SO$_4$, and concentrated under reduced pressure. The crude product was purified by silica gel flash column chromatography (petroleum ether/EtOAc 1:0→20:1) to give 96 (0.59 g).
$^1$H-NMR (400 MHz, CDCl$_3$): δ=5.17-5.13 (m, 1H), 4.18 (s, 1H), 4.15-4.04 (m, 1H), 2.63-2.60 (m, 2H), 2.16-2.00 (m, 15H), 1.86-1.74 (m, 2H), 1.68-1.50 (m, 5H), 1.25 ppm (s, 3H).

Step j. Synthesis of (S,E)-2-(11,11-difluoro-3-hydroxy-3,7-dimethylundeca-6,10-dien-1-yl)-3,5,6-trimethylcyclohexa-2,5-diene-1,4-dione (Compound L)

To a cooled (ice bath) solution of 96 (590 mg, 1.61 mmol) in $^i$PrOAc (15 mL) was added solution of ammonium cerium(IV) nitrate (2.66 g, 4.85 mmol) in water (3.5 mL) and the reaction mixture was stirred at r.t. for 25 min. After cooling to 0° C., the reaction mixture was quenched by brine (60 mL) and EtOAc (400 mL). The resulting mixture was stirred at r.t. for 5 min. Then, aqueous phase was separated and the organic phase was washed with water (80 mL) and brine (80 mL), dried over anh. Na$_2$SO$_4$ and concentrated under reduced pressure. The crude product was purified by silica gel flash column chromatography using a mixture of petroleum ether and EtOAc (1:0→10:1) as an eluent and re-purified by reversed phase flash chromatography (100% MeCN) to give Compound L (300 mg) in 74% yield.
$^1$H-NMR (CDCl$_3$, 400 MHz): δ=5.18-5.14 (m, 1H), 4.14-4.04 (m, 1H), 2.57-2.53 (m, 2H), 2.13-2.01 (m, 15H), 1.62-1.48 (m, 7H), 1.25 ppm (s, 3H). MS (M+H$^+$): 381.2244.

Example 15: Synthesis of (R)-2-(3-hydroxy-3-methyl-4-(3-(trimethylsilyl)propoxy)butyl)-3,5,6-trimethylcyclohexa-2,5-diene-1,4-dione (Compound M)

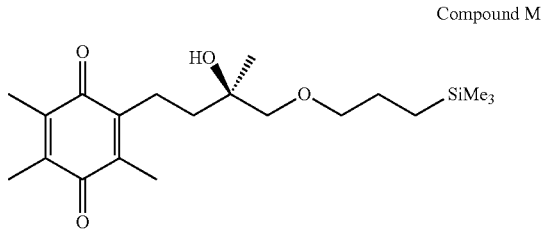 [SMILES: CC1=C(C)C(=O)C(CC[C@@](C)(O)COCCC[Si](C)(C)C)=C(C)C1=O]

Compound M

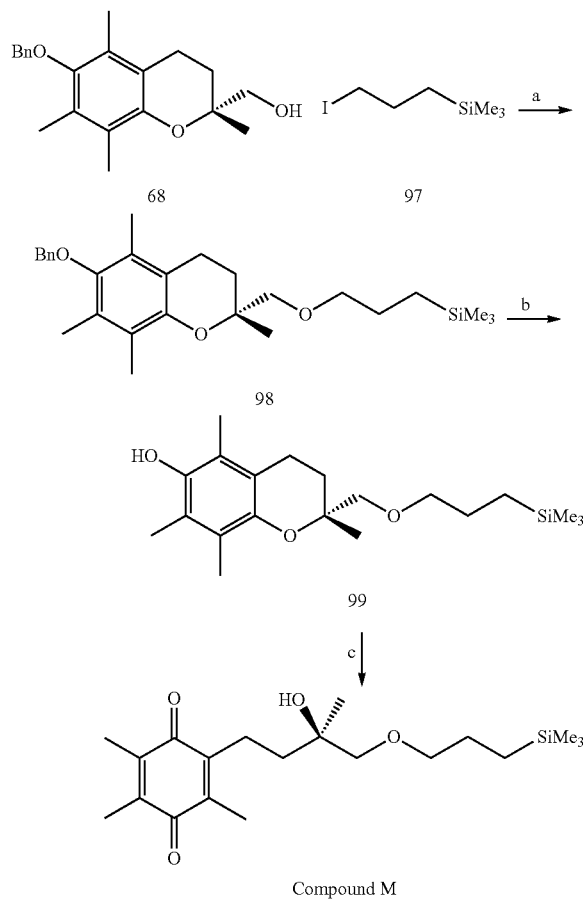

Scheme 18

Step a. Synthesis of (R)-(3-((6-(benzyloxy)-2,5,7,8-tetramethylchroman-2-yl)methoxy)propyl)trimethylsilane (98)

To a solution of 68 (0.38 g, 1.16 mmol) and NaH (72 mg, 1.5 mmol) in dry DMF (2 mL) was added (3-iodopropyl)trimethylsilane (97, 0.6 g, 2.5 mmol) and reaction mixture allowed to stir at r.t. for 24 hrs. To reaction mixture was added EtOAc (50 mL) and washed first with water (50 mL) and then brine (3×50 mL). Then the organic phase was separated, dried over anh. Na$_2$SO$_4$, filtered and evaporated. Crude product was purified by flash column chromatography (SiO$_2$, hexane-EtOAc (10:1, R$_f$(PR) 0.6)) to yield 98 (180 mg) as a colorless oil.

$^1$H-NMR (400 MHz, Chloroform-d) δ 7.54-7.48 (m, 2H), 7.44-7.38 (m, 2H), 7.37-7.31 (m, 1H), 4.70 (s, 2H), 3.53-3.45 (m, 3H), 3.44-3.36 (m, 1H), 2.61 (t, J=6.8 Hz, 2H), 2.23 (s, 3H), 2.21-2.16 (m, 3H), 2.11 (s, 3H), 2.00 (dt, J=14.1, 7.2 Hz, 1H), 1.79 (dt, J=13.3, 6.5 Hz, 1H), 1.62-1.50 (m, 3H), 1.31 (s, 3H), 1.29-1.13 (m, 2H), 0.97-0.86 (m, 1H), 0.53-0.44 (m, 2H), −0.00 (s, 9H).

Step b. Synthesis of (R)-2,5,7,8-tetramethyl-2-((3-(trimethylsilyl)propoxy)methyl)chroman-6-ol (99)

To a solution of 98 (180 mg) in MeOH (10 mL) was added 10% Pd/C (8 mg) and through the reaction mixture was bubbled hydrogen gas at room temperature for 2 hrs. After filtration and evaporation, 90 mg of 99 was obtained was obtained as white solid. This material was used in next step without purification.

$^1$H-NMR (400 MHz, Chloroform-d) δ 3.51-3.42 (m, 3H), 3.38 (d, J=9.8 Hz, 1H), 2.61 (t, J=6.9 Hz, 2H), 2.16 (s, 3H), 2.12 (s, 3H), 2.11 (s, 3H), 1.97 (dt, J=14.1, 7.2 Hz, 1H), 1.76 (dt, J=13.3, 6.5 Hz, 1H), 1.61-1.50 (m, 3H), 0.52-0.43 (m, 2H), −0.01 (s, 9H).

Step c. Synthesis of (R)-2-(3-hydroxy-3-methyl-4-(3-(trimethylsilyl)propoxy)butyl)-3,5,6-trimethylcyclohexa-2,5-diene-1,4-dione (Compound M)

To a solution of 99 (90 mg, 0.257 mmol) in mixture of i-PrOAc (3 mL) and water (0.7 mL) was added ceric ammonium nitrate (423 mg, 0.771 mmol) at room temp and stirred for 1 h. After cooling to 0° C., the reaction mixture was quenched by brine (5 mL) and EtOAc (20 mL). The resulting mixture was stirred at r.t. for 5 min. Then, aqueous phase was separated and the organic phase was washed with brine (10 mL), dried over anh. Na$_2$SO$_4$ and concentrated under reduced pressure. The crude product purified by flash column chromatography (SiO$_2$, DCM-MeOH (50:1, R$_f$(PR) 0.3)) to yield 75 mg (80%) of Compound M as a yellow oil (HPLC purity 96.2%).

$^1$H-NMR (400 MHz, CDCl$_3$) δ: 3.42 (t, J=6.9 Hz, 2H), 3.34-3.25 (m, 2H), 2.63-2.46 (m, 2H), 2.38 (s, 1H), 2.03 (s, 3H), 1.99 (s, 6H), 1.63-1.44 (m, 4H), 1.23 (s, 3H), 0.50-0.43 (m, 2H), −0.02 (s, 9H). MS (M−H): 365.3.

Example 16: Synthesis of (R)-2,3,5-trimethyl-6-(12,12,12-trifluoro-3-hydroxy-3-methyldodecyl)cyclohexa-2,5-diene-1,4-dione (Compound N)

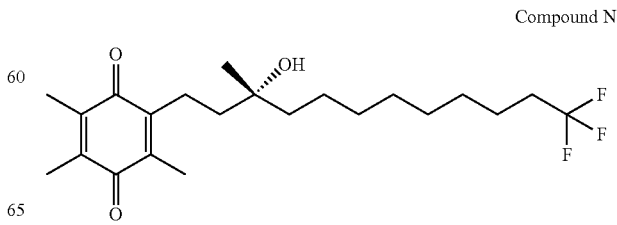

Compound N

Scheme 19

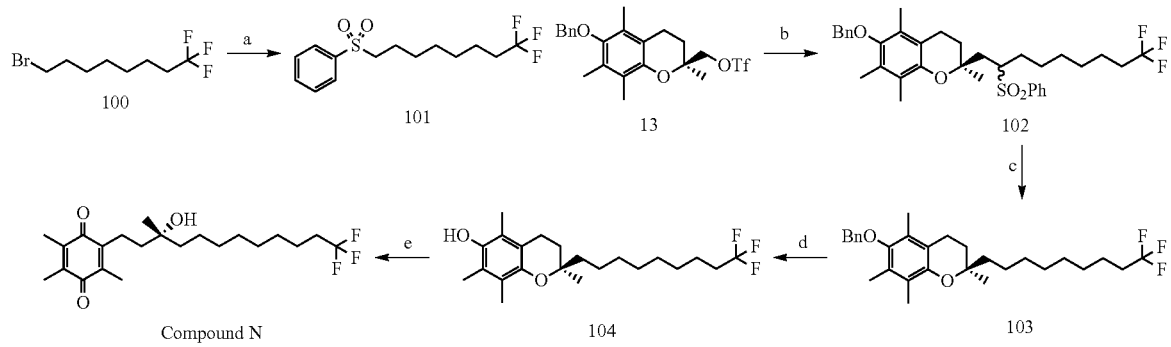

Step a. Synthesis of ((8,8,8-trifluorooctyl)sulfonyl)benzene (101)

8-Bromo-1,1,1-trifluorooctane (100, 5.00 g, 20.2 mmol) was added to a solution of sodium benzene sulfonate (NaSO$_2$Ph, 4.31 g, 26.3 mmol) in DMF (15 mL) at 0° C. The reaction mixture was stirred at room temperature overnight and was then diluted with ethyl acetate (100 mL), washed with 1 M aq. HCl (30 mL), saturated aqueous solution of NaHCO$_3$ (30 mL), water (30 mL) and brine (30 mL) and then dried over anh. Na$_2$SO$_4$. The solvent was removed under reduced pressure to give yellow oil which was purified by flash column chromatography on silica gel (EtOAc/PE=15:85) to give 101 as a colorless oil (3.57 g, 57%).

$^1$H-NMR (400 MHz, Chloroform-d) δ 7.95-7.86 (m, 2H), 7.68-7.62 (m, 1H), 7.60-7.53 (m, 2H), 3.14-2.99 (m, 2H), 2.09-1.95 (m, 2H), 1.78-1.67 (m, 2H), 1.56-1.45 (m, 2H), 1.41-1.24 (m, 6H). $^{19}$F NMR (376 MHz, Chloroform-d) δ −66.39 (t, J=11.0 Hz).

Step b. Synthesis of (2S)-6-(benzyloxy)-2,5,7,8-tetramethyl-2-(9,9,9-trifluoro-2-(phenylsulfonyl)-nonyl)chromane (102)

To a solution of 101 (1.78 g, 5.76 mmol) in dry THF (20 mL) under argon was added hexamethylphosphoramide (814 µl, 4.68 mmol) and resulting mixture was cooled to −78° C. Then $^n$-BuLi (2.3 M in hexane, 2.03 mL, 4.68 mmol) was added dropwise and reaction mixture was stirred at the same temperature for 30 min. After dropwise addition of 13 (1.65 µg, 3.60 mmol) dissolved in dry THF (20 mL), the reaction mixture was stirred at −78° C. for 8 hrs. and stirring was continued at r.t. for 20 hrs. The reaction mixture was diluted with Et$_2$O (125 mL), washed with brine (2×50 mL) and dried over anh. Na$_2$SO$_4$. After evaporation of the solvent, the crude product was purified by silica gel flash column chromatography using a mixture of EtOAc (0-10%) in petroleum ether (PE) as eluent to give 102 as a mixture of diastereomers in 1.96 g (yield 88%).

$^1$H-NMR (400 MHz, Chloroform-d) δ 7.86-7.80 (m, 3H), 7.70-7.64 (m, 2H), 7.62-7.55 (m, 1H), 7.53-7.47 (m, 4H), 7.44-7.38 (m, 5H), 7.37-7.31 (m, 5H), 4.64-4.56 (m, 4H), 3.33-3.26 (m, 1H), 3.11-3.05 (m, 1H), 3.03-2.97 (m, 1H), 2.54-2.44 (m, 3H), 2.28-2.21 (m, 1H), 2.20 (s, 3H), 2.19 (s, 3H), 2.15 (s, 3H), 2.14 (s, 3H), 2.00-1.59 (m, 17H), 1.92 (s, 6H), 1.57-1.16 (m, 20H).

Step c. Synthesis of (R)-6-(benzyloxy)-2,5,7,8-tetramethyl-2-(9,9,9-rifluorononyl)chromane (103)

To a mixture of 102 (1.00 g, 1.62 mmol) in MeOH (50 mL) at r.t. was added NiCl$_2$ (21.0 mg, 0.162 mmol). After being warmed to 60° C., Mg powder (1.71 g, 64.9 mmol) was added in three batches. After 2 hrs., the reaction mixture was quenched by the addition of aq. HCl (1 µM, 25 mL) and extracted with EtOAc (2×45 mL). The combined organic solution was washed with brine (25 mL), dried over anh. Na$_2$SO$_4$, filtered, and concentrated. The residue was purified by silica gel flash column chromatography (0-30% of EtOAc in PE) to give 103 (390 mg) as colorless glass.

$^1$H-NMR (400 MHz, Chloroform-d) δ 7.53-7.48 (m, 2H), 7.44-7.38 (m, 2H), 7.36-7.31 (m, 1H), 4.70 (s, 2H), 2.59 (t, J=6.8 Hz, 2H), 2.22 (s, 3H), 2.17 (s, 3H), 2.10 (s, 3H), 2.09-2.00 (m, 2H), 1.87-1.73 (m, 2H), 1.65-1.50 (m, 5H), 1.46-1.28 (m, 8H), 1.24 (s, 3H). $^{19}$F NMR (376 MHz, Chloroform-d) δ −66.39 (t, J=11.0 Hz).

Step d. Synthesis of (R)-2,5,7,8-tetramethyl-2-(9,9,9-trifluorononyl)chroman-6-ol (104)

To solution of 103 (370 mg, 0.776 mmol) in a MeOH (10 mL) was added Pd/C (10% w/w, 70 mg). The hydrogen was purged in reaction mixture at room temperature for 2 hrs. Then the reaction mixture was filtrated through a Celite pad and washed with MeOH (10 mL). The solvent was removed by evaporation to give 290 mg of 104. The resulting oil (290 mg, 96%) was used to next step without purification.

$^1$H-NMR (400 MHz, Chloroform-d) δ 4.17 (s, 1H), 2.60 (t, J=6.9 Hz, 2H), 2.16 (s, 3H), 2.11 (s, 6H), 2.09-1.98 (m, 2H), 1.85-1.71 (m, 2H), 1.63-1.49 (m, 5H), 1.44-1.26 (m, 9H), 1.22 (s, 3H). $^{19}$F NMR (376 MHz, Chloroform-d) δ −66.40 (t, J=11.1 Hz).

Step e. Synthesis of (R)-2,3,5-trimethyl-6-(12,12,12-trifluoro-3-hydroxy-3-methyldodecyl)cyclo-hexa-2,5-diene-1,4-dione (Compound N)

To a solution of 104 (280 mg, 0.725 mmol) in i-PrOAc (7 mL) at r.t. was added solution of ammonium cerium(IV) nitrate (1.19 g, 2.17 mmol) in water (2 mL). After a stirring for 0.5 hrs. at r.t, the reaction mixture was cooled to 0° C. and quenched by the addition of brine (30 mL) and EtOAc (50 mL). The resulting mixture was stirred at r.t. for 5 min. The organic layer was separated and dried over anh. Na$_2$SO$_4$. After evaporation of the solvent, the crude product was purified by column chromatography on silica gel (hexane/ethyl acetate—25/1) to afford the Compound N (250 mg, 85%) as yellow oil.

$^1$H-NMR (400 MHz, Chloroform-d) δ 2.57-2.49 (m, 2H), 2.12-1.99 (m, 11H), 1.59-1.45 (m, 8H), 1.32 (s, 9H), 1.22 (s, 3H). $^{19}$F NMR (376 MHz, Chloroform-d) δ −66.40 (t, J=11.0 Hz). MS (M−H): 401.2.

Example 17: Frataxin Deficient Fibroblast Viability Assay (the "BSO Assay")

Reference: Matthias L. Jauslin, Thomas Wirth, Thomas Meier and Fabrice Schoumacher, A cellular model for Friederichs Ataxia reveals small-molecule glutathione peroxidase mimetics as novel treatment strategy, Human Molecular Genetics, 2002, Vol. 11 (24): 3055-3063.

This Example was used to evaluate the various new compositions (and to rank order them) for their potential efficacy in the treatment of Friedreich's Ataxia—substantially as described in the above cited Reference (Matthias et al.). This data can be used to select candidates for further testing, including animal studies directed to development of active therapeutic agents.

INTRODUCTION

The assay utilizes frataxin deficient fibroblasts (i.e., fibroblasts from Friedreich's ataxia (FRDA) patient material) as a means to assay cell viability by determining how compounds of interest can potentially inhibit/delay/prevent L-buthionine-sulfoximine-induced (BSO-induced) cell death in diseased and control (healthy) cells.

Test Articles

Figure 5:
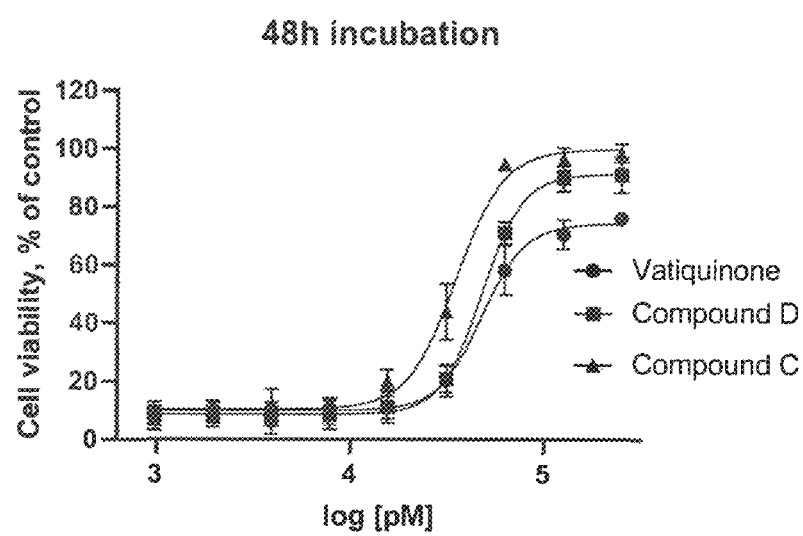
FIG. 5 is a graphic illustration of data obtained for the analysis of the effects of various compounds disclosed herein on cells obtained from a patient confirmed to have Friedreich's ataxia.

The stock solutions of the test articles were prepared in dimethyl sulfoxide (DMSO at 10 mM). Working stock solutions (2 times concentrated) were prepared on the day of the experiment in respective cell culture medium to be used for assay (detailed medium description below). The following compounds (Table 1) were used to produce the data presented in FIG. 5. Additional data for these and other compounds examined is presented below in Table 2.

TABLE 1

| Compound ID | MW | Purity by HPLC |
| --- | --- | --- |
| Vatiquinone | 440.67 | 98.4 |
| Compound C | 448.59 | 96.1 |
| Compound D | 452.68 | 94.4 |

Vatiquinone is a known compound (See: PCT/US2011/061540 (WO 2012/068552)) of formula:

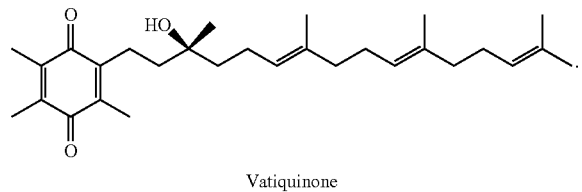 [SMILES: CC(C)=CCC/C(C)=C/CC/C(C)=C/CC[C@@](C)(O)CCC1=C(C)C(=O)C(C)=C(C)C1=O]

Vatiquinone

Assay Experimental

A patient derived frataxin deficient fibroblast cell line was obtained from Coriell Institute. More specifically, the following cell lines/DNA samples were obtained from the NIGMS Human Genetic Cell Repository at the Coriell Institute for Medical Research: GM03665. To evaluate importance of various growth conditions on cell susceptibility to BSO toxicity cells were grown on:

MEM (Sigma-Aldrich) 15% Fetal Bovine Serum (FBS) without growth factors;

MEM (Sigma-Aldrich) 15% FBS with growth factors (Catalogue number 100-181B, Recombinant Human FGF-basic (154 a.a.) and catalogue number AF-100-15, Animal-Free Recombinant Human EGF from Peprotech);

MEM199/MEM EBS (Bioconcept Ltd) 10% FBS, insulin 10 µg/ml, L-glutamine 2 mM with growth factors (Catalogue number 100-18B, Recombinant Human FGF-basic (154 a.a.) and catalogue number AF-100-15, Animal-Free Recombinant Human EGF from Peprotech).

To conduct an experiment, fibroblast cells (from all growth conditions) were seeded (100 µL (cells 3×10^3/well) on 96-well plates in MEM199/MEM EBS medium 10% FBS, insulin 10 µg/mL, L-glutamine 2 mM with growth factors and allowed to grow on plate for 24 hrs. After 24 hrs., media was removed and then test compounds of interest were added (100 µL, 2 times concentrated stock) to 96-well plates (end DMSO concentration not exceeding 0.5%) and incubated for 24 hours. Then L-buthionine-sulfoximine (BSO, from Acros Organics, Cat. No. 235520010) was added (100 µL, 2 times concentrated stock) at end concentrations ranging from 1 to 10 mM. Both test compounds and BSO were dissolved in MEM199/MEM EBS medium 10% FBS, insulin 10 µg/mL, L-glutamine 2 mM with growth factors. Cell viability was monitored and either after 24- or 48-hours cell viability was assayed by MTT (Thiazolyl blue tetrazolium bromide) assay. For the MTT assay, media was removed and 100 µL of MTT 1 mg/mL was added, incubated for 2 hours at +37° C., then medium was removed and 100 µL of isopropanol added to dissolve sediment. Absorption was measured at 570 (OD570) and 650 (OD650) nm wavelengths. Control cells (vehicle instead of BSO and compound) and vehicle control (with BSO, but vehicle instead of test compound) were treated in the same manner as cells with BSO and compound. All cell media contained penicillin and streptomycin 100 U/mL each.

Calculations

Absorption readouts were processed as follows: Value$_A$=Value$_{OD570}$−Value$_{OD650}$ and the obtained values were used to calculate cell viability as % of control cell (i.e., no BSO, no compound, just vehicle) viability.

Replicates

All samples were run in at least 3 replicates for test compounds and at least 8 replicates for controls (i.e., both control (no BSO, no compound) and vehicle control (i.e., with BSO, no compound). Exact N per data points are indicated in the figures/table legends. Results for the compounds listed in Table 1, above, are presented in FIG. 5. Additional data for other compounds tested can be found in Table 2, below. In some cases intermediates (e.g. (56) and (67)) were also tested.

Discussion

This is a cell-based assay measuring cytotoxicity which results from oxidative stress subsequent to depletion of endogenous glutathione defense mechanisms. The cells were primary Friedreich Ataxia (FA) patient fibroblasts which were incubated for 48 hrs. in BSO, an inhibitor of gamma glutamylsynthetase, an enzyme required for glutathione production. Relative to healthy control fibroblasts, FA patient fibroblasts are more susceptible to the BSO induced cell death due to the loss of frataxin and subsequent accumulation of cytosolic iron, which accelerates the process of ROS driven lipid peroxidation. In the assay, cells were pretreated with drug at decreasing doses from 250 nM down to 6.125 nM the day before the BSO was added at a fixed dose of 10 mM. Cytotoxicity was measured with MTT assay 48 hrs. later and reported as the percent of MTT absorbance normalized to cells grown in media without BSO for 48 hrs. Unless otherwise indicated, each data point was performed in triplicate wells of a 96 well plate. Data obtained is presented below in Table 2. With respect to the data, any compound exhibiting an EC50 less than 100 nM in this assay was identified with an A in the Table and is considered to exhibit good activity in protecting against BSO-induced cell death. Any compound exhibiting an EC50 between 100 nm and 1000 nM in this assay was identified with a B in the Table and is considered to have fair activity in protecting against BSO-induced cell death. Any compound exhibiting an EC50 greater than 1000 nM in this assay was identified with a C in the Table and is considered to have poor activity in protecting against BSO-induced cell death.

Example 18: Rotenone ATP-Assay

Introduction

This assay has been adapted from Haefeli R H, Erb M, Gemperli A C, Robay D, Courdier Fruh I, et al. (2011) NQO1-Dependent Redox Cycling of Idebenone: Effects on Cellular Redox Potential and Energy Levels. PLoS ONE 6(3): e17963. HepG2 human hepatocarcinoma cells were co-incubated with the electron transport chain Complex I toxin rotenone +/− compounds of interest and the corresponding effect on ATP synthesis was measured with a bioluminescent substrate. The assay was useful in identifying compounds which can "by-pass" the rotenone induced block of Complex I, which significantly impairs mitochondrial respiration and results in a net reduction of ATP generated from endogenous substrates.

Test Articles

The stock solutions of the test articles (See Table 2, below for a list of the test articles examined using this assay) were prepared in dimethyl sulfoxide (DMSO at 10 mM). Working stock solutions were prepared on the day of the experiment in glucose free, serum free Dulbecco's modified Eagles medium (DMEM) supplemented with 50 micromolar rotenone.

Assay Experimental

In brief, HepG2 cells were plated at 25,000 cells per well in low glucose (1 gram/Liter) DMEM medium+10% fetal calf serum and incubated for 24 hours. The following day, the media was decanted and subsequently replaced with glucose free/serum free DMEM which has been supplemented with 50 micromolar rotenone and compound of interest. Serial dilutions of compound were prepared in 3× dilutions beginning at 25 micromolar. The cells were incubated for 60 minutes in a humidified tissue culture incubator. Following incubation, ATP levels were quantified via bioluminescent assay (Promega TiterMax Glo Assay kit) and readings were captured on a standard microplate reader.

Calculations

ATP bioluminescence is plotted versus the log of compound of interest and data were used to generate EC50 values. Curve fitting was performed using a sigmoidal dose response curve fit function (GraphPad Prism software).

Replicates

EC50 values were derived from seven-point dose response curves performed on n=3 technical replicates per dose. Robustness of curve fit was assessed as a quality control measure, with an R squared value of at least 0.80 being required for a successful curve fit. Compounds of interest showing an increase in ATP bioluminescence relative to vehicle control were verified in an independent biological replicate of n=3 technical replicates per dose.

Discussion

This assay is a direct measure of the ability of compounds of interest to restore ATP production under conditions of inhibition of Complex I of the mitochondrial electron transport chain. As the majority of ATP produced via the electron transport chain is thought to derive from Complex I activity, significant impairment in Complex I function has dire biological consequences. Of note, Complex I mutations are thought to drive pathophysiology in multiple mitochondrial diseases, including Leigh syndrome and Leber's Hereditary Optic Neuropathy (LHON), while diminished Complex I activity and the resultant attenuation of ATP production has been shown in neurodegenerative diseases, including Friedreich's Ataxia, Parkinson's Disease and Huntington's Disease. Data are presented in Table 2 below. With respect to the data, any compound exhibiting an EC50 less than 1000 nM in this assay was identified with an A in the Table and was considered to exhibit good Complex I by-pass activity. Any compound exhibiting an EC50 between 1000 nm and 3000 nM in this assay was identified with a B in the Table and was considered to have fair Complex I by-pass activity. Any compound exhibiting an EC50 greater than 3000 nM in this assay was identified with a C in the Table and was considered to exhibit poor Complex I by-pass activity.

Discussion of Significance to High Scores in Both the BSO Assay and the Rotenone ATP Assay Compounds with activity in both the BSO Assay and the Rotenone ATP Assay are thought to possess polypharmacology which is uniquely efficacious. Benchmark compounds (e.g. Vatiquinone, Idebenone and Omaveloxolone) assessed in our screening assays appear to possess either the ability to circumvent BSO induced cell death (vatiquinone, omaveloxolone) or the ability to restore ATP production when Complex I is inhibited (idebenone). However, these benchmark compounds (i.e. Vatiquinone, Idebenone and Omaveloxolone) do not possess both activities. Significantly, we have discovered and characterized multiple compounds which possess both activities (e.g. Compounds E, (67), L and N), and we believe these compounds will provide superior efficacy over therapeutic approaches which target one pathway alone in indications in which ferroptosis/lipid peroxidation driven cell death co-exists with bioenergetic impairment due to dysfunctional Complex I activity. Several debilitating mitochondrial and neurodegenerative diseases of high unmet medical need fit this profile, including Friedreich's ataxia.

TABLE 2

EC$_{50}$ of BSO Assay & EC50 of Rotenone ATP Assay:

| Compound ID | EC50 (nM) BSO Assay* | EC50 Rotenone ATP Assay** |
|---|---|---|
| Compound A | A | |
| Compound B | A | |
| Compound C | A | |
| Compound D | A | C |
| Compound E | A | B |
| Compound F | A | |
| Compound G | A | |
| Compound 56 | A | |
| Compound H | B | A |
| Compound 67 | A | |
| Compound I | B | C |
| Compound J | A | |
| Compound K | A | C**** |
| Compound L | A | A |
| Compound M | Nd | B**** |
| Compound N | B | B |
| Vatiquinone | A | C |
| Idebenone | Nd | B |
| Omaveloxolone | A*** | C |

Nd = not determined (signal too low to calculate an EC50)
*BSO Assay: EC50: A < 100 nM; 100 nM ≤ B ≥ 1000 nM; C > 1000 nM
**Complex I Assay: EC50: A < 1000 nM; 1000 nM ≤ B ≥ 3000 nM; C > 3000 nM
***Toxic above 1000 nM
****Only one assay performed (at least n = 2 performed for all others)
Compounds A, B, C, D, E, F, G, H, I, J, K, L and N were prepared as described above.

8 Example 19: RSL3 Toxicity Assay (RSL3 Assay)

This assay has been adapted from: Hinman, A., Holst, C. R., Latham, J. C., Bruegger, J. J., Ulas, G., McCusker, K. P., Amagata, A., Davis, D., Hoff, K. G., Kahn-Kirby, A. H., Kim, V., Kosaka, Y., Lee, E., Malone, S. A., Mei, J. J., Richards, S. J., Rivera, V., Miller, G., Trimmer, J. K., Shrader, W. D., "Vitamin E hydroquinone is an endogenous regulator of ferroptosis via redox control of 15-lipoxygenase", (2018) PLoS ONE 13(8): e0201369. This assay is designed to determine if the novel compounds disclosed herein exhibit protective effects when fibroblasts from a subject with Friedreich's ataxia are subjected to the toxic effects of RSL3, a known inducer of the iron and lipid peroxidation catalyzed process of regulated cell death known as ferroptosis.

In brief, GM03665 cells (Coriell Institute) were seeded in 96-well plates (Sarstedt) in DMEM cell culture media containing 10% Fetal Bovine serum and 1% Penicillin-Streptomycin (Pen-Strep) antibiotic mix at the amount of 2×10^4/mL (100 μL or 2×10^3 cells per well). Cells were left to rest overnight at 37° C. in a humidified atmosphere with 5% $CO_2$ to allow attachment of the cells to the culture plate. Test compounds were prepared as DMSO stocks (10 mM) and were serially diluted in cell culture media to obtain 2× working solutions. Cell media was discarded and replaced by 50 μL of test compound solutions or cell media with vehicle for control wells. Within 15 minutes, 2× working solution (4 μM) of 1S,3R-RSL3 (CAS #1219810-16-8, Sigma-Aldrich) (diluted from 5 mM DMSO stock in cell culture media) was added. Final reaction volume was 100 μL and final DMSO concentration in reaction was kept below 0.2% (v/v) and equal in all wells. Final RSL3 concentration was 2 μM and test compound final concentrations in reaction were up to 1000 nM. After 24 hours of incubation cell viability was assessed by MTT test. MTT (Sigma-Aldrich) solution 1 mg/mL in 1×PBS (pH=7,4) was prepared 1 hour before the assay and filtered through Filtropur S 0.2 filters (Sarstedt). Cell media with test compounds was discarded and 100 μL of MTT solution was added to cells. The plates were incubated for 2 hours at +37° C. Thereafter, the MTT solution was removed and 100 μL of isopropanol was added to dissolve sediment. Absorption at 570 and 650 nm was measured using Hidex Sense microplate reader. Obtained data were analyzed using GraphPad Prism software to calculate EC50 values that are reported in Table 3, below.

The data presented in Table 3 indicates that all five of the novel compounds examined (i.e. Compounds E, H, L, M and N) were active in the assay. Several were roughly equivalent to Vatiquinone (perhaps some were slightly better) and a few were slightly less active as compared with Vatiquinone. Omaveloxolone was inactive in the assay. In summary, all of the novel compounds tested in this assay were found to be protective of the Friedreich's ataxia fibroblasts when exposed to the toxic effects of RSL3.

Discussion—Both BSO and RSL3 are frequently utilized to induce the regulated cell death pathway known as ferroptosis. Ferroptosis is thought to require the joint activity of iron catalyzed oxidative stress and lipid peroxidation and has been described in cell and animal models of multiple neurodegenerative diseases, including Friedreich's Ataxia, Huntington Disease, Parkinson Disease and Alzheimer's Disease. Compounds active in both assays should in theory possess strong anti-ferroptotic activity. Surprisingly, the reference compound omaveloxolone displayed anti-ferroptotic activity in the BSO assay, but not the RSL3 assay. These data suggest that the downstream mechanisms of ferroptosis may be differentially regulated based upon the experimental insult and some compounds—such as omaveloxolone—may not be effective in all contexts. Of note, compounds E, H, L, M and N were able to prevent ferroptotic cell death when either BSO or RSL3 were used as initiating stimulus, differentiating these compounds from omaveloxolone.

TABLE 3

| | Omav | Vatiq | Ideb | Cmpd E | Cmpd H | Cmpd L | Cmpd M | Cmpd N |
|---|---|---|---|---|---|---|---|---|
| Mean* | Inactive | 56.0 | ND | 73.2 | 178.6 | 41.9 | 41.2 | 93.0 |
| SD | | 25.5 | | 31.1 | 27.3 | 15.9 | 17.5 | 65.6 |

*Mean of at least three measurements; SD is standard deviation; Vatiq is the abbreviation for vatiquinone; Omav is the abbreviation for omaveloxolone ; Ideb is the abbreviation for idebenone; ND is not determined.

Example 20: Rotenone Oxygraph Assay
(High-Resolution Respirometry of Intact HepG2 Cells)

The Oxygraph-2 k (O2k, OROBOROS INSTRUMENTS, Austria) was used for measurements of respiration of intact cells. The respirometry was performed in Dulbecco's Modified Eagle Medium (DMEM) high glucose without supplements. All experiments were performed at 37° C.

HepG2 cells (ATCC collection code HB-8065™) were cultured in 10 $cm^2$ culture dishes in DMEM high glucose medium supplemented with 10% fetal bovine serum (FBS) and 100 units/mL penicillin and 100 μg/mL streptomycin until approximately 90% confluence was reached. Immediately prior to performing the respirometric assay, the cells were washed with media without FBS, trypsinized and resuspended in DMEM high glucose without FBS.

The final concentration of intact cells in the O2k-chamber was 0.5·$10^6$/mL. After stabilization of respiration, the Complex I inhibitor, rotenone, at 1 μM final concentration was added to inhibit electron flux via Complex I. Then, compound to be tested was added at 10 μM final concentration, and the change in respiration rate of intact cells was monitored. The increase in respiration rate indicates that Complex I by-pass is occurring.

The data presented in Table 4 indicates that all five of the novel test compounds examined were active in the assay. Vatiquinone and omaveloxolone were inactive in the assay. In summary, all of the novel test compounds examined in this assay were found to exhibit reasonably strong Complex I by-pass activity.

TABLE 4

| | | | Percent increase in ATP | | | | |
|---|---|---|---|---|---|---|---|
| Vatiq | Omav | Ideb | Cmpd E | Cmpd H | Cmpd L | Cmpd M | Cmpd N |
| Mean Inactive | Inactive | 70.2 +/– 15 | 37.9 +/– 10.7 | 54.3 +/– 13 | 58.6 +/– 15.5 | 56.6 +/– 11.3 | 44.8 +/– 10.3 |

Example 21: Nrf-2 Activation Assay (Nrf-2 Assay)

This assay was developed internally and was designed to determine if the novel test compounds disclosed herein active Nrf-2 and thereby promote resolution of inflammation by the mechanism believed to be responsible for the activity of omaveloxolone.

Briefly, GM03665 Friedreich Ataxia patient fibroblasts were grown in 12 Well Plates (TC Cell+F) (Sarstedt, Numbrecht Germany), at a density of 12×10∝cells/per well in DMEM/F12 (Gibco, ThermoFisher Scientific, Waltham, MA, USA) cell media supplemented with 10% FBS and 1% Pen/Strep. Cells were left to rest overnight at 37° C. in a humidified atmosphere with 5% $CO_2$ to allow attachment of the cells to the culture plate. Before continuing assay visual inspection of each well was done by light microscopy to detect any possible bacterial and fungal contamination. After inspection, cells were treated with test compounds (test compound DMSO stocks were further diluted with cell media/DMSO in order to keep the final DMSO concentration in reaction below 0.2% and equal in all wells) dissolved in cell media (1 μM as final concentration,) for 24 hours. After incubation, cell media was removed and total RNA from the cells was isolated using E.Z.N.A.® Total RNA Kit I (Omega Bio-tek, Norcross, Georgia, USA) spin columns, and first-strand cDNA synthesis was carried out using a High Capacity cDNA Reverse Transcription Kit (Applied Biosystems™, Foster City, CA) following the manufacturer's instructions. qPCR analysis of gene expression was performed by mixing SYBR® Green Master Mix (Applied Biosystems™) with synthesized cDNA and forward and reverse primers. Primers were designed using the Primer-BLAST tool (Ye et al., 2012) and are listed in Table 5, below. Reactions were run on a Bio-Molecular Systems MIC qPCR Cycler according to the manufacturer's protocol and using the following conditions: 95° C. for 10 min, [95° C. for 15 seconds, 60° C. for 60 seconds] (60 cycles), and 95° C. for 60 seconds, followed by melt curve analysis at 72-95° C., 0.3° C./sec. The relative expression levels for each gene were calculated with the ΔΔCt method and normalized to the expression of REEP5 and SNRPD3 genes. Data obtained is summarized in FIG. 7.

TABLE 5

Primers used in this study

| Gene name | Full name | NCBI Accession number | Forward primer sequence (5'->3') | Reverse primer sequence (5'->3') | Amplicon length, bp |
|---|---|---|---|---|---|
| NRF-2 | Nuclear factor erythroid 2-related factor 2 | >NM_006164.5 | AACTACTCCC AGGTTGCCCA (SEQ ID NO: 1) | AATGTCTGCG CCAAAAGCTG (SEQ ID NO: 9) | 80 |
| SNRPD3 | Small nuclear ribonucleo-protein D3 | >NM_004175.5 | AACATGAACT GCCAGATGTC CA (SEQ ID NO: 2) | AGAAAGCGGA TTTTGCTGCC (SEQ ID NO: 10) | 101 |
| REEP5 | Receptor accessory protein 5 | >NM_005669.5 | CCATGAGGGA GAGGTTCGAC (SEQ ID NO: 3) | CACCAGTCCG ATGACACCAA (SEQ ID NO: 11) | 125 |
| Nqo1 | NAD(P)H dehydro-genase [quinone] 1 | >NM_000903.3 | AAAGGCTGGT TTGAGCGAGT (SEQ ID NO: 4) | GCCTTCTTAC TCCGGAAGGG (SEQ ID NO: 12) | 89 |
| GCLC | Glutamate-cysteine ligase | >NM_001498.4 | GACAATGAGA TTTAAGCCCC CTCC | TTCTGTGCTA CCTTCATGTT CTCA | 204 |

TABLE 5-continued

Primers used in this study

| Gene name | Full name | NCBI Accession number | Forward primer sequence (5'->3') | Reverse primer sequence (5'->3') | Amplicon length, bp |
|---|---|---|---|---|---|
| | catalytic subunit | | (SEQ ID NO: 5) | (SEQ ID NO: 13) | |
| SRXN1 | Sulfiredoxin-1 | >NM_080725.3 | TGGACACGAT CCGGGAGG (SEQ ID NO: 6) | ATGGTCTCTC GCTGCAGTTG (SEQ ID NO: 14) | 142 |
| TXNRD1 | Thioredoxin reductase 1, cytoplasmic | >NM_182729.3 | TGGACGATTC CGTCAAGAGA TAA (SEQ ID NO: 7) | AGCCCACAAC ACGTTCATTG (SEQ ID NO: 15) | 82 |
| HMOX | Heme oxygenase 1 | >NM_002133.3 | GACAGCATGC CCCAGGATTT (SEQ ID NO: 8) | ATCACCAGCT TGAAGCCGTC (SEQ ID NO: 16) | 134 |

Figure 7:
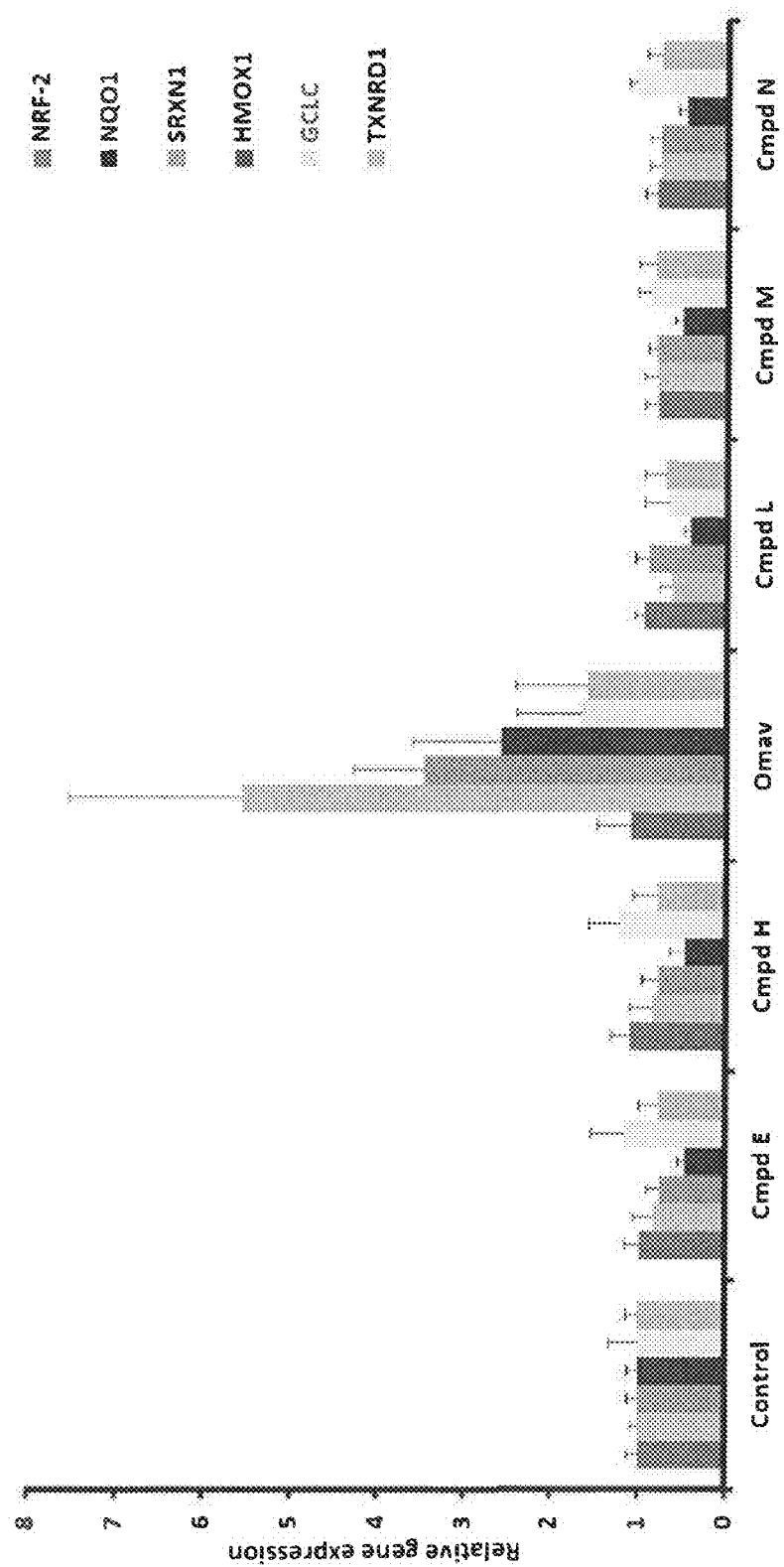
FIG. 7 is a bar graph summarizing the results obtained for a Nrf-2 activation assay comparing the activity of Ovameloxolone with various of the novel compounds disclosed herein.

The data presented in FIG. 7 demonstrates that all five of the novel test compounds examined were inactive in the assay—specifically they did not appear to activate Nrf-2 responsive genes and thereby promote resolution of inflammation. The assay was positive for omaveloxolone as would be expected based on literature reports. In summary, all of the novel test compounds examined in this assay were found to be differentiated from omaveloxolone in their mechanism of action.

Example 22: Lipoxygenase-15 Assay
(LO-15-Assay)

This assay has been adapted from: Hinman, A., Holst, C. R., Latham, J. C., Bruegger, J. J., Ulas, G., McCusker, K. P., Amagata, A., Davis, D., Hoff, K. G., Kahn-Kirby, A. H., Kim, V., Kosaka, Y., Lee, E., Malone, S. A., Mei, J. J., Richards, S. J., Rivera, V., Miller, G., Trimmer, J. K., Shrader, W. D., "Vitamin E hydroquinone is an endogenous regulator of ferroptosis via redox control of 15-lipoxygenase", (2018) PLoS ONE 13(8): e0201369. This assay was designed to determine if the novel compounds disclosed herein could be used to target 15-lipoxygenase and thereby inhibit 15-lipoxygenase-induced ferroptosis associated with mitochondrial disease.

Briefly, reactions were carried out in Corning 96 half-well black, flat bottom assay plates and contained final concentrations of 50 μM arachidonic acid (Cayman Chemical) as a substrate, 1:10 (v:v) cholate mix (2% (w:v) sodium cholate (Sigma-Aldrich) and 2% (v:v) DMSO with or without test compounds), 40 μM dihydrorhodamine 123 (Sigma-Aldrich) and 1:200 lipoxygenase-15 enzyme (soybean enzyme from Lipoxygenase Inhibitor Screening Assay Kit Item No. 760700 (Cayman Chemical)) in 100 mM Tris-HCl, pH 7.5. Cholate mix contained 2% (w:v) sodium cholate dissolved in 2% (v:v) DMSO. Cholate mix is used for the positive control wells (100% enzymatic activity). Due to the fact, that test compound stocks were dissolved in 100% DMSO, cholate mix was adjusted (sodium cholate was dissolved in water) and test compound DMSO stocks were further diluted with this solution in order to keep the final DMSO concentration in reaction below 0.2% and equal in all wells. Assay buffers and DMSO were deoxygenated to keep test compounds in the reduced state**. Stock solutions of test compounds were prepared in DMSO and then diluted to final assay concentrations in cholate mix such that final cholate and DMSO concentrations were maintained at 0.2%. Reactions were initiated by the addition of 50 μL of enzyme mix (80 μM dihydrorhodamine 123 and 1:100 lipoxygenase-15 enzyme in 100 mM Tris-HCl, pH 7.5) to wells containing 50 L substrate and cholate mix in 100 mM Tris-HCl, pH 7.5 and linear rates were assessed by measuring fluorescence, using excitation/emission of 485/535 nm on a Hidex Sense microplate reader every 10 seconds for 5 minutes at room temperature. First minute was used as a complete linear range for calculations of $IC_{50}$ values using GraphPad Prism software. For initial run compounds were tested at 100 μM and 10 μM concentrations and $IC_{50}$ values were determined for compounds where Lipoxygenase-15 activity in the presence of 10 μM compound was below 50% of vehicle control. Results of the assay are provided in Table 6.

The data presented in Table 6 indicates that four of the five novel test compounds examined were active in the LO-15 assay. Compound M gave the best result and it was approximately equivalent to Vatiquinone. Compounds H, L and N were active but not quite as good as vatiquinone or Compound M. The result for Compound E was outside of the range of the assay so an $IC_{50}$ could not be determined. Omaveloxolone and idebenone were not examined in this assay. In summary, ⅘ of the novel test compounds examined in this assay were found to be protective of the HepG2 cells when subjected to rotenone-induced oxidative stress and apoptosis.

TABLE 6

| | $IC_{50}$, μM |
|---|---|
| Compound E | NM |
| Compound H | 2.93 |
| Compound L | 5.76 |
| Compound M | 0.83 |
| Compound N | 2.67 |
| Vatiquinone | 0.59 |

NM is not meaningful.

** This assay requires use of the reduced form of each compound. Accordingly, this assay was performed with the hydroquinone version of each of the compounds listed in Table 6.

TABLE 7

Summary Data Table

| Compound | Structure | BSO Assay | Rotenone ATP Assay EC50, nM | RSL3 Assay EC50, nM | Rotenone Oxygraph Assay % Increase | Nrf-2 Assay | LO-15 Assay IC$_{50}$, μM |
|---|---|---|---|---|---|---|---|
| Vatiquinone | Vatiquinone | 44.3 +/− 17.5 | Inactive | 56.0 +/− 25.5 | Inactive | — | 0.59 |
| Omaveloxolone | Omaveloxolone | 48.6 +/− 10.5* | Inactive | Inactive | Inactive | Active | — |
| Idebenone | Idebenone | >1000 nM | 1561 +/− 910 | — | 70.2 +/− 15 | — | — |
| Compound E | Compound E | 65.1 +/− 20.5 | 2808 +/− 1126 | 73.2 +/− 31.11 | 37.9 +/− 10.7 | Inactive | NM |
| Compound H | Compound H | 164 +/− 44 | 1141 +/− 552 | 179 +/− 27 | 54.3 +/− 13 | Inactive | 2.93 |
| Compound L | Compound L | 39.1 +/− 2 | 891 +/− 448 | 41.9 +/− 16 | 58.6 +/− 15.5 | Inactive | 5.76 |
| Compound M | Compound M | 61.2 +/− 20.6 | 1336 +/− 1153 | 41.2 +/− 17.5 | 56.6 +/− 11.3 | Inactive | 0.83 |

TABLE 7-continued

Summary Data Table

| Compound | Structure | BSO Assay | Rotenone ATP Assay EC50, nM | RSL3 Assay EC50, nM | Rotenone Oxygraph Assay % Increase | Nrf-2 Assay | LO-15 Assay $IC_{50}$, μM |
|---|---|---|---|---|---|---|---|
| Compound N | Compound N | 144.2 +/− 28.5 | 2365 +/− 798.9 | 93.0 +/− 65.6 | 44.8 +/− 10.3 | Inactive | 2.67 |

*Omaveloxolone is toxic to cells at doses higher than 330 nM

The data in Table 7 can be summarized as follows:
a. Compounds E, H, L, M, N and idebenone are active in Complex I by-pass. Omaveloxolone and vatiquinone are not.
b. Compounds E, H, L, M, N and vatiquinone are active in BOTH ferroptosis assays (BSO and RSL3 Assays). Idebenone is very weakly active/borderline inactive in the BSO assay and was never tested in the RSL3 assay. Omaveloxolone is active in the BSO assay but completely inactive in the RSL3 assay.
c. Compounds E, H, L, M, and N do not activate the Nrf-2 pathway, while omaveloxolone does. Idebenone and vatiquinone were not tested.
d. Compounds E, H, L, M and N exhibit properties that are distinct from the benchmark compounds of Vatiquinone, Omaveloxolone and Idebenone, and that compounds E,H,L,M and N may exhibit a broader range of therapeutic activity as the only compounds that satisfy all of the following criteria: protection from BSO induced ferroptosis; protection from RSL3 induced ferroptosis; and complex I by-pass activity. In addition, at least compounds H, L, M and N are effective inhibitors of lipoxygenase-15.

Equivalents

The present application is not to be limited in terms of the particular embodiments described in this application, which are intended as single illustrations of individual aspects of the inventive compositions and methods presented herein. Many modifications and variations of the present technology can be made without departing from its spirit and scope, as will be apparent to those skilled in the art. Functionally equivalent methods and apparatuses within the scope of the present application, in addition to those enumerated herein, will be apparent to those skilled in the art from the foregoing descriptions. Such modifications and variations are intended to fall within the scope of the appended claims. The present application is to be limited only by the terms of the appended claims, along with the full scope of equivalents to which such claims are entitled. It is to be understood that the present application is not limited to particular methods, reagents, compounds compositions or biological systems, which can, of course, vary. It is also to be understood that the terminology used herein is for the purpose of describing particular embodiments only and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible sub-ranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

What is claimed is:

1. A compound of formula E-G, or pharmaceutically acceptable salts, stereoisomers, mixtures of stereoisomers, tautomers, hydrates, and/or solvates thereof, wherein E is 21 or 22:

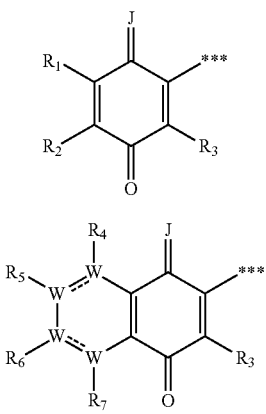

and G is 23 or 24:

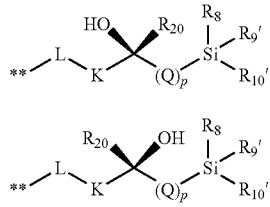

wherein,
J is O, S or N—$R_{11}$;
K is absent or —$(CR_{12}R_{13})$—;
L is —$(CR_{12}R_{13})$—;
each W is independently C (carbon) or N (nitrogen) and wherein for each use of W⚌W, the bond between each W can be a single bond or double bond and further provided that if a single bond, each C (carbon) atom will have a hydrogen atom linked hereto in addition to one of $R_4$, $R_5$, $R_6$ or $R_7$ and in either case each of $R_4$, $R_5$, $R_6$ and $R_7$ attached thereto is independently selected from H, D, F, Cl, Br, I, $C_1$-$C_6$ alkyl and $C_1$-$C_6$ alkoxy, and if W is N (nitrogen), each of $R_4$, $R_5$, $R_6$ and $R_7$ attached thereto is independently absent (if W⚌W is a double bond) or selected from H, D and $C_1$-$C_6$ alkyl (if W⚌W is a single bond);
each Q is independently a group of formula —$(CR_{12}R_{13})$-, O or Si provided that each O and each Si is not directly bonded to O or Si;

each of $R_1$, $R_2$ and $R_3$ is independently H, D, F, Cl, Br, I, $C_1$-$C_6$ alkyl or $C_1$-$C_6$ alkoxy;
or $R_1$ and $R_2$ together form a 5-membered carbocyclic ring, a 5-membered heterocyclic ring, a 5-membered aromatic or heteroaromatic ring, or a 6-membered heterocyclic ring;
each $R_8'$, $R_9'$ and $R_{10}'$ is independently a $C_1$-$C_4$ alkyl; or taken together $R_8'$ and $R_9'$ form a 3-, 4-, 5-, 6- or 7-membered carbocyclic or heterocyclic ring;
$R_{11}$ is H, D or $C_1$-$C_6$ alkyl;
each of $R_{12}$ and $R_{13}$ is independently H, D, F, Cl, Br, I, $C_1$-$C_6$ alkyl or $C_1$-$C_6$ alkoxy;
$R_{20}$ is H, D, F or $C_1$-$C_{12}$ alkyl;
p is an integer from 0 to 20, inclusive; and
* indicates the point of attachment of E to G and  indicates the point of attachment of G to E.

2. The compound of claim 1, wherein E is 21.

3. The compound of claim 2, wherein the compound is of formula Compound M-0:

Compound M-0

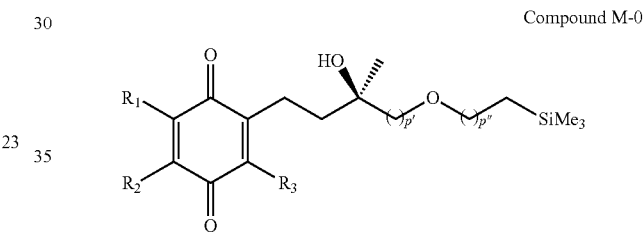

wherein each of $R_1$, $R_2$ and $R_3$ is independently H, F, —$CH_3$, —$OCH_3$, —$CH_2CH_3$, —$OCH_2CH_3$, or —$OCF_3$, p' is an integer from 1 to 9, inclusive and p" is an integer from 1 to 9, inclusive.

4. The compound of claim 2, wherein the compound is

Compound M

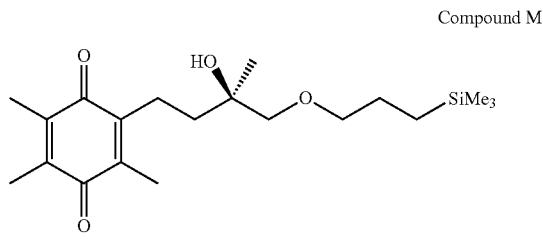 [SMILES: CC1=C(C)C(=O)C(CC[C@@](C)(O)COCCC[Si](C)(C)C)=C(C)C1=O]

or a pharmaceutically acceptable salt, a stereoisomer, a mixture of stereoisomers, a tautomer, a hydrate, and/or a solvate thereof.

5. A composition or medicament comprising a compound of claim 1.

* * * * *

SEQUENCE LISTING

Sequence total quantity: 16
SEQ ID NO: 1          moltype = DNA  length = 20

```
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 1
aactactccc aggttgccca                                                    20

SEQ ID NO: 2            moltype = DNA  length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 2
aacatgaact gccagatgtc ca                                                 22

SEQ ID NO: 3            moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 3
ccatgaggga gaggttcgac                                                    20

SEQ ID NO: 4            moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 4
aaaggctggt ttgagcgagt                                                    20

SEQ ID NO: 5            moltype = DNA  length = 24
FEATURE                 Location/Qualifiers
misc_feature            1..24
                        note = Description of Artificial Sequence: Synthetic primer
source                  1..24
                        mol_type = other DNA
                        organism = synthetic construct
SEQUENCE: 5
gacaatgaga tttaagcccc ctcc                                               24

SEQ ID NO: 6            moltype = DNA  length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 6
tggacacgat ccgggagg                                                      18

SEQ ID NO: 7            moltype = DNA  length = 23
FEATURE                 Location/Qualifiers
misc_feature            1..23
                        note = Description of Artificial Sequence: Synthetic primer
source                  1..23
                        mol_type = other DNA
                        organism = synthetic construct
SEQUENCE: 7
tggacgattc cgtcaagaga taa                                                23

SEQ ID NO: 8            moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 8
gacagcatgc cccaggattt                                                    20
```

```
SEQ ID NO: 9              moltype = DNA   length = 20
FEATURE                   Location/Qualifiers
misc_feature              1..20
                          note = Description of Artificial Sequence: Synthetic primer
source                    1..20
                          mol_type = other DNA
                          organism = synthetic construct
SEQUENCE: 9
aatgtctgcg ccaaaagctg                                                    20

SEQ ID NO: 10             moltype = DNA   length = 20
FEATURE                   Location/Qualifiers
misc_feature              1..20
                          note = Description of Artificial Sequence: Synthetic primer
source                    1..20
                          mol_type = other DNA
                          organism = synthetic construct
SEQUENCE: 10
agaaagcgga ttttgctgcc                                                    20

SEQ ID NO: 11             moltype = DNA   length = 20
FEATURE                   Location/Qualifiers
misc_feature              1..20
                          note = Description of Artificial Sequence: Synthetic primer
source                    1..20
                          mol_type = other DNA
                          organism = synthetic construct
SEQUENCE: 11
caccagtccg atgacaccaa                                                    20

SEQ ID NO: 12             moltype = DNA   length = 20
FEATURE                   Location/Qualifiers
misc_feature              1..20
                          note = Description of Artificial Sequence: Synthetic primer
source                    1..20
                          mol_type = other DNA
                          organism = synthetic construct
SEQUENCE: 12
gccttcttac tccggaaggg                                                    20

SEQ ID NO: 13             moltype = DNA   length = 24
FEATURE                   Location/Qualifiers
misc_feature              1..24
                          note = Description of Artificial Sequence: Synthetic primer
source                    1..24
                          mol_type = other DNA
                          organism = synthetic construct
SEQUENCE: 13
ttctgtgcta ccttcatgtt ctca                                               24

SEQ ID NO: 14             moltype = DNA   length = 20
FEATURE                   Location/Qualifiers
misc_feature              1..20
                          note = Description of Artificial Sequence: Synthetic primer
source                    1..20
                          mol_type = other DNA
                          organism = synthetic construct
SEQUENCE: 14
atggtctctc gctgcagttg                                                    20

SEQ ID NO: 15             moltype = DNA   length = 20
FEATURE                   Location/Qualifiers
misc_feature              1..20
                          note = Description of Artificial Sequence: Synthetic primer
source                    1..20
                          mol_type = other DNA
                          organism = synthetic construct
SEQUENCE: 15
agcccacaac acgttcattg                                                    20

SEQ ID NO: 16             moltype = DNA   length = 20
FEATURE                   Location/Qualifiers
misc_feature              1..20
                          note = Description of Artificial Sequence: Synthetic primer
source                    1..20
                          mol_type = other DNA
                          organism = synthetic construct
```

```
SEQUENCE: 16
atcaccagct tgaagccgtc                                           20
```